(12) United States Patent
Bachand et al.

(10) Patent No.: US 7,745,636 B2
(45) Date of Patent: Jun. 29, 2010

(54) HEPATITIS C VIRUS INHIBITORS

(75) Inventors: Carol Bachand, Candiac (CA); Makonen Belema, North Haven, CT (US); Daniel H. Deon, Brossard (CA); Andrew C. Good, Wallingford, CT (US); Jason Goodrich, Meriden, CT (US); Clint A. James, Longueuil (CA); Rico Lavoie, Candiac (CA); Omar D. Lopez, Wallingford, CT (US); Alain Martel, Delson (CA); Nicholas A. Meanwell, East Hampton, CT (US); Van N. Nguyen, Meriden, CT (US); Jeffrey Lee Romine, Meriden, CT (US); Edward H. Ruediger, Greenfield Park (CA); Lawrence B. Snyder, Killingworth, CT (US); Denis R. St. Laurent, Newington, CT (US); Fukang Yang, Madison, CT (US); David R. Langley, Meriden, CT (US); Gan Wang, Wallingford, CT (US); Lawrence G. Hamann, North Grafton, MA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 180 days.

(21) Appl. No.: 12/029,680

(22) Filed: Feb. 12, 2008

(65) Prior Publication Data
US 2008/0299075 A1    Dec. 4, 2008

Related U.S. Application Data

(63) Continuation-in-part of application No. 11/835,524, filed on Aug. 8, 2007.

(60) Provisional application No. 60/837,247, filed on Aug. 11, 2006.

(51) Int. Cl.
*C07D 233/02*    (2006.01)
*A01N 43/50*    (2006.01)

(52) U.S. Cl. .................................. 548/300.1; 514/396
(58) Field of Classification Search .................. None
See application file for complete search history.

(56) References Cited

U.S. PATENT DOCUMENTS

| 5,654,451 A | 8/1997 | Kari |
| 2004/0142985 A1 | 7/2004 | Singh et al. |
| 2005/0119318 A1 | 6/2005 | Hudyma et al. |

FOREIGN PATENT DOCUMENTS

| WO | WO 94/15909 | 7/1994 |
| WO | WO 2004/002940 A1 | 1/2004 |
| WO | WO 2005/047288 A1 | 5/2005 |
| WO | WO 2005/105761 A1 | 11/2005 |
| WO | WO 2006/022442 A1 | 3/2006 |
| WO | WO 2006/093867 A1 | 9/2006 |
| WO | WO2006/133326 | 12/2006 |
| WO | WO 2007/031791 A1 | 3/2007 |
| WO | WO 2007/058384 A1 | 5/2007 |
| WO | WO 2007/077186 A1 | 7/2007 |
| WO | WO 2007/080401 A1 | 7/2007 |
| WO | WO 2007/081517 A2 | 7/2007 |
| WO | WO 2007/082554 A1 | 7/2007 |
| WO | WO2007/138242 | 12/2007 |
| WO | WO2008/021927 | 2/2008 |
| WO | WO2008/021936 | 2/2008 |
| WO | WO2008021928 | 2/2008 |

OTHER PUBLICATIONS

U.S. Appl. No. 12/120,494, filed May 14, 2008, Bachand, et al.
U.S. Appl. No. 12/030,232, filed Feb. 13, 2008, Bachand et al.

*Primary Examiner*—Frederick Krass
*Assistant Examiner*—Marcos Sznaidman
(74) *Attorney, Agent, or Firm*—Pamela A. Mingo

(57) ABSTRACT

The present disclosure relates to compounds, compositions and methods for the treatment of hepatitis C virus (HCV) infection. Also disclosed are pharmaceutical compositions containing such compounds and methods for using these compounds in the treatment of HCV infection.

26 Claims, No Drawings

HEPATITIS C VIRUS INHIBITORS

CROSS REFERENCE TO RELATED APPLICATIONS

This application is a continuation-in-part of U.S. non-provisional application Ser. No. 11/835,524, filed Aug. 8, 2007, and claims the benefit of U.S. provisional application No. 60/837,247, filed Aug. 11, 2006.

The present disclosure is generally directed to antiviral compounds, and more specifically directed to compounds which can inhibit the function of the NS5A protein encoded by Hepatitis C virus (HCV), compositions comprising such compounds, and methods for inhibiting the function of the NS5A protein.

HCV is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma.

Presently, the most effective HCV therapy employs a combination of alpha-interferon and ribavirin, leading to sustained efficacy in 40% of patients. Recent clinical results demonstrate that pegylated alpha-interferon is superior to unmodified alpha-interferon as monotherapy. However, even with experimental therapeutic regimens involving combinations of pegylated alpha-interferon and ribavirin, a substantial fraction of patients do not have a sustained reduction in viral load. Thus, there is a clear and long-felt need to develop effective therapeutics for treatment of HCV infection.

HCV is a positive-stranded RNA virus. Based on a comparison of the deduced amino acid sequence and the extensive similarity in the 5' untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. At least six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2-NS3 junction; the second one is a serine protease contained within the N-terminal region of NS3 (also referred to herein as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities. NS5B (also referred to herein as HCV polymerase) is a RNA-dependent RNA polymerase that is involved in the replication of HCV.

Compounds useful for treating HCV-infected patients are desired which selectively inhibit HCV viral replication. In particular, compounds which are effective to inhibit the function of the NS5A protein are desired. The HCV NS5A protein is described, for example, in Tan, S.-L., Katzel, M. G. *Virology* 2001, 284, 1-12; and in Park, K.-J.; Choi, S.-H, *J. Biological Chemistry* 2003.

In its first aspect the present disclosure provides a compound of Formula (I)

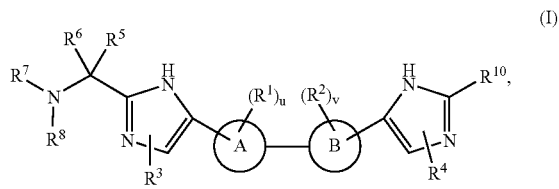

(I)

or a pharmaceutically acceptable salt thereof, wherein u and v are independently 0, 1, 2, or 3;

A and B are independently selected from phenyl and a six-membered heteroaromatic ring containing one, two, or three nitrogen atoms;

each $R^1$ and $R^2$ is independently selected from alkoxy, alkoxyalkyl, alkoxycarbonyl, alkyl, arylalkoxycarbonyl, carboxy, formyl, halo, haloalkyl, hydroxy, hydroxyalkyl, —$NR^aR^b$, $(NR^aR^b)$alkyl, and $(NR^aR^b)$carbonyl;

$R^3$ and $R^4$ are each independently selected from hydrogen, alkoxycarbonyl, alkyl, arylalkoxycarbonyl, carboxy, haloalkyl, $(NR^aR^b)$carbonyl, and trialkylsilylalkoxyalkyl;

$R^5$ and $R^6$ are each independently selected from hydrogen, alkenyl, alkoxyalkyl, alkyl, haloalkyl, and $(NR^aR^b)$alkyl; or, $R^5$ and $R^6$, together with the carbon atom to which they are attached, form a five or six membered saturated ring optionally containing one or two heteroatoms selected from $NR^z$, O, and S; wherein $R^z$ is selected from hydrogen and alkyl;

$R^7$ is selected from hydrogen, $R^9$—C(O)—, and $R^9$—C(S)—;

$R^8$ is selected from hydrogen and alkyl;

$R^9$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —$NR^cR^d$, $(NR^cR^d)$alkenyl, $(NR^cR^d)$alkyl, and $(NR^cR^d)$carbonyl;

$R^{10}$ is selected from

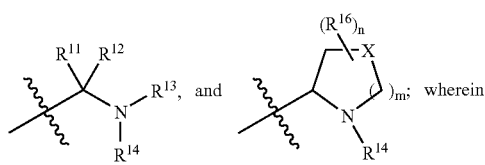

and wherein $R^{11}$ and $R^{12}$ are each independently selected from hydrogen, alkenyl, alkoxyalkyl, alkyl, haloalkyl, and $(NR^aR^b)$alkyl; or, $R^{11}$ and $R^{12}$, together with the carbon atom to which they are attached, form a five or six membered saturated ring optionally containing one or two heteroatoms selected from $NR^z$, O, and S; wherein $R^z$ is selected from hydrogen and alkyl;

$R^{13}$ is selected from hydrogen and alkyl;

$R^{14}$ is selected from hydrogen, $R^{15}$—C(O)—, and $R^{15}$—C(S)—;

$R^{15}$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —$NR^cR^d$, $(NR^cR^d)$alkenyl, $(NR^c R^d)$alkyl, and $(NR^cR^d)$carbonyl;

m is 0, 1, or 2;

n is 0, 1, 2, 3, or 4;

X is selected from O, S, S(O), $SO_2$, $CH_2$, $CHR^{16}$, and $C(R^{16})_2$; provided that when m is 0, X is selected from $CH_2$, $CHR^{16}$, and $C(R^{16})_2$;

each $R^{16}$ is independently selected from alkoxy, alkyl, aryl, halo, haloalkyl, hydroxy, and —$NR^aR^b$, wherein the alkyl can optionally form a fused three- to six-membered ring with an adjacent carbon atom, wherein the three- to six-membered ring is optionally substituted with one or two alkyl groups.

In a first embodiment of the first aspect m is 0.

In a second embodiment of the first aspect u and v are each independently 0 or 1; and each $R^1$ and $R^2$ is independently selected from alkyl and halo.

In a third embodiment of the first aspect u and v are each 0.

In a fourth embodiment of the first aspect X is selected from $CH_2$ and $CHR^{16}$. In a fifth embodiment of the first aspect X is $CH_2$.

In a sixth embodiment of the first aspect $R^3$ and $R^4$ are each independently selected from hydrogen, haloalkyl, and trialkylsilylalkoxyalkyl. In a seventh embodiment $R^3$ and $R^4$ are each independently selected from hydrogen and haloalkyl.

In an eighth embodiment of the first aspect n is 0, 1, or 2; and, when present, each $R^{16}$ is halo. In a ninth embodiment n is 0.

In a tenth embodiment of the first aspect $R^5$ and $R^6$ are independently selected from hydrogen and alkyl.

In an eleventh embodiment of the first aspect $R^{11}$ and $R^{12}$ are independently selected from hydrogen and alkyl.

In a twelfth embodiment of the first aspect at least one of $R^7$ and $R^{14}$ is hydrogen.

In a thirteenth embodiment of the first aspect $R^7$ is $R^9$—C(O)—; and $R^{14}$ is $R^{15}$—C(O)—. In a fourteenth embodiment $R^9$ and $R^{15}$ are each independently selected from alkoxy, alkoxyalkyl, alkyl, alkylcarbonylalkyl, aryl, arylalkenyl, arylalkoxy, arylalkyl, aryloxyalkyl, cycloalkyl, (cycloalkyl)alkyl, cycloalkyloxyalkyl, heterocyclyl, heterocyclylalkyl, hydroxyalkyl, —$NR^cR^d$, $(NR^cR^d)$alkenyl, $(NR^cR^d)$alkyl, and $(NR^cR^d)$carbonyl. In a fifteenth embodiment $R^9$ and $R^{15}$ are each independently selected from alkoxy, arylalkoxy, arylalkyl, and $(NR^cR^d)$alkyl.

In a second aspect the present disclosure provides a compound of Formula (II)

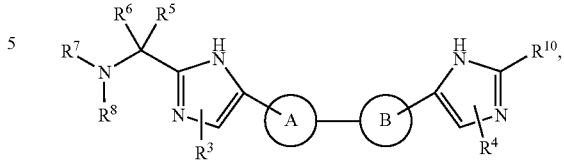

(II)

or a pharmaceutically acceptable salt thereof, wherein

A and B are independently selected from phenyl and a six-membered heteroaromatic ring containing one, two, or three nitrogen atoms;

$R^3$ and $R^4$ are each independently selected from hydrogen, haloalkyl, and trialkylsilylalkoxyalkyl;

$R^5$ and $R^6$ are each independently selected from hydrogen, and alkyl;

$R^7$ is selected from hydrogen and $R^9$—C(O)—;

$R^8$ is selected from hydrogen and alkyl;

$R^9$ is independently selected from alkoxy, arylalkoxy, arylalkyl, and $(NR^cR^d)$alkyl;

$R^{10}$ is selected from

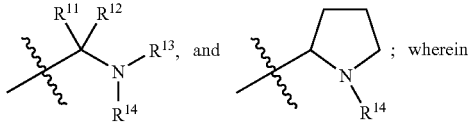

$R^{11}$ and $R^{12}$ are each independently selected from hydrogen and alkyl;

$R^{13}$ is selected from hydrogen and alkyl;

$R^{14}$ is selected from hydrogen and $R^{15}$—C(O)—; and $R^{15}$ is independently selected from alkoxy, arylalkoxy, arylalkyl, and $(NR^cR^d)$alkyl.

In a third aspect the present disclosure provides a composition comprising a compound of Formula (I), or a pharmaceutically acceptable salt thereof, and a pharmaceutically acceptable carrier. In a first embodiment of the third aspect, the composition comprises one or two additional compounds having anti-HCV activity. In a second embodiment of the third aspect at least one of the additional compounds is an interferon or a ribavirin. In a third embodiment of the third aspect the interferon is selected from interferon alpha 2B, pegylated interferon alpha, consensus interferon, interferon alpha 2A, and lymphoblastoid interferon tau.

In a fourth embodiment of the third aspect the present disclosure provides a composition comprising a compound of Formula (I), or a pharmaceutically acceptable salt thereof, a pharmaceutically acceptable carrier, and one or two additional compounds having anti-HCV activity, wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5'-monophosphate dehydrogenase inhibitor, amantadine, and rimantadine.

In a fifth embodiment of the third aspect the present disclosure provides a composition comprising a compound of Formula (I), or a pharmaceutically acceptable salt thereof, a pharmaceutically acceptable carrier, and one or two additional compounds having anti-HCV activity, wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

In a fourth aspect the present disclosure provides a method of treating an HCV infection in a patient, comprising administering to the patient a therapeutically effective amount of a compound of Formula (I), or a pharmaceutically acceptable salt thereof. In a first embodiment of the fourth aspect the method further comprises administering one or two additional compounds having anti-HCV activity prior to, after or simultaneously with the compound of Formula (I), or a pharmaceutically acceptable salt thereof. In a second embodiment of the fourth aspect at least one of the additional compounds is an interferon or a ribavirin. In a third embodiment of the fourth aspect the interferon is selected from interferon alpha 2B, pegylated interferon alpha, consensus interferon, interferon alpha 2A, and lymphoblastoid interferon tau.

In a fourth embodiment of the fourth aspect the present disclosure provides a method of treating an HCV infection in a patient, comprising administering to the patient a therapeutically effective amount of a compound of Formula (I), or a pharmaceutically acceptable salt thereof and administering one or two additional compounds having anti-HCV activity prior to, after or simultaneously with the compound of Formula (I), or a pharmaceutically acceptable salt thereof, wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5'-monophosphate dehydrogenase inhibitor, amantadine, and rimantadine.

In a fifth embodiment of the fourth aspect the present disclosure provides a method of treating an HCV infection in a patient, comprising administering to the patient a therapeutically effective amount of a compound of Formula (I), or a pharmaceutically acceptable salt thereof and administering one or two additional compounds having anti-HCV activity prior to, after or simultaneously with the compound of Formula (I), or a pharmaceutically acceptable salt thereof, wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

Other embodiments of the present disclosure may comprise suitable combinations of two or more of embodiments and/or aspects disclosed herein.

Yet other embodiments and aspects of the disclosure will be apparent according to the description provided below.

The compounds of the present disclosure also exist as tautomers; therefore the present disclosure also encompasses all tautomeric forms.

The description of the present disclosure herein should be construed in congruity with the laws and principals of chemical bonding. In some instances it may be necessary to remove a hydrogen atom in order accommodate a substituent at any given location. For example, in the structure shown below

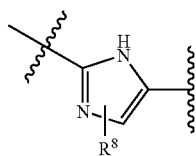

$R^8$ may be attached to either the carbon atom in the imidazole ring or, alternatively, $R^8$ may take the place of the hydrogen atom on the nitrogen ring to form an N-substituted imidazole.

It should be understood that the compounds encompassed by the present disclosure are those that are suitably stable for use as pharmaceutical agent.

It is intended that the definition of any substituent or variable (e.g., $R^1$, $R^2$, $R^5$, $R^6$, etc.) at a particular location in a molecule be independent of its definitions elsewhere in that molecule. For example, when u is 2, each of the two $R^1$ groups may be the same or different.

All patents, patent applications, and literature references cited in the specification are herein incorporated by reference in their entirety. In the case of inconsistencies, the present disclosure, including definitions, will prevail.

As used in the present specification, the following terms have the meanings indicated:

As used herein, the singular forms "a", "an", and "the" include plural reference unless the context clearly dictates otherwise.

Unless stated otherwise, all aryl, cycloalkyl, and heterocyclyl groups of the present disclosure may be substituted as described in each of their respective definitions. For example, the aryl part of an arylalkyl group may be substituted as described in the definition of the term 'aryl'.

The term "alkenyl," as used herein, refers to a straight or branched chain group of two to six carbon atoms containing at least one carbon-carbon double bond.

The term "alkenyloxy," as used herein, refers to an alkenyl group attached to the parent molecular moiety through an oxygen atom.

The term "alkenyloxycarbonyl," as used herein, refers to an alkenyloxy group attached to the parent molecular moiety through a carbonyl group.

The term "alkoxy," as used herein, refers to an alkyl group attached to the parent molecular moiety through an oxygen atom.

The term "alkoxyalkyl," as used herein, refers to an alkyl group substituted with one, two, or three alkoxy groups.

The term "alkoxyalkylcarbonyl," as used herein, refers to an alkoxyalkyl group attached to the parent molecular moiety through a carbonyl group.

The term "alkoxycarbonyl," as used herein, refers to an alkoxy group attached to the parent molecular moiety through a carbonyl group.

The term "alkoxycarbonylalkyl," as used herein, refers to an alkyl group substituted with one, two, or three alkoxycarbonyl groups.

The term "alkyl," as used herein, refers to a group derived from a straight or branched chain saturated hydrocarbon containing from one to six carbon atoms. In the compounds of the present disclosure, when m and/or n is 1 or 2; X and/or Y is $CHR^5$ and/or $CHR^6$, respectively, and $R^5$ and/or $R^6$ is alkyl, each alkyl can optionally form a fused three- to six-membered ring with an adjacent carbon atom to provide one of the structures shown below:

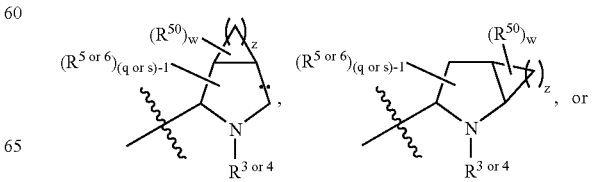

-continued

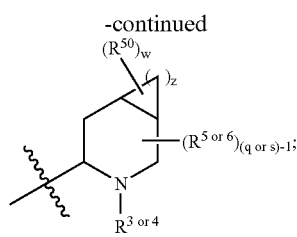

where z is 1, 2, 3, or 4, w is 0, 1, or 2, and $R^{50}$ is alkyl. When w is 2, the two $R^{50}$ alkyl groups may be the same or different.

The term "alkylcarbonyl," as used herein, refers to an alkyl group attached to the parent molecular moiety through a carbonyl group.

The term "alkylcarbonylalkyl," as used herein, refers to an alkyl group substituted with one, two, or three alkylcarbonyl groups.

The term "alkylcarbonyloxy," as used herein, refers to an alkylcarbonyl group attached to the parent molecular moiety through an oxygen atom.

The term "alkylsulfanyl," as used herein, refers to an alkyl group attached to the parent molecular moiety through a sulfur atom.

The term "alkylsulfonyl," as used herein, refers to an alkyl group attached to the parent molecular moiety through a sulfonyl group.

The term "aryl," as used herein, refers to a phenyl group, or a bicyclic fused ring system wherein one or both of the rings is a phenyl group. Bicyclic fused ring systems consist of a phenyl group fused to a four- to six-membered aromatic or non-aromatic carbocyclic ring. The aryl groups of the present disclosure can be attached to the parent molecular moiety through any substitutable carbon atom in the group. Representative examples of aryl groups include, but are not limited to, indanyl, indenyl, naphthyl, phenyl, and tetrahydronaphthyl. The aryl groups of the present disclosure are optionally substituted with one, two, three, four, or five substituents independently selected from alkoxy, alkoxyalkyl, alkoxycarbonyl, alkyl, alkylcarbonyl, a second aryl group, arylalkoxy, arylalkyl, arylcarbonyl, cyano, halo, haloalkoxy, haloalkyl, heterocyclyl, heterocyclylalkyl, heterocyclylcarbonyl, hydroxy, hydroxyalkyl, nitro, —$NR^xR^y$, ($NR^xR^y$)alkyl, oxo, and —$P(O)OR_2$, wherein each R is independently selected from hydrogen and alkyl; and wherein the alkyl part of the arylalkyl and the heterocyclylalkyl are unsubstituted and wherein the second aryl group, the aryl part of the arylalkyl, the aryl part of the arylcarbonyl, the heterocyclyl, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro.

The term "arylalkenyl," as used herein, refers to an alkenyl group substituted with one, two, or three aryl groups.

The term "arylalkoxy," as used herein, refers to an aryl group attached to the parent molecular moiety through an alkoxy group.

The term "arylalkoxyalkyl," as used herein, refers to an alkyl group substituted with one, two, or three arylalkoxy groups.

The term "arylalkoxyalkylcarbonyl," as used herein, refers to an arylalkoxyalkyl group attached to the parent molecular moiety through a carbonyl group.

The term "arylalkoxycarbonyl," as used herein, refers to an arylalkoxy group attached to the parent molecular moiety through a carbonyl group.

The term "arylalkyl," as used herein, refers to an alkyl group substituted with one, two, or three aryl groups. The alkyl part of the arylalkyl is further optionally substituted with one or two additional groups independently selected from alkoxy, alkylcarbonyloxy, halo, haloalkoxy, haloalkyl, heterocyclyl, hydroxy, and —$NR^cR^d$, wherein the heterocyclyl is further optionally substituted with one or two substituents independently selected from alkoxy, alkyl, unsubstituted aryl, unsubstituted arylalkoxy, unsubstituted arylalkoxycarbonyl, halo, haloalkoxy, haloalkyl, hydroxy, and —$NR^xR^y$.

The term "arylalkylcarbonyl," as used herein, refers to an arylalkyl group attached to the parent molecular moiety through a carbonyl group.

The term "arylcarbonyl," as used herein, refers to an aryl group attached to the parent molecular moiety through a carbonyl group.

The term "aryloxy," as used herein, refers to an aryl group attached to the parent molecular moiety through an oxygen atom.

The term "aryloxyalkyl," as used herein, refers to an alkyl group substituted with one, two, or three aryloxy groups.

The term "aryloxycarbonyl," as used herein, refers to an aryloxy group attached to the parent molecular moiety through a carbonyl group.

The term "arylsulfonyl," as used herein, refers to an aryl group attached to the parent molecular moiety through a sulfonyl group.

The terms "Cap" and "cap" as used herein, refer to the group which is placed on the nitrogen atom of the terminal nitrogen-containing ring, i.e., the pyrrolidine rings of compound 1e. It should be understood that "Cap" or "cap" can refer to the reagent used to append the group to the terminal nitrogen-containing ring or to the fragment in the final product, i.e., "Cap-51" or "The Cap-51 fragment found in LS-19".

The term "carbonyl," as used herein, refers to —C(O)—.

The term "carboxy," as used herein, refers to —$CO_2H$.

The term "cyano," as used herein, refers to —CN.

The term "cycloalkyl," as used herein, refers to a saturated monocyclic, hydrocarbon ring system having three to seven carbon atoms and zero heteroatoms. Representative examples of cycloalkyl groups include, but are not limited to, cyclopropyl, cyclopentyl, and cyclohexyl. The cycloalkyl groups of the present disclosure are optionally substituted with one, two, three, four, or five substituents independently selected from alkoxy, alkyl, aryl, cyano, halo, haloalkoxy, haloalkyl, heterocyclyl, hydroxy, hydroxyalkyl, nitro, and —$NR^xR^y$, wherein the aryl and the heterocyclyl are further optionally substituted with one, two, or three substituents independently selected from alkoxy, alkyl, cyano, halo, haloalkoxy, haloalkyl, hydroxy, and nitro.

The term "(cycloalkyl)alkenyl," as used herein, refers to an alkenyl group substituted with one, two, or three cycloalkyl groups.

The term "(cycloalkyl)alkyl," as used herein, refers to an alkyl group substituted with one, two, or three cycloalkyl groups. The alkyl part of the (cycloalkyl)alkyl is further optionally substituted with one or two groups independently selected from hydroxy and —$NR^cR^d$.

The term "cycloalkyloxy," as used herein, refers to a cycloalkyl group attached to the parent molecular moiety through an oxygen atom.

The term "cycloalkyloxyalkyl," as used herein, refers to an alkyl group substituted with one, two, or three cycloalkyloxy groups.

The term "cycloalkylsulfonyl," as used herein, refers to a cycloalkyl group attached to the parent molecular moiety through a sulfonyl group.

The term "formyl," as used herein, refers to —CHO.

The terms "halo" and "halogen," as used herein, refer to F, Cl, Br, or I.

The term "haloalkoxy," as used herein, refers to a haloalkyl group attached to the parent molecular moiety through an oxygen atom.

The term "haloalkoxycarbonyl," as used herein, refers to a haloalkoxy group attached to the parent molecular moiety through a carbonyl group.

The term "haloalkyl," as used herein, refers to an alkyl group substituted by one, two, three, or four halogen atoms.

The term "heterocyclyl," as used herein, refers to a four-, five-, six-, or seven-membered ring containing one, two, three, or four heteroatoms independently selected from nitrogen, oxygen, and sulfur. The four-membered ring has zero double bonds, the five-membered ring has zero to two double bonds, and the six- and seven-membered rings have zero to three double bonds. The term "heterocyclyl" also includes bicyclic groups in which the heterocyclyl ring is fused to another monocyclic heterocyclyl group, or a four- to six-membered aromatic or non-aromatic carbocyclic ring; as well as bridged bicyclic groups such as 7-azabicyclo[2.2.1]hept-7-yl, 2-azabicyclo[2.2.2]oc-2-tyl, and 2-azabicyclo[2.2.2]oc-3-tyl. The heterocyclyl groups of the present disclosure can be attached to the parent molecular moiety through any carbon atom or nitrogen atom in the group. Examples of heterocyclyl groups include, but are not limited to, benzothienyl, furyl, imidazolyl, indolinyl, indolyl, isothiazolyl, isoxazolyl, morpholinyl, oxazolyl, piperazinyl, piperidinyl, pyrazolyl, pyridinyl, pyrrolidinyl, pyrrolopyridinyl, pyrrolyl, thiazolyl, thienyl, thiomorpholinyl, 7-azabicyclo[2.2.1]hept-7-yl, 2-azabicyclo[2.2.2]oc-2-tyl, and 2-azabicyclo[2.2.2]oc-3-tyl. The heterocyclyl groups of the present disclosure are optionally substituted with one, two, three, four, or five substituents independently selected from alkoxy, alkoxyalkyl, alkoxycarbonyl, alkyl, alkylcarbonyl, aryl, arylalkyl, arylcarbonyl, cyano, halo, haloalkoxy, haloalkyl, a second heterocyclyl group, heterocyclylalkyl, heterocyclylcarbonyl, hydroxy, hydroxyalkyl, nitro, —$NR^xR^y$, ($NR^xR^y$)alkyl, and oxo, wherein the alkyl part of the arylalkyl and the heterocyclylalkyl are unsubstituted and wherein the aryl, the aryl part of the arylalkyl, the aryl part of the arylcarbonyl, the second heterocyclyl group, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro.

The term "heterocyclylalkenyl," as used herein, refers to an alkenyl group substituted with one, two, or three heterocyclyl groups.

The term "heterocyclylalkoxy," as used herein, refers to a heterocyclyl group attached to the parent molecular moiety through an alkoxy group.

The term "heterocyclylalkoxycarbonyl," as used herein, refers to a heterocyclylalkoxy group attached to the parent molecular moiety through a carbonyl group.

The term "heterocyclylalkyl," as used herein, refers to an alkyl group substituted with one, two, or three heterocyclyl groups. The alkyl part of the heterocyclylalkyl is further optionally substituted with one or two additional groups independently selected from alkoxy, alkylcarbonyloxy, aryl, halo, haloalkoxy, haloalkyl, hydroxy, and —$NR^cR^d$, wherein the aryl is further optionally substituted with one or two substituents independently selected from alkoxy, alkyl, unsubstituted aryl, unsubstituted arylalkoxy, unsubstituted arylalkoxycarbonyl, halo, haloalkoxy, haloalkyl, hydroxy, and —$NR^xR^y$.

The term "heterocyclylalkylcarbonyl," as used herein, refers to a heterocyclylalkyl group attached to the parent molecular moiety through a carbonyl group.

The term "heterocyclylcarbonyl," as used herein, refers to a heterocyclyl group attached to the parent molecular moiety through a carbonyl group.

The term "heterocyclyloxy," as used herein, refers to a heterocyclyl group attached to the parent molecular moiety through an oxygen atom.

The term "heterocyclyloxyalkyl," as used herein, refers to an alkyl group substituted with one, two, or three heterocyclyloxy groups.

The term "heterocyclyloxycarbonyl," as used herein, refers to a heterocyclyloxy group attached to the parent molecular moiety through a carbonyl group.

The term "hydroxy," as used herein, refers to —OH.

The term "hydroxyalkyl," as used herein, refers to an alkyl group substituted with one, two, or three hydroxy groups.

The term "hydroxyalkylcarbonyl," as used herein, refers to a hydroxyalkyl group attached to the parent molecular moiety through a carbonyl group.

The term "nitro," as used herein, refers to —$NO_2$.

The term "—$NR^aR^b$," as used herein, refers to two groups, $R^a$ and $R^b$, which are attached to the parent molecular moiety through a nitrogen atom. $R^a$ and $R^b$ are independently selected from hydrogen, alkenyl, and alkyl.

The term "($NR^aR^b$)alkyl," as used herein, refers to an alkyl group substituted with one, two, or three —$NR^aR^b$ groups.

The term "($NR^aR^b$)carbonyl," as used herein, refers to an —$NR^aR^b$ group attached to the parent molecular moiety through a carbonyl group.

The term "$NR^cR^d$," as used herein, refers to two groups, $R^c$ and $R^d$, which are attached to the parent molecular moiety through a nitrogen atom. $R^c$ and $R^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, ($NR^eR^f$)alkyl, ($NR^eR^f$)alkylcarbonyl, ($NR^eR^f$)carbonyl, ($NR^eR^f$)sulfonyl, —C(NCN)OR', and —C(NCN)$NR^xR^y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —$NR^eR^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro.

The term "($NR^cR^d$)alkenyl," as used herein, refers to an alkenyl group substituted with one, two, or three —$NR^cR^d$ groups.

The term "($NR^cR^d$)alkyl," as used herein, refers to an alkyl group substituted with one, two, or three —$NR^cR^d$ groups. The alkyl part of the ($NR^cR^d$)alkyl is further optionally substituted with one or two additional groups selected from alkoxy, alkoxyalkylcarbonyl, alkoxycarbonyl, alkylsulfanyl, arylalkoxyalkylcarbonyl, carboxy, heterocyclyl, heterocyclylcarbonyl, hydroxy, and $(NR^eR^f)$carbonyl; wherein the heterocyclyl is further optionally substituted with one, two, three, four, or five substituents independently selected from alkoxy, alkyl, cyano, halo, haloalkoxy, haloalkyl, and nitro.

The term "$(NR^cR^d)$carbonyl," as used herein, refers to an —$NR^cR^d$ group attached to the parent molecular moiety through a carbonyl group.

The term "—$NR^eR^f$," as used herein, refers to two groups, $R^e$ and $R^f$ which are attached to the parent molecular moiety through a nitrogen atom. $R^e$ and $R^f$ are independently selected from hydrogen, alkyl, unsubstituted aryl, unsubstituted arylalkyl, unsubstituted cycloalkyl, unsubstituted (cycloalkyl)alkyl, unsubstituted heterocyclyl, unsubstituted heterocyclylalkyl, $(NR^xR^y)$alkyl, and $(NR^xR^y)$carbonyl.

The term "$(NR^eR^f)$alkyl," as used herein, refers to an alkyl group substituted with one, two, or three —$NR^eR^f$ groups.

The term "$(NR^eR^f)$alkylcarbonyl," as used herein, refers to an $(NR^eR^f)$alkyl group attached to the parent molecular moiety through a carbonyl group.

The term "$(NR^eR^f)$carbonyl," as used herein, refers to an —$NR^eR^f$ group attached to the parent molecular moiety through a carbonyl group.

The term "$(NR^eR^f)$sulfonyl," as used herein, refers to an —$NR^eR^f$ group attached to the parent molecular moiety through a sulfonyl group.

The term "—$NR^xR^y$," as used herein, refers to two groups, $R^x$ and $R^y$, which are attached to the parent molecular moiety through a nitrogen atom. $R^x$ and $R^y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and $(NR^{x'}R^{y'})$carbonyl, wherein $R^{x'}$ and $R^{y'}$ are independently selected from hydrogen and alkyl.

The term "$(NR^xR^y)$alkyl," as used herein, refers to an alkyl group substituted with one, two, or three —$NR^xR^y$ groups.

The term "oxo," as used herein, refers to =O.

The term "sulfonyl," as used herein, refers to —$SO_2$—.

The term "trialkylsilyl," as used herein, refers to —$SiR_3$, wherein R is alkyl. The R groups may be the same or different.

The term "trialkylsilylalkyl," as used herein, refers to an alkyl group substituted with one, two, or three trialkylsilyl groups.

The term "trialkylsilylalkoxy," as used herein, refers to a trialkylsilylalkyl group attached to the parent molecular moiety through an oxygen atom.

The term "trialkylsilylalkoxyalkyl," as used herein, refers to an alkyl group substituted with one, two, or three trialkylsilylalkoxy groups.

Asymmetric centers exist in the compounds of the present disclosure. These centers are designated by the symbols "R" or "S", depending on the configuration of substituents around the chiral carbon atom. It should be understood that the disclosure encompasses all stereochemical isomeric forms, or mixtures thereof, which possess the ability to inhibit NS5A. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, or direct separation of enantiomers on chiral chromatographic columns. Starting compounds of particular stereochemistry are either commercially available or can be made and resolved by techniques known in the art.

Certain compounds of the present disclosure may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

The term "compounds of the present disclosure", and equivalent expressions, are meant to embrace compounds of Formula (I), and pharmaceutically acceptable enantiomers, diastereomers, and salts thereof. Similarly, references to intermediates are meant to embrace their salts where the context so permits.

The compounds of the present disclosure can exist as pharmaceutically acceptable salts. The term "pharmaceutically acceptable salt," as used herein, represents salts or zwitterionic forms of the compounds of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use The salts can be prepared during the final isolation and purification of the compounds or separately by reacting a suitable nitrogen atom with a suitable acid. Representative acid addition salts include acetate, adipate, alginate, citrate, aspartate, benzoate, benzenesulfonate, bisulfate, butyrate, camphorate, camphorsulfonate; digluconate, dihydrobromide, dihydrochloride, dihydroiodide, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine. Other representative organic amines useful for the formation of base addition salts include ethylenediamine, ethanolamine, diethanolamine, piperidine, and piperazine.

When it is possible that, for use in therapy, therapeutically effective amounts of a compound of formula (I), as well as pharmaceutically acceptable salts thereof, may be administered as the raw chemical, it is possible to present the active ingredient as a pharmaceutical composition. Accordingly, the disclosure further provides pharmaceutical compositions, which include therapeutically effective amounts of compounds of formula (I) or pharmaceutically acceptable salts thereof, and one or more pharmaceutically acceptable carriers, diluents, or excipients. The term "therapeutically effective amount," as used herein, refers to the total amount of each active component that is sufficient to show a meaningful patient benefit, e.g., a reduction in viral load. When applied to an individual active ingredient, administered alone, the term refers to that ingredient alone. When applied to a combination, the term refers to combined amounts of the active ingredients that result in the therapeutic effect, whether administered in combination, serially, or simultaneously. The compounds of formula (I) and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the present disclosure there is also provided a process for the preparation of a pharmaceutical formulation including admixing a compound of formula (J), or a pharmaceutically acceptable salt thereof, with one or more pharmaceutically acceptable carriers, diluents, or excipients. The term "pharmaceutically acceptable," as used herein, refers to those compounds, materials, compositions, and/or dosage forms which are, within the scope of sound medical judgment, suitable for use in contact with the tissues of patients without excessive toxicity, irritation, allergic response, or other problem or complication commensurate with a reasonable benefit/risk ratio, and are effective for their intended use.

Pharmaceutical formulations may be presented in unit dose forms containing a predetermined amount of active ingredient per unit dose. Dosage levels of between about 0.01 and about 250 milligram per kilogram ("mg/kg") body weight per day, preferably between about 0.05 and about 100 mg/kg body weight per day of the compounds of the present disclosure are typical in a monotherapy for the prevention and treatment of HCV mediated disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Treatment may be initiated with small dosages substantially less than the optimum dose of the compound. Thereafter, the dosage is increased by small increments until the optimum effect under the circumstances is reached. In general, the compound is most desirably administered at a concentration level that will generally afford antivirally effective results without causing any harmful or deleterious side effects.

When the compositions of this disclosure comprise a combination of a compound of the present disclosure and one or more additional therapeutic or prophylactic agent, both the compound and the additional agent are usually present at dosage levels of between about 10 to 150%, and more preferably between about 10 and 80% of the dosage normally administered in a monotherapy regimen.

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s). Oral administration or administration by injection are preferred.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

The compounds of formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research* 1986, 3(6), 318.

Pharmaceutical formulations adapted for topical administration may be formulated as ointments, creams, suspensions, lotions, powders, solutions, pastes, gels, sprays, aerosols, or oils.

Pharmaceutical formulations adapted for rectal administration may be presented as suppositories or as enemas.

Pharmaceutical formulations adapted for nasal administration wherein the carrier is a solid include a course powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

The term "patient" includes both human and other mammals.

The term "treating" refers to: (i) preventing a disease, disorder or condition from occurring in a patient that may be predisposed to the disease, disorder, and/or condition but has not yet been diagnosed as having it; (ii) inhibiting the disease, disorder, or condition, i.e., arresting its development; and (iii) relieving the disease, disorder, or condition, i.e., causing regression of the disease, disorder, and/or condition.

The compounds of the present disclosure can also be administered with a cyclosporin, for example, cyclosporin A. Cyclosporin A has been shown to be active against HCV in clinical trials (*Hematology* 2003, 38, 1282; *Biochem. Biophys. Res. Commun.* 2004, 313, 42; *J. Gastroenterol.* 2003, 38, 567).

Table 1 below lists some illustrative examples of compounds that can be administered with the compounds of this disclosure. The compounds of the disclosure can be administered with other anti-HCV activity compounds in combination therapy, either jointly or separately, or by combining the compounds into a composition.

TABLE 1

| Brand Name | Physiological Class | Type of Inhibitor or Target | Source Company |
| --- | --- | --- | --- |
| NIM811 | | Cyclophilin Inhibitor | Novartis |
| Zadaxin | | Immunomodulator | Sciclone |
| Suvus | | Methylene blue | Bioenvision |
| Actilon (CPG10101) | | TLR9 agonist | Coley |
| Batabulin (T67) | Anticancer | β-tubulin inhibitor | Tularik Inc., South San Francisco, CA |

TABLE 1-continued

| Brand Name | Physiological Class | Type of Inhibitor or Target | Source Company |
|---|---|---|---|
| ISIS 14803 | Antiviral | antisense | ISIS Pharmaceuticals Inc, Carlsbad, CA/Elan Phamaceuticals Inc., New York, NY |
| Summetrel | Antiviral | antiviral | Endo Pharmaceuticals Holdings Inc., Chadds Ford, PA |
| GS-9132 (ACH-806) | Antiviral | HCV Inhibitor | Achillion/Gilead |
| Pyrazolopyrimidine compounds and salts From WO-2005047288 26 May 2005 | Antiviral | HCV Inhibitors | Arrow Therapeutics Ltd. |
| Levovirin | Antiviral | IMPDH inhibitor | Ribapharm Inc., Costa Mesa, CA |
| Merimepodib (VX-497) | Antiviral | IMPDH inhibitor | Vertex Pharmaceuticals Inc., Cambridge, MA |
| XTL-6865 (XTL-002) | Antiviral | monoclonal antibody | XTL Biopharmaceuticals Ltd., Rehovot, Isreal |
| Telaprevir (VX-950, LY-570310) | Antiviral | NS3 serine protease inhibitor | Vertex Pharmaceuticals Inc., Cambridge, MA/Eli Lilly and Co. Inc., Indianapolis, IN |
| HCV-796 | Antiviral | NS5B Replicase Inhibitor | Wyeth/Viropharma |
| NM-283 | Antiviral | NS5B Replicase Inhibitor | Idenix/Novartis |
| GL-59728 | Antiviral | NS5B Replicase Inhibitor | Gene Labs/Novartis |
| GL-60667 | Antiviral | NS5B Replicase Inhibitor | Gene Labs/Novartis |
| 2'C MeA | Antiviral | NS5B Replicase Inhibitor | Gilead |
| PSI 6130 | Antiviral | NS5B Replicase Inhibitor | Roche |
| R1626 | Antiviral | NS5B Replicase Inhibitor | Roche |
| 2'C Methyl adenosine | Antiviral | NS5B Replicase Inhibitor | Merck |
| JTK-003 | Antiviral | RdRp inhibitor | Japan Tobacco Inc., Tokyo, Japan |
| Levovirin | Antiviral | ribavirin | ICN Pharmaceuticals, Costa Mesa, CA |
| Ribavirin | Antiviral | ribavirin | Schering-Plough Corporation, Kenilworth, NJ |
| Viramidine | Antiviral | Ribavirin Prodrug | Ribapharm Inc., Costa Mesa, CA |
| Heptazyme | Antiviral | ribozyme | Ribozyme Pharmaceuticals Inc., Boulder, CO |

TABLE 1-continued

| Brand Name | Physiological Class | Type of Inhibitor or Target | Source Company |
|---|---|---|---|
| BILN-2061 | Antiviral | serine protease inhibitor | Boehringer Ingelheim Pharma KG, Ingelheim, Germany |
| SCH 503034 | Antiviral | serine protease inhibitor | Schering Plough |
| Zadazim | Immune modulator | Immune modulator | SciClone Pharmaceuticals Inc., San Mateo, CA |
| Ceplene | Immunomodulator | immune modulator | Maxim Pharmaceuticals Inc., San Diego, CA |
| CellCept | Immunosuppressant | HCV IgG immunosuppressant | F. Hoffmann-La Roche LTD, Basel, Switzerland |
| Civacir | Immunosuppressant | HCV IgG immunosuppressant | Nabi Biopharmaceuticals Inc., Boca Raton, FL |
| Albuferon-α | Interferon | albumin IFN-α2b | Human Genome Sciences Inc., Rockville, MD |
| Infergen A | Interferon | IFN alfacon-1 | InterMune Pharmaceuticals Inc., Brisbane, CA |
| Omega IFN | Interferon | IFN-ω | Intarcia Therapeutics |
| IFN-β and EMZ701 | Interferon | IFN-β and EMZ701 | Transition Therapeutics Inc., Ontario, Canada |
| Rebif | Interferon | IFN-β1a | Serono, Geneva, Switzerland |
| Roferon A | Interferon | IFN-α2a | F. Hoffmann-La Roche LTD, Basel, Switzerland |
| Intron A | Interferon | IFN-α2b | Schering-Plough Corporation, Kenilworth, NJ |
| Intron A and Zadaxin | Interferon | IFN-α2b/α1-thymosin | RegeneRx Biopharmiceuticals Inc., Bethesda, MD/ SciClone Pharmaceuticals Inc, San Mateo, CA |
| Rebetron | Interferon | IFN-α2b/ribavirin | Schering-Plough Corporation, Kenilworth, NJ |
| Actimmune | Interferon | INF-γ | InterMune Inc., Brisbane, CA |
| Interferon-β | Interferon | Interferon-β-1a | Serono |
| Multiferon | Interferon | Long lasting IFN | Viragen/Valentis |
| Wellferon | Interferon | lymphoblastoid IFN-αn1 | GlaxoSmithKline plc, Uxbridge, UK |
| Omniferon | Interferon | natural IFN-α | Viragen Inc., Plantation, FL |

TABLE 1-continued

| Brand Name | Physiological Class | Type of Inhibitor or Target | Source Company |
|---|---|---|---|
| Pegasys | Interferon | PEGylated IFN-α2a | F. Hoffmann-La Roche LTD, Basel, Switzerland |
| Pegasys and Ceplene | Interferon | PEGylated IFN-α2a/ immune modulator | Maxim Pharmaceuticals Inc., San Diego, CA |
| Pegasys and Ribavirin | Interferon | PEGylated IFN-α2a/ribavirin | F. Hoffmann-La Roche LTD, Basel, Switzerland |
| PEG-Intron | Interferon | PEGylated IFN-α2b | Schering-Plough Corporation, Kenilworth, NJ |
| PEG-Intron/ Ribavirin | Interferon | PEGylated IFN-α2b/ribavirin | Schering-Plough Corporation, Kenilworth, NJ |
| IP-501 | Liver protection | antifibrotic | Indevus Pharmaceuticals Inc., Lexington, MA |
| IDN-6556 | Liver protection | caspase inhibitor | Idun Pharmaceuticals Inc., San Diego, CA |
| ITMN-191 (R-7227) | Antiviral | serine protease inhibitor | InterMune Pharmaceuticals Inc., Brisbane, CA |
| GL-59728 | Antiviral | NS5B Replicase Inhibitor | Genelabs |
| ANA-971 | Antiviral | TLR-7 agonist | Anadys |

The compounds of the present disclosure may also be used as laboratory reagents. Compounds may be instrumental in providing research tools for designing of viral replication assays, validation of animal assay systems and structural biology studies to further enhance knowledge of the HCV disease mechanisms. Further, the compounds of the present disclosure are useful in establishing or determining the binding site of other antiviral compounds, for example, by competitive inhibition.

The compounds of this disclosure may also be used to treat or prevent viral contamination of materials and therefore reduce the risk of viral infection of laboratory or medical personnel or patients who come in contact with such materials, e.g., blood, tissue, surgical instruments and garments, laboratory instruments and garments, and blood collection or transfusion apparatuses and materials.

This disclosure is intended to encompass compounds having formula (I) when prepared by synthetic processes or by metabolic processes including those occurring in the human or animal body (in vivo) or processes occurring in vitro.

The abbreviations used in the present application, including particularly in the illustrative schemes and examples which follow, are well-known to those skilled in the art. Some of the abbreviations used are as follows: HATU for O-(7-azabenzotriazol-1-yl)-N,N,N',N'-tetramethyluronium hexafluorophosphate; Boc or BOC for tert-butoxycarbonyl; NBS for N-bromosuccinimide; tBu or t-Bu for tert-butyl; SEM for -(trimethylsilyl)ethoxymethyl; DMSO for dimethylsulfoxide; MeOH for methanol; TFA for trifluoroacetic acid; RT for room temperature or retention time (context will dictate); $t_R$ for retention time; EDCl for 1-(3-dimethylaminopropyl)-3-ethylcarbodiimide hydrochloride; DMAP for 4-dimethylaminopyridine; THF for tetrahydrofuran; DBU for 1,8-diazabicyclo[5.4.0]undec-7-ene; t-Bu; DEA for diethylamine; HMDS for hexamethyldisilazide; DMF for N,N-dimethylformamide; Bzl for benzyl; EtOH for ethanol; iPrOH or i-PrOH for isopropanol; $Me_2S$ for dimethylsulfide; $Et_3N$ or TEA for triethylamine; Ph for phenyl; OAc for acetate; EtOAc for ethyl acetate; dppf for 1,1'-bis(diphenylphosphino)ferrocene; $iPr_2EtN$ or DIPEA for diisopropylethylamine; Cbz for carbobenzyloxy; n-BuLi for n-butyllithium; ACN for acetonitrile; h or hr for hours; m or min for minutes; s for seconds; LiHMDS for lithium hexamethyldisilazide; DIBAL for diisobutyl aluminum hydride; TBDMSCl for tert-butyldimethylsilyl chloride; Me for methyl; ca. for about; OAc for acetate; iPr for isopropyl; Et for ethyl; Bn for benzyl; and HOAT for 1-hydroxy-7-azabenzotriazole.

The compounds and processes of the present disclosure will be better understood in connection with the following synthetic schemes which illustrate the methods by which the compounds of the present disclosure may be prepared. Starting materials can be obtained from commercial sources or prepared by well-established literature methods known to those of ordinary skill in the art. It will be readily apparent to one of ordinary skill in the art that the compounds defined above can be synthesized by substitution of the appropriate reactants and agents in the syntheses shown below. It will also be readily apparent to one skilled in the art that the selective protection and deprotection steps, as well as the order of the steps themselves, can be carried out in varying order, depending on the nature of the variables to successfully complete the syntheses below. The variables are as defined above unless otherwise noted below.

Scheme 1

Symmetric or Asymmetric Biphenyls

Aryl halide 1 and boronic ester 2 can be coupled to produce biaryl 3 using standard Suzuki-Miayura coupling conditions (*Angew Chem. Int. Ed. Engl* 2001, 40, 4544). It should be noted that the boronic acid analog of 2 may be used in place of the ester. Mono-deprotection of the pyrrolidine moiety may be accomplished when $R^{12}$ and $R^{13}$ are different. When $R^{12}$=benzyl, and $R^{13}$=t-butyl treatment to hydrogenolytic conditions produces 4. For example, Pd/C catalyst in the presence of a base such as potassium carbonate can be used. Acylation of 4 can be accomplished under standard acylation conditions. A coupling reagent such as HATU in combination with an amine base such as Hunig's base can be used in this regard. Alternatively, 4 may be reacted with an isocyanate or carbamoyl chloride to provide compounds of formula 5 where $R^9$ is an amine. Further deprotection of 5 can be accomplished by treatment with strong acid such as HCl or trifluoroacetic acid. Standard conditions analogous to those used to convert 4 to 5 can be used to prepare 7 from 6. In another embodiment where $R^{12}$=$R^{13}$=t-Bu, direct conversion to 8 can be accomplished by treatment of 3 with strong acid such as HCl or trifluoroacetic acid. Conversion of 8 to 7 is accomplished in analogous fashion to the methods used to prepare 5 from 4 or 7 from 6. In this instance however, the caps in 7 will be identical.

Scheme 2: Asymmetrically Capped Biphenyls

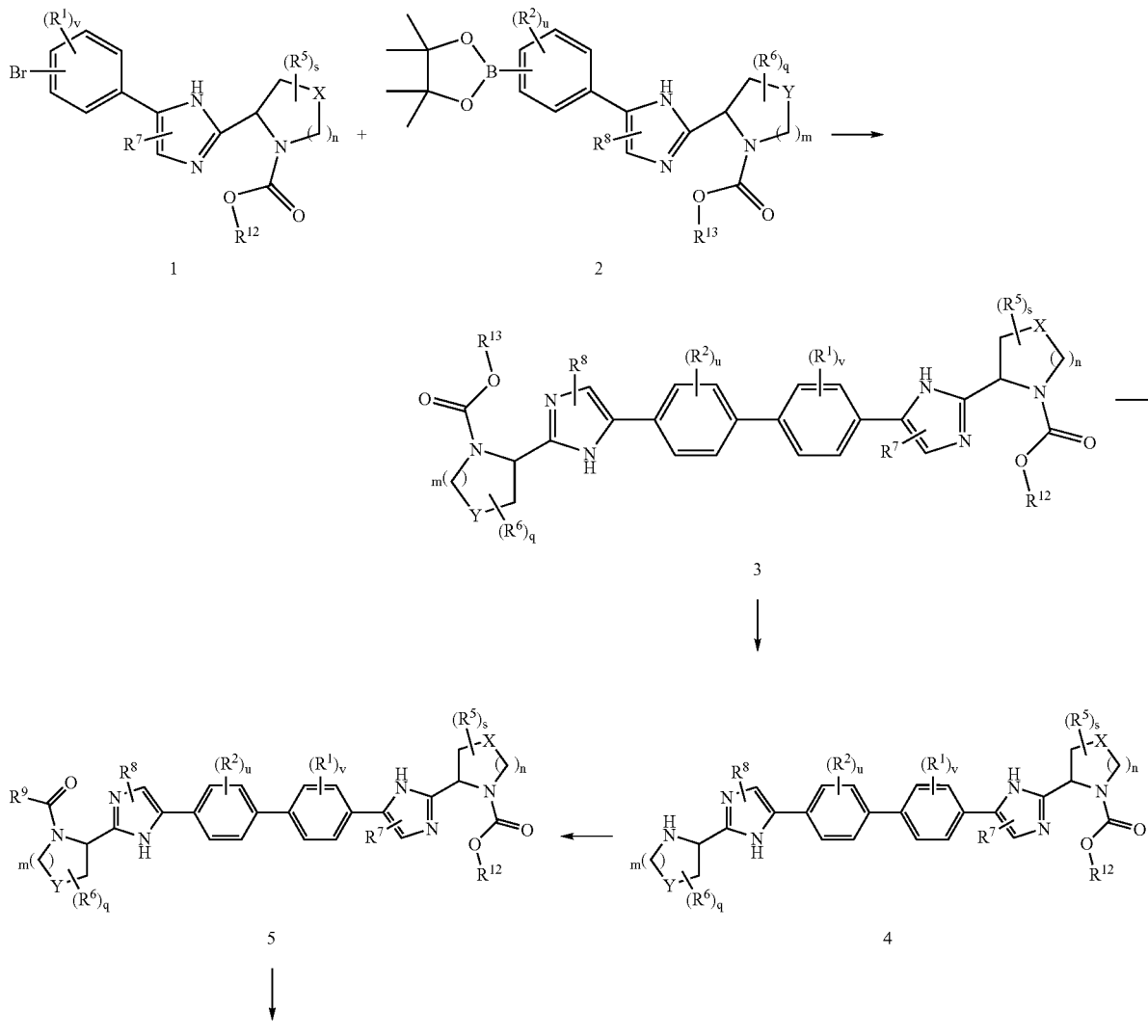

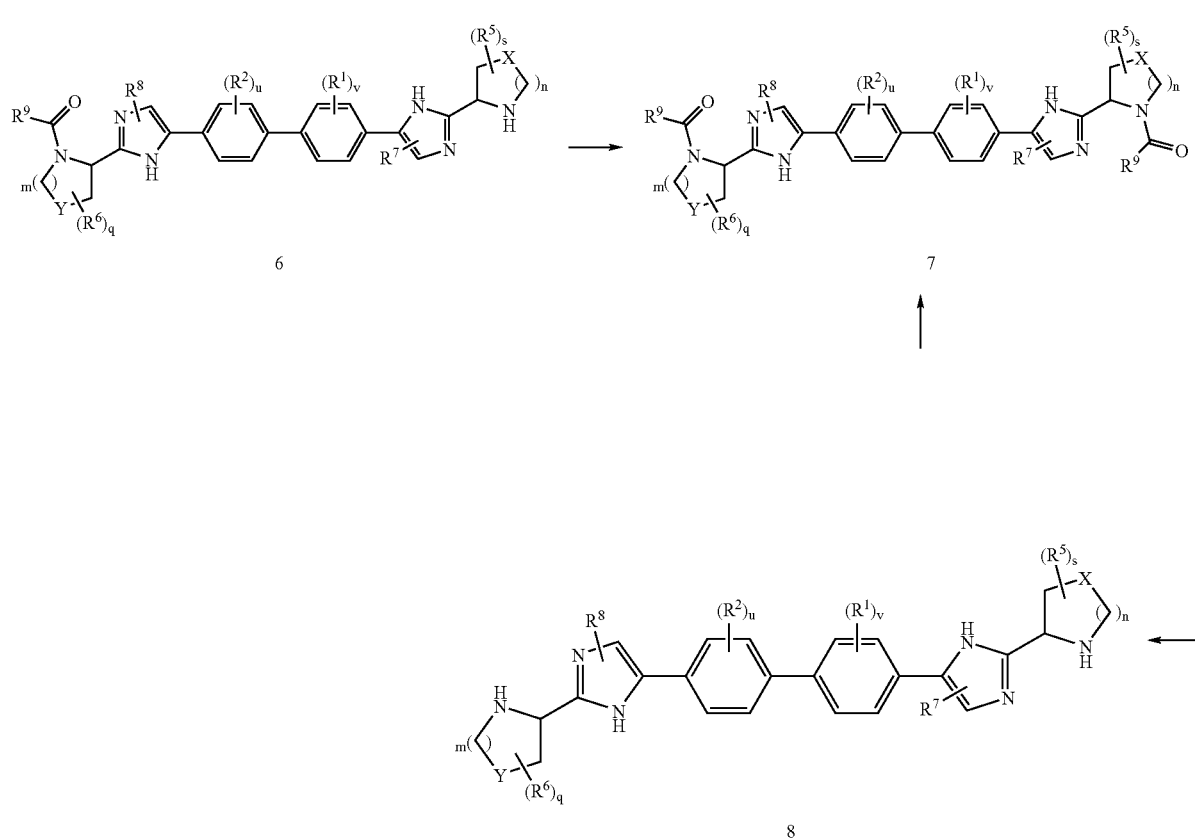

Conversion of 6 (from Scheme 1) to 10 can be done using standard amide coupling conditions such as HATU with an amine base, such as Hunig's base. Deprotection can be accomplished with strong acid such as HCl or trifluoroacetic acid affording 11. Compound 11 can then be converted to 12, 13, or 14 using an acid chloride, an isocyanate or carbamoyl chloride, or a chloroformate respectively.

Scheme 3: Symmetric Cap Elaborated Biphenyls

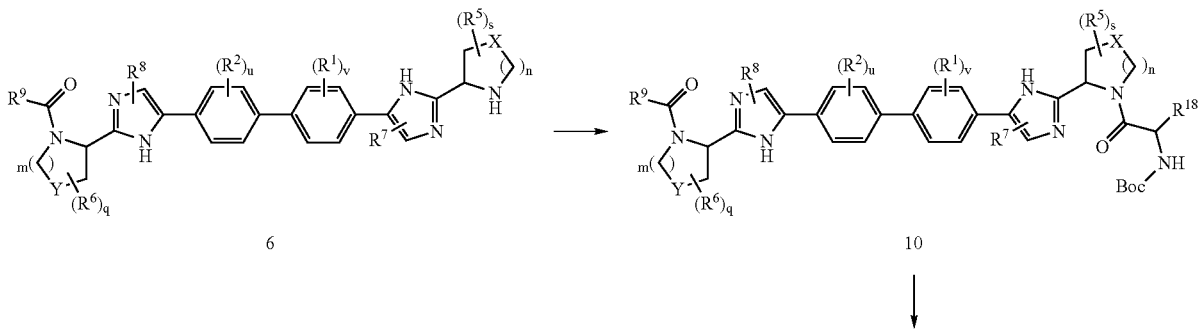

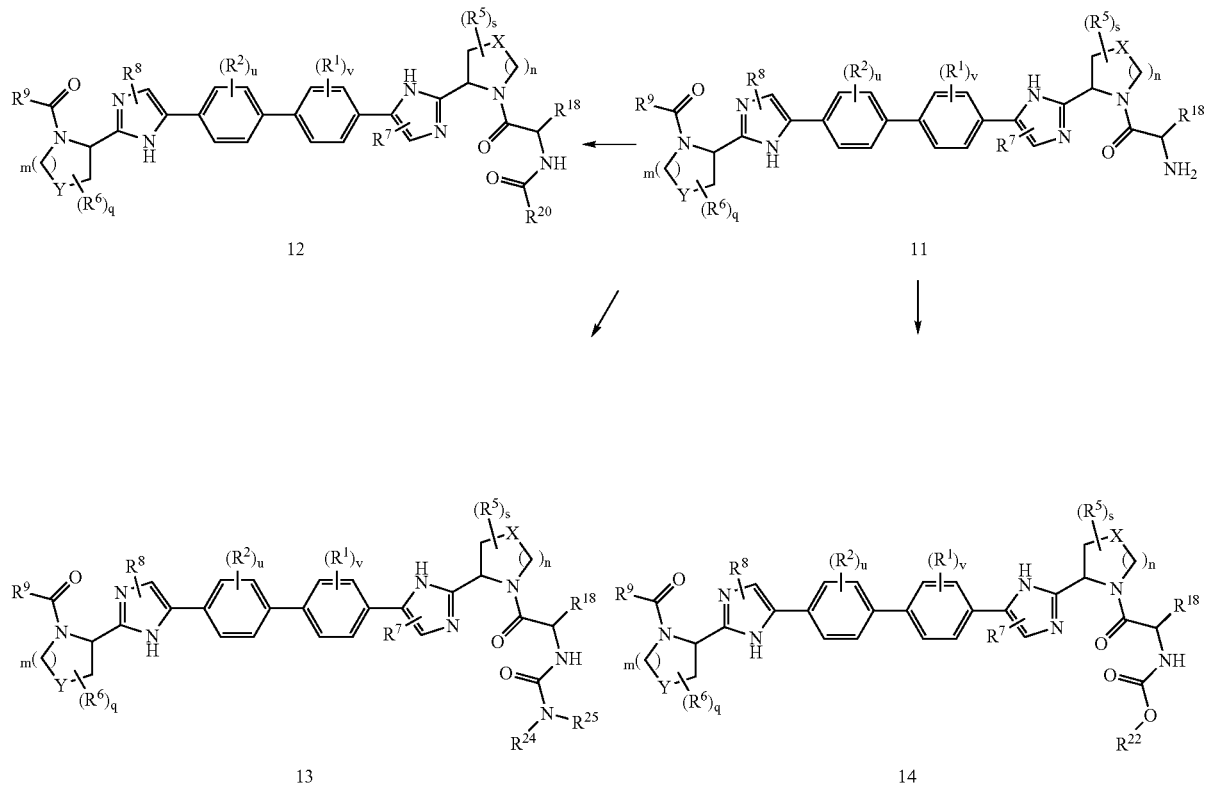
Compound 15 (15=7 (Scheme 1) wherein each R⁹ is —CH(NHBoc)R¹⁸) can be converted to 16 via treatment with strong acid such as HCl or trifluoroacetic acid. Compounds 17, 18, and 19 can be prepared from 16 by treating 16 with an appropriate chloroformate, isocyanate or carbamoyl chloride, or an acid chloride respectively.

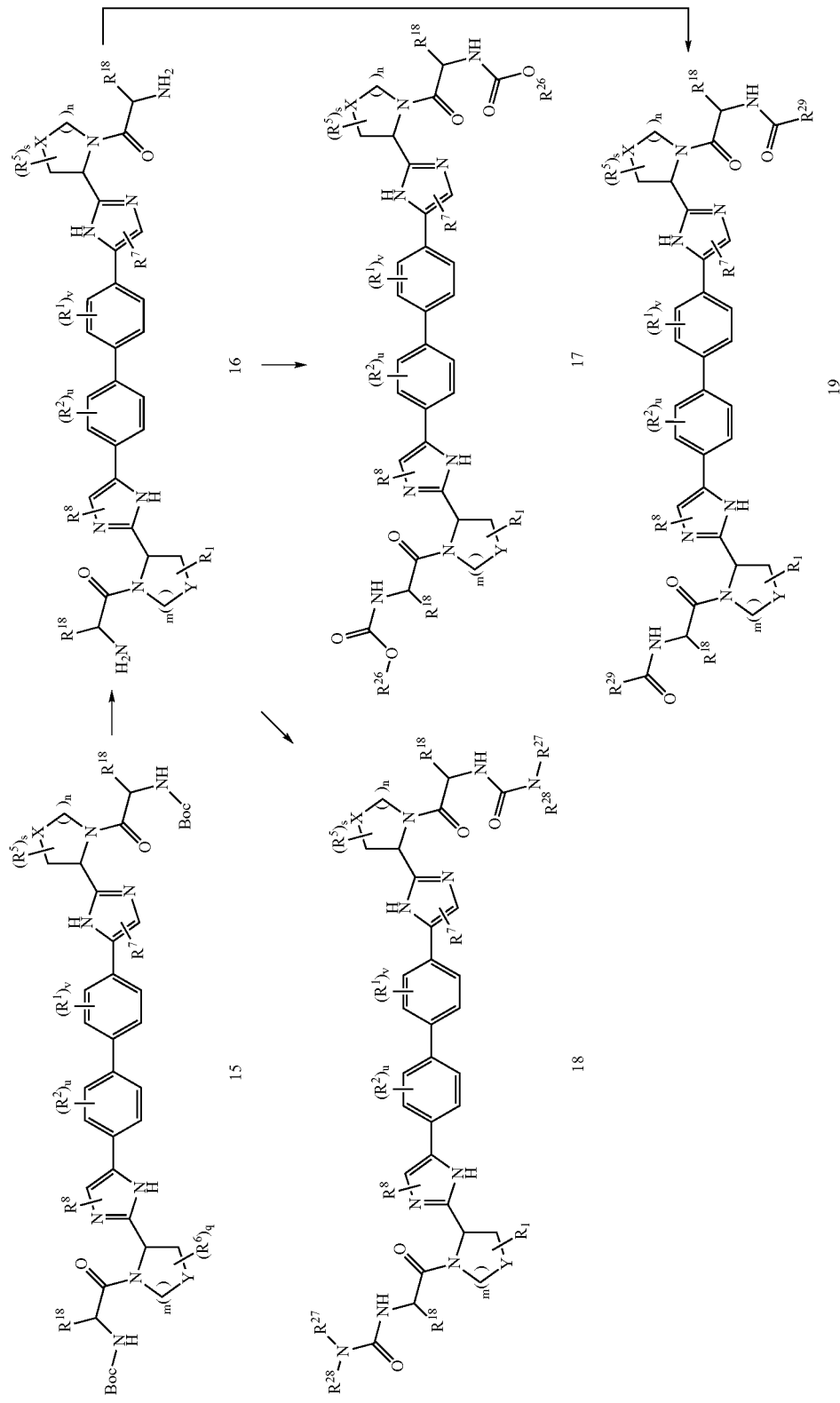
Scheme 4: Symmetric Biphenyls

Symmetrical biphenyl analogs (compounds of formula 7 where both halves of the molecule are equivalent) can be synthesized starting from bromoketone 20. Amination by displacement with a nucleophile such as azide, phthalimide or preferably sodium diformylamide (Yinglin and Hongwen, *Synthesis* 1990, 122) followed by deprotection affords 21. Condensation under standard amination conditions such as HATU and Hunig's base with an appropriately protected amino acid provides 22. Heating with ammonium acetate under thermal or microwave conditions results in the formation of 3 which can be deprotected with strong acid such as HCl or trifluoroacetic acid ($R^{12}$=$R^{13}$=t-Bu) or by hydrogenolysis with hydrogen gas and a transition metal catalyst such as Pd/C ($R^{12}$=$R^{13}$=benzyl). Acylation can be affected with a carboxylic acid ($R^9CO_2H$) in a manner similar to the conversion of 21 to 22. Urea formation can be accomplished by treatment with an appropriate isocyanate ($R^9$=$R^{24}R^{25}N$; $R^{25}$=H) or carbamoyl chloride ($R^9$=$R^{24}R^{25}N$; $R^{25}$ is other than hydrogen).

Scheme 5 describes the preparation of some of the starting materials required for the synthetic sequences depicted in Schemes 1-4. Key intermediate 25 (analogous to 1 in Scheme 1) is prepared from keto-amide 24 or keto-ester 27 via heating with ammonium acetate under thermal or microwave conditions. Keto-amide 24 can be prepared from 23 via condensation with an appropriate cyclic or acyclic amino acid under standard amide formation conditions. Bromide 26 can give rise to 23 by treatment with a nucleophile such as azide, phthalimide or sodium diformylamide (*Synthesis* 1990, 122) followed by deprotection. Bromide 26 can also be converted to 27 by reacting with an appropriate cyclic or acyclic N-protected amino acid in the presence of base such as potassium carbonate or sodium bicarbonate. Bromination of 28 with a source of bromonium ion such as bromine, NBS, or $CBr_4$ results in the formation of 26. Bromide 25 can be converted to boronic ester 2 via treatment with bis-pinacalotodiboron under palladium catalysis according to the method described in *Journal of Organic Chemistry* 1995, 60, 7508, or variations thereof.

Scheme 5: Starting Materials 25 and 2

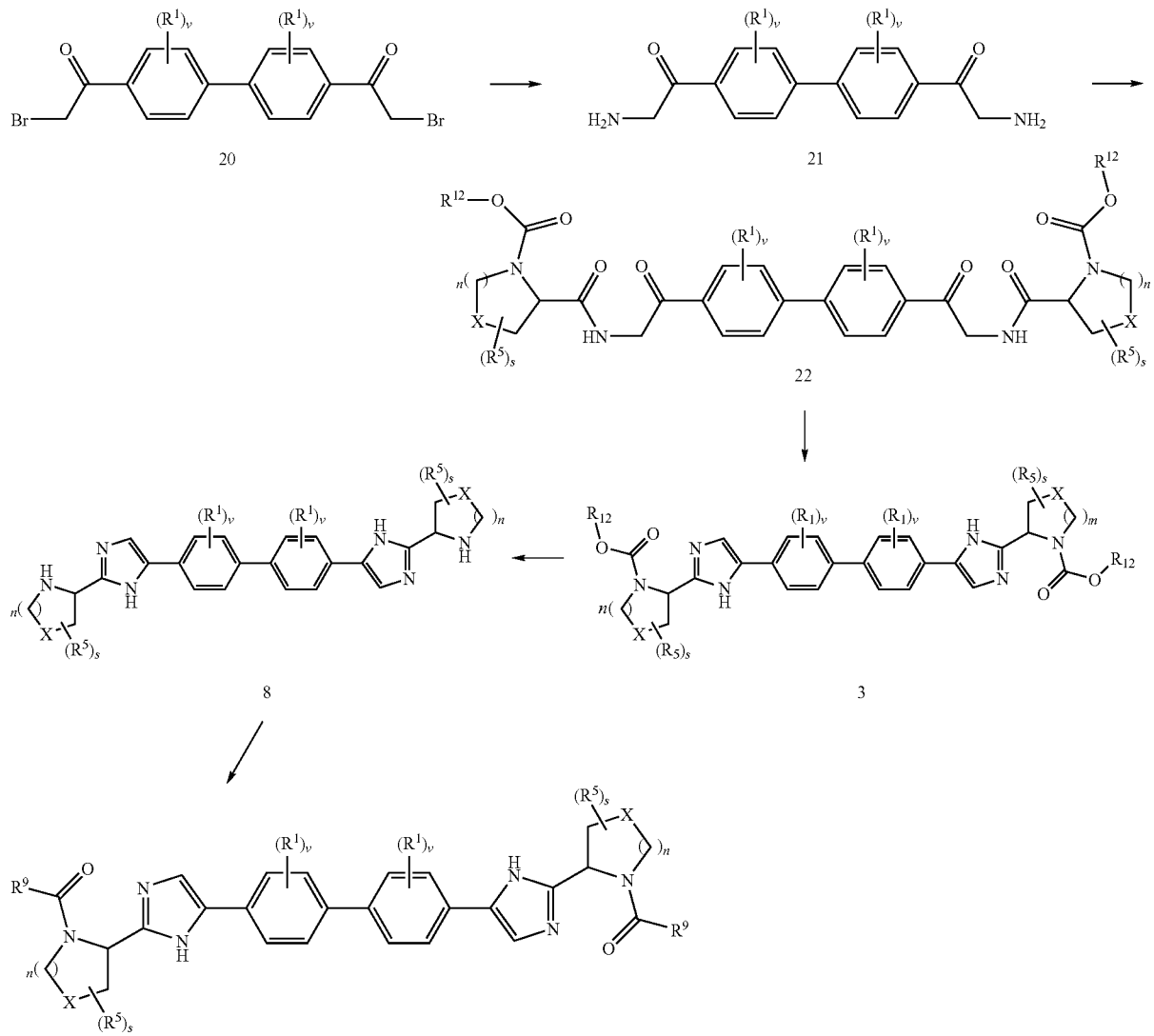

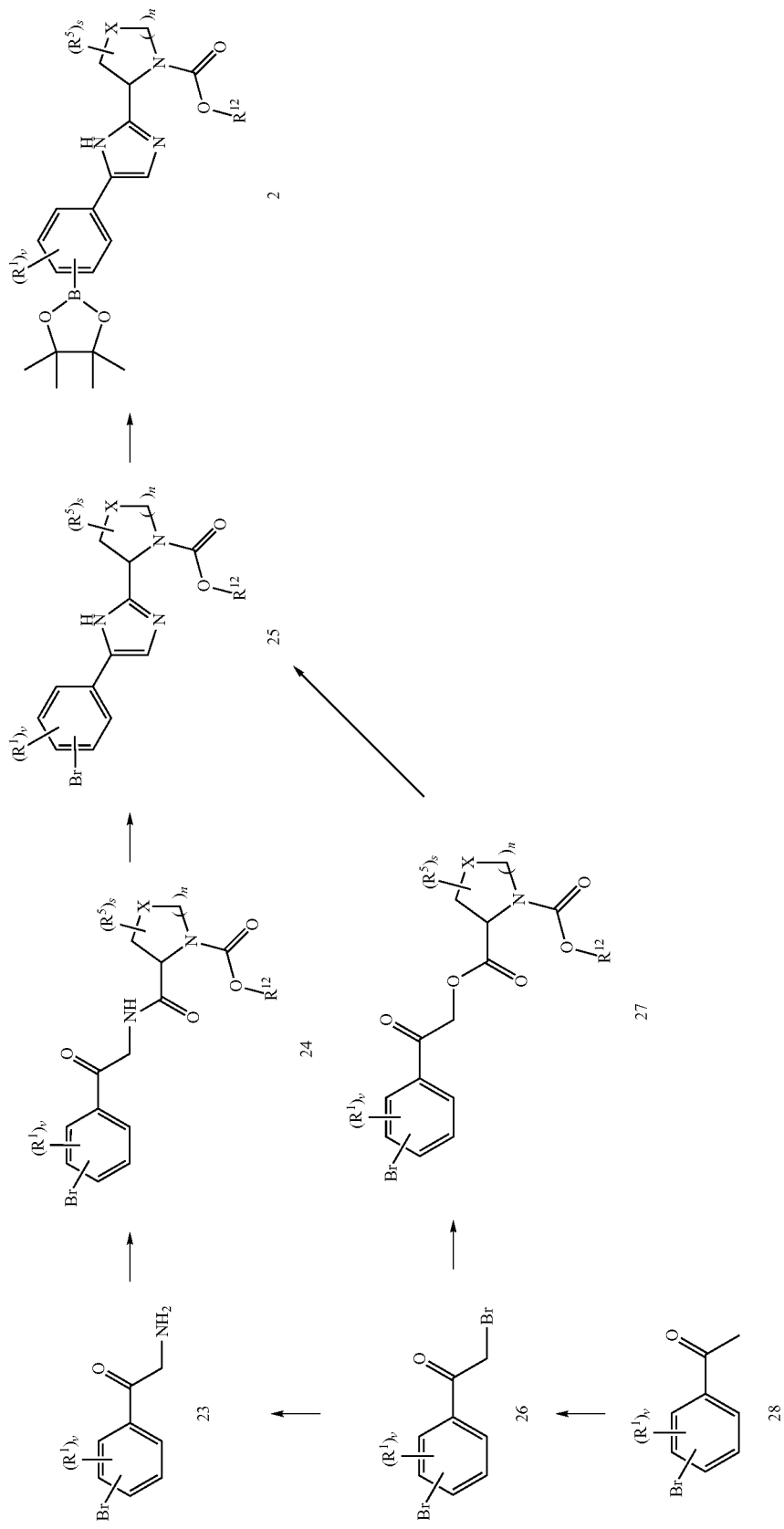
Scheme 6: Starting Material 31a

In another embodiment, starting materials such as 31a (analogous to 25 in Scheme 5 and 1 in Scheme 1) may be prepared by reacting bromoimidazole derivatives 31 under Suzuki-type coupling conditions with a variety of chloro-substituted aryl boronic acids which can either be prepared by standard methodologies (see, for example, *Organic Letters* 2006, 8, 305 and references cited therein) or purchased from commercial suppliers. Bromoimidazole 31 can be obtained by brominating imidazole 30 with a source of bromonium ion such as bromine, $CBr_4$, or N-bromosuccinimide. Imidazole 30 can be prepared from N-protected amino acids which are appropriately substituted by reacting with glyoxal in a methanolic solution of ammonium hydroxide.

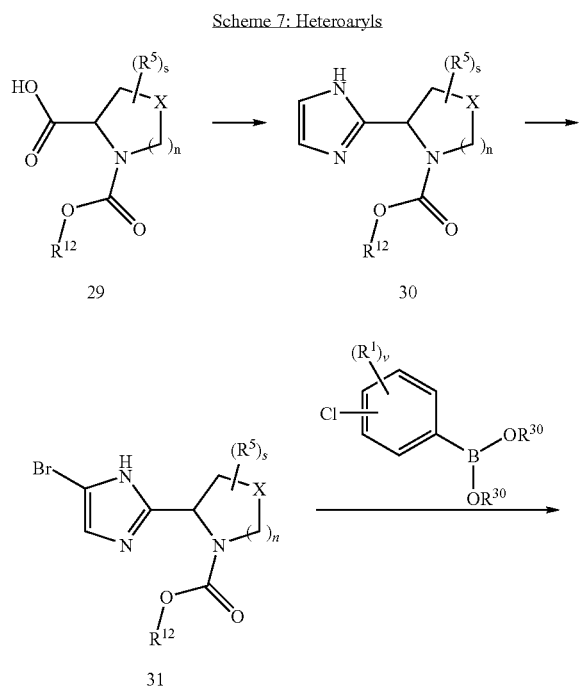

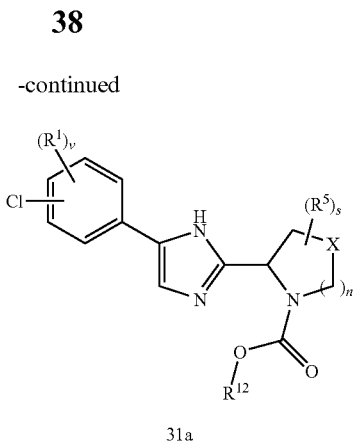

In yet another embodiment of the current disclosure, aryl halide 32 can be coupled under Suzuki-Miyaura palladium catalyzed conditions to form the heteroaryl derivative 34. Compound 34 can be elaborated to 35 by treatment to hydrogenolytic conditions with hydrogen and a transition metal catalyst such as palladium on carbon ($R^{13}$=benzyl). Acylation of 35 can be accomplished with an appropriate acid chloride ($R^9COCl$) in the presence of a base such as triethylamine, with an appropriately substituted carboxylic acid ($R^9CO_2H$) in the presence of a standard coupling reagent such as HATU, or with an isocyanate ($R^{27}NCO$ wherein $R^9$=$R^{27}R^{28}N$—; $R^{28}$=H) or carbamoyl chloride ($R^{27}R^{28}NCOCl$ wherein $R^9$=$R^{27}R^{28}N$—). Compound 37 can be prepared from 36 ($R^{12}$=t-Bu) via treatment with strong acid such as HCl or trifluoroacetic acid. Acylation of the resulting amine in 37 to give 38 can be accomplished as in the transformation of 35 to 36. In cases where $R^{12}$=$R^{13}$, 34 can be directly transformed into 39 by treatment with strong acid such as HCl or trifluoroacetic acid ($R^{12}$=$R^{13}$=t-Bu) or by employing hydrogenolytic conditions with hydrogen and a transition metal catalyst such as palladium on carbon ($R^{12}$=$R^{13}$=benzyl). Acylation of 39 can be accomplished in analogous fashion to that described for the transformation of 35 to 36.

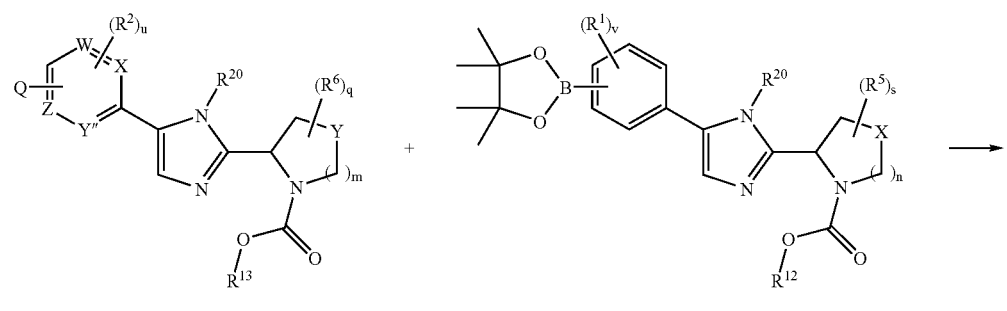

-continued
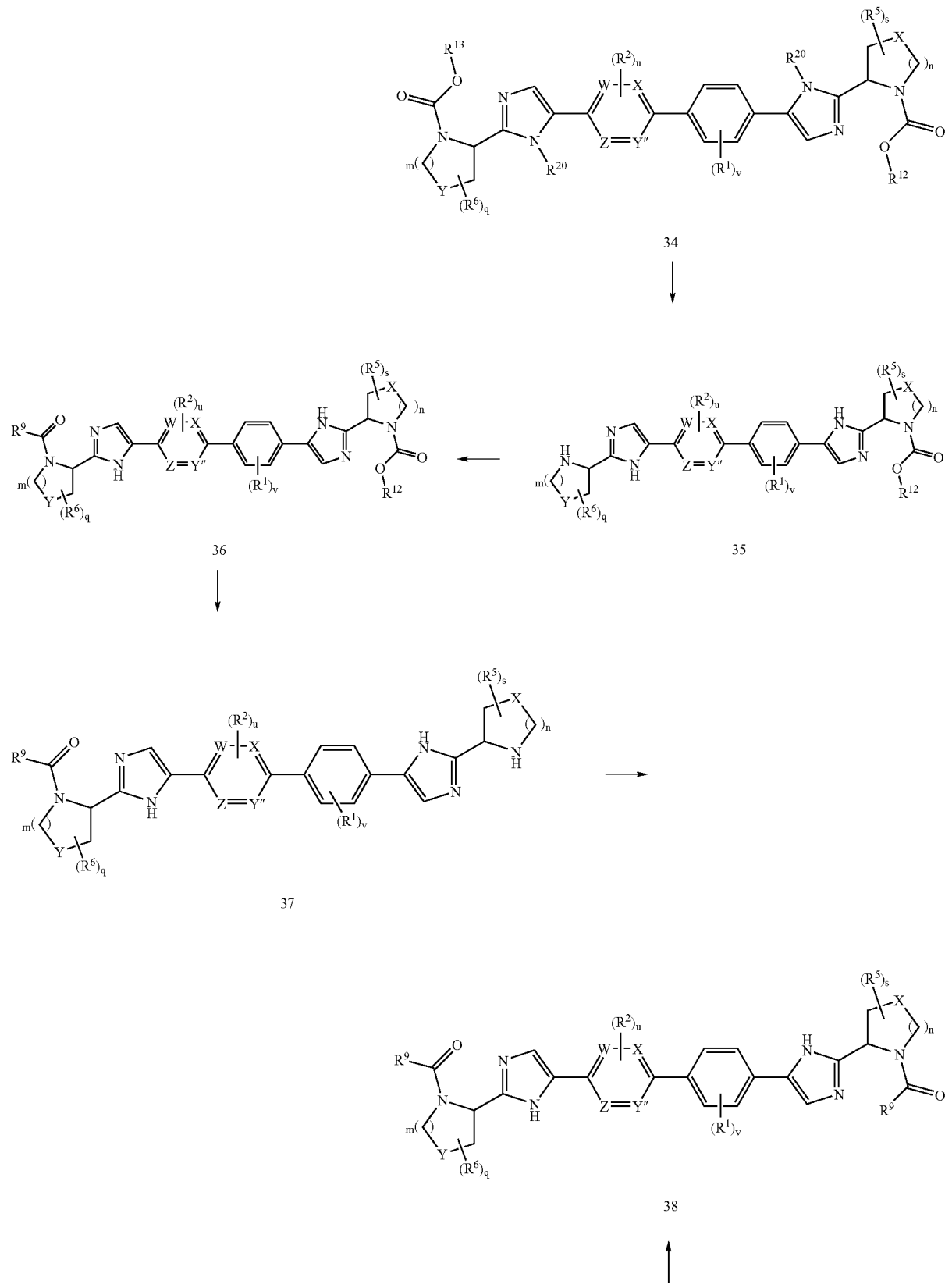

-continued

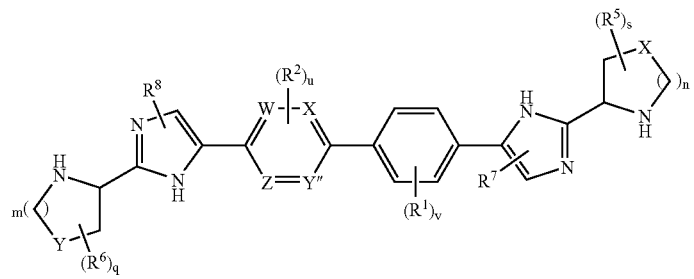

39

$R^{12}$ and $R^{13}$ are independently alkoxymethyl or H
Q = Cl or Br
W, X, Y″, Z = C or N with at least one of W, X, Y, and Z must be C and at least one of W, X, Y″, and Z must be N each $R^9$ can be independently alkyl or $NR^{27}R^{28}$ Heteroaryl chloride 29 can be converted to symmetrical analog 40 via treatment with a source of palladium such as dichlorobis(benzonitrile) palladium in the presence of tetrakis(dimethylamino)ethylene at elevated temperature. Removal of the SEM ether and Boc carbamates found in 40 can be accomplished in one step by treatment with a strong acid such as HCl or trifluoroacetic acid providing 41. Conversion to 42 can be accomplished in similar fashion to the conditions used to convert 38 to 39 in Scheme 7.

Scheme 9: Symmetric Cap Substituted Heteroaryls

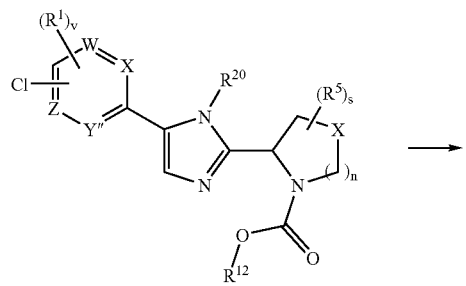

29

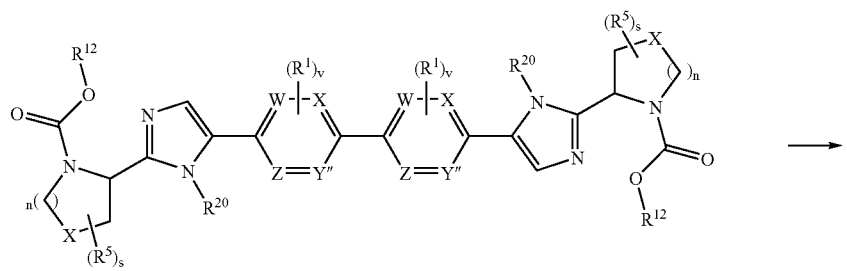

40

-continued

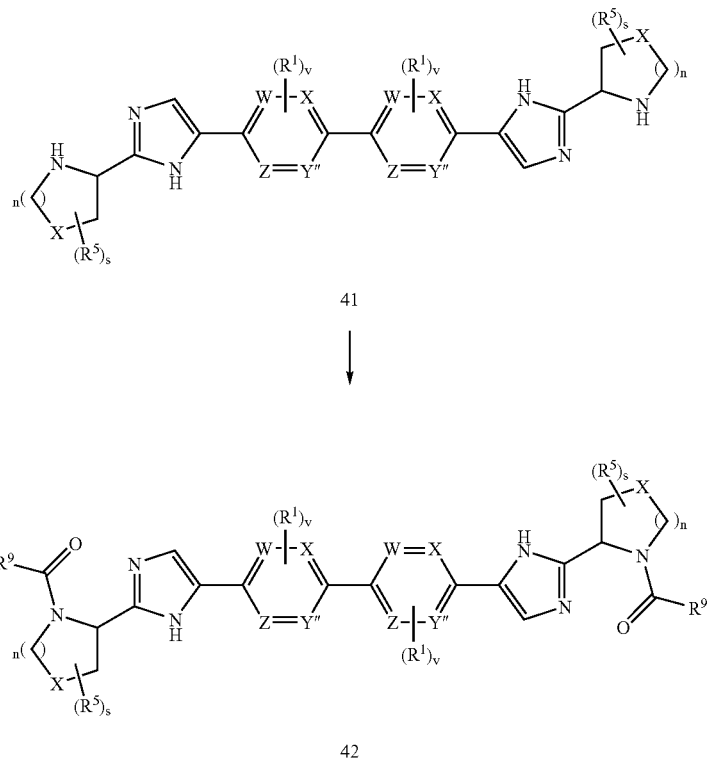

41

↓

42

$R^{20}$ = alkoxymethyl or H
W, X, Y″, Z = C or N with at least one of
W, X, Y″, and Z must be C
$R^9$ can be alkyl or $NR^{27}R^{28}$ Compound 43 (analogous to 42 wherein $R_{23}$=—CH(NH-Boc)$R_{24}$) may be elaborated to 45, 46, and 47 via similar methodologies to those described in Scheme 3. In cases where $R_{20}$=alkoxymethyl (ie; SEM), removal can be accomplished simultaneously with removal of the Boc carbamate (cf, 43 to 44) using strong acid such as HCl or trifluoroacetic acid.

Scheme 10: Starting Material 29
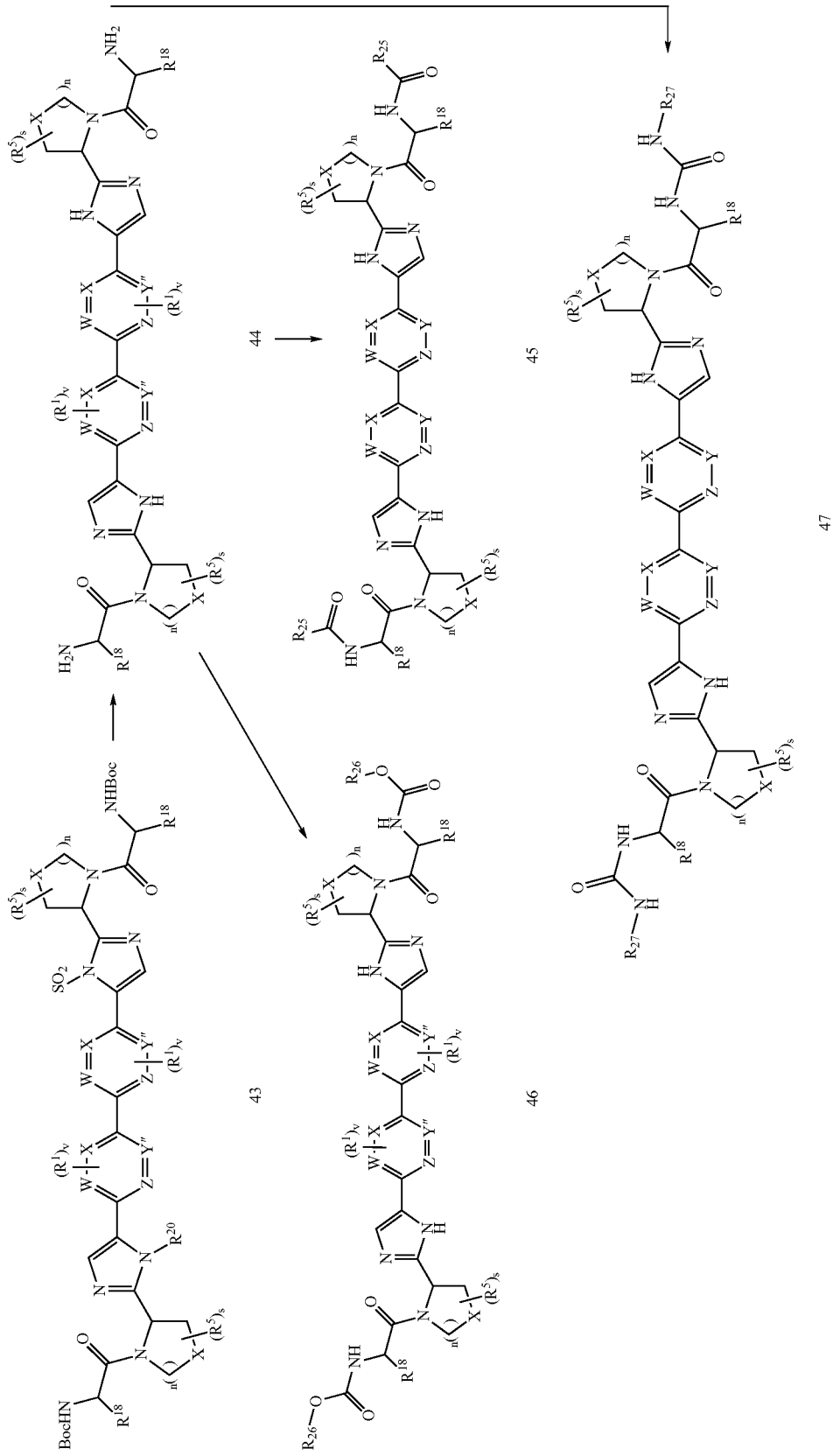
$R_{20}$ = alkoxymethyl or H
W, X, Y, Z = C or N with at least one of
W, X, Y, and Z must be C;
at least one of W, X, Y, and Z must be N Heteroaryl bromides 54 may be reacted with a vinyl stannane such as tributyl(1-ethoxyvinyl)tin in the presence of a source of palladium such as dichlorobis(triphenylphosphine) palladium (II) to provide 55 which can be subsequently transformed into bromoketone 51 via treatment with a source of bromonium ion such as N-bromosuccinimide, $CBr_4$, or bromine. Alternatively, keto-substituted heteroaryl bromides 53 may be directly converted to 51 via treatment with a source of bromonium ion such as bromine, $CBr_4$, or N-bromosuccinimide. Bromide 51 can be converted to aminoketone 48 via addition of sodium azide, potassium phthalimide or sodium diformylamide (*Synthesis* 1990 122) followed by deprotection. Aminoketone 48 can then be coupled with an appropriately substituted amino acid under standard amide formation conditions (i.e.; a coupling reagent such as HATU in the presence of a mild base such as Hunig's base) to provide 49. Compound 49 can then be further transformed into imidazole 50 via reacting with ammonium acetate under thermal or microwave conditions. Alternatively, 51 can be directly reacted with an appropriately substituted amino acid in the presence of a base such as sodium bicarbonate or potassium carbonate providing 52 which can in turn be reacted with ammonium acetate under thermal or microwave conditions to provide 50. Imidazole 50 can be protected with an alkoxymethyl group by treatment with the appropriate alkoxymethyl halide such as 2-(trimethylsilyl)ethoxymethyl chloride after first being deprotonated with a strong base such as sodium hydride.

Scheme 11: Substituted Phenylglycine Derivatives
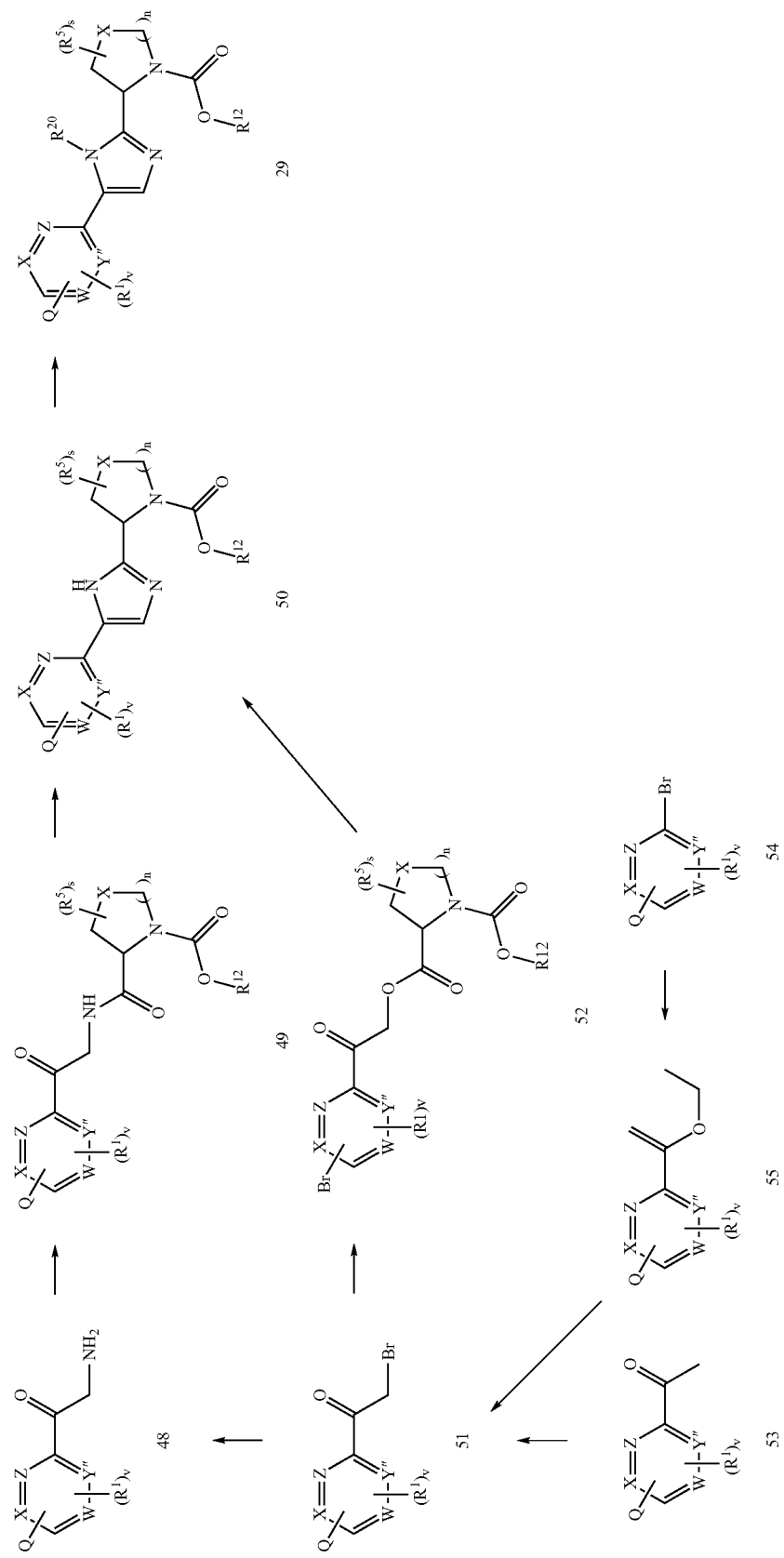
Q = Cl or Br
W, X, Y, Z = C or N;
at least one of W, X, Y, and Z must be C;
at least one of W, X, Y, and Z must be N Substituted phenylglycine derivatives can be prepared by a number of methods shown below. Phenylglycine t-butyl ester can be reductively alkylated (pathway A) with an appropriate aldehyde and a reductant such as sodium cyanoborohydride in acidic medium. Hydrolysis of the t-butyl ester can be accomplished with strong acid such as HCl or trifluoroacetic acid. Alternatively, phenylglycine can be alkylated with an alkyl halide such as ethyl iodide and a base such as sodium bicarbonate or potassium carbonate (pathway B). Pathway C illustrates reductive alkylation of phenylglycine as in pathway A followed by a second reductive alkylation with an alternate aldehyde such as formaldehyde in the presence of a reducing agent and acid. Pathway D illustrates the synthesis of substituted phenylglycines via the corresponding mandelic acid analogs. Conversion of the secondary alcohol to a competent leaving group can be accomplished with p-toluenesulfonyl chloride. Displacement of the tosylate group with an appropriate amine followed by reductive removal of the benzyl ester can provide substituted phenylglycine derivatives. In pathway E a racemic substituted phenylglycine derivative is resolved by esterification with an enantiomerically pure chiral auxiliary such as but not limited to (+)-1-phenylethanol, (−)-1-phenylethanol, an Evan's oxazolidinone, or enantiomerically pure pantolactone. Separation of the diastereomers is accomplished via chromatography (silica gel, HPLC, crystallization, etc) followed by removal of the chiral auxiliary providing enantiomerically pure phenylglycine derivatives. Pathway H illustrates a synthetic sequence which intersects with pathway E wherein the aforementioned chiral auxiliary is installed prior to amine addition. Alternatively, an ester of an arylacetic acid can be brominated with a source of bromonium ion such as bromine, N-bromosuccinimide, or $CBr_4$. The resultant benzylic bromide can be displaced with a variety of mono- or disubstituted amines in the presence of a tertiary amine base such as triethylamine or Hunig's base. Hydrolysis of the methyl ester via treatment with lithium hydroxide at low temperature or 6N HCl at elevated temperature provides the substituted phenylglycine derivatives. Another method is shown in pathway G. Glycine analogs can be derivatized with a variety of aryl halides in the presence of a source of palladium (0) such as palladium bis(tributylphosphine) and base such as potassium phosphate. The resultant ester can then be hydrolyzed by treatment with base or acid. It should be understood that other well known methods to prepare phenylglycine derivatives exist in the art and can be amended to provide the desired compounds in this description. It should also be understood that the final phenylglycine derivatives can be purified to enantiomeric purity greater than 98% ee via preparative HPLC.

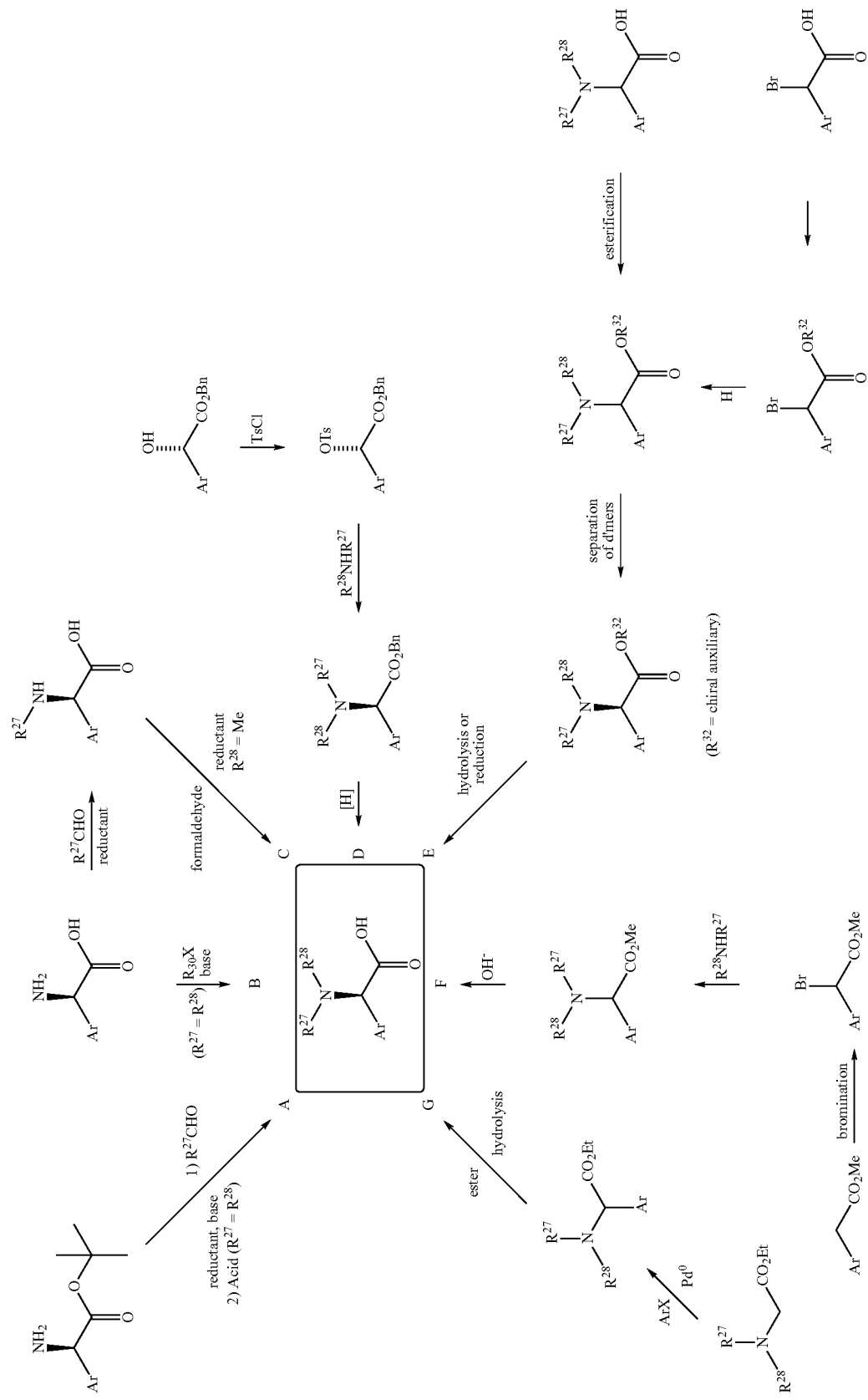
Scheme 12: Acylated Amino Acid Derivatives

In another embodiment of the present disclosure, acylated phenylglycine derivatives may be prepared as illustrated below. Phenylglycine derivatives wherein the carboxylic acid is protected as an easily removed ester, may be acylated with an acid chloride in the presence of a base such as triethylamine to provide the corresponding amides (pathway A). Pathway B illustrates the acylation of the starting phenylglycine derivative with an appropriate chloroformate while pathway C shows reaction with an appropriate isocyanate or carbamoyl chloride. Each of the three intermediates shown in pathways A-C may be deprotected by methods known by those skilled in the art (ie; treatment of the t-butyl ester with strong base such as HCl or trifluoroacetic acid).

| Condition 1 | |
|---|---|
| Column = | Phenomenex-Luna 3.0 × 50 mm S10 |
| Start % B = | 0 |
| Final % B = | 100 |
| Gradient time = | 2 min |
| Stop time = | 3 min |
| Flow Rate = | 4 mL/min |
| Wavelength = | 220 nm |
| Slovent A = | 0.1% TFA in 10% methanol/90% $H_2O$ |
| Solvent B = | 0.1% TFA in 90% methanol/10% $H_2O$ |

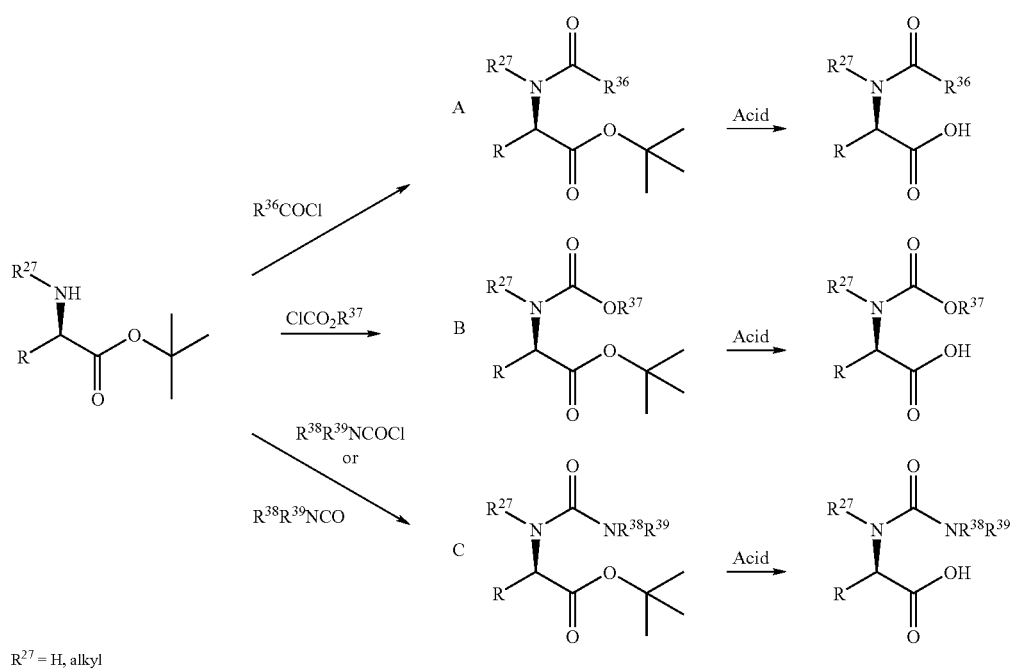

Scheme 13

$R^{27}$ = H, alkyl

Amino-substituted phenylacetic acids may be prepared by treatment of a chloromethylphenylacetic acid with an excess of an amine.

Compound Analysis Conditions

Purity assessment and low resolution mass analysis were conducted on a Shimadzu LC system coupled with Waters Micromass ZQ MS system. It should be noted that retention times may vary slightly between machines. The LC conditions employed in determining the retention time (RT) were:

| -continued | |
|---|---|
| Condition 2 | |
| Column = | Phenomenex-Luna 4.6 × 50 mm S10 |
| Start % B = | 0 |
| Final % B = | 100 |
| Gradient time = | 2 min |
| Stop time = | 3 min |
| Flow Rate = | 5 mL/min |
| Wavelength = | 220 nm |
| Slovent A = | 0.1% TFA in 10% methanol/90% $H_2O$ |
| Solvent B = | 0.1% TFA in 90% methanol/10% $H_2O$ |
| Condition 3 | |
| Column = | HPLC XTERRA C18 3.0 × 50 mm S7 |
| Start % B = | 0 |
| Final % B = | 100 |
| Gradient time = | 3 min |
| Stop time = | 4 min |
| Flow Rate = | 4 mL/min |
| Wavelength = | 220 nm |
| Slovent A = | 0.1% TFA in 10% methanol/90% $H_2O$ |
| Solvent B = | 0.1% TFA in 90% methanol/10% $H_2O$ |

-continued

Condition M1

| | |
|---|---|
| Column: | Luna 4.6 × 50 mm S10 |
| Start % B = | 0 |
| Final % B = | 100 |
| Gradient time = | 3 min |
| Stop time = | 4 min |
| Flow rate = | 4 mL/min |
| Solvent A: = | 95% H$_2$0: 5% CH$_3$CN, 10 mm Ammonium acetate |
| Solvent B: = | 5% H$_2$O: 95% CH$_3$CN; 10 mm Ammonium acetate |

Synthesis of Common Caps

Cap-1

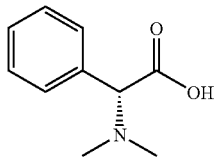

A suspension of 10% Pd/C (2.0 g) in methanol (10 mL) was added to a mixture of (R)-2-phenylglycine (10 g, 66.2 mmol), formaldehyde (33 mL of 37% wt. in water), 1N HCl (30 mL) and methanol (30 mL), and exposed to H$_2$ (60 psi) for 3 hours. The reaction mixture was filtered through diatomaceous earth (Celite®), and the filtrate was concentrated in vacuo. The resulting crude material was recrystallized from isopropanol to provide the HCl salt of Cap-1 as a white needle (4.0 g). Optical rotation: −117.1° [c=9.95 mg/mL in H$_2$O; λ=589 nm]. $^1$H NMR (DMSO-d$_6$, δ=2.5 ppm, 500 MHz): δ 7.43-7.34 (m, 5H), 4.14 (s, 1H), 2.43 (s, 6H); LC (Cond. 1): RT=0.25; LC/MS: Anal. Calcd. for [M+H]$^-$ C$_{10}$H$_{14}$NO$_2$ 180.10; found 180.17; HRMS: Anal. Calcd. for [M+H]$^-$ C$_{10}$H$_{14}$NO$_2$ 180.1025; found 180.1017.

Cap-2

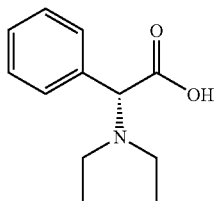

NaBH$_3$CN (6.22 g, 94 mmol) was added in portions over a few minutes to a cooled (ice/water) mixture of (R)-2-Phenylglycine (6.02 g, 39.8 mmol) and MeOH (100 mL), and stirred for 5 min. Acetaldehyde (10 mL) was added drop-wise over 10 min and stirring was continued at the same cooled temperature for 45 min and at ambient temperature for ~6.5 hr. The reaction mixture was cooled back with ice-water bath, treated with water (3 mL) and then quenched with a drop-wise addition of concentrated HCl over ~45 min until the pH of the mixture is ~1.5-2.0. The cooling bath was removed and the stirring was continued while adding concentrated HCl in order to maintain the pH of the mixture around 1.5-2.0. The reaction mixture was stirred over night, filtered to remove the white suspension, and the filtrate was concentrated in vacuo. The crude material was recrystallized from ethanol to afford the HCl salt of Cap-2 as a shining white solid in two crops (crop-1: 4.16 g; crop-2: 2.19 g). $^1$H NMR (DMSO-d$_6$, δ=2.5 ppm, 400 MHz): 10.44 (1.00, br s, 1H), 7.66 (m, 2H), 7.51 (m, 3H), 5.30 (s, 1H), 3.15 (br m, 2H), 2.98 (br m, 2H), 1.20 (app br s, 6H). Crop-1: [α]$^{25}$ −102.21° (c=0.357, H$_2$O); crop-2: [α]$^{25}$ −99.7° (c=0.357, H$_2$O). LC (Cond. 1): RT=0.43 min; LC/MS: Anal. Calcd. for [M+H]$^+$ C$_{12}$H$_{18}$NO$_2$: 208.13; found 208.26

Cap-3

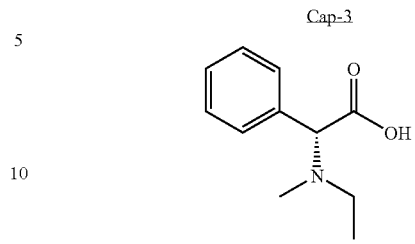

Acetaldehyde (5.0 mL, 89.1 mmol) and a suspension of 10% Pd/C (720 mg) in methanol/H$_2$O (4 mL/1 mL) was sequentially added to a cooled (~15° C.) mixture of (R)-2-phenylglycine (3.096 g, 20.48 mmol), 1N HCl (30 mL) and methanol (40 mL). The cooling bath was removed and the reaction mixture was stirred under a balloon of H$_2$ for 17 hours. An additional acetaldehyde (10 mL, 178.2 mmol) was added and stirring continued under H$_2$ atmosphere for 24 hours [Note: the supply of H$_2$ was replenished as needed throughout the reaction]. The reaction mixture was filtered through diatomaceous earth (Celite®), and the filtrate was concentrated in vacuo. The resulting crude material was recrystallized from isopropanol to provide the HCl salt of (R)-2-(ethylamino)-2-phenylacetic acid as a shining white solid (2.846 g). $^1$H NMR (DMSO-d$_6$, δ=2.5 ppm, 400 MHz): δ 14.15 (br s, 1H), 9.55 (br s, 2H), 7.55-7.48 (m, 5H), 2.88 (br m, 1H), 2.73 (br m, 1H), 1.20 (app t, J=7.2, 3H). LC (Cond. 1): RT=0.39 min; >95% homogeneity index; LC/MS: Anal. Calcd. for [M+H]$^+$ C$_{10}$H$_{14}$NO$_2$: 180.10; found 180.18.

A suspension of 10% Pd/C (536 mg) in methanol/H$_2$O (3 mL/1 mL) was added to a mixture of (R)-2-(ethylamino)-2-phenylacetic acid/HCl (1.492 g, 6.918 mmol), formaldehyde (20 mL of 37% wt. in water), 1N HCl (20 mL) and methanol (23 mL). The reaction mixture was stirred under a balloon of H$_2$ for ~72 hours, where the H$_2$ supply was replenished as needed. The reaction mixture was filtered through diatomaceous earth (Celite®) and the filtrate was concentrated in vacuo. The resulting crude material was recrystallized from isopropanol (50 mL) to provide the HCl salt of Cap-3 as a white solid (985 mg). $^1$H NMR (DMSO-d$_6$, δ=2.5 ppm, 400 MHz): δ 10.48 (br s, 1H), 7.59-7.51 (m, 5H), 5.26 (s, 1H), 3.08 (app br s, 2H), 2.65 (br s, 3H), 1.24 (br m, 3H). LC (Cond. 1): RT=0.39 min; >95% homogeneity index; LC/MS: Anal. Calcd. for [M+H]$^+$ C$_{11}$H$_{16}$NO$_2$: 194.12; found 194.18; HRMS: Anal. Calcd. for [M+H]$^+$ C$_{11}$H$_{16}$NO$_2$: 194.1180; found 194.1181.

Cap-4

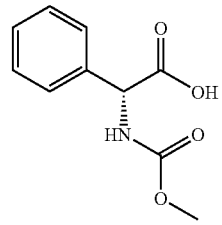

ClCO$_2$Me (3.2 mL, 41.4 mmol) was added dropwise to a cooled (ice/water) THF (410 mL) semi-solution of (R)-tert-butyl 2-amino-2-phenylacetate/HCl (9.877 g, 40.52 mmol) and diisopropylethylamine (14.2 mL, 81.52 mmol) over 6 min, and stirred at similar temperature for 5.5 hours. The volatile component was removed in vacuo, and the residue was partitioned between water (100 mL) and ethyl acetate (200 mL). The organic layer was washed with 1N HCl (25 mL) and saturated NaHCO₃ solution (30 mL), dried (MgSO₄), filtered, and concentrated in vacuo. The resultant colorless oil was triturated from hexanes, filtered and washed with hexanes (100 mL) to provide (R)-tert-butyl 2-(methoxycarbonylamino)-2-phenylacetate as a white solid (7.7 g). $^1$H NMR (DMSO-d₆, δ=2.5 ppm, 400 MHz): 7.98 (d, J=8.0, 1H), 7.37-7.29 (m, 5H), 5.09 (d, J=8, 1H), 3.56 (s, 3H), 1.33 (s, 9H). LC (Cond. 1): RT=1.53 min; ~90% homogeneity index; LC/MS: Anal. Calcd. for [M+Na]⁺ C₁₄H₁₉NNaO₄:288.12; found 288.15.

TFA (16 mL) was added dropwise to a cooled (ice/water) CH₂Cl₂ (160 mL) solution of the above product over 7 minutes, and the cooling bath was removed and the reaction mixture was stirred for 20 hours. Since the deprotection was still not complete, an additional TFA (1.0 mL) was added and stirring continued for an additional 2 hours. The volatile component was removed in vacuo, and the resulting oil residue was treated with diethyl ether (15 mL) and hexanes (12 mL) to provide a precipitate. The precipitate was filtered and washed with diethyl ether/hexanes (~1:3 ratio; 30 mL) and dried in vacuo to provide Cap-4 as a fluffy white solid (5.57 g). Optical rotation: −176.9° [c=3.7 mg/mL in H₂O; λ=589 nm]. $^1$H NMR (DMSO-d₆, δ=2.5 ppm, 400 MHz): δ 12.84 (br s, 1H), 7.96 (d, J=8.3, 1H), 7.41-7.29 (m, 5H), 5.14 (d, J=8.3, 1H), 3.55 (s, 3H). LC (Cond. 1): RT=1.01 min; >95% homogeneity index; LC/MS: Anal. Calcd. for [M+H]⁺ C₁₀H₁₂NO₄ 210.08; found 210.17; HRMS: Anal. Calcd. for [M+H]⁺ C₁₀H₁₂NO₄ 210.0766; found 210.0756.

Cap-5

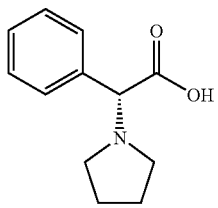

A mixture of (R)-2-phenylglycine (1.0 g, 6.62 mmol), 1,4-dibromobutane (1.57 g, 7.27 mmol) and Na₂CO₃ (2.10 g, 19.8 mmol) in ethanol (40 mL) was heated at 100° C. for 21 hours. The reaction mixture was cooled to ambient temperature and filtered, and the filtrate was concentrated in vacuo. The residue was dissolved in ethanol and acidified with 1N HCl to pH 3-4, and the volatile component was removed in vacuo. The resulting crude material was purified by a reverse phase HPLC (water/methanol/TFA) to provide the TFA salt of Cap-5 as a semi-viscous white foam (1.0 g). $^1$H NMR (DMSO-d₆, δ=2.5, 500 MHz) δ 10.68 (br s, 1H), 7.51 (m, 5H), 5.23 (s, 1H), 3.34 (app br s, 2H), 3.05 (app br s, 2H), 1.95 (app br s, 4H); RT=0.30 min (Cond. 1); >98% homogeneity index; LC/MS: Anal. Calcd. for [M+H]⁺ C₁₂H₁₆NO₂: 206.12; found 206.25.

Cap-6

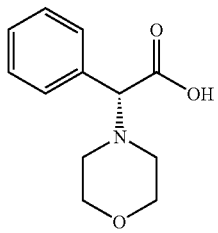

The TFA salt of Cap-6 was synthesized from (R)-2-phenylglycine and 1-bromo-2-(2-bromoethoxy)ethane by using the method of preparation of Cap-5. $^1$H NMR (DMSO-d₆, δ=2.5, 500 MHz) δ 12.20 (br s, 1H), 7.50 (m, 5H), 4.92 (s, 1H), 3.78 (app br s, 4H), 3.08 (app br s, 2H), 2.81 (app br s, 2H); RT=0.32 min (Cond. 1); >98%; LC/MS: Anal. Calcd. for [M+H]⁺ C₁₂H₁₆NO₃: 222.11; found 222.20; HRMS: Anal. Calcd. for [M+H]⁺ C₁₂H₁₆NO₃: 222.1130; found 222.1121.

Cap-7

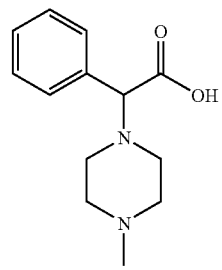

Cap-7a: enantiomer-1
Cap-7b: enantiomer-2

A CH₂Cl₂ (200 mL) solution of p-toluenesulfonyl chloride (8.65 g, 45.4 mmol) was added dropwise to a cooled (−5° C.) CH₂Cl₂ (200 mL) solution of (S)-benzyl 2-hydroxy-2-phenylacetate (10.0 g, 41.3 mmol), triethylamine (5.75 mL, 41.3 mmol) and 4-dimethylaminopyridine (0.504 g, 4.13 mmol), while maintaining the temperature between −5° C. and 0° C. The reaction was stirred at 0° C. for 9 hours, and then stored in a freezer (−25° C.) for 14 hours. It was allowed to thaw to ambient temperature and washed with water (200 mL), 1N HCl (100 mL) and brine (100 mL), dried (MgSO₄), filtered, and concentrated in vacuo to provide benzyl 2-phenyl-2-(tosyloxy)acetate as a viscous oil which solidified upon standing (16.5 g). The chiral integrity of the product was not checked and that product was used for the next step without further purification. $^1$H NMR (DMSO-d₆, δ=2.5, 500 MHz) δ 7.78 (d, J=8.6, 2H), 7.43-7.29 (m, 10H), 7.20 (m, 2H), 6.12 (s, 1H), 5.16 (d, J=12.5, 1H), 5.10 (d, J=12.5, 1H), 2.39 (s, 3H). RT=3.00 (Cond. 3); >90% homogeneity index; LC/MS: Anal. Calcd. for [M+H]⁺ C₂₂H₂₀NaO₅S: 419.09. found 419.04.

A THF (75 mL) solution of benzyl 2-phenyl-2-(tosyloxy) acetate (6.0 g, 15.1 mmol), 1-methylpiperazine (3.36 mL, 30.3 mmol) and N,N-diisopropylethylamine (13.2 mL, 75.8 mmol) was heated at 65° C. for 7 hours. The reaction was allowed to cool to ambient temperature and the volatile component was removed in vacuo. The residue was partitioned between ethylacetate and water, and the organic layer was washed with water and brine, dried (MgSO₄), filtered, and concentrated in vacuo. The resulting crude material was purified by flash chromatography (silica gel, ethyl acetate) to provide benzyl 2-(4-methylpiperazin-1-yl)-2-phenylacetate as an orangish-brown viscous oil (4.56 g). Chiral HPLC analysis (Chiralcel OD-H) indicated that the sample is a mixture of enantiomers in a 38.2 to 58.7 ratio. The separation of the enantiomers were effected as follow: the product was dissolved in 120 mL of ethanol/heptane (1:1) and injected (5 mL/injection) on chiral HPLC column (Chiracel OJ, 5 cm ID×50 cm L, 20 µm) eluting with 85:15 Heptane/ethanol at 75 mL/min, and monitored at 220 nm. Enantiomer-1 (1.474 g) and enantiomer-2 (2.2149 g) were retrieved as viscous oil. $^1$H NMR (CDCl₃, δ=7.26, 500 MHz) 7.44-7.40 (m, 2H), 7.33-7.24 (m, 6H), 7.21-7.16 (m, 2H), 5.13 (d, J=12.5, 1H), 5.08 (d, J=12.5, 1H), 4.02 (s, 1H), 2.65-2.38 (app br s, 8H), 2.25 (s, 3H). RT=2.10 (Cond. 3); >98% homogeneity index; LC/MS: Anal. Calcd. for [M+H]⁺ C₂₀H₂₅N₂O₂: 325.19; found 325.20.

A methanol (10 mL) solution of either enantiomer of benzyl 2-(4-methylpiperazin-1-yl)-2-phenylacetate (1.0 g, 3.1 mmol) was added to a suspension of 10% Pd/C (120 mg) in methanol (5.0 mL). The reaction mixture was exposed to a balloon of hydrogen, under a careful monitoring, for <50 min. Immediately after the completion of the reaction, the catalyst was filtered through diatomaceous earth (Celite®) and the filtrate was concentrated in vacuo to provide Cap-7, contaminated with phenylacetic acid as a tan foam (867.6 mg; mass is above the theoretical yield). The product was used for the next step without further purification. $^1$H NMR (DMSO-d$_6$, δ=2.5, 500 MHz) δ 7.44-7.37 (m, 2H), 7.37-7.24 (m, 3H), 3.92 (s, 1H), 2.63-2.48 (app. bs, 2H), 2.48-2.32 (m, 6H), 2.19 (s, 3H); RT=0.31 (Cond. 2); >90% homogeneity index; LC/MS: Anal. Calcd. for $[M+H]^+$ $C_{13}H_{19}N_2O_2$: 235.14; found 235.15; HRMS: Anal. Calcd. for $[M+H]^+$ $C_{13}H_{19}N_2O_2$: 235.1447; found 235.1440.

The synthesis of Cap-8 and Cap-9 was conducted according to the synthesis of Cap-7 by using appropriate amines for the SN$_2$ displacement step (i.e., 4-hydroxypiperidine for Cap-8 and (S)-3-fluoropyrrolidine for Cap-9) and modified conditions for the separation of the respective stereoisomeric intermediates, as described below.

Cap-8

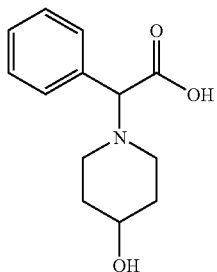

8a: enantiomer-1
8b: enantiomer-2

The enantiomeric separation of the intermediate benzyl 2-(4-hydroxypiperidin-1-yl)-2-phenyl acetate was effected by employing the following conditions: the compound (500 mg) was dissolved in ethanol/heptane (5 mL/45 mL). The resulting solution was injected (5 mL/injection) on a chiral HPLC column (Chiracel OJ, 2 cm ID×25 cm L, 10 μm) eluting with 80:20 heptane/ethanol at 10 mL/min, monitored at 220 nm, to provide 186.3 mg of enantiomer-1 and 209.1 mg of enantiomer-2 as light-yellow viscous oils. These benzyl ester was hydrogenolysed according to the preparation of Cap-7 to provide Cap-8: $^1$H NMR (DMSO-d$_6$, δ=2.5, 500 MHz) 7.40 (d, J=7, 2H), 7.28-7.20 (m, 3H), 3.78 (s 1H), 3.46 (m, 1H), 2.93 (m, 1H), 2.62 (m, 1H), 2.20 (m, 2H), 1.70 (m, 2H), 1.42 (m, 2H). RT=0.28 (Cond. 2); >98% homogeneity index; LC/MS: Anal. Calcd. for $[M+H]^+$ $C_{13}H_{18}NO_3$: 236.13; found 236.07; HRMS: Calcd. for $[M+H]^+$ $C_{13}H_{18}NO_3$: 236.1287; found 236.1283.

Cap-9

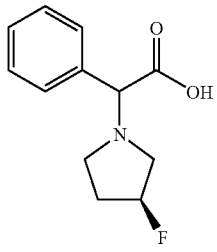

9a: diastereomer-1
9b: diastereomer-2

The diastereomeric separation of the intermediate benzyl 2-((S)-3-fluoropyrrolidin-1-yl)-2-phenylacetate was effected by employing the following conditions: the ester (220 mg) was separated on a chiral HPLC column (Chiracel OJ-H, 0.46 cm ID×25 cm L, 5 μm) eluting with 95% CO$_2$/5% methanol with 0.1% TFA, at 10 bar pressure, 70 mL/min flow rate, and a temperature of 35° C. The HPLC elute for the respective stereoisomers was concentrated, and the residue was dissolved in CH$_2$Cl$_2$ (20 mL) and washed with an aqueous medium (10 mL water+1 mL saturated NaHCO$_3$ solution). The organic phase was dried (MgSO$_4$), filtered, and concentrated in vacuo to provide 92.5 mg of fraction-1 and 59.6 mg of fraction-2. These benzyl esters were hydrogenolysed according to the preparation of Cap-7 to prepare Caps 9a and 9b. Cap-9a (diastereomer-1; the sample is a TFA salt as a result of purification on a reverse phase HPLC using H$_2$O/methanol/TFA solvent): $^1$H NMR (DMSO-d$_6$, δ=2.5, 400 MHz) 7.55-7.48 (m, 5H), 5.38 (d of m, J=53.7, 1H), 5.09 (br s, 1H), 3.84-2.82 (br m, 4H), 2.31-2.09 (m, 2H). RT=0.42 (Cond. 1); >95% homogeneity index; LC/MS: Anal. Calcd. for $[M+H]^+$ $C_{12}H_{15}FNO_2$: 224.11; found 224.14; Cap-9b (diastereomer-2): $^1$H NMR (DMSO-d$_6$, δ=2.5, 400 MHz) 7.43-7.21 (m, 5H), 5.19 (d of m, J=55.9, 1H), 3.97 (s, 1H), 2.95-2.43 (m, 4H), 2.19-1.78 (m, 2H). RT=0.44 (Cond. 1); LC/MS: Anal. Calcd. for $[M+H]^+$ $C_{12}H_{15}FNO_2$: 224.11; found 224.14.

Cap-10

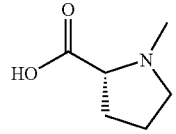

To a solution of D-proline (2.0 g, 17 mmol) and formaldehyde (2.0 mL of 37% wt. in H$_2$O) in methanol (15 mL) was added a suspension of 10% Pd/C (500 mg) in methanol (5 mL). The mixture was stirred under a balloon of hydrogen for 23 hours. The reaction mixture was filtered through diatomaceous earth (Celite®) and concentrated in vacuo to provide Cap-10 as an off-white solid (2.15 g). $^1$H NMR (DMSO-d$_6$, δ=2.5, 500 MHz) 3.42 (m, 1H), 3.37 (dd, J=9.4, 6.1, 1H), 2.85-2.78 (m, 1H), 2.66 (s, 3H), 2.21-2.13 (m, 1H), 1.93-1.84 (m, 2H), 1.75-1.66 (m, 1H). RT=0.28 (Cond. 2); >98% homogeneity index; LC/MS: Anal. Calcd. for $[M+H]^+$ $C_6H_{12}NO_2$: 130.09; found 129.96.

Cap-11

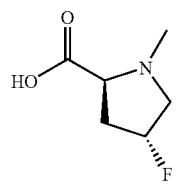

A mixture of (2S,4R)-4-fluoropyrrolidine-2-carboxylic acid (0.50 g, 3.8 mmol), formaldehyde (0.5 mL of 37% wt. in H$_2$O), 12 N HCl (0.25 mL) and 10% Pd/C (50 mg) in methanol (20 mL) was stirred under a balloon of hydrogen for 19 hours. The reaction mixture was filtered through diatomaceous earth (Celite®) and the filtrate was concentrated in vacuo. The residue was recrystallized from isopropanol to provide the HCl salt of Cap-11 as a white solid (337.7 mg). $^1$H NMR (DMSO-d$_6$, δ=2.5, 500 MHz) 5.39 (d m, J=53.7, 1H), 4.30 (m, 1H), 3.90 (ddd, J=31.5, 13.5, 4.5, 1H), 3.33 (dd, J=25.6, 13.4, 1H), 2.85 (s, 3H), 2.60-2.51 (m, 1H), 2.39-2.26 (m, 1H). RT=0.28 (Cond. 2); >98% homogeneity index; LC/MS: Anal. Calcd. for [M+H]$^+$ C$_6$H$_{11}$FNO$_2$: 148.08; found 148.06.

Cap-12

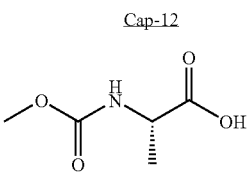

L-Alanine (2.0 g, 22.5 mmol) was dissolved in 10% aqueous sodium carbonate solution (50 mL), and a THF (50 mL) solution of methyl chloroformate (4.0 mL) was added to it. The reaction mixture was stirred under ambient conditions for 4.5 hours and concentrated in vacuo. The resulting white solid was dissolved in water and acidified with 1N HCl to a pH ~2-3. The resulting solutions was extracted with ethyl acetate (3×100 mL), and the combined organic phase was dried (Na$_2$SO$_4$), filtered, and concentrated in vacuo to provide a colorless oil (2.58 g). 500 mg of this material was purified by a reverse phase HPLC (H$_2$O/methanol/TFA) to provide 150 mg of Cap-12 as a colorless oil. $^1$H NMR (DMSO-d$_6$, δ=2.5, 500 MHz) 7.44 (d, J=7.3, 0.8H), 7.10 (br s, 0.2H), 3.97 (m, 1H), 3.53 (s, 3H), 1.25 (d, J=7.3, 3H).

Cap-13

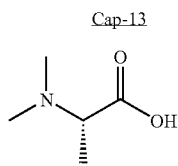

A mixture of L-alanine (2.5 g, 28 mmol), formaldehyde (8.4 g, 37 wt. %), 1N HCl (30 mL) and 10% Pd/C (500 mg) in methanol (30 mL) was stirred under a hydrogen atmosphere (50 psi) for 5 hours. The reaction mixture was filtered through diatomaceous earth (Celite®) and the filtrate was concentrated in vacuo to provide the HCl salt of Cap-13 as an oil which solidified upon standing under vacuum (4.4 g; the mass is above theoretical yield). The product was used without further purification. $^1$H NMR (DMSO-d$_6$, δ=2.5, 500 MHz) δ 12.1 (br s, 1H), 4.06 (q, J=7.4, 1H), 2.76 (s, 6H), 1.46 (d, J=7.3, 3H).

Cap-14

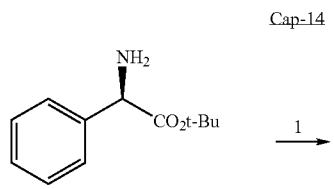

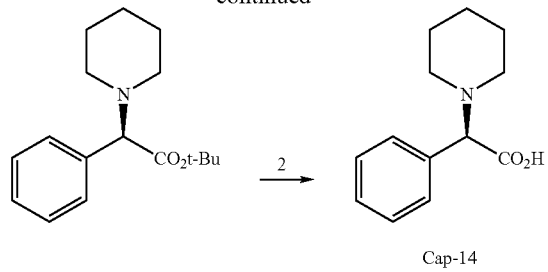

Step 1: A mixture of (R)-(−)-D-phenylglycine tert-butyl ester (3.00 g, 12.3 mmol), NaBH$_3$CN (0.773 g, 12.3 mmol), KOH (0.690 g, 12.3 mmol) and acetic acid (0.352 mL, 6.15 mmol) were stirred in methanol at 0° C. To this mixture was added glutaric dialdehyde (2.23 mL, 12.3 mmol) dropwise over 5 minutes. The reaction mixture was stirred as it was allowed to warm to ambient temperature and stirring was continued at the same temperature for 16 hours. The solvent was subsequently removed and the residue was partitioned with 10% aqueous NaOH and ethyl acetate. The organic phase was separated, dried (MgSO$_4$), filtered and concentrated to dryness to provide a clear oil. This material was purified by reverse-phase preparative HPLC (Primesphere C-18, 30×100 mm; CH$_3$CN—H$_2$O-0.1% TFA) to give the intermediate ester (2.70 g, 56%) as a clear oil. $^1$HNMR (400 MHz, CDCl$_3$) δ 7.53-7.44 (m, 3H), 7.40-7.37 (m, 2H), 3.87 (d, J=10.9 Hz, 1H), 3.59 (d, J=10.9 Hz, 1H), 2.99 (t, J=11.2 Hz, 1H), 2.59 (t, J=11.4 Hz, 1H), 2.07-2.02 (m, 2H), 1.82 (d, J=1.82 Hz, 3H), 1.40 (s, 9H). LC/MS: Anal. Calcd. for C$_{17}$H$_{25}$NO$_2$: 275; found: 276 (M+H)$^+$.

Step 2: To a stirred solution of the intermediate ester (1.12 g, 2.88 mmol) in dichloromethane (10 mL) was added TFA (3 mL). The reaction mixture was stirred at ambient temperature for 4 hours and then it was concentrated to dryness to give a light yellow oil. The oil was purified using reverse-phase preparative HPLC (Primesphere C-18, 30×100 mm; CH$_3$CN—H$_2$O-0.1% TFA). The appropriate fractions were combined and concentrated to dryness in vacuo. The residue was then dissolved in a minimum amount of methanol and applied to applied to MCX LP extraction cartridges (2×6 g). The cartridges were rinsed with methanol (40 mL) and then the desired compound was eluted using 2M ammonia in methanol (50 mL). Product-containing fractions were combined and concentrated and the residue was taken up in water. Lyophilization of this solution provided the title compound (0.492 g, 78%) as a light yellow solid. $^1$HNMR (DMSO-d$_6$) δ 7.50 (s, 5H), 5.13 (s, 1H), 3.09 (br s, 2H), 2.92-2.89 (m, 2H), 1.74 (m, 4H), 1.48 (br s, 2H). LC/MS: Anal. Calcd. for C$_{13}$H$_{17}$NO$_2$: 219; found: 220 (M+H)$^+$.

Cap-15

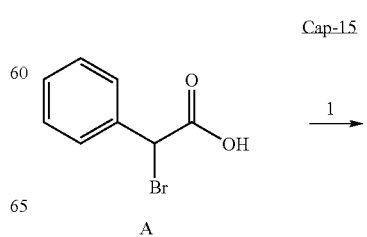

A

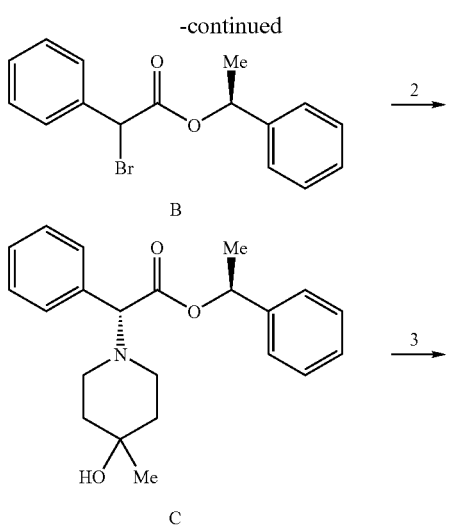

1.71-1.49 (m, 4H), 1.38 (d, J=6.6 Hz, 3H), 1.18 (s, 3H). LCMS: Anal. Calcd. for $C_{22}H_{27}NO_3$: 353; found: 354 (M+H)$^+$. (S,S)-isomer: $^1$HNMR (CD$_3$OD) δ 7.41-7.30 (m, 5H), 7.20-7.14 (m, 3H), 7.06-7.00 (m, 2H), 5.85 (q, J=6.6 Hz, 1H), 4.06 (s, 1H), 2.70-2.60 (m, 1H), 2.51 (dt, J=6.6, 3.3 Hz, 1H), 2.44-2.31 (m, 2H), 1.75-1.65 (m, 1H), 1.65-1.54 (m, 3H), 1.50 (d, J=6.8 Hz, 3H), 1.20 (s, 3H). LCMS: Anal. Calcd. for $C_{22}H_{27}NO_3$: 353; found: 354 (M+H)$^+$.

Step 3; (R)-2-(4-Hydroxy-4-methylpiperidin-1-yl)-2-phenylacetic acid: To a solution of (S)-1-phenylethyl (R)-2-(4-hydroxy-4-methylpiperidin-1-yl)-2-phenylacetate (0.185 g, 0.52 mmol) in dichloromethane (3 mL) was added trifluoroacetic acid (1 mL) and the mixture was stirred at room temperature for 2 hours. The volatiles were subsequently removed in vacuo and the residue was purified by reverse-phase preparative HPLC (Primesphere C-18, 20×100 mm; CH$_3$CN—H$_2$O-0.1% TFA) to give the title compound (as TFA salt) as a pale bluish solid (0,128 g, 98%). LCMS: Anal. Calcd. for $C_{14}H_{19}NO_3$: 249; found: 250 (M+H)$^+$.

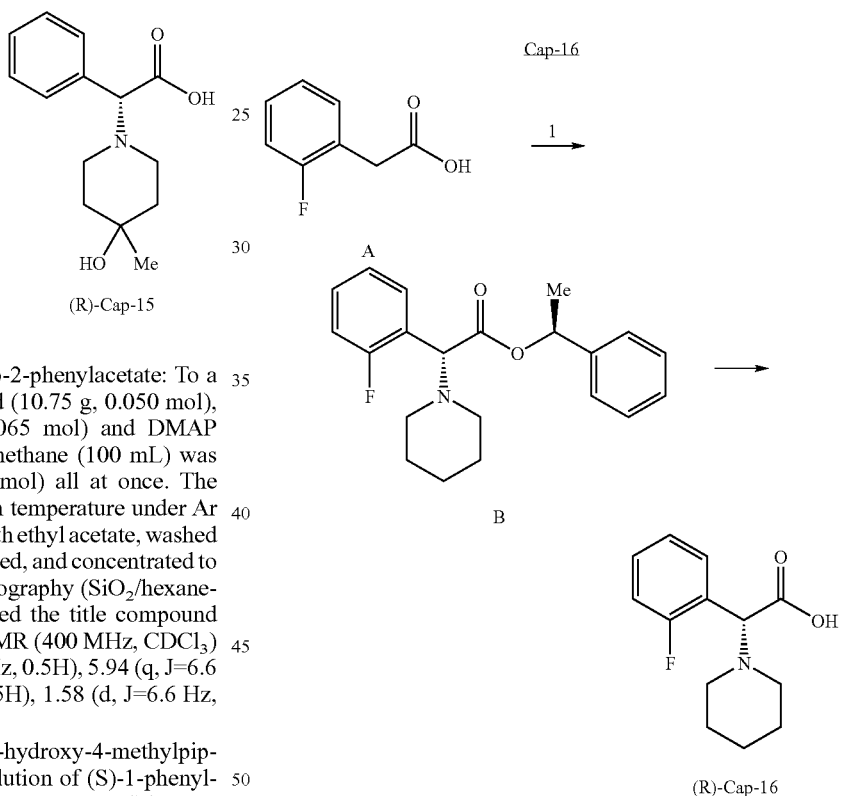

Step 1; (S)-1-Phenylethyl 2-bromo-2-phenylacetate: To a mixture of α-bromophenylacetic acid (10.75 g, 0.050 mol), (S)-(−)-1-phenylethanol (7.94 g, 0.065 mol) and DMAP (0.61 g, 5.0 mmol) in dry dichloromethane (100 mL) was added solid EDCI (12.46 g, 0.065 mol) all at once. The resulting solution was stirred at room temperature under Ar for 18 hours and then it was diluted with ethyl acetate, washed (H$_2$O×2, brine), dried (Na$_2$SO$_4$), filtered, and concentrated to give a pale yellow oil. Flash chromatography (SiO$_2$/hexane-ethyl acetate, 4:1) of this oil provided the title compound (11.64 g, 73%) as a white solid. $^1$HNMR (400 MHz, CDCl$_3$) δ 7.53-7.17 (m, 10H), 5.95 (q, J=6.6 Hz, 0.5H), 5.94 (q, J=6.6 Hz, 0.5H), 5.41 (s, 0.5H), 5.39 (s, 0.5H), 1.58 (d, J=6.6 Hz, 1.5H), 1.51 (d, J=6.6 Hz, 1.5H).

Step 2; (S)-1-Phenylethyl (R)-2-(4-hydroxy-4-methylpiperidin-1-yl)-2-phenylacetate: To a solution of (S)-1-phenylethyl 2-bromo-2-phenylacetate (0.464 g, 1.45 mmol) in THF (8 mL) was added triethylamine (0.61 mL, 4.35 mmol), followed by tetrabutylammonium iodide (0.215 g, 0.58 mmol). The reaction mixture was stirred at room temperature for 5 minutes and then a solution of 4-methyl-4-hydroxypiperidine (0.251 g, 2.18 mmol) in THF (2 mL) was added. The mixture was stirred for 1 hour at room temperature and then it was heated at 55-60° C. (oil bath temperature) for 4 hours. The cooled reaction mixture was then diluted with ethyl acetate (30 mL), washed (H$_2$O×2, brine), dried (MgSO$_4$), filtered and concentrated. The residue was purified by silica gel chromatography (0-60% ethyl acetate-hexane) to provide first the (S,R)-isomer of the title compound (0.306 g, 60%) as a white solid and then the corresponding (S,S)-isomer (0.120 g, 23%), also as a white solid. (S,R)-isomer: $^1$HNMR (CD$_3$OD) δ 7.51-7.45 (m, 2H), 7.41-7.25 (m, 8H), 5.85 (q, J=6.6 Hz, 1H), 4.05 (s, 1H), 2.56-2.45 (m, 2H), 2.41-2.29 (m, 2H), Step 1; (S)-1-Phenylethyl 2-(2-fluorophenyl)acetate: A mixture of 2-fluorophenylacetic acid (5.45 g, 35.4 mmol), (S)-1-phenylethanol (5.62 g, 46.0 mmol), EDCI (8.82 g, 46.0 mmol) and DMAP (0.561 g, 4.60 mmol) in CH$_2$Cl$_2$ (100 mL) was stirred at room temperature for 12 hours. The solvent was then concentrated and the residue partitioned with H$_2$O-ethyl acetate. The phases were separated and the aqueous layer back-extracted with ethyl acetate (2×). The combined organic phases were washed (H$_2$O, brine), dried (Na$_2$SO$_4$), filtered, and concentrated in vacuo. The residue was purified by silica gel chromatography (Biotage/0-20% ethyl acetate-hexane) to provide the title compound as a colorless oil (8.38 g, 92%). $^1$HNMR (400 MHz, CD$_3$OD) δ 7.32-7.23 (m, 7H), 7.10-7.04 (m, 2), 5.85 (q, J=6.5 Hz, 1H), 3.71 (s, 2H), 1.48 (d, J=6.5 Hz, 3H).

Step 2; (R)-((S)-1-Phenylethyl) 2-(2-fluorophenyl)-2-(piperidin-1-yl)acetate: To a solution of (S)-1-phenylethyl 2-(2-fluorophenyl)acetate (5.00 g, 19.4 mmol) in THF (1200 mL) at 0° C. was added DBU (6.19 g, 40.7 mmol) and the solution was allowed to warm to room temperature while stirring for 30 minutes. The solution was then cooled to −78° C. and a solution of $CBr_4$ (13.5 g, 40.7 mmol) in THF (100 mL) was added and the mixture was allowed to warm to −10° C. and stirred at this temperature for 2 hours. The reaction mixture was quenched with saturated aq. $NH_4Cl$ and the layers were separated. The aqueous layer was back-extracted with ethyl acetate (2×) and the combined organic phases were washed ($H_2O$, brine), dried ($Na_2SO_4$), filtered, and concentrated in vacuo. To the residue was added piperidine (5.73 mL, 58.1 mmol) and the solution was stirred at room temperature for 24 hours. The volatiles were then concentrated in vacuo and the residue was purified by silica gel chromatography (Biotage/ 0-30% diethyl ether-hexane) to provide a pure mixture of diastereomers (2:1 ratio by $^1$HNMR) as a yellow oil (2.07 g, 31%), along with unreacted starting material (2.53 g, 51%). Further chromatography of the diastereomeric mixture (Biotage/0-10% diethyl ether-toluene) provided the title compound as a colorless oil (0.737 g, 11%). $^1$HNMR (400 MHz, $CD_3OD$) δ 7.52 (ddd, J=9.4, 7.6, 1.8 Hz, 1H), 7.33-7.40 (m, 1), 7.23-7.23 (m, 4H), 7.02-7.23 (m, 4H), 5.86 (q, J=6.6 Hz, 1H), 4.45 (s, 1H), 2.39-2.45 (m, 4H), 1.52-1.58 (m, 4H), 1.40-1.42 (m, 1H), 1.38 (d, J=6.6 Hz, 3H). LCMS: Anal. Calcd. for $C_{21}H_{24}FNO_2$: 341; found: 342 (M+H)$^+$.

Step 3; (R)-2-(2-fluorophenyl)-2-(piperidin-1-yl)acetic acid: A mixture of (R)—((S)-1-phenylethyl) 2-(2-fluorophenyl)-2-(piperidin-1-yl)acetate (0.737 g, 2.16 mmol) and 20% $Pd(OH)_2$/C (0.070 g) in ethanol (30 mL) was hydrogenated at room temperature and atmospheric pressure ($H_2$ balloon) for 2 hours. The solution was then purged with Ar, filtered through diatomaceous earth (Celite®), and concentrated in vacuo. This provided the title compound as a colorless solid (0.503 g, 98%). $^1$HNMR (400 MHz, $CD_3OD$) δ 7.65 (ddd, J=9.1, 7.6, 1.5 Hz, 1H), 7.47-7.53 (m, 1H), 7.21-7.30 (m, 2H), 3.07-3.13 (m, 4H), 1.84 (br s, 4H), 1.62 (br s, 2H). LCMS: Anal. Calcd. for $C_{13}H_{16}FNO_2$: 237; found: 238 (M+H)$^+$.

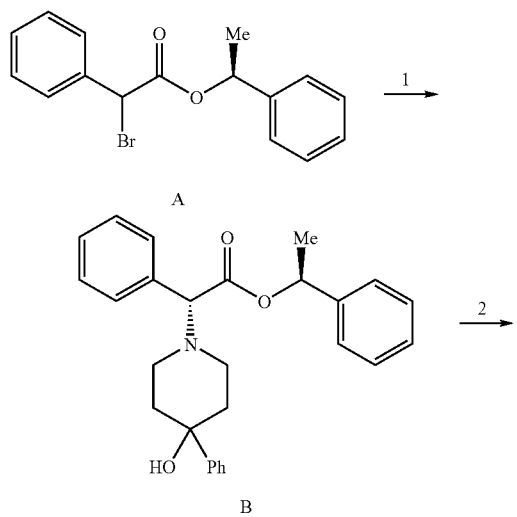

Cap-17

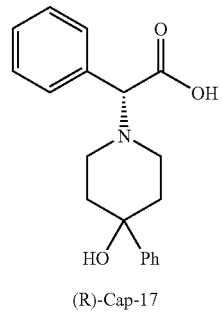

(R)-Cap-17

Step 1; (S)-1-Phenylethyl (R)-2-(4-hydroxy-4-phenylpiperidin-1-yl)-2-phenylacetate: To a solution of (S)-1-phenylethyl 2-bromo-2-phenylacetate (1.50 g, 4.70 mmol) in THF (25 mL) was added triethylamine (1.31 mL, 9.42 mmol), followed by tetrabutylammonium iodide (0.347 g, 0.94 mmol). The reaction mixture was stirred at room temperature for 5 minutes and then a solution of 4-phenyl-4-hydroxypiperidine (1.00 g, 5.64 mmol) in THF (5 mL) was added. The mixture was stirred for 16 hours and then it was diluted with ethyl acetate (100 mL), washed ($H_2O\times2$, brine), dried ($MgSO_4$), filtered and concentrated. The residue was purified on a silica gel column (0-60% ethyl acetate-hexane) to provide an approximately 2:1 mixture of diastereomers, as judged by $^1$HNMR. Separation of these isomers was performed using supercritical fluid chromatography (Chiralcel OJ-H, 30×250 mm; 20% ethanol in $CO_2$ at 35° C.), to give first the (R)-isomer of the title compound (0.534 g, 27%) as a yellow oil and then the corresponding (S)-isomer (0.271 g, 14%), also as a yellow oil. (S,R)-isomer: $^1$HNMR (400 MHz, $CD_3OD$) δ 7.55-7.47 (m, 4H), 7.44-7.25 (m, 10H), 7.25-7.17 (m, 1H), 5.88 (q, J=6.6 Hz, 1H), 4.12 (s, 1H), 2.82-2.72 (m, 1H), 2.64 (dt, J=11.1, 2.5 Hz, 1H), 2.58-2.52 (m, 1H), 2.40 (dt, J=11.1, 2.5 Hz, 1H), 2.20 (dt, J=12.1, 4.6 Hz, 1H), 2.10 (dt, J=12.1, 4.6 Hz, 1H), 1.72-1.57 (m, 2H), 1.53 (d, J=6.5 Hz, 3H). LCMS: Anal. Calcd. for $C_{27}H_{29}NO_3$: 415; found: 416 (M+H)$^+$; (S,S)-isomer: $^1$HNMR (400 MHz, $CD_3OD$) δ 7.55-7.48 (m, 2H), 7.45-7.39 (m, 2H), 7.38-7.30 (m, 5H), 7.25-7.13 (m, 4H), 7.08-7.00 (m, 2H), 5.88 (q, J=6.6 Hz, 1H), 4.12 (s, 1H), 2.95-2.85 (m, 1H), 2.68 (dt, J=11.1, 2.5 Hz, 1H), 2.57-2.52 (m, 1H), 2.42 (dt, J=11.1, 2.5 Hz, 1H), 2.25 (dt, J=12.1, 4.6 Hz, 1H), 2.12 (dt, J=12.1, 4.6 Hz, 1H), 1.73 (dd, J=13.6, 3.0 Hz, 1H), 1.64 (dd, J=13.6, 3.0 Hz, 1H), 1.40 (d, J=6.6 Hz, 3H). LCMS: Anal. Calcd. for $C_{27}H_{29}NO_3$: 415; found: 416 (M+H)$^+$.

The following esters were prepared in similar fashion employing step 1 in the synthesis of Cap-17.

| Intermediate-17a | 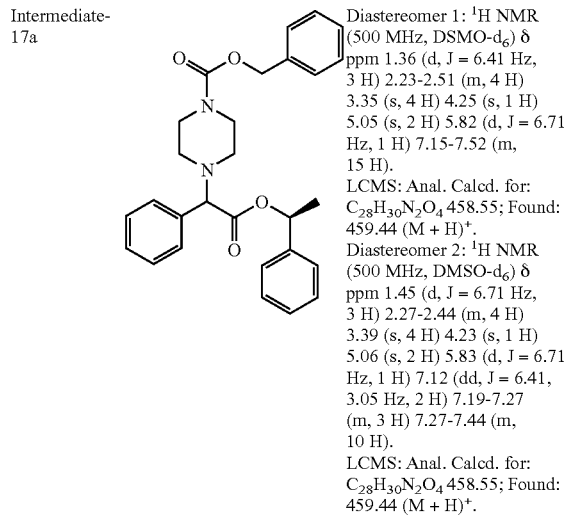 | Diastereomer 1: ¹H NMR (500 MHz, DSMO-d₆) δ ppm 1.36 (d, J = 6.41 Hz, 3 H) 2.23-2.51 (m, 4 H) 3.35 (s, 4 H) 4.25 (s, 1 H) 5.05 (s, 2 H) 5.82 (d, J = 6.71 Hz, 1 H) 7.15-7.52 (m, 15 H). LCMS: Anal. Calcd. for: $C_{28}H_{30}N_2O_4$ 458.55; Found: 459.44 (M + H)⁺. Diastereomer 2: ¹H NMR (500 MHz, DMSO-d₆) δ ppm 1.45 (d, J = 6.71 Hz, 3 H) 2.27-2.44 (m, 4 H) 3.39 (s, 4 H) 4.23 (s, 1 H) 5.06 (s, 2 H) 5.83 (d, J = 6.71 Hz, 1 H) 7.12 (dd, J = 6.41, 3.05 Hz, 2 H) 7.19-7.27 (m, 3 H) 7.27-7.44 (m, 10 H). LCMS: Anal. Calcd. for: $C_{28}H_{30}N_2O_4$ 458.55; Found: 459.44 (M + H)⁺. |
|---|---|---|
| * | * | * |
| * | * | * |
| * | * | * |
| Intermediate-17b | | Diastereomer 1: RT = 11.76 min (Cond'n II); LCMS: Anal. Calcd. for: $C_{20}H_{22}N_2O_3$ 338.4 Found: 339.39 (M + H)⁺; Diastereomer 2: RT = 10.05 min (Cond'n II); LCMS: Anal. Calcd. for: $C_{20}H_{22}N_2O_3$ 338.4; Found: 339.39 (M + H)⁺. |
| * | * | * |
| Intermediate-17c | | Diastereomer 1: $T_R$ = 4.55 min (Cond'n I); LCMS: Anal. Calcd. for: $C_{21}H_{26}N_2O_2$ 338.44 Found: 339.45 (M + H)⁺; Diastereomer 2: $T_R$ 6.00 min (Cond'n I); LCMS: Anal. Calcd. for: $C_{21}H_{26}N_2O_2$ 338.44 Found: 339.45 (M + H)⁺. |
| * | * | * |
| Intermediate-17d | 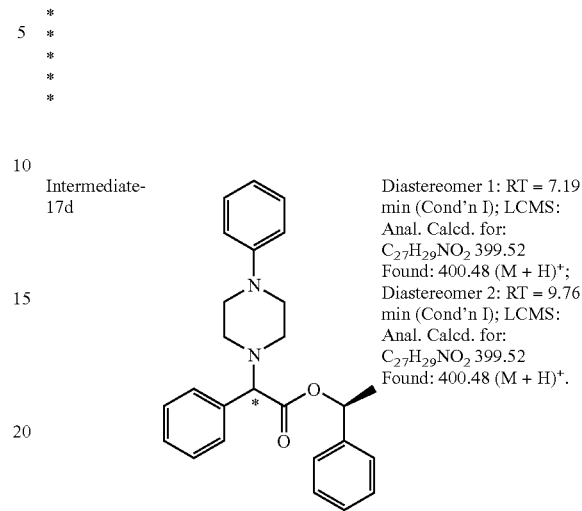 | Diastereomer 1: RT = 7.19 min (Cond'n I); LCMS: Anal. Calcd. for: $C_{27}H_{29}NO_2$ 399.52 Found: 400.48 (M + H)⁺; Diastereomer 2: RT = 9.76 min (Cond'n I); LCMS: Anal. Calcd. for: $C_{27}H_{29}NO_2$ 399.52 Found: 400.48 (M + H)⁺. |

Chiral SFC Conditions for Determining Retention Time for Intermediates 17b-17d

Condition 1

Column: Chiralpak AD-H Column, 4.6×250 mm, 5 μm

Solvents: 90% $CO_2$-10% methanol with 0.1% DEA

Temp: 35° C.

Pressure: 150 bar

Flow rate: 2.0 mL/min.

UV monitored@220 nm

Injection: 1.0 mg/3 mL methanol

Condition 2

Column: Chiralcel OD-H Column, 4.6×250 mm, 5 μm

Solvents: 90% $CO_2$-10% methanol with 0.1% DEA

Temp: 35° C.

Pressure: 150 bar

Flow rate: 2.0 mL/min.

UV monitored@220 nm

Injection: 1.0 mg/mL methanol

Cap-17, Step 2; (R)-2-(4-Hydroxy-4-phenylpiperidin-1-yl)-2-phenylacetic acid: To a solution of (S)-1-phenylethyl (R)-2-(4-hydroxy-4-phenylpiperidin-1-yl)-2-phenylacetate (0.350 g, 0.84 mmol) in dichloromethane (5 mL) was added trifluoroacetic acid (1 mL) and the mixture was stirred at room temperature for 2 hours. The volatiles were subsequently removed in vacuo and the residue was purified by reverse-phase preparative HPLC (Primesphere C-18, 20×100 mm; $CH_3CN$—$H_2O$-0.1% TFA) to give the title compound (as TFA salt) as a white solid (0.230 g, 88%). LCMS: Anal. Calcd. for $C_{19}H_{21}NO_3$: 311; found: 312 (M+H)⁺.

The following carboxylic acids were prepared in a similar fashion:

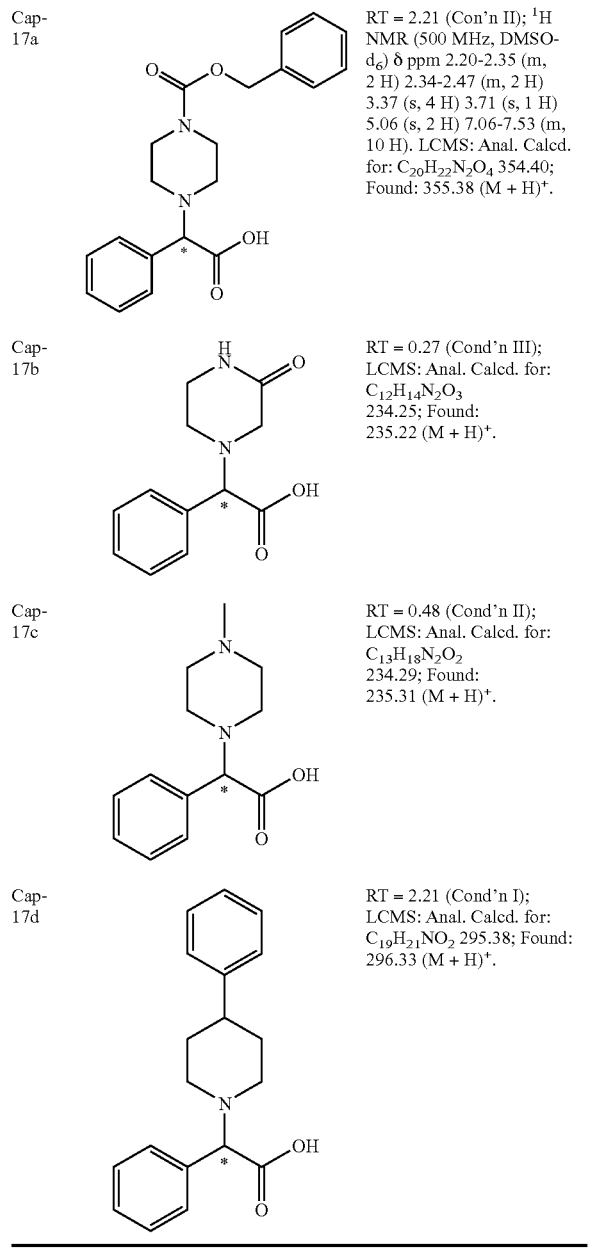

| Cap-17a | RT = 2.21 (Con'n II); ¹H NMR (500 MHz, DMSO-$d_6$) δ ppm 2.20-2.35 (m, 2 H) 2.34-2.47 (m, 2 H) 3.37 (s, 4 H) 3.71 (s, 1 H) 5.06 (s, 2 H) 7.06-7.53 (m, 10 H). LCMS: Anal. Calcd. for: $C_{20}H_{22}N_2O_4$ 354.40; Found: 355.38 (M + H)⁺. |
| Cap-17b | RT = 0.27 (Cond'n III); LCMS: Anal. Calcd. for: $C_{12}H_{14}N_2O_3$ 234.25; Found: 235.22 (M + H)⁺. |
| Cap-17c | RT = 0.48 (Cond'n II); LCMS: Anal. Calcd. for: $C_{13}H_{18}N_2O_2$ 234.29; Found: 235.31 (M + H)⁺. |
| Cap-17d | RT = 2.21 (Cond'n I); LCMS: Anal. Calcd. for: $C_{19}H_{21}NO_2$ 295.38; Found: 296.33 (M + H)⁺. |

LCMS Conditions for Determining Retention Time for Caps 17a-17d

Condition 1

Column: Phenomenex-Luna 4.6×50 mm S10

Start % B=0

Final % B=100

Gradient Time=4 min

Flow Rate=4 mL/min

Wavelength=220

Solvent A=10% methanol–90% $H_2O$–0.1% TFA

Solvent B=90% methanol–10% $H_2O$–0.1% TFA

Condition 2

Column: Waters-Sunfire 4.6×50 mm S5

Start % B=0

Final % B=100

Gradient Time=2 min

Flow Rate=4 mL/min

Wavelength=220

Solvent A=10% methanol–90% $H_2O$–0.1% TFA

Solvent B=90% methanol–10% $H_2O$–0.1% TFA

Condition 3

Column: Phenomenex 10μ 3.0×50 mm

Start % B=0

Final % B=100

Gradient Time=2 min

Flow Rate=4 mL/min

Wavelength=220

Solvent A=10% methanol–90% $H_2O$–0.1% TFA

Solvent B=90% methanol–10% $H_2O$–0.1% TFA

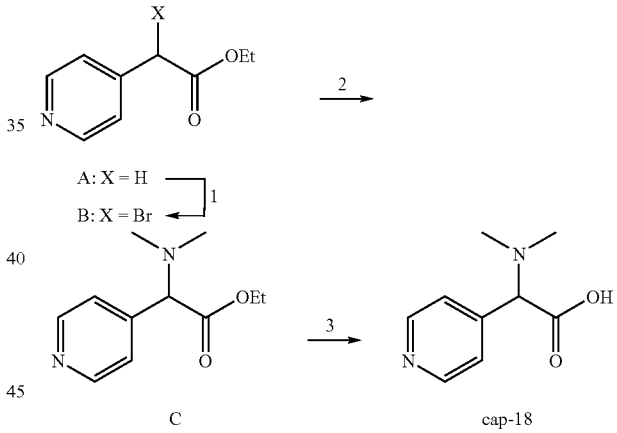

Cap-18

Step 1; (R,S)-Ethyl 2-(4-pyridyl)-2-bromoacetate: To a solution of ethyl 4-pyridylacetate (1.00 g, 6.05 mmol) in dry THF (150 mL) at 0° C. under argon was added DBU (0.99 mL, 6.66 mmol). The reaction mixture was allowed to warm to room temperature over 30 minutes and then it was cooled to –78° C. To this mixture was added $CBr_4$ (2.21 g, 6.66 mmol) and stirring was continued at –78° C. for 2 hours. The reaction mixture was then quenched with sat. aq. $NH_4Cl$ and the phases were separated. The organic phase was washed (brine), dried ($Na_2SO_4$), filtered, and concentrated in vacuo. The resulting yellow oil was immediately purified by flash chromatography ($SiO_2$/hexane-ethyl acetate, 1:1) to provide the title compound (1.40 g, 95%) as a somewhat unstable yellow oil. ¹HNMR (400 MHz, $CDCl_3$) δ 8.62 (dd, J=4.6, 1.8 Hz, 2H), 7.45 (dd, J=4.6, 1.8 Hz, 2H), 5.24 (s, 1H), 4.21-4.29 (m, 2H), 1.28 (t, J=7.1 Hz, 3H). LCMS: Anal. Calcd. for $C_9H_{10}BrNO_2$: 242, 244; found: 243, 245 (M+H)⁺.

Step 2; (R,S)-Ethyl 2-(4-pyridyl)-2-(N,N-dimethylamino) acetate: To a solution of (R,S)-ethyl 2-(4-pyridyl)-2-bromoacetate (1.40 g, 8.48 mmol) in DMF (10 mL) at room temperature was added dimethylamine (2M in THF, 8.5 mL, 17.0 mmol). After completion of the reaction (as judged by tlc) the volatiles were removed in vacuo and the residue was purified by flash chromatography (Biotage, 40+M SiO$_2$ column; 50%-100% ethyl acetate-hexane) to provide the title compound (0.539 g, 31%) as a light yellow oil. $^1$HNMR (400 MHz, CDCl$_3$) δ 8.58 (d, J=6.0 Hz, 2H), 7.36 (d, J=6.0 Hz, 2H), 4.17 (m, 2H), 3.92 (s, 1H), 2.27 (s, 6H), 1.22 (t, J=7.0 Hz). LCMS: Anal. Calcd. for C$_{11}$H$_{16}$N$_2$O$_2$: 208; found: 209 (M+H)$^+$.

Step 3; (R,S)-2-(4-Pyridyl)-2-(N,N-dimethylamino)acetic acid: To a solution of (R,S)-ethyl 2-(4-pyridyl)-2-(N,N-dimethylamino)acetate (0.200 g, 0.960 mmol) in a mixture of THF-methanol-H$_2$O (1:1:1, 6 mL) was added powdered LiOH (0.120 g, 4.99 mmol) at room temperature. The solution was stirred for 3 hours and then it was acidified to pH 6 using 1N HCl. The aqueous phase was washed with ethyl acetate and then it was lyophilized to give the dihydrochloride of the title compound as a yellow solid (containing LiCl). The product was used as such in subsequent steps. $^1$HNMR (400 MHz, DMSO-d$_6$) δ 8.49 (d, J=5.7 Hz, 2H), 7.34 (d, J=5.7 Hz, 2H), 3.56 (s, 1H), 2.21 (s, 6H).

The following examples were prepared in similar fashion using the method described above.

| | | |
|---|---|---|
| Cap-19 | 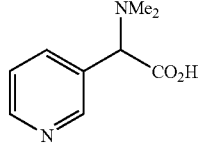 | LCMS: Anal. Calcd. for C$_9$H$_{12}$N$_2$O$_2$: 180; found: 181 (M + H)$^+$. |
| Cap-20 | 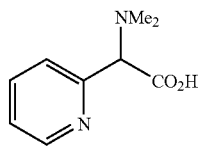 | LCMS: no ionization. $^1$HNMR (400 MHz, CD$_3$OD) δ 8.55 (d, J = 4.3 Hz, 1 H), 7.84 (app t, J = 5.3 Hz, 1 H), 7.61 (d, J = 7.8 Hz, 1 H), 7.37 (app t, J = 5.3 Hz, 1 H), 4.35 (s, 1 H), 2.60 (s, 6 H). |
| Cap-21 | 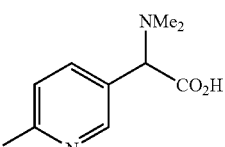 | LCMS: Anal. Calcd. for C$_9$H$_{11}$ClN$_2$O$_2$: 214, 216; found: 215, 217 (M + H)$^+$. |
| Cap-22 | 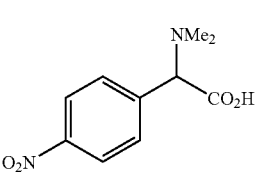 | LCMS: Anal. Calcd. for C$_{10}$H$_{12}$N$_2$O$_4$: 224; found: 225 (M + H)$^+$. |
| Cap-23 | 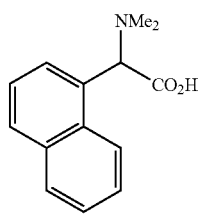 | LCMS: Anal. Calcd. for C$_{14}$H$_{15}$NO$_2$: 247; found: 248 (M + H)$^+$. |
| Cap-24 | 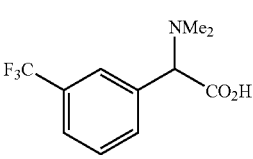 | LCMS: Anal. Calcd. for C$_{11}$H$_{12}$F$_3$NO$_2$: 247; found: 248 (M + H)$^+$. |
| Cap-25 | 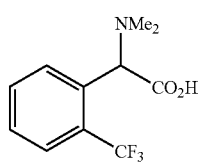 | LCMS: Anal. Calcd. for C$_{11}$H$_{12}$F$_3$NO$_2$: 247; found: 248 (M + H)$^+$. |

-continued

| | | |
|---|---|---|
| Cap-26 | 2-F-C6H4-CH(NMe2)-CO2H | LCMS: Anal. Calcd. for C10H12FNO2: 247; found: 248 (M + H)+. |
| Cap-27 | 3-F-C6H4-CH(NMe2)-CO2H | LCMS: Anal. Calcd. for C10H12FNO2: 247; found: 248 (M + H)+. |
| Cap-28 | 3-Cl-C6H4-CH(NMe2)-CO2H | LCMS: Anal. Calcd. for C10H12ClNO2: 213, 215; found: 214, 217 (M + H)+. |
| Cap-29 | 2-Cl-C6H4-CH(NMe2)-CO2H | LCMS: Anal. Calcd. for C10H12ClNO2: 213, 215; found: 214, 217 (M + H)+. |
| Cap-30 | 4-Cl-C6H4-CH(NMe2)-CO2H | LCMS: Anal. Calcd. for C10H12ClNO2: 213, 215; found: 214, 217 (M + H)+. |
| Cap-31 | (2-methylthiazol-4-yl)-CH(NMe2)-CO2H | LCMS: Anal. Calcd. for C8H11N2O2S: 200; found: 201 (M + H)+. |
| Cap-32 | (thiophen-2-yl)-CH(NMe2)-CO2H | LCMS: Anal. Calcd. for C8H11NO2S: 185; found: 186 (M + H)+. |
| Cap-33 | (thiophen-3-yl)-CH(NMe2)-CO2H | LCMS: Anal. Calcd. for C8H11NO2S: 185; found: 186 (M + H)+. |
| Cap-34 | (benzo[d]isoxazol-3-yl)-CH(NMe2)-CO2H | LCMS: Anal. Calcd. for C11H12N2O3: 220; found: 221 (M + H)+. |
| Cap-35 | (benzo[b]thiophen-3-yl)-CH(NMe2)-CO2H | LCMS: Anal. Calcd. for C12H13NO2S: 235; found: 236 (M + H)+. |

| | | |
|---|---|---|
| Cap-36 | 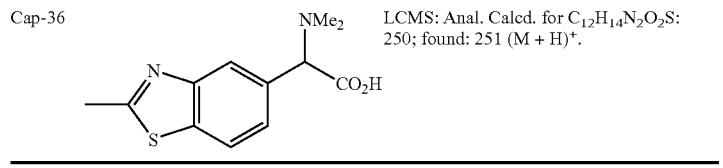 | LCMS: Anal. Calcd. for $C_{12}H_{14}N_2O_2S$: 250; found: 251 (M + H)+. |

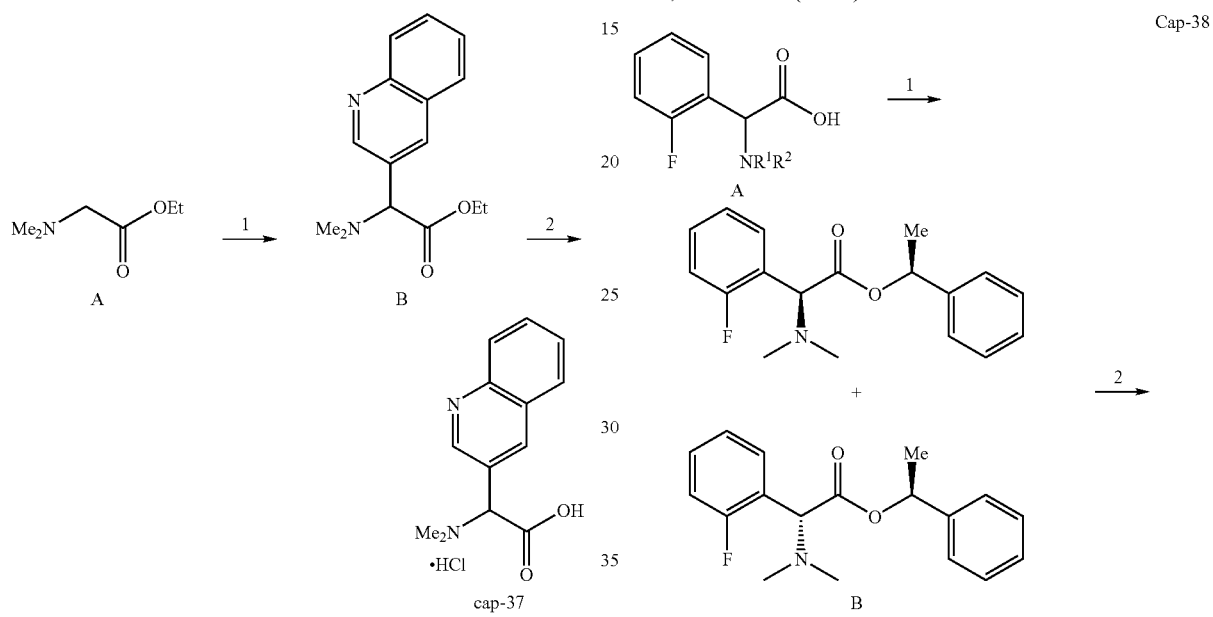

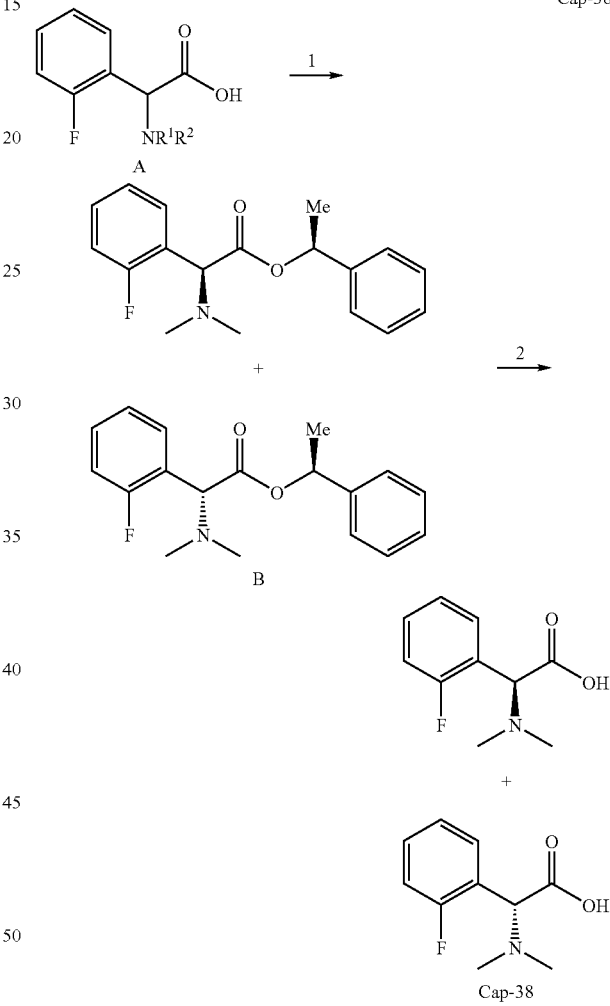

Step 1; (R,S)-Ethyl 2-(quinolin-3-yl)-2-(N,N-dimethylamino)-acetate: A mixture of ethyl N,N-dimethylaminoacetate (0.462 g, 3.54 mmol), $K_3PO_4$ (1.90 g, 8.95 mmol), $Pd(t-Bu_3P)_2$ (0.090 g, 0.176 mmol) and toluene (10 mL) was degassed with a stream of Ar bubbles for 15 minutes. The reaction mixture was then heated at 100° C. for 12 hours, after which it was cooled to room temperature and poured into $H_2O$. The mixture was extracted with ethyl acetate (2x) and the combined organic phases were washed ($H_2O$, brine), dried ($Na_2SO_4$), filtered, and concentrated in vacuo. The residue was purified first by reverse-phase preparative HPLC (Primesphere C-18, 30×100 mm; $CH_3CN$—$H_2O$-5 mM $NH_4OAc$) and then by flash chromatography ($SiO_2$/hexane-ethyl acetate, 1:1) to provide the title compound (0.128 g, 17%) as an orange oil. $^1HNMR$ (400 MHz, $CDCl_3$) δ 8.90 (d, J=2.0 Hz, 1H), 8.32 (d, J=2.0 Hz, 1H), 8.03-8.01 (m, 2H), 7.77 (ddd, J=8.3, 6.8, 1.5 Hz, 1H), 7.62 (ddd, J=8.3, 6.8, 1.5 Hz, 1H), 4.35 (s, 1H), 4.13 (m, 2H), 2.22 (s, 6H), 1.15 (t, J=7.0 Hz, 3H). LCMS: Anal. Calcd. for $C_{15}H_{18}N_2O_2$: 258; found: 259 (M+H)+.

Step 2; (R,S) 2-(Quinolin-3-yl)-2-(N,N-dimethylamino) acetic acid: A mixture of (R,S)-ethyl 2-(quinolin-3-yl)-2-(N,N-dimethylamino)acetate (0.122 g, 0.472 mmol) and 6M HCl (3 mL) was heated at 100° C. for 12 hours. The solvent was removed in vacuo to provide the dihydrochloride of the title compound (0.169 g, >100%) as a light yellow foam. The unpurified material was used in subsequent steps without further purification. LCMS: Anal. Calcd. for $C_{13}H_{14}N_2O_2$: 230; found: 231 (M+H)+.

Step 1; (R)—((S)-1-phenylethyl) 2-(dimethylamino)-2-(2-fluorophenyl)acetate and (S)—((S)-1-phenylethyl) 2-(dimethylamino)-2-(2-fluorophenyl)acetate: To a mixture of (RS)-2-(dimethylamino)-2-(2-fluorophenyl)acetic acid (2.60 g, 13.19 mmol), DMAP (0.209 g, 1.71 mmol) and (S)-1-phenylethanol (2.09 g, 17.15 mmol) in $CH_2Cl_2$ (40 mL) was added EDCI (3.29 g, 17.15 mmol) and the mixture was allowed to stir at room temperature for 12 hours. The solvent was then removed in vacuo and the residue partitioned with ethyl acetate-$H_2O$. The layers were separated, the aqueous layer was back-extracted with ethyl acetate (2x) and the combined organic phases were washed ($H_2O$, brine), dried ($Na_2SO_4$), filtered, and concentrated in vacuo. The residue was purified by silica gel chromatography (Biotage/0-50% diethyl ether-hexane). The resulting pure diastereomeric mixture was then separated by reverse-phase preparative HPLC (Primesphere C-18, 30×100 mm; CH₃CN—H₂O-0.1% TFA) to give first (S)-1-phenethyl (R)-2-(dimethylamino)-2-(2-fluorophenyl)acetate (0.501 g, 13%) and then (S)-1-phenethyl (S)-2-(dimethylamino)-2-(2-fluorophenyl)-acetate (0.727 g. 18%), both as their TFA salts. (S,R)-isomer: ¹HNMR (400 MHz, CD₃OD) δ 7.65-7.70 (m, 1H), 7.55-7.60 (ddd, J=9.4, 8.1, 1.5 Hz, 1H), 7.36-7.41 (m, 2H), 7.28-7.34 (m, 5H), 6.04 (q, J=6.5 Hz, 1H), 5.60 (s, 1H), 2.84 (s, 6H), 1.43 (d, J=6.5 Hz, 3H). LCMS: Anal. Calcd. for $C_{18}H_{20}FNO_2$: 301; found: 302 (M+H)⁺; (S,S)-isomer: ¹HNMR (400 MHz, CD₃OD) δ 7.58-7.63 (m, 1H), 7.18-7.31 (m, 6H), 7.00 (dd, J=8.5, 1.5 Hz, 2H), 6.02 (q, J=6.5 Hz, 1H), 5.60 (s, 1H), 2.88 (s, 6H), 1.54 (d, J=6.5 Hz, 3H). LCMS: Anal. Calcd. for $C_{18}H_{20}FNO_2$: 301; found: 302 (M+H)⁺.

Step 2; (R)-2-(dimethylamino)-2-(2-fluorophenyl)acetic acid: A mixture of (R)—((S)-1-phenylethyl) 2-(dimethylamino)-2-(2-fluorophenyl)acetate TFA salt (1.25 g, 3.01 mmol) and 20% Pd(OH)₂/C (0.125 g) in ethanol (30 mL) was hydrogenated at room temperature and atmospheric pressure (H₂ balloon) for 4 hours. The solution was then purged with Ar, filtered through diatomaceous earth (Celite®), and concentrated in vacuo. This gave the title compound as a colorless solid (0.503 g, 98%). ¹HNMR (400 MHz, CD₃OD) δ 7.53-7.63 (m, 2H), 7.33-7.38 (m, 2H), 5.36 (s, 1H), 2.86 (s, 6H). LCMS: Anal. Calcd. for $C_{10}H_{12}FNO_2$: 197; found: 198 (M+H)⁺.

The S-isomer could be obtained from (S)—((S)-1-phenylethyl) 2-(dimethylamino)-2-(2-fluorophenyl)acetate TFA salt in similar fashion.

Cap-39

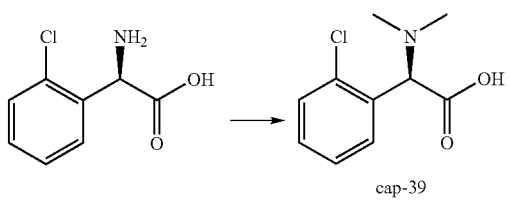

cap-39

A mixture of (R)-(2-chlorophenyl)glycine (0.300 g, 1.62 mmol), formaldehyde (35% aqueous solution, 0.80 mL, 3.23 mmol) and 20% Pd(OH)₂/C (0.050 g) was hydrogenated at room temperature and atmospheric pressure (H₂ balloon) for 4 hours. The solution was then purged with Ar, filtered through diatomaceous earth (Celite®) and concentrated in vacuo. The residue was purified by reverse-phase preparative HPLC (Primesphere C-18, 30×100 mm; CH₃CN—H₂O-0.1% TFA) to give the TFA salt of the title compound (R)-2-(dimethylamino)-2-(2-chlorophenyl)acetic acid as a colorless oil (0.290 g, 55%). ¹H NMR (400 MHz, CD₃OD) δ 7.59-7.65 (m, 2H), 7.45-7.53 (m, 2H), 5.40 (s, 1H), 2.87 (s, 6H). LCMS: Anal. Calcd. for $C_{10}H_{12}ClNO_2$: 213, 215; found: 214, 216 (M+H)⁺.

Cap-40

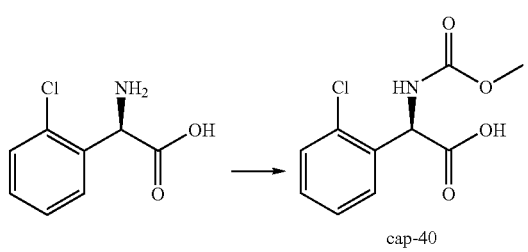

cap-40

To an ice-cold solution of (R)-(2-chlorophenyl)glycine (1.00 g, 5.38 mmol) and NaOH (0.862 g, 21.6 mmol) in H₂O (5.5 mL) was added methyl chloroformate (1.00 mL, 13.5 mmol) dropwise. The mixture was allowed to stir at 0° C. for 1 hour and then it was acidified by the addition of conc. HCl (2.5 mL). The mixture was extracted with ethyl acetate (2×) and the combined organic phase was washed (H₂O, brine), dried (Na₂SO₄), filtered, and concentrated in vacuo to give the title compound (R)-2-(methoxycarbonylamino)-2-(2-chlorophenyl)acetic acid as a yellow-orange foam (1.31 g, 96%). ¹H NMR (400 MHz, CD₃OD) δ 7.39-7.43 (m, 2H), 7.29-7.31 (m, 2H), 5.69 (s, 1H), 3.65 (s, 3H). LCMS: Anal. Calcd. for $C_{10}H_{10}ClNO_4$: 243, 245; found: 244, 246 (M+H)⁺.

Cap-41

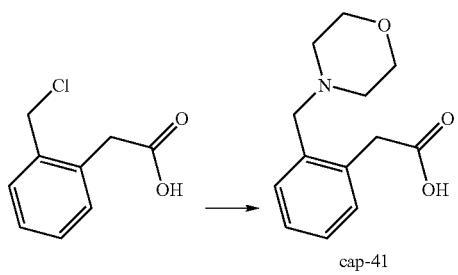

cap-41

To a suspension of 2-(2-(chloromethyl)phenyl)acetic acid (2.00 g, 10.8 mmol) in THF (20 mL) was added morpholine (1.89 g, 21.7 mmol) and the solution was stirred at room temperature for 3 hours. The reaction mixture was then diluted with ethyl acetate and extracted with H₂O (2×). The aqueous phase was lyophilized and the residue was purified by silica gel chromatography (Biotage/0-10% methanol-CH₂Cl₂) to give the title compound 2-(2-(Morpholinomethyl)phenyl)acetic acid as a colorless solid (2.22 g, 87%). ¹HNMR (400 MHz, CD₃OD) δ 7.37-7.44 (m, 3H), 7.29-7.33 (m, 1H), 4.24 (s, 2H), 3.83 (br s, 4H), 3.68 (s, 2H), 3.14 (br s, 4H). LCMS Anal. Calcd. for $C_{13}H_{17}NO_3$: 235; found: 236 (M+H)⁺.

The following caps were similarly prepared using the method described for Cap-41:

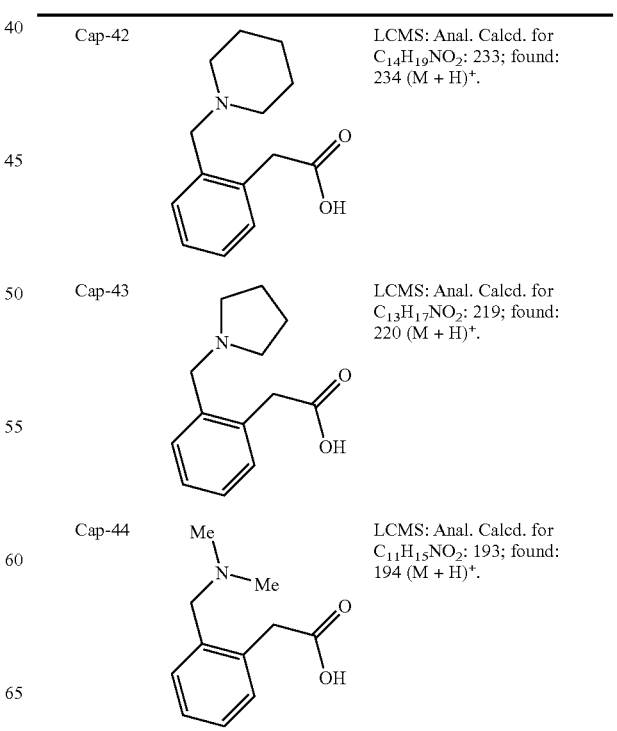

| Cap-42 | LCMS: Anal. Calcd. for $C_{14}H_{19}NO_2$: 233; found: 234 (M + H)⁺. |
| Cap-43 | LCMS: Anal. Calcd. for $C_{13}H_{17}NO_2$: 219; found: 220 (M + H)⁺. |
| Cap-44 | LCMS: Anal. Calcd. for $C_{11}H_{15}NO_2$: 193; found: 194 (M + H)⁺. |

| Cap-45 | 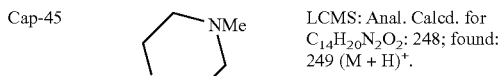 | LCMS: Anal. Calcd. for C₁₄H₂₀N₂O₂: 248; found: 249 (M + H)⁺. |

Cap-45

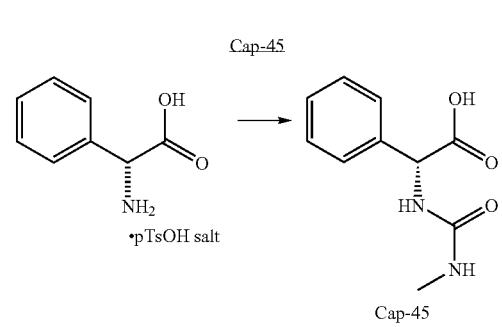

Cap-45

HMDS (1.85 mL, 8.77 mmol) was added to a suspension of (R)-2-amino-2-phenylacetic acid p-toluenesulfonate (2.83 g, 8.77 mmol) in CH₂Cl₂ (10 mL) and the mixture was stirred at room temperature for 30 minutes. Methyl isocyanate (0.5 g, 8.77 mmol) was added in one portion stirring continued for 30 minutes. The reaction was quenched by addition of H₂O (5 mL) and the resulting precipitate was filtered, washed with H₂O and n-hexanes, and dried under vacuum. (R)-2-(3-methylureido)-2-phenylacetic acid (1.5 g; 82%). was recovered as a white solid and it was used without further purification. $^1$H NMR (500 MHz, DMSO-d₆) δ ppm 2.54 (d, J=4.88 Hz, 3H) 5.17 (d, J=7.93 Hz, 1H) 5.95 (q, J=4.48 Hz, 1H) 6.66 (d, J=7.93 Hz, 1H) 7.26-7.38 (m, 5H) 12.67 (s, 1H). LCMS: Anal. Calcd. for C₁₀H₁₂N₂O₃ 208.08 found 209.121 (M+H)⁺; HPLC Phenomenex C-18 3.0×46 mm, 0 to 100% B over 2 minutes, 1 minute hold time, A=90% water, 10% methanol, 0.1% TFA, B=10% water, 90% methanol, 0.1% TFA, RT=1.38 min, 90% homogeneity index.

Cap-46

cap-46

The desired product was prepared according to the method described for Cap-45. $^1$H NMR (500 MHz, DMSO-d₆) δ ppm 0.96 (t, J=7.17 Hz, 3H) 2.94-3.05 (m, 2H) 5.17 (d, J=7.93 Hz, 1H) 6.05 (t, J=5.19 Hz, 1H) 6.60 (d, J=7.63 Hz, 1H) 7.26-7.38 (m, 5H) 12.68 (s, 1H). LCMS: Anal. Calcd. for C₁₁H₁₄N₂O₃ 222.10 found 209.121 (M+H)⁺.

HPLC XTERRA C-18 3.0×506 mm, 0 to 100% B over 2 minutes, 1 minutes hold time, A=90% water, 10% methanol, 0.2% H₃PO₄, B=10% water, 90% methanol, 0.2% H₃PO₄, RT=0.87 min, 90% homogeneity index.

Cap-47

A

B

Cap-47

Step 1; (R)-tert-butyl 2-(3,3-dimethylureido)-2-phenylacetate: To a stirred solution of (R)-tert-butyl-2-amino-2-phenylacetate (1.0 g, 4.10 mmol) and Hunig's base (1.79 mL, 10.25 mmol) in DMF (40 mL) was added dimethylcarbamoyl chloride (0.38 mL, 4.18 mmol) dropwise over 10 minutes. After stirring at room temperature for 3 hours, the reaction was concentrated under reduced pressure and the resulting residue was dissolved in ethyl acetate. The organic layer was washed with H₂O, 1N aq. HCl and brine, dried (MgSO₄), filtered and concentrated under reduced pressure. (R)-tert-butyl 2-(3,3-dimethylureido)-2-phenylacetate was obtained as a white solid (0.86 g; 75%) and used without further purification. $^1$H NMR (500 MHz, DMSO-d₆) δ ppm 1.33 (s, 9H) 2.82 (s, 6H) 5.17 (d, J=7.63 Hz, 1H) 6.55 (d, J=7.32 Hz, 1H) 7.24-7.41 (m, 5H). LCMS: Anal. Calcd. for C₁₅H₂₂N₂O₃ 278.16 found 279.23 (M+H)⁺; HPLC Phenomenex LUNA C-18 4.6×50 mm, 0 to 100% B over 4 minutes, 1 minutes hold time, A=90% water, 10% methanol, 0.1% TFA, B=10% water, 90% methanol, 0.1% TFA, RT=2.26 min, 97% homogeneity index.

Step 2; (R)-2-(3,3-dimethylureido)-2-phenylacetic acid: To a stirred solution of ((R)-tert-butyl 2-(3,3-dimethylureido)-2-phenylacetate (0.86 g, 3.10 mmol) in CH₂Cl₂ (250 mL) was added TFA (15 mL) dropwise and the resulting solution was stirred at rt for 3 h. The desired compound was then precipitated out of solution with a mixture of EtOAC: Hexanes (5:20), filtered off and dried under reduced pressure.

(R)-2-(3,3-dimethylureido)-2-phenylacetic acid was isolated as a white solid (0.59 g, 86%) and used without further purification. $^1$H NMR (500 MHz, DMSO-$d_6$) δ ppm 2.82 (s, 6H) 5.22 (d, J=7.32 Hz, 1H) 6.58 (d, J=7.32 Hz, 1H) 7.28 (t, J=7.17 Hz, 1H) 7.33 (t, J=7.32 Hz, 2H) 7.38-7.43 (m, 2H) 12.65 (s, 1H). LCMS: Anal. Calcd. for $C_{11}H_{14}N_2O_3$: 222.24; found: 223.21 (M+H)$^+$. HPLC XTERRA C-18 3.0×50 mm, 0 to 100% B over 2 minutes, 1 minutes hold time, A=90% water, 10% methanol, 0.2% $H_3PO_4$, B=10% water, 90% methanol, 0.2% $H_3PO_4$, RT=0.75 min, 93% homogeneity index.

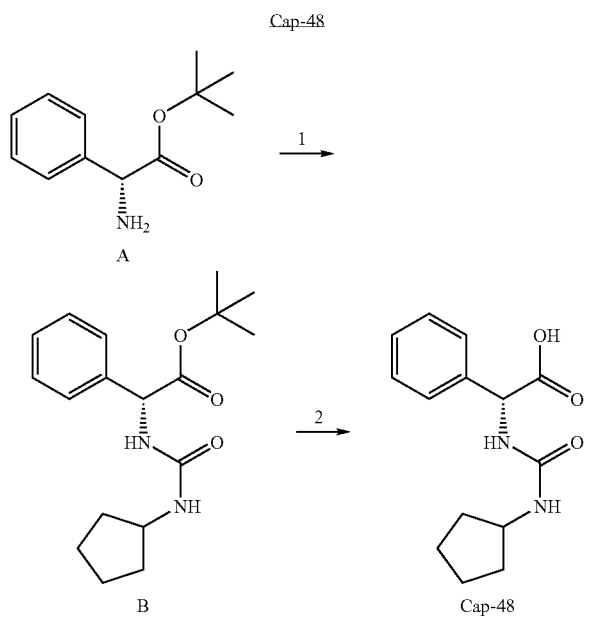

Step 1; (R)-tert-butyl 2-(3-cyclopentylureido)-2-phenylacetate: To a stirred solution of (R)-2-amino-2-phenylacetic acid hydrochloride (1.0 g, 4.10 mmol) and Hunig's base (1.0 mL, 6.15 mmol) in DMF (15 mL) was added cyclopentyl isocyanate (0.46 mL, 4.10 mmol) dropwise and over 10 minutes. After stirring at room temperature for 3 hours, the reaction was concentrated under reduced pressure and the resulting residue was taken up in ethyl acetate. The organic layer was washed with $H_2O$ and brine, dried (MgSO$_4$), filtered, and concentrated under reduced pressure. (R)-tert-butyl 2-(3-cyclopentylureido)-2-phenylacetate was obtained as an opaque oil (1.32 g; 100%) and used without further purification. $^1$H NMR (500 MHz, CD$_3$Cl-D) δ ppm 1.50-1.57 (m, 2H) 1.58-1.66 (m, 2H) 1.87-1.97 (m, 2H) 3.89-3.98 (m, 1H) 5.37 (s, 1H) 7.26-7.38 (m, 5H). LCMS: Anal. Calcd. for $C_{18}H_{26}N_2O_3$ 318.19 found 319.21 (M+H)$^+$; HPLC XTERRA C-18 3.0×50 mm, 0 to 100% B over 4 minutes, 1 minutes hold time, A=90% water, 10% methanol, 0.1% TFA, B=10% water, 90% methanol, 0.1% TFA, RT=2.82 min, 96% homogeneity index.

Step 2; (R)-2-(3-cyclopentylureido)-2-phenylacetic acid: To a stirred solution of (R)-tert-butyl 2-(3-cyclopentylureido)-2-phenylacetate (1.31 g, 4.10 mmol) in CH$_2$Cl$_2$ (25 mL) was added TFA (4 mL) and triethylsilane (1.64 mL; 10.3 mmol) dropwise, and the resulting solution was stirred at room temperature for 6 hours. The volatile components were removed under reduced pressure and the crude product was recrystallized in ethyl acetate/pentanes to yield (R)-2-(3-cyclopentylureido)-2-phenylacetic acid as a white solid (0.69 g, 64%). $^1$H NMR (500 MHz, DMSO-$d_6$) δ ppm 1.17-1.35 (m, 2H) 1.42-1.52 (m, 2H) 1.53-1.64 (m, 2H) 1.67-1.80 (m, 2H) 3.75-3.89 (m, 1H) 5.17 (d, J=7.93 Hz, 1H) 6.12 (d, J=7.32 Hz, 1H) 6.48 (d, J=7.93 Hz, 1H) 7.24-7.40 (m, 5H) 12.73 (s, 1H). LCMS: Anal. Calcd. for $C_{14}H_{18}N_2O_3$: 262.31; found: 263.15 (M+H)$^+$. HPLC XTERRA C-18 3.0×50 mm, 0 to 100% B over 2 minutes, 1 minutes hold time, A=90% water, 10% methanol, 0.2% $H_3PO_4$, B=10% water, 90% methanol, 0.2% $H_3PO_4$, RT=1.24 min, 100% homogeneity index.

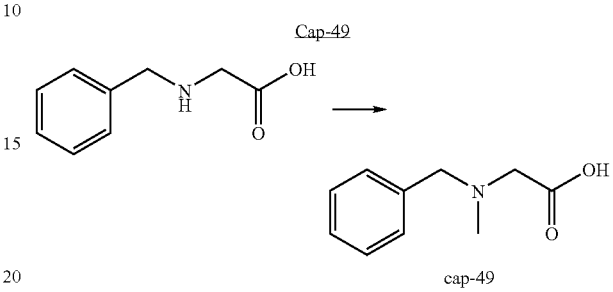

To a stirred solution of 2-(benzylamino)acetic acid (2.0 g, 12.1 mmol) in formic acid (91 mL) was added formaldehyde (6.94 mL, 93.2 mmol). After five hours at 70° C., the reaction mixture was concentrated under reduced pressure to 20 mL and a white solid precipitated. Following filtration, the mother liquors were collected and further concentrated under reduced pressure providing the crude product. Purification by reverse-phase preparative HPLC (Xterra 30×100 mm, detection at 220 nm, flow rate 35 mL/min, 0 to 35% B over 8 min; A=90% water, 10% methanol, 0.1% TFA, B=10% water, 90% methanol, 0.1% TFA) provided the title compound 2-(benzyl(methyl)-amino)acetic acid as its TFA salt (723 mg, 33%) as a colorless wax. $^1$H NMR (300 MHz, DMSO-$d_6$) δ ppm 2.75 (s, 3H) 4.04 (s, 2H) 4.34 (s, 2H) 7.29-7.68 (m, 5H). LCMS: Anal. Calcd. for: $C_{10}H_{13}NO_2$ 179.22;
Found: 180.20 (M+H)$^+$.

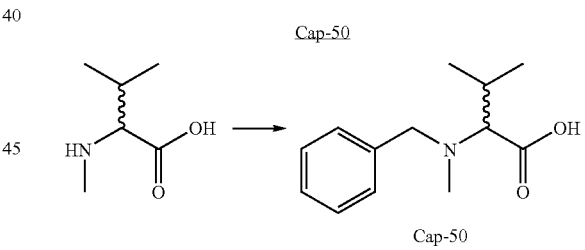

To a stirred solution of 3-methyl-2-(methylamino)butanoic acid (0.50 g, 3.81 mmol) in water (30 mL) was added K$_2$CO$_3$ (2.63 g, 19.1 mmol) and benzyl chloride (1.32 g, 11.4 mmol). The reaction mixture was stirred at ambient temperature for 18 hours. The reaction mixture was extracted with ethyl acetate (30 mL×2) and the aqueous layer was concentrated under reduced pressure providing the crude product which was purified by reverse-phase preparative HPLC (Xterra 30×100 mm, detection at 220 nm, flow rate 40 mL/min, 20 to 80% B over 6 min; A=90% water, 10% methanol, 0.1% TFA, B=10% water, 90% methanol, 0.1% TFA) to provide 2-(benzyl(methyl)amino)-3-methylbutanoic acid, TFA salt (126 mg, 19%) as a colorless wax. $^1$H NMR (500 MHz, DMSO-$d_6$) δ ppm 0.98 (d, 3H) 1.07 (d, 3H) 2.33-2.48 (m, 1H) 2.54-2.78 (m, 3H) 3.69 (s, 1H) 4.24 (s, 2H) 7.29-7.65 (m, 5H). LCMS: Anal. Calcd. for: $C_{13}H_{19}NO_2$ 221.30; Found: 222.28 (M+H)$^+$.

Cap-51

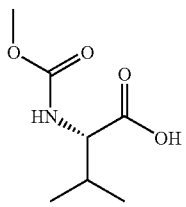

Na$_2$CO$_3$ (1.83 g, 17.2 mmol) was added to NaOH (33 mL of 1M/H$_2$O, 33 mmol) solution of L-valine (3.9 g, 33.29 mmol) and the resulting solution was cooled with ice-water bath. Methyl chloroformate (2.8 mL, 36.1 mmol) was added drop-wise over 15 min, the cooling bath was removed and the reaction mixture was stirred at ambient temperature for 3.25 hr. The reaction mixture was washed with ether (50 mL, 3×), and the aqueous phase was cooled with ice-water bath and acidified with concentrated HCl to a pH region of 1-2, and extracted with CH$_2$Cl$_2$ (50 mL, 3×). The organic phase was dried (MgSO$_4$), filtered, and concentrated in vacuo to afford Cap-51 as a white solid (6 g). $^1$H NMR for the dominant rotamer (DMSO-d$_6$, δ=2.5 ppm, 500 MHz): 12.54 (s, 1H), 7.33 (d, J=8.6, 1H), 3.84 (dd, J=8.4, 6.0, 1H), 3.54 (s, 3H), 2.03 (m, 1H), 0.87 (m, 6H). HRMS: Anal. Calcd. for [M+H]$^+$ C$_7$H$_{14}$NO$_4$: 176.0923; found 176.0922

Cap-52

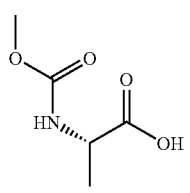

Cap-52 was synthesized from L-alanine according to the procedure described for the synthesis of Cap-51. For characterization purposes, a portion of the crude material was purified by a reverse phase HPLC (H$_2$O/MeOH/TFA) to afford Cap-52 as a colorless viscous oil. $^1$H NMR (DMSO-d$_6$, δ=2.5 ppm, 500 MHz): 12.49 (br s, 1H), 7.43 (d, J=7.3, 0.88H), 7.09 (app br s, 0.12H), 3.97 (m, 1H), 3.53 (s, 3H), 1.25 (d, J=7.3, 3H).

Cap-53 to -64 were prepared from appropriate starting materials according to the procedure described for the synthesis of Cap-51, with noted modifications if any.

| Cap | Structure | Data |
|---|---|---|
| Cap-53a: (R) Cap-53b: (S) | ![structure] | $^1$H NMR (DMSO-d$_6$, δ = 2.5 ppm, 500 MHz): δ 12.51 (br s, 1 H), 7.4 (d, J = 7.9, 0.9 H), 7.06 (app s, 0.1 H), 3.86-3.82 (m, 1 H), 3.53 (s, 3 H), 1.75-1.67 (m, 1 H), 1.62-1.54 (m, 1 H), 0.88 (d, J = 7.3, 3 H). RT = 0.77 minutes (Cond. 2); LC/MS: Anal. Calcd. for [M + Na]$^+$ C$_6$H$_{11}$NNaO$_4$: 184.06; found 184.07. HRMS Calcd. for [M + Na]$^+$ C$_6$H$_{11}$NNaO$_4$: 184.0586; found 184.0592. |
| Cap-54a: (R) Cap-54b: (S) | ![structure] | $^1$H NMR (DMSO-d$_6$, δ = 2.5 ppm, 500 MHz): δ 12.48 (s, 1 H), 7.58 (d, J = 7.6, 0.9 H), 7.25 (app s, 0.1 H), 3.52 (s, 3 H), 3.36-3.33 (m, 1 H), 1.10-1.01 (m, 1 H), 0.54-0.49 (m, 1 H), 0.46-0.40 (m, 1 H), 0.39-0.35 (m, 1 H), 0.31-0.21 (m, 1 H). HRMS Calcd. for [M + H]$^+$ C$_7$H$_{12}$NO$_4$: 174.0766; found 174.0771 |
| Cap-55 | ![structure] | $^1$H NMR (DMSO-d$_6$, δ 2.5 ppm, 500 MHz): δ 12.62 (s, 1 H), 7.42 (d, J = 8.2, 0.9 H), 7.07 (app s, 0.1 H), 5.80-5.72 (m, 1 H), 5.10 (d, J = 17.1, 1 H), 5.04 (d, J = 10.4, 1 H), 4.01-3.96 (m, 1 H), 3.53 (s, 3 H), 2.47-2.42 (m, 1 H), 2.35-2.29 (m, 1 H). |
| Cap-56 | ![structure] | $^1$H NMR (DMSO-d$_6$, δ = 2.5 ppm, 500 MHz): δ 12.75 (s, 1 H), 7.38 (d, J = 8.3, 0.9 H), 6.96 (app s, 0.1 H), 4.20-4.16 (m, 1 H), 3.60-3.55 (m, 2 H), 3.54 (s, 3 H), 3.24 (s, 3 H). |

| Cap | Structure | Data |
|---|---|---|
| Cap-57 | 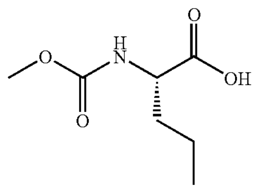 | $^1$H NMR (DMSO-d$_6$, δ = 2.5 ppm, 500 MHz): δ 12.50 (s, 1 H), 8.02 (d, J = 7.7, 0.08 H), 7.40 (d, J = 7.9, 0.76 H), 7.19 (d, J = 8.2, 0.07 H), 7.07 (d, J = 6.7, 0.09 H), 4.21-4.12 (m, 0.08 H), 4.06-3.97 (m, 0.07 H), 3.96-3.80 (m, 0.85 H), 3.53 (s, 3 H), 1.69-1.51 (m, 2 H), 1.39-1.26 (m, 2 H), 0.85 (t, J = 7.4, 3 H). LC (Cond. 2): RT = 1.39 LC/MS: Anal. Calcd. for [M + H]$^+$ C$_7$H$_{14}$NO$_4$: 176.09; found 176.06. |
| Cap-58 | 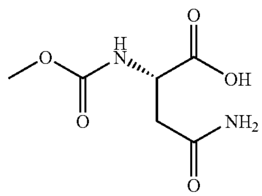 | $^1$H NMR (DMSO-d$_6$, δ = 2.5 ppm, 500 MHz): δ 12.63 (bs, 1 H), 7.35 (s, 1 H), 7.31 (d, J = 8.2, 1 H), 6.92 (s, 1 H), 4.33-4.29 (m, 1 H), 3.54 (s, 3 H), 2.54 (dd, J = 15.5, 5.4, 1 H), 2.43 (dd, J = 15.6, 8.0, 1 H). RT = 0.16 min (Cond. 2); LC/MS: Anal. Calcd. for [M + H]$^+$ C$_6$H$_{11}$N$_2$O$_5$: 191.07; found 191.14. |
| Cap-59a: (R) Cap-59b: (S) | | $^1$H NMR (DMSO-d$_6$, δ = 2.5 ppm, 400 MHz): δ 12.49 (br s, 1 H), 7.40 (d, J = 7.3, 0.89 H), 7.04 (br s, 0.11 H), 4.00-3.95 (m, 3 H), 1.24 (d, J = 7.3, 3 H), 1.15 (t, J = 7.2, 3 H). HRMS: Anal. Calcd. for [M + H]$^+$ C$_6$H$_{12}$NO$_4$: 162.0766; found 162.0771. |
| Cap-60 | 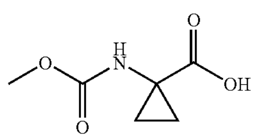 | The crude material was purified with a reverse phase HPLC (H$_2$O/MeOH/TFA) to afford a colorless viscous oil that crystallized to a white solid upon exposure to high vacuum. $^1$H NMR (DMSO-d$_6$, δ = 2.5 ppm, 400 MHz): δ 12.38 (br s, 1 H), 7.74 (s, 0.82 H), 7.48 (s, 0.18 H), 3.54/3.51 (two s, 3 H), 1.30 (m, 2 H), 0.98 (m, 2 H). HRMS: Anal. Calcd. for [M + H]$^+$ C$_6$H$_{10}$NO$_4$: 160.0610; found 160.0604. |
| Cap-61 | 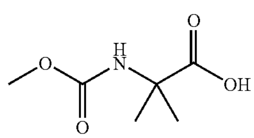 | $^1$H NMR (DMSO-d$_6$, δ = 2.5 ppm, 400 MHz): δ 12.27 (br s, 1 H), 7.40 (br s, 1 H), 3.50 (s, 3 H), 1.32 (s, 6 H). HRMS: Anal. Calcd. for [M + H]$^+$ C$_6$H$_{12}$NO$_4$: 162.0766; found 16.0765. |
| Cap-62 | 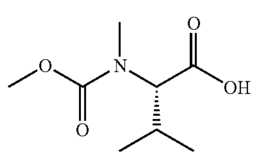 | $^1$H NMR (DMSO-d$_6$, δ = 2.5 ppm, 400 MHz); δ 12.74 (br s, 1 H), 4.21 (d, J = 10.3, 0.6 H), 4.05 (d, J = 10.0, 0.4 H), 3.62/3.60 (two singlets, 3 H), 3.0 (s, 3 H), 2.14-2.05 (m, 1 H), 0.95 (d, J = 6.3, 3 H), 0.81 (d, J = 6.6, 3 H). LC/MS: Anal. Calcd. for [M − H]$^-$ C$_8$H$_{14}$NO$_4$: 188.09; found 188.05. |
| Cap-63 | 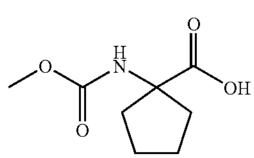 | [Note: the reaction was allowed to run for longer than what was noted for the general procedure.] $^1$H NMR (DMSO-d$_6$, δ = 2.5 ppm, 400 MHz): 12.21 (br s, 1 H), 7.42 (br s, 1 H), 3.50 (s, 3 H), 2.02-1.85 (m, 4 H), 1.66-1.58 (m, 4 H). LC/MS: Anal. Calcd. for [M + H]$^+$ C$_8$H$_{14}$NO$_4$: 188.09; found 188.19. |
| Cap-64 | 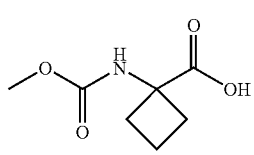 | [Note: the reaction was allowed to run for longer than what was noted for the general procedure.] $^1$H NMR (DMSO-d$_6$, δ = 2.5 ppm, 400 MHz): 12.35 (br s, 1 H), 7.77 (s, 0.82 H), 7.56/7.52 (overlapping br s, 0.18 H), 3.50 (s, 3 H), 2.47-2.40 (m, 2 H), 2.14-2.07 (m, 2 H), 1.93-1.82 (m, 2 H). |

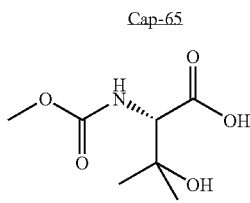

Cap-65

Methyl chloroformate (0.65 mL, 8.39 mmol) was added dropwise over 5 min to a cooled (ice-water) mixture of $Na_2CO_3$ (0.449 g, 4.23 mmol), NaOH (8.2 mL of $1M/H_2O$, 8.2 mmol) and (S)-3-hydroxy-2-(methoxycarbonylamino)-3-methylbutanoic acid (1.04 g, 7.81 mmol). The reaction mixture was stirred for 45 min, and then the cooling bath was removed and stirring was continued for an additional 3.75 hr. The reaction mixture was washed with $CH_2Cl_2$, and the aqueous phase was cooled with ice-water bath and acidified with concentrated HCl to a pH region of 1-2. The volatile component was removed in vacuo and the residue was taken up in a 2:1 mixture of $MeOH/CH_2Cl_2$ (15 mL) and filtered, and the filterate was rotervaped to afford Cap-65 as a white semi-viscous foam (1.236 g). $^1H$ NMR (DMSO-$d_6$, δ=2.5 ppm, 400 MHz): δ 6.94 (d, J=8.5, 0.9H), 6.53 (br s, 0.1H), 3.89 (d, J=8.8, 1H), 2.94 (s, 3H), 1.15 (s, 3H), 1.13 (s, 3H).

Cap-66 and -67 were prepared from appropriate commercially available starting materials by employing the procedure described for the synthesis of Cap-65.

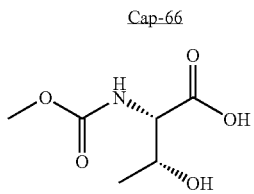

Cap-66

$^1H$ NMR (DMSO-$d_6$, δ=2.5 ppm, 400 MHz): δ 12.58 (br s, 1H), 7.07 (d, J=8.3, 0.13H), 6.81 (d, J=8.8, 0.67H), 4.10-4.02 (m, 1.15H), 3.91 (dd, J=9.1, 3.5, 0.85H), 3.56 (s, 3H), 1.09 (d, J=6.2, 3H). [Note: only the dominant signals of NH were noted]

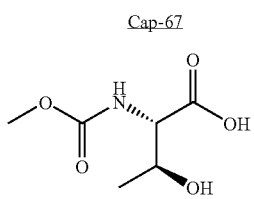

Cap-67

$^1H$ NMR (DMSO-$d_6$, δ=2.5 ppm, 400 MHz): 12.51 (br s, 1H), 7.25 (d, J=8.4, 0.75H), 7.12 (br d, J=0.4, 0.05H), 6.86 (br s, 0.08H), 3.95-3.85 (m, 2H), 3.54 (s, 3H), 1.08 (d, J=6.3, 3H). [Note: only the dominant signals of NH were noted]

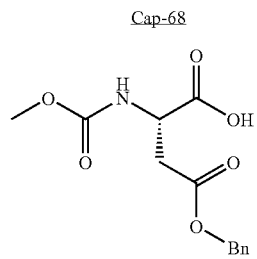

Cap-68

Methyl chloroformate (0.38 ml, 4.9 mmol) was added drop-wise to a mixture of 1N NaOH (aq) (9.0 ml, 9.0 mmol), 1M $NaHCO_3$ (aq) (9.0 ml, 9.0 mol), L-aspartic acid β-benzyl ester (1.0 g, 4.5 mmol) and Dioxane (9 ml). The reaction mixture was stirred at ambient conditions for 3 hr, and then washed with Ethyl acetate (50 ml, 3×). The aqueous layer was acidified with 12N HCl to a pH ~1-2, and extracted with ethyl acetate (3×50 ml). The combined organic layers were washed with brine, dried ($Na_2SO_4$), filtered, and concentrated in vacuo to afford Cap-68 as a light yellow oil (1.37 g; mass is above theoretical yield, and the product was used without further purification). $^1H$ NMR (DMSO-$d_6$, δ=2.5 ppm, 500 MHz): δ 12.88 (br s, 1H), 7.55 (d, J=8.5, 1H), 7.40-7.32 (m, 5H), 5.13 (d, J=12.8, 1H), 5.10 (d, J=12.9, 1H), 4.42-4.38 (m, 1H), 3.55 (s, 3H), 2.87 (dd, J=16.2, 5.5, 1H), 2.71 (dd, J=16.2, 8.3, 1H). LC (Cond. 2): RT=1.90 min; LC/MS: Anal. Calcd. For $[M+H]^+$ $C_{13}H_{16}NO_6$: 282.10; found 282.12.

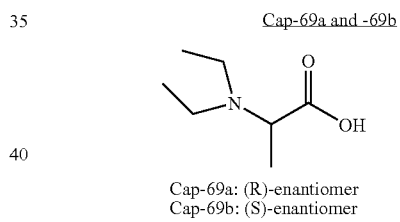

Cap-69a and -69b

Cap-69a: (R)-enantiomer
Cap-69b: (S)-enantiomer $NaCNBH_3$ (2.416 g, 36.5 mmol) was added in batches to a chilled (~15° C.) water (17 mL)/MeOH (10 mL) solution of alanine (1.338 g, 15.0 mmol). A few minutes later acetaldehyde (4.0 mL, 71.3 mmol) was added drop-wise over 4 min, the cooling bath was removed, and the reaction mixture was stirred at ambient condition for 6 hr. An additional acetaldehyde (4.0 mL) was added and the reaction was stirred for 2 hr. Concentrated HCl was added slowly to the reaction mixture until the pH reached ~1.5, and the resulting mixture was heated for 1 hr at 40° C. Most of the volatile component was removed in vacuo and the residue was purified with a Dowex® 50WX8-100 ion-exchange resin (column was washed with water, and the compound was eluted with dilute $NH_4OH$, prepared by mixing 18 ml of $NH_4OH$ and 282 ml of water) to afford Cap-69 (2.0 g) as an off-white soft hygroscopic solid. $^1H$ NMR (DMSO-$d_6$, δ=2.5 ppm, 400 MHz): δ 3.44 (q, J=7.1, 1H), 2.99-2.90 (m, 2H), 2.89-2.80 (m, 2H), 1.23 (d, J=7.1, 3H), 1.13 (t, J=7.3, 6H).

Cap-70 to -74x were prepared according to the procedure described for the synthesis of Cap-69 by employing appropriate starting materials.

| | | |
|---|---|---|
| Cap-70a: (R)<br>Cap-70b: (S) | 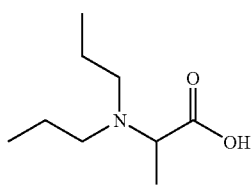 | $^1$H NMR (DMSO-$d_6$, δ = 2.5 ppm, 400 MHz):<br>δ 3.42 (q, J = 7.1, 1 H), 2.68-2.60 (m, 4 H),<br>1.53-1.44 (m, 4 H), 1.19 (d, J = 7.3, 3 H), 0.85<br>(t, J = 7.5, 6 H). LC/MS: Anal. Calcd. for<br>[M + H]$^+$ C$_9$H$_{20}$NO$_2$: 174.15; found 174.13. |
| Cap-71a: (R)<br>Cap-71b: (S) | 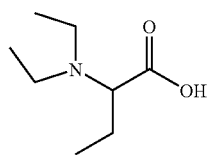 | $^1$H NMR (DMSO-$d_6$, δ = 2.5 ppm, 500 MHz):<br>δ 3.18-3.14 (m, 1 H), 2.84-2.77 (m, 2 H), 2.76-<br>2.68 (m, 2 H), 1.69-1.54 (m, 2 H), 1.05 (t, J =<br>7.2, 6 H), 0.91 (t, J = 7.3, 3 H). LC/MS: Anal.<br>Calcd. for [M + H]$^+$ C$_8$H$_{18}$NO$_2$: 160.13; found<br>160.06. |
| Cap-72 | 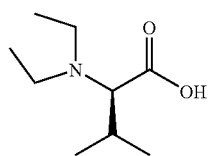 | $^1$H NMR (DMSO-$d_6$, δ = 2.5 ppm, 400 MHz):<br>δ 2.77-2.66 (m, 3 H), 2.39-2.31 (m, 2 H), 1.94-<br>1.85 (m, 1 H), 0.98 (t, J = 7.1, 6 H), 0.91 (d, J =<br>6.5, 3 H), 0.85 (d, J = 6.5, 3 H).<br>LC/MS: Anal. Calcd. for<br>[M + H]$^+$ C$_9$H$_{20}$NO$_2$: 174.15; found 174.15. |
| Cap-73 | 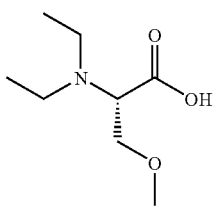 | $^1$H NMR (DMSO-$d_6$, δ = 2.5 ppm, 500 MHz):<br>δ 9.5 (br s, 1 H), 3.77 (dd, J = 10.8, 4.1, 1 H),<br>3.69-3.61 (m, 2 H), 3.26 (s, 3 H), 2.99-2.88 (m,<br>4 H), 1.13 (t, J = 7.2, 6 H). |
| Cap-74 | 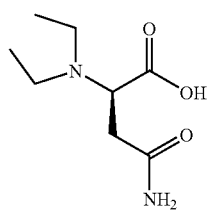 | $^1$H NMR (DMSO-$d_6$, δ = 2.5 ppm, 500 MHz):<br>δ 7.54 (s, 1 H), 6.89 (s, 1 H), 3.81 (t, J = 6.6,<br>k, 1 H), 2.82-2.71 (m, 4 H), 2.63 (dd, J = 15.6,<br>7.0, 1 H), 2.36 (dd, J = 15.4, 6.3, 1 H), 1.09 (t,<br>J = 7.2, 6 H). RT = 0.125 minutes (Cond. 2);<br>LC/MS: Anal. Calcd. for [M + H]$^+$ C$_8$H$_{17}$N$_2$O$_3$:<br>189.12; found 189.13. |
| Cap-74x | 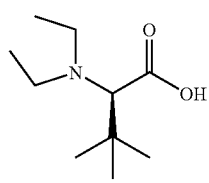 | LC/MS: Anal. Calcd. for [M + H]$^+$ C$_{10}$H$_{22}$NO$_2$:<br>188.17; found 188.21 |

| | |
|---|---|
| Cap-75<br>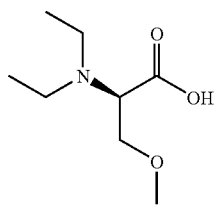<br><br>Cap-75, step a<br>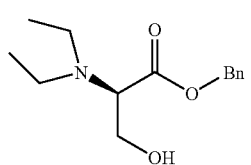 | NaBH$_3$CN (1.6 g, 25.5 mmol) was added to a cooled (ice/water bath) water (25 ml)/methanol (15 ml) solution of H-D-Ser-OBzl HCl (2.0 g, 8.6 mmol). Acetaldehyde (1.5 ml, 12.5 mmol) was added drop-wise over 5 min, the cooling bath was removed, and the reaction mixture was stirred at ambient condition for 2 hr. The reaction was carefully quenched with 12N HCl and concentrated in vacuo. The residue was dissolved in water and purified with a reverse phase HPLC (MeOH/H$_2$O/TFA) to afford the TFA salt of (R)-benzyl 2-(diethylamino)-3-hydroxypropanoate as a colorless viscous oil (1.9 g). $^1$H NMR (DMSO-$d_6$, δ=2.5 ppm, 500 MHz): δ 9.73 (br s, 1H), 7.52-7.36 (m, 5H), 5.32 (d, J=12.2, 1H), 5.27 (d, J=12.5, 1H), 4.54-4.32 (m, 1H), 4.05-3.97 (m, 2H), 3.43-3.21 (m, 4H), 1.23 (t, J=7.2, 6H). LC/MS (Cond. 2): RT=1.38 min; LC/MS: Anal. Calcd. for [M+H]$^+$ C$_{14}$H$_{22}$NO$_3$: 252.16; found 252.19. |

Cap-75

NaH (0.0727 g, 1.82 mmol, 60%) was added to a cooled (ice-water) THF (3.0 mL) solution of the TFA salt (R)-benzyl 2-(diethylamino)-3-hydroxypropanoate (0.3019 g, 0.8264 mmol) prepared above, and the mixture was stirred for 15 min. Methyl iodide (56 μL, 0.90 mmol) was added and stirring was continued for 18 hr while allowing the bath to thaw to ambient condition. The reaction was quenched with water and loaded onto a MeOH pre-conditioned MCX (6 g) cartridge, and washed with methanol followed by compound elution with 2N $NH_3$/Methanol. Removal of the volatile component in vacuo afforded Cap-75, contaminated with (R)-2-(diethylamino)-3-hydroxypropanoic acid, as a yellow semi-solid (100 mg). The product was used as is without further purification.

Cap-76

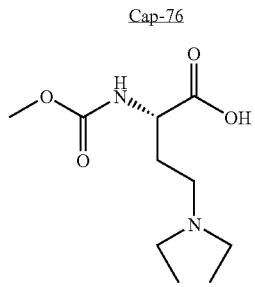

$NaCNBH_3$ (1.60 g, 24.2 mmol) was added in batches to a chilled (~15° C.) water/MeOH (12 mL each) solution of (S)-4-amino-2-(tert-butoxycarbonylamino)butanoic acid (2.17 g, 9.94 mmol). A few minutes later acetaldehyde (2.7 mL, 48.1 mmol) was added drop-wise over 2 min, the cooling bath was removed, and the reaction mixture was stirred at ambient condition for 3.5 hr. An additional acetaldehyde (2.7 mL, 48.1 mmol) was added and the reaction was stirred for 20.5 hr. Most of the MeOH component was removed in vacuo, and the remaining mixture was treated with concentrated HCl until its pH reached ~1.0 and then heated for 2 hr at 40° C. The volatile component was removed in vacuo, and the residue was treated with 4 M HCl/dioxane (20 mL) and stirred at ambient condition for 7.5 hr. The volatile component was removed in vacuo and the residue was purified with Dowex® 50WX8-100 ion-exchange resin (column was washed with water and the compound was eluted with dilute $NH_4OH$, prepared from 18 ml of $NH_4OH$ and 282 ml of water) to afford intermediate (S)-2-amino-4-(diethylamino) butanoic acid as an off-white solid (1.73 g).

Methyl chloroformate (0.36 mL, 4.65 mmol) was added drop-wise over 11 min to a cooled (ice-water) mixture of $Na_2CO_3$ (0.243 g, 2.29 mmol), NaOH (4.6 mL of 1M/$H_2O$, 4.6 mmol) and the above product (802.4 mg). The reaction mixture was stirred for 55 min, and then the cooling bath was removed and stirring was continued for an additional 5.25 hr. The reaction mixture was diluted with equal volume of water and washed with $CH_2Cl_2$ (30 mL, 2×), and the aqueous phase was cooled with ice-water bath and acidified with concentrated HCl to a pH region of 2. The volatile component was then removed in vacuo and the crude material was free-based with MCX resin (6.0 g; column was washed with water, and sample was eluted with 2.0 M $NH_3$/MeOH) to afford impure Cap-76 as an off-white solid (704 mg). $^1$H NMR (MeOH-$d_4$, δ=3.29 ppm, 400 MHz): δ 3.99 (dd, J=7.5, 4.7, 1H), 3.62 (s, 3H), 3.25-3.06 (m, 6H), 2.18-2.09 (m, 1H), 2.04-1.96 (m, 1H), 1.28 (t, J=7.3, 6H). LC/MS: Anal. Calcd. for [M+H]$^+$ $C_{10}H_{21}N_2O_4$: 233.15; found 233.24.

Cap-77a and -77b

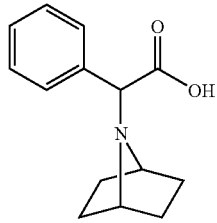

Cap-77a: enantiomer-1
Cap-77b: enantiomer-2

The synthesis of Cap-77 was conducted according to the procedure described for Cap-7 by using 7-azabicyclo[2.2.1] heptane for the $SN_2$ displacement step, and by effecting the enantiomeric separation of the intermediate benzyl 2-(7-azabicyclo[2.2.1]heptan-7-yl)-2-phenylacetate using the following condition: the intermediate (303.7 mg) was dissolved in ethanol, and the resulting solution was injected on a chiral HPLC column (Chiracel AD-H column, 30×250 mm, 5 um) eluting with 90% $CO_2$-10% EtOH at 70 mL/min, and a temperature of 35° C. to provide 124.5 mg of enantiomer-1 and 133.8 mg of enantiomer-2. These benzyl esters were hydrogenolysed according to the preparation of Cap-7 to provide Cap-77: $^1$H NMR (DMSO-$d_6$, δ=2.5 ppm, 400 MHz): δ 7.55 (m, 2H), 7.38-7.30 (m, 3H), 4.16 (s, 1H), 3.54 (app br s, 2H), 2.08-1.88 (m, 4H), 1.57-1.46 (m, 4H). LC (Cond. 1): RT=0.67 min; LC/MS: Anal. Calcd. for [M+H]$^+$ $C_{14}H_{18}BrNO_2$: 232.13; found 232.18. HRMS: Anal. Calcd. for [M+H]$^+$ $C_{14}H_{18}BrNO_2$: 232.1338; found 232.1340.

Cap-78

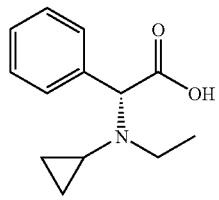

$NaCNBH_3$ (0.5828 g, 9.27 mmol) was added to a mixture of the HCl salt of (R)-2-(ethylamino)-2-phenylacetic acid (an intermediate in the synthesis of Cap-3; 0.9923 mg, 4.60 mmol) and (1-ethoxycyclopropoxy)trimethylsilane (1.640 g, 9.40 mmol) in MeOH (10 mL), and the semi-heterogeneous mixture was heated at 50° C. with an oil bath for 20 hr. More (1-ethoxycyclopropoxy)trimethylsilane (150 mg, 0.86 mmol) and $NaCNBH_3$ (52 mg, 0.827 mmol) were added and the reaction mixture was heated for an additional 3.5 hr. It was then allowed to cool to ambient temperature and acidified to a ~pH region of 2 with concentrated HCl, and the mixture was filtered and the filtrate was rotervaped. The resulting crude material was taken up in i-PrOH (6 mL) and heated to effect dissolution, and the non-dissolved part was filtered off and the filtrate concentrated in vacuo. About ⅓ of the resultant crude material was purified with a reverse phase HPLC ($H_2O$/MeOH/TFA) to afford the TFA salt of Cap-78 as a colorless viscous oil (353 mg). $^1$H NMR (DMSO-$d_6$, δ=2.5 ppm, 400 MHz; after $D_2O$ exchange): δ 7.56-7.49 (m, 5H), 5.35 (S, 1H), 3.35 (m, 1H), 3.06 (app br s, 1H), 2.66 (m, 1H), 1.26 (t, J=7.3, 3H), 0.92 (m, 1H), 0.83-0.44 (m, 3H). LC (Cond. 1): RT=0.64 min; LC/MS: Anal. Calcd. for [M+H]$^+$ C$_{13}$H$_{18}$NO$_2$: 220.13; found 220.21. HRMS: Anal. Calcd. for [M+H]$^+$ C$_{13}$H$_{18}$NO$_2$: 220.1338; found 220.1343.

Cap-79

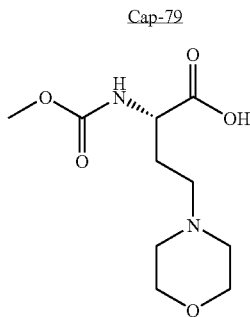

Ozone was bubbled through a cooled (−78° C.) CH$_2$Cl$_2$ (5.0 mL) solution Cap-55 (369 mg, 2.13 mmol) for about 50 min until the reaction mixture attained a tint of blue color. Me$_2$S (10 pipet drops) was added, and the reaction mixture was stirred for 35 min. The −78° C. bath was replaced with a −10° C. bath and stirring continued for an additional 30 min, and then the volatile component was removed in vacuo to afford a colorless viscous oil.

NaBH$_3$CN (149 mg, 2.25 mmol) was added to a MeOH (5.0 mL) solution of the above crude material and morpholine (500 μL, 5.72 mmol) and the mixture was stirred at ambient condition for 4 hr. It was cooled to ice-water temperature and treated with concentrated HCl to bring its pH to ~2.0, and then stirred for 2.5 hr. The volatile component was removed in vacuo, and the residue was purified with a combination of MCX resin (MeOH wash; 2.0 N NH$_3$/MeOH elution) and a reverse phase HPLC (H$_2$O/MeOH/TFA) to afford Cap-79 containing unknown amount of morpholine.

In order to consume the morpholine contaminant, the above material was dissolved in CH$_2$Cl$_2$ (1.5 mL) and treated with Et$_3$N (0.27 mL, 1.94 mmol) followed by acetic anhydride (0.10 mL, 1.06 mmol) and stirred at ambient condition for 18 hr. THF (1.0 mL) and H$_2$O (0.5 mL) were added and stirring continued for 1.5 hr. The volatile component was removed in vacuo, and the resultant residue was passed through MCX resin (MeOH wash; 2.0 N NH$_3$/MeOH elution) to afford impure Cap-79 as a brown viscous oil, which was used for the next step without further purification.

Cap-80a and -80b

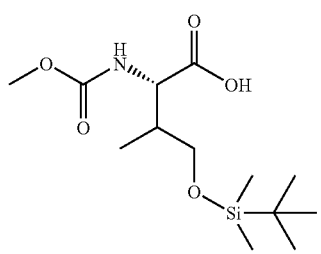

Cap-80a: S/S-diastereomer
Cap-80b: S/R-diastereomer

SOCl$_2$ (6.60 mL, 90.5 mmol) was added drop-wise over 15 min to a cooled (ice-water) mixture of (S)-3-amino-4-(benzyloxy)-4-oxobutanoic acid (10.04 g, 44.98 mmol) and MeOH (300 mL), the cooling bath was removed and the reaction mixture was stirred at ambient condition for 29 hr. Most of the volatile component was removed in vacuo and the residue was carefully partitioned between EtOAc (150 mL) and saturated NaHCO$_3$ solution. The aqueous phase was extracted with EtOAc (150 mL, 2×), and the combined organic phase was dried (MgSO$_4$), filtered, and concentrated in vacuo to afford (S)-1-benzyl 4-methyl 2-aminosuccinate as a colorless oil (9.706 g). $^1$H NMR (DMSO-d$_6$, δ=2.5 ppm, 400 MHz): δ 7.40-7.32 (m, 5H), 5.11 (s, 2H), 3.72 (app t, J=6.6, 1H), 3.55 (s, 3H), 2.68 (dd, J=15.9, 6.3, 1H), 2.58 (dd, J=15.9, 6.8, 1H), 1.96 (s, 2H). LC (Cond. 1): RT=0.90 min; LC/MS: Anal. Calcd. for [M+H]$^+$ C$_{12}$H$_{16}$NO$_4$: 238.11; found 238.22.

Pb(NO$_3$)$_2$ (6.06 g, 18.3 mmol) was added over 1 min to a CH$_2$Cl$_2$ (80 mL) solution of (S)-1-benzyl 4-methyl 2-aminosuccinate (4.50 g, 19.0 mmol), 9-bromo-9-phenyl-9H-fluorene (6.44 g, 20.0 mmol) and Et$_3$N (3.0 mL, 21.5 mmol), and the heterogeneous mixture was stirred at ambient condition for 48 hr. The mixture was filtered and the filtrate was treated with MgSO$_4$ and filtered again, and the final filtrate was concentrated. The resulting crude material was submitted to a Biotage purification (350 g silica gel, CH$_2$Cl$_2$ elution) to afford (S)-1-benzyl 4-methyl 2-(9-phenyl-9H-fluoren-9-ylamino)succinate as highly viscous colorless oil (7.93 g). $^1$H NMR (DMSO-d$_6$, δ=2.5 ppm, 400 MHz): δ 7.82 (m, 2H), 7.39-7.13 (m, 16H), 4.71 (d, J=12.4, 1H), 4.51 (d, J=12.6, 1H), 3.78 (d, J=9.1, NH), 3.50 (s, 3H), 2.99 (m, 1H), 2.50-2.41 (m, 2H, partially overlapped with solvent). LC (Cond. 1): RT=2.16 min; LC/MS: Anal. Calcd. for [M+H]$^+$ C$_{31}$H$_{28}$NO$_4$: 478.20; found 478.19.

LiHMDS (9.2 mL of 1.0 M/THF, 9.2 mmol) was added drop-wise over 10 min to a cooled (−78° C.) THF (50 mL) solution of (S)-1-benzyl 4-methyl 2-(9-phenyl-9H-fluoren-9-ylamino)succinate (3.907 g, 8.18 mmol) and stirred for ~1 hr. MeI (0.57 mL, 9.2 mmol) was added drop-wise over 8 min to the mixture, and stirring was continued for 16.5 hr while allowing the cooling bath to thaw to room temperature. After quenching with saturated NH$_4$Cl solution (5 mL), most of the organic component was removed in vacuo and the residue was partitioned between CH$_2$Cl$_2$ (100 mL) and water (40 mL). The organic layer was dried (MgSO$_4$), filtered, and concentrated in vacuo, and the resulting crude material was purified with a Biotage (350 g silica gel; 25% EtOAc/hexanes) to afford 3.65 g of a 2S/3S and 2S/3R diastereomeric mixtures of 1-benzyl 4-methyl 3-methyl-2-(9-phenyl-9H-fluoren-9-ylamino)succinate in ~1.0:0.65 ratio ($^1$H NMR). The stereochemistry of the dominant isomer was not determined at this juncture, and the mixture was submitted to the next step without separation. Partial $^1$H NMR data (DMSO-d$_6$, δ=2.5 ppm, 400 MHz): major diastereomer, δ 4.39 (d, J=12.3, 1H of CH$_2$), 3.33 (s, 3H, overlapped with H$_2$O signal), 3.50 (d, J=10.9, NH), 1.13 (d, J=7.1, 3H); minor diastereomer, δ 4.27 (d, J=12.3, 1H of CH$_2$), 3.76 (d, J=10.9, NH), 3.64 (s, 3H), 0.77 (d, J=7.0, 3H). LC (Cond. 1): RT=2.19 min; LC/MS: Anal. Calcd. for [M+H]$^+$ C$_{32}$H$_{30}$NO$_4$: 492.22; found 492.15.

Diisobutylaluminum hydride (20.57 ml of 1.0 M in hexanes, 20.57 mmol) was added drop-wise over 10 min to a cooled (−78° C.) THF (120 mL) solution of (2S)-1-benzyl 4-methyl 3-methyl-2-(9-phenyl-9H-fluoren-9-ylamino)succinate (3.37 g, 6.86 mmol) prepared above, and stirred at −78° C. for 20 hr. The reaction mixture was removed from the cooling bath and rapidly poured into ~1M H$_3$PO$_4$/H$_2$O (250 mL) with stirring, and the mixture was extracted with ether (100 mL, 2×). The combined organic phase was washed with brine, dried (MgSO$_4$), filtered and concentrated in vacuo. A silica gel mesh of the crude material was prepared and submitted to chromatography (25% EtOAc/hexanes; gravity elution) to afford 1.1 g of (2S,3S)-benzyl 4-hydroxy-3-methyl-2-(9-phenyl-9H-fluoren-9-ylamino)butanoate, contaminated with benzyl alcohol, as a colorless viscous oil and (2S,3R)-benzyl 4-hydroxy-3-methyl-2-(9-phenyl-9H-fluoren-9-ylamino)butanoate containing the (2S,3R) stereoisomer as an impurity. The later sample was resubmitted to the same column chromatography purification conditions to afford 750 mg of purified material as a white foam. [Note: the (2S,3S) isomer elutes before the (2S,3R) isomer under the above condition]. (2S,3S) isomer: $^1$H NMR (DMSO-d$_6$, δ=2.5 ppm, 400 MHz): 7.81 (m, 2H), 7.39-7.08 (m, 16H), 4.67 (d, J=12.3, 1H), 4.43 (d, J=12.4, 1H), 4.21 (app t, J=5.2, OH), 3.22 (d, J=10.1, NH), 3.17 (m, 1H), 3.08 (m, 1H), ~2.5 (m, 1H, overlapped with the solvent signal), 1.58 (m, 1H), 0.88 (d, J=6.8, 3H). LC (Cond. 1): RT=2.00 min; LC/MS: Anal. Calcd. for [M+H]$^+$ C$_{31}$H$_{30}$NO$_3$: 464.45; found 464.22. (2S,3R) isomer: $^1$H NMR (DMSO-d$_6$, δ=2.5 ppm, 400 MHz): 7.81 (d, J=7.5, 2H), 7.39-7.10 (m, 16H), 4.63 (d, J=12.1, 1H), 4.50 (app t, J=4.9, 1H) 4.32 (d, J=12.1, 1H), 3.59-3.53 (m, 2H), 3.23 (m, 1H), 2.44 (dd, J=9.0, 8.3, 1H), 1.70 (m, 1H), 0.57 (d, J=6.8, 3H). LC (Cond. 1): RT=1.92 min; LC/MS: Anal. Calcd. for [M+H]$^+$ C$_{31}$H$_{30}$NO$_3$: 464.45; found 464.52.

The relative stereochemical assignments of the DIBAL-reduction products were made based on NOE studies conducted on lactone derivatives prepared from each isomer by employing the following protocol: LiHMDS (50 μL of 1.0 M/THF, 0.05 mmol) was added to a cooled (ice-water) THF (2.0 mL) solution of (2S,3S)-benzyl 4-hydroxy-3-methyl-2-(9-phenyl-9H-fluoren-9-ylamino)butanoate (62.7 mg, 0.135 mmol), and the reaction mixture was stirred at similar temperature for ~2 hr. The volatile component was removed in vacuo and the residue was partitioned between CH$_2$Cl$_2$ (30 mL), water (20 mL) and saturated aqueous NH$_4$Cl solution (1 mL). The organic layer was dried (MgSO$_4$), filtered, and concentrated in vacuo, and the resulting crude material was submitted to a Biotage purification (40 g silica gel; 10-15% EtOAc/hexanes) to afford (3S,4S)-4-methyl-3-(9-phenyl-9H-fluoren-9-ylamino)dihydrofuran-2(3H)-one as a colorless film of solid (28.1 mg). (2S,3R)-benzyl 4-hydroxy-3-methyl-2-(9-phenyl-9H-fluoren-9-ylamino)butanoate was elaborated similarly to (3S,4R)-4-methyl-3-(9-phenyl-9H-fluoren-9-ylamino)dihydrofuran-2(3H)-one. (3S,4S)-lactone isomer: $^1$H NMR (DMSO-d$_6$, δ=2.5 ppm, 400 MHz), 7.83 (d, J=7.5, 2H), 7.46-7.17 (m, 11H), 4.14 (app t, J=8.3, 1H), 3.60 (d, J=5.8, NH), 3.45 (app t, J=9.2, 1H), ~2.47 (m, 1H, partially overlapped with solvent signal), 2.16 (m, 1H), 0.27 (d, J=6.6, 3H). LC (Cond. 1): RT=1.98 min; LC/MS: Anal. Calcd. for [M+Na]$^+$ C$_{24}$H$_{21}$NNaO$_2$: 378.15; found 378.42. (3S,4R)-lactone isomer: $^1$H NMR (DMSO-d$_6$, δ=2.5 ppm, 400 MHz), 7.89 (d, J=7.6, 1H), 7.85 (d, J=7.3, 1H), 7.46-7.20 (m, 11H), 3.95 (dd, J=9.1, 4.8, 1H), 3.76 (d, J=8.8, 1H), 2.96 (d, J=3.0, NH), 2.92 (dd, J=6.8, 3, NCH), 1.55 (m, 1H), 0.97 (d, J=7.0, 3H). LC (Cond. 1): RT=2.03 min; LC/MS: Anal. Calcd. for [M+Na]$^+$ C$_{24}$H$_{21}$NNaO$_2$: 378.15; found 378.49.

TBDMS-Cl (48 mg, 0.312 mmol) followed by imidazole (28.8 mg, 0.423 mmol) were added to a CH$_2$Cl$_2$ (3 ml) solution of (2S,3S)-benzyl 4-hydroxy-3-methyl-2-(9-phenyl-9H-fluoren-9-ylamino)butanoate (119.5 mg, 0.258 mmol), and the mixture was stirred at ambient condition for 14.25 hr. The reaction mixture was then diluted with CH$_2$Cl$_2$ (30 mL) and washed with water (15 mL), and the organic layer was dried (MgSO$_4$), filtered, and concentrated in vacuo. The resultant crude material was purified with a Biotage (40 g silica gel; 5% EtOAc/hexanes) to afford (2S,3S)-benzyl 4-(tert-butyldimethylsilyloxy)-3-methyl-2-(9-phenyl-9H-fluoren-9-ylamino)butanoate, contaminated with TBDMS based impurities, as a colorless viscous oil (124.4 mg). (2S,3R)-benzyl 4-hydroxy-3-methyl-2-(9-phenyl-9H-fluoren-9-ylamino)butanoate was elaborated similarly to (2S,3R)-benzyl 4-(tert-butyldimethylsilyloxy)-3-methyl-2-(9-phenyl-9H-fluoren-9-ylamino)butanoate. (2S,3S)-silyl ether isomer: $^1$H NMR (DMSO-d$_6$, δ=2.5 ppm, 400 MHz), 7.82 (d, J=4.1, 1H), 7.80 (d, J=4.0, 1H), 7.38-7.07 (m, 16H), 4.70 (d, J=12.4, 1H), 4.42 (d, J=12.3, 1H), 3.28-3.19 (m, 3H), 2.56 (dd, J=10.1, 5.5, 1H), 1.61 (m, 1H), 0.90 (d, J=6.8, 3H), 0.70 (s, 9H), −0.13 (s, 3H), −0.16 (s, 3H). LC (Cond. 1, where the run time was extended to 4 min): RT=3.26 min; LC/MS: Anal. Calcd. for [M+H]$^+$ C$_{37}$H$_{44}$NO$_3$Si: 578.31. found 578.40. (2S,3R)-silyl ether isomer: $^1$H NMR (DMSO-d$_6$, δ=2.5 ppm, 400 MHz), 7.82 (d, J=3.0, 1H), 7.80 (d, J=3.1, 1H), 7.39-7.10 (m, 16H), 4.66 (d, J=12.4, 1H), 4.39 (d, J=12.4, 1H), 3.61 (dd, J=9.9, 5.6, 1H), 3.45 (d, J=9.5, 1H), 3.41 (dd, J=10, 6.2, 1H), 2.55 (dd, J=9.5, 7.3, 1H), 1.74 (m, 1H), 0.77 (s, 9H), 0.61 (d, J=7.1, 3H), −0.06 (s, 3H), −0.08 (s, 3H).

A balloon of hydrogen was attached to a mixture of (2S,3S)-benzyl 4-(tert-butyldimethylsilyloxy)-3-methyl-2-(9-phenyl-9H-fluoren-9-ylamino)butanoate (836 mg, 1.447 mmol) and 10% Pd/C (213 mg) in EtOAc (16 mL) and the mixture was stirred at room temperature for ~21 hr, where the balloon was recharged with H$_2$ as necessary. The reaction mixture was diluted with CH$_2$Cl$_2$ and filtered through a pad of diatomaceous earth (Celite-545®), and the pad was washed with EtOAc (200 mL), EtOAc/MeOH (1:1 mixture, 200 mL) and MeOH (750 mL). The combined organic phase was concentrated, and a silica gel mesh was prepared from the resulting crude material and submitted to a flash chromatography (8:2:1 mixture of EtOAc/i-PrOH/H$_2$O) to afford (2S,3S)-2-amino-4-(tert-butyldimethylsilyloxy)-3-methylbutanoic acid as a white fluffy solid (325 mg). (2S,3R)-benzyl 4-(tert-butyldimethylsilyloxy)-3-methyl-2-(9-phenyl-9H-fluoren-9-ylamino)butanoate was similarly elaborated to (2S,3R)-2-amino-4-(tert-butyldimethylsilyloxy)-3-methylbutanoic acid. (2S,3S)-amino acid isomer: $^1$H NMR (Methanol-d$_4$, δ=3.29 ppm, 400 MHz), 3.76 (dd, J=10.5, 5.2, 1H), 3.73 (d, J=3.0, 1H), 3.67 (dd, J=10.5, 7.0, H), 2.37 (m, 1H), 0.97 (d, J=7.0, 3H), 0.92 (s, 9H), 0.10 (s, 6H). LC/MS: Anal. Calcd. for [M+H]$^+$C$_{11}$H$_{26}$NO$_3$Si: 248.17. found 248.44. (2S,3R)-amino acid isomer: $^1$H NMR (Methanol-d$_4$, δ=3.29 ppm, 400 MHz), 3.76-3.75 (m, 2H), 3.60 (d, J=4.1, 1H), 2.16 (m, 1H), 1.06 (d, J=7.3, 3H), 0.91 (s, 9H), 0.09 (s, 6H). Anal. Calcd. for [M+H]$^+$C$_{11}$H$_{26}$NO$_3$Si: 248.17; found 248.44.

Water (1 mL) and NaOH (0.18 mL of 1.0 M/H$_2$O, 0.18 mmol) were added to a mixture of (2S,3S)-2-amino-4-(tert-butyldimethylsilyloxy)-3-methylbutanoic acid (41.9 mg, 0.169 mmol) and Na$_2$CO$_3$ (11.9 mg, 0.112 mmol), and sonicated for about 1 min to effect dissolution of reactants. The mixture was then cooled with an ice-water bath, methyl chloroformate (0.02 mL, 0.259 mmol) was added over 30 s, and vigorous stirring was continued at similar temperature for 40 min and then at ambient temperature for 2.7 hr. The reaction mixture was diluted with water (5 mL), cooled with ice-water bath and treated drop-wise with 1.0 N HCl aqueous solution (~0.23 mL). The mixture was further diluted with water (10 mL) and extracted with CH$_2$Cl$_2$ (15 mL, 2×). The combined organic phase was dried (MgSO$_4$), filtered, and concentrated in vacuo to afford Cap-80a as an off-white solid. (2S,3R)-2-amino-4-(tert-butyldimethylsilyloxy)-3-methylbutanoic acid was similarly elaborated to Cap-80b. Cap-80a: $^1$H NMR (DMSO-d$_6$, δ=2.5 ppm, 400 MHz), 12.57 (br s, 1H), 7.64 (d, J=8.3, 0.3H), 7.19 (d, J=8.8, 0.7H), 4.44 (dd, J=8.1, 4.6, 0.3H), 4.23 (dd, J=8.7, 4.4, 0.7H), 3.56/3.53 (two singlets, 3H), 3.48-3.40 (m, 2H), 2.22-2.10 (m, 1H), 0.85 (s, 9H), ~0.84 (d, 0.9H, overlapped with t-Bu signal), 0.79 (d, J=7, 2.1H), 0.02/0.01/0.00 (three overlapping singlets, 6H). LC/MS: Anal. Calcd. for [M+Na]$^+$ C$_{13}$H$_{27}$NNaO$_5$Si: 328.16; found 328.46. Cap-80b: $^1$H NMR (CDCl$_3$, δ=7.24 ppm, 400 MHz), 6.00 (br d, J=6.8, 1H), 4.36 (dd, J=7.1, 3.1, 1H), 3.87 (dd, J=10.5, 3.0, 1H), 3.67 (s, 3H), 3.58 (dd, J=10.6, 4.8, 1H), 2.35 (m, 1H), 1.03 (d, J=7.1, 3H), 0.90 (s, 9H), 0.08 (s, 6H). LC/MS: Anal. Calcd. for [M+Na]$^+$ C$_{13}$H$_{27}$NNaO$_5$Si: 328.16; found 328.53. The crude products were utilized without further purification.

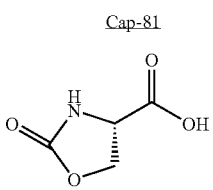

Cap-81

Prepared according to the protocol described by Falb et al. *Synthetic Communications* 1993, 23, 2839.

Cap-82 to Cap-85

Cap-82 to Cap-85 were synthesized from appropriate starting materials according to the procedure described for Cap-51. The samples exhibited similar spectral profiles as that of their enantiomers (i.e., Cap-4, Cap-13, Cap-51 and Cap-52, respectively)

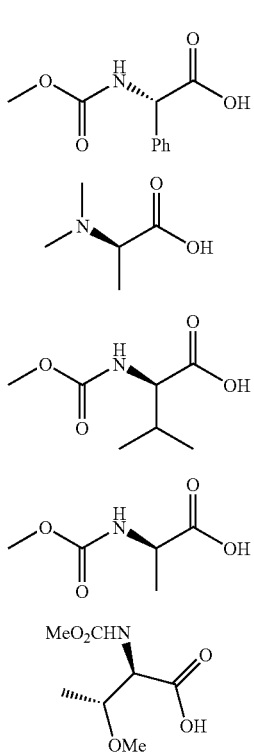

Cap-82

Cap-83

Cap-84

Cap-85

Cap-86

To a mixture of O-methyl-L-threonine (3.0 g, 22.55 mmol), NaOH (0.902 g, 22.55 mmol) in H$_2$O (15 mL) was added ClCO$_2$Me (1.74 mL, 22.55 mmol) dropwise at 0° C. The mixture was allowed to stir for 12 h and acidified to pH 1 using 1N HCl. The aqueous phase was extracted with EtOAc and (2×250 mL) and 10% MeOH in CH$_2$Cl$_2$ (250 mL) and the combined organic phases were concentrated under in vacuo to afford a colorless oil (4.18 g, 97%) which was of sufficient purity for use in subsequent steps. $^1$HNMR (400 MHz, CDCl$_3$) δ 4.19 (s, 1H), 3.92-3.97 (m, 1H), 3.66 (s, 3H), 1.17 (d, J=7.7 Hz, 3H). LCMS: Anal. Calcd. for C$_7$H$_{13}$NO$_5$: 191; found: 190 (M−H)$^-$.

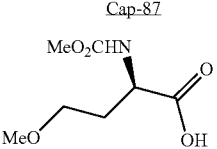

Cap-87

To a mixture of L-homoserine (2.0 g, 9.79 mmol), Na$_2$CO$_3$ (2.08 g, 19.59 mmol) in H$_2$O (15 mL) was added ClCO$_2$Me (0.76 mL, 9.79 mmol) dropwise at 0° C. The mixture was allowed to stir for 48 h and acidified to pH 1 using 1N HCl. The aqueous phase was extracted with EtOAc and (2×250 mL) and the combined organic phases were concentrated under in vacuo to afford a colorless solid (0.719 g, 28%) which was of sufficient purity for use in subsequent steps. $^1$HNMR (400 MHz, CDCl$_3$) δ 4.23 (dd, J=4.5, 9.1 Hz, 1H), 3.66 (s, 3H), 3.43-3.49 (m, 2H), 2.08-2.14 (m, 1H), 1.82-1.89 (m, 1H). LCMS: Anal. Calcd. for C$_7$H$_{13}$NO$_5$: 191; found: 192 (M+H)$^+$.

Cap-88

A mixture of L-valine (1.0 g, 8.54 mmol), 3-bromopyridine (1.8 mL, 18.7 mmol), K$_2$CO$_3$ (2.45 g, 17.7 mmol) and CuI (169 mg, 0.887 mmol) in DMSO (10 mL) was heated at 100° C. for 12 h. The reaction mixture was cooled to rt, poured into H$_2$O (ca. 150 mL) and washed with EtOAc (×2). The organic layers were extracted with a small amount of H$_2$O and the combined aq phases were acidified to ca. pH 2 with 6N HCl. The volume was reduced to about one-third and 20 g of cation exchange resin (Strata) was added. The slurry was allowed to stand for 20 min and loaded onto a pad of cation exchange resin (Strata) (ca. 25 g). The pad was washed with H$_2$O (200 mL), MeOH (200 mL), and then NH$_3$ (3M in MeOH, 2×200 mL). The appropriate fractions was concentrated in vacuo and the residue (ca. 1.1 g) was dissolved in H$_2$O, frozen and lyophilized. The title compound was obtained as a foam (1.02 g, 62%). $^1$HNMR (400 MHz, DMSO-d$_6$) δ 8.00 (s, br, 1H), 7.68-7.71 (m, 1H), 7.01 (s, br, 1H), 6.88 (d, J=7.5 Hz, 1H), 5.75 (s, br, 1H), 3.54 (s, 1H), 2.04-2.06 (m, 1H), 0.95 (d, J=6.0 Hz, 3H), 0.91 (d, J=6.6 Hz, 3H). LCMS: Anal. Calcd. for C$_{10}$H$_{14}$N$_2$O$_2$: 194; found: 195 (M+H)$^+$.

Cap-89

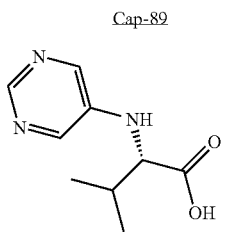

A mixture of L-valine (1.0 g, 8.54 mmol), 5-bromopyrimidine (4.03 g, 17.0 mmol), $K_2CO_3$ (2.40 g, 17.4 mmol) and CuI (179 mg, 0.94 mmol) in DMSO (10 mL) was heated at 100° C. for 12 h. The reaction mixture was cooled to RT, poured into $H_2O$ (ca. 150 mL) and washed with EtOAc (×2). The organic layers were extracted with a small amount of $H_2O$ and the combined aq phases were acidified to ca. pH 2 with 6N HCl. The volume was reduced to about one-third and 20 g of cation exchange resin (Strata) was added. The slurry was allowed to stand for 20 min and loaded onto a pad of cation exchange resin (Strata) (ca. 25 g). The pad was washed with $H_2O$ (200 mL), MeOH (200 mL), and then $NH_3$ (3M in MeOH, 2×200 mL). The appropriate fractions was concentrated in vacuo and the residue (ca. 1.1 g) was dissolved in $H_2O$, frozen and lyophilized. The title compound was obtained as a foam (1.02 g, 62%). $^1$HNMR (400 MHz, $CD_3OD$) showed the mixture to contain valine and the purity could not be estimated. The material was used as is in subsequent reactions. LCMS: Anal. Calcd. for $C_9H_{13}N_3O_2$: 195; found: 196 $(M+H)^+$.

Cap-90

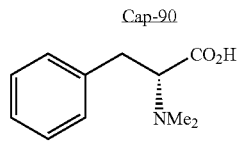

Cap-90 was prepared according to the method described for the preparation of Cap-1. The crude material was used as is in subsequent steps. LCMS: Anal. Calcd. for $C_{11}H_{15}NO_2$: 193; found: 192 $(M-H)^-$.

The following caps were prepared according to the method of Cap-51:

| Cap | Structure | LCMS |
|---|---|---|
| Cap-91 | NHCO₂Me, CO₂H (phenyl) | LCMS: Anal. Calcd. for $C_{11}H_{13}NO_4$: 223; found 222 $(M-H)^-$. |
| Cap-92 | NHCO₂Me, CO₂H (phenyl) | LCMS: Anal. Calcd. for $C_{11}H_{13}NO_4$: 223; found 222 $(M-H)^-$. |
| Cap-93 | (pyridyl, NHCO₂Me, COOH) | LCMS: Anal. Calcd. for $C_{10}H_{12}N_2O_4$: 224; found 225 $(M+H)^+$. |
| Cap-94 | (imidazolyl, NHCO₂Me, COOH) | LCMS: Anal. Calcd. for $C_8H_{11}N_3O_4$: 213; found 214 $(M+H)^+$. |

-continued

| Cap | Structure | LCMS |
|---|---|---|
| Cap-95 | 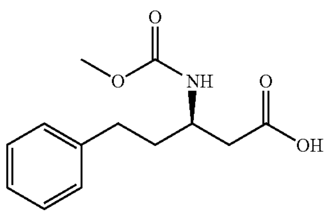 | LCMS: Anal. Calcd. for $C_{13}H_{17}NO_4$: 251; found 250 $(M - H)^-$. |
| Cap-96 | 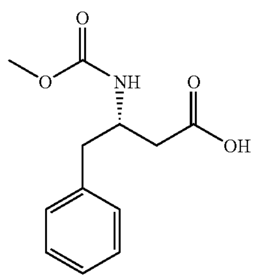 | LCMS: Anal. Calcd. for $C_{12}H_{50}NO_4$: 237; found 236 $(M - H)^-$. |
| Cap-97 | 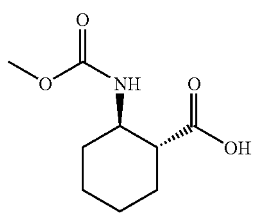 | LCMS: Anal. Calcd. for $C_9H_{15}NO_4$: 201; found 200 $(M - H)^-$. |
| Cap-98 | 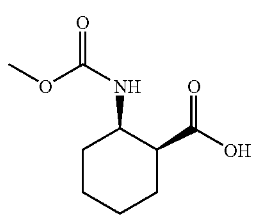 | LCMS: Anal. Calcd. for $C_9H_{15}NO_4$: 201; found 202 $(M + H)^+$. |
| Cap-99 | 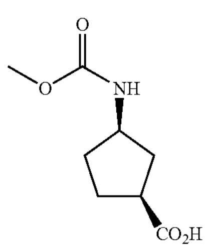 | $^1$HNMR (400 MHz, CD$_3$OD) δ 3.88-3.94 (m, 1 H), 3.60, 3.61 (s, 3 H), 2.80 (m, 1 H), 2.20 (m 1 H), 1.82-1.94 (m, 3 H), 1.45-1.71 (m, 2 H). |
| Cap-99a | 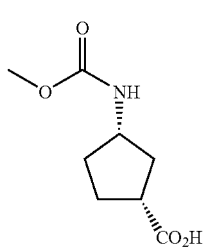 | $^1$HNMR (400 MHz, CD$_3$OD) δ 3.88-3.94 (m, 1 H), 3.60, 3.61 (s, 3 H), 2.80 (m, 1 H), 2.20 (m 1 H), 1.82-1.94 (m, 3 H), 1.45-1.71 (m, 2 H). |

-continued

| Cap | Structure | LCMS |
|---|---|---|
| Cap-100 | 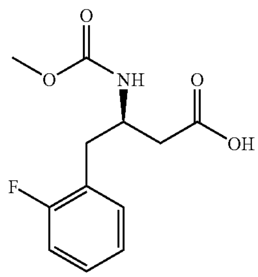 | LCMS: Anal. Calcd. for $C_{12}H_{14}NO_4F$: 255; found 256 $(M + H)^+$. |
| Cap-101 | 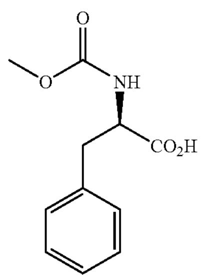 | LCMS: Anal. Calcd. for $C_{11}H_{13}NO_4$: 223; found 222 $(M - H)^-$. |
| Cap-102 | 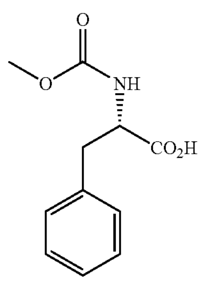 | LCMS: Anal. Calcd. for $C_{11}H_{13}NO_4$: 223; found 222 $(M - H)^-$. |
| Cap-103 | 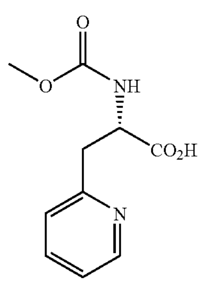 | LCMS: Anal. Calcd. for $C_{10}H_{12}NO_4$: 224; found 225 $(M + H)^+$. |
| Cap-104 | 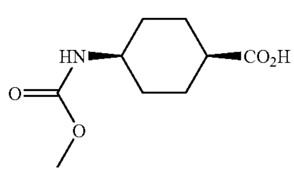 | $^1$HNMR (400 MHz, CD$_3$OD) δ 3.60 (s, 3 H), 3.50-3.53 (m, 1 H), 2.66-2.69 and 2.44-2.49 (m, 1 H), 1.91-2.01 (m, 2 H), 1.62-1.74 (m, 4 H), 1.51-1.62 (m, 2 H). |
| Cap-105 | 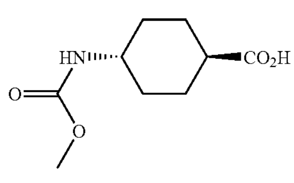 | $^1$HNMR (400 MHz, CD$_3$OD) δ 3.60 (s, 3 H), 3.33-3.35 (m, 1 H, partially obscured by solvent), 2.37-2.41 and 2.16-2.23 (m, 1 H), 1.94-2.01 (m, 4 H), 1.43-1.53 (m, 2 H), 1.17-1.29 (m, 2 H). |

-continued

| Cap | Structure | LCMS |
|---|---|---|
| Cap-106 (prepared following the procedure described for Cap-2)) | Et₂N-cyclohexyl-CO₂H (trans-4-(diethylamino)cyclohexanecarboxylic acid) | $^1$HNMR (400 MHz, CD$_3$OD) δ 3.16 (q, J = 7.3 Hz, 4 H), 2.38-2.41 (m, 1 H), 2.28-2.31 (m, 2 H), 1.79-1.89 (m, 2 H), 1.74 (app, ddd J = 3.5, 12.5, 15.9 Hz, 2 H), 1.46 (app dt J = 4.0, 12.9 Hz, 2 H), 1.26 (t, J = 7.3 Hz, 6 H). |
| Cap-107 | (thiazol-4-yl)-CH₂-CH(NHC(O)OMe)-CO₂H | LCMS: Anal. Calcd. for C$_8$H$_{10}$N$_2$O$_4$S: 230; found: 231 (M + H)$^+$. |
| Cap-108 | (1-benzyl-1H-imidazol-4-yl)-CH₂-CH(NHC(O)OMe)-CO₂H | LCMS: Anal. Calcd. for C$_{15}$H$_{17}$N$_3$O$_4$: 303; found: 304 (M + H)$^+$. |
| Cap-109 | MeO-C(O)-NH-CH(CO₂H)-CH₂-(pyridin-3-yl) | LCMS: Anal. Calcd. for C$_{10}$H$_{12}$N$_2$O$_4$: 224; found: 225 (M + H)$^+$. |
| Cap-110 | MeO-C(O)-NH-CH(CO₂H)-CH₂-(pyridin-4-yl) | LCMS: Anal. Calcd. for C$_{10}$H$_{12}$N$_2$O$_4$: 224; found: 225 (M + H)$^+$. |
| Cap-111 | MeO-C(O)-NH-CH(CO₂H)-CH₂-(4-(OP(O)(OMe)(OH))phenyl) | LCMS: Anal. Calcd. for C$_{12}$H$_{16}$NO$_8$P: 333; found: 334 (M + H)$^+$. |

-continued

| Cap | Structure | LCMS |
|---|---|---|
| Cap-112 | 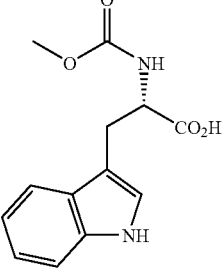 | LCMS: Anal. Calcd. for $C_{13}H_{14}N_2O_4$: 262; found: 263 $(M + H)^+$. |
| Cap-113 | 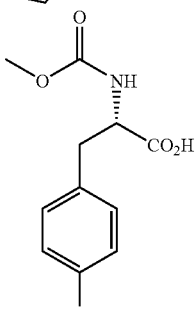 | LCMS: Anal. Calcd. for $C_{18}H_{19}NO_5$: 329; found: 330 $(M + H)^+$. |
| Cap-114 | 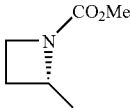 | $^1$HNMR (400 MHz, CDCl$_3$) δ 4.82-4.84 (m, 1 H), 4.00-4.05 (m, 2 H), 3.77 (s, 3 H), 2.56 (s, br, 2 H) |
| Cap-115 | 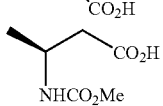 | $^1$HNMR (400 MHz, CDCl$_3$) δ 5.13 (s, br, 1 H), 4.13 (s, br, 1 H), 3.69 (s, 3 H), 2.61 (d, J = 5.0 Hz, 2 H), 1.28 (d, J = 9.1 Hz, 3 H). |
| Cap-116 | 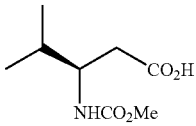 | $^1$HNMR (400 MHz, CDCl$_3$) δ 5.10 (d, J = 8.6 Hz, 1 H), 3.74-3.83 (m, 1 H), 3.69 (s, 3 H), 2.54-2.61 (m, 2 H), 1.88 (sept, J = 7.0 Hz, 1 H), 0.95 (d, J = 7.0 Hz, 6 H). |

Cap-117 to Cap-123

For the preparation of caps Cap-117 to Cap-123 the Boc amino acids were commercially available and were deprotected by treatment with 25% TFA in CH$_2$Cl$_2$. After complete reaction as judged by LCMS the solvents were removed in vacuo and the corresponding TFA salt of the amino acid was carbamoylated with methyl chloroformate according to the procedure for Cap-51.

| Cap | Structure | LCMS |
|---|---|---|
| Cap-117 | 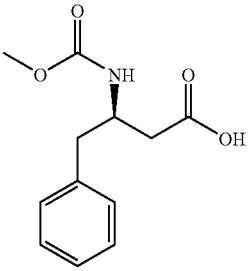 | LCMS: Anal. Calcd. for $C_{12}H_{15}NO_4S$: 237; found: 238 $(M + H)^+$. |

-continued

| Cap | Structure | LCMS |
|---|---|---|
| Cap-118 | 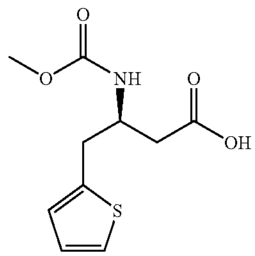 | LCMS: Anal. Calcd. for $C_{10}H_{13}NO_4S$: 243; found: 244 $(M + H)^+$. |
| Cap-119 | 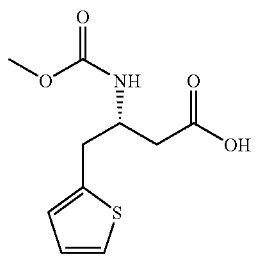 | LCMS: Anal. Calcd. for $C_{10}H_{13}NO_4S$: 243; found: 244 $(M + H)^+$. |
| Cap-120 | 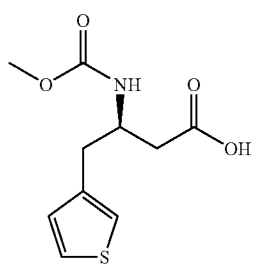 | LCMS: Anal. Calcd. for $C_{10}H_{13}NO_4S$: 243; found: 244 $(M + H)^+$. |
| Cap-121 | 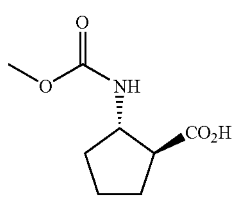 | $^1$HNMR (400 MHz, CDCl$_3$) δ 4.06-4.16 (m, 1 H), 3.63 (s, 3 H), 3.43 (s, 1 H), 2.82 and 2.66 (s, br, 1 H), 1.86-2.10 (m, 3 H), 1.64-1.76 (m, 2 H), 1.44-1.53 (m, 1 H). |
| Cap-122 | 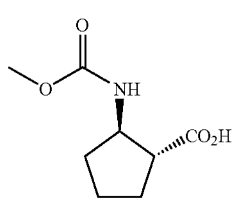 | $^1$HNMR (400 MHz, CDCl$_3$) δ 5.28 and 5.12 (s, br, 1 H), 3.66 (s, 3 H), 2.64-2.74 (m, 1 H), 1.86-2.12 (m, 3 H), 1.67-1.74 (m, 2 H), 1.39-1.54 (m, 1 H). |
| Cap-123 | 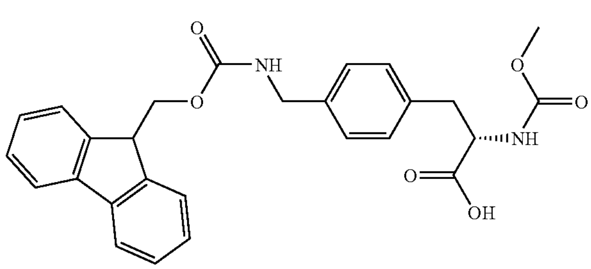 | LCMS: Anal. Calcd. for $C_{27}H_{26}N_2O_6$: 474; found: 475 $(M + H)^+$. |

Preparation of Cap-124.
(4S,5R)-5-methyl-2-oxooxazolidine-4-carboxylic acid

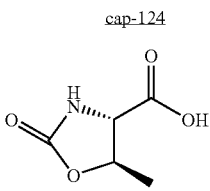
cap-124

The hydrochloride salt of L-threonine tert-butyl ester was carbamoylated according to the procedure for Cap-51. The crude reaction mixture was acidified with 1N HCl to pH ~1 and the mixture was extracted with EtOAc (2×50 mL). The combined organic phases were concentrated in vacuo to give a colorless which solidified on standing. The aqueous layer was concentrated in vacuo and the resulting mixture of product and inorganic salts was triturated with EtOAc-$CH_2Cl_2$-MeOH (1:1:0.1) and then the organic phase concentrated in vacuo to give a colorless oil which was shown by LCMS to be the desired product. Both crops were combined to give 0.52 g of a solid. $^1$HNMR (400 MHz, $CD_3OD$) δ 4.60 (m, 1H), 4.04 (d, J=5.0 Hz, 1H), 1.49 (d, J=6.3 Hz, 3H). LCMS: Anal. Calcd. for $C_5H_7NO_4$: 145; found: 146 $(M+H)^+$.

Preparation of Cap-125. (S)-2-(tert-butoxycarbonylamino)-4-(dimethylamino)butanoic acid

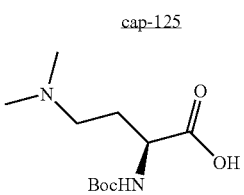
cap-125

Cap-125 was prepared according to the procedure for the preparation of Cap-1. The crude product was used as is in subsequent reactions. LCMS: Anal. Calcd. for $C_{11}H_{22}N_2O_4$: 246; found: 247 $(M+H)^+$.

Preparation of (S)-2-(methoxycarbonylamino)-3-(1-methyl-1H-imidazol-2-yl)propanoic acid (Cap-126)

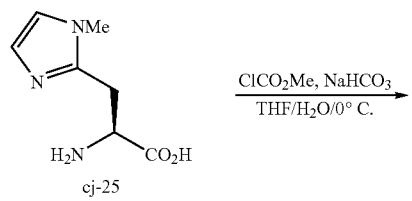

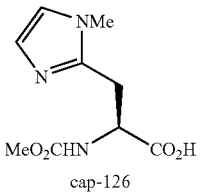
cap-126

This procedure is a modification of that used to prepare Cap-51. To a suspension of (S)-2-amino-3-(1-methyl-1H-imidazol-2-yl)propanoic acid (0.80 g, 4.70 mmol) in THF (10 mL) and $H_2O$ (10 mL) at 0° C. was added $NaHCO_3$ (0.88 g, 10.5 mmol). The resulting mixture was treated with $ClCO_2Me$ (0.40 mL, 5.20 mmol) and the mixture allowed to stir at 0° C. After stirring for ca. 2 h LCMS showed no starting material remaining. The reaction was acidified to pH 2 with 6 N HCl.

The solvents were removed in vacuo and the residue was suspended in 20 mL of 20% MeOH in $CH_2Cl_2$. The mixture was filtered and concentrated to give a light yellow foam (1.21 g). LCMS and $^1$H NMR showed the material to be a 9:1 mixture of the methyl ester and the desired product. This material was taken up in THF (10 mL) and $H_2O$ (10 mL), cooled to 0° C. and LiOH (249.1 mg, 10.4 mmol) was added. After stirring ca. 1 h LCMS showed no ester remaining. Therefore the mixture was acidified with 6N HCl and the solvents removed in vacuo. LCMS and $^1$H NMR confirm the absence of the ester. The title compound was obtained as its HCl salt contaminated with inorganic salts (1.91 g, >100%). The compound was used as is in subsequent steps without further purification.

$^1$HNMR (400 MHz, $CD_3OD$) δ 8.84, (s, 1H), 7.35 (s, 1H), 4.52 (dd, J=5.0, 9.1 Hz, 1H), 3.89 (s, 3H), 3.62 (s, 3H), 3.35 (dd, J=4.5, 15.6 Hz, 1H, partially obscured by solvent), 3.12 (dd, J=9.0, 15.6 Hz, 1H).

LCMS: Anal. Calcd. for $C_{17}H_{15}NO_2$: 392; found: 393 $(M+H)^+$.

Preparation of (S)-2-(methoxycarbonylamino)-3-(1-methyl-1H-imidazol-4-yl)propanoic acid (Cap-127)

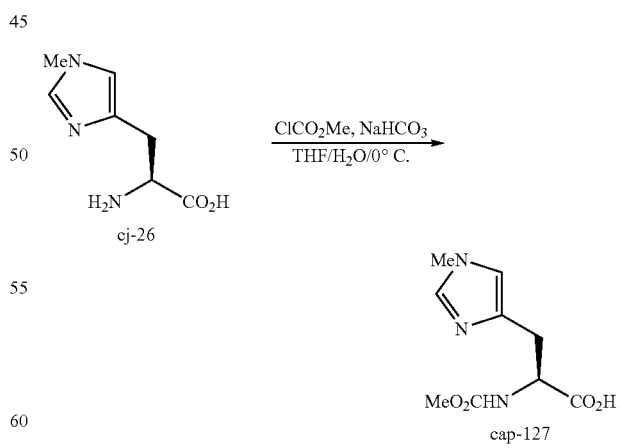

Cap-127 was prepared according to the method for Cap-126 above starting from (S)-2-amino-3-(1-methyl-1H-imidazol-4-yl)propanoic acid (1.11 g, 6.56 mmol), $NaHCO_3$ (1.21 g, 14.4 mmol) and $ClCO_2Me$ (0.56 mL, 7.28 mmol). The title compound was obtained as its HCl salt (1.79 g, >100%)

contaminated with inorganic salts. LCMS and ¹H NMR showed the presence of ca. 5% of the methyl ester. The crude mixture was used as is without further purification.

¹HNMR (400 MHz, CD₃OD) δ 8.90 (s, 1H), 7.35 (s, 1H), 4.48 (dd, J=5.0, 8.6 Hz, 1H), 3.89 (s, 3H), 3.62 (s, 3H), 3.35 (m, 1H), 3.08 (m, 1H).

LCMS: Anal. Calcd. for $C_{17}H_{15}NO_2$: 392; found: 393 (M+H)⁺.

Preparation of (S)-2-(methoxycarbonylamino)-3-(1H-1,2,3-triazol-4-yl)propanoic acid (Cap-128)

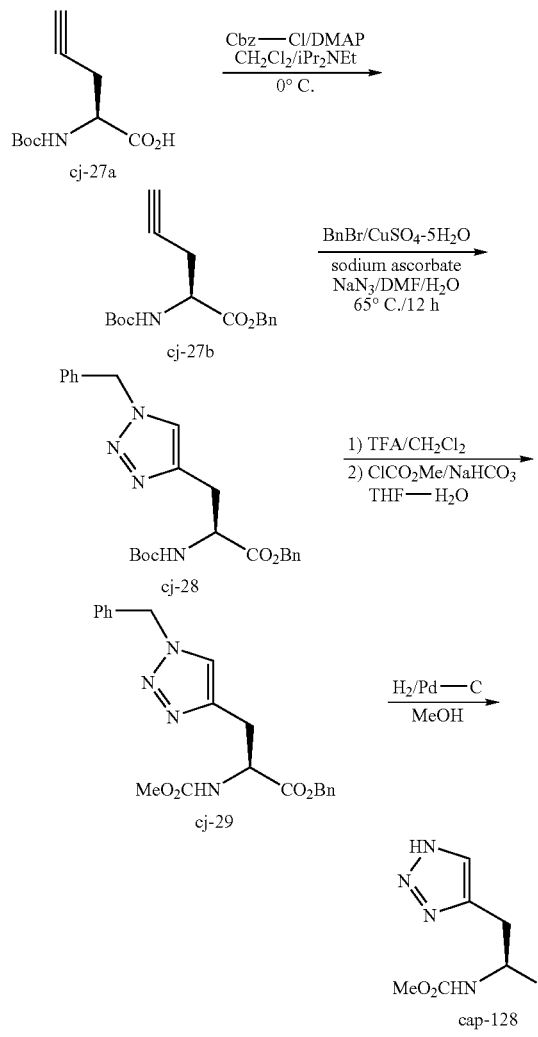

Step 1. Preparation of (S)-benzyl 2-(tert-butoxycarbonylamino)pent-4-ynoate (cj-27b)

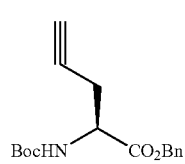

To a solution of cj-27a (1.01 g, 4.74 mmol), DMAP (58 mg, 0.475 mmol) and iPr₂NEt (1.7 mL, 9.8 mmol) in CH₂Cl₂ (100 mL) at 0° C. was added Cbz-Cl (0.68 mL, 4.83 mmol). The solution was allowed to stir for 4 h at 0° C., washed (1N KHSO₄, brine), dried (Na₂SO₄), filtered, and concentrated in vacuo. The residue was purified by flash column chromatography (TLC 6:1 hex:EtOAc) to give the title compound (1.30 g, 91%) as a colorless oil. ¹HNMR (400 MHz, CDCl₃) δ 7.35 (s, 5H), 5.35 (d, br, J=8.1 Hz, 1H), 5.23 (d, J=12.2 Hz, 1H), 5.17 (d, J=12.2 Hz, 1H), 4.48-4.53 (m, 1H), 2.68-2.81 (m, 2H), 2.00 (t, J=2.5 Hz, 1H), 1.44 (s, 9H). LCMS: Anal. Calcd. for $C_{17}H_{21}NO_4$: 303; found: 304 (M+H)⁺.

Step 2. Preparation of (S)-benzyl 3-(1-benzyl-1H-1,2,3-triazol-4-yl)-2-(tert-butoxycarbonylamino)propanoate (cj-28)


To a mixture of (S)-benzyl 2-(tert-butoxycarbonylamino)pent-4-ynoate (0.50 g, 1.65 mmol), sodium ascorbate (0.036 g, 0.18 mmol), CuSO₄·5H₂O (0.022 g, 0.09 mmol) and NaN₃ (0.13 g, 2.1 mmol) in DMF-H₂O (5 mL, 4:1) at rt was added BnBr (0.24 mL, 2.02 mmol) and the mixture was warmed to 65° C. After 5 h LCMS indicated low conversion. A further portion of NaN₃ (100 mg) was added and heating was continued for 12 h. The reaction was poured into EtOAc and H₂O and shaken. The layers were separated and the aqueous layer extracted 3× with EtOAc and the combined organic phases washed (H₂O×3, brine), dried (Na₂SO₄), filtered, and concentrated. The residue was purified by flash (Biotage, 40+M 0-5% MeOH in CH₂Cl₂; TLC 3% MeOH in CH₂Cl₂) to afford a light yellow oil which solidified on standing (748.3 mg, 104%). The NMR was consistent with the desired product but suggests the presence of DMF. The material was used as is without further purification. ¹HNMR (400 MHz, DMSO-d₆) δ 7.84 (s, 1H), 7.27-7.32 (m, 10H), 5.54 (s, 2H), 5.07 (s, 2H), 4.25 (m, 1H), 3.16 (dd, J=1.0, 5.3 Hz, 1H), 3.06 (dd, J=5.3, 14.7 Hz), 2.96 (dd, J=9.1, 14.7 Hz, 1H), 1.31 (s, 9H).

LCMS: Anal. Calcd. for $C_{24}H_{28}N_4O_4$: 436; found: 437 (M+H)⁺.

Step 2. Preparation of (S)-benzyl 3-(1-benzyl-1H-1,2,3-triazol-4-yl)-2-(methoxycarbonylamino)propanoate (cj-29)


A solution of (S)-benzyl 3-(1-benzyl-1H-1,2,3-triazol-4-yl)-2-(tert-butoxycarbonylamino)propanoate (0.52 g, 1.15 mmol) in CH$_2$Cl$_2$ was added TFA (4 mL). The mixture was allowed to stir at room temperature for 2 h. The mixture was concentrated in vacuo to give a colorless oil which solidified on standing. This material was dissolved in THF-H$_2$O and cooled to 0° C. Solid NaHCO$_3$ (0.25 g, 3.00 mmol) was added followed by ClCO$_2$Me (0.25 mL, 3.25 mmol). After stirring for 1.5 h the mixture was acidified to pH ~2 with 6N HCl and then poured into H$_2$O-EtOAc. The layers were separated and the aq phase extracted 2× with EtOAc. The combined org layers were washed (H$_2$O, brine), dried (Na$_2$SO$_4$), filtered, and concentrated in vacuo to give a colorless oil (505.8 mg, 111%, NMR suggested the presence of an unidentified impurity) which solidified while standing on the pump. The material was used as is without further purification. $^1$HNMR (400 MHz, DMSO-d$_6$) δ 7.87 (s, 1H), 7.70 (d, J=8.1 Hz, 1H), 7.27-7.32 (m, 10H), 5.54 (s, 2H), 5.10 (d, J=12.7 Hz, 1H), 5.06 (d, J=12.7 Hz, 1H), 4.32-4.37 (m, 1H), 3.49 (s, 3H), 3.09 (dd, J=5.6, 14.7 Hz, 1H), 2.98 (dd, J=9.6, 14.7 Hz, 1H). LCMS: Anal. Calcd. for C$_{21}$H$_{22}$N$_4$O$_4$: 394; found: 395 (M+H)$^+$.

Step 3. Preparation of (S)-2-(methoxycarbonylamino)-3-(1H-1,2,3-triazol-4-yl)propanoic acid (Cap-128)

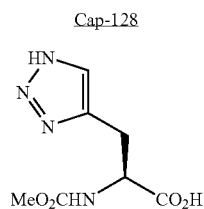

(S)-benzyl 3-(1-benzyl-1H-1,2,3-triazol-4-yl)-2-(methoxycarbonylamino)propanoate (502 mg, 1.11 mmol) was hydrogenated in the presence of Pd—C (82 mg) in MeOH (5 mL) at atmospheric pressure for 12 h. The mixture was filtered through diatomaceous earth (Celite®) and concentrated in vacuo. (S)-2-(methoxycarbonylamino)-3-(1H-1,2,3-triazol-4-yl)propanoic acid was obtained as a colorless gum (266 mg, 111%) which was contaminated with ca. 10% of the methyl ester. The material was used as is without further purification.

$^1$HNMR (400 MHz, DMSO-d$_6$) δ 12.78 (s, br, 1H), 7.59 9 s, 1H), 7.50 (d, J=8.0 Hz, 1H), 4.19-4.24 (m, 1H), 3.49 (s, 3H), 3.12 (dd, J=4.8 Hz, 14.9 Hz, 1H), 2.96 (dd, J=9.9, 15.0 Hz, 1H). LCMS: Anal. Calcd. for C$_7$H$_{10}$N$_4$O$_4$: 214; found: 215 (M+H)$^+$.

Preparation of (S)-2-(methoxycarbonylamino)-3-(1H-pyrazol-1-yl)propanoic acid (Cap-129)

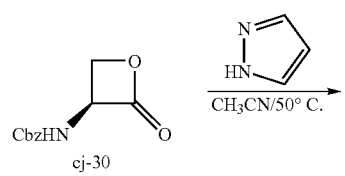

Step 1. Preparation of (S)-2-(benzyloxycarbonylamino)-3-(1H-pyrazol-1-yl)propanoic acid (cj-31)

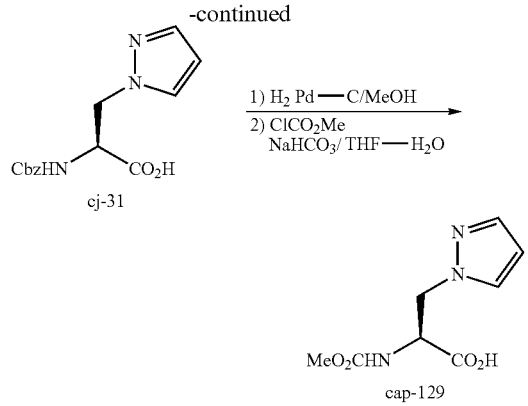

A suspension of (S)-benzyl 2-oxooxetan-3-ylcarbamate (0.67 g, 3.03 mmol), and pyrazole (0.22 g, 3.29 mmol) in CH$_3$CN (12 mL) was heated at 50° C. for 24 h. The mixture was cooled to rt overnight and the solid filtered to afford (S)-2-(benzyloxycarbonylamino)-3-(1H-pyrazol-1-yl)propanoic acid (330.1 mg). The filtrate was concentrated in vacuo and then triturated with a small amount of CH$_3$CN (ca. 4 mL) to afford a second crop (43.5 mg). Total yield 370.4 mg (44%).

m.p. 165.5-168° C. lit m.p. 168.5-169.5 Vederas et al. *J. Am. Chem. Soc.* 1985, 107, 7105.

$^1$HNMR (400 MHz, CD$_3$OD) δ 7.51 (d, J=2.0, 1H), 7.48 (s, J=1.5 Hz, 1H), 7.24-7.34 (m, 5H), 6.23 m, 1H), 5.05 (d, 12.7H, 1H), 5.03 (d, J=12.7 Hz, 1H), 4.59-4.66 (m, 2H), 4.42-4.49 (m, 1H). LCMS: Anal. Calcd. for C$_{14}$H$_{15}$N$_3$O$_4$: 289; found: 290 (M+H)$^+$.

Step 2. Preparation of (S)-2-(methoxycarbonylamino)-3-(1H-pyrazol-1-yl)propanoic acid (Cap-129)

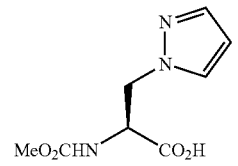

(S)-2-(benzyloxycarbonylamino)-3-(1H-pyrazol-1-yl)propanoic acid (0.20 g, 0.70 mmol) was hydrogenated in the presence of Pd—C (45 mg) in MeOH (5 mL) at atmospheric pressure for 2 h. The product appeared to be insoluble in MeOH, therefore the rxn mixture was diluted with 5 mL H$_2$O and a few drops of 6N HCl. The homogeneous solution was filtered through diatomaceous earth (Celite®), and the MeOH removed in vacuo. The remaining solution was frozen and lyophilized to give a yellow foam (188.9 mg). This material was suspended in THF-H$_2$O (1:1, 10 mL) and then cooled to 0° C. To the cold mixture was added NaHCO$_3$ (146.0 mg, 1.74 mmol) carefully (evolution of CO$_2$). After gas evolution had ceased (ca. 15 min) ClCO₂Me (0.06 mL, 0.78 mmol) was added dropwise. The mixture was allowed to stir for 2 h and was acidified to pH ~2 with 6N HCl and poured into EtOAc. The layers were separated and the aqueous phase extract with EtOAC (×5). The combined organic layers were washed (brine), dried (Na$_2$SO$_4$), filtered, and concentrated to give the title compound as a colorless solid (117.8 mg, 79%).

$^1$HNMR (400 MHz, DMSO-d$_6$) δ 13.04 (s, 1H), 7.63 (d, J=2.6 Hz, 1H), 7.48 (d, J=8.1 Hz, 1H), 7.44 (d, J=1.5 Hz, 1H), 6.19 (app t, J=2.0 Hz, 1H), 4.47 (dd, J=3.0, 12.9 Hz, 1H), 4.29-4.41 (m, 2H), 3.48 (s, 3H). LCMS: Anal. Calcd. for C$_8$H$_{11}$N$_3$O$_4$: 213; found: 214 (M+H)$^+$.

cap-130

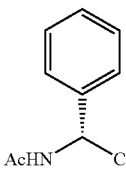

Cap-130. N-Acetyl-(R)-Phenylglycine

Cap-130 was prepared by acylation of commercially available (R)-phenylglycine analogous to the procedure given in: Calmes, M.; Daunis, J.; Jacquier, R.; Verducci, J. *Tetrahedron*, 1987, 43(10), 2285.

EXAMPLES

The present disclosure will now be described in connection with certain embodiments which are not intended to limit its scope. On the contrary, the present disclosure covers all alternatives, modifications, and equivalents as can be included within the scope of the claims. Thus, the following examples, which include specific embodiments, will illustrate one practice of the present disclosure, it being understood that the examples are for the purposes of illustration of certain embodiments and are presented to provide what is believed to be the most useful and readily understood description of its procedures and conceptual aspects.

Solution percentages express a weight to volume relationship, and solution ratios express a volume to volume relationship, unless stated otherwise. Nuclear magnetic resonance (NMR) spectra were recorded either on a Bruker 300, 400, or 500 MHz spectrometer; the chemical shifts (δ) are reported in parts per million. Flash chromatography was carried out on silica gel (SiO$_2$) according to Still's flash chromatography technique (*J. Org. Chem.* 1978, 43, 2923).

Purity assessment and low resolution mass analysis were conducted on a Shimadzu LC system coupled with Waters Micromass ZQ MS system. It should be noted that retention times may vary slightly between machines. The LC conditions employed in determining the retention time (RT) were:

| Condition 1 | |
|---|---|
| Column = | Phenomenex-Luna 3.0 × 50 mm S10 |
| Start % B = | 0 |
| Final % B = | 100 |
| Gradient time = | 2 min |
| Stop time = | 3 min |
| Flow Rate = | 4 mL/min |
| Wavelength = | 220 nm |
| Solvent A = | 0.1% TFA in 10% methanol/90% H$_2$O |
| Solvent B = | 0.1% TFA in 90% methanol/10% H$_2$O |
| Condition 2 | |
| Column = | Phenomenex-Luna 4.6 × 50 mm S10 |
| Start % B = | 0 |
| Final % B = | 100 |
| Gradient time = | 2 min |
| Stop time = | 3 min |
| Flow Rate = | 5 mL/min |
| Wavelength = | 220 nm |
| Solvent A = | 0.1% TFA in 10% methanol/90% H$_2$O |
| Solvent B = | 0.1% TFA in 90% methanol/10% H$_2$O |
| Condition 3 | |
| Column = | HPLC XTERRA C18 3.0 × 50 mm S7 |
| Start % B = | 0 |
| Final % B = | 100 |
| Gradient time = | 3 min |
| Stop time = | 4 min |
| Flow Rate = | 4 mL/min |
| Wavelength = | 220 nm |
| Solvent A = | 0.1% TFA in 10% methanol/90% H$_2$O |
| Solvent B = | 0.1% TFA in 90% methanol/10% H$_2$O |

Method A: LCMS—Xterra MS C-18 3.0×50 mm, 0 to 100% B over 30.0 minute gradient, 1 minute hold time, A=5% acetonitrile, 95% water, 10 mm ammonium acetate, B=95% acetonitrile, 5% water, 10 mm ammonium acetate.

Method B: HPLC—X-Terra C-18 4.6×50 mm, 0 to 100% B over 10.0 minute gradient, 1 minute hold time, A=10% methanol 90% water 0.1% TFA, B=90% methanol 10% water 0.1% TFA Method C: HPLC—YMC C-18 4.6×50 mm, 0 to 100% B over 10.0 minute gradient, 1 minute hold time, A=10% methanol 90% water 0.2% H$_3$PO$_4$, B=90% methanol 10% water 0.2% H$_3$PO$_4$.

Method D: HPLC—Phenomenex C-18 4.6×150 mm, 0 to 100% B over 10.0 minute gradient, 1 minute hold time, A=10% methanol 90% water 0.2% H$_3$PO$_4$, B=90% methanol 10% water 0.2% H$_3$PO$_4$.

Method E: LCMS—Gemini C-18 4.6×50 mm, 0 to 100% B over 10.0 minute gradient, 1 minute hold time, A=5% acetonitrile, 95% water, 10 mm ammonium acetate, B=95% acetonitrile, 5% water, 10 mm ammonium acetate.

Method F: LCMS—Luna C-18 3.0×50 mm, 0 to 100% B over 7.0 minute gradient, 1 minute hold time, A=5% acetonitrile, 95% water, 10 mm ammonium acetate, B=95% acetonitrile, 5% water, 10 mm ammonium acetate.

Example 1

(1R,1'R)-2,2'-(4,4'-biphenyldiylbis(1H-imidazole-5,2-diyl(2S)-2,1-pyrrolidinediyl))bis(N,N-dimethyl-2-oxo-1-phenylethanamine)

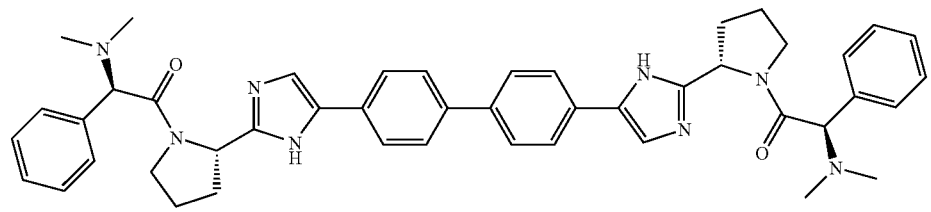

Example 1

Step a

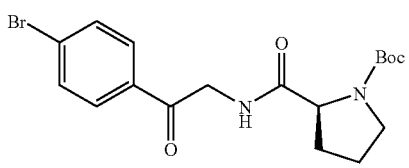

1a

N,N-Diisopropylethylamine (18 mL, 103.3 mmol) was added dropwise, over 15 minutes, to a heterogeneous mixture of N-Boc-L-proline (7.139 g, 33.17 mmol), HATU (13.324 g, 35.04 mmol), the HCl salt of 2-amino-1-(4-bromophenyl)ethanone (8.127 g, 32.44 mmol), and DMF (105 mL), and stirred at ambient condition for 55 minutes. Most of the volatile component was removed in vacuo, and the resulting residue was partitioned between ethyl acetate (300 mL) and water (200 mL). The organic layer was washed with water (200 mL) and brine, dried (MgSO$_4$), filtered, and concentrated in vacuo. A silica gel mesh was prepared from the residue and submitted to flash chromatography (silica gel; 50-60% ethyl acetate/hexanes) to provide ketoamide 1a as a white solid (12.8 g). $^1$H NMR (DMSO-d$_6$, δ=2.5 ppm, 400 MHz): δ 8.25-8.14 (m, 1H), 7.92 (br d, J=8.0, 2H), 7.75 (br d, J=8.6, 2H), 4.61 (dd, J=18.3, 5.7, 1H), 4.53 (dd, J=18.1, 5.6, 1H), 4.22-4.12 (m, 1H), 3.43-3.35 (m, 1H), 3.30-3.23 (m, 1H), 2.18-2.20 (m, 1H), 1.90-1.70 (m, 3H), 1.40/1.34 (two app br s, 9H). LC (Cond. 1): RT=1.70 min; LC/MS: Anal. Calcd. for [M+Na]$^+$ C$_{18}$H$_{23}$BrN$_2$NaO$_4$: 433.07; found 433.09.

Analogous compounds such as intermediate 1-1a to 1-5a can be prepared by incorporating the appropriately substituted amino acid and aryl bromide isomer.

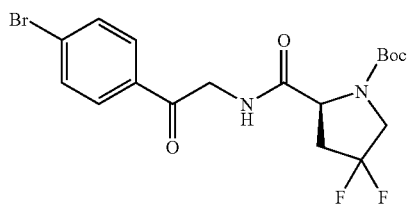

1-1a $^1$H NMR (500 MHz, DMSO-d$_6$) δ ppm 1.35/1.40 (two br s, 9H), 2.27-2.42 (m, 1H), 2.73-2.95 (m, 1H), 3.62-3.89 (m, 2H), 4.36-4.50 (m, 1H), 4.51-4.60 (m, 1H), 4.62-4.73 (m, 1H), 7.75 (d, J=8.24 Hz, 2H), 7.92 (d, J=7.63 Hz, 2H), 8.31-8.49 (m, 1H). HPLC XTERRA C-18 4.6×30 mm, 0 to 100% B over 4 minutes, 1 minute hold time, A=90% water, 10% methanol, 0.2% H$_3$PO$_4$, B=10% water, 90% methanol, 0.2% H$_3$PO$_4$, RT=1.59 minutes, 99% homogeneity index. LCMS: Anal. Calcd. for C$_{18}$H$_{21}$BrF$_2$N$_2$O$_4$: 446.06; found: 445.43 (M-H)$^-$.

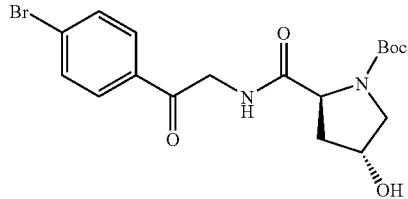

1-2a $^1$H NMR (500 MHz, DMSO-d$_6$) δ ppm (8.25 1H, s), 7.91 (2H, d, J=8.24 Hz), 7.75 (2H, d, J=8.24 Hz), 4.98 (1H, s), 4.59-4.63 (1H, m), 4.46-4.52 (1H, m), 4.23 (1H, m), 3.37 (1H, s), 3.23-3.28 (1H, m), 2.06 (1H, m), 1.88 (1H, s), 1.38 (3H, s), 1.33 (6H, s). LCMS—Phenomenex C-18 3.0×50 mm, 0 to 100% B over 4.0 minute gradient, 1 minute hold time, A=10% methanol 90% water 0.1% TFA, B=90% methanol 10% water 0.1% TFA mobile phase, RT=3.34 minutes, Anal Calcd. for C$_{18}$H$_{23}$BrN$_2$O$_5$ 427.30; found 428.08 (M+H)$^-$.

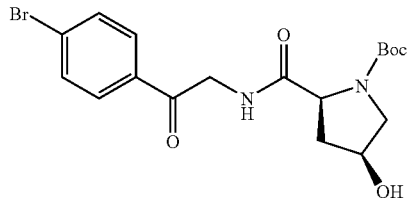

1-3a $^1$H NMR (500 MHz, DMSO-d$_6$) δ ppm 8.30 (1H, s) 7.93-7.96 (2H, m) 7.76 (2H d, J=8.24 Hz) 5.13 (1H, s) 4.66-4.71 (1H, m) 4.52-4.55 (1H, m) 4.17 (1H, m) 3.51 (1H, s) 3.16-3.19 (1H, m) 2.36 (1H, m) 1.78 (1H, s) 1.40 (s, 3H), 1.34 (s, 6H). LCMS—Phenomenex C-18 3.0×50 mm, 0 to 100% B over 4.0 minute gradient, 1 minute hold time, A=10% methanol 90% water 0.1% TFA, B=90% methanol 10% water 0.1% TFA, RT=3.69 minutes, Anal Calcd. for C$_{18}$H$_{23}$BrN$_2$O$_5$ 427.30; found 428.16 (M+H)$^+$.

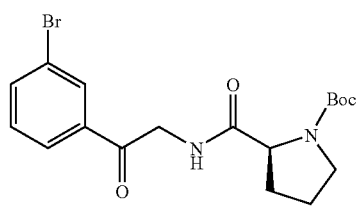

1-4a $^1$H NMR (500 MHz, DMSO-d$_6$) δ ppm 1.29-1.47 (m, 9H), 1.67-1.90 (m, 3H), 2.00-2.20 (m, 1H), 3.23-3.30 (m, 1H), 3.34-3.44 (m, 1H), 4.16 (dd, 1H), 4.57 (q, 2H), 7.51 (t, J=7.78 Hz, 1H), 7.86 (dd, J=7.93, 1.22 Hz, 1H), 7.98 (d, J=7.63 Hz, 1H), 8.11 (s, 1H), 8.15-8.29 (m, 1H). LC/MS (M+Na)$^+$= 433.12/435.12.

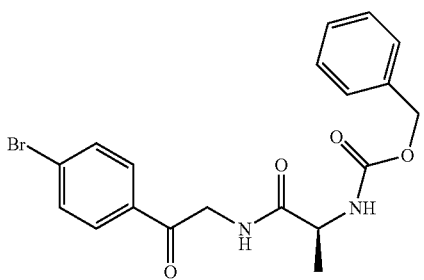

1-5a

LCMS conditions: Phenomenex LUNA C-18 4.6×50 mm, 0 to 100% B over 2 minutes, 1 minute hold time, A=90% water, 10% methanol, 0.1% TFA, B=10% water, 90% methanol, 0.1% TFA, 220 nm, 5 µL injection volume. RT=1.93 min; LRMS: Anal. Calcd. for $C_{19}H_{18}BrN_2O_4$ 418.05; found: 419.07 $(M+H)^+$.

Example 1

Step b

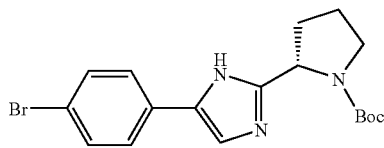

1b

A mixture of ketoamide 1a (12.8 g, 31.12 mmol) and $NH_4OAc$ (12.0 g, 155.7 mmol) in xylenes (155 mL) was heated in a sealed tube at 140° C. for 2 hours. The volatile component was removed in vacuo, and the residue was partitioned carefully between ethyl acetate and water, whereby enough saturated $NaHCO_3$ solution was added so as to make the pH of the aqueous phase slightly basic after the shaking of the biphasic system. The layers were separated, and the aqueous layer was extracted with an additional ethyl acetate. The combined organic phase was washed with brine, dried ($MgSO_4$), filtered, and concentrated in vacuo. The resulting material was recrystallized from ethyl acetate/hexanes to provide two crops of imidazole 1b as a light-yellow dense solid, weighing 5.85 g. The mother liquor was concentrated in vacuo and submitted to a flash chromatography (silica gel; 30% ethyl acetate/hexanes) to provide an additional 2.23 g of imidazole 1b. $^1$H NMR (DMSO-$d_6$, δ=2.5 ppm, 400 MHz): δ 12.17/11.92/11.86 (m, 1H), 7.72-7.46/7.28 (m, 5H), 4.86-4.70 (m, 1H), 3.52 (app br s, 1H), 3.36 (m, 1H), 2.30-1.75 (m, 4H), 1.40/1.15 (app br s, 9H). LC (Cond. 1): RT=1.71 min; >98% homogeneity index; LC/MS: Anal. Calcd. for $[M+H]^+$ $C_{18}H_{23}BrN_3O_2$: 392.10; found 391.96; HRMS: Anal. Calcd. for $[M+H]^+$ $C_{18}H_{23}BrN_3O_2$: 392.0974; found 392.0959

The optical purity of the two samples of 1b were assessed using the chiral HPLC conditions noted below (ee>99% for the combined crops; ee=96.7% for the sample from flash chromatography):

Column: Chiralpak AD, 10 um, 4.6×50 mm

Solvent: 2% ethanol/heptane (isocratic)

Flow rate: 1 mL/min

Wavelength: either 220 or 254 nm

Relative retention time: 2.83 minutes (R), 5.34 minutes (S)

Analogous compounds such as intermediates 1-1b to 1-4b can be prepared by incorporating the appropriate ketoamide.

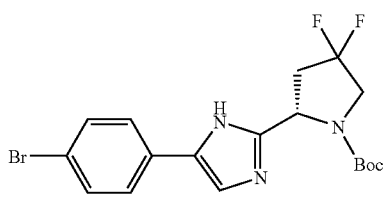

1-1b $^1$H NMR (500 MHz, DMSO-$d_6$) δ ppm 1.17/1.40 (two br s, 9H), 2.50-2.74 (m, J=25.64 Hz, 1H), 2.84-3.07 (m, 1H), 3.88 (d, J=10.07 Hz, 2H), 5.03 (s, 1H), 7.50 (d, J=8.55 Hz, 2H), 7.60 (s, 1H), 7.70 (d, J=8.55 Hz, 2H), 12.10 (s, 1H). HPLC XTERRA C-18 4.6×30 mm, 0 to 100% B over 4 minutes, 1 minute hold time, A=90% water, 10% methanol, 0.2% $H_3PO_4$, B=10% water, 90% methanol, 0.2% $H_3PO_4$, RT=1.59 minutes, 99% homogeneity index; LCMS: Anal. Calcd. for $C_{18}H_{20}BrF_2N_3O_2$: 428.27; found: 428.02 $(M)^+$.

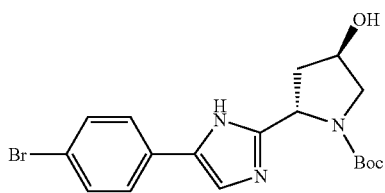

1-2b $^1$H NMR (500 MHz, DMSO-$d_6$) δ ppm 11.89-11.99 (1H, m), 7.68 (2H, d, J=8.54 Hz), 7.52-7.59 (1H, m), 7.48 (2H, d, J=8.54 Hz), 4.80 (1H, m), 4.33 (1H, s), 3.51-3.60 (1H, m), 3.34 (1H, d, J=10.99 Hz), 2.14 (1H, s), 1.97-2.05 (1H, m), 1.37 (3H, s), 1.10 (6H, s); LCMS—Phenomenex C-18 3.0×50 mm, 0 to 100% B over 4.0 minute gradient, 1 minute hold time, A=10% methanol 90% water 0.1% TFA, B=90% methanol 10% water 0.1% TFA, (RT=3.23 min) Anal Calcd. for $C_{18}H_{22}BrN_3O_3$ 408.30; found 409.12 $(M+H)^+$.

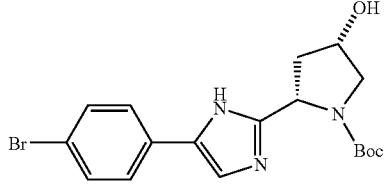

1-3b $^1$H NMR (500 MHz, DMSO-$d_6$) δ ppm 12.06-12.24 (1H, m), 7.58-7.69 (5H, m), 4.84-4.95 (1H, m), 4.34 (1H, s), 3.61 (1H, s), 3.34-3.40 (1H, m), 2.52 (1H, s), 1.92-2.20 (1H, m), 1.43 (3H, s), 1.22 (6H, s); LCMS—Phenomenex C-18 3.0×50 mm, 0 to 100% B over 4.0 minute gradient, 1 minute hold time, A=10% methanol 90% water 0.1% TFA, B=90% methanol 10% water 0.1% TFA, (RT=3.41 min) Anal Calcd. for $C_{18}H_{22}BrN_3O_3$ 408.30; found 409.15 $(M+H)^+$.

1-4b

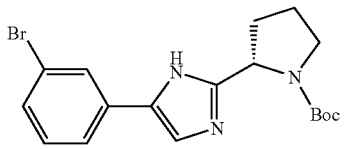

¹H NMR (500 MHz, DMSO-d₆) δ ppm 0.98-1.51 (m, 9H), 1.82-2.12 (m, 3H), 2.31-2.48 (m, 1H), 3.30-3.51 (m, 1H), 3.52-3.66 (m, 1H), 4.88-5.16 (m, 1H), 7.47 (t, J=7.93 Hz, 1H), 7.61 (d, J=7.93 Hz, 1H), 7.81 (d, J=7.93 Hz, 1H), 8.04 (s, 1H), 8.12 (d, J=28.38 Hz, 1H), 14.65 (s, 1H). LC/MS (M+H)⁺= 391.96/393.96.

Additional imidazole analogs made following procedures similar to those described above.

LC conditions: Condition 1: Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, 220 nm, 5 μL injection volume.

Condition 2: Phenomenex LUNA C-18 4.6×50 mm, 0 to 100% B over 2 minutes, 1 minute hold time, A=90% water, 10% methanol, 0.1% TFA, B=10% water, 90% methanol, 0.1% TFA, 220 nm, 5 μL injection volume.

Example 1

Step c

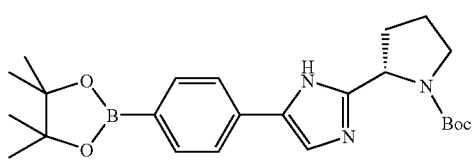

Pd(Ph₃P)₄ (469 mg, 0.406 mmol) was added to a pressure tube containing a mixture of bromide 1b (4.008 g, 10.22 mmol), bis(pinacolato)diboron (5.422 g, 21.35 mmol), potassium acetate (2.573 g, 26.21 mmol) and 1,4-dioxane (80 mL). The reaction flask was purged with nitrogen, capped and heated with an oil bath at 80° C. for 16.5 hours. The reaction mixture was filtered and the filtrate was concentrated in vacuo. The crude material was partitioned carefully between CH₂Cl₂ (150 mL) and an aqueous medium (50 mL water+10 mL saturated NaHCO₃ solution). The aqueous layer was extracted with CH₂Cl₂, and the combined organic phase was dried (MgSO₄), filtered, and concentrated in vacuo. The resulting material was purified with flash chromatography (sample was loaded with eluting solvent; 20-35% ethyl acetate/CH₂Cl₂) to provide boronate 1c, contaminated with

| Example | Structure | Data |
|---|---|---|
| 1-5b | 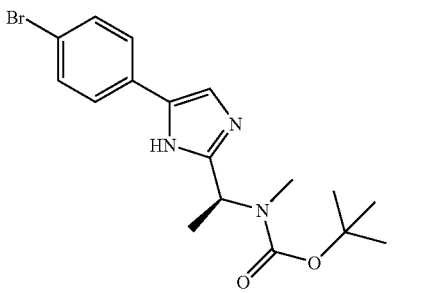 | RT = 1.70 minutes (condition 2, 98%); LRMS: Anal. Calcd. for C₁₉H₁₈BrN₃O₂ 399.05; found: 400.08 (M + H)⁺. |
| 1-6b | 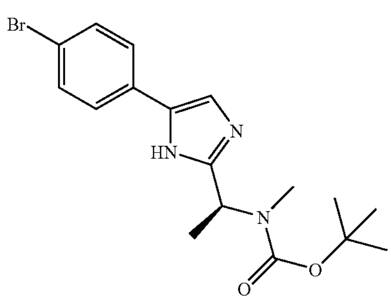 | RT = 1.64 minutes (condition 2, 98%); LRMS: Anal. Calcd. for C₁₇H₂₂N₃O₂ 379.09; found: 380.06 (M + H)⁺. |
| 1-7b | 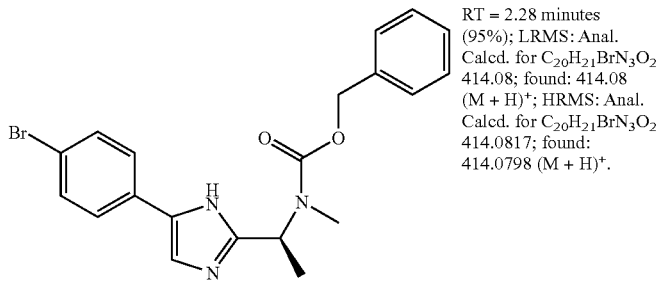 | RT = 2.28 minutes (95%); LRMS: Anal. Calcd. for C₂₀H₂₁BrN₃O₂ 414.08; found: 414.08 (M + H)⁺; HRMS: Anal. Calcd. for C₂₀H₂₁BrN₃O₂ 414.0817; found: 414.0798 (M + H)⁺. | pinacol, as an off-white dense solid; the relative mole ratio of 1c to pinacol was about 10:1 ($^1$H NMR). The sample weighed 3.925 g after ~2.5 days exposure to high vacuum. $^1$H NMR (DMSO-d$_6$, δ=2.5 ppm, 400 MHz): 12.22/11.94/11.87 (m, 1H), 7.79-7.50/7.34-7.27 (m, 5H), 4.86-4.70 (m, 1H), 3.52 (app br s, 1H), 3.36 (m, 1H), 2.27-1.77 (m, 4H), 1.45-1.10 (m, 21H). LC (Cond. 1): RT=1.64 min; LC/MS: Anal. Calcd. for [M+H]$^+$ C$_{24}$H$_{35}$BN$_3$O$_4$: 440.27; found 440.23.

Analogous compounds such as intermediates 1-1c to 1-4c can be prepared by incorporating the appropriate aryl bromide.

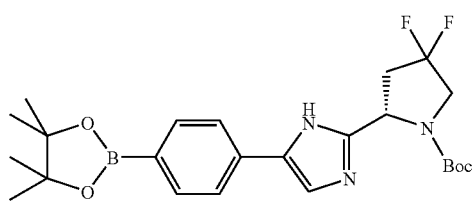

1-1c $^1$H NMR (500 MHz, DMSO-d$_6$) δ ppm 1.16 (s, 8H), 1.29 (s, 13H), 2.51-2.72 (m, 1H), 2.84-3.03 (m, 1H), 3.79-4.00 (m, 2H), 4.88-5.21 (m, 1H), 7.62 (d, J=7.93 Hz, 2H), 7.67 (s, 1H), 7.76 (d, J=7.93 Hz, 2H), 12.11/12.40 (two br s, 1H). HPLC GEMINI C-18 4.6×50 mm, 0 to 100% B over 4 minutes, 1 minute hold time, A=95% water, 5% acetonitrile, 0.1% NH$_4$OAc, B=5% water, 95% acetonitrile, 0.1% NH$_4$OAc, RT=1.62 minutes, 99% homogeneity index. LCMS: Anal. Calcd. for C$_{34}$H$_{32}$BF$_2$N$_3$O$_4$: 475.34; found: 474.78 (M–H)$^-$.

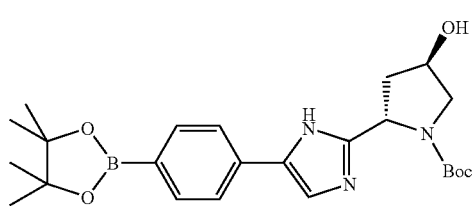

1-2c $^1$H NMR (500 MHz, DMSO-d$_6$) δ ppm 11.97 (1H, m), 7.62-7.75 (5H, m), 5.05 (1H d, J=3.36 Hz), 4.82 (m, 1H), 4.35 (m, 1H), 3.58 (1H, m), 2.389 (1H, s), 2.17 (1 H, m), 1.38 (3H, s), 1.30 (12H, s), 1.1 (6H, s); LCMS—Phenomenex C-18 3.0×50 mm, 0 to 100% B over 4.0 minute gradient, 1 minute hold time, A=5% acetonitrile, 95% water, 10 mm ammonium acetate, B=95% acetonitrile, 5% water, 10 mm ammonium acetate, RT=3.63 minutes, Anal. Calcd. for C$_{24}$H$_{34}$BN$_3$O$_5$ 455.30; found 456.31 (M+H)$^+$.

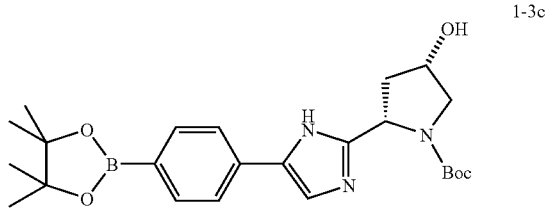

1-3c $^1$H NMR (500 MHz, DMSO-d$_6$) δ ppm 12.05-12.24 (1H, m), 7.61-7.73 (5H, m), 4.83-5.01 (1H, m), 4.33 (1H, s), 3.54-3.63 (1H, m), 3.39-3.80 (1H, m), 2.38-2.49 (1H, m), 1.98-2.01 (1H, m), 1.42 (3H, s), 1.34 (12H, s), 1.21 (6H, s); LCMS—Phenomenex C-18 3.0×50 mm, 0 to 100% B over 4.0 minute gradient, 1 minute hold time, A=10% methanol 90% water 0.1% TFA, B=90% methanol 10% water 0.1% TFA, RT=3.64 minutes, Anal. Calcd. for C$_{24}$H$_{34}$BN$_3$O$_5$ 455.30; found 456.30 (M+H)$^+$.

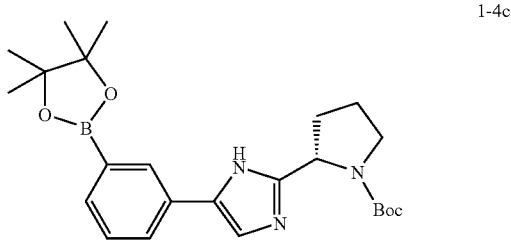

1-4c $^1$H NMR (500 MHz, DMSO-d$_6$) δ ppm 1.02-1.54 (m, 21H), 1.75-2.07 (m, 3H), 2.09-2.33 (m, 1H), 3.32-3.44 (m, 1H), 3.55 (s, 1H), 4.69-4.94 (m, 1H), 7.33 (t, J=7.32 Hz, 1H), 7.41-7.57 (m, 2H), 7.84 (d, J=7.32 Hz, 1H), 8.08 (s, 1H), 11.62-12.07 (m, 1H). LC/MS (M+H)$^+$=440.32.

Additional boronic esters: Conditions for 1-5c through 1-10c

LCMS conditions: Condition 1: Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, 220 nm, 5 μL injection volume.

Condition 2: Phenomenex LUNA C-18 4.6×50 mm, 0 to 100% B over 2 minutes, 1 minute hold time, A=90% water, 10% methanol, 0.1% TFA, B=10% water, 90% methanol, 0.1% TFA, 220 nm, 5 μL injection volume.

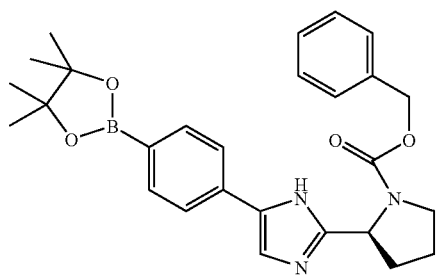

1-5c

RT = 1.84 minutes (condition 2); LCMS: Anal. Calcd. for C$_{27}$H$_{32}$BN$_3$O$_4$ 473; found: 474 (M + H)$^+$.

-continued

| | | |
|---|---|---|
| 1-6c | 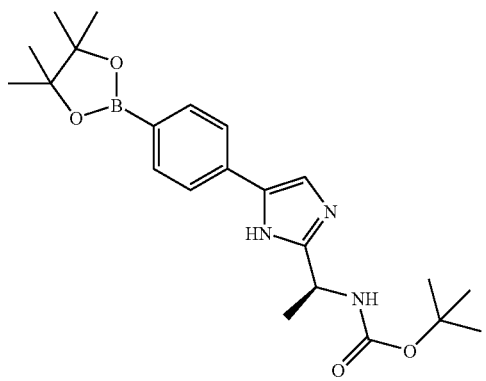 | RT = 1.84 minutes (condition 2); LCMS: Anal. Calcd. for $C_{22}H_{32}BN_3O_4$ 413; found: 414 $(M + H)^+$. |
| 1-7c | 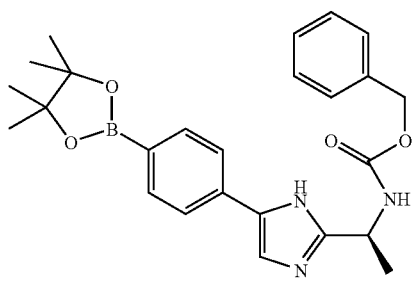 | RT = 1.85 minutes (condition 2); LRMS: Anal. Calcd. for $C_{25}H_{31}BN_3O_4$ 448; found: 448 $(M + H)^+$. |
| 1-8c | 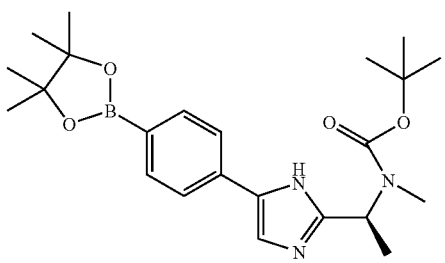 | RT = 2.49 (76%, boronic ester) and 1.81 (21.4%, boronic acid); LCMS: Anal. Calcd. for $C_{23}H_{35}N_3O_4B$ 428.27; found: 428.27 $(M + H)^+$; HRMS: Anal. Calcd. for $C_{23}H_{35}N_3O_4B$ 428.2721; found: 428.2716 $(M + H)^+$. |
| 1-9c | 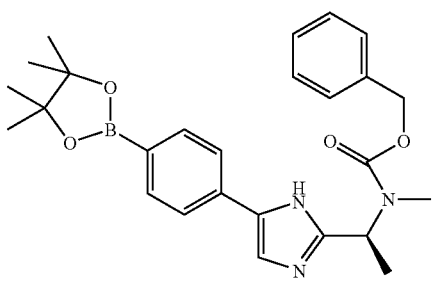 | RT = 2.54 (74.2%, boronic ester) and 1.93 (25.8%, boronic acid); LRMS: Anal. Calcd. for $C_{26}H_{33}N_3O_4B$ 462.26; found: 462.25 $(M + H)^+$; HRMS: Anal. Calcd. for $C_{26}H_{33}N_3O_4B$ 462.2564; found: 462.2570 $(M + H)^+$. |
| 1-10c | 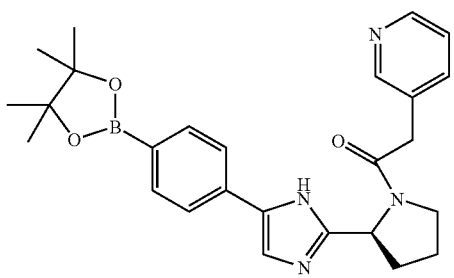 | RT = 1.91 (64.5%, boronic ester) and 1.02 (33.8%, boronic acid); LRMS: Anal. Calcd. for $C_{26}H_{32}N_4O_3{}^{10}B$ 458.26; found: 458.28 $(M + H)^+$; HRMS: Anal. Calcd. for $C_{26}H_{32}N_4O_3{}^{10}B$ 458.2604; found 458.2617 $(M + H)^+$. |

Example 1

Step d di-tert-butyl (2S,2'S)-2,2'-(4,4'-biphenyldiylbis(1H-imidazole-5,2-diyl))di(1-pyrrolidinecarboxylate)

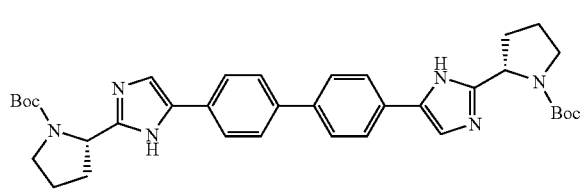

1d

Pd(Ph₃P)₄ (59.9 mg, 0.0518 mmol) was added to a mixture of bromide 1b (576.1 mg, 1.469 mmol), boronate 1c (621.8 mg, 1.415 mmol), NaHCO₃ (400.4 mg, 4.766 mmol) in 1,2-dimethoxyethane (12 mL) and water (4 mL). The reaction mixture was flushed with nitrogen, heated with an oil bath at 80° C. for 5.75 hours, and then the volatile component was removed in vacuo. The residue was partitioned between 20% methanol/CHCl₃ (60 mL) and water (30 mL), and the aqueous phase was extracted with 20% methanol/CHCl₃ (30 mL). The combined organic phase was washed with brine, dried (MgSO₄), filtered, and concentrated in vacuo. A silica gel mesh was prepared from the resulting crude material and submitted to flash chromatography (ethyl acetate) to provide dimer 1d, contaminated with Ph₃PO, as an off-white solid (563 mg). $^1$H NMR (DMSO-$d_6$, δ=2.5 ppm, 400 MHz): δ 12.21-12-16/11.95-11.78 (m, 2H), 7.85-7.48/7.32-7.25 (m, 10H), 4.90-4.71 (m, 2H), 3.60-3.32 (m, 4H), 2.30-1.79 (m, 8H), 1.46-1.10 (m, 18H). LC (Cond. 1b): RT=1.77 min; LC/MS: Anal. Calcd. for [M+H]$^+$ $C_{36}H_{45}BN_6O_4$: 625.35; found 625.48.

Additional biphenyl analogs were prepared similarly.

LC conditions for Examples 1-5d through 1-7d: Condition 1: Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, 220 nm, 5 μL injection volume.

Condition 2: Phenomenex LUNA C-18 4.6×50 mm, 0 to 100% B over 2 minutes, 1 minute hold time, A=90% water, 10% methanol, 0.1% TFA, B=10% water, 90% methanol, 0.1% TFA, 220 nm, 5 μL injection volume.

| Example | Compound Name | Structure | Characterization Data |
|---|---|---|---|
| 1-5d | di-tert-butyl (4,4'-biphenyldiylbis(1H-imidazol-5,2-diyl(1S)-1,1-ethanediyl))bis(methylcarbamate) | 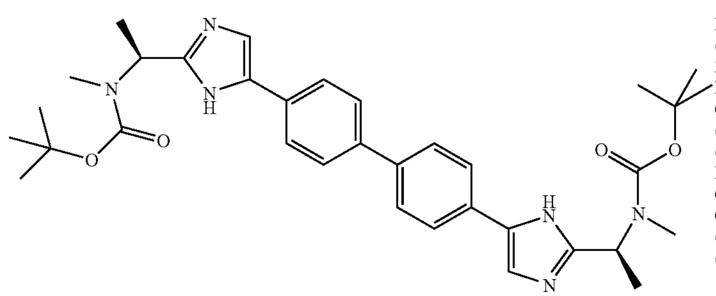 | RT = 1.64 minutes (>95%); Condition 2; LCMS: Anal. Calcd $C_{34}H_{45}N_6O_4$ 601.35; found: 601.48 (M + H)$^+$; LRMS: Anal. Calcd. for $C_{34}H_{44}N_6O_4$ 600.34; found: 601.32 (M + H)$^+$. |
|  | Prepared from 1-8c and 1-6b | | |
| 1-6d | tert-butyl (2S)-2-(5-(4'-(2-((1S)-1-((tert-butoxycarbonyl)(methyl)amino)ethyl)-1H-imidazol-5-yl)-4-biphenylyl)-1H-imidazol-2-yl)-1-pyrrolidinecarboxylate | 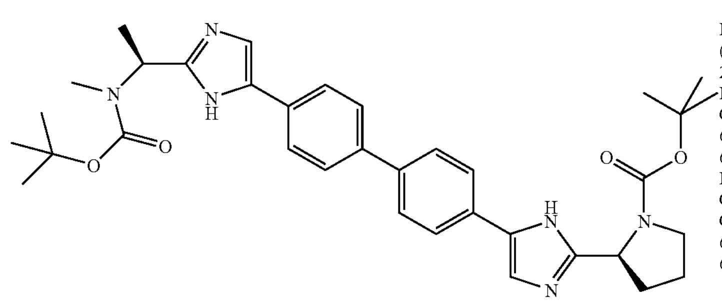 | RT = 1.63 minutes (>95%); Condition 2; LCMS: Anal. Calcd $C_{35}H_{45}N_6O_4$ 613.34; found: 613.56 (M + H)$^+$; LRMS: Anal. Calcd. for $C_{35}H_{44}N_6O_4$ 612.34; found 613.33 (M + H)$^+$. |
|  | Prepared from 1-8c and 1b | | |

| Example | Compound Name | Structure | Characterization Data |
|---|---|---|---|
| 1-7d | benzyl (2S)-2-(5-(4'-(2-((1S)-1-((tert-butoxycarbonyl)(methyl)amino)ethyl)-1H-imidazol-5-yl)-4-biphenylyl)-1H-imidazol-2-yl)-1-pyrrolidinecarboxylate | 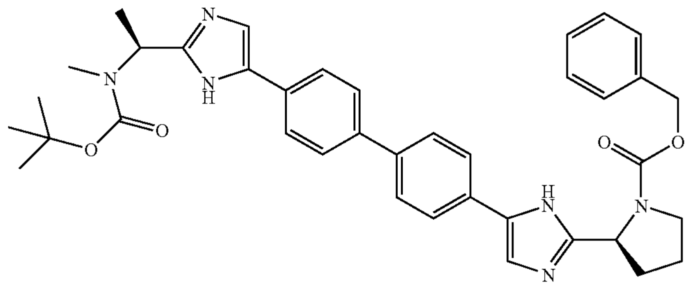 | RT = 1.65 minutes (>95%); Condition 2; LCMS: Anal. Calcd $C_{38}H_{43}N_6O_4$ 647.33; found: 647.44 (M + H)$^+$; LRMS: Anal. Calcd. for $C_{38}H_{42}N_6O_4$ 646.33; found 647.34 (M + H)$^+$. |

Prepared from 1-6b and 1-5c

Example 1

Step e 5,5'-(4,4'-biphenyldiyl)bis(2-((2S)-2-pyrrolidinyl)-1H-imidazole)

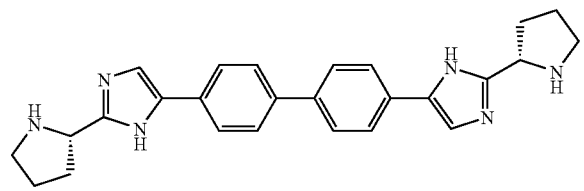

1e

A mixture of carbamate 1d (560 mg) and 25% TFA/$CH_2Cl_2$ (9.0 mL) was stirred at ambient condition for 3.2 hours. The volatile component was removed in vacuo, and the resulting material was free based using an MCX column (methanol wash; 2.0 M $NH_3$/methanol elution) to provide pyrrolidine 1e as a dull yellow solid (340 mg). $^1$H NMR (DMSO-$d_6$, δ=2.5 ppm, 400 MHz): δ 11.83 (br s, 2H), 7.80 (d, J=8.1, 4H), 7.66 (d, J=8.3, 4H), 7.46 (br s, 2H), 4.16 (app t, J=7.2, 2H), 2.99-2.69 (m, 6H), 2.09-2.00 (m, 2H), 1.94-1.66 (m, 6H). LC (Cond. 1): RT=1.27 min; >98% homogeneity index; LC/MS: Anal. Calcd. for [M+H]$^-$ $C_{26}H_{29}N_6$: 425.25; found 425.25; HRMS: Anal. Calcd. for [M+H]$^-$ $C_{26}H_{29}N_6$: 425.2454; found 425.2448

Additional analogs were prepared similarly:

| Example | Compound Name | Structure | Data |
|---|---|---|---|
| 1-5e | | 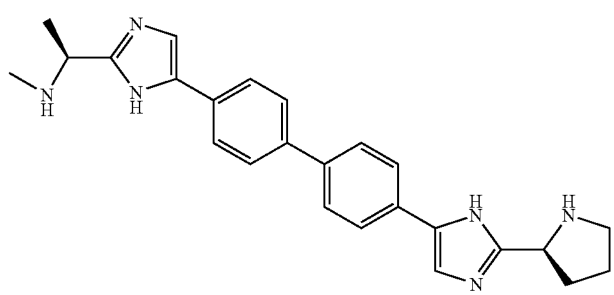 | RT = 1.37 min; LCMS: Anal. Calcd. for $C_{25}H_{28}N_6$ 412; found: 413 (M + H)$^+$. |

Prepared from 1-6d

-continued

| Example | Compound Name | Structure | Data |
|---|---|---|---|
| 1-6e | | 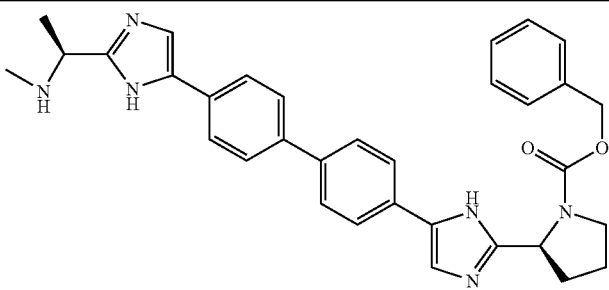<br>Prepared from 1-7d | RT = 1.43 min;<br>LCMS: Anal.<br>Calcd. for<br>$C_{33}H_{35}N_6O_2$ 547;<br>found: 547<br>$(M + H)^+$. |
| 1-7e | | 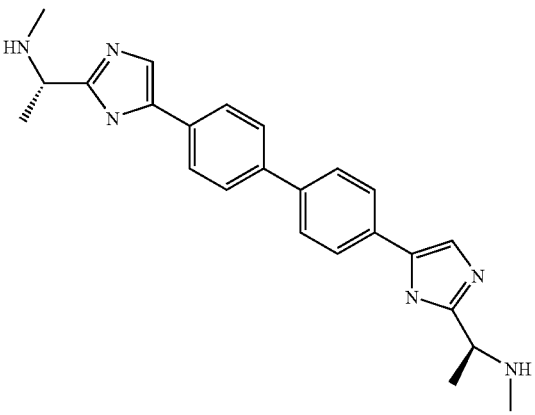<br>Prepared from 1-5d | RT = 1.12 min;<br>LRMS: Anal.<br>Calcd. for<br>$C_{24}H_{28}N_6$ 400.24;<br>found 401.22<br>$(M + H)^+$. |

LC Conditions for 1-5e through 1-7e: Phenomenex LUNA C-18 4.6×50 mm, 0 to 100% B over 2 minutes, 1 minute hold time, A=90% water, 10% methanol, 0.1% TFA, B=10% water, 90% methanol, 0.1% TFA, 220 nm, 5 μL injection volume.

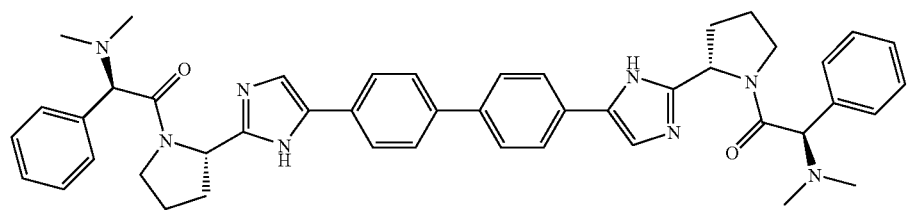

Example 1

(1R,1'R)-2,2'-(4,4'-biphenyldiylbis(1H-imidazole-5,2-diyl(2S)-2,1-pyrrolidinediyl))bis(N,N-dimethyl-2-oxo-1-phenylethanamine)

HATU (44.6 mg, 0.117 mmol) was added to a mixture of pyrrolidine 1e (22.9 mg, 0.054 mmol), diisopropylethylamine (45 μL, 0.259 mmol) and Cap-1 (28.1 mg, 0.13 mmol) in DMF (1.5 mL), and the resulting mixture was stirred at ambient for 90 minutes. The volatile component was removed in vacuo, and the residue was purified first by MCX (methanol wash; 2.0 M $NH_3$/methanol elution) and then by a reverse phase HPLC system ($H_2O$/methanol/TFA) to provide the TFA salt of Example 1 as an off-white foam (44.1 mg). $^1$H NMR (DMSO-$d_6$, δ=2.5 ppm, 400 MHz): δ 10.25 (br s, 2H), 8.20-7.10 (m, 20H), 5.79-5.12 (m, 4H), 4.05-2.98 (m, 4H), 2.98-2.62 (m, 6H), 2.50-1.70 (m, 14H), [Note: the signal of the imidazole NH was too broad to assign a chemical shift]; LC (Cond. 1): RT=1.40 min; >98% homogeneity index; LC/MS: Anal. Calcd. for $[M+H]^+$ $C_{46}H_{51}N_8O_2$: 747.41; found 747.58

| Example | Compound Name | Structure | Characterization Data |
|---|---|---|---|
| 24-18-1 | dimethyl (4,4'-biphenyldiylbis(1H-imidazole-5,2-diyl(1S)-1,1-ethanediyl(methylimino)((1R)-2-oxo-1-phenyl-2,1-ethanediyl)))biscarbamate | from 1-7e and Cap-4 | RT = 1.55 min[1]; LRMS: Anal. Calcd. for $C_{44}H_{46}N_8O_6$ 782.35; found: 783.37 (M + H)$^+$; HRMS: Anal. Calcd. for $C_{44}H_{47}N_8O_6$ 783.3619 found: 783.3630 (M + H)$^+$. |
| 24-18-2 | (2R,2'R)-N,N'-(4,4'-biphenyldiylbis(1H-imidazole-5,2-diyl(1S)-1,1-ethanediyl))bis(2-(dimethylamino)-N-methyl-2-phenylacetamide) | from 1-7e and Cap-1 | RT = 1.16 min[1]; LRMS: Anal. Calcd. for $C_{44}H_{50}N_8O_2$ 722.41; found: 723.41 (M + H)$^+$; HRMS: Anal. Calcd. for $C_{44}H_{51}N_8O_2$ 723.4135 found: 723.4152 (M + H)$^+$. |

-continued

| Example | Compound Name | Structure | Characterization Data |
|---|---|---|---|
| 24-18-3 | (2R,2'R)-N,N'-(4,4'-biphenyldiylbis(1H-imidazol-5,2-diyl(1S)-1,1-ethanediyl))bis(N-methyl-2-phenyl-2-(1-piperidinyl)acetamide) | from 1-7e and Cap-14 | RT = 1.28 min[1]; LRMS: Anal. Calcd. for $C_{50}H_{58}N_8O_2$ 802.47; found: 803.50 $(M + H)^+$; HRMS: Anal. Calcd. for $C_{50}H_{59}N_8O_2$ 803.4761 found: 803.4778 $(M + H)^+$. |
| 24-18-4 | methyl ((1R)-2-((2S)-2-(5-(4'-(2-((1S)-1-(((2R)-2-((methoxycarbonyl)amino)-2-phenylacetyl)(methyl)amino)ethyl)-1H-imidazol-5-yl)-4-biphenylyl)-1H-imidazol-2-yl)-1-pyrrolidinyl)-2-oxo-1-phenylethyl)carbamate | Prepared from 1-5e and Cap-4 | RT = 1.53 min[1]; LRMS: Anal. Calcd. for $C_{45}H_{46}N_8O_6$ 794.35; found: 795.39 $(M + H)^+$; HRMS: Anal. Calcd. for $C_{45}H_{47}N_8O_6$ 795.3619 found: 795.3616 $(M + H)^+$. |
| 24-18-5 | (2R)-2-(dimethylamino)-N-((1S)-1-(5-(4'-(2-((2S)-1-((2R)-2-(dimethylamino)-2-phenylacetyl)-2-pyrrolidinyl)-1H-imidazol-5-yl)-4-biphenylyl)-1H-imidazol-2-yl)ethyl)-N-methyl-2-phenylacetamide | Prepared from 1-5e and Cap-1 | RT = 1.21[1]; LRMS: Anal. Calcd. for $C_{45}H_{50}N_8O_2$ 734.41; found: 735.46 $(M + H)^+$; HRMS: Anal. Calcd. for $C_{45}H_{51}N_8O_2$ 735.4135 found: 735.4136 $(M + H)^+$. |

[1]LC Conditions for 24-18-1 through 24-18-5: Phenomenex LUNA C-18 4.6 x 50 mm, 0 to 100% B over 2 minutes, 1 minute hold time, A = 90% water, 10% methanol, 0.1% TFA, B = 10% water, 90% methanol, 0.1% TFA, 220 nm, 5 µL injection volume.

Example 28 methyl((1R)-2-oxo-1-phenyl-2-((2S)-2-(5-(4'-(2-((2S)-1-(phenylacetyl)-2-pyrrolidinyl)-1H-imidazol-5-yl)-4-biphenylyl)-1H-imidazol-2-yl)-1-pyrrolidinyl)ethyl)carbamate


Example 28

Step a

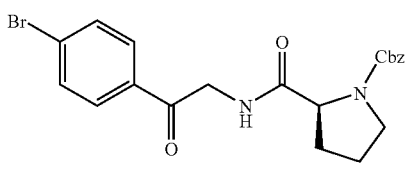

28a

HATU (19.868 g, 52.25 mmol) was added to a heterogeneous mixture of N-Cbz-L-proline (12.436 g, 49.89 mmol) and the HCl salt of 2-amino-1-(4-bromophenyl)ethanone (12.157 g, 48.53 mmol) in DMF (156 mL). The mixture was lowered in an ice-water bath, and immediately afterward N,N-diisopropylethylamine (27 mL, 155 mmol) was added dropwise to it over 13 minutes. After the addition of the base was completed, the cooling bath was removed and the reaction mixture was stirred for an additional 50 minutes. The volatile component was removed in vacuo; water (125 mL) was added to the resulting crude solid and stirred for about 1 hour. The off-white solid was filtered and washed with copious water, and dried in vacuo to provide ketoamide 28a as a white solid (20.68 g). $^1$H NMR (DMSO-d$_6$, δ=2.5 ppm, 400 MHz): δ 8.30 (m, 1H), 7.91 (m, 2H), 7.75 (d, J=8.5, 2H), 7.38-7.25 (m, 5H), 5.11-5.03 (m, 2H), 4.57-4.48 (m, 2H), 4.33-4.26 (m, 1H), 3.53-3.36 (m, 2H), 2.23-2.05 (m, 1H), 1.94-1.78 (m, 3H); LC (Cond. 1): RT=1.65 min; 98% homogeneity index; LC/MS: Anal. Calcd. for [M+H]$^+$ $C_{21}H_{22}BrN_2O_4$: 445.08; found 445.31.

Example 28

Step b

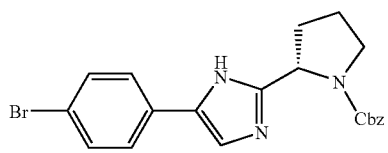

28b

Ketoamide 28a (10.723 g, 24.08 mmol) was converted to 28b according to the procedure described for the synthesis of carbamate 1b, with the exception that the crude material was purified by flash chromatography (sample was loaded with eluting solvent; 50% ethyl acetate/hexanes). Bromide 28b was retrieved as an off-white foam (7.622 g). $^1$H NMR (DMSO-d$_6$, δ=2.5 ppm, 400 MHz): δ 12.23/12.04/11.97 (m, 1H), 7.73-6.96 (m, 10H), 5.11-4.85 (m, 3H), 3.61 (m, 1H), 3.45 (m, 1H), 2.33-184 (m, 4H). LC (Cond. 1): RT=1.42 min; >95% homogeneity index; LC/MS: Anal. Calcd. for [M+H]$^+$ $C_{21}H_{21}BrN_3O_2$: 426.08; found 426.31; HRMS: Anal. Calcd. for [M+H]$^+$ $C_{21}H_{21}BrN_3O_2$: 426.0817; found: 426.0829. The optical purity of 28b was assessed using the following chiral HPLC methods, and an ee of 99% was observed.

Column: Chiralpak AD, 10 um, 4.6×50 mm

Solvent: 20% ethanol/heptane (isocratic)

Flow rate: 1 mL/min

Wavelength: 254 nm

Relative retention time: 1.82 minutes (R), 5.23 minutes (S)

Example 28

Step c benzyl tert-butyl(2S,2'S)-2,2'-(4,4'-biphenyldiylbis(1H-imidazole-5,2-diyl))di(1-pyrrolidinecarboxylate)

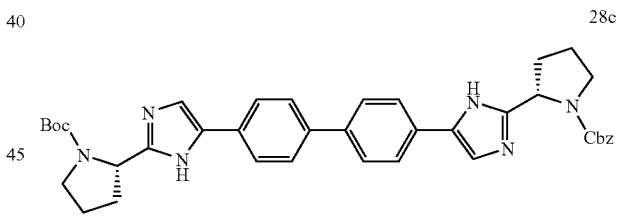

28c

Pd(Ph$_3$P)$_4$ (711.4 mg, 0.616 mmol) was added to a mixture of boronate ester 1c (7.582 g, ~17 mmol), bromide 28b (7.62 g, 17.87 mmol), NaHCO$_3$ (4.779 g, 56.89 mmol) in 1,2-dimethoxyethane (144 mL) and water (48 mL). The reaction mixture was purged with N$_2$ and heated with an oil bath at 80° C. for 15.5 hours, and then the volatile component was removed in vacuo. The residue was partitioned between CH$_2$Cl$_2$ and water, and the aqueous layer was extracted with CH$_2$Cl$_2$. The combined organic phase was dried (MgSO$_4$), filtered, and concentrated in vacuo. The resulting material was submitted to flash chromatography (sample was loaded as a silica gel mesh; ethyl acetate used as eluent) to provide biphenyl 28c as an off-white foam containing Ph$_3$PO impurity (7.5 g). $^1$H NMR (DMSO-d$_6$, δ=2.5 ppm, 400 MHz): δ 12.24-12.19 (m, 0.36H), 12.00-11.82 (m, 1.64H), 7.85-6.98 (15H), 5.12-4.74 (4H), 3.68-3.34 (4H), 2.34-1.79 (8H), 1.41/1.17 (two brS, 9H); LC (Cond. 1): RT=1.41 minutes; LC/MS: Anal. Calcd. for [M+H]$^+$ $C_{39}H_{43}N_6O_4$: 659.34; found 659.52; HRMS: Anal. Calcd. for [M+H]$^+$ $C_{39}H_{43}N_6O_4$: 659.3346; found 659.3374.

Example 28

Step d tert-butyl(2S)-2-(5-(4'-(2-((2S)-2-pyrrolidinyl)-1H-imidazol-5-yl)-4-biphenylyl)-1H-imidazol-2-yl)-1-pyrrolidinecarboxylate

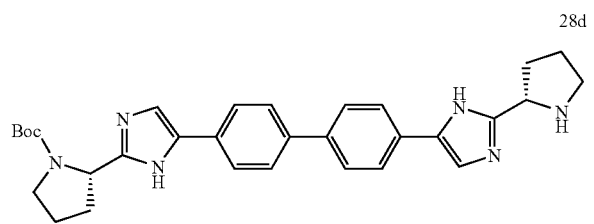

K$_2$CO$_3$ (187.8 mg, 1.36 mmol) was added to a mixture of catalyst (10% Pd/C; 205.3 mg), carbamate 28c (1.018 g, ~1.5 mmol), methanol (20 mL) and 3 pipet-drops of water. A balloon of H$_2$ was attached and the mixture was stirred for 6 hours. Then, additional catalyst (10% Pd/C, 100.8 mg) and K$_2$CO$_3$ (101.8 mg, 0.738 mmol) were added and stirring continued for 3.5 hours. During the hydrogenation process, the balloon of H$_2$ was changed at intervals three times. The reaction mixture was filtered through a pad of diatomaceous earth (Celite® 521), and the filterate was removed in vacuo. The resulting crude material was submitted to flash chromatography using a short column (sample was loaded as a silica gel mesh; 0-20% methanol/CH$_2$Cl$_2$ used as eluent) to provide 28d as a light-yellow foam (605.6 mg). $^1$H NMR (DMSO-d$_6$, δ=2.5 ppm, 400 MHz): δ 12.18/11.89/11.82 (three br s, 2H), 7.83-7.29 (m, 10H), 4.89-4.73 (m, 1H), 4.19 (app t, J=7.2, 1H), 3.55 (app br s 1H), 3.40-3.35 (m, 1H), 3.02-2.96 (m, 1H), 2.91-2.84 (m, 1H), 2.30-1.69 (m, 8H), 1.41/1.16 (two br s, 9H). Note: the signal of pyrrolidine NH appears to have overlapped with signals in the 3.6-3.2 ppm region; LC (Cond. 1): RT=1.21 min; >95% homogeneity index; LC/MS: Anal. Calcd. for [M+H]$^+$C$_{31}$H$_{37}$N$_6$O$_2$: 525.30; found 525.40.

Example 28

Step e-f

Example 28

Step e tert-butyl(2S)-2-(5-(4'-(2-((2S)-1-((2R)-2-((methoxycarbonyl)amino)-2-phenylacetyl)-2-pyrrolidinyl)-1H-imidazol-5-yl)-4-biphenylyl)-1H-imidazol-2-yl)-1-pyrrolidinecarboxylate

Example 28

Step f methyl((1R)-2-oxo-1-phenyl-2-((2S)-2-(5-(4'-(2-((2S)-2-pyrrolidinyl)-1H-imidazol-5-yl)-4-biphenylyl)-1H-imidazol-2-yl)-1-pyrrolidinyl)ethyl)carbamate

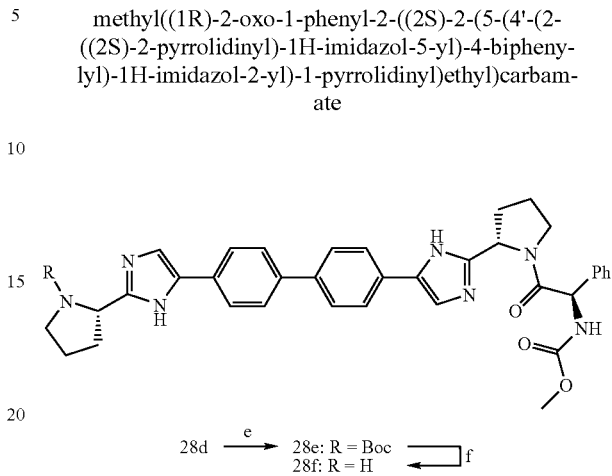

Step e: HATU (316.6 mg, 0.833 mmol) was added to a DMF (7.0 mL) solution of pyrrolidine 28d (427 mg, 0.813 mmol), Cap-4 (177.6 mg, 0.849 mmol) and diisopropylethylamine (0.32 mL, 1.84 mmol), and the reaction mixture was stirred for 45 minutes. The volatile component was removed in vacuo, and the residue was partitioned between CH$_2$Cl$_2$ (50 mL) and an aqueous medium (20 mL H$_2$O+1 mL saturated NaHCO$_3$ solution). The aqueous phase was re-extracted with CH$_2$Cl$_2$, and the combined organic phase was dried (MgSO$_4$), filtered, and concentrated in vacuo. The resulting yellow oil was purified by flash chromatography (silica gel; ethyl acetate) to provide 28e as a yellow foam (336 mg). LC (Cond. 1): RT=1.68 min; 91% homogeneity index; LC/MS: Anal. Calcd. for [M+H]$^+$ C$_{41}$H$_{46}$N$_7$O$_5$: 716.35; found 716.53.

Step f: Carbamate 28e was elaborated to amine 28f by employing the procedure described in the conversion of 1d to 1e. LC (Cond. 1): RT=1.49 min; >98% homogeneity index. LC/MS: Anal. Calcd. for [M+H]$^+$ C$_{36}$H$_{38}$N$_7$O$_3$: 616.30; found 616.37; HRMS: Anal. Calcd. for [M+H]$^+$ C$_{36}$H$_{38}$N$_7$O$_3$: 616.3036; found 616.3046.

Example 28 methyl((1R)-2-oxo-1-phenyl-2-((2S)-2-(5-(4'-(2-((2S)-1-(phenylacetyl)-2-pyrrolidinyl)-1H-imidazol-5-yl)-4-biphenylyl)-1H-imidazol-2-yl)-1-pyrrolidinyl)ethyl)carbamate

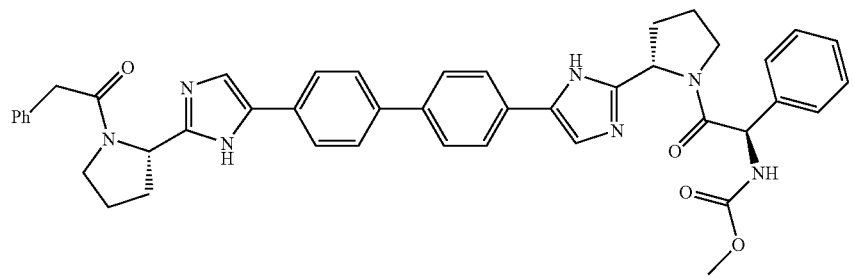

Amine 28f was converted to the TFA salt of Example 28 by employing the last step of the synthesis of Example 1. $^1$H NMR (DMSO-$d_6$, δ=2.5 ppm, 400 MHz): δ 8.21-7.03 (m, 21H), 5.78-5.14 (3H), 3.98-3.13 (m, 9H; includes the signal for OCH$_3$ at 3.54 & 3.53), 2.45-1.72 (m, 8H). LC (Cond. 1): RT=1.66 minutes, >98% homogeneity index; LC/MS: Anal. Calcd. for [M+H]$^+$ C$_{44}$H$_{44}$N$_7$O$_4$: 734.35; found 734.48; HRMS: Anal. Calcd. for [M+H]$^+$ C$_{44}$H$_{44}$N$_7$O$_4$: 734.3455; 734.3455.

Example 121

(1R,1'R)-2,2'-((2,2'-dimethyl-4,4'-biphenyldiyl)bis(1H-imidazole-5,2-diyl(2S)-2,1-pyrrolidinediyl))bis(N,N-dimethyl-2-oxo-1-phenylethanamine)

(3.01 g, 10.13 mmol) and tri-n-butyl(1-ethoxyvinyl)stannane (3.826 g, 10.59 mmol) and heated at 80° C. for ~17 hours. The reaction mixture was treated with water (15 mL), cooled to ~0° C. (ice/water), and then NBS (1.839 g, 10.3 mmol) was added in batches over 7 minutes. After about 25 minutes of stirring, the volatile component was removed in vacuo, and the residue was partitioned between CH$_2$Cl$_2$ and water. The aqueous layer was extracted with CH$_2$Cl$_2$, and the combined organic phase was dried (MgSO$_4$), filtered, and concentrated in vacuo. The resulting crude material was purified by a gravity chromatography (silica gel; 4% ethyl acetate/hexanes) to provide bromide 121a as a brownish-yellow solid (2.699 g); the sample is impure and contains stannane-derived impurities, among others. $^1$H NMR (CDCl$_3$, δ=7.24,

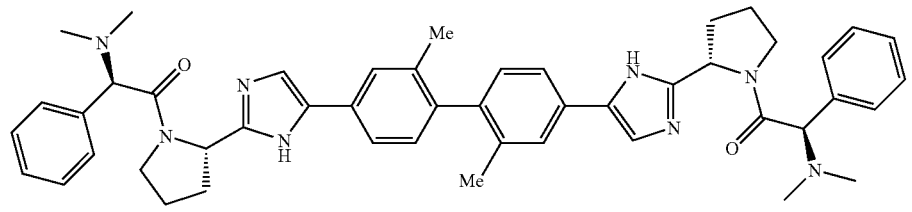

Example 121

Step a-b

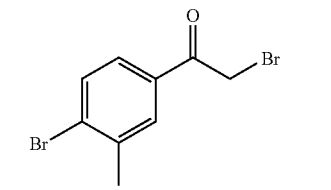
121a

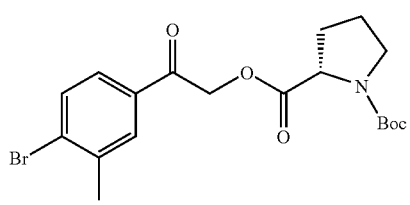
121b

PdCl$_2$(Ph$_3$P)$_2$ (257 mg, 0.367 mmol) was added to a dioxane (45 mL) solution of 1-bromo-4-iodo-2-methylbenzene 400 MHz): 7.83 (s, 1H), 7.63 (s, 2H), 4.30 (s, 2H), 2.46 (s, 3H).

A CH$_3$CN (15 mL) solution of 121a (2.69 g, <9.21 mmol) was added dropwise over 3 minutes to a CH$_3$CN (30 mL) solution of (S)-Boc-proline (2.215 g, 10.3 mmol) and triethylamine (1.40 mL, 10.04 mmol), and stirred for 90 minutes. The volatile component was removed in vacuo, and the residue was partitioned between water and CH$_2$Cl$_2$, and the organic phase was dried (MgSO$_4$), filtered, and concentrated in vacuo. The resulting crude material was purified by a flash chromatography (silica gel; 15-20% ethyl acetate/hexanes) to provide 121b as a colorless viscous oil (2.74 g). $^1$H NMR (DMSO-$d_6$, δ=2.50, 400 MHz): δ 7.98 (m, 1H), 7.78 (d, J=8.3, 1H), 7.72-7.69 (m, 1H), 5.61-5.41 (m, 2H), 4.35-4.30 (m, 1H), 3.41-3.30 (m, 2H), 2.43 (s, 3H), 2.33-2.08 (m, 2H), 1.93-1.83 (m, 2H), 1.40/1.36 (s, 9H); LC (Cond. 1): RT=1.91 min; >95% homogeneity index; LC/MS: Anal. Calcd. for [M+Na]$^+$ C$_{19}$H$_{24}$BrNNaO$_5$ 448.07; found 448.10.

Additional keto-esters can be prepared in analogous fashion.

LC conditions: Condition 1: Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, 220 nm, 5 μL injection volume.

Condition 2: Phenomenex LUNA C-18 4.6×50 mm, 0 to 100% B over 2 minutes, 1 minute hold time, A=90% water, 10% methanol, 0.1% TFA, B=10% water, 90% methanol, 0.1% TFA, 220 nm, 5 μL injection volume.

| Example | Structure | Data |
|---|---|---|
| 121b-1 | 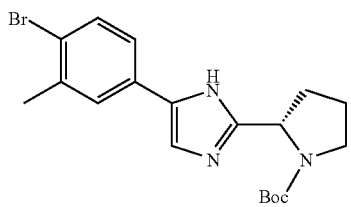 | RT = 2.15 minutes (condition 2, 98%); LRMS: Anal. Calcd. for $C_{17}H_{22}NO_5$ 399.07; found: 400.10 $(M + H)^+$. |
| 121b-2 | 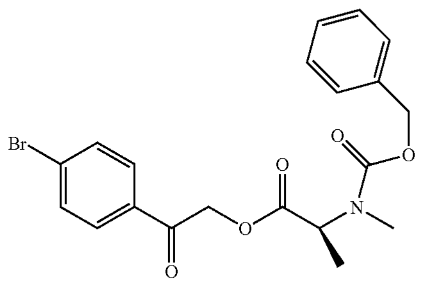 | RT = 2.78 minutes (condition 1, >90%); LRMS: Anal. Calcd. for $C_{20}H_{20}{}^{37}BrNO_5$ 435.05.; found: 458.02 $(M + Na)^+$. |

Example 121

Step c


121c

A mixture of ketoester 121b (1.445 g, 3.39 mmol) and $NH_4OAc$ (2.93 g, 38.0 mmol) in xylenes (18 mL) was heated with a microwave at 140° C. for 80 minutes. The volatile component was removed in vacuo, and the residue was carefully partitioned between $CH_2Cl_2$ and water, where enough saturated $NaHCO_3$ solution was added to neutralize the aqueous medium. The aqueous phase was extracted with $CH_2Cl_2$, and the combined organic phase was dried ($MgSO_4$), filtered, and concentrated in vacuo. The crude product was purified by a flash chromatography (silica gel, 40% ethyl acetate/hexanes) to provide imidazole 121c as an off-white solid (1.087 g). $^1$H NMR (DMSO-$d_6$, δ=2.50, 400 MHz): 12.15/11.91/11.84 (br s, 1H), 7.72-7.24 (m, 4H), 4.78 (m, 1H), 3.52 (m, 1H), 3.38-3.32 (m, 1H), 2.35 (s, 3H), 2.28-1.77 (m, 4H), 1.40/1.14 (s, 9H); LC (Cond. 1): RT=1.91 min; >98% homogeneity index; LC/MS: Anal. Calcd. for $[M+H]^+$ $C_{19}H_{25}BrN_3O_2$ 405.96; found 406.11.

Example 121

Step d $PdCl_2dppf·CH_2Cl_2$ (50.1 mg, 0.061 mmol) was added to a pressure tube containing a mixture of bromide 121c (538.3 mg, 1.325 mmol), bis(pinacolato)diboron (666.6 mg, 2.625 mmol), potassium acetate (365.8 mg, 3.727 mmol) and DMF (10 mL). The reaction mixture was flushed with $N_2$ and heated at 80° C. for 24.5 hours. The volatile component was removed in vacuo and the residue was partitioned between $CH_2Cl_2$ and water, where enough saturated $NaHCO_3$ solution was added to make the pH of the aqueous medium neutral. The aqueous phase was extracted with $CH_2Cl_2$, and the combined organic phase was dried ($MgSO_4$), filtered, and concentrated in vacuo. The resulting material was purified by a Biotage system (silica gel, 40-50% ethyl acetate/hexanes) to provide boronate 121d as a white foam (580 mg). According to $^1$H NMR the sample contains residual pinacol in a product/pinacol ratio of ~3. $^1$H NMR (DMSO-$d_6$, δ=2.50, 400 MHz): δ 12.16/11.91/11.83 (br s, 1H), 7.63-7.25 (m, 4H), 4.78 (m, 1H), 3.53 (m, 1H), 3.39-3.32 (m, 1H), 2.48/2.47 (s, 3H), 2.28-1.78 (m, 4H), 1.40/1.14/1.12 (br s, 9H), 1.30 (s, 12H); LC (Cond. 1): RT=1.62 min; LC/MS: Anal. Calcd. for $[M+H]^+$ $C_{25}H_{37}BN_3O_4$ 454.29; found 454.15

Example 121

Step e and

Example 121

Step f

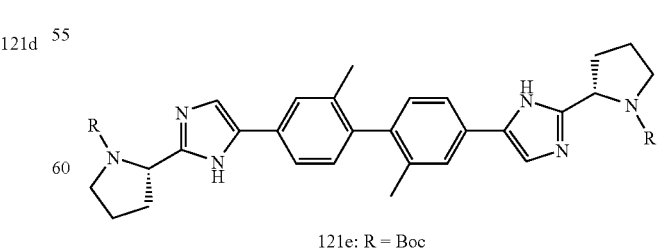

121e: R = Boc
121f: R = H

Carbamate 121e was prepared from bromide 121c and boronate 121d according to the preparation of dimer 1d; LC (Cond. 1): RT=1.43 min; LC/MS: Anal. Calcd. for [M+H]$^+$ C$_{38}$H$_{49}$N$_6$O$_4$ 653.38; found 653.65.

The deprotection of carbamate 121e, according to the preparation of pyrrolidine 1e, provided 121f as an off-white foam. $^1$H NMR (DMSO-d$_6$, δ=2.50, 400 MHz): 11.79 (br s, 2H), 7.66 (s, 2H), 7.57 (d, J=7.8, 2H), 7.41 (br s, 2H), 7.02 (d, J=7.8, 2H), 4.15 (app t, J=7.2, 2H), 3.00-2.94 (m, 2H), 2.88- 2.82 (m, 2H), 2.09-2.01 (m, 2H), 2.04 (s, 6H), 1.93-1.85 (m, 2H), 1.82-1.66 (m, 4H). Note: although broad signals corresponding to the pyrrolidine NH appear in the 2.8-3.2 ppm region, the actual range for their chemical shift could not be determined. LC (Cond. 1): RT=1.03 min; LC/MS: Anal. Calcd. for [M+H]$^+$ C$_{28}$H$_{33}$N$_6$ 453.28; found 453.53

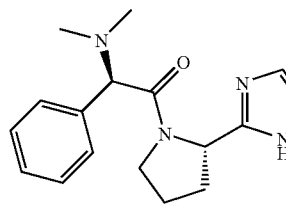
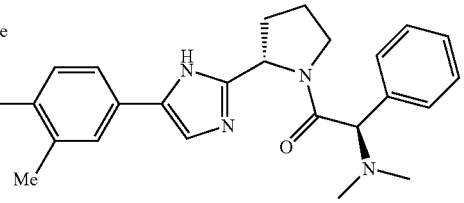

Example 121

(1R,1'R)-2,2'-((2,2'-dimethyl-4,4'-biphenyldiyl)bis(1H-imidazole-5,2-diyl(2S)-2,1-pyrrolidinediyl))bis(N,N-dimethyl-2-oxo-1-phenylethanamine)

Example 121 (TFA salt) was synthesized from 121f according to the preparation of Example 1 from 1e; LC (Cond. 1): RT=1.14 min; >98% homogeneity index; LC/MS: Anal. Calcd. for [M+H]$^+$ C$_{48}$H$_{55}$N$_8$O$_2$ 775.45; 775.75; HRMS: Anal. Calcd. for [M+H]$^+$ C$_{48}$H$_{55}$N$_8$O$_2$ 775.4448; found 775.4473

Examples 126-128

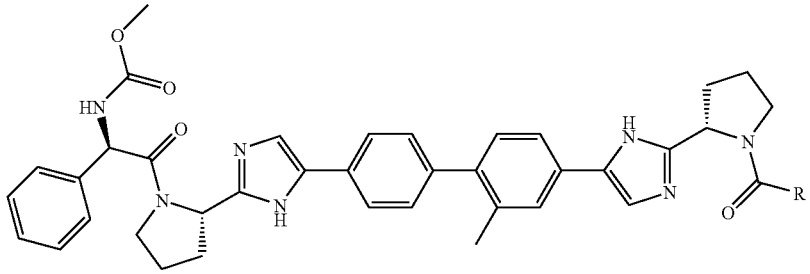

Example 126-128 were prepared starting from bromide 28b and boronate 121d by using the methods described in Example 28 starting with step c.

| Example | Compound Name | R $\overset{\overset{O}{\|\|}}{C}$ ~~~ | RT (LC-Cond.); % homogeneity index; MS data |
|---|---|---|---|
| 126 | methyl ((1R)-2-((2S)-2-(5-(4'-(2-((2S)-1-((2R)-2-(dimethylamino)-2-phenylacetyl)-2-pyrrolidinyl)-1H-imidazol-5-yl)-2'-methyl-4-biphenylyl)-1H-imidazol-2-yl)-1-pyrrolidinyl)-2-oxo-1-phenylethyl)carbamate | Ph, N (Cap-1) | 1.22 min (Cond. 1); >98%; LC/MS: Anal. Calcd. for [M + H]$^+$ C$_{47}$H$_{51}$N$_8$O$_4$: 791.40; found 791.70; HRMS: Anal. Calcd. for [M + H]$^+$ C$_{47}$H$_{51}$N$_8$O$_4$: 791.4033; found 791.4061 |

-continued

| Example | Compound Name | R (acyl group) | RT (LC-Cond.); % homogeneity index; MS data |
|---|---|---|---|
| 127 | methyl ((1R)-2-((2S)-2-(5-(2'-methyl-4'-(2-((2S)-1-(3-pyridinylacetyl)-2-pyrrolidinyl)-1H-imidazol-5-yl)-4-biphenylyl)-1H-imidazol-2-yl)-1-pyrrolidinyl)-2-oxo-1-phenylethyl)carbamate | 3-pyridinyl-CH$_2$-C(O)- | 1.19 minutes (Cond. 1); >98%; LC/MS: Anal. Calcd. for [M + H]$^+$ C$_{44}$H$_{45}$N$_8$O$_4$: 749.36; found 749.62; HRMS: Anal. Calcd. for [M + H]$^+$ C$_{44}$H$_{45}$N$_8$O$_4$: 749.3564; found 749.3592 |
| 128 | methyl ((1R)-2-((2S)-2-(5-(2'-methyl-4'-(2-((2S)-1-((2S)-tetrahydro-2-furanylcarbonyl)-2-pyrrolidinyl)-1H-imidazol-5-yl)-4-biphenylyl)-1H-imidazol-2-yl)-1-pyrrolidinyl)-2-oxo-1-phenylethyl)carbamate | (2S)-tetrahydrofuran-2-yl-C(O)- | 1.27 minutes (Cond. 1); >98%; LC/MS: Anal. Calcd. for [M + H]$^+$ C$_{42}$H$_{46}$N$_7$O$_5$: 728.36; found 728.59; HRMS: Anal. Calcd. for [M + H]$^+$ C$_{42}$H$_{46}$N$_7$O$_5$: 728.3560; found 728.3593 |

Example 130

(1R,1'R)-2,2'-((2-(trifluoromethyl)-4,4'-biphenyldiyl)bis(1H-imidazole-5,2-diyl(2S)-2,1-pyrrolidinediyl))bis(N,N-dimethyl-2-oxo-1-phenylethanamine)

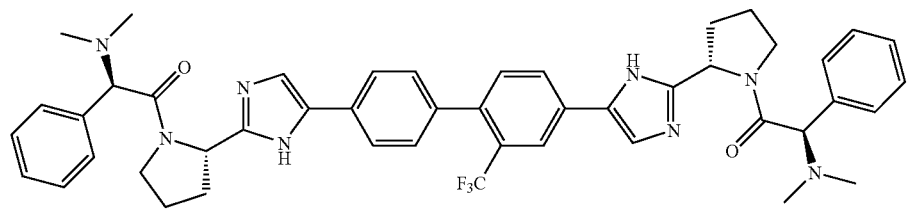

Example 130

Step a

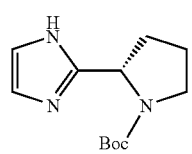

130a

Glyoxal (2.0 mL of 40% in water) was added dropwise over 11 minutes to a methanol solution of NH$_4$OH (32 mL) and (S)-Boc-prolinal (8.564 g, 42.98 mmol) and stirred at ambient temperature for 19 hours. The volatile component was removed in vacuo and the residue was purified by a flash chromatography (silica gel, ethyl acetate) followed by a recrystallization (ethyl acetate, room temperature) to provide imidazole 130a as a white fluffy solid (4.43 g). $^1$H NMR (DMSO-d$_6$, δ=2.50, 400 MHz): 11.68/11.59 (br s, 1H), 6.94 (s, 1H), 6.76 (s, 1H), 4.76 (m, 1H), 3.48 (m, 1H), 3.35-3.29 (m, 1H), 2.23-1.73 (m, 4H), 1.39/1.15 (s, 9H). LC (Cond. 1): RT=0.87 min; >95% homogeneity index; LC/MS: Anal. Calcd. for [M+H]$^+$ C$_{12}$H$_{20}$N$_3$O$_2$ 238.16; found 238.22. Imidazole 130a had an ee of 98.9% when analyzed under chiral HPLC condition noted below.

Column: Chiralpak AD, 10 um, 4.6×50 mm
Solvent: 1.7% ethanol/heptane (isocratic)
Flow rate: 1 mL/min
Wavelength: either 220 or 256 nm
Relative retention time: 3.25 min (R), 5.78 minutes (S)

Example 130

Step b

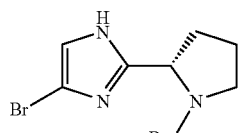

130b

N-Bromosuccinimide (838.4 mg, 4.71 mmol) was added in batches, over 15 minutes, to a cooled (ice/water) CH$_2$Cl$_2$ (20 mL) solution of imidazole 130a (1.0689 g, 4.504 mmol), and stirred at similar temperature for 75 minutes. The volatile component was removed in vacuo. The crude material was purified by a reverse phase HPLC system (H$_2$O/methanol/

TFA) to separate bromide 130b from its dibromo-analog and the non-consumed starting material. The HPLC elute was neutralized with excess NH$_3$/methanol and the volatile component was removed in vacuo. The residue was partitioned between CH$_2$Cl$_2$ and water, and the aqueous layer was extracted with water. The combined organic phase was dried (MgSO$_4$), filtered, and concentrated in vacuo to provide 130b as a white solid (374 mg). $^1$H NMR (DMSO-d$_6$, δ=2.50, 400 MHz): 12.12 (br s, 1H), 7.10 (m, 1H), 4.70 (m, 1H), 3.31 (m, 1H; overlapped with water signal), 2.25-1.73 (m, 4H), 1.39/1.17 (s, 3.8H+5.2H). LC (Cond. 1): RT=1.10 min; >95% homogeneity index; LC/MS: Anal. Calcd. for [M+H]$^+$ C$_{12}$H$_{19}$BrN$_3$O$_2$ 316.07; found 316.10.

Example 130

Step c

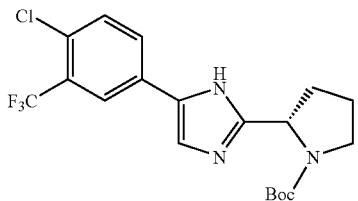

130c

Pd(Ph$_3$P)$_4$ (78.5 mg, 0.0679 mmol) was added to a mixture of bromide 130b (545 mg, 1.724 mmol), 2-(4-chloro-3-(trifluoromethyl)phenyl-4,4,5,5-tetramethyl-1,3,2-dioxaborolane (542.8 mg, 1.771 mmol) (commercially available), NaHCO$_3$ (477 mg, 5.678 mmol) in 1,2-dimethoxyethane (12.5 mL) and water (4.2 mL). The reaction mixture was purged with nitrogen, heated with an oil bath at 80° C. for 27 hours, and then the volatile component was removed in vacuo. The residue was partitioned between CH$_2$Cl$_2$ and water, and the organic layer was dried (MgSO$_4$), filtered, and concentrated in vacuo. The resulting crude material was purified by a Biotage system (silica gel, 40-50% ethyl acetate/hexanes) followed by a reverse phase HPLC (water/methanol/TFA). The HPLC elute was treated with excess NH$_3$/methanol and concentrated. The residue was partitioned between water and CH$_2$Cl$_2$, and the organic layer was dried (MgSO$_4$), filtered, and concentrated in vacuo to provide 130c as a white foam (317.4 mg). $^1$H NMR (DMSO-d$_6$, δ=2.50, 400 MHz): 12.36/12.09/12.03 (br s, 1H), 8.15 (d, J=1.8, 0.93H), 8.09 (br s, 0.07H), 8.01 (dd, J=8.3/1.3, 0.93H), 7.93 (m, 0.07H), 7.74 (m, 1H), 7.66 (d, J=8.3, 0.93H), 7.46 (m, 0.07H), 4.80 (m, 1H), 3.53 (m, 1H), 3.36 (m, 1H), 2.30-1.77 (m, 4 h), 1.40/1.15 (s, 3.8H+5.2H). LC (Cond. 1): RT=1.52 min; >95% homogeneity index; LC/MS: Anal. Calcd. for [M+H]$^+$ C$_{19}$H$_{22}$ClF$_3$N$_3$O$_2$ 416.14; found 416.17.

Example 130

Step d-e

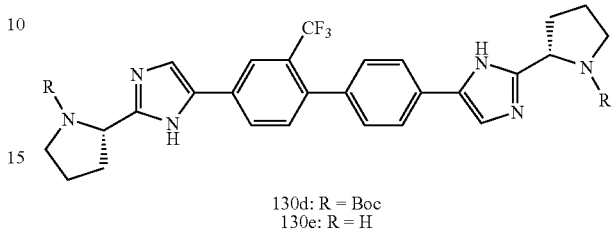

130d: R = Boc
130e: R = H

Pd[P(t-Bu)$_3$]$_2$ (48 mg, 0.094 mmol) was added to a mixture of chloride 130c (245 mg, 0.589 mmol), boronate 1c (277.1 mg, 0.631 mmol), KF (106.7 mg, 1.836 mmol) in DMF (6 mL), and heated at 110° C. for ~30 hours. The volatile component was removed in vacuo, and the residue was partitioned between CH$_2$Cl$_2$ (50 mL), water (20 mL) and saturated NaHCO$_3$ (1 mL). The aqueous layer was extracted with CH$_2$Cl$_2$ (2×), and the combined organic phase was dried (MgSO$_4$), filtered, and concentrated in vacuo. The resulting material was purified by a Biotage system (silica gel, ethyl acetate) to provide carbamate 130d as an off-white foam (297 mg). LC (Cond. 1): RT=1.44 min; >95% homogeneity index; LC/MS: Anal. Calcd. for [M+H]$^+$ C$_{37}$H$_{44}$F$_3$N$_6$O$_4$ 693.34; found 693.34.

The deprotection of 130d, which was conducted according to the preparation of pyrrolidine 1e, provided 130e as a light yellow foam. $^1$H NMR (DMSO-d$_6$, δ=2.50, 400 MHz): 11.88 (br s, 2H), 8.16 (d, J=1.5, 1H), 8.02 (d, J=7.8, 1H), 7.78 (d, J=8.1, 2H), 7.66 (br s, 1H), 7.48 (br s, 1H), 7.37 (d, J=8.1, 1H), 7.28 (d, J=8.3, 2H), 4.18 (m, 2H), 2.99-2.93 (m, 2H), 2.89-2.83 (m, 2H), 2.11-2.01 (m, 2H), 1.94-1.85 (m, 2H), 1.82-1.67 (m, 4H). Note: although broad signals corresponding to the pyrrolidine NH appear in the 2.8-3.2 ppm region, the actual range for their chemical shift could not be determined. LC (Cond. 1): RT=1.12 min; >95% homogeneity index; LC/MS: Anal. Calcd. for [M+H]$^+$ C$_{27}$H$_{28}$F$_3$N$_6$ 493.23; found 493.14.

Example 130

(1R,1'R)-2,2'-((2-(trifluoromethyl)-4,4'-biphenyldiyl)bis(1H-imidazole-5,2-diyl(2S)-2,1-pyrrolidinediyl))bis(N,N-dimethyl-2-oxo-1-phenylethanamine)

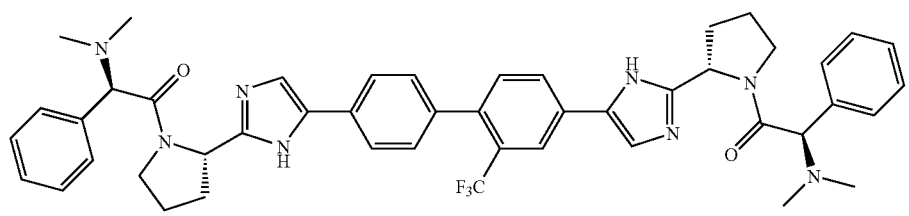

Example 130 (TFA salt) was prepared from 130e and Cap-1 according to the preparation of Example 1 from pyrrolidine 1e. LC (Cond. 1): RT=1.17 min; >98% homogeneity index; LC/MS: Anal. Calcd. for [M+H]$^+$ $C_{47}H_{50}F_3N_8O_2$ 815.40; found 815.44; HRMS: Anal. Calcd. for [M+H]$^+$ $C_{47}H_{50}F_3N_8O_2$ 815.4009; found 815.4013

Example 131.1-1 to 131.1-2

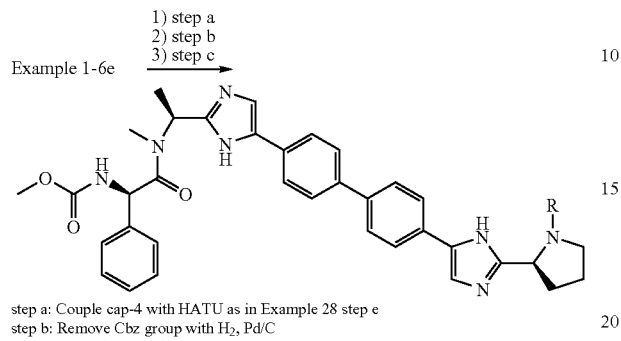

step a: Couple cap-4 with HATU as in Example 28 step e
step b: Remove Cbz group with H$_2$, Pd/C
step c: Append appropriate cap Examples 131.1-1 through 131.1-2 were prepared in similar fashion to example 28 via the intermediacy of intermediate 1-6e after appending Cap-4.

Example 131.1-1 methyl((1R)-2-(((1S)-1-(5-(4'-(2-((2S)-1-((2R)-2-(dimethylamino)-2-phenylacetyl)-2-pyrrolidinyl)-1H-imidazol-5-yl)-4-biphenylyl)-1H-imidazol-2-yl)ethyl)(methyl)amino)-2-oxo-1-phenylethyl)carbamate

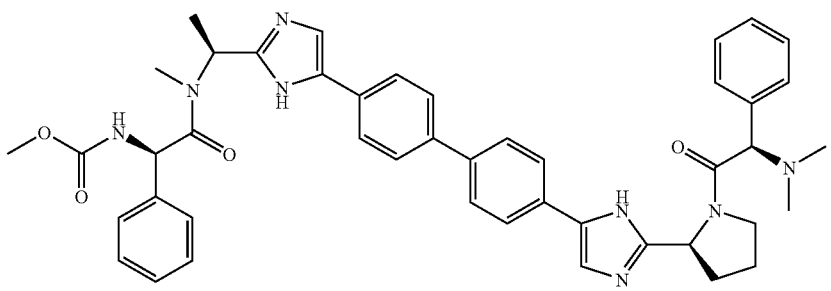

Cap-1 was appended after the CBz carbamate was removed from 1-6e with Pd/C/H$_2$.

LCMS conditions: Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, 220 nm, 5 μL injection volume. t$_R$=1.42 min LRMS: Anal. Calcd. for $C_{45}H_{49}N_8O_4$ 765.39; found: 765.38 (M+H)$^+$.

HRMS: Anal. Calcd. for $C_{45}H_{49}N_8O_4$ Calcd 765.3877 found: 765.3905 (M+H)$^+$.

Example 131.1-1.2 methyl((1R)-2-(methyl((1S)-1-(5-(4'-(2-((2S)-1-((2R)-2-phenyl-2-(1-piperidinyl)acetyl)-2-pyrrolidinyl)-1H-imidazol-5-yl)-4-biphenylyl)-1H-imidazol-2-yl)ethyl)amino)-2-oxo-1-phenylethyl)carbamate

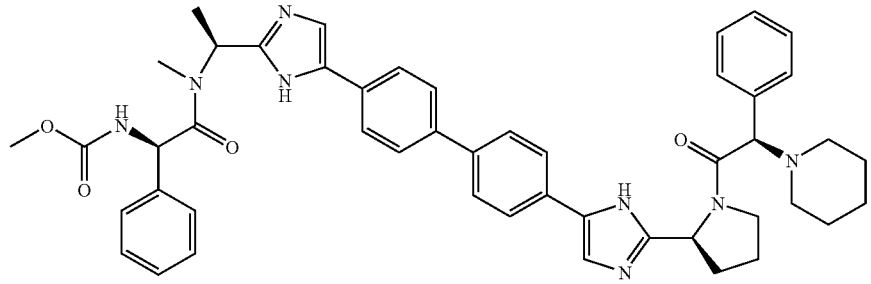

Cap-14 was appended after the CBz carbamate was removed from 1-6e with Pd/C/H$_2$.

LCMS conditions: Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, 220 nm, 5 μL injection volume. $t_R$=1.45 min (>95%)

LRMS: Anal. Calcd. for C$_{48}$H$_{52}$N$_8$O$_4$ 805.42; found: 805.41 (M+H)$^+$.

HRMS: Anal. Calcd. C$_{48}$H$_{52}$N$_8$O$_4$ Calcd 805.4190 found: 805.4214 (M+H)$^+$.

Example 131.2

(2R)-2-(dimethylamino)-N-methyl-2-phenyl-N-((1S)-1-(5-(4'-(2-((2S)-1-((2R)-2-phenyl-2-(1-piperidinyl)acetyl)-2-pyrrolidinyl)-1H-imidazol-5-yl)-4-biphenylyl)-1H-imidazol-2-yl)ethyl)acetamide

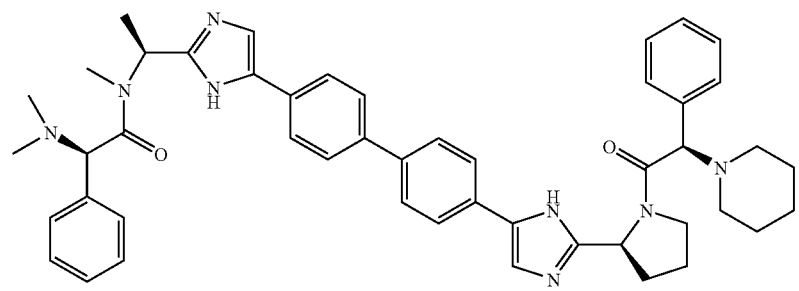

Example 131.2 was prepared in similar fashion to example 131.1-1 and example 131.1-2 via the intermediacy of intermediate 1-6e after appending Cap-1. Cap-14 was appended after the CBz carbamate was removed with Pd/C/H$_2$. LCMS conditions: Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, 220 nm, 5 μL injection volume. $t_R$=1.28 min LRMS: Anal. Calcd. for C$_{48}$H$_{54}$N$_8$O$_2$ 775.44; found: 775.45 (M+H)$^+$.

HRMS: Anal. Calcd. C$_{48}$H$_{54}$N$_8$O$_2$ Calcd 775.4448 found: 775.4460 (M+H)$^+$.

Example 132

(1R)-2-((2S)-2-(5-(6-(4-(2-((2S)-1-((2R)-2-(dimethylamino)-2-phenylacetyl)-2-pyrrolidinyl)-1H-imidazol-5-yl)phenyl)-3-pyridinyl)-1H-imidazol-2-yl)-1-pyrrolidinyl)-N,N-dimethyl-2-oxo-1-phenylethanamine

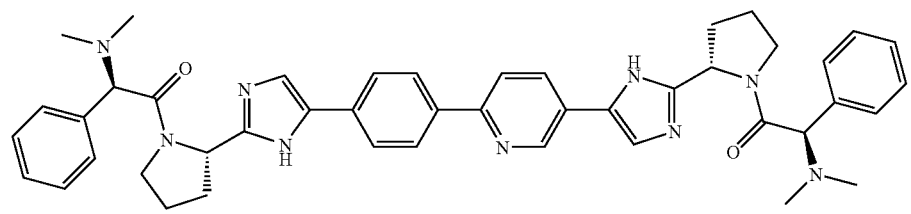

Example 132

Step a-b

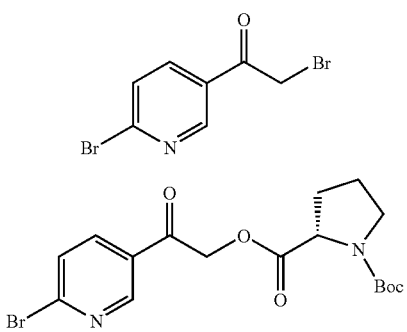

A CH$_2$Cl$_2$ (10 mL) solution of Br$_2$ (7.63 g, 47.74 mmol) was added-drop wise over 5 min to a cooled (ice/water) CH$_2$Cl$_2$ (105 mL) solution of 1-(6-bromopyridine-3-yl)ethanone (9.496 g, 47.47 mmol) and 48% HBr (0.4 mL). The cooling bath was removed 40 min later, and stirring was continued at ambient temperature for about 66 hr. The cake of solid that formed was filtered, washed with CH$_2$Cl$_2$ and dried in vacuo to afford impure 132a as an off-white solid (15.94 g).

Boc-L-proline (9.70 g, 45.06 mmol) was added in one batch to a heterogeneous mixture of crude 132a (15.4 g) and CH$_3$CN (150 mL), and immediately afterward Et$_3$N (13.0 mL, 93.2 mmol) was added drop-wise over 6 min. The reaction mixture was stirred for 50 min, the volatile component was removed in vacuo and the residue was partitioned between CH$_2$Cl$_2$ and water. The CH$_2$Cl$_2$ layer was dried (MgSO$_4$), filtered and concentrated in vacuo, and the resultant material was purified by flash chromatography (silica gel; sample was loaded with eluting solvent; 25% EtOAc/hexanes) to afford 132b as a highly viscous yellow oil (11.44 g). $^1$H NMR (DMSO, δ=2.5 ppm; 400 MHz): 8.95 (m, 1H), 8.25-8.21 (m, 1H), 7.88 (d, J=8.3, 1H), 5.65-5.46 (m, 2H), 4.36-4.31 (m, 1H), 3.41-3.29 (m, 2H), 2.36-2.22 (m, 1H), 2.14-2.07 (m, 1H), 1.93-1.83 (m, 2H), 1.40 & 1.36 (two s, 9H).

LC (Cond. 1): RT=2.01 min; >90% homogeneity index
LC/MS: Anal. Calcd. for [M+Na]$^+$ C$_{17}$H$_{21}$NaBrN$_2$O$_5$: 435.05; found 435.15
HRMS: Anal. Calcd. for [M+H]$^+$ C$_{17}$H$_{22}$BrN$_2$O$_5$: 413.0712; found 413.0717

Example 132

Step c

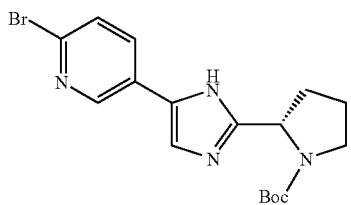

A mixture of ketoester 132b (1.318 g, 3.19 mmol) and NH$_4$OAc (2.729 g, 35.4 mmol) in xylenes (18 mL) was heated with a microwave at 140° C. for 90 min. The volatile component was removed in vacuo and the residue was partitioned between CH$_2$Cl$_2$ and water, where enough saturated NaHCO$_3$ solution was added to neutralize the aqueous medium. The aqueous phase was extracted with CH$_2$Cl$_2$, and the combined organic phase was dried (MgSO$_4$), filtered, and concentrated in vacuo. The resulting crude material was purified by a Biotage system (silica gel; 50% EtOAc/hexanes) to afford imidazole 132c as an off-white foam (1.025 g). $^1$H NMR (DMSO, δ=2.5 ppm, 400 MHz): 12.33/12.09/12.02 (br m, 1H), 8.74 (d, J=2.3, 0.93H), 8.70 (app br s, 0.07H), 8.03/7.98 (dd for the first peak, J=8.3, 1H), 7.69/7.67 (br m, 1H), 7.58/7.43 (d for the first peak, J=8.3, 1H), 4.80 (m, 1H), 3.53 (m, 1H), 3.36 (m, 1H), 2.33-2.11 (m, 1H), 2.04-1.79 (m, 3H), 1.39/1.15 (app br s, 3.9H+5.1H).

LC (Cond. 1): RT=1.52 min; >98% homogeneity index
LC/MS: Anal. Calcd. for [M+H]$^+$ C$_{17}$H$_{22}$BrN$_4$O$_2$: 393.09; found 393.19
HRMS: Anal. Calcd. for [M+H]$^+$ C$_{17}$H$_{22}$BrN$_4$O$_2$: 393.0926; found 393.0909

Example 132

Step d-e

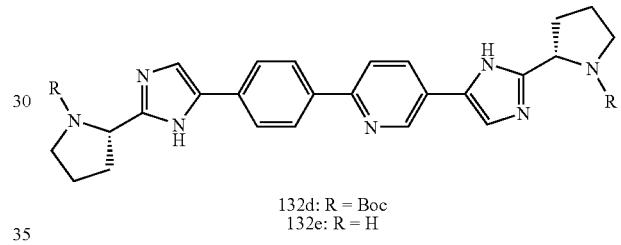

132d: R = Boc
132e: R = H

Pd(Ph$_3$P)$_4$ (115.1 mg, 0.10 mmol) was added to a mixture of bromide 132c (992 mg, 2.52 mmol), boronate 1c (1.207 g, 2.747 mmol), NaHCO$_3$ (698.8 mg, 8.318 mmol) in 1,2-dimethoxyethane (18 mL) and water (4 mL). The reaction mixture was flushed with nitrogen, heated with an oil bath at 90° C. for 37 hr and allowed to cool to ambient temperature. The suspension that formed was filtered and washed with water followed by 1,2-dimethoxyethane, and dried in vacuo. A silica gel mesh was prepared from the crude solid and submitted to flash chromatography (silica gel; EtOAc) to afford carbamate 132d as a white solid, which yellowed slightly upon standing at ambient conditions (1.124 g). $^1$H NMR indicated that the sample contains residual MeOH in a product/MeOH mole ratio of 1.3.

LC (Cond. 1): RT=1.71 min; >98% homogeneity index
LC/MS: Anal. Calcd. for [M+H]$^+$ C$_{35}$H44N$_7$O$_4$: 626.35; found 626.64
HRMS: Anal. Calcd. for [M+H]$^+$ C$_{35}$H$_{44}$N$_7$O$_4$: 626.3455; 626.3479

Carbamate 132d (217 mg) was treated with 25% TFA/CH$_2$Cl$_2$ (3.6 mL) and stirred at ambient condition for 6 hr. The volatile component was removed in vacuo, and the resultant material was free based by MCX column (MeOH wash; 2.0 M NH$_3$/MeOH elution) to afford 132e as a dull yellow foam that solidified gradually upon standing (150.5 mg; mass is above theoretical yield). $^1$H NMR (DMSO, δ=2.5 ppm; 400 MHz): 11.89 (very broad, 2H), 9.01 (d, J=1.8, 1H), 8.13 (dd, J=8.3, 2.2, 1H), 8.07 (d, J=8.6, 2H), 7.92 (d, J=8.3, 1H), 7.83 (d, J=8.5, 2H), 7.61 (br s, 1H), 7.50 (br s, 1H), 4.18 (m, 2H), 3.00-2.93 (m, 2H), 2.90-2.82 (m, 2H), 2.11-2.02 (m, 2H), 1.94-1.85 (m, 2H), 1.83-1.67 (m, 4H). [Note: the exchangeable pyrrolidine hydrogens were not observed]

LC (Cond. 1): RT=1.21 min; >98% homogeneity index
LC/MS: Anal. Calcd. for [M+H]+ $C_{25}H_{28}N_7$: 426.24; found 426.40
HRMS: Anal. Calcd. for [M+H]+ $C_{25}H_{28}N_7$: 426.2406; found 426.2425

Example 132

(1R)-2-((2S)-2-(5-(6-(4-(2-((2S)-1-((2R)-2-(dimethylamino)-2-phenylacetyl)-2-pyrrolidinyl)-1H-imidazol-5-yl)phenyl)-3-pyridinyl)-1H-imidazol-2-yl)-1-pyrrolidinyl)-N,N-dimethyl-2-oxo-1-phenylethanamine

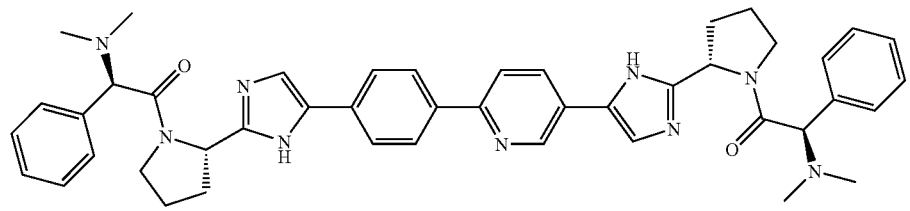

HATU (41.4 mg, 0.109 mmol) was added to a mixture of pyrrolidine 132e (23.1 mg, 0.054 mmol), (i-Pr)$_2$EtN (40 µL, 0.23 mmol) and Cap-1 (25.3 mg, 0.117 mmol) in DMF (1.5 mL), and the mixture was stirred at ambient for 1 hr. The volatile component was removed in vacuo, and the residue was purified first by MCX (MeOH wash; 2.0 M NH$_3$/MeOH elution) and then by a reverse phase HPLC (H$_2$O/MeOH/TFA) to afford the TFA salt of Example 132 as a yellow foam (39.2 mg).

LC (Cond. 1): RT=1.37 min; >98% homogeneity index
LC/MS: Anal. Calcd. for [M+H]+ $C_{45}H_{50}N_9O_2$: 748.41; found 748.53
HRMS: Anal. Calcd. for [M+H]+ $C_{45}H_{50}N_9O_2$: 748.4087; found 748.4090

Example 133-135 were prepared as TFA salts from 132e by using the same method of preparations as Example 132 and appropriate reagents.

Example 133-135

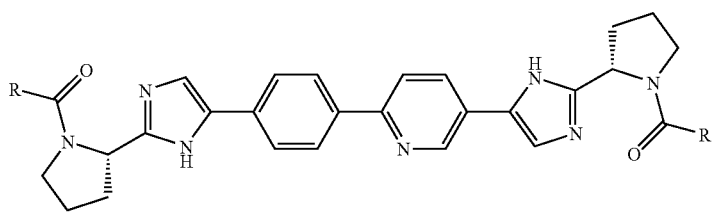

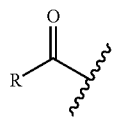

| Example | Compound Name | R | RT(LC-Cond.); % homogeneity index; MS data |
|---|---|---|---|
| 133 | (1R)-2-((2S)-2-(5-(6-(4-(2-((2S)-1-((2R)-2-hydroxy-2-phenylacetyl)-2-pyrrolidinyl)-1H-imidazol-5-yl)phenyl)-3-pyridinyl)-1H-imidazol-2-yl)-1-pyrrolidinyl)-2-oxo-1-phenylethanol | Ph-CH(OH)-C(O)- | 1.49 min (Cond. 1); >98% LC/MS: Anal. Calcd. for [M + H]+ $C_{41}H_{40}N_7O_4$: 694.31; found 694.42 HRMS: Anal. Calcd. for [M + H]+ $C_{41}H_{40}N_7O_4$: 694.3142, found: 694.3164 |
| 134 | methyl ((1R)-2-((2S)-2-(5-(6-(4-(2-((2S)-1-((2R)-2-((methoxycarbonyl)amino)-2-phenylacetyl)-2-pyrrolidinyl)-1H-imidazol-5-yl)phenyl)-3-pyridinyl)-1H-imidazol-2-yl)-1-pyrrolidinyl)-2-oxo-1-phenylethyl)carbamate | Ph-CH(NHC(O)OMe)-C(O)- | 1.60 min (Cond. 1); >98% LC/MS: Anal. Calcd. for [M + H]+ $C_{45}H_{46}N_9O_6$: 808.36; found 808.51 HRMS: Anal. Calcd. for [M + H]+ $C_{45}H_{46}N_9O_6$: 808.3571; found 808.3576 |

Cap-4

-continued

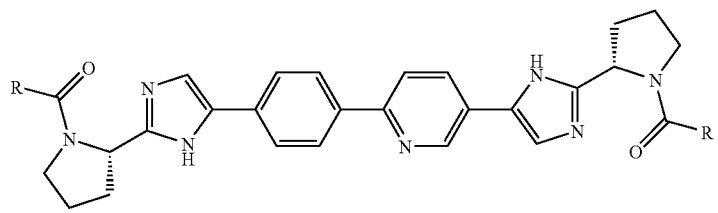

| Example | Compound Name | 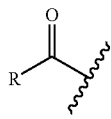 | RT(LC-Cond.); % homogeneity index; MS data |
|---|---|---|---|
| 135 | 5-(2-((2S)-1-((2R)-2-methoxy-2-phenylacetyl)-2-pyrrolidinyl)-1H-imidazol-5-yl)-2-(4-(2-((2S)-1-((2R)-2-methoxy-2-phenylacetyl)-2-pyrrolidinyl)-1H-imidazol-5-yl)phenyl)pyridine | (Ph, OMe structure) | 1.60 min (Cond. 1); >98% LC/MS: Anal. Calcd. for [M + H]$^+$ C$_{43}$H$_{44}$N$_7$O$_4$: 722.35; found 722.40 HRMS: Anal. Calcd. for [M + H]$^+$ C$_{43}$H$_{44}$N$_7$O$_4$: 722.3455; found 722.3464 |

Example 136

(1R)-2-((2S)-2-(5-(6-(4-(2-((2S)-1-((2R)-2-(dimethylamino)-2-phenylacetyl)-2-pyrrolidinyl)-1H-imidazol-5-yl)-2-methylphenyl)-3-pyridinyl)-1H-imidazol-2-yl)-1-pyrrolidinyl)-N,N-dimethyl-2-oxo-1-phenylethanamine

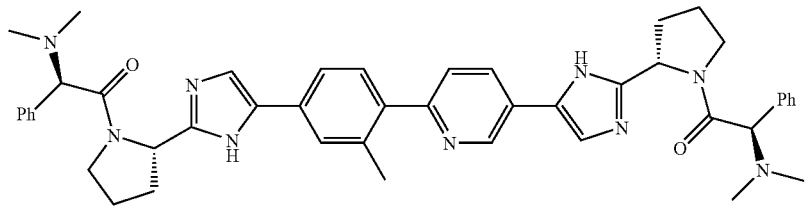

Example 136

Steps a and b

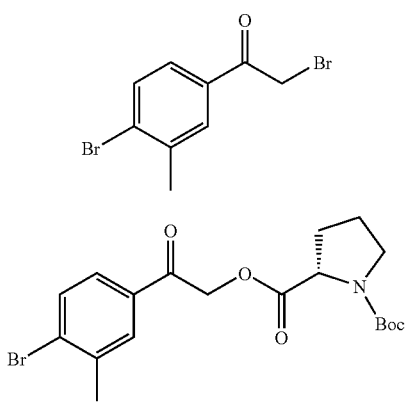

136a

136b

PdCl$_2$(Ph$_3$P)$_2$ (257 mg, 0.367 mmol) was added to a dioxane (45 mL) solution of 1-bromo-4-iodo-2-methylbenzene (3.01 g, 10.13 mmol) and tri-n-butyl(1-ethoxyvinyl)stannane (3.826 g, 10.59 mmol) and heated at 80° C. for ~17 hr. The reaction mixture was treated with water (15 mL), cooled to ~0° C. (ice/water), and then NBS (1.839 g, 10.3 mmol) was added in batches over 7 min. About 25 min of stirring, the volatile component was removed in vacuo, and the residue was partitioned between CH$_2$Cl$_2$ and water. The aqueous layer was extracted with CH$_2$Cl$_2$, and the combined organic phase was dried (MgSO$_4$), filtered, and concentrated in vacuo. The resulting crude material was purified by a gravity chromatography (silica gel; 4% EtOAc/hexanes) to afford bromide 136a as a brownish-yellow solid (2.699 g); the sample is impure and contains stannane-derived impurities, among others. $^1$H NMR (CDCl$_3$, δ=7.24, 400 MHz): 7.83 (s, 1H), 7.63 (s, 2H), 4.30 (s, 2H), 2.46 (s, 3H).

An CH$_3$CN (15 mL) solution of 136a (2.69 g, <9.21 mmol) was added drop wise over 3 min to a CH$_3$CN (30 mL) solution of (S)-Boc-proline (2.215 g, 10.3 mmol) and Et$_3$N (1.40 mL, 10.04 mmol), and stirred for 90 min. The volatile component was removed in vacuo, and the residue was partitioned between water and CH$_2$Cl$_2$, and the organic phase was dried (MgSO$_4$), filtered, and concentrated in vacuo. The resultant crude material was purified by a flash chromatography (silica gel; 15-20% EtOAc/hexanes) to afford 136b as a colorless viscous oil (2.74 g). $^1$H NMR (DMSO-d$_6$, δ=2.50, 400 MHz): 7.98 (m, 1H), 7.78 (d, J=8.3, 1H), 7.72-7.69 (m, 1H), 5.61-5.41 (m, 2H), 4.35-4.30 (m, 1H), 3.41-3.30 (m, 2H), 2.43 (s, 3H), 2.33-2.08 (m, 2H), 1.93-1.83 (m, 2H), 1.40/1.36 (s, 9H).

LC (Cond. 1): RT=1.91 min; >95% homogeneity index
LC/MS: Anal. Calcd. for [M+Na]$^+$ C$_{19}$H$_{24}$BrNNaO$_5$ 448.07; found 448.10

Example 136

Step c

136c

A mixture of ketoester 136b (1.445 g, 3.39 mmol) and NH₄OAc (2.93 g, 38.0 mmol) in xylenes (18 mL) was heated with a microwave at 140° C. for 80 min. The volatile component was removed in vacuo, and the residue was carefully partitioned between $CH_2Cl_2$ and water, where enough saturated NaHCO₃ solution was added to neutralize the aqueous medium. The aqueous phase was extracted with $CH_2Cl_2$, and the combined organic phase was dried (MgSO₄), filtered, and concentrated in vacuo. The crude was purified by a flash chromatography (silica gel, 40% EtOAc/hexanes) to afford imidazole 136c as an off-white solid (1.087 g). ¹H NMR (DMSO-d₆, δ=2.50, 400 MHz): 12.15/11.91/11.84 (br s, 1H), 7.72-7.24 (m, 4H), 4.78 (m, 1H), 3.52 (m, 1H), 3.38-3.32 (m, 1H), 2.35 (s, 3H), 2.28-1.77 (m, 4H), 1.40/1.14 (s, 9H).

LC (Cond. 1): RT=1.91 min; >98% homogeneity index
LC/MS: Anal. Calcd. for [M+H]⁺ $C_{19}H_{25}BrN_3O_2$ 405.96; found 406.11

Example 136

Step d

136d

PdCl₂dppf.CH₂Cl₂ (50.1 mg, 0.061 mmol) was added to a pressure tube containing a mixture of bromide 136c (538.3 mg, 1.325 mmol), bis(pinacolato)diboron (666.6 mg, 2.625 mmol), KOAc (365.8 mg, 3.727 mmol) and DMF (10 mL). The reaction mixture was flushed with N₂ and heated at 80° C. for 24.5 hr. The volatile component was removed in vacuo and the residue was partitioned between $CH_2Cl_2$ and water, where enough saturated NaHCO₃ solution was added to make the pH of the aqueous medium neutral. The aqueous phase was extracted with $CH_2Cl_2$, and the combined organic phase was dried (MgSO₄), filtered, and concentrated in vacuo. The resulting material was purified by a Biotage system (silica gel, 40-50% EtOAc/hexanes) to afford boronate 136d as a white foam (580 mg). According to ¹H NMR the sample contains residual pinacol in a product/pinacol ratio of ~3. ¹H NMR (DMSO-d₆, δ=2.50, 400 MHz): 12.16/11.91/11.83 (br s, 1H), 7.63-7.25 (m, 4H), 4.78 (m, 1H), 3.53 (m, 1H), 3.39-3.32 (m, 1H), 2.48/2.47 (s, 3H), 2.28-1.78 (m, 4H), 1.40/1.14/1.12 (br s, 9H), 1.30 (s, 12H).

LC (Cond. 1): RT=1.62 min
LC/MS: Anal. Calcd. for [M+H]⁺ $C_{25}H_{37}BN_3O_4$ 454.29; found 454.15

Example 136

Step e-f

136e: R = Boc
136f: R = H

Biaryl 136e was prepared from bromide 132c and boronate 136d according to the coupling condition described for the preparation of biaryl 132d.

LC (Cond. 1a): RT=1.32 min; >90% homogeneity index
LC/MS: Anal. Calcd. for [M+H]⁺ $C_{36}H_{45}N_7O_4$ 640.36; found 640.66

The deprotection of biaryl 136e was done according to the preparation of pyrrolidine 132e to afford 136f as a light yellow foam. ¹H NMR (DMSO-d₆, δ=2.50, 400 MHz): 11.88 (br s, 2H), 9.02 (d, J=2, 1H), 8.12 (dd, J=8.4, 2.3, 1H), 7.67 (s, 1H), 7.64-7.62 (m, 2H), 7.50 (d, J=8.3, 1H), 7.46 (br s, 1H), 7.40 (d, J=7.8, 1H), 4.21-4.14 (m, 2H), 3.00-2.93 (m, 2H), 2.90-2.82 (m, 2H), 2.40 (s, 3H), 2.11-2.01 (m, 2H), 1.94-1.85 (m, 2H), 1.82-1.66 (m, 4H). [Note: the signal for the pyrrolidine NH appears in the region 3.22-2.80 and is too broad to make a chemical shift assignment.]

LC (Cond. 1): RT=0.84 min
LC/MS: Anal. Calcd. for [M+H]⁺ $C_{26}H_{30}N_7$ 440.26; found 440.50

Example 136

(1R)-2-((2S)-2-(5-(6-(4-(2-((2S)-1-((2R)-2-(dimethylamino)-2-phenylacetyl)-2-pyrrolidinyl)-1H-imidazol-5-yl)-2-methylphenyl)-3-pyridinyl)-1H-imidazol-2-yl)-1-pyrrolidinyl)-N,N-dimethyl-2-oxo-1-phenylethanamine Example 136 (TFA salt) was synthesized from 136f according to the preparation of Example 132 from 132e.
1.05 min (Cond. 1); >98%
LC/MS: Anal. Calcd. for [M+H]+ C46H52N9O2: 762.42, found: 762.77
HRMS: Anal. Calcd. for [M+H]+ C46H52N9O2: 762.4244; found 762.4243

Example 138 methyl((1R)-2-((2S)-2-(5-(6-(4-(2-((2S)-1-((2R)-2-((methoxycarbonyl)amino)-2-phenylacetyl)-2-pyrrolidinyl)-1H-imidazol-5-yl)-2-methylphenyl)-3-pyridinyl)-1H-imidazol-2-yl)-1-pyrrolidinyl)-2-oxo-1-phenylethyl)carbamate

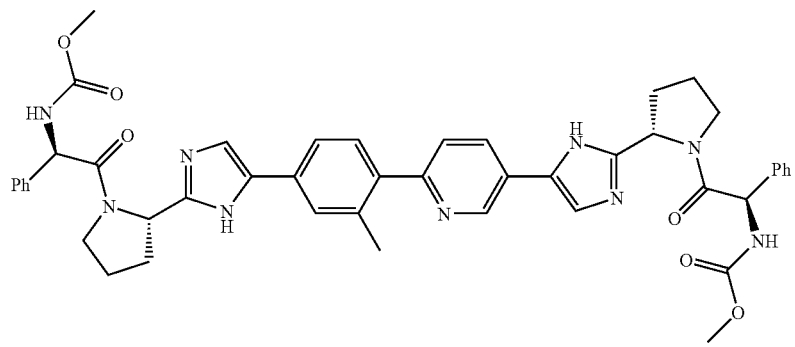

Example 138 was prepared similarly from pyrrolidine 136f and Cap-4. 1.60 min (Cond. 1); >98%
LC/MS: Anal. Calcd. for [M+H]+ C46H48N9O6: 822.37; found 822.74
HRMS: Anal. Calcd. for [M+H]+ C46H48N9O6: 822.3728; found 822.3760

Example 139

N-((1R)-2-((2S)-2-(5-(6-(4-(2-((2S)-1-((2R)-2-acetamido-2-phenylacetyl)-2-pyrrolidinyl)-1H-imidazol-5-yl)phenyl)-3-pyridinyl)-1H-imidazol-2-yl)-1-pyrrolidinyl)-2-oxo-1-phenylethyl)acetamide

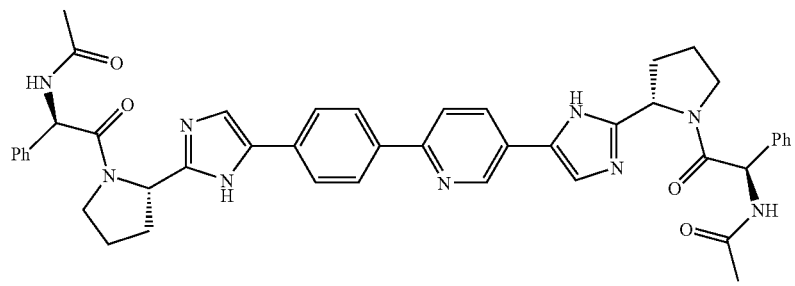

Example 139

Step a

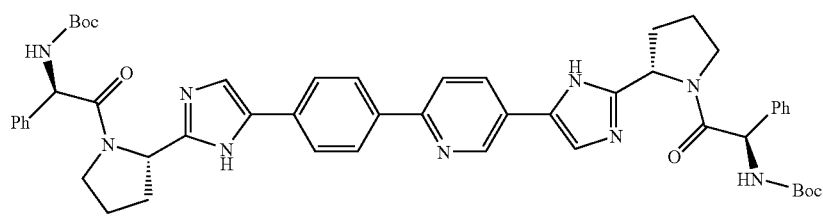

139a

HATU (99.8 mg, 0.262 mmol) was added to a mixture of 132e (54.1 mg, 0.127 mmol), (R)-2-(t-butoxycarbonylamino)-2-phenylacetic acid (98.5 mg, 0.392 mmol) and i-Pr$_2$EtN (100 μL, 0.574 mol), and the reaction mixture was stirred for 70 min. The volatile component was removed in vacuo, and the residue was purified by a reverse phase HPLC (H$_2$O/MeOH/TFA), where the HPLC elute was treated with excess 2.0 N NH$_3$/MeOH before the removal of the volatile component in vacuo. The resulting material was partitioned between CH$_2$Cl$_2$ and water, and the aqueous phase was extracted with CH$_2$Cl$_2$ (2×). The combined organic phase was dried (MgSO$_4$), filtered, and concentrated in vacuo. Carbamate 139a was obtained as a white film of foam (82.3 mg).

LC (Cond. 1): RT=1.97 min; >95% homogeneity index.
LC/MS: Anal. Calcd. for [M+H]$^+$ C$_{51}$H$_{58}$N$_9$O$_6$: 892.45; found 892.72

Example 139b

Step b

Acetic anhydride (20 μL, 0.212 mmol) was added to a DMF (1.5 mL) solution of 139b (31.2 mg, 0.045 mmol), and the reaction mixture was stirred for 1 hr. NH$_3$/MeOH (1.0 mL of 2N) was added to the reaction mixture and stirring continued for 100 min. The volatile component was removed in vacuo and the resulting crude material was purified by a reverse phase HPLC (H$_2$O/MeOH/TFA) to afford the TFA salt of Example 139 as a light yellow solid (24.1 mg).

LC (Cond. 1): RT=1.53 min; >98% homogeneity index

LC/MS: Anal. Calcd. for [M+H]$^+$ C$_{45}$H$_{46}$N$_9$O$_4$: 776.37; found 776.38

HRMS: Anal. Calcd. for [M+H]$^+$ C$_{45}$H$_{46}$N$_9$O$_4$: 776.3673; found 776.3680

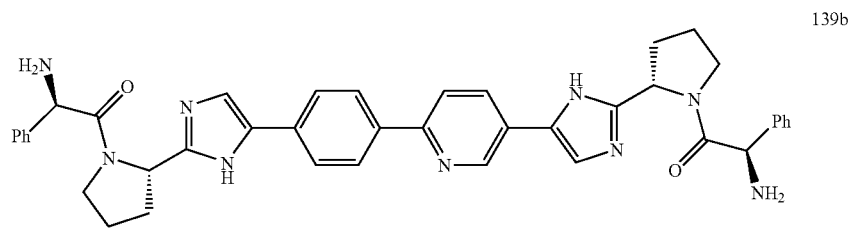

139b

Carbamate 139a was deprotected to amine 139b by using the procedure described for the preparation of pyrrolidine 132e from 132d.

LC (Cond. 1): RT=1.37 min; >95% homogeneity index
LC/MS: Anal. Calcd. for [M+H]$^+$ C$_{41}$H$_{42}$N$_9$O$_2$: 692.35; found 692.32

Example 139

N-((1R)-2-((2S)-2-(5-(6-(4-(2-((2S)-1-((2R)-2-acetamido-2-phenylacetyl)-2-pyrrolidinyl)-1H-imidazol-5-yl)phenyl)-3-pyridinyl)-1H-imidazol-2-yl)-1-pyrrolidinyl)-2-oxo-1-phenylethyl)acetamide

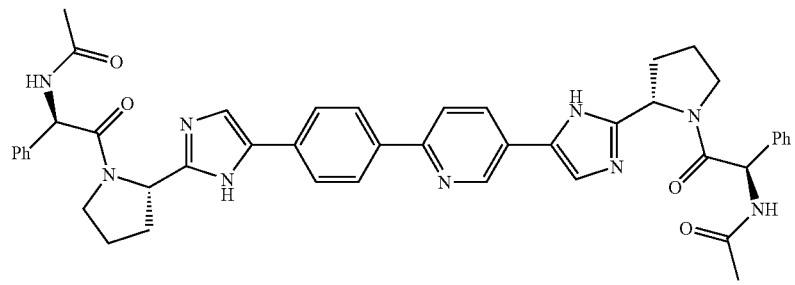

Example 140 methyl((1R)-2-((2S)-2-(5-(4-(5-(2-((2S)-1-((2R)-2-(dimethylamino)-2-phenylacetyl)-2-pyrrolidinyl)-1H-imidazol-5-yl)-2-pyridinyl)phenyl)-1H-imidazol-2-yl)-1-pyrrolidinyl)-2-oxo-1-phenylethyl)carbamate

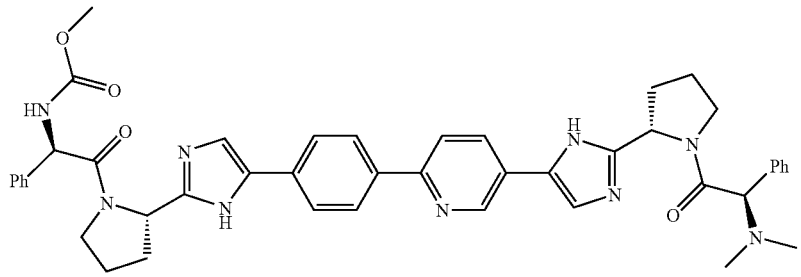

Example 140

Step a

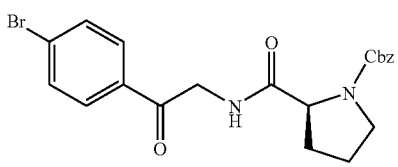

140a

HATU (19.868 g, 52.25 mmol) was added to a heterogeneous mixture of N-Cbz-L-proline (12.436 g, 49.89 mmol) and the HCl salt of 2-amino-1-(4-bromophenyl)ethanone (12.157 g, 48.53 mmol) in DMF (156 mL). The mixture was lowered in an ice-water bath, and immediately afterward N,N-diisopropylethylamine (27 mL, 155 mmol) was added drop wise to it over 13 min. After the addition of the base was completed, the cooling bath was removed and the reaction mixture was stirred for an additional 50 min. The volatile component was removed in vacuo; water (125 mL) was added to the resultant crude solid and stirred for about 1 hr. The off-white solid was filtered and washed with copious water, and dried in vacuo to afford ketoamide 140a as a white solid (20.68 g). $^1$H NMR (DMSO-$d_6$, δ=2.5 ppm, 400 MHz): 8.30 (m, 1H), 7.91 (m, 2H), 7.75 (d, J=8.5, 2H), 7.38-7.25 (m, 5H), 5.11-5.03 (m, 2H), 4.57-4.48 (m, 2H), 4.33-4.26 (m, 1H), 3.53-3.36 (m, 2H), 2.23-2.05 (m, 1H), 1.94-1.78 (m, 3H).

LC (Cond. 1): RT=1.65 min; 98% homogeneity index

LC/MS: Anal. Calcd. for [M+H]$^+$ $C_{21}H_{22}BrN_2O_4$: 445.08; found 445.31

Example 140

Step b

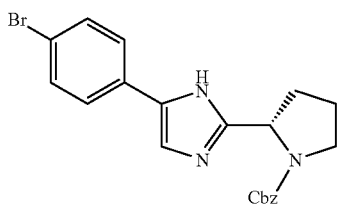

140b

Ketoamide 140a (10.723 g, 24.08 mmol) was converted to 140b according to the procedure described for the synthesis of carbamate 132c, with the exception that the crude material was purified by flash chromatography (silica gel; 50% EtOAc/hexanes). Bromide 140b was retrieved as an off-white foam (7.622 g). $^1$H NMR (DMSO-$d_6$, δ=2.5 ppm, 400 MHz): 12.23/12.04/11.97 (m, 1H), 7.73-6.96 (m, 10H), 5.11-4.85 (m, 3H), 3.61 (m, 1H), 3.45 (m, 1H), 2.33-184 (m, 4H).

LC (Cond. 1): RT=1.42 min; >95% homogeneity index

LC/MS: Anal. Calcd. for [M+H]$^+$ $C_{21}H_{21}BrN_3O_2$: 426.08; found 426.31

HRMS: Anal. Calcd. for [M+H]$^+$ $C_{21}H_{21}BrN_3O_2$: 426.0817; found: 426.0829

The optical purity of 140b was assessed using the following chiral HPLC methods, and an ee of 99% was observed.

Column: Chiralpak AD, 10 um, 4.6×50 mm

Solvent: 20% ethanol/heptane (isocratic)

Flow rate: 1 ml/min

Wavelength: 254 nm

Relative retention time: 1.82 min (R), 5.23 min (S)

Example 140

Step c

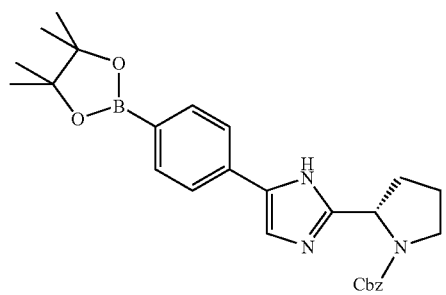

140c

Pd(Ph$_3$P)$_4$ (208 mg, 0.180 mmol) was added to a pressure tube containing a mixture of bromide 140b (1.80 g, 4.22 mmol), bis(pinacolato)diboron (2.146 g, 8.45 mmol), KOAc (1.8 g, 11.0 mmol) and 1,4-dioxane (34 mL). The reaction flask was purged with nitrogen, capped and heated with an oil bath at 80° C. for 23 hr. The volatile component was removed in vacuo, and the residue was partitioned carefully between CH$_2$Cl$_2$ (70 mL) and an aqueous medium (22 mL water+5 mL saturated NaHCO$_3$ solution). The aqueous layer was extracted with CH$_2$Cl$_2$, and the combined organic phase was dried (MgSO$_4$), filtered, and concentrated in vacuo. The oily residue was crystallized from EtOAc/hexanes to afford two crops of boronate 140c as a yellow solid (1.52 g). The mother liquor was evaporated in vacuo and the resulting material was purified by flash chromatography (silica gel; 20-35% EtOAc/

CH₂Cl₂) to afford additional 140c as an off-white solid, containing residual pinacol (772 mg).

LC (Cond. 1): RT=1.95 min

LC/MS: Anal. Calcd. for [M+H]⁺ C₂₇H₃₃BN₃O₄: 474.26; found 474.31

Example 140

Steps d-e

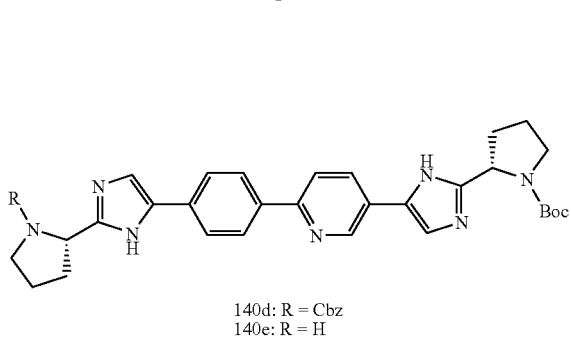

140d: R = Cbz
140e: R = H

Arylbromide 132c was coupled with boronate 140c to afford 140d by using the same procedure described for the synthesis of biaryl 132d. The sample contains the desbromo version of 132c as an impurity. Proceeded to the next step without further purification.

LC (Cond. 1): RT=1.72 min; ~85% homogeneity index

LC/MS: Anal. Calcd. for [M+H]⁺C₃₈H₄₂N₇O₄: 660.33; found 660.30

A mixture of 10% Pd/C (226 mg), biaryl 140d (1.25 g) and MeOH (15 mL) was stirred under a balloon of hydrogen for ~160 hr, where the hydrogen supply was replenished periodically as needed. The reaction mixture was filtered through a pad of diatomaceous earth (Celite®), and the filtrate was evaporated in vacuo to afford crude 140e as a yellowish-brown foam (911 mg). Proceeded to the next step without further purification.

LC (Cond. 1): RT=1.53 min

LC/MS: Anal. Calcd. for [M+H]⁺ C₃₀H₃₆N₇O₂: 526.29; found 526.23

Example 140

Steps f-g

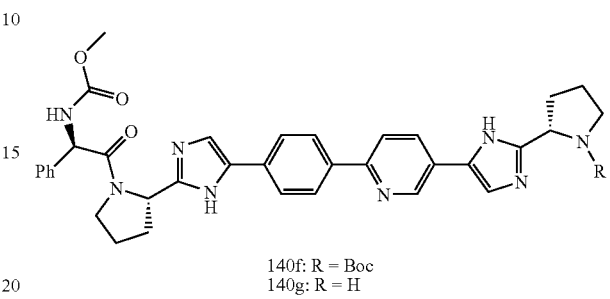

140f: R = Boc
140g: R = H

Pyrrolidine 140g was prepared from 140e and Cap-4, via the intermediacy of carbamate 140f, by sequentially employing the amide forming and Boc-deprotection protocols used in the synthesis of Example 132.

LC (Cond. 1): RT=1.09 min; ~94% homogeneity index

LC/MS: Anal. Calcd. for [M+H]⁺ C₃₅H₃₇N₈O₃: 617.30; found 617.38

Example 140 methyl((1R)-2-((2S)-2-(5-(4-(5-(2-((2S)-1-((2R)-2-(dimethylamino)-2-phenylacetyl)-2-pyrrolidinyl)-1H-imidazol-5-yl)-2-pyridinyl)phenyl)-1H-imidazol-2-yl)-1-pyrrolidinyl)-2-oxo-1-phenylethyl)carbamate

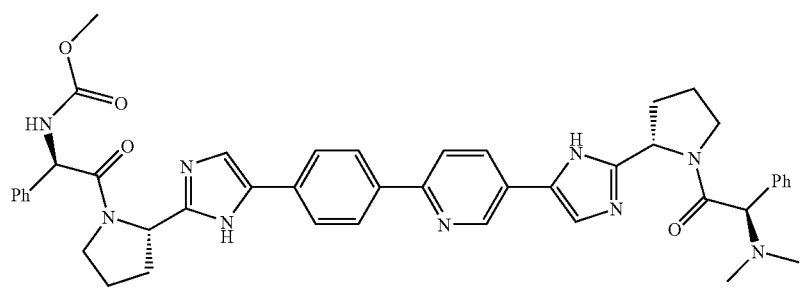

The TFA salt of Example 140 was synthesized from pyrrolidine 140 g and Cap-1 by using the procedure described for the preparation of Example 132 from intermediate 132e.

1.15 min (Cond. 1); >98% homogeneity index

LC/MS: Anal. Calcd. for $[M+H]^+$ $C_{45}H_{40}N_7O_4$: 778.38; found 778.48

HRMS: Anal. Calcd. for $[M+H]^+$ $C_{45}H_{40}N_7O_4$: 778.3829; found 778.3849

The TFA salt of Example 141-143 were synthesized from intermediate 140 g and appropriate reagents in a similar manner.

Examples 141-143

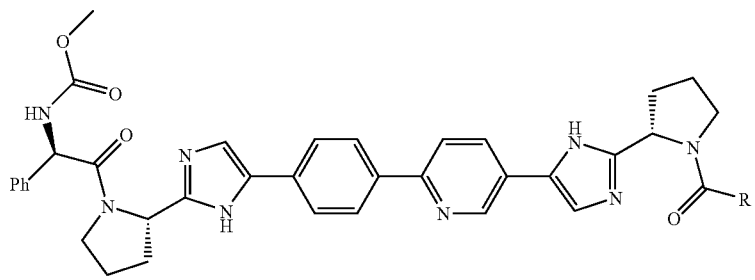

| Example | Compound Name | R group | RT (LC-Cond.); % homogeneity index; MS data |
|---|---|---|---|
| 141 | methyl ((1R)-2-oxo-1-phenyl-2-((2S)-2-(5-(4-(5-(2-((2S)-1-((2R)-tetrahydro-2-furanylcarbonyl)-2-pyrrolidinyl)-1H-imidazol-5-yl)-2-pyridinyl)phenyl)-1H-imidazol-2-yl)-1-pyrrolidinyl)ethyl)carbamate | 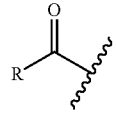 | 1.15 min (Cond. 1); >98% LC/MS: Anal. Calcd. for $[M + H]^+$ $C_{40}H_{43}N_8O_5$: 715.34; found 715.44 HRMS: Anal. Calcd. for $[M + H]^+$ $C_{40}H_{43}N_8O_5$: 715.3356; found 715.3381 |
| 142 | methyl ((1R)-2-((2S)-2-(5-(4-(5-(2-((2S)-1-((1-methyl-4-piperidinyl)carbonyl)-2-pyrrolidinyl)-1H-imidazol-5-yl)-2-pyridinyl)phenyl)-1H-imidazol-2-yl)-1-pyrrolidinyl)-2-oxo-1-phenylethyl)carbamate | 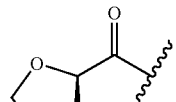 | 1.07 min (Cond. 1); >98% LC/MS: Anal. Calcd. for $[M + H]^+$ $C_{42}H_{48}N_9O_4$: 742.38; found 742.48 HRMS: Anal. Calcd. for $[M + H]^+$ $C_{42}H_{48}N_9O_4$: 742.3829; found 742.3859 |
| 143 | methyl ((1R)-2-oxo-1-phenyl-2-((2S)-2-(5-(4-(5-(2-((2S)-1-(3-pyridinylacetyl)-2-pyrrolidinyl)-1H-imidazol-5-yl)-2-pyridinyl)phenyl)-1H-imidazol-2-yl)-1-pyrrolidinyl)ethyl)carbamate | 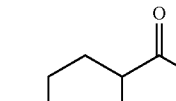 | 1.09 min (Cond. 1); >98% LC/MS: Anal. Calcd. for $[M + H]^+$ $C_{42}H_{42}N_9O_4$: 736.34; found 736.44 HRMS: Anal. Calcd. for $[M + H]^+$ $C_{42}H_{42}N_9O_4$: 736.3360; 736.3344 |

Example 144 methyl((1R)-2-((2S)-2-(5-(4-(5-(2-((2S)-1-(4-morpholinylcarbonyl)-2-pyrrolidinyl)-1H-imidazol-5-yl)-2-pyridinyl)phenyl)-1H-imidazol-2-yl)-1-pyrrolidinyl)-2-oxo-1-phenylethyl)carbamate

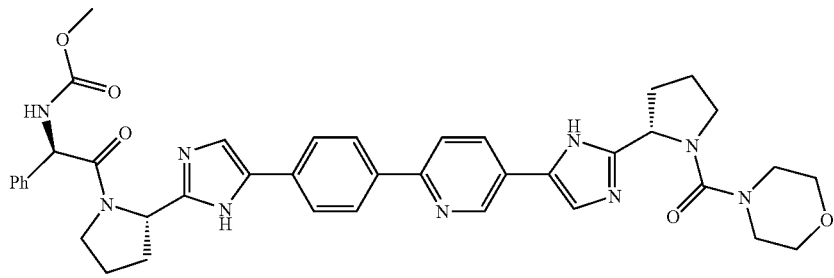

A DMF (1.5 mL) solution of morpholine-4-carbonyl chloride (8.5 mg, 0.057 mmol) was added to a mixture of i-Pr$_2$EtN (20 µL, 0.115 mmol) and 140 g (27.3 mg, 0.044 mmol), and stirred for 100 min. The volatile component was removed in vacuo and the residue was purified by a reverse phase HPLC (H$_2$O/MeOH/TFA) to afford the TFA salt of Example 144 as a yellow foam (34.6 mg).

1.17 min (Cond. 1); >98%

LC/MS: Anal. Calcd. for [M+H]$^+$ C$_{40}$H$_{44}$N$_9$O$_5$: 730.35; found 730.42

HRMS: Anal. Calcd. for [M+H]$^+$ C$_{40}$H$_{44}$N$_9$O$_5$: 730.3465; found 730.3477

Example 145 dimethyl(2,2'-bipyridine-5,5'-diylbis(1H-imidazole-5,2-diyl(2S)-2,1-pyrrolidinediyl((1R)-2-oxo-1-phenyl-2,1-ethanediyl)))biscarbamate Pd(Ph$_3$P)$_4$ (9.6 mg, 0.008 mmol) and LiCl (28 mg, 0.67 mmol) were added to a mixture of arylbromide 132c (98.7 mg, 0.251 mmol) and hexamethylditin (51.6 mg, 0.158 mmol), and heated at 80° C. for ~3 days. The volatile component was removed in vacuo and the resultant crude material was purified by flash chromatography (silica gel; 0-10% MeOH/EtOAc) followed by a reverse phase HPLC (H$_2$O/MeOH/TFA). The HPLC elute was neutralized with excess 2.0 N NH$_3$/MeOH, and the volatile component was removed in vacuo. The residue was partitioned between CH$_2$Cl$_2$ and water, and the aqueous phase was washed with CH$_2$Cl$_2$ (2×). The combined organic phase was dried (MgSO$_4$), filtered, and concentrated in vacuo to afford carbamate 145a as a film of oil (8.7 mg).

LC (Cond. 1): RT=1.68 min; >98% homogeneity index

LC/MS: Anal. Calcd. for [M+H]$^+$ C$_{34}$H$_{43}$N$_8$O$_4$: 627.34; found 627.47

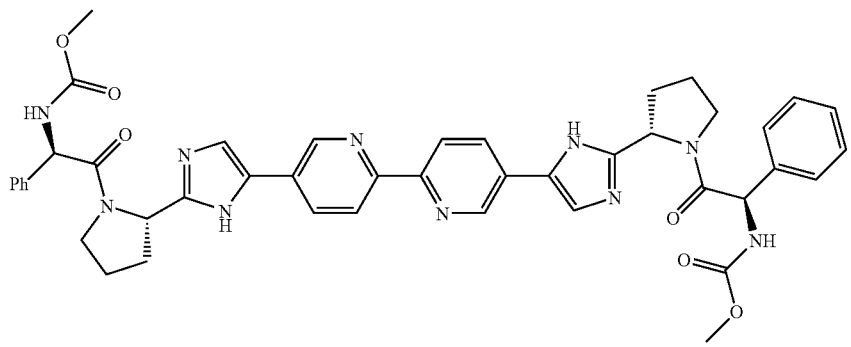

Example 145

Step a-b

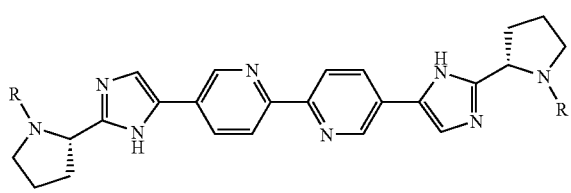

145a: R = Boc
145b: R = H

Carbamate 145a was elaborated to pyrrolidine 145b according to the preparation of 132e from 132d. $^1$H NMR (DMSO, δ=2.5 ppm; 400 MHz): 12.02 (br signal, 2H), 9.04 (d, J=1.6, 2H), 8.34 (d, J=8.3, 2H), 8.20 (dd, J=8.3, 2.3, 2H), 7.67 (br s, 1H), 4.21 (m, 2H), 3.00-2.85 (m, 4H), 2.12-2.04 (m, 2H), 1.95-1.68 (m, 6H). [Note: the pyrrolidine-NH signal was not observed].

LC (Cond. 1): RT=1.17 min; >98% homogeneity index

LC/MS: Anal. Calcd. for [M+H]$^+$ C$_{24}$H$_{27}$N$_8$: 427.24; found 427.13

Example 145 dimethyl (2,2'-bipyridine-5,5'-diylbis(1H-imidazole-5,2-diyl(2S)-2,1-pyrrolidinediyl((1R)-2-oxo-1-phenyl-2,1-ethanediyl)))biscarbamate

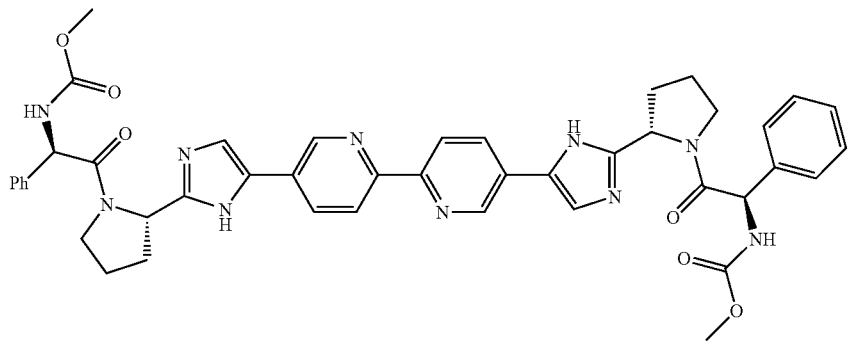

Example 145 (TFA salt) was synthesized from 145b according to the preparation of Example 132 from 132e.

LC (Cond. 1): RT=1.63 min; 98% homogeneity index
LC/MS: Anal. Calcd. for [M+H]$^+$ C$_{44}$H$_{45}$N$_{10}$O$_6$: 809.35; found 809.40

Example 146

(1R)-2-((2S)-2-(5-(5-(4-(2-((2S)-1-((2R)-2-(dimethylamino)-2-phenylacetyl)-2-pyrrolidinyl)-1H-imidazol-5-yl)phenyl)-2-pyridinyl)-1H-imidazol-2-yl)-1-pyrrolidinyl)-N,N-dimethyl-2-oxo-1-phenylethanamine

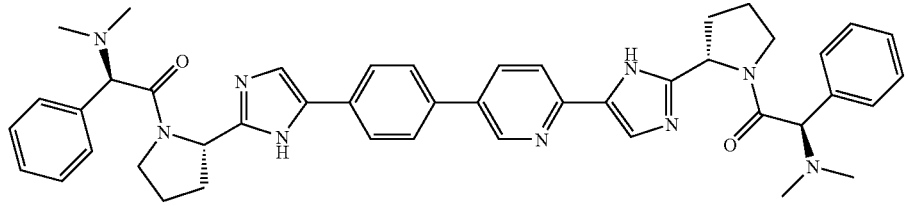

Example 146

Step a

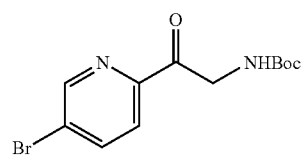

146a n-BuLi (12.0 mL of 2.5M/hexanes, 30 mmol) was added drop-wise over 15 min to a cooled (−78° C.) toluene (300 mL) semi-solution of 2,5-dibromopyridine (6.040 g, 25.5 mmol), and stirred for 2.5 hr. t-Butyl 2-(methoxy(methyl)amino)-2-oxoethylcarbamate (2.809 g, 12.87 mmol) was added in batches over 7 min, and stirring continued for 1.5 hr at −78° C. The −78° C. bath was replaced with −60° C. bath, which was allowed to warm up to −15° C. over 2.5 hr. The reaction was quenched with saturated NH$_4$Cl solution (20 mL), and the mixture was allowed to thaw to ambient temperature and the organic layer was separated and evaporated in vacuo. The resulting crude material was purified by flash chromatography (silica gel; 15% EtOAc/hexanes) to afford a reddish brown semisolid, which was washed with hexanes to removed the colored residue. Pyridine 146a was retrieved as an ash colored solid (842 mg). $^1$H NMR (DMSO, δ=2.5 ppm; 400 MHz): 8.89 (d, J=2.3, 1H), 8.30 (dd, J=8.4, 2.4, 1H), 7.90 (d, J=8.3, 1H), 7.03 (br t, J=5.7; 0.88H), 6.63 (app br s, 0.12H), 4.55 (d, J=5.8, 2H), 1.40/1.28 (two app s, 7.83H+1.17H).

LC (Cond. 1): RT=2.00 min; >95% homogeneity index

LC/MS: Anal. Calcd. for [M+Na]$^+$ C$_{12}$H$_{15}$BrNaN$_2$O$_3$: 337.02; found 337.13

Example 146

Step b

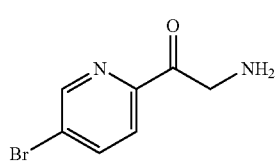

146b

48% HBr (1.0 mL) was added drop-wise to a dioxane (5.0 mL) solution of carbamate 146a (840 mg, 2.66 mmol) over 3 min, and the reaction mixture was stirred at ambient temperature for 17.5 hr. The precipitate was filtered and washed with dioxane, and dried in vacuo to afford amine the HBr salt of 146b as an off-white solid (672.4 mg; the exact mole equivalent of the HBr salt was not determined). $^1$H NMR (DMSO, δ=2.5 ppm; 400 MHz): 8.95 (d, J=2.3, 1H), 8.37 (dd, J=8.4, 2.3, 1H), 8.2 (br s, 3H), 8.00 (d, J=8.3, 1H), 4.61 (s, 2H).

LC (Cond. 1): RT=0.53 min

LC/MS: Anal. Calcd. for [M+H]$^+$ $C_7H_8BrN_2O$: 214.98; found 215.00

Example 146

Step c

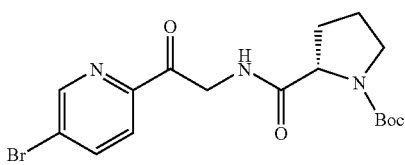

146c i-Pr$_2$EtN (2.3 mL, 13.2 mmol) was added drop-wise over 15 min to a heterogeneous mixture of amine 146b (1.365 g), (S)-Boc-proline (0.957 g, 4.44 mmol) and HATU (1.70 g, 4.47 mmol) in DMF (13.5 mL), and stirred at ambient temperature for 1 hr. The volatile component was removed in vacuo and the residue was partitioned between EtOAc (40 mL) and an aqueous medium (20 mL water+1 ml saturated NaHCO$_3$ solution). The aqueous layer was washed with EtOAc (20 mL), and the combined organic phase was dried (MgSO$_4$), filtered, and concentrated in vacuo. The resultant crude material was purified by flash chromatography (silica gel; 40-50% EtOAc/hexanes) to afford ketoamide 146c as a faint-yellow foam (1.465 g). $^1$H NMR (DMSO, δ=2.5 ppm; 400 MHz): 8.90 (d, J=2.3, 1H), 8.30 (dd, J=8.5, 2.4, 1H), 8.01-8.07 (m, 1H), 7.90 (d, J=8.3, 1H), 4.6 (m, 1H), 4.64 (dd, J=19.1, 5.5, 1H); 4.19 (m, 1H), 3.39 (m, 1H), 3.32-3.26 (m, 1H), 2.20-2.01 (m, 1H), 1.95-1.70 (m, 3H), 1.40/1.35 (two app s, 9H).

LC (Cond. 1): RT=1.91 min

LC/MS: Anal. Calcd. for [M+Na]$^+$ $C_{17}H_{22}BrN_3NaO_4$: 434.07; found 433.96.

Example 146

Step d

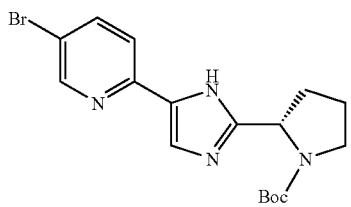

146d

A mixture of ketoamide 146c (782.2 mg, 1.897 mmol) and NH$_4$OAc (800 mg, 10.4 mmol) in xylenes was heated with a microwave (140° C.) for 90 min. The volatile component was removed in vacuo and the residue was carefully partitioned between CH$_2$Cl$_2$ and water, where enough saturated NaHCO$_3$ solution was added to neutralize it. The aqueous phase was extracted with CH$_2$Cl$_2$ (2×), and the combined organic phase was dried (MgSO$_4$), filtered, and concentrated in vacuo. The resultant crude material was purified by flash chromatography (silica gel; 50% CH$_2$Cl$_2$/EtOAc) to afford imidazole 146d as an off-white solid (552.8 mg). $^1$H NMR (DMSO, δ=2.5 ppm; 400 MHz): 12.49/12.39/12.15/12.06 (br s, 1H), 8.62 (app br s, 0.2H), 8.56 (d, J=2, 0.8H), 8.02 (br d, J=8.5, 0.2H), 7.97 (br d, J=7.8, 0.8H), 7.77 (d, J=8.6, 0.8H), 7.72 (d, J=8.6, 0.2H), 7.61-7.49 (m, 1H), 4.93-4.72 (m, 1H), 3.53 (m, 1H), 3.41-3.32 (m, 1H), 2.33-1.77 (m, 4H), 1.39/1.14 (app br s, 3.7H+5.3H).

LC (Cond. 1): RT=1.67 min; >95% homogeneity index

LC/MS: Anal. Calcd. for [M+Na]$^+$ $C_{17}H_{21}BrN_4NaO_2$: 415.08; found 415.12

Example 146

Step e

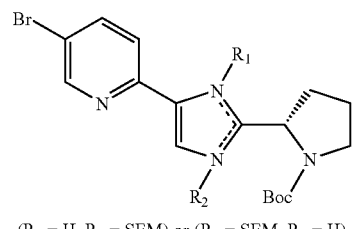

146e (R$_1$ = H, R$_2$ = SEM) or (R$_1$ = SEM, R$_2$ = H)

NaH (60%; 11.6 mg, 0.29 mmol) was added in one batch to a heterogeneous mixture of imidazole 146d (80 mg, 0.203 mmol) and DMF (1.5 mL), and stirred at ambient condition for 30 min. SEM-Cl (40 μL, 0.226 mmol) was added drop-wise over 2 min to the above reaction mixture, and stirring was continued for 14 hr. The volatile component was removed in vacuo and the residue was partitioned between water and CH$_2$Cl$_2$. The aqueous layer was extracted with CH$_2$Cl$_2$, and the combined organic phase was dried (MgSO$_4$), filtered, and concentrated in vacuo. The crude material was purified by a flash chromatography (silica gel; 20% EtOAc/hexanes) to afford 146e as a colorless viscous oil (87.5 mg). The exact regiochemistry of 146e was not determined. $^1$H NMR (CDCl$_3$, δ=7.4 ppm; 400 MHz): 8.53 (d, J=2.2, 1H), 7.90-7.72 (m, 2H), 7.52 (s, 1H), 5.87 (m, 0.46H), 5.41 (m, 0.54H), 5.16 (d, J=10.8, 1H), 5.03-4.85 (m, 1H), 3.76-3.42 (m, 4H), 2.54-1.84 (m, 4H), 1.38/1.19 (br s, 4.3H+4.7H), 0.97-0.81 (m, 2H), −0.03 (s, 9H).

LC (Cond. 1): RT=2.1 min

LC/MS: Anal. Calcd. for [M+H]$^+$ $C_{23}H_{36}BrN_4O_3Si$: 523.17; found 523.24

Example 146

Step f

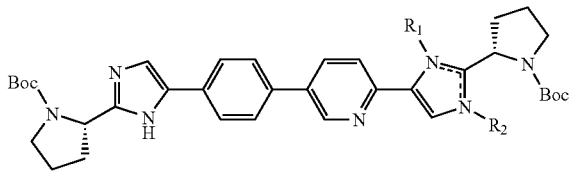

146f: (R₁ = H, R₂ = SEM) or (R₁ = SEM, R₂ = H)

Pd(Ph₃P)₄ (24.4 mg, 0.021 mmol) was added to a mixture of imidazole 146e (280 mg, 0.535 mmol), 1c (241.5 mg, 0.55 mmol) and NaHCO₃ (148.6 mg, 1.769 mmol) in 1,2-dimethoxyethane (4.8 mL) and water (1.6 mL). The reaction mixture was flushed with nitrogen, heated with an oil bath at 80° C. for ~24 hr and then the volatile component was removed in vacuo. The residue was partitioned between CH₂Cl₂ and water, and the organic phase was dried (MgSO₄), filtered, and concentrated in vacuo. The crude material was purified by a Biotage system (silica gel; 75-100% EtOAc/hexanes) followed by a reverse phase HPLC (H₂O/MeOH/TFA). The HPLC elute was neutralized with 2M NH₃/MeOH and evaporated in vacuo, and the residue was partitioned between water and CH₂Cl₂. The organic layer was dried (MgSO₄), filtered, and concentrated in vacuo to afford 146f as a white foam (162 mg).

LC (Cond. 1): RT=2.1 min

LC/MS: Anal. Calcd. for [M+H]⁺ $C_{41}H_{58}N_7O_5Si$: 756.43; found 756.55

Step g

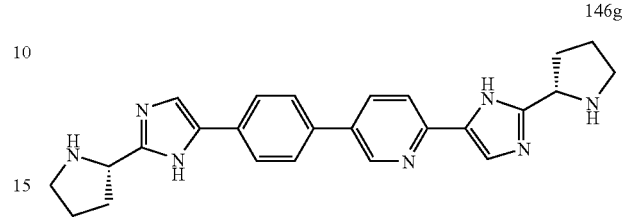

Carbamate 146f (208 mg, 0.275 mmol) was treated with 25% TFA/CH₂Cl₂ (4.0 mL) and stirred at ambient temperature for 10 hr. The volatile component was removed in vacuo and the residue was first free-based by MCX (MeOH wash; 2.0 M NH₃/MeOH elution) and then purified by a reverse phase HPLC (H₂O/MeOH/TFA), and the resultant material was free-based again (MCX) to afford pyrrolidine 146 g as a film of oil (53.7 mg). ¹H NMR (DMSO, δ=2.5 ppm; 400 MHz): 1.88 (app br s, 2H), 8.83 (d, J=2.1, 1H), 8.07 (dd, J=8.3/2.3, 1H0, 7.87 (d, J=8.5, 1H), 7.84 (d, J=8.3, 2H), 7.71 (d, J=8.3, 2H), 7.55 (s, 1H), 7.50 (br s, 1H), 4.18 (m, 2H), 3.00-2.94 (m, 2H), 2.89-2.83 (m, 2H), 2.11-2.02 (m, 2H), 1.95-1.86 (m, 2H), 1.83-1.67 (m, 4H).

LC (Cond. 1): RT=0.95 min; >98% homogeneity index

LC/MS: Anal. Calcd. for [M+H]⁺ $C_{25}H_{28}N_7$: 426.24; found 426.27

Example 146

(1R)-2-((2S)-2-(5-(5-(4-(2-((2S)-1-((2R)-2-(dimethylamino)-2-phenylacetyl)-2-pyrrolidinyl)-1H-imidazol-5-yl)phenyl)-2-pyridinyl)-1H-imidazol-2-yl)-1-pyrrolidinyl)-N,N-dimethyl-2-oxo-1-phenylethanamine

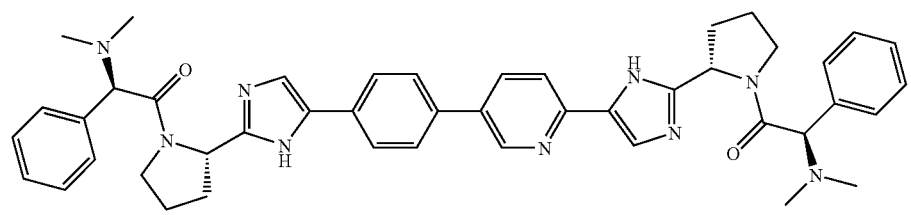

Example 146 (TFA salt) was synthesized from pyrrolidine 146 g according to the preparation of Example 132 from intermediate 132e.

LC (Cond. 1): RT=1.42 min; 96.5% homogeneity index
LC/MS: Anal. Calcd. for [M+H]+ $C_{45}H_{50}N_9O_2$: 748.41; found 748.57
HRMS: Anal. Calcd. for [M+H]+ $C_{45}H_{50}N_9O_2$: 748.4087; found 748.4100

Example 147 methyl((1R)-2-((2S)-2-(5-(5-(4-(2-((2S)-1-((2R)-2-((methoxycarbonyl)amino)-2-phenylacetyl)-2-pyrrolidinyl)-1H-imidazol-5-yl)phenyl)-2-pyridinyl)-1H-imidazol-2-yl)-1-pyrrolidinyl)-2-oxo-1-phenylethyl) carbamate

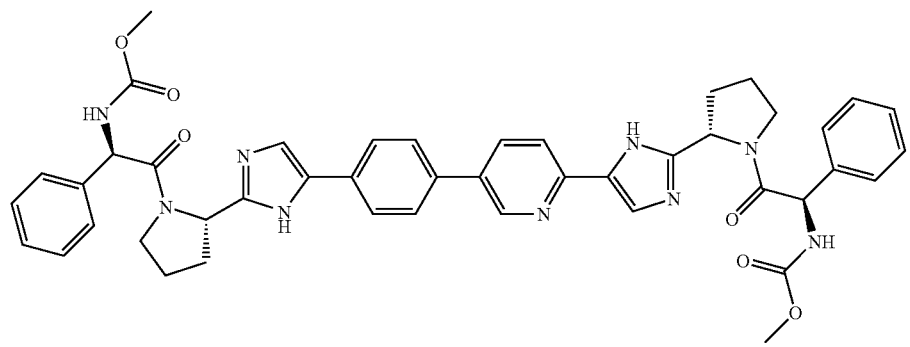

The TFA salt of Example 147 was prepared similarly from intermediate 146 g by using Cap-4.

LC (Cond. 1): RT=1.66 min; 95% homogeneity index
LC/MS: Anal. Calcd. for [M+H]+ $C_{45}H_{46}N_9O_6$: 808.36; found 808.55

Example 148

(1R,1'R)-2,2'-(4,4'-biphenyldiylbis(1H-imidazole-5,2-diyl(4R)-1,3-thiazolidine-4,3-diyl))bis(N,N-dimethyl-2-oxo-1-phenylethanamine)

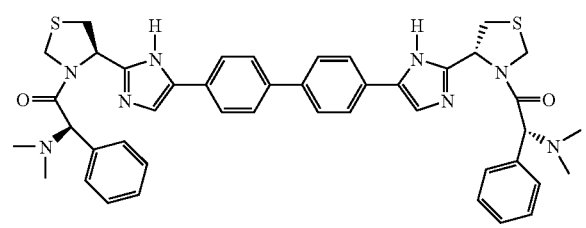

Example 148

Step a

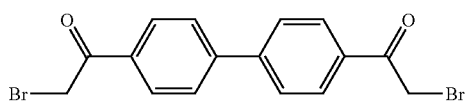

A solution of bromine (1.3 mL, 25.0 mmol) in 15 mL glacial acetic acid was added drop-wise to a solution of 4-4'-diacetylbiphenyl (3.0 g, 12.5 mmol) in 40 mL acetic acid at 50° C. Upon completion of addition the mixture was stirred at room temperature overnight. The precipitated product was filtered off and re-crystallized from chloroform to give 1,1'-(biphenyl-4,4'-diyl)bis(2-bromoethanone) (3.84 g, 77.5%) as a white solid.

$^1$H NMR (500 MHz, CHLOROFORM-D) δ ppm 8.09 (4H, d, J=7.93 Hz) 7.75 (4H, d, J=8.24 Hz) 4.47 (4H, s)

Nominal/LRMS—Anal. Calcd. for 369.07 found; (M+H)+ −397.33, (M−H)− −395.14

Example 148

Step b

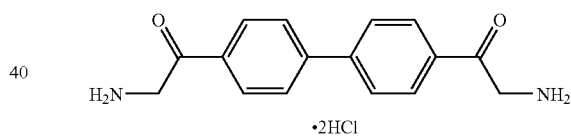

Sodium diformylamide (3.66 g, 38.5 mmol) was added to a suspension of 1,1'-(biphenyl-4,4'-diyl)bis(2-bromoethanone) (6.1 g, 15.4 mmol) in 85 mL acetonitrile. The mixture was heated at reflux for 4 hours and concentrated under reduced pressure. The residue was suspended in 300 mL 5% HCl in ethanol and heated at reflux for 3.5 hours. Reaction was cooled to room temperature and placed in the freezer for 1 hour. Precipitated solid was collected, washed with 200 mL 1:1 ethanol/ether followed by 200 mL pentane, and dried under vacuum to give 1,1'-(biphenyl-4,4'-diyl)bis(2-aminoethanone)dihydrochloride (4.85 g, 92%). Carried on without further purification.

$^1$H NMR (300 MHz, DMSO-d$_6$) δ ppm 8.47-8.55 (4H, m) 8.11-8.17 (4H, m) 8.00 (4H, d, J=8.42 Hz) 4.59-4.67 (4H, m).

LCMS—Phenomenex C-18 3.0×50 mm, 0 to 100% B over 4.0 minute gradient, 1 minute hold time, A=10% methanol 90% water 0.1% TFA, B=90% methanol 10% water 0.1% TFA, $t_R$=0.44 minutes, Anal. Calcd. for $C_{16}H_{16}N_2O_2$ 268.31 found; 269.09 (M+H)+.

Example 148

Step c

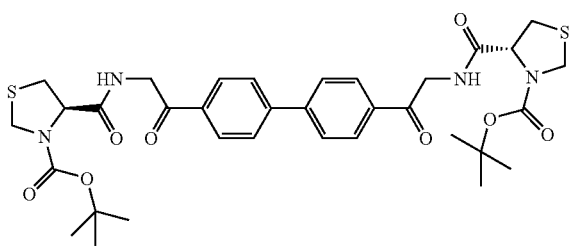

To a stirred solution of 1,1'-(biphenyl-4,4'-diyl)bis(2-aminoethanone)dihydrochloride (0.7 g, 2.1 mmol), N-(tert-butoxy carbonyl)-L-thioproline (0.96 g, 4.2 mmol), and HATU (1.68 g, 4.4 mmol) in 14 mL DMF was added diisopropylethyl amine (1.5 mL, 8.4 mmol) drop-wise over 5 minutes. The resulting clear yellow solution was stirred at room temperature overnight (14 hours) and concentrated under reduced pressure. The residue was partitioned between 20% methanol/chloroform and water. The aqueous phase was washed once with 20% methanol/chloroform. The combined organics were washed with brine, dried (MgSO$_4$), filtered, and concentrated under reduced pressure. The crude product was chromatographed on silica gel by gradient elution with 10-50% ethyl acetate/CH$_2$Cl$_2$ to give (4S,4'S)-tert-butyl 4,4'-(2,2'-(biphenyl-4,4'-diyl)bis(2-oxoethane-2,1-diyl))bis(azanediyl)bis(oxomethylene)dithiazolidine-3-carboxylate (0.39 g, 27%) as an orange foam.

$^1$H NMR (400 MHz, DMSO-d$_6$) δ ppm 8.38 (2H, s) 8.12 (4H, d, J=8.56 Hz) 7.94 (4 H, d, J=8.56 Hz) 4.60-4.68 (4H, m) 4.33-4.38 (2H, m) 3.58-3.68 (2H, m) 3.38 (2H, s) 3.08-3.18 (2H, m) 1.40 (18H, s)

LCMS—Water-Sunfire C-18 4.6×50 mm, 0 to 100% B over 4.0 minute gradient, 1 minute hold time, A=10% methanol 90% water 0.1% TFA, B=90% methanol 10% water 0.1% TFA, t$_R$=3.69 min., Anal. Calcd. for C$_{34}$H$_{42}$N$_4$O$_8$S$_2$ 698.85 found; 699.12 (M+H)$^+$.

Example 148

Step d

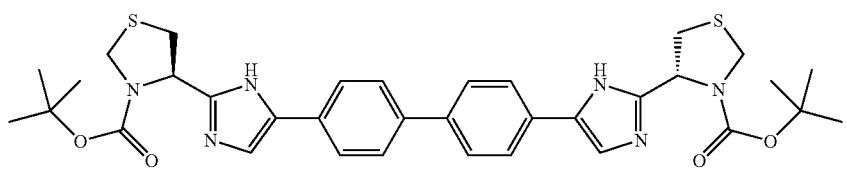

(4S,4'S)-tert-butyl 4,4'-(5,5'-(biphenyl-4,4'-diyl)bis(1H-imidazole-5,2-diyl))dithiazolidine-3-carboxylate (0.39 g, 0.56 mmol) and ammonium acetate (0.43 g, 5.6 mmol) were suspended in 8 mL o-xylene in a microwave reaction vessel. The mixture was heated under standard microwave conditions at 140° C. for 70 minutes and concentrated under reduced pressure. The residue was dissolved in 30 mL 20% methanol/chloroform and washed with 10% NaHCO$_3$(aq). The organic layer was washed with brine, dried (MgSO$_4$), filtered, and concentrated under reduced pressure. The crude product was chromatographed on silica gel by gradient elution with 1-6% methanol/CH$_2$Cl$_2$ to give (4S,4'S)-tert-butyl 4,4'-(5,5'-(biphenyl-4,4'-diyl)bis(1H-imidazole-5,2-diyl))dithiazolidine-3-carboxylate (0.15 g, 41%) as a yellow solid.

$^1$H NMR (500 MHz, DMSO-d$_6$) δ ppm 12.02 (2H, s) 7.70-7.88 (10H, m) 5.28-5.37 (2H, m) 4.68 (2H, d, J=9.16 Hz) 4.47-4.55 (2H, m) 3.46 (2H, s) 3.23 (2H, s) 1.26-1.43 (18H, m)

LCMS—Luna C-18 3.0×50 mm, 0 to 100% B over 3.0 minute gradient, 1 minute hold time, A=5% acetonitrile, 95% water, 10 mm ammonium acetate, B=95% acetonitrile, 5% water, 10 mm ammonium acetate, t$_R$=1.96 min., Anal. Calcd. for C$_{34}$H$_{40}$N$_6$O$_4$S$_2$ 660.85 found; 661.30 (M+H)$^+$, 659.34 (M−H)$^−$

Example 148

Step e

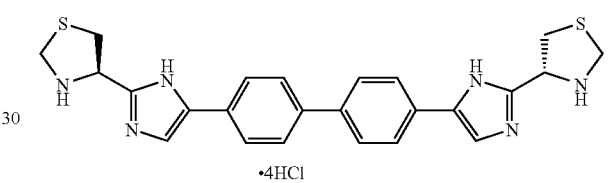

·4HCl

To a solution of (4S,4'S)-tert-butyl 4,4'-(5,5'-(biphenyl-4,4'-diyl)bis(1H-imidazole-5,2-diyl))dithiazolidine-3-carboxylate in 1 mL dioxane was added 0.3 mL of a 4.0M solution of HCl in dioxane. The reaction was stirred for 3 hours at room temperature and concentrated under reduced pressure. The resulting tan solid was dried under vacuum to give 4,4'-bis(2-((S)-thiazolidin-4-yl)-1H-imidazol-5-yl)biphenyl tetrahydrochloride (0.12 g, 100%) as a yellow solid.

$^1$H NMR (500 MHz, DMSO-d$_6$) δ ppm 8.09 (2H, s) 8.01 (4H, d, J=8.55 Hz) 7.90 (4 H, d, J=8.55 Hz) 5.08 (2H, t, J=6.10 Hz) 4.38 (2H, d, J=9.16 Hz) 4.23 (2H, d, J=9.46 Hz) 3.48-3.54 (2H, m) 3.35-3.41 (2H, m)

LCMS—Luna C-18 3.0×50 mm, 0 to 100% B over 4.0 minute gradient, 1 minute hold time, A=5% acetonitrile, 95% water, 10 mm ammonium acetate, B=95% acetonitrile, 5% water, 10 mm ammonium acetate, t$_R$=1.70 min., Anal. Calcd. for C$_{24}$H$_{24}$N$_6$S$_2$ 460.62 found; 461.16 (M+H)$^+$, 459.31 (M−H)$^−$

Example 148

(1R,1'R)-2,2'-(4,4'-biphenyldiylbis(1H-imidazole-5, 2-diyl(4R)-1,3-thiazolidine-4,3-diyl))bis(N,N-dimethyl-2-oxo-1-phenylethanamine)

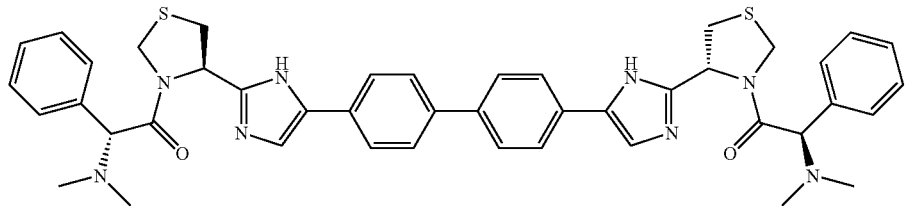

To a stirred solution of (4,4'-bis(2-((S)-thiazolidin-4-yl)-1H-imidazol-5-yl)biphenyl tetrahydrochloride (0.028 g, 0.046 mmol), (R)-2-(dimethylamino)-2-phenylacetic acid (Cap-1, 0.017 g, 0.0.10 mmol), and HATU (0.039 g, 0.10 mmol) in 2 mL DMF was added diisopropylethyl amine (0.05 mL, 0.28 mmol). The reaction was stirred at room temperature overnight (16 hours) and concentrated under reduced pressure. The crude product was purified by reverse-phase preparative HPLC to provide (2R,2'R)-1,1'-((4S,4'S)-4,4'-(5, 5'-(biphenyl-4,4'-diyl)bis(1H-imidazole-5,2-diyl))bis(thiazolidine-4,3-diyl))bis(2-(dimethylamino)-2-phenylethanone), TFA salt (0.012 g, 21%)

$^1$H NMR (500 MHz, DMSO-d$_6$) δ ppm 7.59-7.91 (20H, m) 5.62 (2H, dd, J=6.56, 2.59 Hz) 4.99 (2H, d, J=8.85 Hz) 4.82/4.35 (2H, s) 4.22 (2H, s) 3.42 (2H, s) 3.25 (2H, s) 2.35-2.61 (12H, m)

LCMS—Luna C-18 3.0×50 mm, 0 to 100% B over 7.0 minute gradient, 1 minute hold time, A=5% acetonitrile, 95% water, 10 mm ammonium acetate, B=95% acetonitrile, 5% water, 10 mm ammonium acetate mobile phase $t_R$=3.128 min.

Nominal/LRMS—Calcd. for C$_{44}$H$_{46}$N$_8$O$_2$S$_2$ 783.03; found 783.28 (M+H)$^+$ Accurate/HRMS—Calcd. for C$_{44}$H$_{47}$N$_8$O$_2$S$_2$ 783.3263; 783.3246 (M+H)$^+$

Example 151

(1R,1'R)-2,2'-(4,4'-biphenyldiylbis((1-methyl-1H-imidazole-4,2-diyl)(2S)-2,1-pyrrolidinediyl))bis(N,N-dimethyl-2-oxo-1-phenylethanamine)

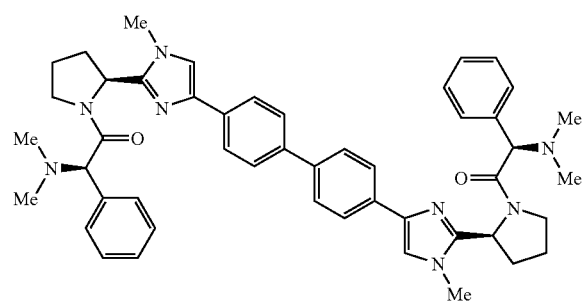

Example 151

Step a

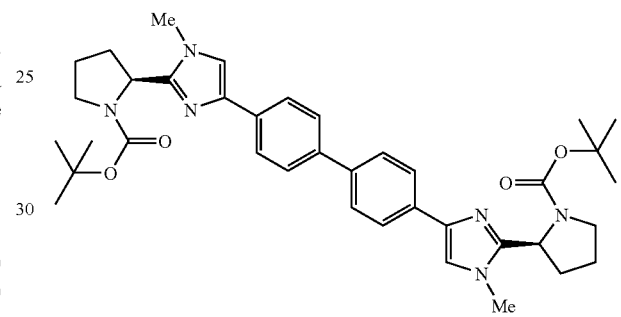

To a stirred solution of 1d, (2S,2'S)-tert-butyl 2,2'-(4,4'-(biphenyl-4,4'-diyl)bis(1H-imidazole-4,2-diyl))dipyrrolidine-1-carboxylate (100 mg, 0.16 mmole) and iodomethane (40 µL, 0.16 mmole) in CH$_2$Cl$_2$ (2 mL) was added sodium hydride (40%) (21.2 mg, 0.352 mmole). After five hours at ambient temperature, it was concentrated under reduced pressure. The crude reaction product 151a, (2S,2'S)-tert-butyl 2,2'-(4,4'-(biphenyl-4,4'-diyl)bis(1-methyl-1H-imidazole-4, 2-diyl))dipyrrolidine-1-carboxylate (~90 mg) was moved onto next step without further purification (purity ~85%)
LCMS: Anal. Calcd. for: C$_{38}$H$_{48}$N$_6$O$_4$ 652.83;
Found: 653.51 (M+H)$^+$. It should be recognized that multiple methylation isomers are possible in this reaction and no attempt to assign these was made.

Example 151

Step b

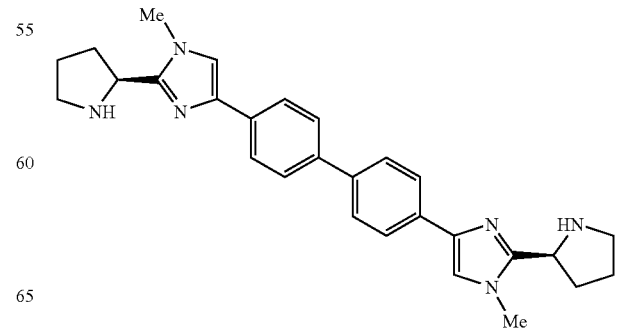

151a, (2S,2'S)-tert-butyl 2,2'-(4,4'-(biphenyl-4,4'-diyl)bis(1-methyl-1H-imidazole-4,2-diyl))dipyrrolidine-1-carboxylate (100 mg, 0.153 mmole) treated with 4 M HCl/dioxane (20 mL). After three hours at ambient temperature, it was concentrated under reduced pressure. The crude reaction product, 4,4'-bis(1-methyl-2-((S)-pyrrolidin-2-yl)-1H-imidazol-4-yl)biphenyl(~110 mg, HCl salt) was moved onto the next step without further purification (purity ~85%) LCMS: Anal. Calcd. for: $C_{28}H_{32}N_6$ 452.59; Found: 453.38 $(M+H)^+$. Multiple imidazole isomers were present and carried forward.

Example 151

HATU (58.9 mg, 0.150 mmol) was added to a mixture of 151b, 4,4'-bis(1-methyl-2-((S)-pyrrolidin-2-yl)-1H-imidazol-4-yl)biphenyl (45.0 mg, 0.075 mmol), (i-Pr)$_2$EtN (78 μL, 0.451 mmol) and Cap-1, (R)-2-(dimethylamino)-2-phenylacetic acid (0.026 mg 0.150 mmol) in DMF (1.0 mL). The resultant mixture was stirred at ambient temperature until the coupling was complete as determined by LC/MS analysis. Purification was accomplished by reverse-phase preparative HPLC (Waters-Sunfire 30×100 mm S5, detection at 220 nm, flow rate 30 mL/min, 0 to 90% B over 14 min; A=90% water, 10% ACN, 0.1% TFA, B=10% water, 90% ACN, 0.1% TFA) to provide two isomer of 151, (2R,2'R)-1,1'-((2S,2'S)-2,2'-(4,4'-(biphenyl-4,4'-diyl)bis(1-methyl-1H-imidazole-4,2-diyl))bis(pyrrolidine-2,1-diyl))bis(2-(dimethylamino)-2-phenylethanone), TFA salts.

Isomer 1: (1R,1'R)-2,2'-(4,4'-biphenyldiylbis((1-methyl-1H-imidazole-4,2-diyl)(2S)-2,1-pyrrolidinediyl))bis(N,N-dimethyl-2-oxo-1-phenylethanamine)

(8 mg, 8.6%) as a colorless wax.

$^1$H NMR (500 MHz, DMSO-d$_6$) δ ppm 1.84-2.25 (m, 8H) 2.32-2.90 (m, 12H) 3.67-3.92 (m, 8H) 4.07 (s, 2H) 5.23 (s, 2H) 5.51 (s, 2H) 7.51-7.91 (m, 20H)

HPLC Xterra 4.6×50 mm, 0 to 100% B over 10 minutes, one minutes hold time, A=90% water, 10% methanol, 0.2% phosphoric acid, B=10% water, 90% methanol, 0.2% phosphoric acid, RT=2.74 min, 98%.

LCMS: Anal. Calcd. for: $C_{48}H_{54}N_8O_2$ 775.02; Found: 775.50 $(M+H)^+$.

Isomer 2: (1R,1'R)-2,2'-(4,4'-biphenyldiylbis((1-methyl-1H-imidazole-4,2-diyl)(2S)-2,1-pyrrolidinediyl))bis(N,N-dimethyl-2-oxo-1-phenylethanamine)

(10.2 mg, 11%) as a colorless wax.

$^1$H NMR (500 MHz, DMSO-d$_6$) δ ppm 1.83-2.26 (m, 8H) 2.30-2.92 (m, 12H) 3.68-3.94 (m, 8H) 4.06 (s, 2H) 5.25 (d, J=2.14 Hz, 2H) 5.50 (s, 2H) 7.52-7.91 (m, 20H).

HPLC Xterra 4.6×50 mm, 0 to 100% B over 10 minutes, one minutes hold time, A=90% water, 10% methanol, 0.2% phosphoric acid, B=10% water, 90% methanol, 0.2% phosphoric acid, RT=2.75 min, 90%.

LCMS: Anal. Calcd. for: $C_{48}H_{54}N_8O_2$ 775.02; Found: 775.52 $(M+H)^+$.

Example 152

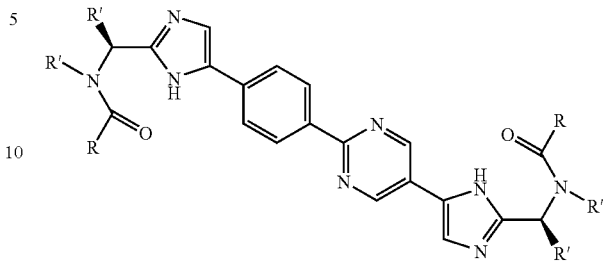

Example 152a-1

Step a

2-Chloro-5-(1-ethoxyvinyl)pyrimidine

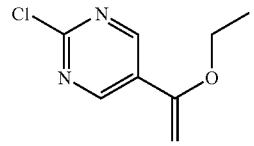

To a solution of 5-bromo-2-chloropyrimidine (12.5 g, 64.62 mmol) in dry DMF (175 mL) under N$_2$ was added tributyl(1-ethoxyvinyl)tin (21.8 mL, 64.62 mmol) and dichlorobis(triphenylphosphine)palladium (II) (2.27 g, 3.23 mmol). The mixture was heated at 100° C. for 3 h before being allowed to stir at room temperature for 16 hr. The mixture was then diluted with ether (200 mL) and treated with aqueous KF soln (55 g of potassium fluoride in 33 mL of water). The two phase mixture was stirred vigorously for 1 h at room temperature before being filtered through diatomaceous earth (Celite®). The filtrate was washed with sat'd NaHCO$_3$ soln and brine prior to drying (Na$_2$SO$_4$). The original aqueous phase was extracted with ether (2×) and the organic phase was treated as above. Repetition on 13.5 g of 5-bromo-2-chloropyrimidine and combined purification by Biotage™ flash chromatography on silica gel (gradient elution on a 65M column using 3% ethyl acetate in hexanes to 25% ethyl acetate in hexanes with 3.0 L) afforded the title compound as a white, crystalline solid (18.2 g, 73%).

$^1$H NMR (500 MHz, DMSO-d$_6$) δ 8.97 (s, 2H), 5.08 (d, J=3.7 Hz, 1H), 4.56 (d, J=3.4 Hz, 1H), 3.94 (q, J=7.0 Hz, 2H), 1.35 (t, J=7.0 Hz, 3H).

LCMS Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, RT=2.53 min, 98.8% homogeneity index.

LCMS: Anal. Calcd. for $C_8H_{10}ClN_2O$ 185.05; found: 185.04 $(M+H)^+$.

HRMS: Anal. Calcd. for $C_8H_{10}ClN_2O$ 185.0482; found: 185.0490 $(M+H)^+$.

The same method was used for the preparation of Examples 152a-2 & 152a-3:

LC conditions: Condition 1: Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, 220 nm, 5 μL injection volume.

Condition 2: Phenomenex LUNA C-18 4.6×50 mm, 0 to 100% B over 2 minutes, 1 minute hold time, A=90% water, 10% methanol, 0.1% TFA, B=10% water, 90% methanol, 0.1% TFA, 220 nm, 5 µL injection volume.

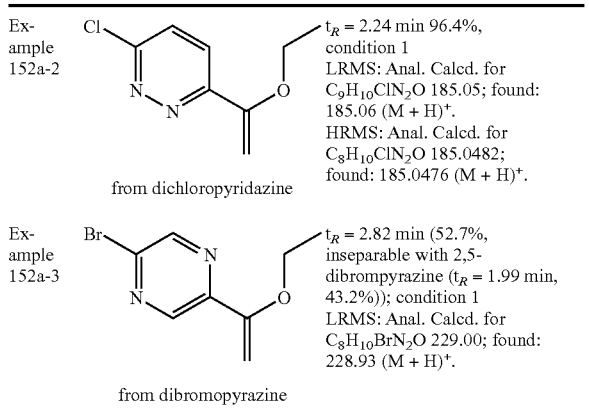

| Example 152a-2 | from dichloropyridazine | $t_R$ = 2.24 min 96.4%, condition 1 LRMS: Anal. Calcd. for $C_9H_{10}ClN_2O$ 185.05; found: 185.06 (M + H)⁺. HRMS: Anal. Calcd. for $C_8H_{10}ClN_2O$ 185.0482; found: 185.0476 (M + H)⁺. |
|---|---|---|
| Example 152a-3 | from dibromopyrazine | $t_R$ = 2.82 min (52.7%, inseparable with 2,5-dibrompyrazine ($t_R$ = 1.99 min, 43.2%)); condition 1 LRMS: Anal. Calcd. for $C_8H_{10}BrN_2O$ 229.00; found: 228.93 (M + H)⁺. |

Example 152b-1

Step b (S)-tert-Butyl 2-(5-(2-chloropyrimidin-5-yl)-1H-imidazol-2-yl)pyrrolidine-1-carboxylate or (S)-2-[5-(2-Chloro-pyrimidin-5-yl)-1H-imidazol-2-yl]-pyrrolidine-1-carboxylic acid tert-butyl ester

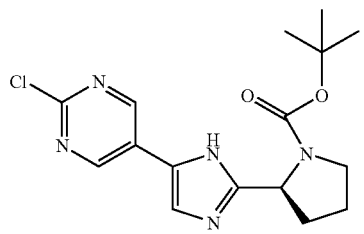

NBS (16.1 g, 90.7 mmol) was added in one portion to a stirred solution of 2-chloro-5-(1-ethoxyvinyl)pyrimidine (152a-1, 18.2 g, 98.6 mmol) in THF (267 mL) and $H_2O$ (88 mL) at 0° C. under $N_2$. The mixture was stirred for 1 h at 0° C. before it was diluted with more $H_2O$ and extracted with ethyl acetate (2×). The combined extracts were washed with sat'd $NaHCO_3$ soln and brine prior to drying ($Na_2SO_4$), filtration, and solvent evaporation. LCMS Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, RT=1.52 min (unsymmetrical peak).

LCMS: Anal. Calcd. for $C_6H_{14}BrClN_2O$ 235.92; found: 236.85 (M+H)⁺.

Example 152c-1

Step c

Half of the crude residue (2-bromo-1-(2-chloropyrimidin-5-yl)ethanone, ~14.5 g) was dissolved into anhydrous acetonitrile (150 mL) and treated directly with N-Boc-L-proline (9.76 g, 45.35 mmol) and diisopropylethylamine (7.9 mL, 45.35 mmol). After being stirred for 3 h, the solvent was removed in vacuo and the residue was partitioned into ethyl acetate and water. The organic phase was washed with 0.1N hydrochloric acid, sat'd $NaHCO_3$ soln and brine prior to drying ($Na_2SO_4$), filtration, and concentration. LCMS Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, RT=2.66 min.

The same method was used to prepare Examples 152c-2 through 152c-6.

LC conditions: Condition 1: Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, 220 nm, 5 µL injection volume.

Condition 2: Phenomenex LUNA C-18 4.6×50 mm, 0 to 100% B over 2 minutes, 1 minute hold time, A=90% water, 10% methanol, 0.1% TFA, B=10% water, 90% methanol, 0.1% TFA, 220 nm, 5 µL injection volume.

| Example 152c-2 | 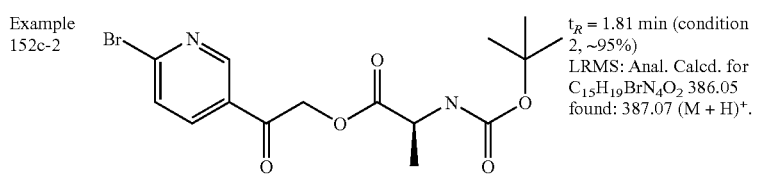 | $t_R$ = 1.81 min (condition 2, ~95%) LRMS: Anal. Calcd. for $C_{15}H_{19}BrN_4O_2$ 386.05 found: 387.07 (M + H)⁺. |
|---|---|---|
| Example 152c-3 | 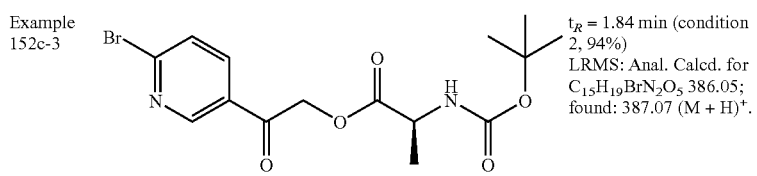 | $t_R$ = 1.84 min (condition 2, 94%) LRMS: Anal. Calcd. for $C_{15}H_{19}BrN_2O_5$ 386.05; found: 387.07 (M + H)⁺. |

-continued

| Example 152c-3a | 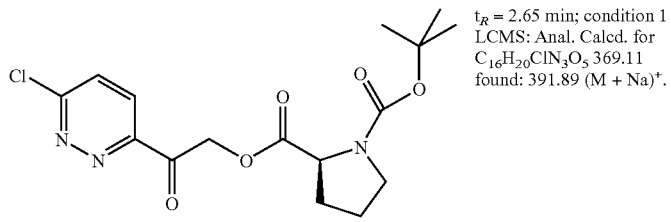 | $t_R$ = 2.65 min; condition 1<br>LCMS: Anal. Calcd. for<br>$C_{16}H_{20}ClN_3O_5$ 369.11<br>found: 391.89 (M + Na)$^+$. |
|---|---|---|
| Example 152c-4 | 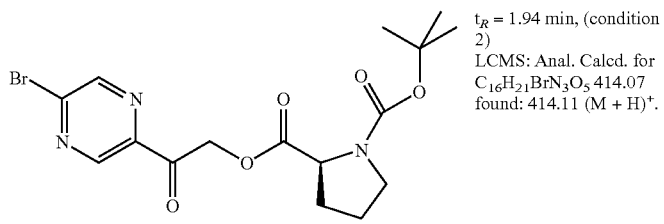 | $t_R$ = 1.94 min, (condition 2)<br>LCMS: Anal. Calcd. for<br>$C_{16}H_{21}BrN_3O_5$ 414.07<br>found: 414.11 (M + H)$^+$. |
| Example 152c-5 | 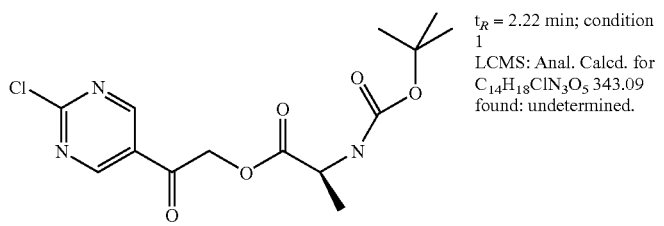 | $t_R$ = 2.22 min; condition 1<br>LCMS: Anal. Calcd. for<br>$C_{14}H_{18}ClN_3O_5$ 343.09<br>found: undetermined. |
| Example 152c-6 | 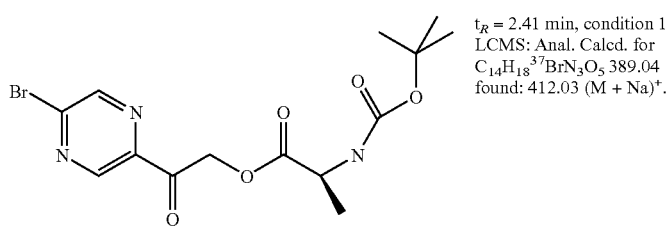 | $t_R$ = 2.41 min, condition 1<br>LCMS: Anal. Calcd. for<br>$C_{14}H_{18}{}^{37}BrN_3O_5$ 389.04<br>found: 412.03 (M + Na)$^+$. |

Example 152d-1

Step d

This residue ((S)-1-tert-butyl 2-(2-(2-chloropyrimidin-5-yl)-2-oxoethyl)pyrrolidine-1,2-dicarboxylate) was taken up in xylenes (200 mL) and treated to NH$_4$OAc (17.5 g, 0.23 mol). The mixture was heated at 140° C. for 2 hr in a thick-walled, screw-top flask before it was cooled to ambient temperature and suction-filtered. The filtrate was then concentrated, partitioned into ethyl acetate and sat'd NaHCO$_3$ soln and washed with brine prior to drying (Na$_2$SO$_4$), filtration, and concentration The original precipitate was partitioned into aqueous NaHCO$_3$ soln and ethyl acetate and sonicated for 2 min before being suction-filtered. The filtrate was washed with brine, dried over (Na$_2$SO$_4$), filtered, and concentrated to dryness. Purification of the combined residues by Biotage™ flash chromatography on silica gel (65M column, preequilibration with 2% B for 900 mL followed by gradient elution with 2% B to 2% B for 450 ml followed by 2% B to 40% B for 300 mL where B=methanol and A=dichloromethane) afforded the title compound (7.0 g, 44% yield, 2 steps, pure fraction) as an yellowish orange foam. The mixed fractions were subjected to a second Biotage™ chromatography on silica gel (40M column, preequilibration with 1% B for 600 mL followed by gradient elution with 1% B to 1% B for 150 ml followed by 1% B to 10% B for 1500 mL where B=MeOH and A=CH$_2$Cl$_2$) afforded additional title compound (2.8 g, 18%) as a brownish-orange foam. $^1$H NMR (500 MHz, DMSO-d$_6$) δ 12.24-12.16 (m, 1H), 9.05 (s, 2H), 7.84-7.73 (m, 1H), 4.90-4.73 (m, 1H), 3.59-3.46 (m, 1H), 3.41-3.31 (m, 1H), 2.32-2.12 (m, 1H), 2.03-1.77 (m, 3H), 1.39 and 1.15 (2s, 9H).

LCMS Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, RT=1.92 min, 94.7% homogeneity index.

LRMS: Anal. Calcd. for $C_{16}H_{21}ClN_5O_2$ 350.14; found: 350.23 (M+H)$^+$.

HRMS: Anal. Calcd. for $C_{16}H_{21}ClN_5O_2$ 350.1384; found: 350.1398 (M+H)$^+$.

The same method was used to prepare Examples 152d-2 through 152d-6.

LC conditions: Condition 1: Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, 220 nm, 5 μL injection volume.

Condition 2: Phenomenex LUNA C-18 4.6×50 mm, 0 to 100% B over 2 minutes, 1 minute hold time, A=90% water, 10% methanol, 0.1% TFA, B=10% water, 90% methanol, 0.1% TFA, 220 nm, 5 μL injection volume.

| Example 152d-2 | 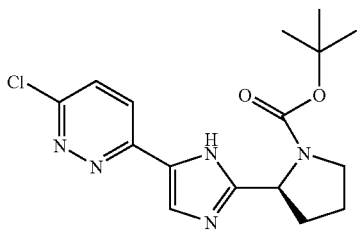 from 152c-3a | $t_R$ = 1.92 min (86.5%); condition 1<br>LRMS: Anal. Calcd. for $C_{16}H_{21}ClN_5O_2$ 350.14; found: 350.23 (M + H)$^+$.<br>HRMS: Anal. Calcd. for $C_{16}H_{21}ClN_5O_2$ 350.1384; found: 350.1393 (M + H)$^+$. |
|---|---|---|
| Example 152d-3 | 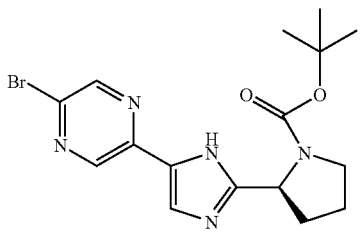 from 152c-4 | $t_R$ = 1.90 min (>95%); condition 1<br>LRMS: Anal. Calcd. for $C_{16}H_{21}BrN_5O_2$ 394.09; found: 393.82 (M + H)$^+$.<br>HRMS: Anal. Calcd. for $C_{16}H_{21}BrN_5O_2$ 394.0879; found: 394.0884 (M + H)$^+$. |
| Example 152d-4 | 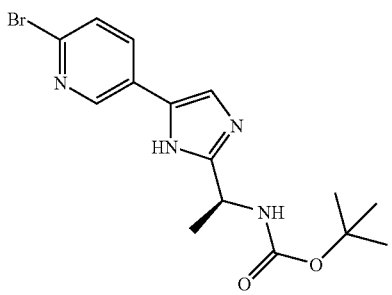 from 152c-3 | $t_R$ = 1.45 min (condition 2, 100%)<br>LRMS: Anal. Calcd. for $C_{15}H_{19}BrN_4O_2$ 366.07 found: 367.07 (M + H)$^+$. |
| Example 152d-5 | 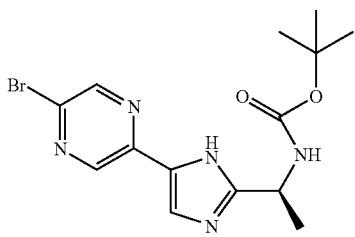 from 152c-6 | $t_R$ = 1.88 min (>95%); condition 1<br>LRMS: Anal. Calcd. for $C_{14}H_{18}BrN_5O_2$ 367.06; found: 368.10 (M + H)$^+$. |
| Example 152d-6 | 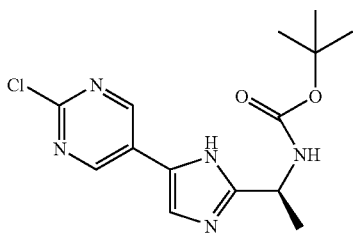 from 152c-5 | $t_R$ = 1.66 min (85%); condition 1<br>LRMS: Anal. Calcd. for $C_{14}H_{18}ClN_5O_2$ 323.11; found: 324.15 (M + H)$^+$. |

Example 152e-1

Step e

Example 152e-1

(S)-tert-Butyl 2-(5-(2-chloropyrimidin-5-yl)-1-((2-(trimethyl-silyl)ethoxy)methyl)-1H-imidazol-2-yl)pyrrolidine-1-carboxylate

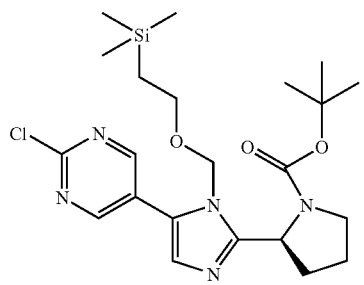

Sodium hydride (60% dispersion in mineral oil, 0.23 g, 5.72 mmol) was added in one portion to a stirred solution of (S)-tert-butyl 2-(5-(2-chloropyrimidin-5-yl)-1H-imidazol-2-yl)pyrrolidine-1-carboxylate (152d-1, 2.0 g, 5.72 mmol) in dry DMF (45 mL) at ambient temperature under $N_2$. The mixture was stirred for 5 min. before SEM chloride (1.01 mL, 5.72 mmol) was added in approx. 0.1 mL increments. The mixture was stirred for 3 h before being quenched with sat'd $NH_4Cl$ soln and diluted with ethyl acetate. The organic phase was washed with sat'd $NaHCO_3$ soln and brine, dried over ($Na_2SO_4$), filtered, and concentrated. The original aqueous phase was extracted twice more and the combined residue was purified by Biotage™ flash chromatography (40M column, 50 mL/min, preequilibration with 5% B for 750 mL, followed by step gradient elution with 5% B to 5% B for 150 mL, 5% B to 75% B for 1500 mL, then 75% B to 100% B for 750 mL where solvent B is ethyl acetate and solvent A is hexanes). Concentration of the eluant furnished the title compound as a pale yellow foam (2.35 g, 85%).

$^1$H NMR (500 MHz, DMSO-$d_6$) δ 9.04 (s, 2H), 7.98-7.95 (m, 1H), 5.70-5.31 (3 m, 2H), 5.02-4.91 (m, 1H), 3.59-3.49 (m, 3H), 3.45-3.35 (m, 1H), 2.30-2.08 (m, 2H), 1.99-1.83 (m, 2H), 1.36 and 1.12 (2s, 9H), 0.93-0.82 (m, 2H), −0.02 (s, 9H).

LCMS Phenomenex LUNA C-18 4.6×50 mm, 0 to 100% B over 2 minutes, 2 minute hold time, A=90% water, 10% methanol, 0.1% TFA, B=10% water, 90% methanol, 0.1% TFA, RT=2.38 min, 95% homogeneity index.

LRMS: Anal. Calcd. for $C_{22}H_{35}ClN_5O_3Si$ 480.22; found: 480.23 (M+H)$^+$.

HRMS: Anal. Calcd. for $C_{22}H_{35}ClN_5O_3Si$ 480.2198; found: 480.2194 (M+H)$^+$.

The same method was used to prepare 152e-2 through 152e-4

LC conditions: Condition 1: Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, 220 nm, 5 μL injection volume.

Condition 2: Phenomenex LUNA C-18 4.6×50 mm, 0 to 100% B over 2 minutes, 1 minute hold time, A=90% water, 10% methanol, 0.1% TFA, B=10% water, 90% methanol, 0.1% TFA, 220 nm, 5 μL injection volume.

Example 152e-2

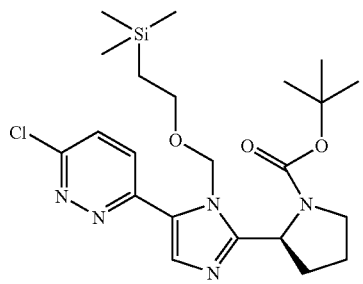

from 152d-2

$t_R$ = 2.34 min (85.7%); condition 1
LCMS: Anal. Calcd. for $C_{22}H_{35}ClN_5O_3Si$ 480.22; found: 480.22 (M + H)$^+$.
HRMS: Anal. Calcd. for $C_{22}H_{35}ClN_5O_3Si$ 480.2198 found: 480.2198 (M + H)$^+$.

Example 152e-3

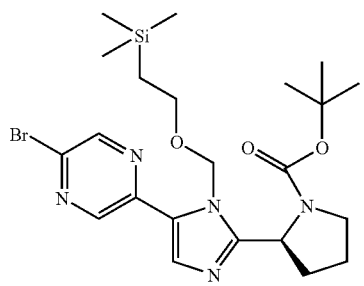

from 152d-3

$t_R$ = 3.18 min (>95%); condition 1
LCMS: Anal. Calcd. for $C_{22}H_{35}^{37}BrN_5O_3Si$ 526.17; found: 525.99 (M + H)$^+$.
HRMS: Anal. Calcd. for $C_{22}H_{35}^{37}BrN_5O_3Si$ 526.1692; found: 526.1674 (M + H)$^+$.

| Example 152e-4 | 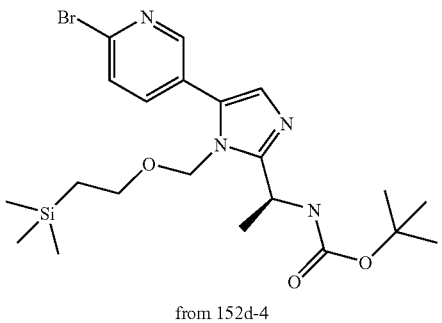<br>from 152d-4 | $t_R$ = 2.14 min (condition 2, 96%)<br>LRMS: Anal. Calcd. For $C_{21}H_{33}BrN_4O_3Si$ 495.15 found: 497.13 (M + H)$^+$. |
|---|---|---|

Examples 152f-1 to 152f-2

Example 152f-1

(S)-1-(2-(5-(2-chloropyrimidin-5-yl)-1H-imidazol-2-yl)pyrrolidin-1-yl)-2-(pyridin-3-yl)ethanone

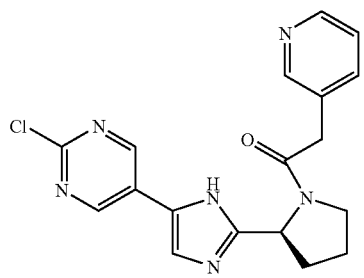

Cold (0° C.) 4 NHCl in dioxanes (5 mL) was added via syringe to (S)-tert-butyl 2-(5-(2-chloropyrimidin-5-yl)-1H-imidazol-2-yl)pyrrolidine-1-carboxylate (152d-1, 0.50 g, 1.43 mmol) in a 100 mL pear-shaped flask followed by MeOH (1.0 mL). The suspension was stirred at room temperature for 4 h before it was concentrated down to dryness and placed under high vacuum for 1 h. There was isolated intermediate (S)-2-chloro-5-(2-(pyrrolidin-2-yl)-1H-imidazol-5-yl)pyrimidine trihydrochloride as a pale yellow solid (with an orange tint) which was used without further purification.

HATU (0.60 g, 1.57 mmol) was added in one portion to a stirred solution of intermediate (S)-2-chloro-5-(2-(pyrrolidin-2-yl)-1H-imidazol-5-yl)pyrimidine trihydrochloride (0.46 g, 1.43 mmol, theoretical amount), 2-(pyridin-3-yl)acetic acid (0.25 g, 1.43 mmol) and DIEA (1.0 mL, 5.72 mmol) in anhydrous DMF (10 mL) at ambient temperature. The mixture was stirred at room temperature for 2 h before the DMF was removed in vacuo. The residue was taken up in $CH_2Cl_2$ and subjected to Biotage™ flash chromatography on silica gel (40M column, preequilibration with 0% B for 600 mL followed by step gradient elution with 0% B to 0% B for 150 mL followed by 0% B to 15% B for 1500 mL followed by 15% B to 25% B for 999 mL where B=MeOH and A=$CH_2Cl_2$). There was isolated the title compound (0.131 g, 25%, 2 steps) as a yellow solid.

$^1$H NMR (500 MHz, DMSO-d$_6$) δ 9.10-9.08 (2s, 2H), 8.72-8.55 (series of m, 2H), 8.21-8.20 and 8.11-8.10 (2m, 1H), 8.00 and 7.93 (2s, 1H), 7.84-7.77 (series of m, 1H), 5.43-5.41 and 5.17-5.15 (2m, 1H), 4.02-3.94 (3 m, 2H), 3.90-3.58 (3 m, 2H), 2.37-2.26 (m, 1H), 2.16-1.85 (2m, 3H).

LCRMS Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, RT=0.92 min, 95.1% homogeneity index.

LRMS: Anal. Calcd. for $C_{18}H_{18}ClN_6O$ 369.12; found: 369.11 (M+H)$^+$.

HRMS: Anal. Calcd. for $C_{18}H_{18}ClN_6O$ 369.1231; found: 369.1246 (M+H)$^+$.

Examples 152g-1 to 152g-17

Example 152g-1 From 1c and 152e-1

(S)-2-[5-(2-{4-[2-((S)-1-tert-Butoxycarbonyl-pyrrolidin-2-yl)-3H-imidazol-4-yl]-phenyl}-pyrimidin-5-yl)-1-(2-trimethylsilanyl-ethoxymethyl)-1H-imidazol-2-yl]-pyrrolidine-1-carboxylic acid tert-butyl ester

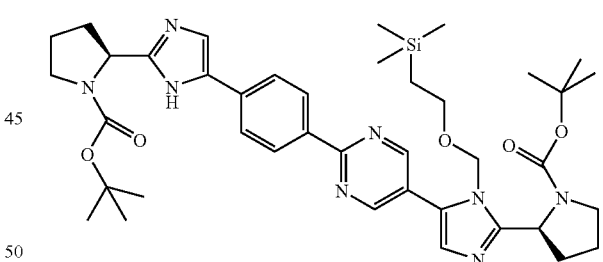

Pd (Ph$_3$)$_4$ (0.12 g, 0.103 mmol) was added in one portion to a stirred suspension of (S)-tert-butyl 2-(5-(4-(4,4,5,5-tetramethyl-1,3,2-dioxaborolan-2-yl)phenyl)-1H-imidazol-2-yl) pyrrolidine-1-carboxylate (1c, 1.00 g, 2.27 mmol), (S)-tert-butyl 2-(5-(2-chloropyrimidin-5-yl)-1-((2-(trimethylsilyl)ethoxy)methyl)-1H-imidazol-2-yl)pyrrolidine-1-carboxylate (152c-1, 0.99 g, 2.06 mmol) and NaHCO$_3$ (0.87 g, 10.3 mmol) in a solution of DME (20 mL) and H$_2$O (6 mL) at room temperature under N$_2$. The vessel was sealed and the mixture was placed into a preheated (80° C.) oil bath and stirred at 80° C. for 16 h before additional catalyst (0.12 g) was added. After heating the mixture for an additional 12 h at 80° C., the mixture was cooled to ambient temperature, diluted with ethyl acetate and washed with sat'd NaHCO$_3$ soln and brine prior to drying over anhydrous sodium sulfate and solvent concentration. Purification of the residue by Biotage™ flash chromatography on silica gel using a 40M column (preequilibrated with 40% B followed by step gradient elution with 40% B to 40% B for 150 mL, 40% B to 100% B for 1500 mL, 100% B to 100% B for 1000 mL where B=ethyl acetate and A=hexanes) furnished the title compound as a yellow foam (1.533 g, 98%). A small amount of the yellow foam was further purified for characterization purposes by pHPLC (Phenomenex GEMINI, 30×100 mm, S10, 10 to 100% B over 13 minutes, 3 minute hold time, 40 mL/min, A=95% water, 5% acetonitrile, 10 mM NH$_4$OAc, B=10% water, 90% acetonitrile, 10 mM NH$_4$OAc) to yield 95% pure title compound as a white solid.

$^1$HNMR (500 MHz, DMSO-d$_6$) δ 12.30-11.88 (3 m, 1H), 9.17-9.16 (m, 2H), 8.43-8.31 (m, 2H), 7.99-7.35 (series of m, 4H), 5.72-5.30 (3 m, 2H), 5.03-4.76 (2m, 2H), 3.64-3.50 (m, 4H), 3.48-3.31 (m, 2H), 2.36-2.07 (m, 2H), 2.05-1.80 (m, 4H), 1.46-1.08 (2m, 18H), 0.95-0.84 (m, 2H), −0.01 (s, 9H).

HPLC Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, RT=2.91 min, 95% homogeneity index.

LRMS: Anal. Calcd. for $C_{40}H_{57}N_8O_5Si$ 757.42; found: 757.42 (M+H)$^+$.

HRMS: Anal. Calcd. for $C_{40}H_{57}N_8O_5Si$ 757.4221; found: 757.4191 (M+H)$^+$.

The same procedure was used to prepare Examples 152g-2 through 152g-17:

LC conditions: Condition 1: Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, 220 nm, 5 μL injection volume.

Condition 2: Phenomenex LUNA C-18 4.6×50 mm, 0 to 100% B over 2 minutes, 1 minute hold time, A=90% water, 10% methanol, 0.1% TFA, B=10% water, 90% methanol, 0.1% TFA, 220 nm, 5 μL injection volume.

Example 152g-2

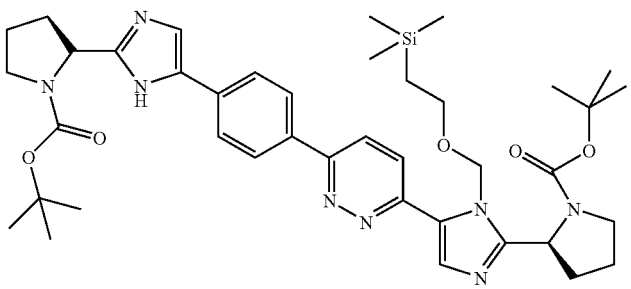

Prepared from 1c and 152e-2

$t_R$ = 2.81 min (79%); Condition 1
LRMS: Anal. Calcd. for $C_{40}H_{57}N_8O_5Si$ 757.42; found: 758.05 (M + H)$^+$.
HRMS: Anal. Calcd. for $C_{40}H_{57}N_8O_5Si$ 757.4221; found: 757.4196 (M + H)$^+$.

Example 152g-3

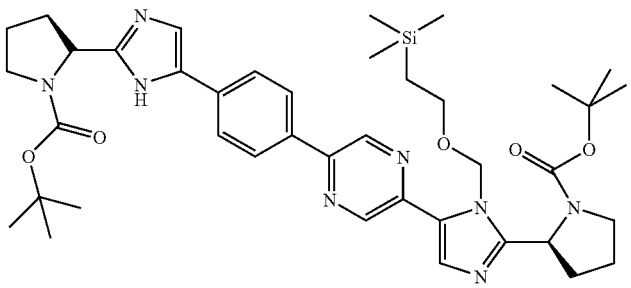

Prepared from 1c and 152e-3

$t_R$ = 2.89 min (>95%); Condition 1
LRMS: Anal. Calcd. for $C_{40}H_{57}N_8O_5Si$ 757.42; found: 757.35 (M + H)$^+$.
HRMS: Anal. Calcd. for $C_{40}H_{57}N_8O_5Si$ 757.4221; found: 757.4191 (M + H)$^+$.

Example 152g-4

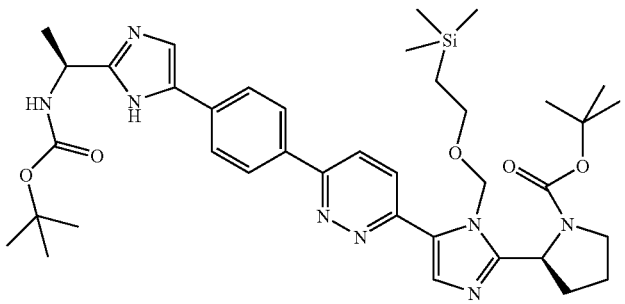

Prepared from 1-6c and 152e-2

$t_R$ = 2.87 min (97%); Condition 1
LRMS: Anal. Calcd. for $C_{38}H_{55}N_8O_5S_i$ 731.41; found: 731.26 (M + H)$^+$.
HRMS: Anal. Calcd. for $C_{38}H_{55}N_8O_5S_i$ 731.4065; found: 731.4070 (M + H)$^+$.

| Example 152g-5 | 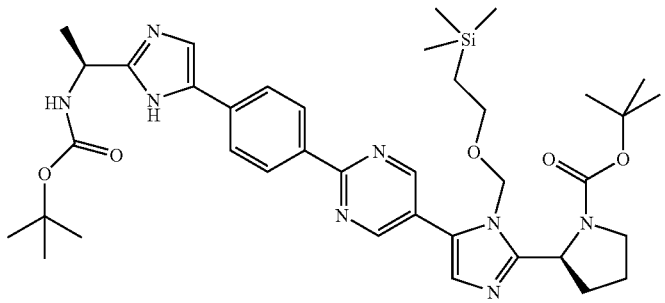 Prepared from 1-6c and 152e-1 | $t_R$ = 2.94 min (>95%); Condition 1<br>LRMS: Anal. Calcd. for<br>$C_{38}H_{55}N_8O_5Si$ 731.41; found:<br>731.26 (M + H)$^+$.<br>HRMS: Anal. Calcd. for<br>$C_{38}H_{55}N_8O_5Si$ 731.4065; found:<br>731.4046 (M + H)$^+$. |
|---|---|---|
| Example 152g-6 | 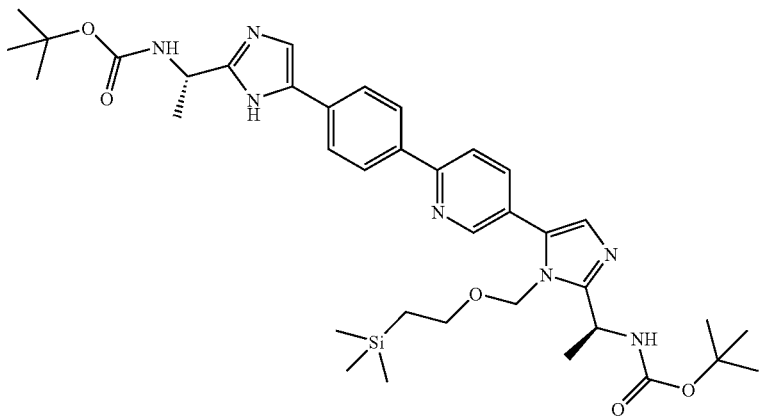 Prepared from 1-6c and 152e-4 | $t_R$ = 1.99 min (condition 2, 96%)<br>LRMS: Anal. Calcd. for<br>$C_{37}H_{53}N_7O_2Si$ 703.39; found:<br>704.34 (M + H)$^+$. |
| Example 152g-7 | 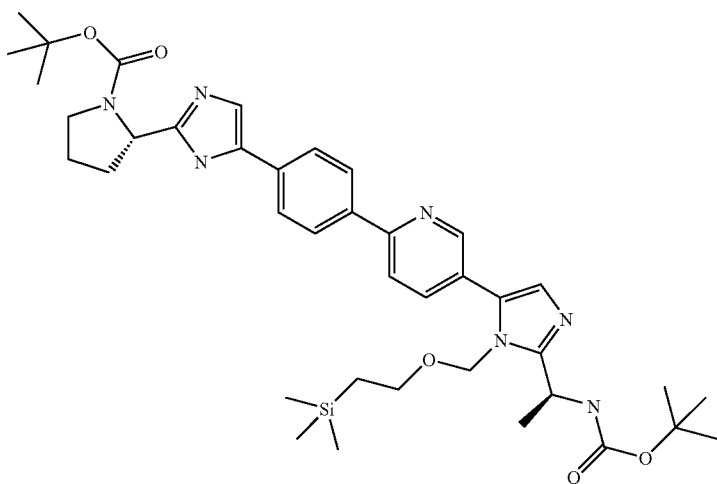 Prepared from 1c and 152e-4 | $t_R$ = 1.99 min (condition 2, 96%)<br>LRMS: Anal. Calcd. for<br>$C_{39}H_{55}N_7O_5Si$ 729.40<br>found: 730.42<br>(M + H)$^+$. |

| Example 152g-8 | 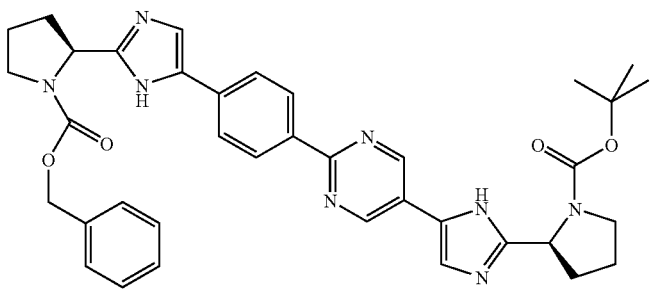  Prepared from 1-5c and 152d-1 | $t_R$ = 2.15 min (>95%); Condition 1<br>LRMS: Anal. Calcd. for $C_{37}H_{41}N_8O_4$ 661.33; found: 661.39 $(M + H)^+$.<br>HRMS: Anal. Calcd. for $C_{37}H_{41}N_8O_4$ 661.3251; found: 661.3268 $(M + H)^+$. |
|---|---|---|
| Example 152g-9 | 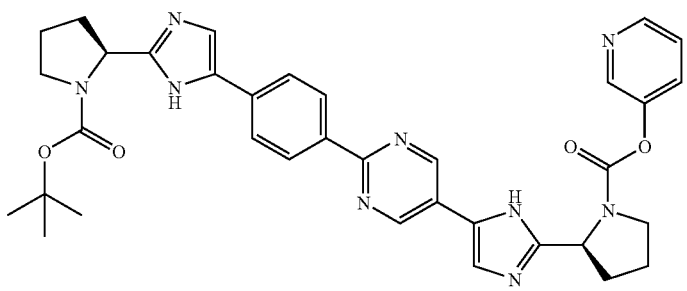  Prepared from 1c and 152f-1 | $t_R$ = 1.71 min (>95%); Condition 1<br>LRMS: Anal. Calcd. for $C_{36}H_{40}N_9O_3$ 646.76; found: 646.47 $(M + H)^+$.<br>HRMS: Anal. Calcd. for $C_{36}H_{40}N_9O_3$ not done found: not done $(M + H)^+$. |
| Example 152g-10 | 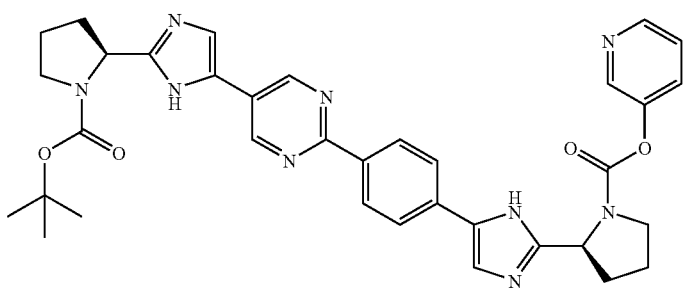  Prepared from 152d-1 and 1-10c | $t_R$ = 1.71 min (>95%); Condition 1<br>LRMS: Anal. Calcd. for $C_{36}H_{40}N_9O_3$ 646.33; found: 646.37 $(M + H)^+$.<br>HRMS: Anal. Calcd. for $C_{36}H_{40}N_9O_3$ 646.3254; found: 646.3240 $(M + H)^+$. |
| Example 152g-11 | 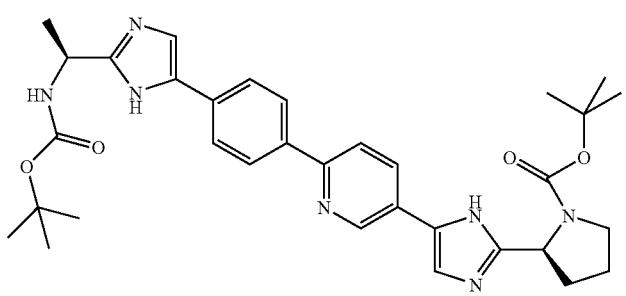  Prepared from 1-6c and 152e-4 | $t_R$ = 2.12 min (>93.9%); Condition 1<br>LRMS: Anal. Calcd. for $C_{33}H_{42}N_7O_4$ 600.33; found: 600.11 $(M + H)^+$.<br>HRMS: Anal. Calcd. for $C_{33}H_{42}N_7O_4$ 600.3298; found: 600.3312 $(M + H)^+$. |

| | | |
|---|---|---|
| Example 152g-12 | 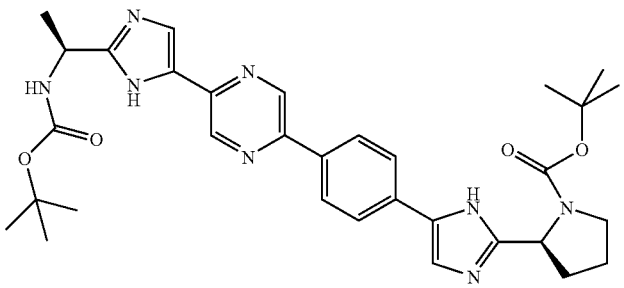<br>Prepared from 1c and 152d-5 | $t_R$ = 2.13 min (97.3%); Condition 1<br>LRMS: Anal. Calcd. for<br>$C_{32}H_{41}N_8O_4$ 601.33; found: 601.36 $(M + H)^+$.<br>HRMS: Anal. Calcd. for<br>$C_{32}H_{41}N_8O_4$ 601.3251; found:<br>601.3253 $(M + H)^+$. |
| Example 152g-13 | 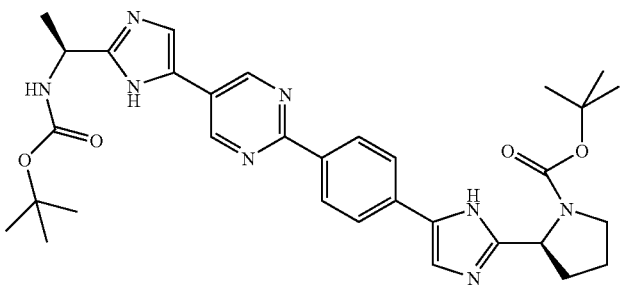<br>Prepared from 1c and 152d-6 | $t_R$ = 2.11 min (98.5%); Condition 1<br>LRMS: Anal. Calcd. for<br>$C_{32}H_{41}N_8O_4$ 601.33; found: 601.36 $(M + H)^+$.<br>HRMS: Anal. Calcd. for<br>$C_{32}H_{41}N_8O_4$ 601.3251; found:<br>601.3253 $(M + H)^+$. |
| Example 152g-14 | 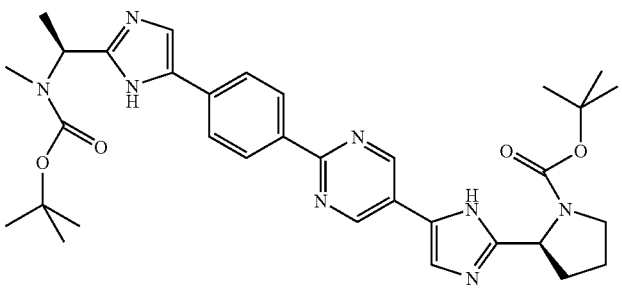<br>Prepared from 1-8c and 152d-1 | $t_R$ = 2.18 min (>95%); Condition 1<br>LRMS: Anal. Calcd. for<br>$C_{33}H_{43}N_8O_4$ 615.34; found: 615.38 $(M + H)^+$.<br>HRMS: Anal. Calcd. for<br>$C_{33}H_{43}N_8O_4$ 615.3407; found:<br>615.3433 $(M + H)^+$. |
| Example 152g-15 | 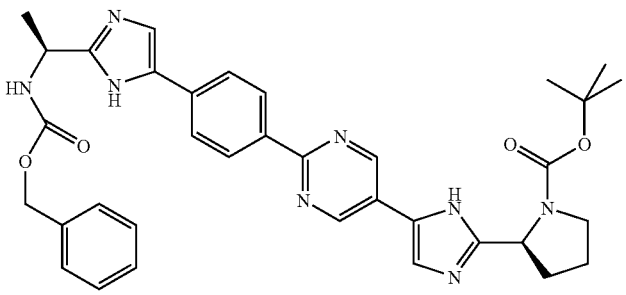<br>Prepared from 1c and 152d-1 | $t_R$ = 2.20 min (97.7%); Condition 1<br>LRMS: Anal. Calcd. for<br>$C_{35}H_{39}N_8O_4$ 635.31; found: 635.36 $(M + H)^+$.<br>HRMS: Anal. Calcd. for<br>$C_{35}H_{39}N_8O_4$ 635.3094; found:<br>635.3119 $(M + H)^+$. |

-continued

Example 152g-16

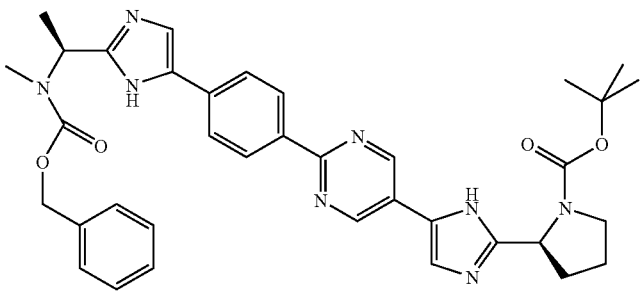

Prepared from 1-9c and 152d-1

$t_R$ = 2.26 min (>95%); Condition 1
LRMS: Anal. Calcd $C_{36}H_{41}N_8O_4$ 649.33; found: 649.39 (M + H)$^+$.
HRMS: Anal. Calcd. for $C_{36}H_{41}N_8O_4$ 649.3251; found: 649.3276 (M + H)$^+$.

Example 152g-17

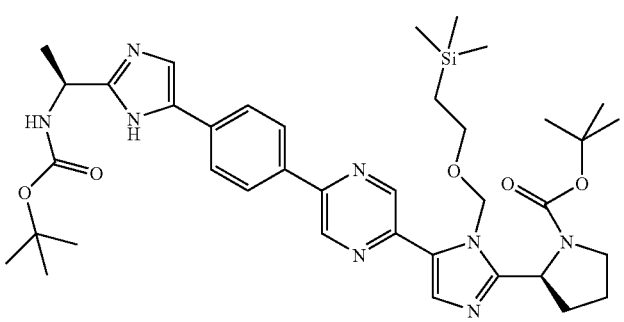

Prepared from 1-6c and 152e-3

$t_R$ = 2.98 min (98.5%); Condition 1
LRMS: Anal. Calcd. for $C_{38}H_{54}N_8O_5Si$ 730.39; found: 731.40 (M + H)$^+$.
HRMS: Anal. Calcd. for $C_{38}H_{54}N_8O_5Si$ 731.4065; found: 731.4045 (M + H)$^+$.

Example 152h-1-152h-7

Example 152h-1 from 152g-1

5-((S)-2-Pyrrolidin-2-yl-3H-imidazol-4-yl)-2-[4-((S)-2-pyrrolidin-2-yl-3H-imidazol-4-yl)-phenyl]-pyrimidine

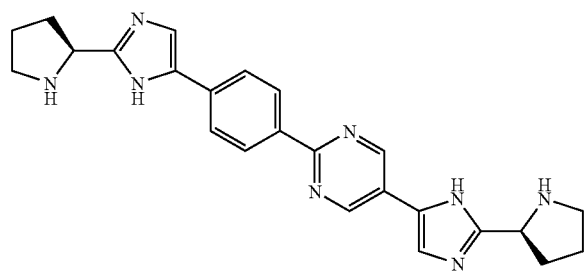

TFA (8 mL) was added in one portion to a stirred solution of (S)-2-[5-(2-{4-[2-((S)-1-tert-butoxycarbonyl-pyrrolidin-2-yl)-3H-imidazol-4-yl]-phenyl}-pyrimidin-5-yl)-1-(2-trimethylsilanyl-ethoxymethyl)-1H-imidazol-2-yl]-pyrrolidine-1-carboxylic acid tert-butyl ester (1.50 g, 1.98 mmol) in dry CH$_2$Cl$_2$ (30 mL) at room temperature. The flask was sealed and the mixture was stirred at room temperature for 16 h before the solvent(s) were removed in vacuo. The residue was taken up in methanol, filtered through a PVDF syringe filter (13 mm×0.45 µm), distributed to 8 pHPLC vials and chromatographed by HPLC (gradient elution from 10% B to 100% B over 13 min on a Phenomenex C18 column, 30×100 mm, 10 µm, where A=90% water, 10% methanol, 0.1% TFA, B=10% water, 90% methanol, 0.1% TFA). After concentration of the selected test tubes by speed vacuum evaporation, the product was dissolved in methanol and neutralized by passing the solution through an UCT CHQAX 110M75 anion exchange cartridge. There was isolated the title compound as a yellow mustard-colored solid (306.7 mg, 36% yield) upon concentration of the eluant.

$^1$H NMR (500 MHz, DMSO-d$_6$) µ 12.50-11.80 (br m, 2H), 9.18 (s, 2H), 8.36 (d, J=8.5 Hz, 2H), 7.89 (d, J=8.2 Hz, 2H), 7.77 (s, 1H), 7.61 (s, 1H), 4.34-4.24 (m, 2H), 3.09-2.89 (m, 4H), 2.18-2.07 (m, 2H), 2.02-1.89 (m, 2H), 1.88-1.72 (m, 4H).

LCMS Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, RT=1.33 min, >95% homogeneity index.

LRMS: Anal. Calcd. for $C_{24}H_{27}N_8$ 427.24; found: 427.01 (M+H)$^+$.

HRMS: Anal. Calcd. for $C_{24}H_{27}N_8$ 427.2359; found: 427.2363 (M+H)$^+$.

The same conditions were used to prepare Examples 152h-2 through 152h-14.

LC conditions: Condition 1: Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, 220 nm, 5 µL injection volume.

Condition 2: Phenomenex LUNA C-18 4.6×50 mm, 0 to 100% B over 2 minutes, 1 minute hold time, A=90% water, 10% methanol, 0.1% TFA, B=10% water, 90% methanol, 0.1% TFA, 220 nm, 5 µL injection volume.

Example 152h-2 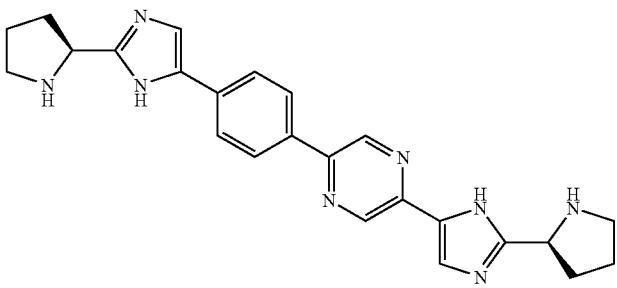

Prepared from 152g-3

$t_R$ = 1.36 min (98%);
Condition 1
LRMS: Anal. Calcd.
for $C_{24}H_{27}N_8$ 427.24;
found: 427.48 $(M + H)^+$.
HRMS: Anal. Calcd.
for $C_{24}H_{27}N_8$ 427.2359;
found: 427.2339
$(M + H)^+$.

Example 152h-3 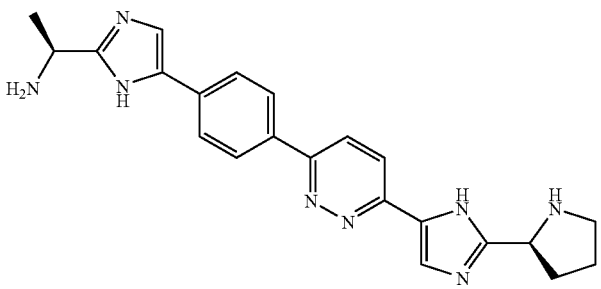

Prepared from 152g-4

$t_R$ = 1.17 min (>95%);
Condition 1
LRMS: Anal. Calcd.
for $C_{22}H_{25}N_8$ 401.22;
found: 401.16 $(M + H)^+$.
HRMS: Anal. Calcd.
for $C_{22}H_{25}N_8$ 401.2202;
found: 401.2193
$(M + H)^+$.

Example 152h-4 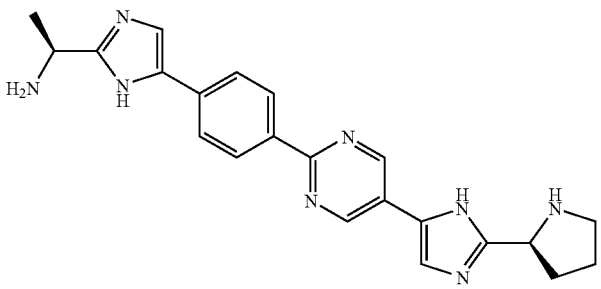

Prepared from 152g-5

$t_R$ = 1.28 min (89.3%);
Condition 1
LRMS: Anal. Calcd.
for $C_{22}H_{25}N_8$ 401.22;
found: 401.16 $(M + H)^+$.
HRMS: Anal. Calcd.
for $C_{22}H_{25}N_8$ 401.2202;
found: 401.2201
$(M + H)^+$.

Example 152h-5 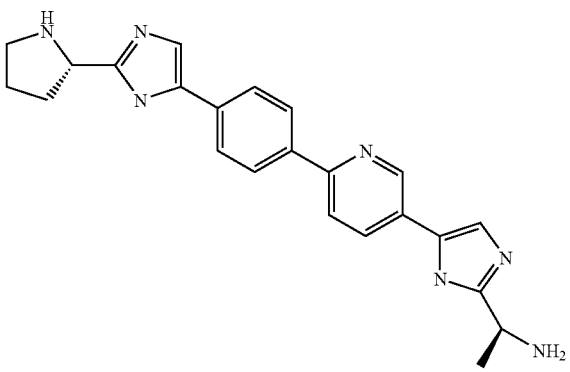

Prepared from 152g-7

$t_R$ = 0.93 min;
Condition 2
LRMS: Anal. Calcd.
for $C_{23}H_{25}N_7$ 399; found:
400 $(M + H)^+$.

-continued

Example 152h-6 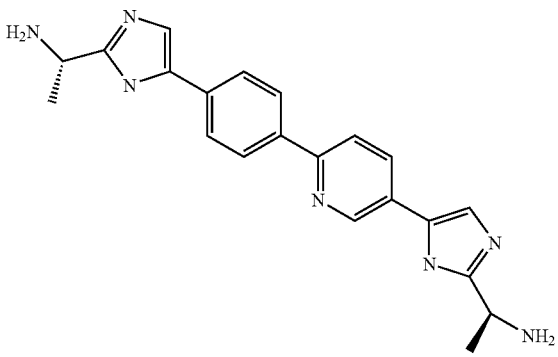
Prepared from 152g-6

$t_R$ = 0.81 min;
Condition 2
LRMS: Anal. Calcd.
for $C_{21}H_{23}N_7$ 373; found:
374 $(M + H)^+$.

Example 152h-7 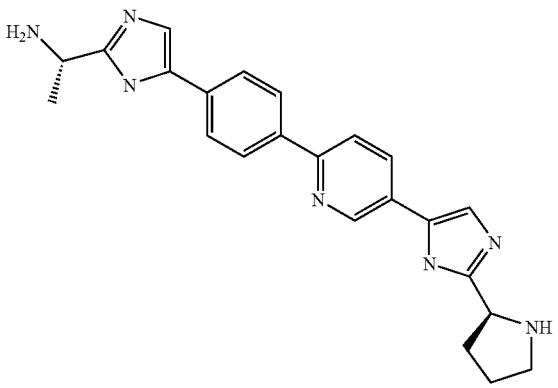
Prepared from 152g-11

$t_R$ = 1.14 min (>95%);
Condition 1
LRMS: Anal. Calcd.
for $C_{23}H_{26}N_7$ 400.23;
found: 400.14 $(M + H)^+$.
HRMS: Anal. Calcd.
for $C_{23}H_{26}N_7$ 400.2250;
found: 400.2234
$(M + H)^+$.

Example 152h-8 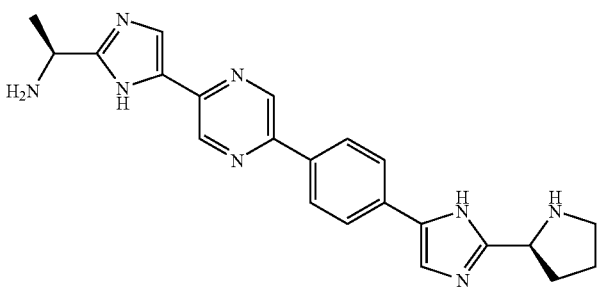
Prepared from 152g-12

$t_R$ = 1.29 min (>95%);
Condition 1
LRMS: Anal. Calcd.
for $C_{22}H_{25}N_8$ 401.22;
found: 401.21 $(M + H)^+$.
HRMS: Anal. Calcd.
for $C_{22}H_{25}N_8$ 401.2202;
found: 401.2204
$(M + H)^+$.

Example 152h-9 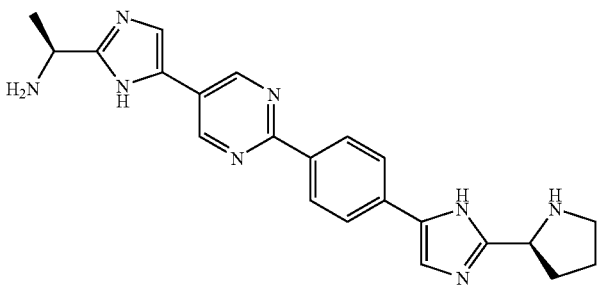
Prepared from 152g-13

$t_R$ = 1.29 min (97.6%);
Condition 1
LRMS: Anal. Calcd.
for $C_{22}H_{25}N_8$ 401.22;
found: 401.21 $(M + H)^+$.
HRMS: Anal. Calcd.
for $C_{22}H_{25}N_8$ 401.2202;
found: 401.2220
$(M + H)^+$.

-continued

Example 152h-10 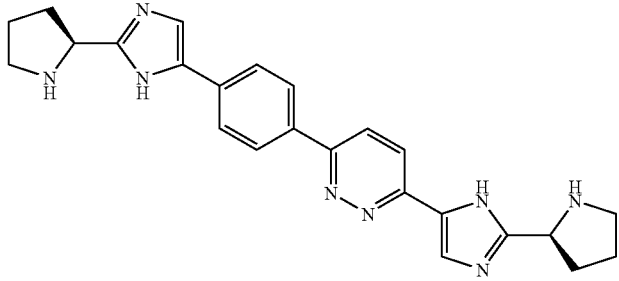

Prepared from 152g-2

$t_R$ = 1.26 min (86.4%); Condition 1
LRMS: Anal. Calcd. for $C_{24}H_{27}N_8$ 427.24; found: 427.48 (M + H)+.
HRMS: Anal. Calcd. for $C_{24}H_{27}N_8$ 427.2359; found: 427.2339 (M + H)+.

Example 152h-11 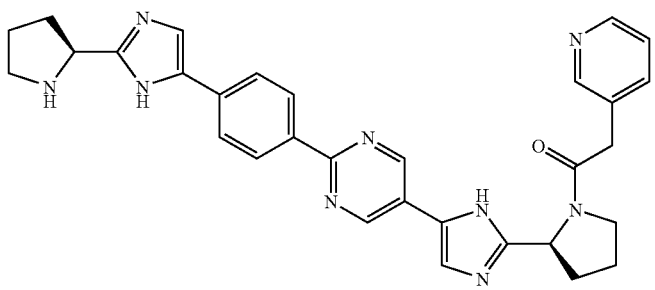

Prepared from 152g-9

$t_R$ = 1.26 min (>95%); Condition 1
LRMS: Anal. Calcd. for $C_{31}H_{32}N_9O$ 546.27; found: 546.28 (M + H)+.
HRMS: Anal. Calcd. for $C_{31}H_{32}N_9O$ 546.2730 found: 546.2739 (M + H)+.

Example 152h-12 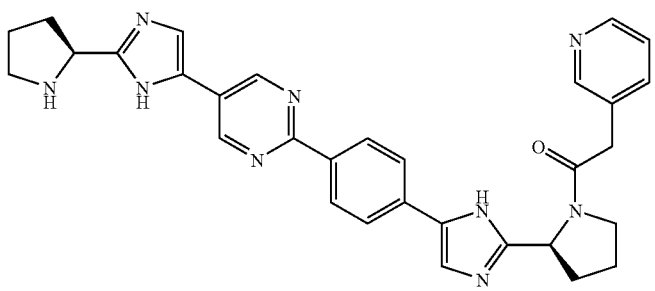

Prepared from 152g-10

$t_R$ = 1.39 min (95%); Condition 1
LRMS: Anal. Calcd. for $C_{31}H_{32}N_9O$ 546.27; found: 546.32 (M + H)+.
HRMS: Anal. Calcd. for $C_{31}H_{32}N_9O$ 546.2730; found: 546.2719 (M + H)+.

Example 152h-13 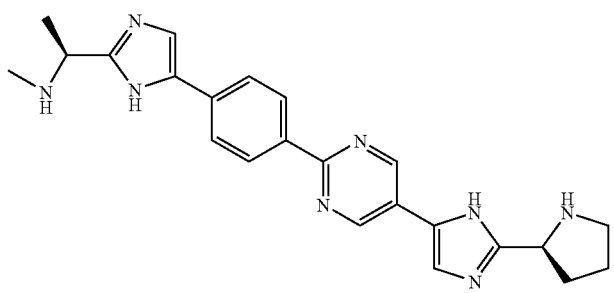

Prepared from 152g-14

$t_R$ = 1.42 min; Condition 1
LRMS: Anal. Calcd. for $C_{23}H_{26}N_8$ 414.24; found: 415.27 (M + H)+.
HRMS: Anal. Calcd. for $C_{23}H_{26}N_8$ 415.2359; found: 415.2371 (M + H)+.

| | | |
|---|---|---|
| Example 152h-14 | 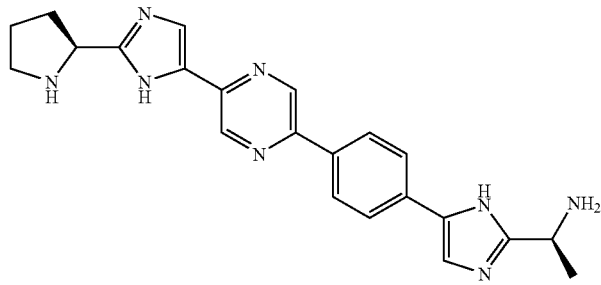 Prepared from 152g-17 | $t_R$ = 1.30 min; Condition 1<br>LRMS: Anal. Calcd. for $C_{22}H_{24}N_8$ 400.21; found: 401.24 (M + H)⁺.<br>HRMS: Anal. Calcd. for $C_{22}H_{24}N_8$ 401.2202; found: 401.2198 (M + H)⁺. |

Example 152i-1 to 152i-3

Example 152i-1 from 152g-8

(S)-2-(5-{2-[4-((S)-2-Pyrrolidin-2-yl-3H-imidazol-4-yl)-phenyl]-pyrimidin-5-yl}-1H-imidazol-2-yl)-pyrrolidine-1-carboxylic acid tert-butyl ester

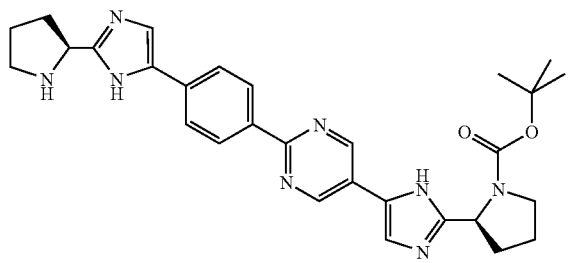

A solution of (S)-2-[5-(2-{4-[2-((S)-1-Benzyloxycarbonyl-pyrrolidin-2-yl)-3H-imidazol-4-yl]-phenyl}-pyrimidin-5-yl)-1H-imidazol-2-yl]-pyrrolidine-1-carboxylic acid tert-butyl ester (317.1 mg, 0.48 mmol) in MeOH (1 mL) was added to a stirred suspension of 10% palladium on carbon (60 mg) and $K_2CO_3$ (70 mg) in a solution of MeOH (5 mL) and $H_2O$ (0.1 mL) at room temperature under $N_2$. The flask was charged and evacuated three times with $H_2$ and stirred for 3 h at atmosphere pressure. Additional catalyst (20 mg) was then added and the reaction mixture was stirred further for 3 h before it was suction-filtered through diatomaceous earth (Celite®) and concentrated. The residue was diluted with MeOH, filtered through a PVDF syringe filter (13 mm×0.45 µm), distributed into 4 pHPLC vials and chromatographed (gradient elution from 20% B to 100% B over 10 min on a Phenomenex-Gemini C18 column (30×100 mm, 10 µm) where A=95% water, 5% acetonitrile, 10 mM $NH_4OAc$, B=10% water, 90% acetonitrile, 10 mM $NH_4OAc$). After concentration of the selected test tubes by speed vacuum evaporation, there was isolated the title compound as a yellow solid (142.5 mg, 56% yield).

$^1$H NMR (400 MHz, DMSO-$d_6$) δ 12.35-12.09 (br m, 1H), 9.17 (s, 2H), 8.35 (d, J=8.3 Hz, 2H), 7.87 (d, J=8.3 Hz, 2H), 7.80-7.72 (m, 1H), 7.56 (s, 1H), 4.92-4.77 (m, 1H), 4.21-4.13 (m, 1H), 3.61-3.05 (2m, 4H), 3.02-2.80 (2m, 2H), 2.37-1.67 (series of m, 6H), 1.41 and 1.17 (2s, 9H).

LCMS Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, RT=1.77 min, >95% homogeneity index.

LRMS: Anal. Calcd. for $C_{29}H_{35}N_8O_2$ 527.29; found: 527.34 (M+H)⁺.

HRMS: Anal. Calcd. for $C_{29}H_{35}N_8O_2$ 527.2883; found: 527.2874 (M+H)⁺.

The same procedure was used to prepare Examples 152i-2 through 152i-3.

LC conditions: Condition 1: Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, 220 nm, 5 µL injection volume.

Condition 2: Phenomenex LUNA C-18 4.6×50 mm, 0 to 100% B over 2 minutes, 1 minute hold time, A=90% water, 10% methanol, 0.1% TFA, B=10% water, 90% methanol, 0.1% TFA, 220 nm, 5 µL injection volume.

| | | |
|---|---|---|
| Example 152i-2 | 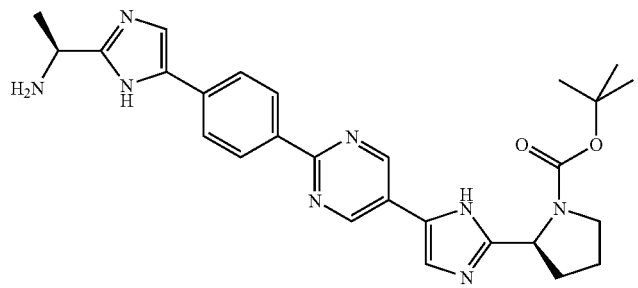 Prepared from 152g-15 | $t_R$ = 1.70 min (95.7%); Condition 1<br>LRMS: Anal. Calcd. for $C_{27}H_{33}N_8O_2$ 501.27; found: 501.35 (M + H)⁺.<br>HRMS: Anal. Calcd. for $C_{27}H_{33}N_8O_2$ 501.2726 found: 501.2709 (M + H)⁺. |

-continued

| Example | | | |
|---|---|---|---|
| Example 152i-3 | 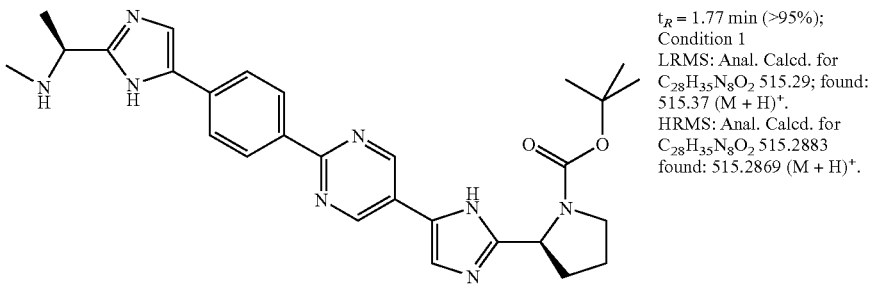 | | $t_R$ = 1.77 min (>95%);<br>Condition 1<br>LRMS: Anal. Calcd. for $C_{28}H_{35}N_8O_2$ 515.29; found: 515.37 $(M + H)^+$.<br>HRMS: Anal. Calcd. for $C_{28}H_{35}N_8O_2$ 515.2883 found: 515.2869 $(M + H)^+$. |

Prepared from 152g-16

Examples 152j-1 to 152j-28

Examples 152j were isolated as TFA or AcOH salts prepared using the procedure to convert Example 148e to 148.

LC conditions: Condition 1: Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, 220 nm, 5 µL injection volume.

Condition 2: Phenomenex LUNA C-18 4.6×50 mm, 0 to 100% B over 2 minutes, 1 minute hold time, A=90% water, 10% methanol, 0.1% TFA, B=10% water, 90% methanol, 0.1% TFA, 220 nm, 5 µL injection volume.

| Example | Compound Name | Structure | Data |
|---|---|---|---|
| Example 152j-1 | (1R)-2-((2S)-2-(5-(2-(4-(2-((2S)-1-((2R)-2-(dimethylamino)-2-phenylacetyl)-2-pyrrolidinyl)-1H-imidazol-5-yl)phenyl)-5-pyrimidinyl)-1H-imidazol-2-yl)-1-pyrrolidinyl)-N,N-dimethyl-2-oxo-1-phenylethanamine | 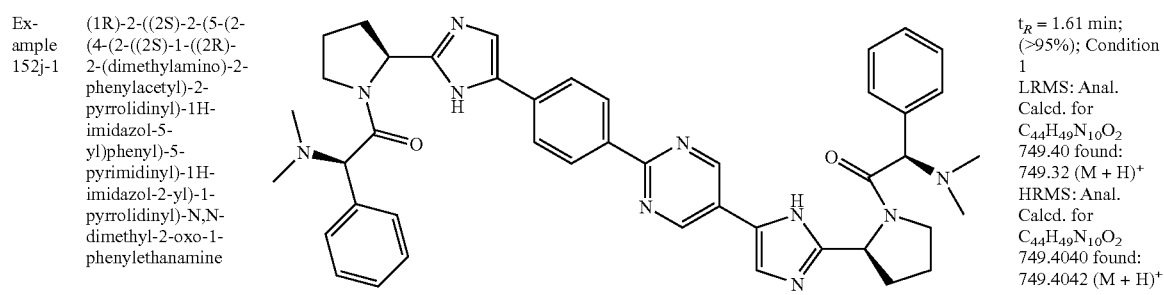<br>Prepared from 152h-1 and Cap-1. | $t_R$ = 1.61 min; (>95%); Condition 1<br>LRMS: Anal. Calcd. for $C_{44}H_{49}N_{10}O_2$ 749.40 found: 749.32 $(M + H)^+$<br>HRMS: Anal. Calcd. for $C_{44}H_{49}N_{10}O_2$ 749.4040 found: 749.4042 $(M + H)^+$ |
| Example 152j-2 | methyl ((1R)-2-((2S)-2-(5-(2-(4-(2-((2S)-1-((2R)-2-((methoxycarbonyl)amino)-2-phenylacetyl)-2-pyrrolidinyl)-1H-imidazol-5-yl)phenyl)-5-pyrimidinyl)-1H-imidazol-2-yl)-1-pyrrolidinyl)-2-oxo-1-phenylethyl)carbamate | 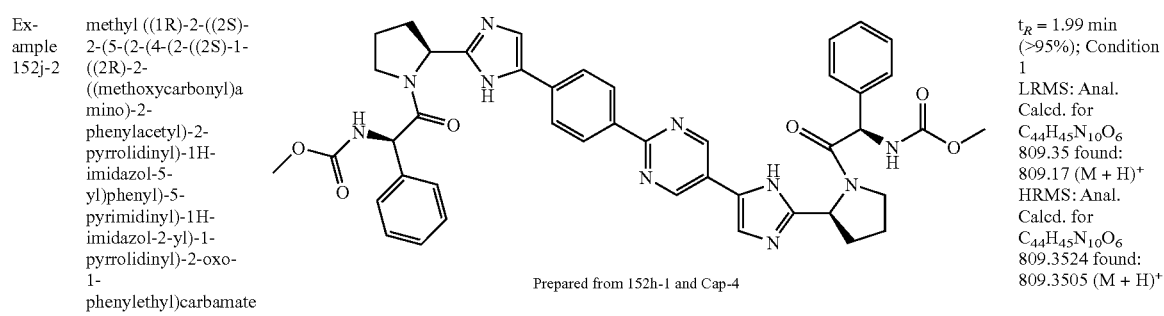<br>Prepared from 152h-1 and Cap-4 | $t_R$ = 1.99 min (>95%); Condition 1<br>LRMS: Anal. Calcd. for $C_{44}H_{45}N_{10}O_6$ 809.35 found: 809.17 $(M + H)^+$<br>HRMS: Anal. Calcd. for $C_{44}H_{45}N_{10}O_6$ 809.3524 found: 809.3505 $(M + H)^+$ |

-continued

| Example | Compound Name | Structure | Data |
|---|---|---|---|
| Example 152j-3 | methyl ((1R)-2-oxo-1-phenyl-2-((2S)-2-(5-(4-(5-(2-((2S)-1-(3-pyridinylacetyl)-2-pyrrolidinyl)-1H-imidazol-5-yl)-2-pyrimidinyl)phenyl)-1H-imidazol-2-yl)-1-pyrrolidinyl)ethyl)carbamate | Prepared from 152h-11 and Cap-4 | $t_R$ = 1.65 min (92.3%); Condition 1 LRMS: Anal. Calcd. for $C_{41}H_{41}N_{10}O_2$ 737.33 found: 737.49 (M + H)$^+$ HRMS: Anal. Calcd. for $C_{41}H_{41}N_{10}O_4$ 737.3312 found: 737.3342 (M + H)$^+$ |
| Example 152j-4 | methyl ((1R)-2-oxo-1-phenyl-2-((2S)-2-(5-(2-(4-(2-((2S)-1-(3-pyridinylacetyl)-2-pyrrolidinyl)-1H-imidazol-5-yl)phenyl)-5-pyrimidinyl)-1H-imidazol-2-yl)-1-pyrrolidinyl)ethyl)carbamate | Prepared from 152h-12 and Cap-4 | $t_R$ = 1.64 min (>95%); Condition 1 LRMS: Anal. Calcd. for $C_{41}H_{41}N_{10}O_4$ 737.33 found: 737.75 (M + H)$^+$ HRMS: Anal. Calcd. for $C_{41}H_{41}N_{10}O_4$ 737.3312 found: 737.3284 (M + H)$^+$ |
| Example 152j-5 | 5-(2-((2S)-1-((2R)-2-phenyl-2-(1-piperidinyl)acetyl)-2-pyrrolidinyl)-1H-imidazol-5-yl)-2-(4-(2-((2S)-1-((2R)-2-phenyl-2-(1-piperidinyl)acetyl)-2-pyrrolidinyl)-1H-imidazol-4-yl)phenyl)pyrimidine | Prepared from 152h-1 and Cap-14 | $t_R$ = 1.70 min (>95%); Condition 1 LRMS: Anal. Calcd. for $C_{50}H_{57}N_{10}O_2$ 829.47 found: 829.39 (M + H)$^+$ HRMS: Anal. Calcd. for $C_{50}H_{57}N_{10}O_2$ 829.4666 found: 829.4658 (M + H)$^+$ |
| Example 152j-6 | (2R)-N-methyl-2-phenyl-N-((1S)-1-(4-(4-(5-(2-((2S)-1-((2R)-2-phenyl-2-(1-piperidinyl)acetyl)-2-pyrrolidinyl)-1H-imidazol-5-yl)-2-pyrimidinyl)phenyl)-1H-imidazol-2-yl)ethyl)-2-(1-piperidinyl)acetamide | Prepared from 152h-13 and Cap-14 | $t_R$ = 1.66 min (>95%); Condition 1 LRMS: Anal. Calcd. for $C_{49}H_{57}N_{10}O_2$ 817.47 found: 817.44 (M + H)$^+$ HRMS: Anal. Calcd. for $C_{49}H_{57}N_{10}O_2$ 817.4666 found: 817.4673 (M + H)$^+$ |

-continued

| Example | Compound Name | Structure | Data |
|---|---|---|---|
| Example 152j-7 | (1R)-2-((2S)-2-(5-(5-(4-(2-((2S)-1-((2R)-2-(dimethylamino)-2-phenylacetyl)-2-pyrrolidinyl)-1H-imidazol-5-yl)phenyl)-2-pyrazinyl)-1H-imidazol-2-yl)-1-pyrrolidinyl)-N,N-dimethyl-2-oxo-1-phenylethanamine | Prepared from 152h-2 and Cap-1 | $t_R$ = 1.60 min (>95%); Condition 1<br>LRMS: Anal. Calcd. for $C_{41}H_{49}N_{10}O_2$ 749.40 found: 749.31 (M + H)$^+$<br>HRMS: Anal. Calcd. for $C_{44}H_{49}N_{10}O_2$ 749.4040 found: 749.4031 (M + H)$^+$ |
| Example 152j-8 | methyl ((1R)-2-((2S)-2-(5-(5-(4-(2-((2S)-1-((2R)-2-((methoxycarbonyl)amino)-2-phenylacetyl)-2-pyrrolidinyl)-1H-imidazol-5-yl)phenyl)-2-pyrazinyl)-1H-imidazol-2-yl)-1-pyrrolidinyl)-2-oxo-1-phenylethyl)carbamate | Prepared from 152h-2 and Cap-4 | $t_R$ = 2.01 min (>95%); Condition 1<br>LRMS: Anal. Calcd. for $C_{44}H_{45}N_{10}O_6$ 809.35 found: 809.24 (M + H)$^+$<br>HRMS: Anal. Calcd. for $C_{44}H_{45}N_{10}O_6$ 809.3523 found: 809.3493 (M + H)$^+$ |
| Example 152j-9 | (1R)-2-((2S)-2-(5-(6-(4-(2-((2S)-1-((2R)-2-(dimethylamino)-2-phenylacetyl)-2-pyrrolidinyl)-1H-imidazol-5-yl)phenyl)-3-pyridazinyl)-1H-imidazol-2-yl)-1-pyrrolidinyl)-N,N-dimethyl-2-oxo-1-phenylethanamine | Prepared from 152h-10 and Cap-1 | $t_R$ = 1.76 min (>95%); Condition 1<br>LRMS: Anal. Calcd. for $C_{44}H_{49}N_{10}O_2$ 749.40 found: not obsd (M + H)$^+$<br>HRMS: Anal. Calcd. for $C_{44}H_{49}N_{10}O_2$ 749.4040 found: 749.4056 (M + H)$^+$ |
| Example 152j-10 | methyl ((1R)-2-((2S)-2-(5-(6-(4-(2-((2S)-1-((2R)-2-((methoxycarbonyl)amino)-2-phenylacetyl)-2-pyrrolidinyl)-1H-imidazol-5-yl)phenyl)-3-pyridazinyl)-1H-imidazol-2-yl)-1-pyrrolidinyl)-2-oxo-1-phenylethyl)carbamate | Prepared from 152h-10 and Cap-4 | $t_R$ = 2.17 min (>95%); Condition 1<br>LRMS: Anal. Calcd. for $C_{44}H_{45}N_{10}O_6$ 809.35 found: 809.59 (M + H)$^+$<br>HRMS: Anal. Calcd. for $C_{44}H_{45}N_{10}O_6$ 809.3524 found: 809.3499 (M + H)$^+$ |

| Example | Compound Name | Structure | Data |
|---|---|---|---|
| Example 152j-11 | (2R)-2-(dimethylamino)-N-((1S)-1-(5-(4-(5-(2-((2S)-1-((2R)-2-(dimethylamino)-2-phenylacetyl)-2-pyrrolidinyl)-1H-imidazol-5-yl)-2-pyridinyl)phenyl)-1H-imidazol-2-yl)ethyl)-2-phenylacetamide | Prepared from 152h-7 and Cap-1 | $t_R$ = 1.56 min (>95%); Condition 1 LRMS: Anal. Calcd. for $C_{43}H_{48}N_9O_2$ 722.39 found: 722.89 $(M + H)^+$ HRMS: Anal. Calcd. for $C_{43}H_{48}N_9O_2$ 722.3931 found: 722.3930 $(M + H)^+$ |
| Example 152j-12 | methyl ((1R)-2-((2S)-2-(5-(6-(4-(2-((1S)-1-(((2R)-2-((methoxycarobnyl)amino)-2-phenylacetyl)amino)ethyl)-1H-imidazol-5-yl)phenyl)-3-pyridinyl)-1H-imidazol-2-yl)-1-pyrrolidinyl)-2-oxo-1-phenylethyl)carbamate | Prepared from 152h-7 and Cap-4 | $t_R$ = 1.95 min (>95%); Condition 1 LRMS: Anal. Calcd. for $C_{43}H_{44}N_9O_6$ 782.34 found: 782.93 $(M + H)^+$ HRMS: Anal. Calcd. for $C_{43}H_{44}N_9O_6$ 782.3415 found: 782.3398 $(M + H)^+$ |
| Example 152j-13 | (2R)-2-(dimethylamino)-N-((1S)-1-(5-(4-(6-(2-((2S)-1-((2R)-2-(dimethylamino)-2-phenylacetyl)-2-pyrrolidinyl)-1H-imidazol-5-yl)-3-pyridazinyl)phenyl)-1H-imidazol-2-yl)ethyl)-2-phenylacetamide | Prepared from 152h-3 and Cap-1 | $t_R$ = 1.55 min (>95%); Condition 1 LRMS: Anal. Calcd. for $C_{42}H_{47}N_{10}O_2$ 723.39 found: 723.88 $(M + H)^+$ HRMS: Anal. Calcd. for $C_{42}H_{47}N_{10}O_2$ 723.3883 found: 723.3903 $(M + H)^+$ |
| Example 152j-14 | methyl ((1R)-2-((2S)-2-(5-(6-(4-(2-((1S)-1-(((2R)-2-((methoxycarobnyl)amino)-2-phenylacetyl)amino)ethyl)-1H-imidazol-5-yl)phenyl)-3-pyridazinyl)-1H-imidazol-2-yl)-1-pyrrolidinyl)-2-oxo-1-phenylethyl)carbamate | Prepared from 152h-3 and Cap-4 | $t_R$ = 1.95 min (>95%); Condition 1 LRMS: Anal. Calcd. for $C_{42}H_{43}N_{10}O_6$ 783.34 found: 783.95 $(M + H)^+$ HRMS: Anal. Calcd. for $C_{42}H_{43}N_{10}O_6$ 783.3367 found: 783.3337 $(M + H)^+$ |

-continued

| Example | Compound Name | Structure | Data |
|---|---|---|---|
| Example 152j-15 | methyl ((1R)-2-((2S)-2-(5-(2-(4-(2-((1S)-1-(((2R)-2-((methoxycarbonyl)amino)-2-phenylacetyl)amino)ethyl)-1H-imidazol-5-yl)phenyl)-5-pyrimidinyl)-1H-imidazol-2-yl)-1-pyrrolidinyl)-2-oxo-1-phenylethyl)carbamate | Prepared from 152h-4 and Cap-4 | $t_R$ = 1.97 min (>95%); Condition 1<br>LRMS: Anal. Calcd. for $C_{42}H_{43}N_{10}O_6$ 783.34 found: 783.97 (M + H)$^+$<br>HRMS: Anal. Calcd. for $C_{42}H_{43}N_{10}O_6$ 783.3367 found: 783.3357 (M + H)$^+$ |
| Example 152j-16 | (2R)-2-(dimethylamino)-N-((1S)-1-(5-(2-(4-(2-((2S)-1-((2R)-2-(dimethylamino)-2-phenylacetyl)-2-pyrrolidinyl)-1H-imidazol-5-yl)phenyl)-5-pyrimidinyl)-1H-imidazol-2-yl)ethyl)-2-phenylacetamide | Prepared from 152h-9 and Cap-1 | $t_R$ = 1.61 min (>95%); Condition 1<br>LRMS: Anal. Calcd. for $C_{42}H_{47}N_{10}O_2$ 723.39 found: 723.52 (M + H)$^+$<br>HRMS: Anal. Calcd. for $C_{42}H_{47}N_{10}O_2$ 723.3883 found: 723.3893 (M + H)$^+$ |
| Example 152j-17 | methyl ((1R)-2-((2S)-2-(5-(4-(5-(2-((1S)-1-(((2R)-2-((methoxycarbonyl)amino)-2-phenylacetyl)amino)ethyl)-1H-imidazol-5-yl)-2-pyrimidinyl)phenyl)-1H-imidazol-2-yl)-1-pyrrolidinyl)-2-oxo-1-phenylethyl)carbamate | Prepared from 152h-9 and Cap-4 | $t_R$ = 1.99 min (95.6%); Condition 1<br>LRMS: Anal. Calcd. for $C_{42}H_{43}N_{10}O_6$ 783.34 found: 783.44 (M + H)$^+$<br>HRMS: Anal. Calcd. for $C_{42}H_{43}N_{10}O_6$ 783.3367 found: 783.3328 (M + H)$^+$ |
| Example 152j-18 | (2R)-2-(dimethylamino)-N-((1S)-1-(5-(5-(4-(2-((2S)-1-((2R)-2-(dimethylamino)-2-phenylacetyl)-2-pyrrolidinyl)-1H-imidazol-5-yl)phenyl)-2-pyrazinyl)-1H-imidazol-2-yl)ethyl)-2-phenylacetamide | Prepared from 152h-8 and Cap-1 | $t_R$ = 1.60 min (>95%); Condition 1<br>LRMS: Anal. Calcd. for $C_{42}H_{47}N_{10}O_2$ 723.39 found: 723.47 (M + H)$^+$<br>HRMS: Anal. Calcd. for $C_{42}H_{47}N_{10}O_2$ 723.3883 found: 723.3861 (M + H)$^+$ |

-continued

| Example | Compound Name | Structure | Data |
|---|---|---|---|
| Example 152j-19 | methyl ((1R)-2-((2S)-2-(5-(4-(5-(2-((1S)-1-(((2R)-2-((methoxycarbonyl)amino)-2-phenylacetyl)amino)ethyl)-1H-imidazol-5-yl)-2-pyrazinyl)phenyl)-1H-imidazol-2-yl)-1-pyrrolidinyl)-2-oxo-1-phenylethyl)carbamate | Prepared from 152h-8 and Cap-4 | $t_R$ = 1.97 min (94.7%); Condition 1<br>LRMS: Anal. Calcd. for $C_{42}H_{43}N_{10}O_6$ 783.34 found: 783.69 (M + H)$^+$<br>HRMS: Anal. Calcd. for $C_{42}H_{43}N_{10}O_6$ 783.3367 found: 783.3345 (M + H)$^+$ |
| Example 152j-20 | (2R)-2-(dimethylamino)-N-((1S)-1-(5-(4-(5-(2-((2S)-1-((2R)-2-(dimethylamino)-2-phenylacetyl)-2-pyrrolidinyl)-1H-imidazol-5-yl)-2-pyrimidinyl)phenyl)-1H-imidaozl-2-yl)ethyl)-N-methyl-2-phenylacetamide | Prepared from 152h-13 and Cap-1 | $t_R$ = 1.54 min (>95%); Condition 1<br>LRMS: Anal. Calcd. for $C_{43}H_{49}N_{10}O_2$ 737.40 found: 737.54 (M + H)$^+$<br>HRMS: Anal. Calcd. for $C_{43}H_{49}N_{10}O_2$ 737.4040 found: 7374066 (M + H)$^+$ |
| Example 152j-21 | methyl ((1R)-2-((2S)-2-(5-(2-(4-(2-((1S)-1-(((2R)-2-((methoxycarbonyl)amino)-2-phenylacetyl)(methyl)amino)ethyl)-1H-imidazol-5-yl)phenyl)-5-pyrimidinyl)-1H-imidazol-2-yl)-1-pyrrolidinyl)-2-oxo-1-phenylethyl)carbamate | Prepared from 152h-13 and Cap-4 | $t_R$ = 2.00 min (>95%); Condition 1<br>LRMS: Anal. Calcd. for $C_{43}H_{45}N_{10}O_6$ 797.35 found: 797.38 (M + H)$^+$<br>HRMS: Anal. Calcd. for $C_{43}H_{45}N_{10}O_6$ 797.3524 found: 797.3528 (M + H)$^+$ |

| Example | Compound Name | Structure | Data |
|---|---|---|---|
| Example 152j-22 | methyl ((1R)-2-((2S)-2-(5-(4-(5-(2-((1S)-1-(((2R)-2-((methoxycarbonyl)amino)-2-phenylacetyl)amino)ethyl)-1H-imidazol-5-yl)-2-pyridinyl)phenyl)-1H-imidazol-2-yl)-1-pyrrolidinyl)-2-oxo-1-phenylethyl)carbamate | Prepared from 152h-5 and Cap-4 | $t_R$ = 1.46 min (condition 2, 98%) LRMS: Anal. Calcd. for $C_{43}H_{43}N_9O_6$ 781.33; found: 782.34 (M + H)$^+$. HRMS: Anal. Calcd. for $C_{43}H_{44}N_9O_6$ 782.3415 found: 782.3417 (M + H)$^+$ |
| Example 152j-23 | methyl ((1R)-2-(((1S)-1-(5-(6-(4-(2-((1S)-1-(((2R)-2-((methoxycarbonyl)amino)-2-phenylacetyl)amino)ethyl)-1H-imidazol-5-yl)phenyl)-3-pyridinyl)-1H-imidazol-2-yl)ethyl)amino)-2-oxo-1-phenylethyl)carbamate | Prepared from 152h-6 and Cap-4 | $t_R$ = 1.44 min condition 2, 90%) LRMS: Anal. Calcd. for $C_{41}H_{41}N_9O_6$ 755.32; found: 756.35 (M + H)$^+$. HRMS: Anal. Calcd. for $C_{41}H_{42}N_9O_6$ 756.3258 found: 756.3239 (M + H)$^+$. |

-continued

| Example | Compound Name | Structure | Data |
|---|---|---|---|
| Example 152j-24 | (2R)-2-(dimethylamino)-N-((1S)-1-(5-(6-(4-(2-((1S)-1-(((2R)-2-(dimethylamino)-2-phenylacetyl)amino)ethyl)-1H-imidazol-5-yl)phenyl)-3-pyridinyl)-1H-imidazol-2-yl)ethyl)-2-phenylacetamide | Prepared from 152h-6 and Cap1 | $t_R$ = 1.18 min (condition 2, 91%) LRMS: Anal. Calcd. for $C_{41}H_{45}N_9O_2$ 695.37; found: 696.37 (M + H)⁺. HRMS: Anal. Calcd. for $C_{41}H_{46}N_9O_2$ 696.3774 found: 696.3806 (M + H)⁺. |
| Example 152j-25 | Prepared from 152i-3 and Cap-4 | 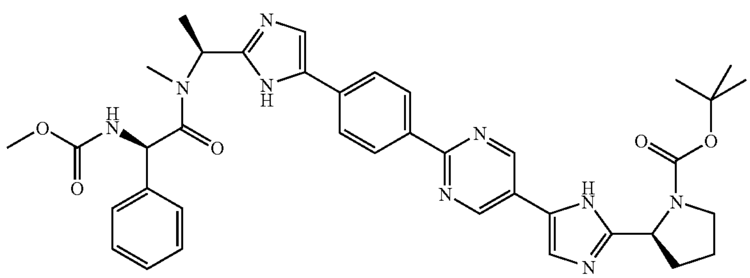 | $t_R$ = 2.08 min (95.8%); Condition 1 LRMS: Anal. Calcd. for $C_{38}H_{44}N_9O_5$ 706.35; found: 706.53 (M + H)⁺. HRMS: Anal. Calcd. for $C_{38}H_{44}N_9O_5$ 706.3465; found: 706.3492 (M + H)⁺. |
| Example 152j-26 | Prepared from 152i-2 and Cap-4 | 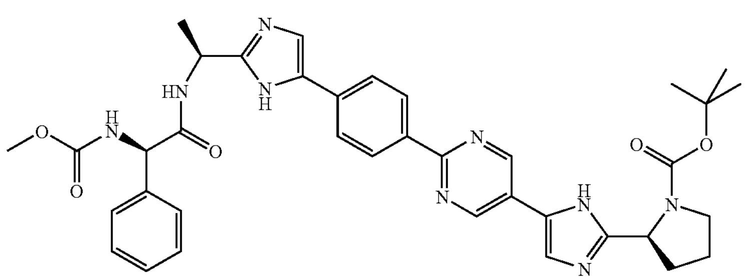 | $t_R$ = 2.04 min (96.4%); Condition 1 LRMS: Anal. Calcd. for $C_{37}H_{42}N_9O_5$ 692.33; found: 692.49 (M + H)⁺. HRMS: Anal. Calcd. for $C_{37}H_{42}N_9O_5$ 692.3309; found: 692.3322 (M + H)⁺. |
| Example 152j-27 | Prepared from 152i-1 and Cap-4 | 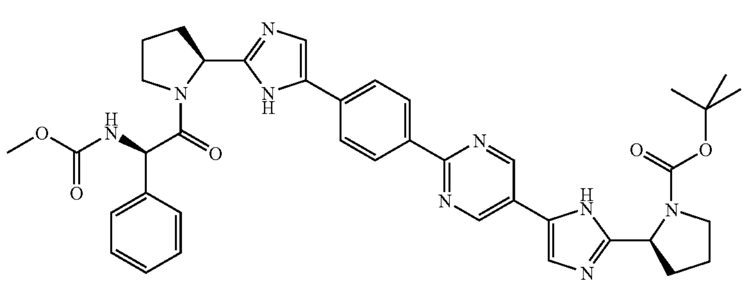 | $t_R$ = 2.04 min (>95%); Condition 1 LRMS: Anal. Calcd. for $C_{39}H_{44}N_9O_5$ 718.35; found: 718.49 (M + H)⁺. HRMS: Anal. Calcd. for $C_{39}H_{44}N_9O_5$ 718.3465; found: 718.3483 (M + H)⁺. |

| Example | Compound Name | Structure | Data |
|---|---|---|---|
| Example 152j-28 | methyl ((1R)-2-((2S)-2-(5-(5-(4-(2-(((1S)-1-(((2R)-2-((methoxycarbonyl)amino)-2-phenylacetyl)amino)ethyl)-1H-imidazol-5-yl)phenyl)-2-pyrazinyl)-1H-imidazol-2-yl)-1-pyrrolidinyl)-2-oxo-1-phenylethyl)carbamate | Prepared from 152h-14 and Cap-4 | $t_R$ = 2.00 min (>95%); Condition 1<br>LRMS: Anal. Calcd. for $C_{42}H_{43}N_{10}O_6$ 783.34 found: 783.96 (M + H)$^+$<br>HRMS: Anal. Calcd. for $C_{42}H_{43}N_{10}O_6$ 783.3367 found: 783.3375 (M + H)$^+$ |

Examples 152k-1 to 152k-

Example 152k-1 from 152j-27

{(R)-2-Oxo-1-phenyl-2-[(S)-2-(5-{4-[5-((S)-2-pyrrolidin-2-yl-3H-imidazol-4-yl)-pyrimidin-2-yl]-phenyl}-1H-imidazol-2-yl)-pyrrolidin-1-yl]-ethyl}-carbamic acid methyl ester

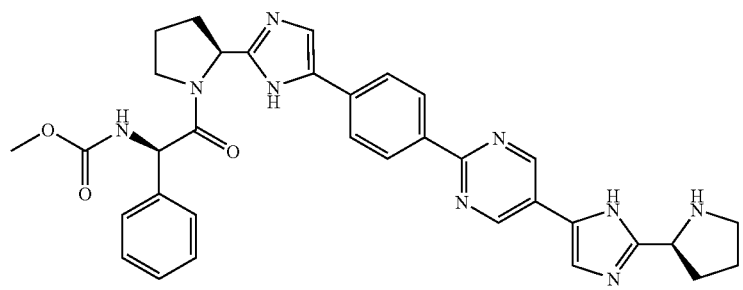

Cold (0° C.) 4 NHCl in dioxanes (4 mL) was added via syringe to (S)-2-{5-[2-(4-{2-[(S)-1-((R)-2-methoxycarbonylamino-2-phenyl-acetyl)-pyrrolidin-2-yl]-3H-imidazol-4-yl}-phenyl)-pyrimidin-5-yl]-1H-imidazol-2-yl}-pyrrolidine-1-carboxylic acid tert-butyl ester (104.6 mg, 0.146 mmol) in a 100 mL pear-shaped flask followed by MeOH (0.5 mL). The homogeneous mixture was stirred at room temperature for 15 min before a precipitate was observed. After stirring further for 1.75 h, the suspension was diluted with ether and hexanes. Suction-filtration of a small portion of the suspension yielded the title compound as a yellow solid which was used for characterization purposes. The balance of the suspension was concentrated down to dryness and placed under high vacuum for 16 h. There was isolated the rest of the title compound also as a yellow solid (137.7 mg, 123%) which was used without further purification.

$^1$H NMR (500 MHz, DMSO-$d_6$) δ 15.20 and 14.66 (2m, 1H), 10.29 (br s, 0.7H), 9.38-9.36 (m, 2H), 8.55-8.00 (series of m, 4H), 7.42-7.28 (2m, 3H), 5.53-4.00 (series of m, 7H), 3.99-3.13 (series of m, 4H), 3.57 and 3.52 (2s, 3H), 2.50-1.84 (series of m, 8H).

LCMS Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, RT=1.79 min, >95% homogeneity index.

LRMS: Anal. Calcd. for $C_{34}H_{36}N_9O_3$ 618.29; found: 618.42 (M+H)$^+$.

HRMS: Anal. Calcd. for $C_{34}H_{36}N_9O_3$ 618.2921; found: 618.2958 (M+H)$^+$.

The same procedure was used to prepare Examples 152k-2 through 152k-3.

LC conditions: Condition 1: Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, 220 nm, 5 μL injection volume.

Condition 2: Phenomenex LUNA C-18 4.6×50 mm, 0 to 100% B over 2 minutes, 1 minute hold time, A=90% water, 10% methanol, 0.1% TFA, B=10% water, 90% methanol, 0.1% TFA, 220 nm, 5 μL injection volume.

| Example | Compound Name | Structure | Data |
|---|---|---|---|
| Example 152k-2 | | Prepared from 152j-26 | $t_R$ = 1.74 min (>95%); Condition 1 LRMS: Anal. Calcd. for $C_{32}H_{34}N_9O_3$ 592.28; found: 592.41 $(M + H)^+$. HRMS: Anal. Calcd. for $C_{32}H_{34}N_9O_3$ 592.2785; found: 592.2775 $(M + H)^+$. |
| Example 152k-3 | | Prepared from 152j-25 | $t_R$ = 1.79 min (>95%); Condition 1 LRMS: Anal. Calcd. for $C_{33}H_{36}N_9O_3$ 606.29; found: 606.43 $(M + H)^+$. HRMS: Anal. Calcd. for $C_{33}H_{36}N_9O_3$ 606.2941; found: 606.2925 $(M + H)^+$. |

Examples 152l-1 to 152l-3

Examples 152l-1 through 152l-3 were isolated as TFA or AcOH salts prepared using the same procedure to convert Example 148e to 148.

LC conditions: Condition 1: Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, 220 nm, 5 µL injection volume.

Condition 2: Phenomenex LUNA C-18 4.6×50 mm, 0 to 100% B over 2 minutes, 1 minute hold time, A=90% water, 10% methanol, 0.1% TFA, B=10% water, 90% methanol, 0.1% TFA, 220 nm, 5 µL injection volume.

| Example | Compound Name | Structure | Data |
|---|---|---|---|
| Example 152l-1 | methyl ((1R)-2-(methyl((1S)-1-(4-(4-(5-(2-((2S)-1-((2R)-2-phenyl-2-(1-piperidinyl)acetyl)-2-pyrrolidinyl)-1H-imidazol-5-yl)-2-pyrimidinyl)phenyl)-1H-imidazol-2-yl)ethyl)amino)-2-oxo-1-phenylethyl)carbamate | Prepared from 152k-3 and Cap-14 | $t_R$ = 1.87 min (>95%); Condition 1 LRMS: Anal. Calcd. for $C_{46}H_{51}N_{10}O_4$ 807.41 found: 807.57 $(M + H)^+$ HRMS: Anal. Calcd. for $C_{46}H_{51}N_{10}O_4$ 807.4095 found: 807.4128 $(M + H)^+$ |

| Example | Compound Name | Structure | Data |
|---|---|---|---|
| Example 152l-2 | methyl ((1R)-2-oxo-1-phenyl-2-(((1S)-1-(4-(4-(5-(2-((2S)-1-((2R)-2-phenyl-2-(1-piperidinyl)acetyl)-2-pyrrolidinyl)-1H-imidazol-5-yl)-2-pyrimidinyl)phenyl)-1H-imidazol-2-yl)ethyl)amino)ethyl)carbamate | Prepared from 152k-2 and Cap-14 | $t_R$ = 1.83 min (>95%); Condition 1 LRMS: Anal. Calcd. for $C_{45}H_{49}N_{10}O_4$ 793.39 found: 793.52 (M + H)$^+$ HRMS: Anal. Calcd. for $C_{45}H_{49}N_{10}O_4$ 793.3938 found: 793.3934 (M + H)$^+$ |
| Example 152l-3 | methyl ((1R)-2-oxo-1-phenyl-2-((2S)-2-(4-(4-(5-(2-((2S)-1-((2R)-2-phenyl-2-(1-piperidinyl)acetyl)-2-pyrrolidinyl)-1H-imidazol-5-yl)-2-pyrimidinyl)phenyl)-1H-imidazol-2-yl)-1-pyrrolidinyl)ethyl)carbamate | Prepared from 152k-1 and Cap-14 | $t_R$ = 1.87 min (>95%); Condition 1 LRMS: Anal. Calcd. for $C_{47}H_{51}N_{10}O_4$ 819.41 found: 819.50 (M + H)$^+$ HRMS: Anal. Calcd. for $C_{47}H_{51}N_{10}O_4$ 819.4095 found: 819.4127 (M + H)$^+$ |

Examples 153a-1 Through 153a-4

Example 153a-1 Prepared From 152e-1

(S)-2-[5-{5'-[2-((S)-1-tert-Butoxycarbonyl-pyrrolidin-2-yl)-3-(2-trimethylsilanyl-ethoxymethyl)-3H-imidazol-4-yl]-[2,2']bipyrimidinyl-5-yl}-1-(2-trimethylsilanyl-ethoxymethyl)-1H-imidazol-2-yl]-pyrrolidine-1-carboxylic acid tert-butyl ester

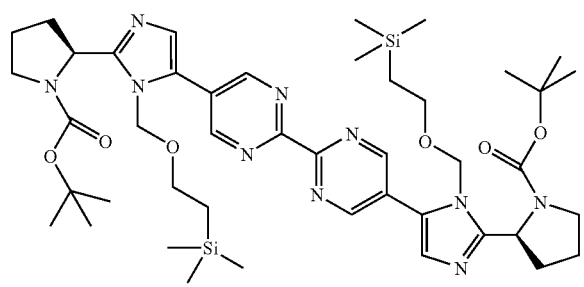

To a stirred solution of (S)-tert-butyl 2-(5-(2-chloropyrimidin-5-yl)-1-((2-(trimethylsilyl)ethoxy)methyl)-1H-imidazol-2-yl)pyrrolidine-1-carboxylate (1.0 g, 2.08 mmol) and dichlorobis(benzonitrile) palladium (40 mg, 0.104 mmol) in dry DMF (10 mL) at room temperature under argon was added neat tetrakis(dimethylamino)ethylene (1.0 mL, 4.16 mmol). The mixture was heated to 60° C. for 15 h before it was diluted with ethyl acetate and suction-filtered through diatomaceous earth (Celite®). The filtrate was washed with sat'd NaHCO$_3$ soln and brine prior to drying over Na$_2$SO$_4$ and solvent evaporation. Purification of the residue by Biotage™ flash chromatography on silica gel (step gradient elution with 15% B to 15% B for 150 mL, 15% B to 75% B for 1500 mL, 75% B to 100% B for 1000 mL, 100% B to 100% B for 1000 mL where B=ethyl acetate and A=hexane followed by a second gradient elution with 10% B to 100% B for 700 mL where B=methanol and A=ethyl acetate) furnished the title compound as a caramel-colored, viscous oil (487.8 mg, 26% yield).

$^1$H NMR (500 MHz, DMSO-d$_6$) δ 9.27 (s, 4H), 8.09-8.06 (m, 2H), 5.73-5.66 and 5.50-5.44 (2m, 2H), 5.06-4.93 (m, 2H), 3.60-3.39 (2m, 8H), 2.32-2.08 (3 m, 4H), 2.00-1.85 (m, 4H), 1.37 and 1.14 (2s, 18H), 0.95-0.84 (m, 4H), −0.01 (s, 18H).

LCMS Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, RT=3.37 min, >95% homogeneity index.

LRMS: Anal. Calcd. for $C_{44}H_{69}N_{10}O_6S_{i2}$ 889.49; found: 889.57 (M+H)$^+$.

HRMS: Anal. Calcd. for $C_{44}H_{69}N_{10}O_6S_{i2}$ 889.4940; found: 889.4920 (M+H)$^+$.

The same procedure was used to prepare Examples 153a-2 through 153a-4.

LC conditions: Condition 1: Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, 220 nm, 5 μL injection volume.

Condition 2: Phenomenex LUNA C-18 4.6×50 mm, 0 to 100% B over 2 minutes, 1 minute hold time, A=90% water, 10% methanol, 0.1% TFA, B=10% water, 90% methanol, 0.1% TFA, 220 nm, 5 μL injection volume.

| Example | Compound Name | Structure | Data |
|---|---|---|---|
| Example 153a-2 | | Prepared from 152e-2 | $t_R$ = 3.37 min (89.6%); Condition 1<br>LRMS: Anal. Calcd. for $C_{44}H_{69}N_{10}O_6Si_2$ 889.49; found: 889.56 $(M + H)^+$.<br>HRMS: Anal. Calcd. for $C_{44}H_{69}N_{10}O_6Si_2$ 889.494; found: 889.4951 $(M + H)^+$. |
| Example 153a-3 | | Prepared from 152e-3 | $t_R$ = 3.37 min (95%); Condition 1<br>LRMS: Anal. Calcd. for $C_{44}H_{69}N_{10}O_6Si_2$ 889.49; found: 889.51 $(M + H)^+$.<br>HRMS: Anal. Calcd. for $C_{44}H_{69}N_{10}O_6Si_2$ 889.4940; found: 889.4915 $(M + H)^+$. |
| Example 153a-4 | | Prepared from 152e-4 | $t_R$ = 2.3 min (condition 2)<br>LRMS: Anal. Calcd. for $C_{42}H_{66}N_8Si_2$ 834; found: 835 $(M + H)^-$. |

Example 153b-1-153b-3

The hydrolysis reactions was performed as above for Example 152h.

LC conditions: Condition 1: Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, 220 nm, 5 µL injection volume.

Condition 2: Phenomenex LUNA C-18 4.6×50 mm, 0 to 100% B over 2 minutes, 1 minute hold time, A=90% water, 10% methanol, 0.1% TFA, B=10% water, 90% methanol, 0.1% TFA, 220 nm, 5 µL injection volume.

| Example | Compound Name | Structure | Data |
|---|---|---|---|
| Example 153b-1 | | Prepared from 153a-1 | $t_R$ = 1.18 min (>95%); Condition 1 LRMS: Anal. Calcd. for $C_{22}H_{25}N_{10}$ 429.23; found: 429.01 $(M + H)^+$. HRMS: Anal. Calcd. for $C_{22}H_{25}N_{10}$ 429.2264; found: 429.2259 $(M + H)^+$. |
| Example 153b-2 | | Prepared from 153a-2 | $t_R$ = 1.26 min (>95%); Condition 1 LRMS: Anal. Calcd. for $C_{41}H_{41}N_{10}O_2$ 737.33 found: 737.49 $(M + H)^+$ HRMS: Anal. Calcd. for $C_{41}H_{41}N_{10}O_4$ 737.3312 found: 737.3342 $(M + H)^+$ |
| Example 153b-3 | | Prepared from 153a-3 | $t_R$ = 1.40 min (>95%); Condition 1 LRMS: Anal. Calcd. for $C_{22}H_{25}N_{10}$ 429.23; found: 429.20 $(M + H)^+$. HRMS: Anal. Calcd. for $C_{22}H_{25}N_{10}$: 429.2264; Found: 429.2254 $(M + H)^+$ |
| Example 153b-4 | | Prepared from 153a-4 | $t_R$ = 0.85 min (condition 1) LCMS: Anal. Calcd. for $C_{20}H_{22}N_8$ 374; found: 375 $(M + H)^+$. |

Examples 153c-1 to 153c-7

Examples 153c-1 through 153c-7 were isolated as TFA or AcOH salts using the procedure used to convert Example 148e to 148.

LC conditions: Condition 1: Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, 220 nm, 5 µL injection volume.

Condition 2: Phenomenex LUNA C-18 4.6×50 mm, 0 to 100% B over 2 minutes, 1 minute hold time, A=90% water, 10% methanol, 0.1% TFA, B=10% water, 90% methanol, 0.1% TFA, 220 nm, 5 µL injection volume.

| Example | Compound Name | Structure | Data |
|---|---|---|---|
| Example 153c-1 | (1R,1'R)-2,2'-(3,3'-bipyridazine-6,6'-diylbis(1H-imidazole-5,2-diyl(2S)-2,1-pyrrolidinediyl))bis(N,N-dimethyl-2-oxo-1-phenylethanamine) | Prepared from 153b-2 and Cap-1 | $t_R$ = 1.55 min (>95%); Condition 1 LRMS: Anal. Calcd. for $C_{42}H_{47}N_{12}O_2$ 751.39 found: 751.64 $(M + H)^+$ HRMS: Anal. Calcd. for $C_{42}H_{47}N_{12}O_2$ 751.3945 found: 751.3936 $(M + H)^+$ |
| Example 153c-2 | dimethyl (3,3'-bipyridazine-6,6'-diylbis(1H-imidazole-5,2-diyl(2S)-2,1-pyrrolidinediyl((1R)-2-oxo-1-phenyl-2,1-ethanediyl))) biscarbamate | Prepared from 153b-2 and Cap-4 | $t_R$ = 1.95 min (>95%); Condition 1 LRMS: Anal. Calcd. for $C_{42}H_{43}N_{12}O_6$ 811.34 found: 811.22 $(M + H)^+$ HRMS: Anal. Calcd. for $C_{42}H_{43}N_{12}O_6$ 811.3429 found: 811.3406 $(M + H)^+$ |
| Example 153c-3 | (1R,1'R)-2,2'-(2,2'-bipyrimidine-5,5'-diylbis(1H-imidazole-5,2-diyl(2S)-2,1-pyrrolidinediyl))bis(N,N-dimethyl-2-oxo-1-phenylethanamine) | Prepared from 153b-1 and Cap-1 | $t_R$ = 1.51 min (>90%*); Condition 1 LRMS: Anal. Calcd. for $C_{42}H_{47}N_{12}O_2$ 751.39 found: 751.21 $(M + H)^+$ HRMS: Anal. Calcd. for $C_{42}H_{47}N_{12}O_2$ 751.3945 found: 751.3921 $(M + H)^+$ |
| Example 153c-4 | dimethyl (2,2'-bipyrimidine-5,5'-diylbis(1H-imidazole-5,2-diyl(2S)-2,1-pyrrolidinediyl((1R)-2-oxo-1-phenyl-2,1-ethanediyl))) biscarbamate | Prepared from 153b-1 and Cap-4 | $t_R$ = 1.88 min (>95%); Condition 1 LRMS: Anal. Calcd. for $C_{42}H_{43}N_{12}O_6$ 811.34 found: 811.10 $(M + H)^+$ HRMS: Anal. Calcd. for $C_{42}H_{43}N_{12}O_6$ 811.3429 found: 811.3401 $(M + H)^+$ |

-continued

| Example | Compound Name | Structure | Data |
|---|---|---|---|
| Example 153c-5 | (1R,1'R)-2,2'-(2,2'-bipyrazine-5,5'-diylbis(1H-imidazole-5,2-diyl(2S)-2,1-pyrrolidinediyl))bis(N,N-dimethyl-2-oxo-1-phenylethanamine) | Prepared from 153b-3 and Cap-1 | $t_R$ = 1.61 min (>95%); Condition 1 LRMS: Anal. Calcd. for $C_{42}H_{47}N_{12}O_2$ 751.39 found: 751.30 $(M + H)^+$ HRMS: Anal. Calcd. for $C_{42}H_{47}N_{12}O_2$ 751.3945 found: 751.3943 $(M + H)^+$ |
| Example 153c-6 | dimethyl (2,2'-bipyrazine-5,5'-diylbis(1H-imidazole-5,2-diyl(2S)-2,1-pyrrolidinediyl((1R)-2-oxo-1-phenyl-2,1-ethanediyl))) biscarbamate | Prepared from 153b-3 and Cap-4 | $t_R$ = 2.00 min (>95%); Condition 1 LRMS: Anal. Calcd. for $C_{42}H_{43}N_{12}O_6$ 811.34 found: 811.23 $(M + H)^+$ HRMS: Anal. Calcd. for $C_{42}H_{43}N_{12}O_6$ 811.3429 found: 811.3407 $(M + H)^+$ |
| Example 153c-7 | dimethyl (2,2'-bipyridine-5,5'-diylbis(1H-imidazole-5,2-diyl(1S)-1,1-ethanediylimino((1R)-2-oxo-1-phenyl-2,1-ethanediyl))) biscarbamate | Prepared from 153b-4 and Cap-4 | $t_R$ = 1.42 min (condition 2, 94%) LRMS: Anal. Calcd. for $C_{40}H_{40}N_{10}O_6$ 756.31; found: 757.34 $(M + H)^+$. HRMS: Anal. Calcd. for $C_{40}H_{41}N_{10}O_6$ 757.3211 found: 747.3180 $(M + H)^+$. |

Section F LC Conditions for Determining Retention Time

Condition 7

Column: Phenomenex C18 10u 4.6×30 mm

Start % B=0

Final % B=100

Gradient Time=3 min

Flow Rate=4 mL/Min

Wavelength=220

Solvent A=10% methanol-90% H₂O-0.1% TFA

Solvent B=90% methanol-10% H₂O-0.1% TFA

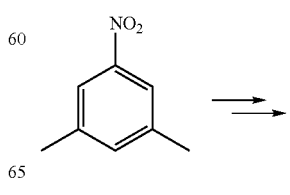

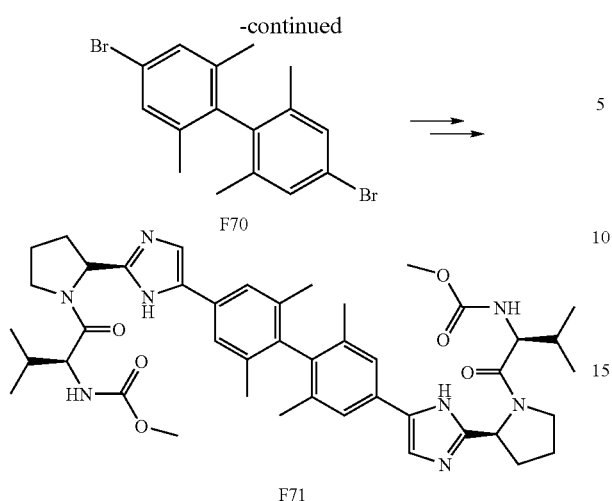

Compound F70 was prepared following the procedure described in Anna Helms et al., *J. Am. Chem. Soc.* 1992 114(15) pp 6227-6238.

Compound F71 was prepared in analogous fashion to the procedure used to synthesize Example 1.

$^1$H NMR (500 MHz, DMSO-d$_6$) δ ppm 0.69-0.95 (m, 12H) 1.92 (s, 12H) 1.97-2.27 (m, 8H) 2.40 (s, 2H) 3.55 (s, 6H) 3.73-3.97 (m, 4H) 4.12 (t, J=7.78 Hz, 2H) 5.14 (t, J=7.02 Hz, 2H) 7.34 (d, J=8.24 Hz, 2H) 7.49-7.70 (m, 4H) 8.04 (s, 2H) 14.59 (s, 2H) RT=2.523 minutes (condition 7, 96%); LRMS: Anal. Calcd. for C44H58N8O6 794.45; found: 795.48 (M+H)$^+$.

Section cj

Synthesis of Carbamate Replacements

Example cj-2 and cj-3

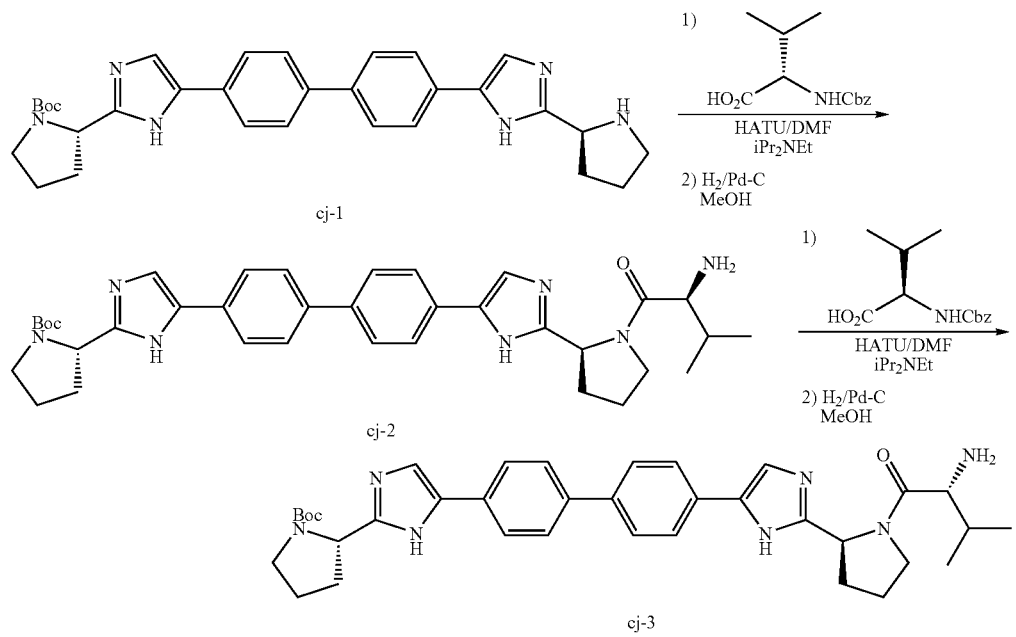

Preparation of (S)-tert-Butyl 2-(5-(4'-(2-((S)-1-((S)-2-amino-3-methylbutanoyl)pyrrolidin-2-yl)-1H-imidazol-5-yl)biphenyl-4-yl)-1H-imidazol-2-yl)pyrrolidine-1-carboxylate (cj-2)

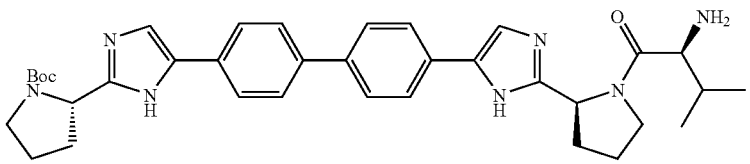

To a solution of (S)-tert-butyl 2-(5-(4'-(2-((S)-pyrrolidin-2-yl)-1H-imidazol-5-yl)biphenyl-4-yl)-1H-imidazol-2-yl)pyrrolidine-1-carboxylate (cj-1) (1.00 g, 1.91 mmol), iPr$_2$NEt (1.60 mL, 9.19 mmol) and N-Z-valine (0.62 g, 2.47 mmol) in DMF (10 mL) was added HATU (0.92 g, 2.42 mmol). The solution was allowed to stir at rt for 1 h and then it was poured into ice water (ca. 250 mL) and allowed to stand for 20 min. The mixture was filtered and the solid washed with water and then dried in vacuo overnight to afford a colorless solid (1.78 g) which was used as such in the next step. LCMS: Anal. Calcd. for C$_{44}$H$_{51}$N$_7$O$_5$: 757; found: 758 (M+H)$^+$.

A mixture of this material (1.70 g) and 10% Pd—C (0.37 g) in MeOH (100 mL) was hydrogenated (balloon pressure) for 12 h. The mixture was then filtered and the solvent removed in vacuo. The residue was purified by silica gel chromatography (Biotage system/0-10% MeOH—CH$_2$Cl$_2$) to afford the title compound as a light yellow foam (0.90 g, 76%).
$^1$HNMR (400 MHz, DMSO-d$_6$) δ 12.18 (s, 0.35H), 11.73 (s, 0.65H), 11.89 (s, 0.65H), 11.82 (s, 0.35H), 7.77-7.81 (m, 3H), 7.57-7.71 (m, 5H), 7.50-7.52 (m, 2H), 5.17 (dd, J=3.6, 6.5 Hz, 0.3H), 5.08 (dd, J=3.6, 6.5 Hz, 0.7H), 4.84 (m, 0.3H), 4.76 (m, 0.7H), 3.67-3.69 (m, 1H), 3.50-3.62 (m, 1H), 3.34-3.47 (m, 2H), 2.22-2.28 (m, 2H), 2.10-2.17 (m, 2H), 1.74-2.05 (m, 6H), 1.40 (s, 4H), 1.15 (s, 5H), 0.85-0.91 (m, 4H), 0.79 (d, J=6.5 Hz, 2H).
LCMS: Anal. Calcd. for C$_{36}$H$_{45}$N$_7$O$_3$: 623; found: 624 (M+H)$^+$.

Preparation of (S)-tert-Butyl 2-(5-(4'-(2-((S)-1-((R)-2-amino-3-methylbutanoyl)pyrrolidin-2-yl)-1H-imidazol-5-yl)biphenyl-4-yl)-1H-imidazol-2-yl)pyrrolidine-1-carboxylate (cj-3)

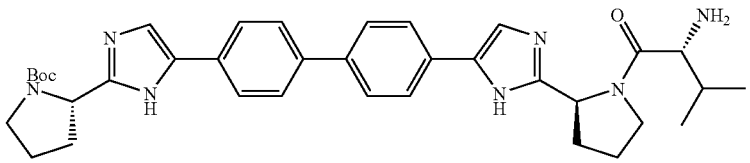

(S)-tert-Butyl 2-(5-(4'-(2-((S)-1-((R)-2-amino-3-methylbutanoyl)pyrrolidin-2-yl)-1H-imidazol-5-yl)biphenyl-4-yl)-1H-imidazol-2-yl)pyrrolidine-1-carboxylate (cj-3) was prepared using the same method used to prepare cj-2 to give a colorless foam (1.15 g, 76%). $^1$HNMR (400 MHz, DMSO-d$_6$) δ 12.17 (s, 0.35H), 12.04 (s, 0.65H), 11.89 (s, 0.65H), 11.81 (s, 0.35H), 7.78-7.83 (m, 3H), 7.60-7.71 (m, 5H), 7.43-7.52 (m, 2H), 5.22-5.25 (m, 0.4H), 5.05-5.07 (m, 0.6H), 4.83-4.86 (m, 0.5H), 4.72-4.78 (m, 0.5H), 3.78-3.84 (m, 1H), 3.49-3.64 (m, 2H), 3.35-3.43 (m, 2H), 2.19-2.32 (m, 1H), 2.04-2.17 (m, 3H), 1.95-2.04 (m, 2H), 1.76-1.90 (m, 3H), 1.40 (s, 4H), 1.15 (s, 5H), 0.85-0.91 (m, 4H), 0.67 (d, J=6.5 Hz, 1H), 0.35 (d, J=6.5 Hz, 1H). LCMS: Anal. Calcd. for C$_{36}$H$_{45}$N$_7$O$_3$: 623; found: 624 (M+H)$^+$.

Example cj-4 and cj-5

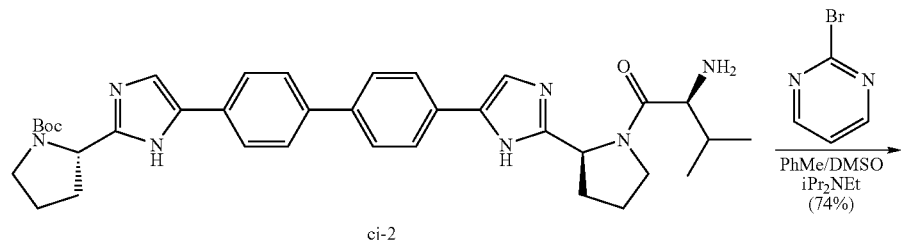

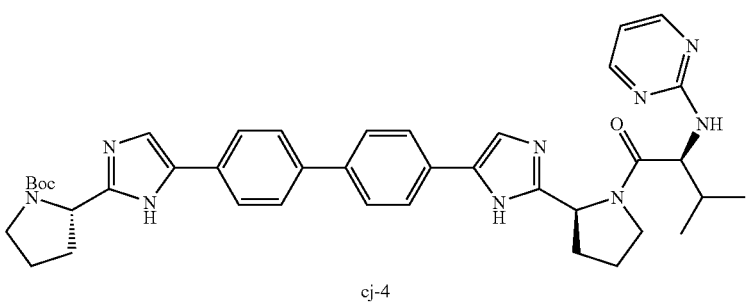

-continued

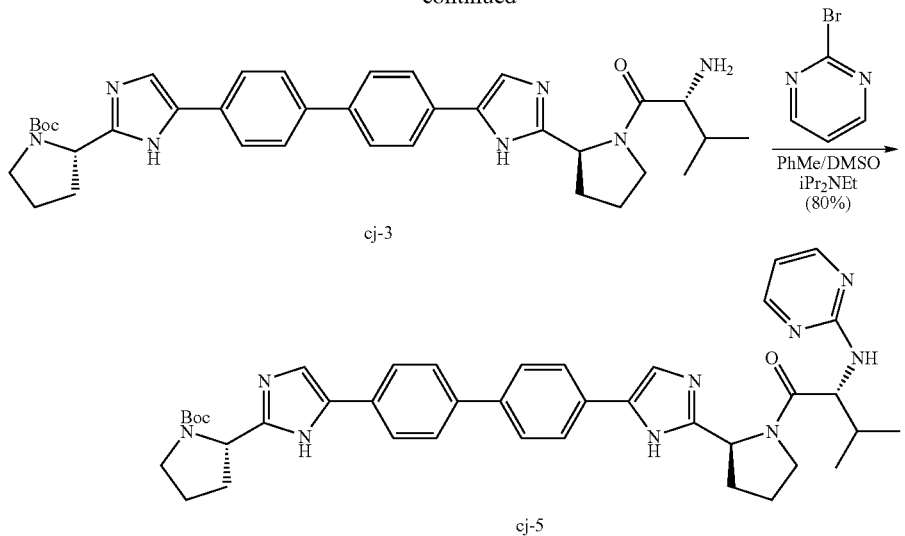

cj-3 cj-5

Preparation of (S)-tert-Butyl 2-(5-(4'-(2-((S)-1-((S)-3-methyl-2-(pyrimidin-2-ylamino)butanoyl)pyrrolidin-2-yl)-1H-imidazol-5-yl)biphenyl-4-yl)-1H-imidazol-2-yl)pyrrolidine-1-carboxylate (cj-4)

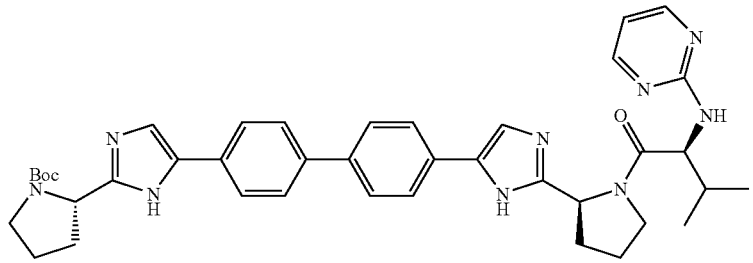

cj-4

A mixture of (S)-tert-butyl 2-(5-(4'-(2-((S)-1-((s)-2-amino-3-methylbutanoyl)pyrrolidin-2-yl)-1H-imidazol-5-yl)biphenyl-4-yl)-1H-imidazol-2-yl)pyrrolidine-1-carboxylate (cj-2) (0.45 g, 0.72 mmol), 2-bromopyrimidine (0.37 g, 2.34 mmol) and iPr₂NEt (0.20 mL, 1.18 mmol) in toluene-DMSO (4:1, 5 mL) was heated at 90° C. overnight. The volatiles were removed in vacuo and the residue was purified by preparative HPLC (YMC Pack C-18, 30×100 mm/MeCN—H₂O-TFA). The title compound (0.56 g, 74%), as its TFA salt, was obtained as a yellow-orange glass.

¹HNMR (400 MHz, DMSO-d₆) δ 14.56 (br s, 2H), 8.28 (d, J=5.0 Hz, 1H), 8.12-8.20 (m, 2H), 7.94-7.97 (m, 3H), 7.83-7.91 (m, 5H), 7.06 (d, J=8.1 Hz, 1H), 6.62 (app t, J=5.0 Hz, 1H), 4.99-5.10 (m, 2H), 4.50 (app t, J=7.7 Hz, 1H), 4.07-4.12 (m, 2H), 3.83-3.87 (m, 1H), 3.56-3.62 (m, 1H), 3.40-3.47 (m, 2H), 2.36-2.41 (m, 1H), 1.94-2.22 (m, 6H), 1.40 (s, 4H), 1.17 (s, 5H), 0.88 (app t, J=6.5 Hz, 6H).

LCMS: Anal. Calcd. for $C_{40}H_{47}N_9O_3$: 701; found: 702 $(M+H)^+$.

Preparation of (S)-tert-Butyl-2-(5-(4'-(2-((S)-1-((R)-3-methyl-2-(pyrimidin-2-ylamino)butanoyl)pyrrolidin-2-yl)-1H-imidazol-5-yl)biphenyl-4-yl)-1H-imidazol-2-yl)pyrrolidine-1-carboxylate (cj-5)

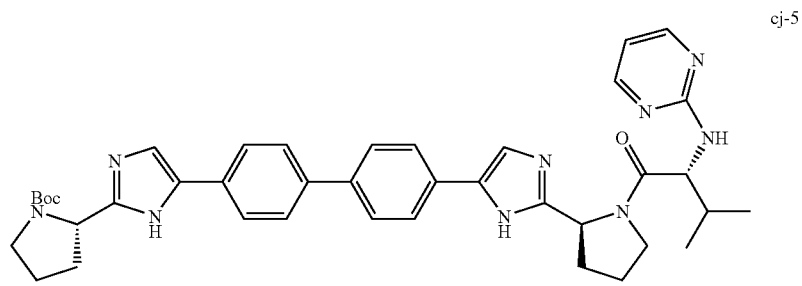

cj-5

The TFA salt of the title compound was prepared following the same method used to prepare cj-4 to give a light yellow solid (0.375 g, 59%).
$^1$HNMR (400 MHz, DMSO-$d_6$) δ 14.67 (br s, 2H), 8.30 (d, J=4.3 Hz, 1H), 8.04-8.19 (m, 2H), 7.84-7.96 (m, 8H), 6.88 (d, J=8.6 Hz, 1H), 6.61 (app t, J=4.5 Hz, 1H), 5.17 (dd, J=4.4, 8.0 Hz, 1H), 5.00-5.07 (m, 1H), 4.67 (dd, J=7.3, 8.1 Hz, 1H), 3.91-3.96 (m, 1H), 3.70-3.75 (m, 1H), 3.56-3.62 (m, 1H), 3.42-3.45 (m, 1H), 2.39-2.43 (m, 2H), 2.04-2.16 (m, 5H), 1.94-1.97 (m, 2H), 1.40 (s, 4H), 1.17 (s, 5H), 0.95 (d, J=6.6 Hz, 2.5H), 0.91 (d, J=6.6 Hz, 2.5H), 0.86 (d, J=6.6 Hz, 0.5H), 0.81 (d, J=6.6 Hz, 0.5H).
LCMS: Anal. Calcd. for $C_{40}H_{47}N_9O_3$: 701; found: 702 (M+H)[+].
Example cj-6 and cj-7
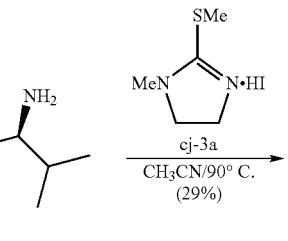
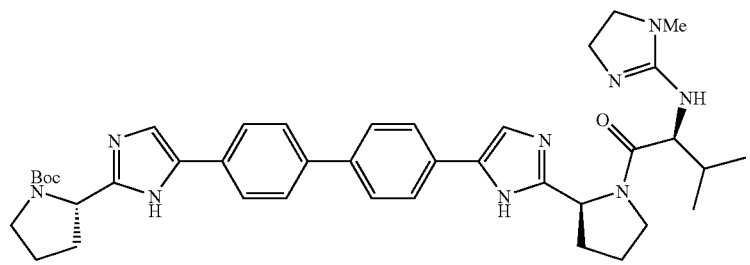
cj-2
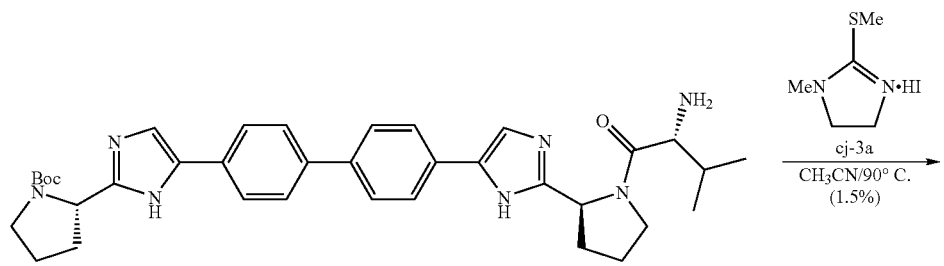
cj-6
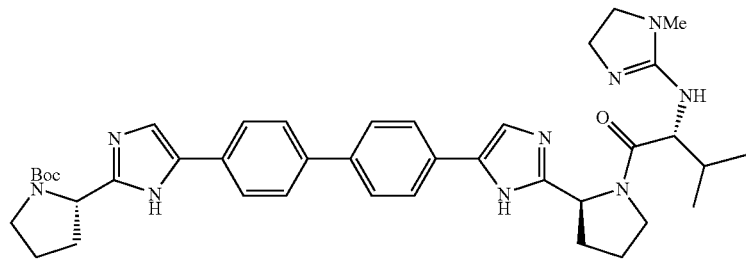
cj-3
cj-7

Preparation of 1-Methyl-2-(methylthio)-4,5-dihydro-1H-imidazole hydroiodide

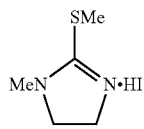

cj-3a

The title compound was prepared according to: Kister, J.; Assef, G.; Dou, H. J.-M.; Metzger, J. *Tetrahedron* 1976, 32, 1395. Thus, a solution of N-methylethylenediamine (10.8 g, 146 mmol) in EtOH-H₂O (1:1, 90 mL) was preheated to 60° C. and CS₂ (9.0 mL, 150 mmol) was added dropwise. The resulting mixture was heated at 60° C. for 3 h and then conc. HCl (4.7 mL) was slowly added. The temperature was raised to 90° C. and stirring was continued for 6 h. After the cooled mixture had been stored at −20° C., it was filtered and the resulting solid dried in vacuo to afford 1-methylimidazolidine-2-thione (8.43 g, 50%) as a beige solid.

¹HNMR (400 MHz, CDCl₃) δ 5.15 (s, br, 1H), 3.67-3.70 (m, 2H), 3.53-3.58 (m, 2H), 3.11 (s, 3H).

To a suspension of 1-methylimidazolidine-2-thione (5.17 g, 44.5 mmol) in acetone (50 mL) was added MeI (2.9 mL, 46.6 mmol). The solution was allowed to stir at room temperature for 4 h and the resulting solid was quickly filtered and then dried in vacuo to give 1-methyl-2-(methylthio)-4,5-dihydro-1H-imidazole hydroiodide (8.79 g, 77%) as beige solid.

¹HNMR (400 MHz, CDCl₃) δ 9.83 (s, br, 1H), 3.99-4.12 (m, 4H), 3.10 (s, 3H), 2.99 (s, 3H).

Preparation of (S)-tert-Butyl 2-(5-(4'-(2-((S)-1-((S)-3-methyl-2-(1-methyl-4-5-dihydroimidazol-2-ylamino)butanoyl)pyrrolidin-2-yl)-1H-imidazol-5-yl)biphenyl-4-yl)-1H-imidazol-2-yl)pyrrolidine-1-carboxylate (cj-6)

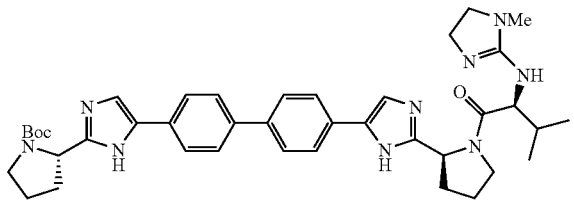

cj-6

A mixture of (s)-tert-butyl 2-(5-(4'-(2-((S)-1-((s)-2-amino-3-methylbutanoyl)pyrrolidin-2-yl)-1H-imidazol-5-yl)biphenyl-4-yl)-1H-imidazol-2-yl)-pyrrolidine-1-carboxylate (cj-2) (0.280 g, 0.448 mmol) and 1-methyl-2-(methylthio)-4,5-dihydro-1H-imidazole hydroiodide (cj-3a) (0.121 g, 0.468 mmol) in CH₃CN (5 mL) was heated at 90° C. for 12 h. Another 0.030 g of 1-methyl-2-(methylthio)-4,5-dihydro-1H-imidazole hydroiodide (cj-3a) was added and heating continued for a further 12 h. The crude reaction mixture was directly purified by prep HPLC (Luna C-18/MeCN—H₂O-TFA) to give the TFA salt of the title compound (0.089 g) as a light yellow solid which was used as such in the subsequent steps.

LCMS: Anal. Calcd. for C₄₀H₅₁N₉O₃: 705; found: 706 (M+H)⁺.

Preparation of (S)-tert-Butyl 2-(5-(4'-(2-((S)-1-((R)-3-methyl-2-(1-methyl-4-5-dihydroimidazol-2-ylamino)butanoyl)pyrrolidin-2-yl)-1H-imidazol-5-yl)biphenyl-4-yl)-1H-imidazol-2-yl)pyrrolidine-1-carboxylate (cj-7)

cj-7

The title compound was prepared from cj-3 according to the method described for the synthesis of cj-6, except that the reaction mixture was initially purified by prep HPLC (YMC-Pack 25×250 mm/MeCN—H₂O—NH₄OAc) and then repurified by prep HPLC (Luna Phenyl-hexyl//MeCN—H₂O—NH₄OAc). This gave the desired product (0.005 g) as a foam which was used as such in the subsequent steps.

LCMS: Anal. Calcd. for C₄₀H₅₁N₉O₃: 705; found: 706 (M+H)⁺.

Example cj-8 and cj-9

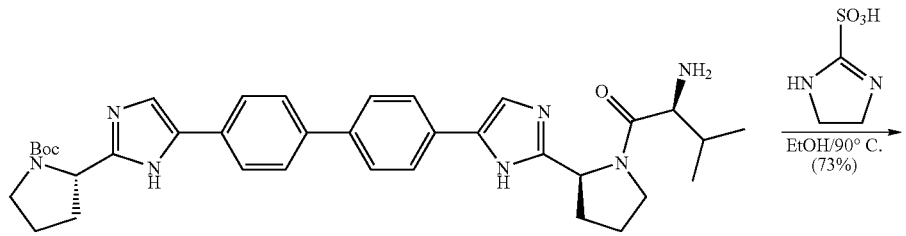

cj-2

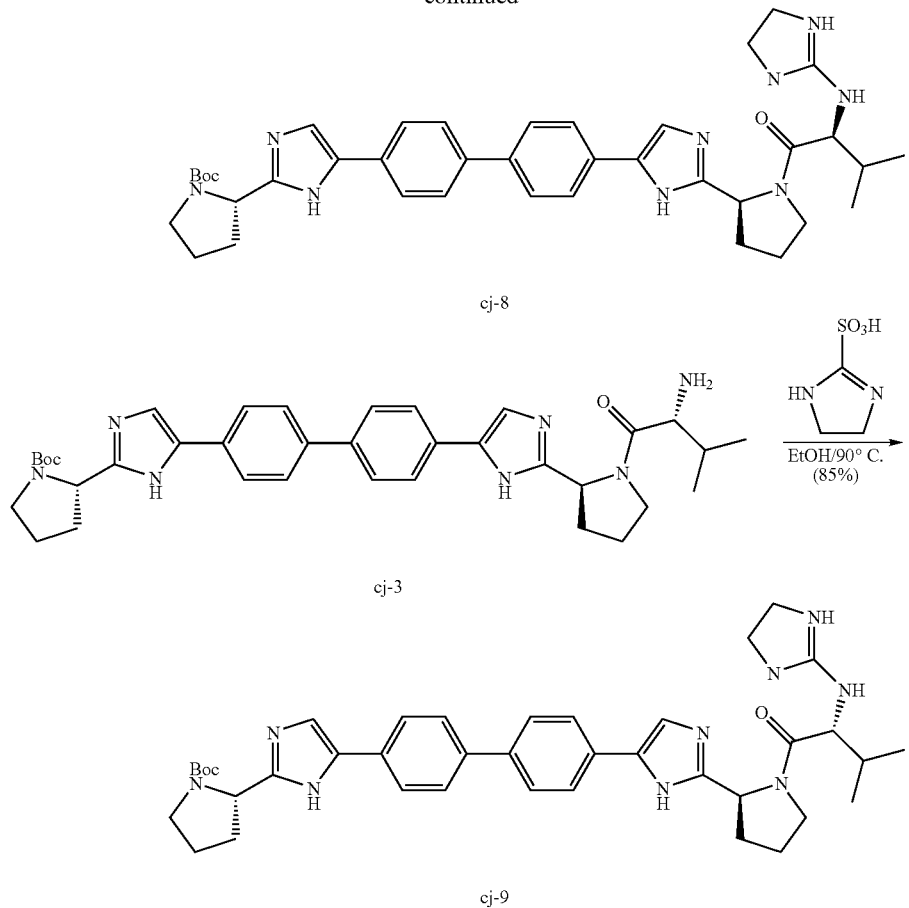

cj-8 cj-3 cj-9

Preparation of (S)-tert-Butyl 2-(5-(4'-(2-((S)-1-((S)-3-methyl-2-(3,4-dihydroimidazol-2-ylamino)butanoyl)pyrrolidin-2-yl)-1H-imidazol-5-yl)biphenyl-4-yl)-1H-imidazol-2-yl)pyrrolidine-1-carboxylate (cj-8)

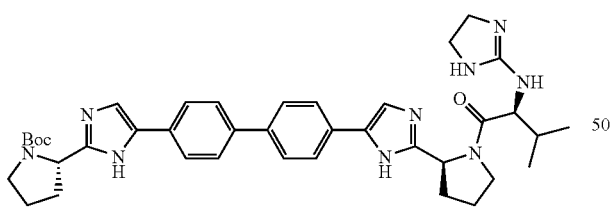

A mixture of (S)-tert-butyl 2-(5-(4'-(2-((S)-1-((S)-2-amino-3-methylbutanoyl)pyrrolidin-2-yl)-1H-imidazol-5-yl)biphenyl-4-yl)-1H-imidazol-2-yl)pyrrolidine-1-carboxylate (cj-2) (0.298 g, 0.480 mmol), 4,5-dihydro-1H-imidazole-2-sulfonic acid (AstaTech) (0.090 g, 0.60 mmol) and iPr₂NEt (0.083 mL, 0.48 mmol) in EtOH (4 mL) was heated at 100° C. for 12 h. The cooled mixture was evaporated to dryness and the residue was purified by prep HPLC (Luna 5u C18/MeCN—H₂O-TFA, ×2) to afford the TFA salt of the title compound (0.390 g, 73%) as a light yellow solid.

¹HNMR (400 MHz, DMSO-d₆) δ 14.66 (br s, 2H), 8.51 (br s, 1H), 8.20 (d, J=10.1 Hz, 2H), 8.10 (br s, 1H), 7.82-7.91 (m, 7H), 7.30 (br s, 1H), 5.12 (t, J=7.1 Hz, 1H), 4.97-5.05 (m, 2H), 4.37 (dd, J=4.3, 10.1 Hz, 2H), 3.82-3.86 (m, 2H), 3.73-3.77 (m, 2H), 3.59 (s, 4H), 3.39-3.48 (m, 2H), 2.15-2.25 (m, 2H), 1.93-2.07 (m, 5H), 1.40 (s, 4H), 1.17 (s, 5H), 0.93 (d, J=6.6 Hz, 3H), 0.69 (br s, 3H).

LCMS: Anal. Calcd. for C₃₉H₄₉N₉O₃: 691; found: 692 (M+H)⁺.

Preparation of (S)-tert-Butyl 2-(5-(4'-(2-((S)-1-((R)-3-methyl-2-(3,4-dihydroimidazol-2-ylamino)butanoyl)pyrrolidin-2-yl)-1H-imidazol-5-yl)biphenyl-4-yl)-1H-imidazol-2-yl)pyrrolidine-1-carboxylate (cj-9)

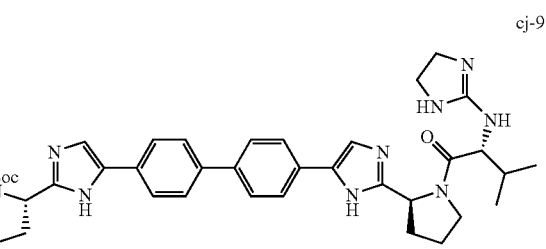

The title compound was prepared from cj-3 according to the same method used to prepare cj-8 to afford the TFA salt (0.199 g, 57%) as a yellow glass.

¹HNMR (400 MHz, DMSO-d₆) δ 14.58 (br s, 4H), 8.23 (d, J=9.6 Hz, 1H), 8.11 (s, 1H), 7.87-7.89 (m, 6H), 7.25 (br s, 1H), 5.17-5.20 (m, 1H), 4.96-5.04 (m, 1H), 4.37 (dd, J=5.5, 9.6 Hz, 1H), 3.91-3.95 (m, 2H), 3.37-3.46 (m, partially obscured by H₂O, 4H), 2.39-2.42 (m, partially obscured by solvent, 2H), 2.01-2.09 (m, 4H), 1.94-1.98 (m, 2H), 1.40 (s, 3H), 1.17 (s, 6H), 0.95 (d, J=6.5 Hz, 2.5H), 0.85 (d, J=6.5 Hz, 2.5H), 0.66 (d, J=7.0 Hz, 0.5H), 0.54 (d, J=6.5 Hz, 0.5H).

LCMS: Anal. Calcd. for $C_{39}H_{49}N_9O_3$: 691; found: 692 $(M+H)^+$.

Example cj-1

Step 1: A solution of the TFA salt of (S)-tert-butyl 2-(5-(4'-(2-((S)-1-((S)-3-methyl-2-(pyrimidin-2-ylamino)butanoyl)pyrrolidin-2-yl)-1H-imidazol-5-yl)biphenyl-4-yl)-1H-imidazol-2-yl)pyrrolidine-1-carboxylate (cj-4) (0.208 g, 0.199 mmol) in a mixture $CH_2Cl_2$ (4 mL) and TFA (3 mL) was stirred at room temperature for 1.5 h. The solvents were then

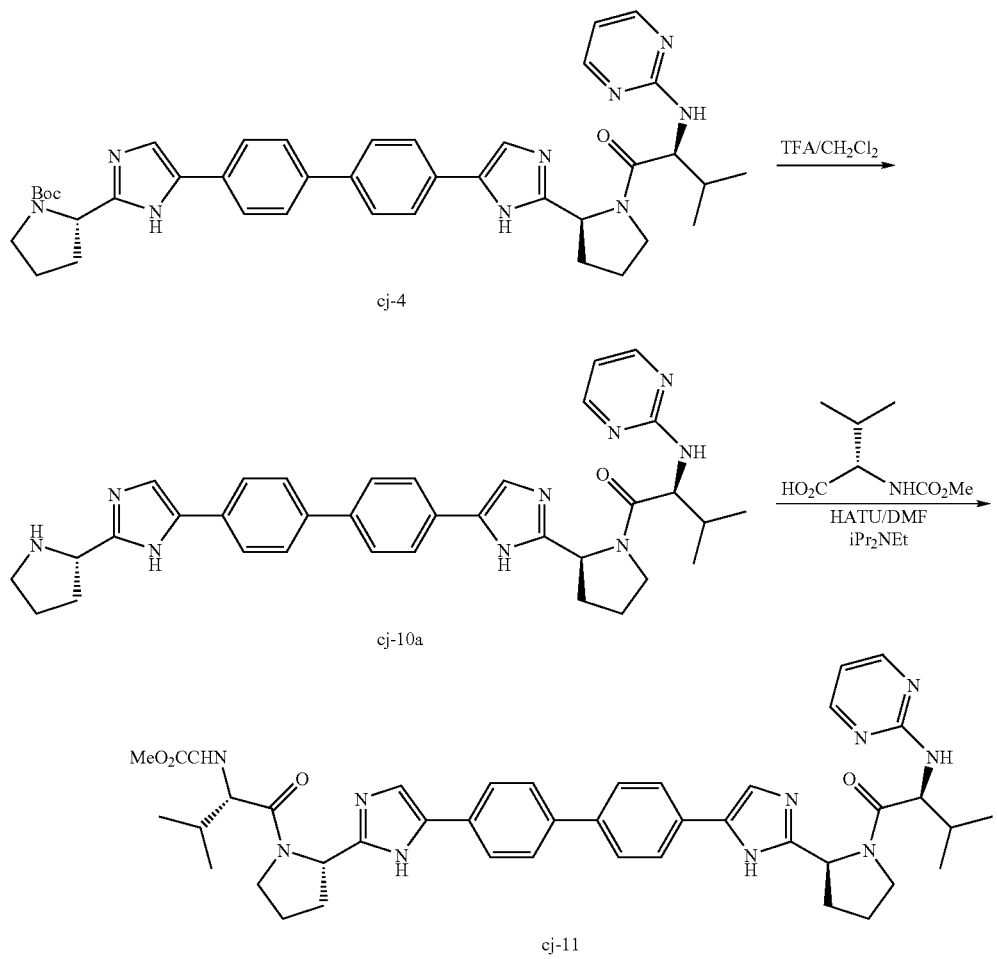

Preparation of (S)-3-Methyl-2-(pyrimidin-2-ylamino)-1-((S)-2-(5-(4'-(2-((S)-pyrrolidin-2-yl)-1H-imidazol-5-yl)biphenyl-4-yl)-1H-imidazol-2-yl)pyrrolidin-1-yl)butan-1-one (cj-10a).

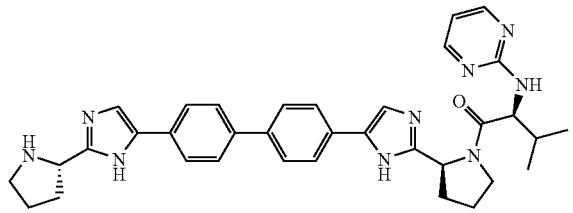

removed in vacuo and the residue was purified by prep HPLC (Luna 5u C18/MeCN—$H_2O$-TFA) to give the TFA salt of the title compound (0.391 g) as an orange gum.

$^1$HNMR (400 MHz, DMSO-$d_6$) δ 14.53 (br s, 3H), 9.52-9.57 (m, 2H), 8.98-9.04 (m, 2H), 8.28 (d, J=4.6 Hz, 2H), 8.13 (br s, 1H), 7.79-7.91 (m, 7H), 7.07 (d, J=8.1 Hz, 1H), 6.62 (app t, J=4.8 Hz, 1H), 5.07 (t, J=7.1 Hz, 1H), 4.72-4.78 (m, 2H), 4.48-4.51 (m, 1H), 4.08-4.12 (m, 2H), 3.28-3.36 (m, 2H), 2.37-2.42 (m, 2H), 1.97-2.22 (m, 6H), 0.88 (app t, J=4.5 Hz, 6H).

LCMS: Anal. Calcd. for $C_{35}H_{39}N_9O$: 601; found: 602 $(M+H)^+$.

Similarly, the following example was prepared according to the representative method above;

| Example | Structure | LCMS |
|---|---|---|
| cj-10a (from cj-3) | 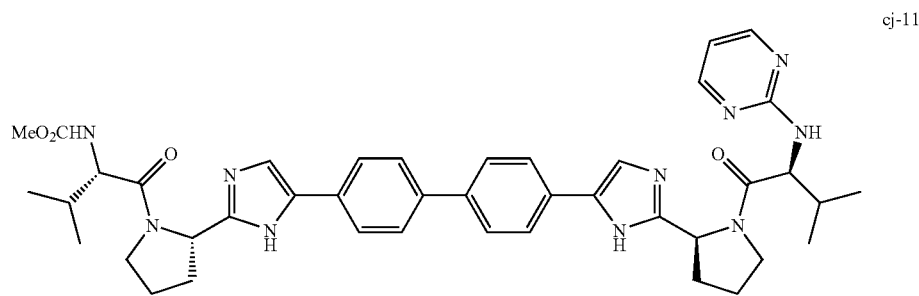 | LCMS: Anal. Calcd. for $C_{35}H_{39}N_9O$: 601; found: 602 $(M + H)^+$. |

Preparation of methyl ((1S)-2-methyl-1-(((2S)-2-(5-(4'-(2-((2S)-1-(N-2-pyrimidinyl-L-valyl)-2-pyrrolidinyl)-1H-imidazol-5-yl)-4-biphenylyl)-1H-imidazol-2-yl)-1-pyrrolidinyl)carbonyl)propyl)carbamate (cj-11)

Step 2: To a solution of the TFA salt of (S)-3-methyl-2-(pyrimidin-2-ylamino)-1-((S)-2-(5-(4'-(2-((S)-pyrrolidin-2-yl)-1H-imidazol-5-yl)biphenyl-4-yl)-1H-imidazol-2-yl)pyrrolidin-1-yl)butan-1-one (cj-10) (0.208 g, 0.197 mmol) in DMF (4 mL) was added iPr$_2$NEt (0.20 mL, 1.15 mmol), (S)-2-(methoxycarbonylamino)-3-methylbutanoic acid (0.049 g, 0.28 mmol) and HATU (0.105 g, 0.276 mmol). The solution was stirred for 1.5 h at room temperature, diluted with MeOH (2 mL) and purified directly by prep HPLC (Luna 5u C18/MeCN—H$_2$O—NH$_4$OAc). This material was repurified by flash chromatography (SiO$_2$/2-10% MeOH—CH$_2$Cl$_2$) to give a solid which was lyophilized from CH$_3$CN—H$_2$O to give the title compound (48.6 mg, 32%) as a colourless solid.

cj-11 methyl((1S)-2-methyl-1-(((2S)-2-(5-(4'-(2-((2S)-1-(N-2-pyrimidinyl-L-valyl)-2-pyrrolidinyl)-1H-imidazol-5-yl)-4-biphenylyl)-1H-imidazol-2-yl)-1-pyrrolidinyl)carbonyl)propyl)carbamate $^1$HNMR (400 MHz, DMSO-d$_6$) δ 11.78 (br s, 1H), 8.28 (d, J=4.5 Hz, 1H), 7.76-7.79 (m, 4H), 7.66-7.69 (m, 4H), 7.48-7.51 (m, 2H), 7.29 (d, J=8.6 Hz, 1H), 6.93 (d, J=8.1 Hz, 1H), 6.60 (app t, J=4.5 Hz, 1H), 5.03-5.09 (m, 2H), 4.48 (t. J=8.1 Hz, 1H), 3.99-4.08 (m, 2H), 3.78-3.85 (m, 2H) 3.53 (s, 3H), 2.12-2.21 (m, 4H), 1.87-2.05 (m, 7H), 0.83-0.97 (m, 12H).

LCMS: Anal. Calcd. for $C_{42}H_{50}N_{10}O_4$:758; found: 759 (M+H)$^+$.

Example-cj-13

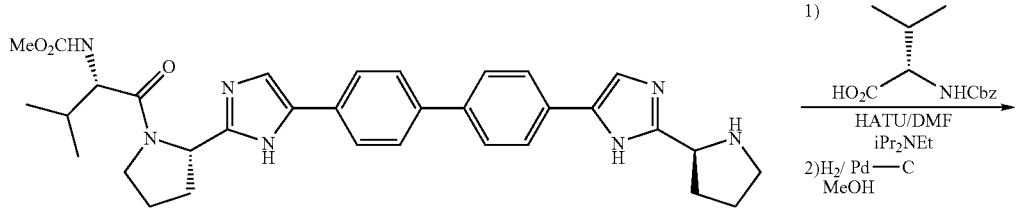

cj-12

-continued

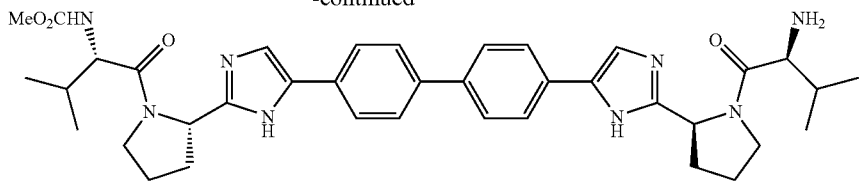

cj-13

Preparation of Methyl (S)-1-((S)-2-(5-(4'-(2-((S)-1-((S)-2-amino-3-methylbutanoyl)pyrrolidin-2-yl)-1H-imidazol-5-yl)biphenyl-4-yl)-1H-imidazol-2-yl)pyrrolidin-1-yl)-3-methyl-1-oxobutan-2-ylcarbamate (cj-13)

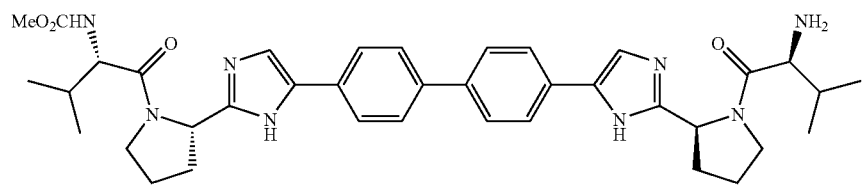

cj-13

To a solution of methyl (S)-3-methyl-1-oxo-1-((S)-2-(5-(4'-(2-((S)-pyrrolidin-2-yl)-1H-imidazol-5-yl)biphenyl-4-yl)-1H-imidazol-2-yl)pyrrolidin-1-yl)butan-2-ylcarbamate (cj-12) (1.16 g, 1.99 mmol), Z-Val-OH (0.712 g, 2.83 mmol) and iPr$_2$NEt (0.70 mL, 5.42 mmol) in DMF (40 mL) was added HATU (1.10 g, 2.89 mmol) portionwise. The mixture was allowed to stir at room temperature for 1 h and was then poured into ice-water (400 mL) and allowed to stand for 20 min. The mixture was filtered and the solid washed with cold water and allowed to air dry overnight to give the Z-protected intermediate. LCMS: Anal. Calcd. for C$_{46}$H$_{54}$N$_8$O$_6$: 814; found: 815 (M+H)$^+$.

The obtained solid was dissolved in MeOH (80 mL), 10% Pd—C (1.0 g) was added and the mixture was hydrogenated at room temperature and atmospheric pressure for 3 h. The mixture was then filtered and the filtrate concentrated in vacuo. The resulting residue was purified by flash chromatography (SiO$_2$/5-20% MeOH—CH$_2$Cl$_2$) to afford the title compound (1.05 g, 77%) as a colorless foam. $^1$HNMR (400 MHz, DMSO-d$_6$) δ 11.75 (s, 1H), 7.75-7.79 (m, 3H), 7.61-7.67 (m, 5H), 7.49 (s, 1H), 7.26-7.28 (m, 1H), 5.05-5.09 (m, 2H), 4.03-4.09 (m, 2H), 3.77-3.80 (m, 1H), 3.66-3.70 (m, 1H), 3.52 (s, 3H), 3.40-3.47 (m, 2H), 2.21-2.26 (m, 1H), 2.10-2.17 (m, 3H), 1.81-2.02 (m, 6H), 0.77-0.92 (m, 12H).

LCMS: Anal. Calcd. for C$_{38}$H$_{48}$N$_8$O$_4$: 680; found: 681 (M+H)$^+$.

Example cj-15

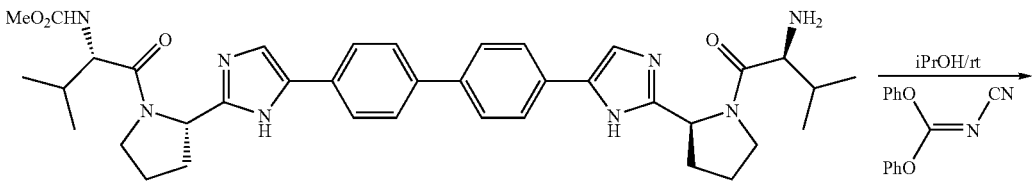

cj-13

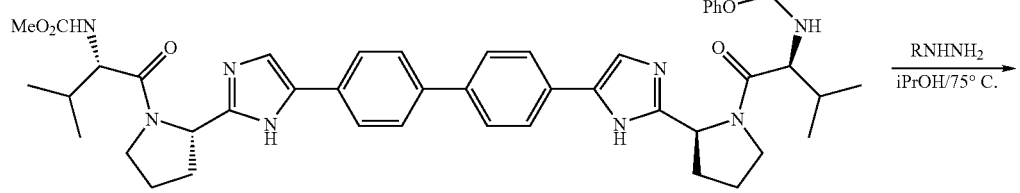

cj-14

-continued

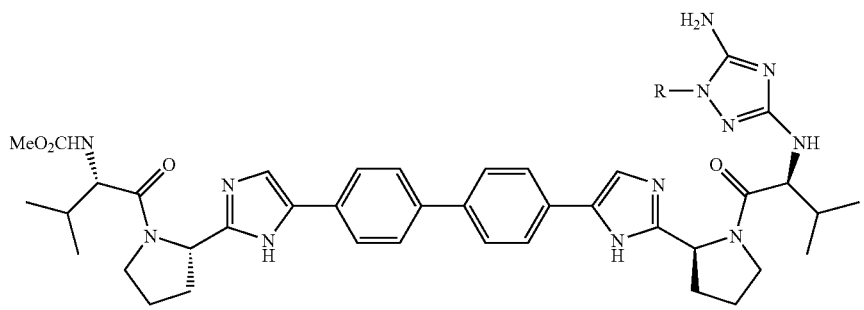

cj-15a R = H
cj-15b R = Me

Preparation of Methyl (S)-1-((S)-2-(5-(4'-(2-((S)-1-((S)-2-((Z/E)-(cyanoimino)(phenoxy)methylamino)-3-methylbutanoyl)pyrrolidin-2-yl)-1H-imidazol-5-yl)biphenyl-4-yl)-1H-imidazol-2-yl)pyrrolidin-1-yl)-3-methyl-1-oxobutan-2-ylcarbamate (cj-14)

title compound (0.187 g, 43%) as a cream-colored solid. This material was used as such in the next step without further purification.

LCMS: Anal. Calcd. for $C_{46}H_{52}N_{10}O_5$: 824; found: 825 $(M+H)^+$.

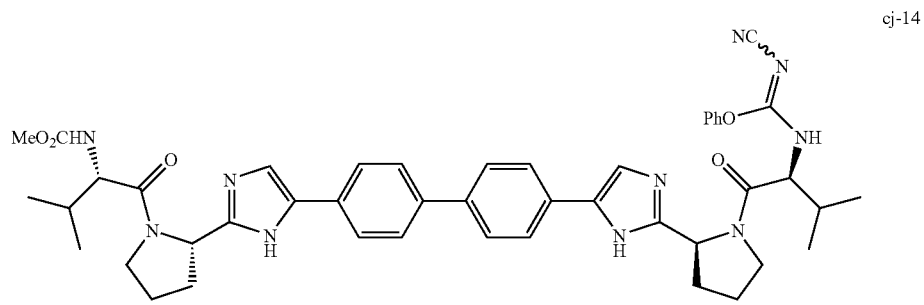

cj-14

A mixture of methyl (S)-1-((S)-2-(5-(4'-(2-((S)-1-((S)-2-amino-3-methylbutanoyl)pyrrolidin-2-yl)-1H-imidazol-5-yl)biphenyl-4-yl)-1H-imidazol-2-yl)pyrrolidin-1-yl)-3-methyl-1-oxobutan-2-ylcarbamate (cj-13) (0.329 g, 0.527 mmol) and diphenyl cyanocarbonimidate (0.128 g, 0.537 mmol) in iPrOH (10 mL) was stirred at room temperature for 12 h. The resulting solid was filtered and air-dried to give the Preparation of methyl((1S)-1-(((2S)-2-(5-(4'-(2-((2S)-1-(N-(5-amino-1-methyl-1H-1,2,4-triazol-3-yl)-L-valyl)-2-pyrrolidinyl)-1H-imidazol-5-yl)-4-biphenylyl)-1H-imidazol-2-yl)-1-pyrrolidinyl)carbonyl)-2-methylpropyl)carbamate (cj-15a, R=H)

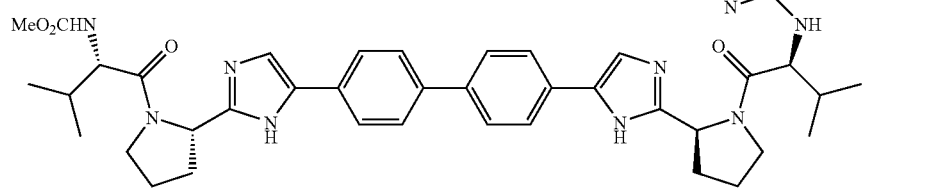

cj-15a

A solution of methyl (S)-1-((S)-2-(5-(4'-(2-((S)-1-((S)-2-((Z/E)-(cyanoimino)(phenoxy)methylamino)-3-methylbutanoyl)pyrrolidin-2-yl)-1H-imidazol-5-yl)biphenyl-4-yl)-1H-imidazol-2-yl)pyrrolidin-1-yl)-3-methyl-1-oxobutan-2-ylcarbamate (cj-14) (0.074 g, 0.090 mmol) and hydrazine hydrate (0.05 mL, 0.88 mmol) in iPrOH (2 mL) was heated at 75° C. for 7 h. The solvent was then removed in vacuo and the residue was purified by prep HPLC (Luna 5u C18/MeCN—$H_2O$—$NH_4OAc$) to give foam which was lyophilized from $CH_3CN$—$H_2O$ to give the title compound (0.032 g, 46%) as a colorless solid.

$^1$HNMR (400 MHz, DMSO-$d_6$) δ 12.17 (s, 1H), 11.75 (m, 2H), 10.66-10.84 (m, 2H), 7.76-7.79 (m, 3H), 7.62-7.74 (m, 4H), 7.49-7.51 (m, 1H), 7.24-7.29 (m, 2H), 5.28-5.32 (m, 1H), 5.05-5.08 (m, 2H), 4.04-4.09 (m, 3H), 3.87-3.94 (m, 2H), 3.72-3.81 (m, 2H), 3.53 (s, 3H), 2.09-2.17 (m, 2H), 1.90-2.02 (m, 6H), 0.81-0.99 (m, 12H).

LCMS: Anal. Calcd. for $C_{40}H_{50}N_{12}O_4$: 762; found: 763 $(M+H)^+$.

Preparation of Methyl (S)-1-((S)-2-(5-(4'-(2-((S)-1-((S)-2-(5-amino-1-methyl-1H-1,2,4-triazol-3-ylamino)-3-methylbutanoyl)pyrrolidin-2-yl)-1H-imidazol-5-yl)biphenyl-4-yl)-1H-imidazol-2-yl)pyrrolidin-1-yl)-3-methyl-1-oxobutan-2-ylcarbamate (cj-15b, R=Me)

A solution of methyl (S)-1-((S)-2-(5-(4'-(2-((S)-1-((S)-2-((Z/E)-(cyanoimino)(phenoxy)methylamino)-3-methylbutanoyl)pyrrolidin-2-yl)-1H-imidazol-5-yl)biphenyl-4-yl)-1H-imidazol-2-yl)pyrrolidin-1-yl)-3-methyl-1-oxobutan-2-ylcarbamate (cj-14) (0.105 g, 0.128 mmol) and N-methylhydrazine (0.010 mL, 0.188 mmol) in iPrOH (2 mL) was heated at 75° C. for 3 h. A second portion of N-methylhydrazine (0.010 mL, 0.188 mmol) was added and heating was continued for 7 h. The volatiles were then removed in vacuo and the residue was purified by prep HPLC (Luna 5u C18/MeCN—$H_2O$—$NH_4OAc$) to give a foam which was further purified by flash chromatography ($SiO_2$/0-20% MeOH—$CH_2Cl_2$). The resulting material was lyophilized from $CH_3CN$—$H_2O$ to give the title compound (0.029 g, 29%) as a colorless solid.

$^1$HNMR (400 MHz, DMSO-$d_6$) δ 13.79 (s, 0.4H), 12.19 (s, 1H), 11.76 (m, 1.6H), 7.77-7.85 (m, 4H), 7.62-7.71 (m, 4H), 7.49-7.51 (m, 1H), 7.24-7.29 (m, 1H), 6.31 (d, J=9.1 Hz, 0.5H), 6.09 (d, J=9.1 Hz, 1.5H), 5.87 (s, 1H), 5.34-5.36 (m, 1H), 5.04-5.08 (m, 2H), 4.89 (s, 1H), 4.75 (s, 2H), 3.53 (s, 3H), 2.10-2.17 (s, 3H), 1.94-2.02 (m, 6H), 0.81-0.98 (m, 12H).

LCMS: Anal. Calcd. for $C_{41}H_{52}N_{12}O_4$: 776; found: 777 $(M+H)^+$.

HRMS: Anal. Calcd. for $C_{41}H_{52}N_{12}O_4$: 776.4234; found: 777.4305 $(M+H)^+$.

Example cj-16 and cj-17

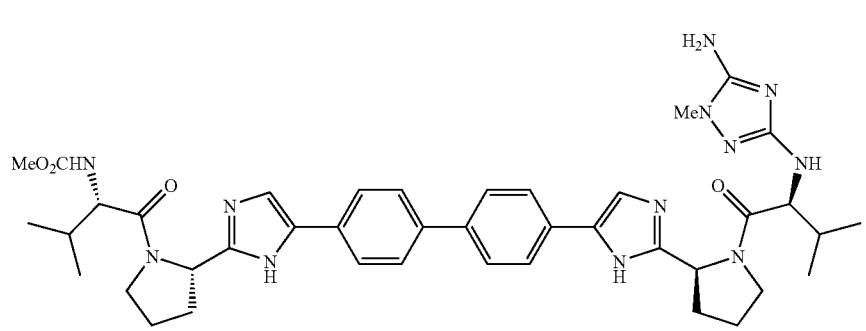

cj-15b

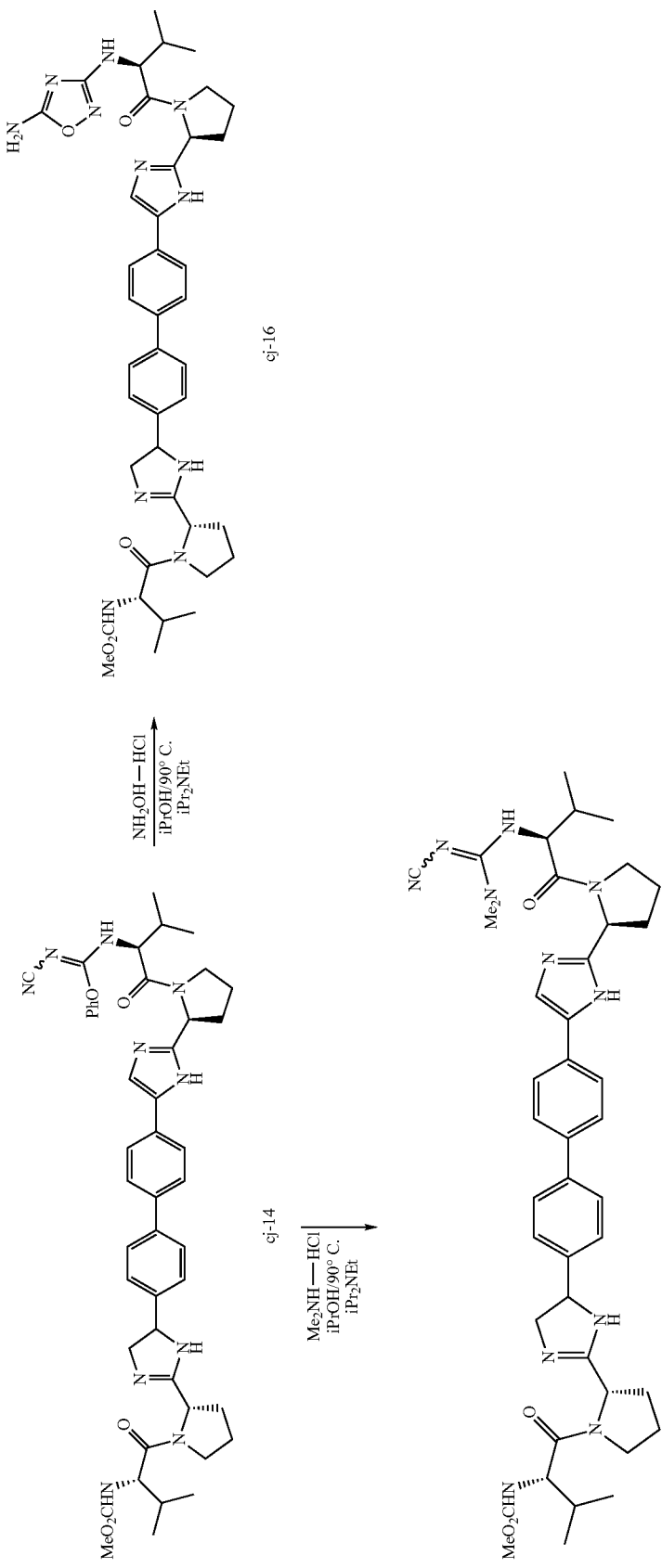

Preparation of methyl((1S)-1-(((2S)-2-(5-(4'-(2-((2S)-1-(N-(5-amino-1,2,4-oxadiazol-3-yl)-L-valyl)-2-pyrrolidinyl)-1H-imidazol-5-yl)-4-biphenylyl)-1H-imidazol-2-yl)-1-pyrrolidinyl)carbonyl)-2-methylpropyl)carbamate (cj-16)

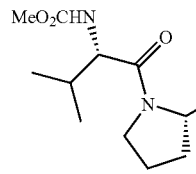

cj-16

A solution of methyl (S)-1-((S)-2-(5-(4'-(2-((S)-1-((S)-2-((Z/E)-(cyanoimino)(phenoxy)methylamino)-3-methylbutanoyl)pyrrolidin-2-yl)-1H-imidazol-5-yl)biphenyl-4-yl)-1H-imidazol-2-yl)pyrrolidin-1-yl)-3-methyl-1-oxobutan-2-ylcarbamate (cj-14) (0.120 g, 0.205 mmol) and hydroxylamine hydrochloride (0.0213 g, 0.307 mmol) in iPrOH (5 mL) was heated at 75° C. for 3 h. A second portion of hydroxylamine hydrochloride (0.0213 g, 0.307 mmol) was added and heating continued for 7 h. The volatiles were then removed in vacuo and the residue was purified by prep HPLC (Luna 5u C18/MeCN—H₂O—NH₄OAc) to give a foam which was further purified by flash chromatography (SiO₂/5% MeOH—CH₂Cl₂). The resulting colorless wax was lyophilized from CH₃CN—H₂O to give the title compound (0.0344 g, 22%) as a colorless solid.

$^1$HNMR (400 MHz, DMSO-$d_6$) δ 12.18-12.22 (m, 1H), 11.80 (s, 1H), 11.75 (s, 1 h), 8.03-8.06 (m, 1H), 7.77 (app d, J=8.1 Hz, 2H), 7.62-7.73 (m, 4H), 7.50 (dd, J=2.0, 5.5 Hz, 1H), 7.24-7.29 (m, 2H), 5.69 (s, 1H), 5.06-5.11 (m, 2H), 4.14 (t, J=8.6 Hz, 1H), 4.06 (unresolved dd, J=8.0, 8.6 Hz, 1H), 3.78-3.90 (m, 3H), 3.53 (s, 3H), 3.01 (br s, 2H), 2.10-2.19 (m, 3H), 1.90-2.04 (m, 5H), 0.81-0.96 (m, 12H).

LCMS: Anal. Calcd. for $C_{40}H_{49}N_{11}O_5$: 763; found: 764 (M+H)⁺.

Preparation of methyl ((1S)-1-(((2S)-2-(5-(4'-(2-((2S)-1-(N-(cyano(dimethyl)carbamimidoyl)-L-valyl)-2-pyrrolidinyl)-1H-imidazol-5-yl)-4-biphenylyl)-1H-imidazol-2-yl)-1-pyrrolidinyl)carbonyl)-2-methylpropyl)carbamate (cj-17)

A solution of methyl (S)-1-((S)-2-(5-(4'-(2-((S)-1-((S)-2-((Z/E)-(cyanoimino)(phenoxy)methylamino)-3-methylbutanoyl)pyrrolidin-2-yl)-1H-imidazol-5-yl)biphenyl-4-yl)-1H-imidazol-2-yl)pyrrolidin-1-yl)-3-methyl-1-oxobutan-2-ylcarbamate (cj-14) (0.115 g, 0.198 mmol) and dimethylamine hydrochloride (0.0257 g, 0.315 mmol) in iPrOH (5 mL) was heated at 90° C. for 12 h. A second portion of dimethylamine hydrochloride (0.0257 g, 0.315 mmol) was added and heating was continued for 48 h. The volatiles were then removed in vacuo and the residue was purified by prep HPLC (Luna 5u C18/MeCN—H₂O—NH₄OAc) and then repurified by flash chromatography (SiO₂/5% MeOH—CH₂Cl₂). The resulting colorless wax was lyophilized from CH₃CN—H₂O to give the title compound (0.0318 g, 21%) as a colorless solid.

$^1$HNMR (400 MHz, DMSO-$d_6$) δ 12.22 (m, 0.6H), 11.81 (s, 1H), 11.75 (s, 1H), 12.17-12.22 (m, 0.5H), 11.99-12.04 (m, 0.5H), 11.75-11.81 (m, 1H), 7.76-7.79 (m, 3H), 7.62-7.73 (m, 5H), 7.50 (t, J=2.0 Hz, 1H), 7.23-7.29 (m, 1H), 6.64 (d, J=8.1 Hz, 1H), 5.06-5.08 (m, 2H), 4.47 (t, J=8.1 Hz, 2H), 4.06 (unresolved dd, J=8.0, 8.6 Hz, 1H), 3.84-3.90 (m, 2H), 3.76-3.82 (m, 3H), 3.53 (s, 3H), 3.00 (s, 6H), 2.11-2.20 (m, 3H), 1.90-2.04 (m, 5H), 0.97 (d, J=6.5 Hz, 3H), 0.89-0.91 (m, 6H), 0.84 (d, J=6.5 Hz, 3H).

LCMS: Anal. Calcd. for $C_{42}H_{53}N_{11}O_4$: 775; found: 776 (M+H)⁺

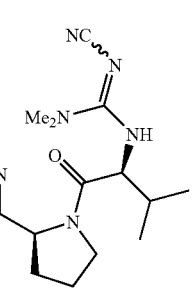

cj-17

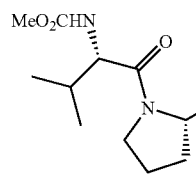

Preparation of Methyl (S)-3-methyl-1-oxo-1-((S)-2-(5-(4'-(2-((S)-pyrrolidin-2-yl)-1H-imidazol-5-yl)biphenyl-4-yl)-1H-imidazol-2-yl)pyrrolidin-1-yl)butan-2-ylcarbamate (cj-12)

Phenomenex 10u C18 3.0×5.0 mm; Wavelength: 220 nM; Flow rate: 4 ml/min; 0% B to 100% B over 2 min with a 1 min hold time cj-12

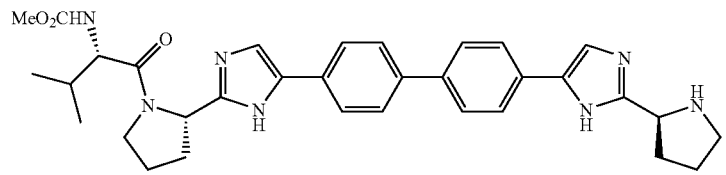

Synthesized from Intermediate-28d and Cap-51 as in Example 28e, followed by Boc removal with TFA/CH$_2$Cl$_2$ and free base formation with MCX resin.

$^1$HNMR (400 MHz, MeOH-d$_4$) δ 7.79-7.82 (m, 3H), 7.65-7.75 (m, 5H), 7.48 (s, 1H), 7.32 (s, 1H), 5.19 (dd, J=5.5, 5.7 Hz, 1H), 4.75 (t, J=7.8 Hz, 1H), 4.25 (d, J=7.3 Hz, 1H), 3.88-4.04 (m, 2H), 3.67 (s, 3H), 3.35-3.51 (m, 3H), 2.43-2.51 (m, 1H), 2.02-2.38 (m, 7H), 0.97 (d, J=6.5 Hz, 3H), 0.92 (d, J=6.9 Hz, 3H).

LCMS: Anal. Calcd. for C$_{33}$H$_{39}$N$_7$O$_3$: 581; found: 582 (M+H)$^+$.

Section OL LC Conditions:

Condition 1: Solvent A: 5% acetonitrile/95% water/10 mmol ammonium acetate; Solvent B: 95% acetonitrile/5% water/10 mmol ammonium acetate; Column: Phenomenex GEMINI 5u C18 4.6×5.0 mm; Wavelength: 220 nM; Flow rate: 4 ml/min; 0% B to 100% B over 3 min with a 1 min hold time.

Condition 2: Solvent A: 5% acetonitrile/95% water/10 mmol ammonium acetate; Solvent B: 95% acetonitrile/5% water/10 mmol ammonium acetate; Column: Phenomenex GEMINI 5u C18 4.6×5.0 mm; Wavelength: 220 nM; Flow rate: 4 ml/min; 0% B to 100% B over 2 min with a 1 min hold time Condition 3: Solvent A: 5% acetonitrile/95% water/10 mmol ammonium acetate; Solvent B: 95% acetonitrile/5% water/10 mmol ammonium acetate; Column: Phenomenex GEMINI 5u C18 4.6×5.0 mm; Wavelength: 220 nM; Flow rate: 4 ml/min; 0% B to 100% B over 4 min with a 1 min hold time Condition 4: Solvent A: 10% MeOH/90% water/0.1% TFA; Solvent B: 90% MeOH/10% water/0.1% TFA; Column: Phenomenex 10u C18 3.0×5.0 mm; Wavelength: 220 nM; Flow rate: 4 ml/min; 0% B to 100% B over 4 min with a 1 min hold time Condition 5: Solvent A: 5% acetonitrile/95% water/10 mmol ammonium acetate; Solvent B: 95% acetonitrile/5% water/10 mmol ammonium acetate; Column: Phenomenex GEMINI 5u C18 4.6×5.0 mm; Wavelength: 220 nM; Flow rate: 4 ml/min; 0% B to 100% B over 9 min with a 1 min hold time Condition 6: Solvent A: 10% MeOH/90% water/0.2% H$_3$PO$_4$; Solvent B: 90% MeOH/10% water/0.2% H$_3$PO$_4$; Column: Phenomenex 5u C-18 4.6×50 mm; Wavelength: 220 nM; Flow rate: 1.5 ml/min; 0% B to 100% B over 14 min with a 3 min hold time Condition 7: Solvent A: 10% MeOH/90% water/0.1% TFA; Solvent B: 90% MeOH/10% water/0.1% TFA; Column: Phenomenex 10u C18 3.0×5.0 mm; Wavelength: 220 nM; Flow rate: 4 ml/min; 0% B to 100% B over 3 min with a 1 min hold time Condition 8: Solvent A: 10% MeOH/90% water/0.1% TFA; Solvent B: 90% MeOH/10% water/0.1% TFA; Column:

Experimentals Caps:

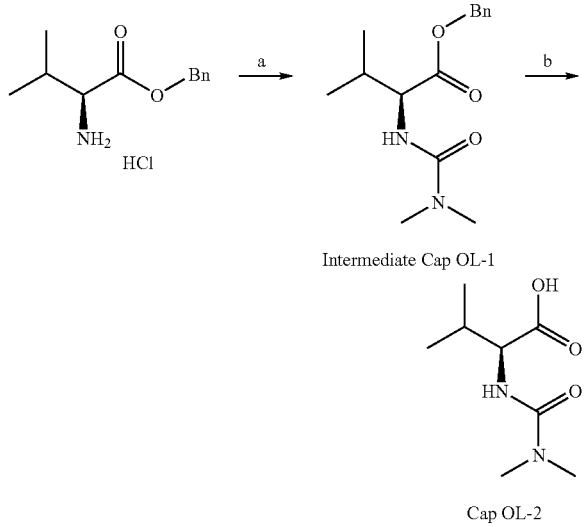

Intermediate Cap OL-1

Cap OL-2

Step a: Dimethylcarbamoyl chloride (0.92 mL, 10 mmol) was added slowly to a solution of (S)-benzyl 2-amino-3-methylbutanoate hydrochloride (2.44 g; 10 mmol) and Hunig's base (3.67 mL, 21 mmol) in THF (50 mL). The resulting white suspension was stirred at room temperature overnight (16 hours) and concentrated under reduced pressure. The residue was partitioned between ethyl acetate and water. The organic layer was washed with brine, dried (MgSO$_4$), filtered, and concentrated under reduced pressure. The resulting yellow oil was purified by flash chromatography, eluting with ethyl acetate:hexanes (1:1). Collected fractions were concentrated under vacuum providing 2.35 g (85%) of Intermediate Cap OL-1 as a clear oil. $^1$H NMR (300 MHz, DMSO-d$_6$) δ ppm 0.84 (d, J=6.95 Hz, 3H) 0.89 (d, J=6.59 Hz, 3H) 1.98-2.15 (m, 1H) 2.80 (s, 6H) 5.01-5.09 (m, J=12.44 Hz, 1H) 5.13 (d, J=12.44 Hz, 1H) 6.22 (d, J=8.05 Hz, 1H) 7.26-7.42 (m, 5H). LC (Cond. 1): RT=1.76 min; MS: Anal. Calcd. for [M+H]$^+$ C$_{16}$H$_{22}$N$_2$O$_3$: 279.17; found 279.03.

Step b: To Intermediate Cap OL-1 (2.35 g; 8.45 mmol) in 50 ml MeOH was added Pd/C (10%; 200 mg) and the resulting black suspension was flushed with N$_2$ (3×) and placed under 1 atm of H$_2$. The mixture was stirred at room temperature overnight and filtered though a microfiber filter to remove the catalyst. The resulting clear solution was then concentrated under reduced pressure to obtain 1.43 g (89%) of Cap OL-2 as a white foam, which was used without further purification. $^1$H NMR (500 MHz, DMSO-d$_6$) δ ppm 0.87 (d, J=4.27 Hz, 3H) 0.88 (d, J=3.97 Hz, 3H) 1.93-2.11 (m, 1H) 2.80 (s, 6H) 3.90 (dd, J=8.39, 6.87 Hz, 1H) 5.93 (d, J=8.54 Hz, 1H) 12.36 (s, 1H).). LC (Cond. 1): RT=0.33 min; MS: Anal. Calcd. for [M+H]$^+$ C$_8$H$_{17}$N$_2$O$_3$: 1898.12; found 189.04.

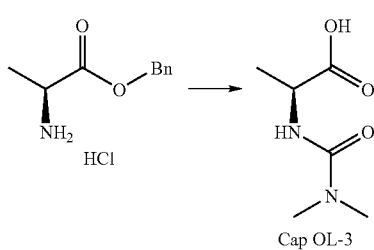

Cap OL-3

Cap OL-3 was prepared from (S)-benzyl 2-aminopropanoate hydrochloride according to the method described for Cap OL-2. $^1$H NMR (500 MHz, DMSO-d$_6$) δ ppm 1.27 (d, J=7.32 Hz, 3H) 2.80 (s, 6H) 4.06 (qt, 1H) 6.36 (d, J=7.32 Hz, 1H) 12.27 (s, 1H). LC (Cond. 1): RT=0.15 min; MS: Anal. Calcd. for [M+H]$^+$ C$_6$H$_{13}$N$_2$O$_3$: 161.09; found 161.00.

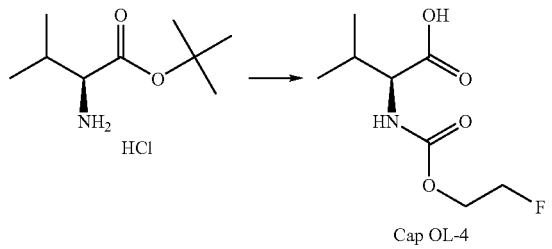

Cap OL-4

Cap OL-4 was prepared from (S)-tert-butyl 2-amino-3-methylbutanoate hydrochloride and 2-fluoroethyl chloroformate according to the method described for Cap-47. $^1$HNMR (500 MHz, DMSO-d$_6$) δ ppm 0.87 (t, J=6.71 Hz, 6H) 1.97-2.10 (m, 1H) 3.83 (dd, J=8.39, 5.95 Hz, 1H) 4.14-4.18 (m, 1H) 4.20-4.25 (m, 1H) 4.50-4.54 (m, 1H) 4.59-4.65 (m, 1H) 7.51 (d, J=8.54 Hz, 1H) 12.54 (s, 1H)

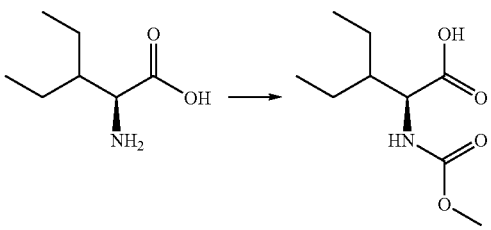

Cap OL-5

Cap OL-5 was prepared from (S)-diethyl alanine and methyl chloroformate according to the method described for Cap-51. $^1$H NMR (500 MHz, DMSO-d$_6$) δ ppm 0.72-0.89 (m, 6H) 1.15-1.38 (m, 4H) 1.54-1.66 (m, 1H) 3.46-3.63 (m, 3H) 4.09 (dd, J=8.85, 5.19 Hz, 1H) 7.24 (d, J=8.85 Hz, 1H) 12.55 (s, 1H). LC (Cond. 2): RT=0.66 min; MS: Anal. Calcd. for [M+H]$^+$ C$_9$H$_{18}$NO$_4$: 204.12; found 204.02.

| Example Number | Compound Name | Heterocycles with New Caps | Analytical Data (Cond 1: 3 min gradient, 4 min run; Cond 2: 2 min gradient, 3 min run) |
|---|---|---|---|
| D71 | tert-butyl (2S)-2-(5-(2-(4-(2-((2S)-1-((2R)-2-(diethylamino)-2-phenylacetyl)-2-pyrrolidinyl)-1H-imidazol-5-yl)phenyl)-5-pyrimidinyl)-1H-imidazol-2-yl)-1-pyrrolidine-carboxylate | 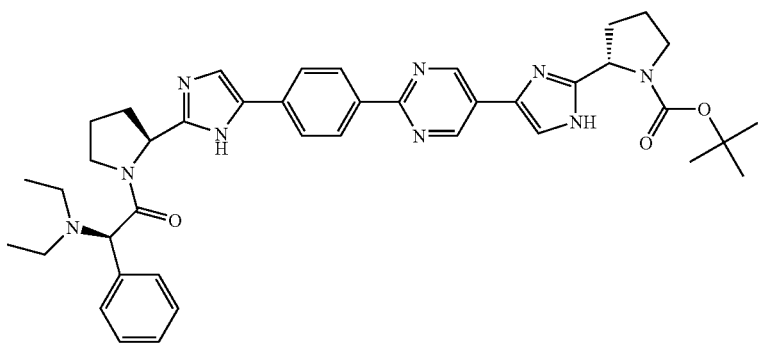<br>Prepared from 152i-1 (in lieu of 148e) and Cap-2 using experimental conditions outlined in Example 148 | $t_R$ = 1.82 min, (97.7%), (Cond 1) LRMS: Anal. Calcd. for C$_{41}$H$_{50}$N$_9$O$_3$ 716.40; found: 716.44 (M + H)$^+$. HRMS: Anal. Calcd. for C$_{41}$H$_{50}$N$_9$O$_3$ 716.4037; found: 716.4056 (M + H)$^+$. |

| | | | |
|---|---|---|---|
| D72 | (1R)-N,N-diethyl-2-oxo-1-phenyl-2-((2S)-2-(5-(4-(5-(2-((2S)-2-pyrrolidinyl)-1H-imidazol-5-yl)-2-pyrimidinyl)phenyl)-1H-imidazol-2-yl)-1-pyrrolidinyl)ethanamine | Prepared from entry 71 (in lieu of 152j-27) using experimental conditions outlined in Example 152k-1. | $t_R$ = 1.56 min, (~95.3%, has shoulder), (Cond 1) LRMS: Anal. Calcd. for $C_{36}H_{42}N_9O$ 616.35; found: 616.37 (M + H)⁺. HRMS: Anal. Calcd. for $C_{36}H_{42}N_9O$ 616.3512; found: 616.3540 (M + H)⁺. |
| D73 | methyl ((1S)-2-((2S)-2-(5-(4-(5-(2-((2S)-1-(N-(methoxycarbonyl)-L-alanyl)-2-pyrrolidinyl)-1H-imidazol-5-yl)-2-pyrimidinyl)phenyl)-1H-imidazol-2-yl)-1-pyrrolidinyl)-1-methyl-2-oxoethyl)carbamate | Prepared from 152h-1 (in lieu of 148e) and Cap-52 using experimental conditions outlined in Example 148 | $t_R$ = 1.52 min, (96.2%), (Cond 1) LRMS: Anal. Calcd. for $C_{34}H_{41}N_{10}O_6$ 685.32; found: 685.21 (M + H)⁺. HRMS: Anal. Calcd. for $C_{34}H_{41}N_{10}O_6$ 685.3211; found: 685.3196 (M + H)⁺. |
| D74 | methyl ((1S)-1-(((2S)-2-(5-(2-(4-(2-((2S)-1-((2S)-2-((methoxycarbonyl)amino)-3-methylbutanoyl)-2-pyrrolidinyl)-1H-imidazol-5-yl)phenyl)-5-pyrimidinyl)-1H-imidazol-2-yl)-1-pyrrolidinyl)carbonyl)-2-methylpropyl)carbamate | Prepared from 152h-1 (in lieu of 148e) and Cap-51 using experimental conditions outlined in Example 148 | $t_R$ = 2.09 min, (95%), (Cond 1) LRMS: Anal. Calcd. for $C_{38}H_{49}N_{10}O_6$ 741.38; found: 741.26 (M + H)⁺. HRMS: Anal. Calcd. for $C_{38}H_{49}N_{10}O_6$ 741.3837; found: 741.3824 (M + H)⁺. |
| D75 | methyl ((1S)-1-cyclopropyl-2-((2S)-2-(5-(2-(4-(2-((2S)-1-((2S)-2-cyclopropyl-2-((methoxycarbonyl)amino)acetyl)-2-pyrrolidinyl)-1H-imidazol-5-yl)phenyl)-5-pyrimidinyl)-1H-imidazol-2-yl)-1-pyrrolidinyl)-2-oxoethyl)carbamate | Prepared from 152h-1 (in lieu of 148e) and Cap-54b using experimental conditions outlined in Example 148 | $t_R$ = 1.98 min, (95%), (Cond 1) LRMS: Anal. Calcd. for $C_{38}H_{45}N_{10}O_6$ 737.35; found: 737.22 (M + H)⁺. HRMS: Anal. Calcd. for $C_{38}H_{45}N_{10}O_6$ 737.3524; found: 737.3555 (M + H)⁺. |

-continued

| | Compound Name | Structure | Analytical Data |
|---|---|---|---|
| D76 | methyl ((1S)-1-(((2S)-2-(5-(2-(4-(2-((2S)-1-((2R)-2-(diethylamino)-2-phenylacetyl)-2-pyrrolidinyl)-1H-imidazol-5-yl)phenyl)-5-pyrimidinyl)-1H-imidazol-2-yl)-1-pyrrolidinyl)carbonyl)-2-methylpropyl)carbamate | 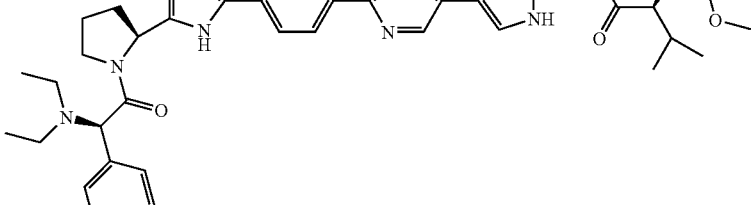<br>Prepared from entry D72 (in lieu of 148e) and Cap-51 using experimental conditions outlined in Example 148 | $t_R$ = 1.69 min, (95%), (Cond 1)<br>LRMS: Anal. Calcd. for $C_{43}H_{53}N_{10}O_4$ 773.43; found: 773.30 $(M + H)^+$.<br>HRMS: Anal. Calcd. for $C_{43}H_{53}N_{10}O_4$ 773.4251; found: 773.4280 $(M + H)^+$. |
| D77 | methyl ((1S)-2-((2S)-2-(5-(2-(4-(2-((2S)-1-((2R)-2-(diethylamino)-2-phenylacetyl)-2-pyrrolidinyl)-1H-imidazol-5-yl)phenyl)-5-pyrimidinyl)-1H-imidazol-2-yl)-1-pyrrolidinyl)-1-methyl-2-oxoethyl)carbamate | 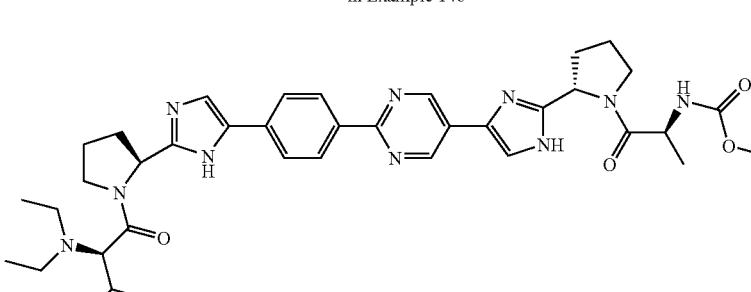<br>Prepared from entry D72 (in lieu of 148e) and Cap-52 using experimental conditions outlined in Example 148 | $t_R$ = 1.81 min, (97.5%), (Cond 1)<br>LRMS: Anal. Calcd. for $C_{41}H_{49}N_{10}O_4$ 745.39; found: 745.27 $(M + H)^+$.<br>HRMS: Anal. Calcd. for $C_{41}H_{49}N_{10}O_4$ 745.3938; found: 745.3939 $(M + H)^+$. |

Section J

| Example Number | Compound Name | Structure | Analytical Data |
|---|---|---|---|
| J.1a | | Prepared from 4-bromoacetophenone and dimethylcarbonate from Bioorg. Med. Chem. Lett (2001)11, 641 | $t_R$ = 1.7 min, (Cond 2);<br>LCMS: $C_{10}H_9BrO_3$ found: 257 $(M + H)^+$. |
| J.1b | | Prepared from 4-bromoacetophenone and diethylcarbonate from Bioorg. Med. Chem. Lett (2001)11, 641. | $t_R$ = 1.9 min, (Cond 2);<br>LCMS: $C_{11}H_{11}BrO_3$ found: 271 $(M + H)^+$. |

| J.1c | 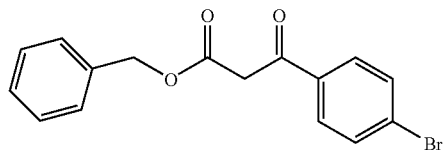 Prepared from 4-bromoactophenone and dibenzylcarbonate from Bioorg. Med. Chem. Lett (2001)11, 641. | $t_R$ = 2.1 min, (Cond 2); LCMS: $C_{16}H_{13}BrO_3$ found: 332 $(M + H)^+$. |
|---|---|---|
| J1 | 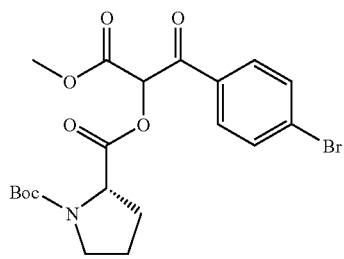 Prepared from entry J.1a (in lieu of J.1b) and proline using experimental conditions in Example J2. | $t_R$ = 2.2 min, (Cond 2); LCMS: $C_{20}H_{24}BrNO_7$ found: 470 $(M + H)^+$. |
| J2 | 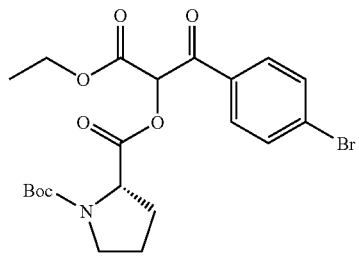 Prepared from entry J.1b and proline using experimental conditions in Example J2. | $t_R$ = 2.2 min, (Cond 2); LCMS: $C_{21}H_{26}BrNO_7$ found: 484 $(M + H)^+$. |
| J3 | 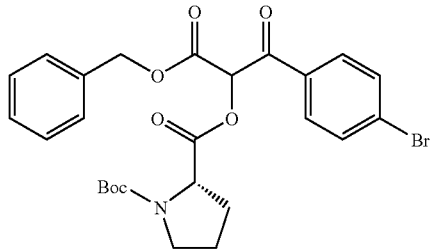 Prepared from entry J.1c (in lieu of J.1b) and proline using experimental conditions in Example J2. | $t_R$ = 2.3 min, (Cond 2); LCMS: $C_{26}H_{28}BrNO_7$ found: 546 $(M + H)^+$. |

| | | |
|---|---|---|
| J4 | 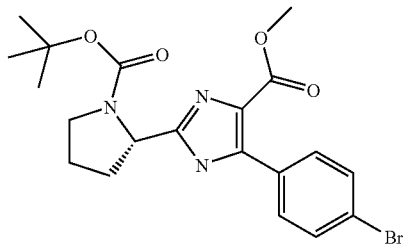<br>Prepared from entry J.1 and (in lieu of J.2) using experimental conditions in Example J2. | $t_R$ = 1.84 min, (100%)(Cond 2); LRMS: Anal. Calcd. for $C_{20}H_{24}BrN_3O_4$; 450.10; found: 450.13 and 452.13 $(M + H)^+$. |
| J5 | 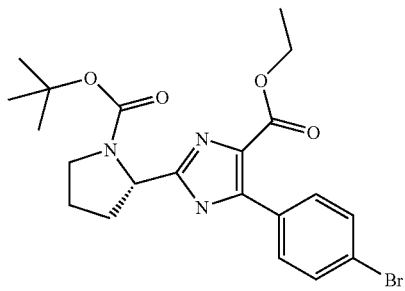<br>Prepared from entry J2 using experimental conditions in J5. | $t_R$ = 1.93 min, (99%) (Cond 2); Reported in J5. |
| J6 | 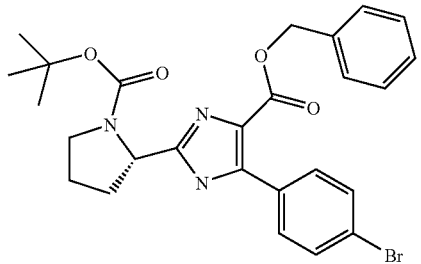<br>Prepared from entry J3 (in lieu of entry J1) using experimental conditions in J5. | $t_R$ = 2.1 min, (93%) (Cond 2); LRMS: Anal. Calcd. for $C_{26}H_{29}BrN_3O_4$ 526.13; found: 526.16 and 528.16 $(M + H)^+$. |
| J7 | 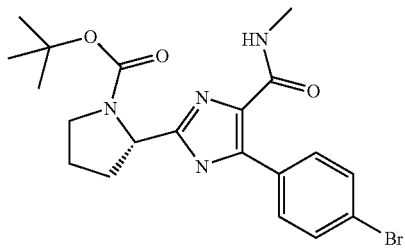<br>Prepared from entry J5 using experimental in J7. | $t_R$ = 1.7 min, (100%) (Cond 2); Reported in J7. |

-continued

J32 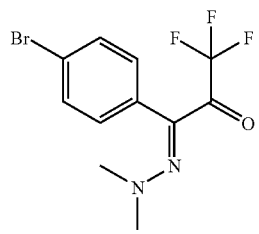

Prepared from 4-bromobenzaldehyde according to procedure described in J. Org. Chem. (1988), 53, 129.

$t_R$ = 1.96 min, (96%) (Cond 2); LRMS: Anal. Calcd. for $C_{11}H_{11}BrF_3N_2O$ 323.00; found: 323.05 and 325.05 $(M + H)^+$. $^1$H NMR (300 MHz, DMSO-$d_6$) δ 7.58(d, J = 8.4 Hz, 2 H), 7.21 (d, J = 8.4 Hz, 2 H), 3.06 (s, 6 H).

J32.a 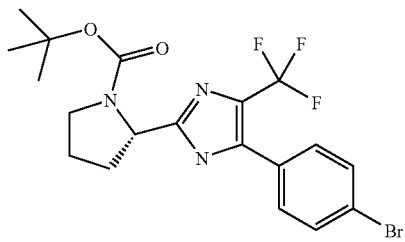

Prepared from entry J32 using experimental conditions in J32.a $t_R$ = 2.19 min, (96%) (Cond 2); Reported in J32.a J32.b 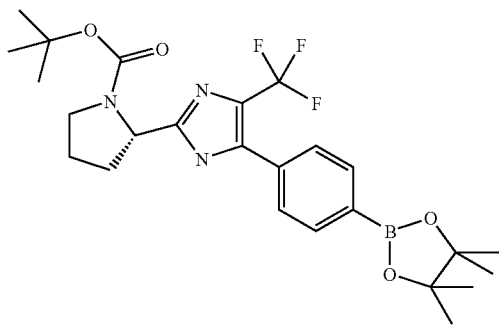

Prepared from entry J32.a (in lieu of 1b) using experimental conditions outlined in Example 1 step c.

$t_R$ = 2.3 min, (73%) (Cond 2); LCMS: $C_{25}H_{34}BF_3N_3O_4$ found: 508 $(M + H)^+$.

J33.a tert-butyl (2S)-2-(5-(4'-(2-((1S)-1-((tert-butoxycarbonyl)(methyl)amino)ethyl)-1H-imidazol-5-yl)-4-biphenylyl)-4-(trifluoromethyl)-1H-imidazol-2-yl)-1-pyrrolidine-carboxylate

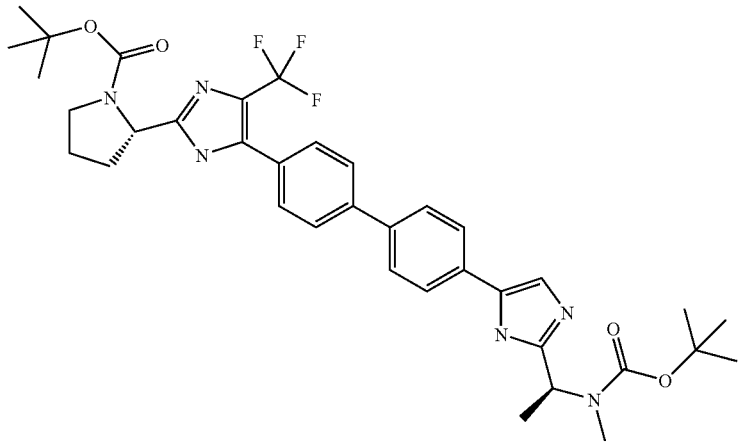

Prepared from entry J32.a (in lieu of 152e-1) and 1-8c using experimental conditions outlined in Example 152g-1.

$t_R$ = 1.97 min, (97%) (Cond 2); LRMS: Anal. Calcd. for $C_{36}H_{44}F_3N_6O_4$ 681.34; found: 681.31 $(M + H)^+$. HRMS: Anal. Calcd. for $C_{36}H_{44}F_3N_6O_4$ 681.3376; found: 681.3383 $(M + H)^+$.

-continued

| | | | |
|---|---|---|---|
| J34.a | tert-butyl (2S)-2-(5-(4-(5-(2-((2S)-1-(tert-butoxycarbonyl)-2-pyrrolidinyl)-1H-imidazol-5-yl)-2-pyrimidinyl)phenyl)-4-(trifluoromethyl)-1H-imidazol-2-yl)-1-pyrrolidine-carboxylate | 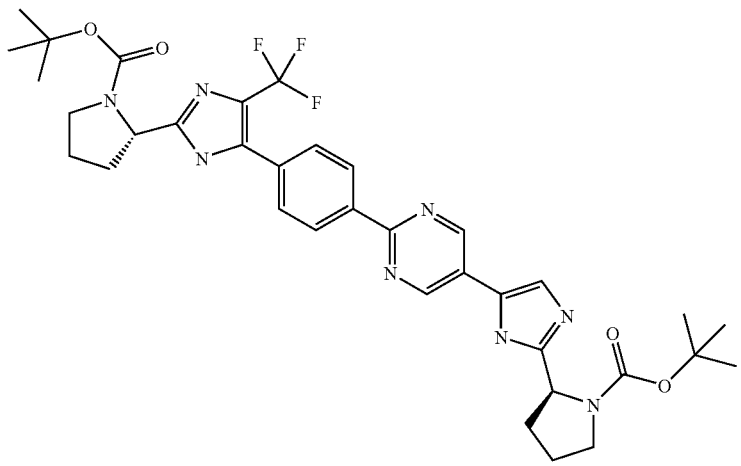 Prepared from entry J32.b (in lieu of 152e-1) and 152d-1 using experimental conditions outlined in Example 152g-1. | $t_R$ = 1.97 min, (93%) (Cond 2); LRMS: Anal. Calcd. for $C_{35}H_{42}F_3N_8O_4$ 695.33; found: 695.28 $(M + H)^+$. |
| J35.a | | 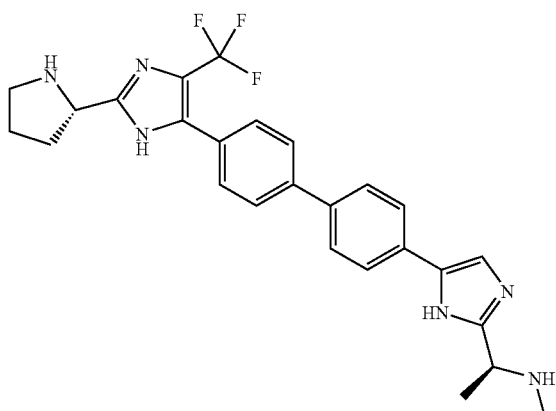 Prepared from entry J33.a (in lieu of 152j-27) using experimental conditions outlined in Example 152k-1. | LCMS: $C_{26}H_{28}F_3N_6$ found: 481 $(M + H)^+$. |
| J36.a | | 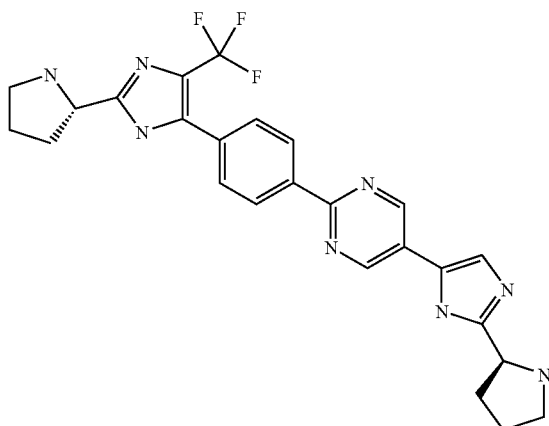 Prepared from entry J34.a (in lieu of 152j-27) using experimental conditions outlined in Example 152k-1. | $t_R$ = 1.45 min, (Cond 2); LCMS: $C_{25}H_{26}F_3N_8$ found: 495 $(M + H)^+$. |

| | | | |
|---|---|---|---|
| J42.a | methyl ((1S)-2-((2S)-2-(5-(4'-(2-((1S)-1-((N-(methoxycarbonyl)-L-alanyl)(methyl)amino)ethyl)-1H-imidazol-5-yl)-4-biphenylyl)-4-(trifluoromethyl)-1H-imidazol-2-yl)-1-pyrrolidinyl)-1-methyl-2-oxoethyl)carbamate | 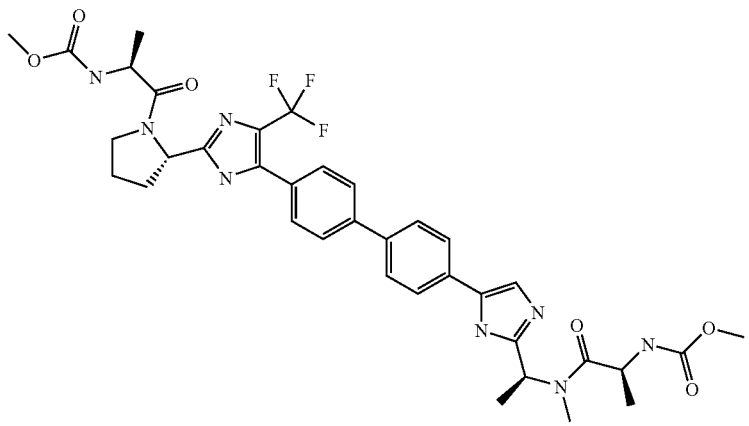<br>Prepared from entry J35.a (in lieu of 148e) and Cap-52 using experimental conditions outlined in Example 148. | $t_R$ = 1.69 min, (100%)(Cond 2); LRMS: Anal. Calcd. for $C_{36}H_{42}F_3N_8O_6$ 739.32; found: 739.31 (M + H)$^+$. HRMS: Anal. Calcd. for $C_{36}H_{42}F_3N_8O_6$ 739.3179; found: 739.3195 (M + H)$^+$. |
| J46 | methyl ((1R)-2-((2S)-2-(5-(4-(5-(2-((2S)-1-((2R)-2-((methoxycarbonyl)amino)-2-phenylacetyl)-2-pyrrolidinyl)-1H-imidazol-5-yl)-2-pyrimidinyl)phenyl)-4-(trifluoromethyl)-1H-imidazol-2-yl)-1-pyrrolidinyl)-2-oxo-1-phenylethyl)carbamate | 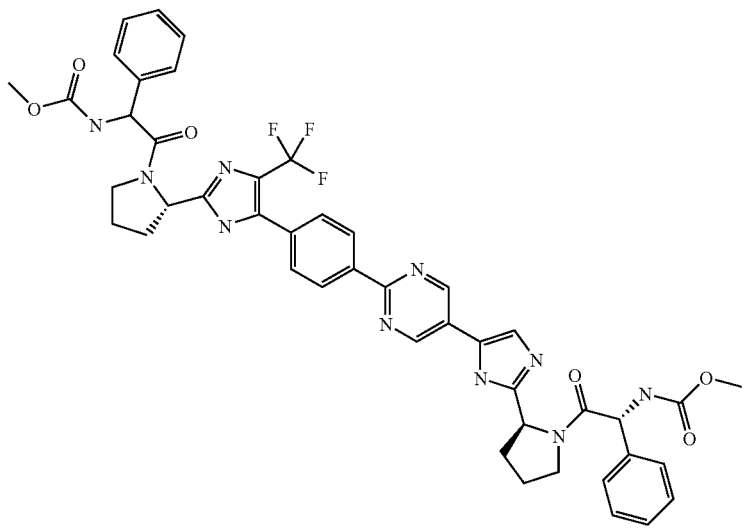<br>Prepared from entry J34.a (in lieu of 148e) and Cap-4 using experimental conditions outlined in Example 148 | $t_R$ = 1.82 min, (98%) (Cond 2); LRMS: Anal. Calcd. for $C_{45}H_{44}F_3N_{10}O_6$ 877.34; found: 877.29 (M + H)$^+$. HRMS: Anal. Calcd. for $C_{45}H_{44}F_3N_{10}O_6$ 877.3397; found: 877.3403 (M + H)$^+$. |

| | | | |
|---|---|---|---|
| J47 | (1R)-2-((2S)-2-(5-(4-(5-(2-((2S)-1-((2R)-2-(diethylamino)-2-phenylacetyl)-2-pyrrolidinyl)-1H-imidazol-5-yl)-2-pyrimidinyl)phenyl)-4-(trifluoromethyl)-1H-imidazol-2-yl)-1-pyrrolidinyl)-N,N-diethyl-2-oxo-1-phenylethanamine | 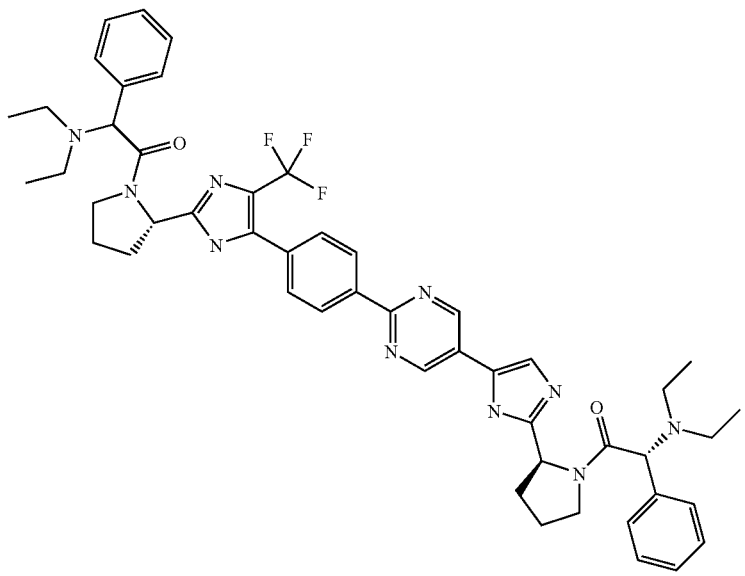<br>Prepared from entry J34.a (in lieu of 148e) and Cap-2 using experimental conditions outlined in Example 148 | $t_R$ = 1.58 min, (97%) (Cond 2);<br>LRMS: Anal. Calcd. for $C_{49}H_{56}F_3N_{10}O_2$ 873.44; found: 873.40 (M + H)$^+$.<br>HRMS: Anal. Calcd. for $C_{49}H_{56}F_3N_{10}O_2$ 873.4540; found: 873.4536 (M + H)$^+$. |
| J48 | methyl ((1S)-1-(((2S)-2-(5-(2-(4-(2-((2S)-1-((2S)-2-((methoxycarbonyl)amino)-3-methylbutanoyl)-2-pyrrolidinyl)-4-(trifluoromethyl)-1H-imidazol-5-yl)phenyl)-5-pyrimidinyl)-1H-imidazol-2-yl)-1-pyrrolidinyl)carbonyl)-2-methylpropyl)carbamate | 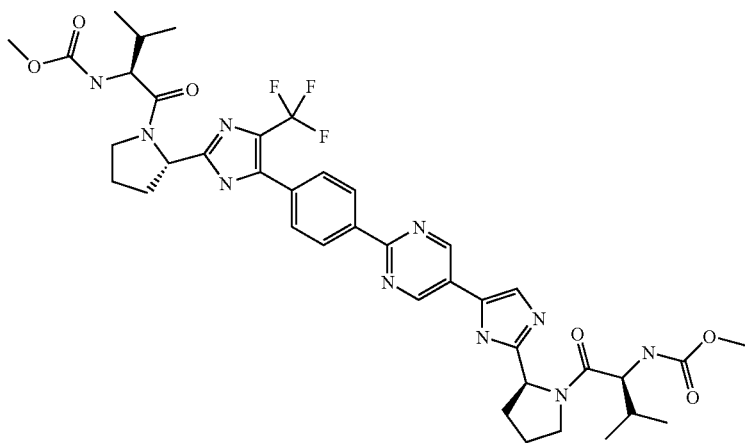<br>Prepared from entry J34.a (in lieu of 148e) and Cap-51 using experimental conditions outlined in Example 148 | $t_R$ = 1.85 min, (99%) (Cond 2);<br>LRMS: Anal. Calcd. for $C_{39}H_{48}F_3N_{10}O_6$ 809.37; found: 809.37 (M + H)$^+$.<br>HRMS: Anal. Calcd. for $C_{39}H_{48}F_3N_{10}O_6$ 809.3710; found: 809.3683 (M + H)$^+$. |

| | | | |
|---|---|---|---|
| J49 | methyl ((1S)-1-cyclopropyl-2-((2S)-2-(5-(4-(5-(2-((2S)-1-((2S)-2-cyclopropyl-2-((methoxycarbonyl)amino)acetyl)-2-pyrrolidinyl)-1H-imidazol-5-yl)-2-pyrimidinyl)phenyl)-4-(trifluoromethyl)-1H-imidazol-2-yl)-1-pyrrolidinyl)-2-oxoethyl)carbamate | 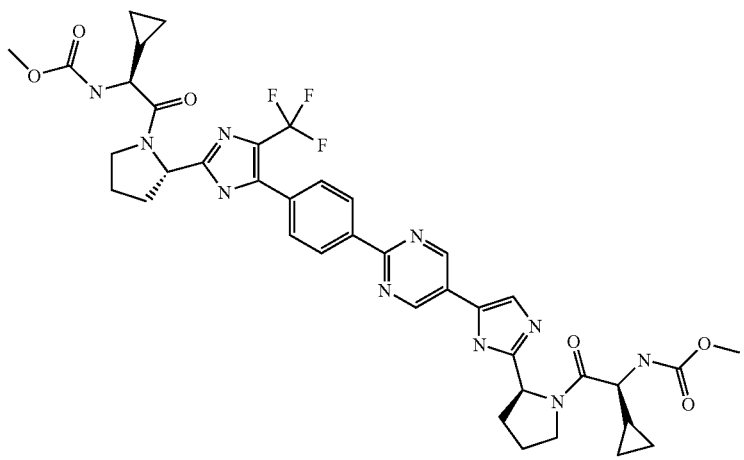<br>Prepared from entry J34.a (in lieu of 148e) and Cap-54b using experimental conditions outlined in Example 148 | $t_R$ = 1.75 min, (100%)(Cond 2); LRMS: Anal. Calcd. for $C_{39}H_{44}F_3N_{10}O_6$ 805.34; found: 805.34 (M + H)$^+$. HRMS: Anal. Calcd. for $C_{39}H_{44}F_3N_{10}O_6$ 805.3397; found: 805.3384 (M + H)$^+$. |
| J50 | methyl ((1S)-2-((2S)-2-(5-(4-(5-(2-((2S)-1-(N-(methoxycarbonyl)-L-alanyl)-2-pyrrolidinyl)-1H-imidazol-5-yl)-2-pyrimidinyl)phenyl)-4-(trifluoromethyl)-1H-imidazol-2-yl)-1-pyrrolidinyl)-1-methyl-2-oxoethyl)carbamate | 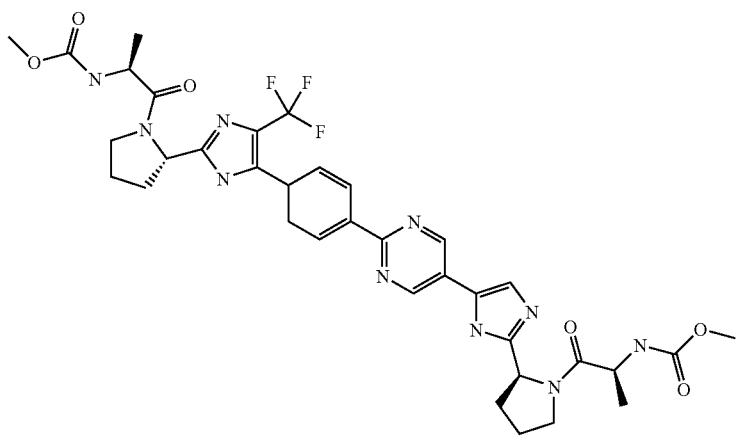<br>Prepared from entry J34.a (in lieu of 148e) and Cap-52 using experimental conditions outlined in Example 148 | $t_R$ = 1.61 min, (94%) (Cond 2); LRMS: Anal. Calcd. for $C_{35}H_{40}F_3N_{10}O_6$ 753.31; found: 753.31 (M + H)$^+$. HRMS: Anal. Calcd. for $C_{35}H_{40}F_3N_{10}O_6$ 753.3084; found: 753.3099 (M + H)$^+$. |

-continued

| | | | |
|---|---|---|---|
| J51 | (2R)-1-((2S)-2-(5-(4-(5-(2-((2S)-1-((2R)-2-(diethylamino)propanoyl)-2-pyrrolidinyl)-1H-imidazol-5-yl)-2-pyrimidinyl)phenyl)-4-(trifluoromethyl)-1H-imidazol-2-yl)-1-pyrrolidinyl)-N,N-diethyl-1-oxo-2-propanamine | 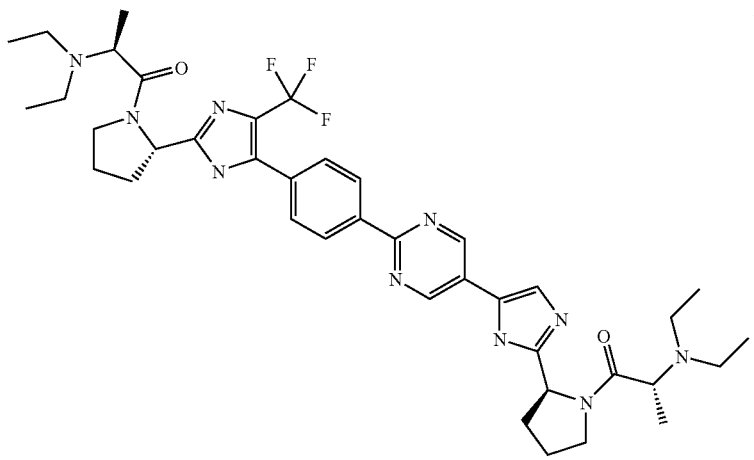 Prepared from entry J34.a (in lieu of 148e) and Cap-70b using experimental conditions outlined in Example 148 | $t_R$ = 1.41 min, (92%) (Cond 2); LRMS: Anal. Calcd. for $C_{39}H_{52}F_3N_{10}O_2$ 749.42; found: 749.37 (M + H)$^+$. HRMS: Anal. Calcd. for $C_{39}H_{52}F_3N_{10}O_2$ 749.4227; found: 749.4223 (M + H)$^+$. |

Cond 1: LCMS conditions: Phenomenex-Luna 4.6×50 mm S10, 0 to 100% B over 3 min, 4 min stop time, 4 mL/min, 220 nm, A: 10% MeOH-90% H2O-0.1% TFA; B: 90% MeOH-10% H2O-0.1% TFA Cond 2: LCMS conditions: Phenomenex-Luna 4.6×50 mm S10, 0 to 100% B over 2 min, 3 min stop time, 4 mL/min, 220 nm, A: 10% MeOH-90% H2O-0.1% TFA; B: 90% MeOH-10% H2O-0.1% TFA Example J2

(2S)-2-(1-(4-bromophenyl)-3-ethoxy-1,3-dioxopropan-2-yl) 1-tert-butyl pyrrolidine-1,2-dicarboxylate

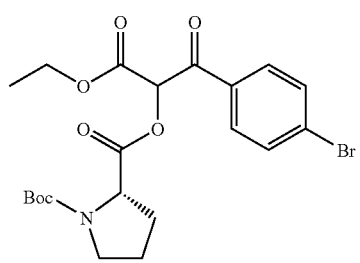

The ethyl 3-(4-bromophenyl)-3-oxopropanoate (15 g, 55 mmol) was dissolved in CH$_2$Cl$_2$ (600 mL) and freshly recrystallized NBS (9.8 g, 55 mmol) was added and the solution stirred 18 hr. The reaction mixture was washed with NaHCO$_3$ solution, brine, and dried (MgSO$_4$), filtered, and concentrated to give a residue which was not purified. Ethyl 2-bromo-3-(4-bromophenyl)-3-oxopropanoate (16.5 g, 48 mmol) and N-Boc-L-proline (10 g, 48 mmol) were taken up in acetonitrile (450 mL) and Hunig's base (16 mL, 95 mmol) was added and the solution stirred 18 hr. The solvent was removed by rotary evaporation and the residue taken up in ethyl acetate, washed with 0.1 N HCl, and brine. $^1$H NMR (300 MHz, DMSO-d$_6$) δ 7.95 (d, J=8.4 Hz, 2H), 7.79 (d, J=8.4 Hz, 2H), 6.68-6.65 (m, 1H), 4.39-4.30 (m, 1H), 4.21-4.12 (m, 2H), 2.27-2.21 (m, 1H), 2.0-1.95 (m, 1H), 1.90-1.76 (m, 2H), 1.39 (s, 2H), 1.31 (s, 9H), 1.11 (t, J=7.3 Hz, 3H).

LRMS: Anal. Calcd. for C$_{21}$H$_{26}$BrNO$_7$ 484.09; found: 410.08 (M+H)$^+$.

Example J5

(S)-ethyl 5-(4-bromophenyl)-2-(1-(tert-butoxycarbonyl)pyrrolidin-2-yl)-1H-imidazole-4-carboxylate

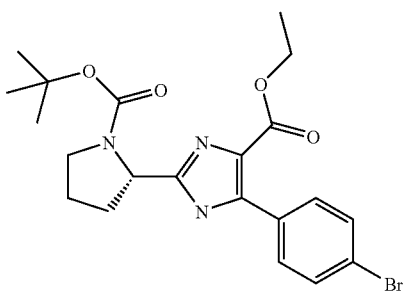

A 1 L pressure bottle was charged with (2S)-2-(1-(4-bromophenyl)-3-ethoxy-1,3-dioxopropan-2-yl) 1-tert-butyl pyrrolidine-1,2-dicarboxylate J2 (7 g, 35 mmol) and 11 g of NH$_4$OAc in 125 mL of Xylene, and the reaction was heated at 140° C. for 3.5 hr. After being cooled, the solution was partition between ethyl acetate and water. The organic layer was concentrated and the resultant residue applied to a Biotage 40 m silica gel cartridge and eluted by 20-100% gradient, ethyl acetate/Hex to give 3 g (45%). $^1$H NMR (300 MHz, CDCl$_3$) δ 12.75 (br. s, 7.82), (br. s, 2H), 7.50 (d, J=8.4 Hz, 2H), 4.96-4.92 (m, 1H), 4.23 (q, J=6.6 Hz, 2H), 3.68-3.50 (m, 1H), 3.40-3.32 (m, 1H), 2.19-2.15 (m, 1H), 1.99-1.89 (m, 3H), 1.48/1.13 (s, 9H), 1.23 (t, J=7.3 Hz, 3H). LRMS: Anal. Calcd. for C$_{21}$H$_{26}$BrN$_3$O$_4$ 464.12; found: 464.15 and 466.15 (M+H)$^+$.

Example J7

(S)-tert-butyl 2-(5-(4-bromophenyl)-4-(methylcarbamoyl)-1H-imidazol-2-yl)pyrrolidine-1-carboxylate

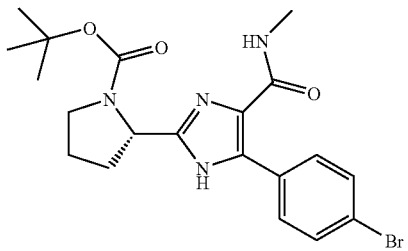

J7

(S)-ethyl 5-(4-bromophenyl)-2-(1-(tert-butoxycarbonyl)pyrrolidin-2-yl)-1H-imidazole-4-carboxylate (1 g, 2.1 mmol) was dissolved in 2M methylamine in MeOH (35 mL) and heated in a pressure vessel at 70° C. for 48 h. The reaction mixture was concentrated and the residue applied to a Biotage 25 m silica gel cartridge and eluted by 10-100% gradient, ethyl acetate/Hex to give 556 mg (57%). $^1$H NMR (300 MHz, DMSO-d$_6$) δ 12.5 (br.s, 1H), 7.86-7.82 (m, 1H), 7.77 (d, J=8.4 Hz, 2H), 7.61 (d, J=8.7 Hz, 2H), 4.83-4.70 (m, 1H), 3.69-3.52 (br.s, 1H), 3.42-3.32 (m, 1H), 2.71 (d, 4.8 Hz, 3H), 2.30-1.78 (m, 4H), 1.19-1.14 (m, 9H).

LRMS: Anal. Calcd. for C$_{20}$H$_{26}$BrN$_4$O$_3$ 449.12; found: 449.15 and 451.14 (M+H)$^+$.

Example J32.a (S)-tert-butyl 2-(5-(4-bromophenyl)-4-(trifluoromethyl)-1H-imidazol-2-yl)pyrrolidine-1-carboxylate

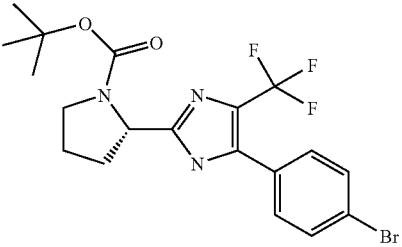

J32.a 3-(4-bromophenyl)-3-(2,2-dimethylhydrazono)-1,1,1-trifluoropropan-2-one (2.0 g, 6.2 mmol) was suspended in 5N sulfuric acid (60 mL) and heated at 45° C. for 6 h. The temperature was raised to 85° C. for 2 h, and upon cooling a precipitate formed. This material which was isolated by filtration to give 1-(4-bromophenyl)-3,3,3-trifluoropropane-1,2-dione 1.6 g (92%) as a yellow solid. The dione (1.6 g, 5.7 mmol) was taken up in methanol (30 mL), N-(tert-butoxycarbonyl)-L-prolinal (1 g, 5.0 mmol) was added, followed by addition of 28% ammonium hydroxide solution (10 mL). The reaction was stirred at room temperature for 18 h, poured onto dichloromethane (200 mL), washed with water and dried with MgSO$_4$. Filtration, concentration and application to a 40 M Biotage cartridge, gradient elution with 5%-30% ethyl acetate/Hexanes, gave J32.a 1.3 g (50%). $^1$H NMR (300 MHz, DMSO-d$_6$) δ 12.88 (br.s, 1H), 7.72 (d, J=8.4 Hz, 2H), 7.39 (d, J=8.0 Hz, 2H), 4.84-4.70 (m, 1H), 3.57-3.49 (m, 1H), 3.39-3.29 (m, 1H), 2.31-2.20 (m, 1H), 1.98-1.78 (m, 3H), 1.39/1.13 (m, 9H). LRMS: Anal. Calcd. for C$_{19}$H$_{20}$BrF$_3$N$_3$O$_2$ 458.07; found: 458.06 and 460.06 (M–H)$^-$. HRMS: Anal. Calcd. for C$_{19}$H$_{22}$BrF$_3$N$_3$O$_2$ 460.0847; found: 460.0866 and 462.0840 (M+H)$^+$.

Section D

| Entry | Compound Name | Structure | **Data |
|---|---|---|---|
| D1 | | ![structure] | $t_R$ = 2.65 min, (86.7%) LCMS: Anal. Calcd. for C$_8$H$_{15}$BrFO 296.88; found: 296.91 (M + H)$^+$. |
| | | Prepared from 1-(4-bromo-2-fluorophenyl)ethanone (Vendor: Marshalton 50043) using bromination conditions outlined in D5. | |

| Entry | Compound Name | Structure | **Data |
|---|---|---|---|
| D2 | | 1-(4-chloro-2,5-difluorophenyl)-2-bromoethanone. Prepared from 1-(4-chloro-2,5-difluorophenyl)ethanone (Vendor: Oakwood products, 001626) using bromination conditions outlined in D5. | $t_R$ = 2.66 min, (80%) LCMS: Anal. Calcd. for $C_8H_4BrClFO$ 270.92; found: ND $(M + H)^+$. |
| D3 | | 2-bromo-1-(5-bromo-2-methoxyphenyl)ethanone. Prepared from 2-bromo-1-(5-bromo-2-methoxyphenyl)ethanone (Andersh et al., Synth. Comm. 2000, 30 (12), 2091-98) using bromination conditions outlined in D5. | $t_R$ = 2.57 min, (95%) LCMS: Anal. Calcd. for $C_9H_9BrO_2$ 228.99; found: 229.00 $(M + H)^+$. |
| D4 | | Prepared from entry D1 and CBz-L-proline (in lieu of Boc-L-proline) using experimental conditions outlined in D5. | $t_R$ = 2.38 min, (95.0%) LRMS: Anal. Calcd. for $C_{19}H_{20}{}^{79}BrFN_3O_2$ 444.07; found: 444.04 $(M + H)^+$. HRMS: Anal. Calcd. for $C_{19}H_{20}{}^{79}BrFN_3O_2$ 444.0721; found: 444.0736 $(M + H)^+$ |
| D5 | | Experimental conditions in D5 | $t_R$ = 2.27 min, (95%) LRMS: Anal. Calcd. for $C_{18}H_{22}BrFN_3O_2$ 410.09 and 412.08; found: 410.08 and 412.08 $(M + H)^+$. HRMS: Anal. Calcd. for $C_{18}H_{22}{}^{79}BrFN_3O_2$ 410.0879; found: 410.0893 $(M + H)^+$. |

-continued

| Entry | Compound Name | Structure | **Data |
|---|---|---|---|
| D6 | | 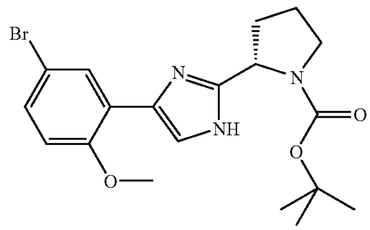 | $t_R$ = 2.26 min, (95%) LRMS: Anal. Calcd. for $C_{19}H_{25}BrN_3O_3$ 422.11 and 424.11; found: 422.10 and 424.10 (M + H)$^+$. HRMS: Anal. Calcd. for $C_{19}H_{25}{}^{79}BrN_3O_3$ 422.1079; found: 422.1089 (M + H)$^+$. |
| | | Prepared from entry D3 (in lieu of entry D1) using experimental conditions outlined in D5. | |
| D7 | | 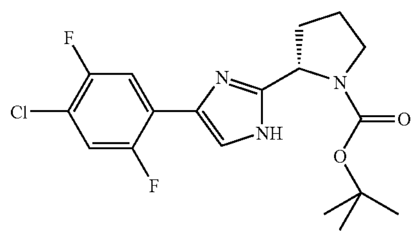 | $t_R$ = 2.28 min, (95%) LRMS: Anal. Calcd. for $C_{18}H_{21}ClF_2N_3O_2$ 384.13; found: 384.13 (M + H)$^+$. HRMS: Anal. Calcd. for $C_{18}H_{21}ClF_2N_3O_2$ 384.1290; found: 384.1301 (M + H)$^+$. |
| | | Prepared from entry D2 (in lieu of entry D1) using experimental conditions outlined in enclosed experiment. | |
| D8 | | 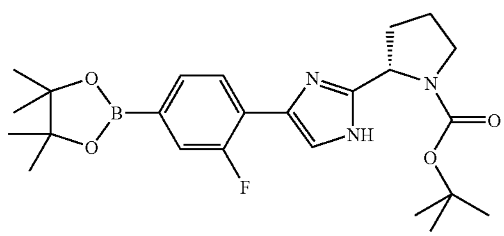 | $t_R$ = 2.62 min, (~50%) and 1.95 min (~50%, boronic acid) LRMS: Anal. Calcd. for $C_{24}H_{34}BFN_3O_4$ 458.26; found: 458.23 (M + H)$^+$. HRMS: Anal. Calcd. for $C_{24}H_{34}BFN_3O_4$ 458.2626; found: 458.2610 (M + H)$^+$. |
| | | Prepared from entry D5 (in lieu of entry 1b) using experimental conditions outlined in Example 1, Step c. | |
| D13 | tert-butyl (2S)-2-(5-(2-(4-(2-((2S)-1-(tert-butoxycarbonyl)-2-pyrrolidinyl)-1H-imidazol-4-yl)-3-fluorophenyl)-5-pyrimidinyl)-1H-imidazol-2-yl)-1-pyrrolidinecarboxylate | 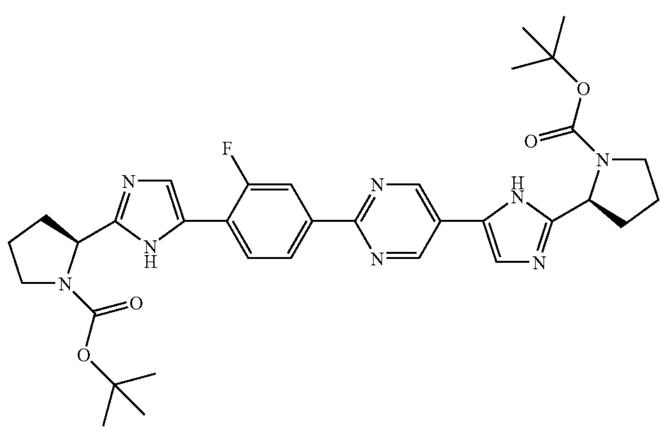 | $t_R$ = 2.27 min, (95%) LRMS: Anal. Calcd. for $C_{34}H_{42}FN_8O_4$ 645.33; found: 645.34 (M + H)$^+$. HRMS: Anal. Calcd. for $C_{34}H_{42}FN_8O_4$ 645.3313; found: 645.3323 (M + H)$^+$. |
| | | Prepared from entry D8 (in lieu of 1c) and 152b-1 using experimental conditions outlined in Example 152g-1. | |

-continued

| Entry | Compound Name | Structure | **Data |
|---|---|---|---|
| D32 | 2-(3-fluoro-4-(2-((2S)-2-pyrrolidinyl)-1H-imidazol-5-yl)phenyl)-5-(2-((2S)-2-pyrrolidinyl)-1H-imidazol-5-yl)pyrimidine | Prepared from entry D13 (in lieu of 152j-27) using experimental conditions outlined in Example 152k-1. | $t_R$ = 1.63 min, (95%) LRMS: Anal. Calcd. for $C_{24}H_{26}FN_8$ 445.23; found: 445.23 (M + H)$^+$. HRMS: Anal. Calcd. for $C_{24}H_{26}FN_8$ 445.2264; found: 445.2268 (M + H)$^+$. |
| D67 | methyl ((1S)-2-((2S)-2-(5-(2-fluoro-4-(5-(2-((2S)-1-(N-(methoxycarbonyl)-L-alanyl)-2-pyrrolidinyl)-1H-imidazol-5-yl)-2-pyrimidinyl)phenyl)-1H-imidazol-2-yl)-1-pyrrolidinyl)-1-methyl-2-oxoethyl)carbamate | Prepared from entry D32 (in lieu of 148e) and Cap-52 using experimental conditions outlined in Example 148. | $t_R$ = 1.58 min, (91.1%) LRMS: Anal. Calcd. for $C_{34}H_{40}FN_{10}O_6$ 703.31; found: 703.27 (M + H)$^+$. HRMS: Anal. Calcd. for $C_{34}H_{40}FN_{10}O_6$ 703.3116; found: 703.3101 (M + H)$^+$. |
| D68 | methyl ((1S)-1-(((2S)-2-(5-(2-fluoro-4-(5-(2-((2S)-1-((2S)-2-((methoxycarbonyl)amino)-3-methylbutanoyl)-2-pyrrolidinyl)-1H-imidazol-5-yl)-2-pyrimidinyl)phenyl)-1H-imidazol-2-yl)-1-pyrrolidinyl)carbonyl)-2-methylpropyl) carbamate | Prepared from entry D32 (in lieu of 148e) and Cap-51 using experimental conditions outlined in Example 148. | $t_R$ = 1.95 min, (99.3%) LRMS: Anal. Calcd. for $C_{38}H_{48}FN_{10}O_6$ 759.37; found: 759.30 (M + H)$^+$. HRMS: Anal. Calcd. for $C_{38}H_{48}FN_{10}O_6$ 759.3742; found: 759.3715 (M + H)$^+$. |
| D69 | methyl ((1R)-2-((2S)-2-(5-(2-(3-fluoro-4-(2-((2S)-1-((2R)-2-((methoxycarbonyl)amino)-2-phenylacetyl)-2-pyrrolidinyl)-1H-imidazol-5-yl)phenyl)-5-pyrimidinyl)-1H-imidazol-2-yl)-1-pyrrolidinyl)-2-oxo-1-phenylethyl) carbamate | Prepared from entry D32 (in lieu of 148e) and Cap-4 using experimental conditions outlined in Example 148. | $t_R$ = 2.05 min, (99.3%) LRMS: Anal. Calcd. for $C_{44}H_{44}FN_{10}O_6$ 827.34; found: 827.27 (M + H)$^+$. HRMS: Anal. Calcd. for $C_{44}H_{44}FN_{10}O_6$ 827.3429; found: 827.3407 (M + H)$^+$. |

| Entry | Compound Name | Structure | **Data |
|---|---|---|---|
| D70 | methyl ((1S,2R)-1-(((2S)-2-(5-(2-fluoro-4-(5-(2-((2S)-1-(N-(methoxycarbonyl)-O-methyl-L-threonyl)-2-pyrrolidinyl)-1H-imidazol-5-yl)-2-pyrimidinyl)phenyl)-1H-imidazol-2-yl)-1-pyrrolidinyl)carbonyl)-2-methoxypropyl) carbamate | Prepared from entry D32 (in lieu of 148e) and Cap-86 using experimental conditions outlined in Example 148. | $t_R$ = 1.79 min, (93.0%) LRMS: Anal. Calcd. for $C_{38}H_{48}FN_{10}O_8$ 791.36; found: 791.31 (M + H)⁺. HRMS: Anal. Calcd. for $C_{38}H_{48}FN_{10}O_8$ 791.3641; found: 791.3636 (M + H)⁺. |

**LCMS conditions: Phenomenex-Luna 4.6 × 50 mm S10, 0 to 100% B over 3 min, 4 min stop time, 4 mL/min, 220 nm, A: 10% MeOH-90% H2O-0.1% TFA; B: 90% MeOH-10% H2O-0.1% TFA Example D5

(S)-tert-butyl 2-(5-(4-bromo-2-fluorophenyl)-1H-imidazol-2-yl)pyrrolidine-1-carboxylate

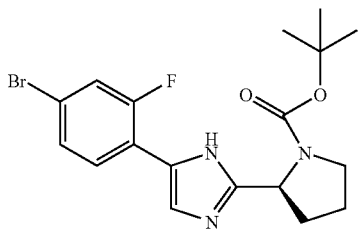

D5

Bromine (0.54 mL, 10.6 mmol) was added dropwise to a cold (0° C.) solution of 4-bromo-2-fluoroacetophenone (2.30 g, 10.6 mmol) in dioxane (80 mL) and tetrahydrofuran (80 mL). The mixture was stirred for 1 h at 0° C. and warmed to RT for 15 h. The mixture was diluted with ethyl acetate, washed with saturated NaHCO₃ solution, 5% sodium thiosulfate solution and brine prior to drying (Na₂SO₄). 2-Bromo-1-(4-bromo-2-fluorophenyl)ethanone (D1) was isolated as a colorless film which solidified upon further concentration under high vacuum. This solid was dissolved into anhydrous acetonitrile (50 mL) and treated with N-Boc-L-proline (2.28 g, 10.6 mmol) and diisopropylethylamine (1.85 mL, 10.6 mmol). After being stirred for 3 h at RT, the solvent was removed in vacuo and the residue was partitioned into ethyl acetate and water. The organic phase was washed with 0.1N hydrochloric acid, saturated NaHCO₃ solution and brine prior to drying (Na₂SO₄), filtration, and concentration. This residue was taken up in xylenes (50 mL) and treated to solid NH₄OAc (4.1 g, 53.0 mmol). The mixture was heated at 140° C. for 2 hr in a thick-walled, screw-top flask before it was cooled to ambient temperature, diluted with ethyl acetate and washed with saturated NaHCO₃ solution and brine prior to drying (Na₂SO₄) and concentration. Purification of the residue by Biotage™ flash chromatography on silica gel (65M column, preequilibration with 16% B for 1800 mL followed by gradient elution with 16% B to 16% B for 450 mL, 16% B to 50% B for 2199 ml and finally 50% B to 100% B for 2199 mL) afforded title compound (D5) (3.61 g, 83%) as a brownish/caramel-colored oil. A small portion (40 mg) of the title compound was further purified by preparative HPLC (20% B to 100% B over 14 min where B is 10 mM NH₄OAc in 10:90 H₂O/ACN and A is 10 mM NH₄OAc in 95:5 H₂O/CAN using a Phenomenex-Gemini 30×100 mm S10 column flowing at 40 mL/min) to afford pure title compound (31.8 mg) as a white solid.

¹H NMR (500 MHz, DMSO-d₆) δ 12.13-11.95 (m, 1H), 7.94 (br s, 1H), 7.54 (d, J=10.7 Hz, 1H), 7.42 (d, J=7.9 Hz, 1H), 7.36-7.34 (m, 1H), 4.86-4.77 (2m, 1H), 3.54 (m, 1H), 3.38-3.32 (m, 1H), 2.28-2.14 (2m, 1H), 2.05-1.78 (2m, 3H), 1.39 and 1.14 (2s, 9H).

HPLC Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, RT=2.27 min, 95% homogeneity index.

LRMS: Anal. Calcd. for $C_{18}H_{22}BrFN_3O_2$ 410.09 and 412.09; found: 410.08 and 412.08 (M+H)⁺.

HRMS: Anal. Calcd. for $C_{18}H_{22}BrFN_3O_2$ 410.0879; found: 410.0893 (M+H)⁺.

Section M: LC Conditions were as follows:

| Condition 1 | |
|---|---|
| Column = | Phenomenex-Luna 3.0 × 50 mm S10 |
| Start % B = | 0 |
| Final % B = | 100 |
| Gradient time = | 2 min |
| Stop time = | 3 min |
| Flow Rate = | 4 mL/min |
| Wavelength = | 220 nm |
| Slovent A = | 0.1% TFA in 10% methanol/90% H₂O |
| Solvent B = | 0.1% TFA in 90% methanol/10% H₂O |
| Condition 2 | |
| Column = | Phenomenex-Luna 4.6 × 50 mm S10 |
| Start % B = | 0 |
| Final % B = | 100 |
| Gradient time = | 2 min |
| Stop time = | 3 min |
| Flow Rate = | 5 mL/min |
| Wavelength = | 220 nm |
| Slovent A = | 0.1% TFA in 10% methanol/90% H₂O |
| Solvent B = | 0.1% TFA in 90% methanol/10% H₂O |
| Condition 3 | |
| Column = | HPLC XTERRA C18 3.0 × 50 mm S7 |
| Start % B = | 0 |
| Final % B = | 100 |

| | |
|---|---|
| Gradient time = | 3 min |
| Stop time = | 4 min |
| Flow Rate = | 4 mL/min |
| Wavelength = | 220 nm |
| Slovent A = | 0.1% TFA in 10% methanol/90% H$_2$O |
| Solvent B = | 0.1% TFA in 90% methanol/10% H$_2$O |
| | Condition M1 |
| Column: | Luna 4.6 × 50 mm S10 |
| Start % B = | 0 |
| Final % B = | 100 |
| Gradient time = | 3 min |
| Stop time = | 4 min |
| Flow rate = | 4 mL/min |
| Solvent A: = | 95% H$_2$O: 5% CH$_3$CN, 10 mm Ammonium acetate |
| Solvent B: = | 5% H$_2$O: 95% CH$_3$CN; 10 mm Ammonium acetate |

Example M114

4,4'-bis(2-((2S)-1-(N-(methoxycarbonyl)-L-valyl)-2-pyrrolidinyl)-1H-imidazol-5-yl)-2-biphenylcarboxylic acid

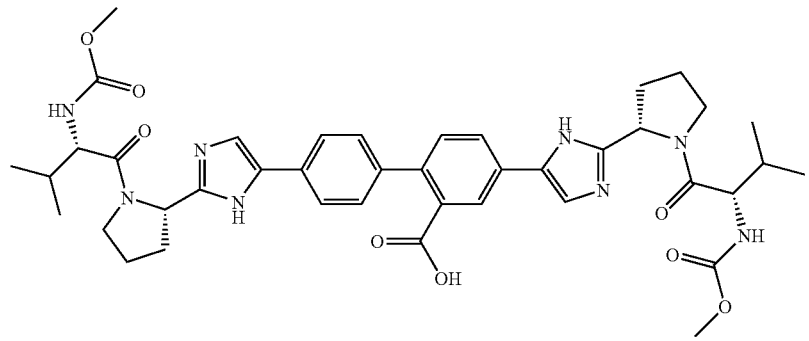

Example M114

Step a

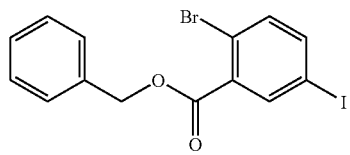

DMF (20 mL) was added to mixture of KHCO$_3$ (1.84 g, 18.4 mmol) and 2-bromo-5-iodobenzoic acid (4.99 g, 15.3 mmol) and the resulting mixture was stirred for 15 min. Benzyl bromide (2.4 mL, 20.2 mmol) was added drop-wise over 5 min and stirring was continued at ambient condition for ~20 hr. Most of the volatile component was removed in vacuo and the residue was partitioned between CH$_2$Cl$_2$ (50 mL) and water (50 mL), and the organic layer was washed with water (50 mL), dried (MgSO$_4$), filtered, and concentrated. The resulting crude material was purified with flash chromatography (7% EtOAc/hexanes) to afford ester M114a as a colorless viscous oil (6.01 g). $^1$H NMR (DMSO-d$_6$, δ=2.5 ppm, 400 MHz): δ 8.07 (d, J=2.0, 1H), 7.81 (dd, J=8.4, 2.1, 1H), 7.53 (d, J=8.4, 1H), 7.48 (m, 2H), 7.43-7.34 (m, 3H), 5.34 (s, 2H). LC (Cond. 1): RT=2.1 min; LC/MS: Anal. Calcd. for [M+Na]$^+$ C$_{14}$H$_{10}$BrINaO$_2$: 438.88; found 438.83.

Example M114

Step b-d

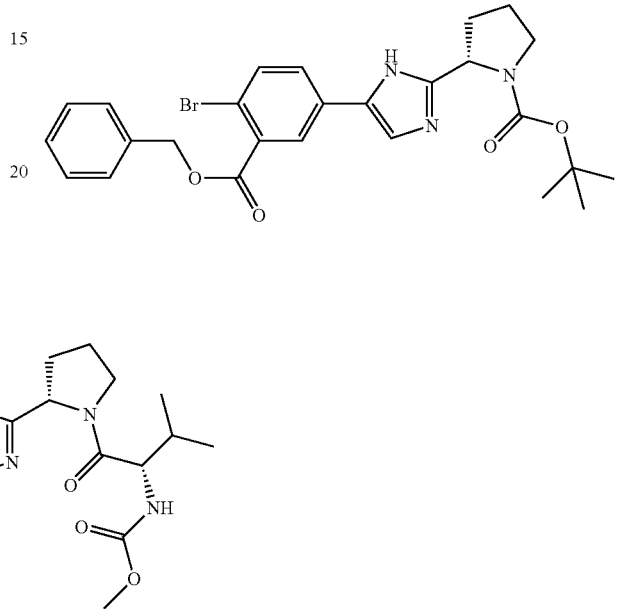

Ester M114a was elaborated to ester M114d by employing a three step protocol employed in the synthesis of bromide 121c from 1-bromo-4-iodo-2-methylbenzene. M114d: $^1$H NMR (DMSO-d$_6$, δ=2.5 ppm, 400 MHz): δ 12.04/11.97 (br s, 1H), 8.12 (d, J=2.0, 0.92H), 7.99 (app br s, 0.08H), 7.81 (dd, J=8.3, 2.0, 0.92H), 7.74-7.62 (m, 2.08H), 7.50 (app br d, J=7.0, 2H), 7.44-7.35 (m, 3H), 5.38 (s, 2H), 4.79 (m, 1H), 3.52 (app br s, 1H), 3.36 (m, 1H), 2.24-1.79 (m, 4H), 1.39/5.11 (two s, 9H). LC (Cond. 1): RT=1.66 min; LC/MS: Anal. Calcd. for [M+H]$^+$ C$_{26}$H$_{29}$BrN$_3$O$_4$: 526.13; found 526.16.

Example M114

Step e

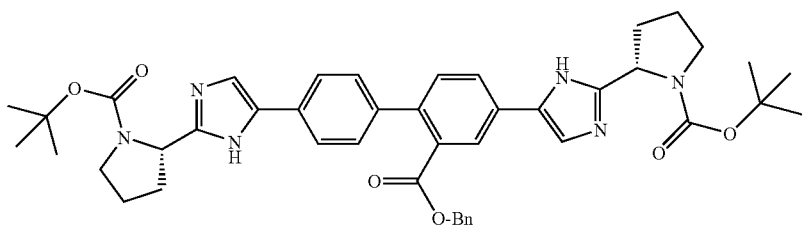

Ester M114e was prepared from bromide M114d and boronate 1c according to the preparation of dimer 1d. ¹H NMR (DMSO-d$_6$, δ=2.5 ppm, 400 MHz): δ 12.18/12.00/11.91/11.83 (four br s, 2H), 8.11-7.03 (m, 14H), 5.10 (s, 2H), 4.85-4.78 (m, 2H), 3.55 (app br s, 2H), 3.37 (m, 2H), 2.29-1.80 (m, 8H), 1.41/1.16 (two s, 18H). LC (Cond. 1): RT=1.54 min; LC/MS: Anal. Calcd. for [M+H]⁺ C$_{44}$H$_{51}$N$_6$O$_6$: 759.39; found 759.63.

Example M114

Step f

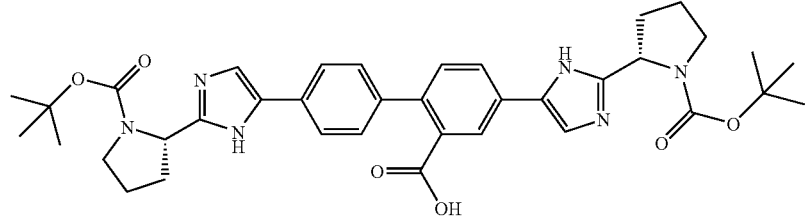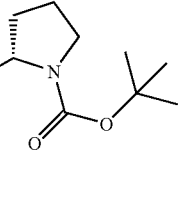

A mixture of benzyl ester M114e (1.005 g, 1.325 mmol) and 10% Pd/C (236 mg) in MeOH (20 mL) was stirred under a balloon of H$_2$ for 5 hr. The reaction mixture was then treated with a 1:1 mixture of MeOH and CH$_2$Cl$_2$, filtered through a pad of diatomaceous earth (Celite®-521), and the filtrate was rotervaped to afford acid M114f (840 mg), contaminated with Ph$_3$PO which was a carryover from the Suzuki coupling step. ¹H NMR (DMSO-d$_6$, δ=2.5 ppm, 400 MHz): δ 12.17/11.98/11.89/11.81 (four app br s, 2H), 8.04-7.31 (m, 9H), 4.85-4.78 (m, 2H), 3.55 (app br s, 2H), ~3.37 (m, 2H, overlapped with water signal) 2.27-1.84 (m, 8H), 1.41/1.16 (two s, 18H). LC (Cond. 1): RT=1.37 min; LC/MS: Anal. Calcd. for [M+H]⁺ C$_{37}$H$_{45}$N$_6$O$_6$: 669.34; found 669.53.

Example M114

Step g

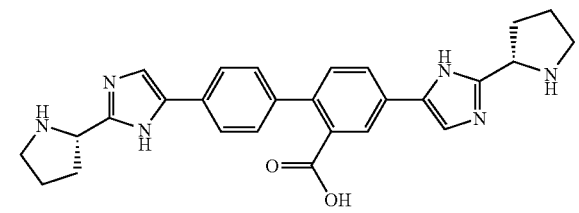

4N HCl/dioxane (8.0 mL) and CH$_2$Cl$_2$ (2.0 mL) were sequentially added to carbamate M114f (417 mg, 0.623 mmol), the mixture was vigorously stirred 5.5 hr, and then the volatile component was removed in vacuo to afford the HCl (0.4×) salt of pyrrolidine M114g (487 mg), contaminated with Ph$_3$PO impurity. ¹H NMR (DMSO-d$_6$, δ=2.5 ppm, 400 MHz) after D$_2$O exchange: δ 8.23 (d, J=1.7, 1H), 8.09-8.04 (m, 3H), 7.92 (d, J=8.3, 2H), 7.53 (d, J=8.1, 1H), 7.48 (d, J=8.3, 2H), 5.00 (app br t, J=8.3, 1H), 4.90 (app br t, J=8.4, 1H), 3.6-3.3 (m, 4H), 2.5-1.99 (m, 8H). LC (Cond. 1): RT=0.92 min; LC/MS: Anal. Calcd. for [M+H]⁺ C$_{27}$H$_{29}$N$_6$O$_2$: 469.24; found 469.31.

Example M114

HATU (79.9 mg, 0.21 mmol) was added to a DMF (3.0 mL) solution of pyrrolidine M114g.4HCl (80 mg, 0.13 mmol), Cap-51 (92.4 mg, 0.527 mmol) and i-Pr$_2$EtN (160 μL, 0.919 mmol), and the reaction mixture was stirred at ambient condition for 2 hr. The volatile component was removed in vacuo and the residue was purified with a combination of MCX (MeOH wash; 2.0 M NH$_3$/MeOH elution) and a reverse phase HPLC (CH$_3$CN/H$_2$O/NH$_4$OAc) to afford the acetic acid salt of Example M 14. LC (Cond. 1): RT=1.20 min; >98 homogeneity index. LC/MS: Anal. Calcd. for [M+H]⁺ C$_{41}$H$_{51}$N$_8$O$_8$: 783.38; found 783.34. HRMS Calcd. for [M+H]⁺ C$_{41}$H$_{51}$N$_8$O$_8$: 783.3830; found 783.3793.

Example M118 methyl((1S)-1-(((2S)-2-(5-(2'-carbamoyl-4'-(2-((2S)-1-((2S)-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl)carbonyl)-2-methylpropyl)carbamate

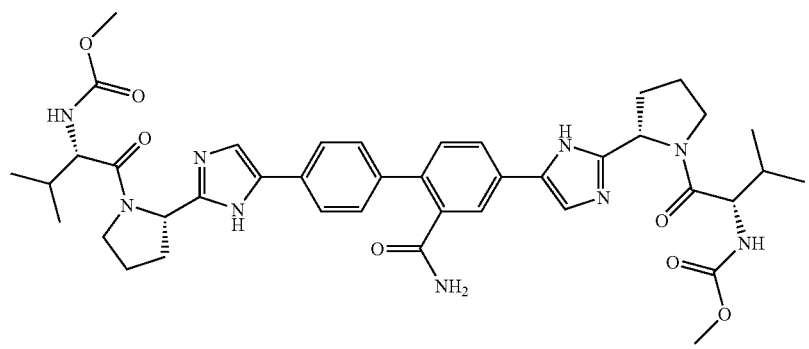

315

Example M118

Step a

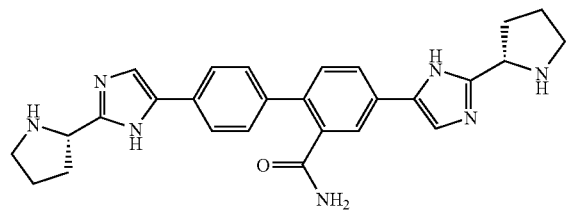

Et₃N (300 μL, 2.15 mmol) was added to a mixture of acid M114f (198.3 mg, 0.297 mmol), HOBt (94.2 mg, 0.697 mmol), EDCI (0.66 mmol), NH₄Cl (101 mg, 1.89 mmol) in DMF (8.0 mL) and stirred for 17 hr at ambient condition. The reaction mixture was filtered through 0.45 μm filter, the volatile component was removed in vacuo and the residue was partitioned between CH₂Cl₂ and water. The organic layer was concentrated and the resulting crude material was purified with a reverse phase HPLC (MeOH/H₂O/TFA).

The above product was treated with 25% TFA/CH₂Cl₂ (4.0 mL) and the reaction mixture was stirred for 2.5 hr at ambient condition. The volatile component was removed in vacuo and the residue was free-based (MCX; MeOH wash; 2.0 M NH₃/MeOH elution) to afford amide M118a (67.2 mg). $^1$H NMR (DMSO-d₆, δ=2.5 ppm, 400 MHz): δ 11.83 (br s, 2H), 7.81-7.80 (m, 2H), 7.73 (d, J=8.3, 2H), 7.65 (br s, 1H), 7.52 (br S, 1H), 7.44 (br s, 1H), 7.41 (d, J=8.3, 2H), 7.36 (d, J=8.3, 1H), 7.31 (br s, 1H), 4.16 (app t, J=7.2, 2H), 3.00-2.94 (m, 2H), 2.88-2.82 (m, 2H), 2.10-2.01 (m, 2H), 1.94-1.85 (m, 2H), 1.83-1.66 (m, 4H). LC (Cond. 1): RT=0.89 min; >95 homogeneity index. LC/MS: Anal. Calcd. for [M+H]⁺ C₂₇H₃₀N₇O: 468.25; found 468.24.

Example M118

The TFA salt of Example M118 was prepared from intermediate M118a and Cap-51 according to the procedure described for Example 1. LC (Cond. 1): RT=1.16 min; 97% homogeneity index. LC/MS: Anal. Calcd. for [M+H]⁺ C₄₁H₅₂N₉O₇: 782.40; found 782.40. HRMS: Anal. Calcd. for [M+H]⁺ C₄₁H₅₂N₉O₇: 782.3990; found 782.3979.

Example M119 methyl((1S)-1-(((2S)-2-(5-(2-(hydroxymethyl)-4'-(2-((2S)-1-((2S)-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl)carbonyl)-2-methylpropyl)carbamate

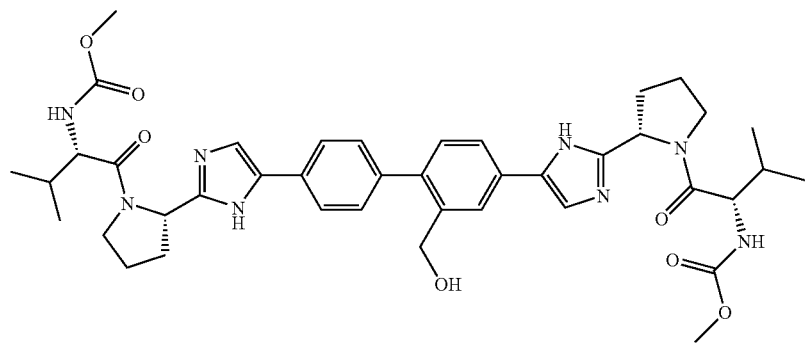

316

Example M119

Step a

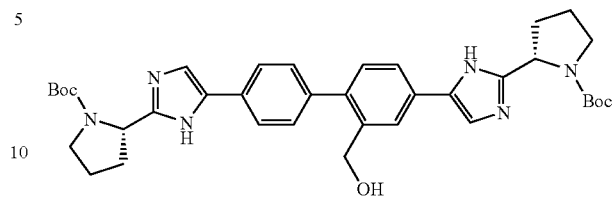

DIBAL-H (8.0 mL of 1.0 M/CH₂Cl₂, 8.0 mmol) was added drop-wise to an ice-water cooled CH₂Cl₂ (20 mL) solution of benzyl ester M114e (1.216 g, 1.60 mmol), and the reaction mixture was stirred for 1 hr and an additional DIBAL-H (0.5 mL of 1.0 M/CH₂Cl₂, 0.5 mmol) was added and stirring was continued for ~2.5 hr. The reaction was quenched with excess saturated NH₄Cl solution and the mixture was diluted with water and extracted with CH₂Cl₂ (3×). The combined organic phase was dried (MgSO₄), filtered, and concentrated in vacuo. The resulting crude material was purified with a Biotage (100 g silica gel; 2-6% MeOH/EtOAc) to afford alcohol M119a as an off-white foam (610 mg). $^1$H NMR (DMSO-d₆, δ=2.5 ppm, 400 MHz): δ 12.23 (brs, 0.19H), 12.17 (brs, 0.19H), 11.89 (brs, 0.81H), 11.82 (brs, 0.81H), 7.97 (s, 0.81H), 7.84 (s, 0.19H), 7.78 (d, J=8.1, 1.62H), 7.69-7.20 (m, 6.38H), 5.21-5.15 (m, 1H), 4.86-4.78 (m, 2H), 4.49-4.45 (m, 2H), ~3.54 (m, 2H), 3.40-3.34 (m, 2H), 2.30-1.80 (m, 8H), 1.41/1.17 (two s, 18H). LC (Cond. 1): RT=1.36 min. LC/MS: Anal. Calcd. for [M+H]⁺ C₃₇H₄₇N₆O₅: 655.36; found 655.34.

Example M119

Step b

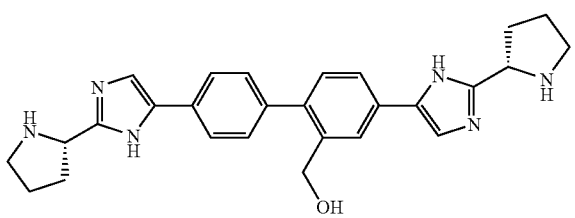

25% TFA/CH₂Cl₂ (3.0 mL) was added to carbamate M119a (105 mg, 0.160 mmol) and the mixture was stirred at ambient condition for 4.5 hr. The volatile component was removed in vacuo and the residue was free-based (MCX; MeOH wash; 2.0 M NH3/MeOH elution) to afford pyrrolidine M119b, contaminated with its trifluoroacetylated derivative of unknown regiochemistry. The sample was dissolved in MeOH (1.5 mL) and treated with 1.0 M NaOH/H₂O (300 μL, 0.3 mmol) and the mixture was stirred for 2.75 hr. It was then directly submitted to MCX purification (MeOH wash; 2.0 M NH₃/MeOH elution) to afford M119b as a film of white solid (63.8 mg). $^1$H NMR (DMSO-d$_6$, δ=2.5 ppm, 400 MHz): δ 11.82 (br s, 2H), 7.96 (s, 1H), 7.77 (d, J=8.0, 2H), 7.66 (d, J=8.0, 1H), 7.46 (br s, 1H), 7.42 (br s, 1H), 7.36 (d, J=8.0, 2H), 7.21 (d, J=8.0, 1H), 5.16 (app br s, 1H), 4.46 (s, 2H), 4.16 (app t, J=7.1, 2H), 3.00-2.82 (two m, 4H; there is a broad base line signal in this region from the pyrrolidine NH that was not included in the integration), 2.10-2.01 (m, 2H), 1.94-1.85 (m, 2H), 1.83-1.67 (m, 4H). LC (Cond. 1): RT=0.78 min. LC/MS: Anal. Calcd. for [M+H]⁺ C$_{27}$H$_{31}$N$_6$O: 455.26; found 455.27.

Example M119

Example M119 was prepared from M119b and Cap-51 according to the procedure described for Example 1, with the exception that a reverse phase HPLC with ACN/H₂O/ NH₄OAC solvent system was employed for the purification step. LC (Cond. 1): RT=1.15 min; 98% homogeneity index. LC/MS: Anal. Calcd. for [M+H]⁺ C$_{41}$H$_{53}$N$_8$O$_7$: 769.40; found 769.40. HRMS: Anal. Calcd. for [M+H]⁺ C$_{41}$H$_{53}$N$_8$O$_7$: 769.4037; found 769.4023.

Example M120 methyl((1S)-1-(((2S)-2-(5-(2-((dimethylamino)methyl)-4'-(2-((2S)-1-((2S)-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl)carbonyl)-2-methylpropyl)carbamate earth (Celite®), the filtrate was rotervaped and the resulting crude material was purified with a Biotage (2% MeOH/EtOAc) to afford aldehyde M120a as a yellow viscous oil (195.6 mg). LC (Cond. 1): RT=1.37 min. LC/MS: Anal. Calcd. for [M+H]⁺ C$_{37}$H$_{45}$N$_6$O$_5$: 653.35; found 653.40.

Example M120

Step b

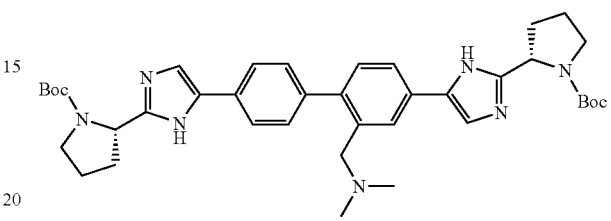

NaCNBH₃ (33 mg, 0.50 mmol) was added in one batch to a MeOH (3.0 mL) solution of aldehyde M120a (195.6 mg, 0.30 mmol) and Me₂NH (200 μL of 40% solution in H₂O), and the reaction mixture was stirred for 4 hr. The volatile component was removed in vacuo and the residue was purified with a flash chromatography (sample was loaded as a silica gel mesh; 3-15% MeOH/CH₂Cl₂) to afford amine M120b as an off-white foam (120 mg). LC (Cond. 1): RT=1.32 min. LC/MS: Anal. Calcd. for [M+H]⁺ C$_{39}$H$_{52}$N$_7$O$_4$: 682.41; found 682.42.

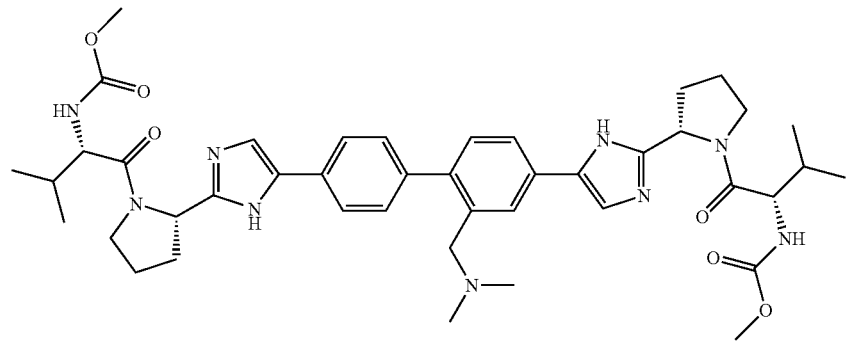

Example M120

Step a

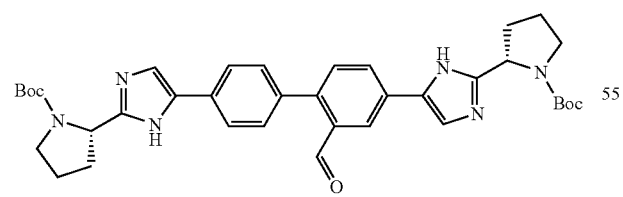

CH₂Cl₂ (6.0 mL) was added to a mixture alcohol M119a (501 mg, 0.765 mmol), TPAP (29.1, 0.083 mmol) and 4-methylmorpholine N-oxide (135.8 mg, 1.159 mmol), and the resultant heterogeneous mixture was vigorously stirred at ambient condition for 14.5 hr. Additional TPAP (11.0 mg, 0.031 mmol) and 4-methylmorpholine N-oxide (39 mg, 0.33 mmol) were added and stirring was continued for an additional 24 hr. The mixture was filtered through diatomaceous Example M120

Step c

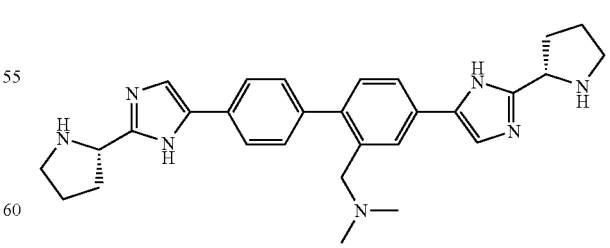

Carbamate M120b was converted to M120c by employing the protocol described for the preparation of 1e from 1d. $^1$H NMR (DMSO-d$_6$, δ=2.5 ppm, 400 MHz): δ 11.82 (br s, 2H), 7.87 (s, 1H), 7.77 (d, J=8.0, 2H), 7.65 (d, J=7.8, 1H), 7.45/7.43 (overlapping two br s, 2H), 7.37 (d, J=7.8, 2H), 7.21 (d, J=7.8, 1H), 4.87 (m, 0.1H), 4.17 (m, 1.90H), ~3.3 (signal of Me$_2$NCH$_2$ overlapped with that of water), 3.01-2.94 (m, 2H), 2.89-2.83 (m, 2H), 2.10 (s, 6H), 2.10-2.01 (m, 2H), 1.94-1.85 (m, 2H), 1.81-1.67 (m, 4H). LC (Cond. 1): RT=0.79 min. LC/MS: Anal. Calcd. for [M+H]$^+$ C$_{29}$H$_{36}$N$_7$: 482.30; found 482.35.

Example M120

The TFA salt of Example M120 was prepared from pyrrolidine M120c and Cap-51 according to the procedure described for Example 1. LC (Cond. 1): RT=1.06 min; 96% homogeneity index. LC/MS: Anal. Calcd. for [M+H]$^+$ C$_{43}$H$_{58}$N$_9$O$_6$: 796.45; found 796.48. HRMS: Anal. Calcd. for [M+H]$^+$ C$_{43}$H$_{58}$N$_9$O$_6$: 796.4510; found 796.4515.

Example M121 dimethyl((2-((dimethylamino)methyl)-4,4'-biphenyldiyl)bis(1H-imidazole-5,2-diyl(2S)-2,1-pyrrolidinediyl((1R)-2-oxo-1-phenyl-2,1-ethanediyl))) biscarbamate

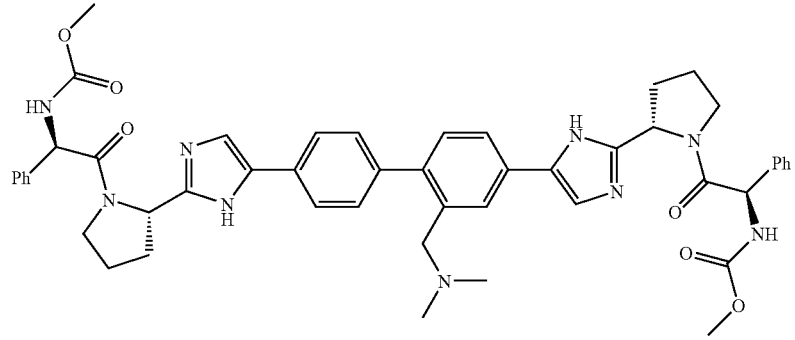

The TFA salt of Example M121 was prepared from M120c and Cap-4 according to the procedure described for Example 1. LC (Cond. 1): RT=1.15 min; >98% homogeneity index. LC/MS: Anal. Calcd. for [M+H]$^+$ C$_{49}$H$_{54}$N$_9$O$_6$: 796.45; found 864.46. HRMS: Anal. Calcd. for [M+H]$^+$ C$_{49}$H$_{54}$N$_9$O$_6$: 864.4197; found 864.4222.

Example M122 methyl((1S)-1-(((1S,3S,5S)-3-(5-(4'-(2-((1S,3S,5S)-2-((2S)-2-((methoxycarbonyl)amino)-3-methylbutanoyl)-2-azabicyclo[3.1.0]hex-3-yl)-1H-imidazol-5-yl)-4-biphenylyl)-1H-imidazol-2-yl)-2-azabicyclo[3.1.0]hex-2-yl)carbonyl)-2-methylpropyl)carbamate

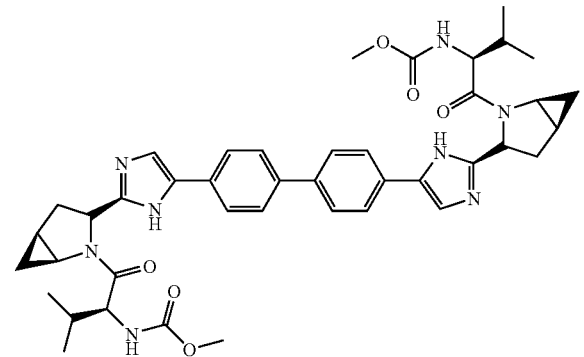

Example M122

Step a

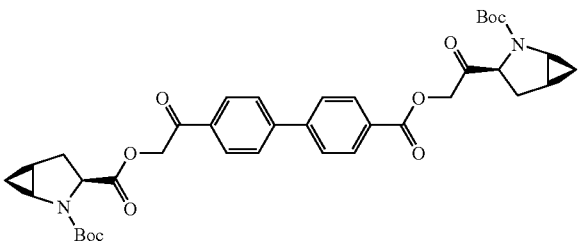

Diisopropyl ethylamine (1.81 mL, 10.4 mmol) was slowly added to acetonitrile (20 mL) solution of (1S,3S,5S)-2-(tert-butoxycarbonyl)-2-azabicyclo[3.10]hexane-3-carboxylic acid (2.36 g, 10.4 mmol) and (2-(4'-(2-bromoacetyl)biphenyl-4-yl)-2-oxoethyl)bromonium (2.0 g, 5.05 mmol), and the reaction mixture was stirred at ambient conditions for 16 hr. The solvent was evaporated and the residue was partitioned between ethyl acetate and water (1:1, 40 mL each). The organic layer was washed with Sat. NaHCO$_3$ (2×10 mL), brine, dried (Na$_2$SO$_4$), filtered, and concentrated in vacuo to afford ketoester M122a (3.58 g) as a viscous amber oil, which solidified upon storage in a refrigerator. $^1$H NMR (DMSO-d$_6$, δ=2.5 ppm, 400 MHz): δ 8.20 (m, 4H), 7.97 (d, J=8.5, 4H), 5.71-5.48 (m, 4H), 4.69 (m, 2H), 3.44 (m, 2H), 3.3 (m, 2H), 2.76-2.67 (m, 2H), 2.27 (m, 2H), 1.60 (m, 2H), 1.44/1.38 (two s, 18H), 0.78 (m, 2H), 0.70 (m, 2H). LC (Cond. 1): RT=1.70 min; LC/MS: the molecular ion was not picked up.

Example M122

Step b

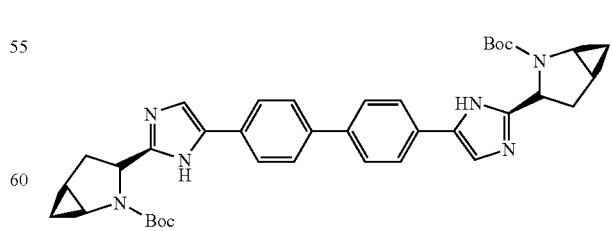

Ammonium acetate (2.89 g, 37.5 mmol) was added to a toluene (20 mL) solution of ketoester M122a (2.58 g, 3.75 mmol), and the resulting mixture was heated at 120° C. for 4.5 hr, while azaetroping the water that is formed with a Dean- Stark set-up. The reaction mixture was cooled to room temperature and the volatile component was removed in vacuo. Sat. NaHCO₃ solution (10 mL) was added to the solid and the mixture was stirred for 30 min, and the solid was filtered, dried in vacuo and submitted to a Biotage purification (28-100% EtOAc/hexanes) to afford imidazole M122b as light yellow solid (0.6 g). LC (Cond. 1): RT=1.52 min; LC/MS: Anal. Calcd. for [M+H]⁺ $C_{38}H_{45}N_6O_4$: 649.35; found 649.78.

Example M1122

Step c

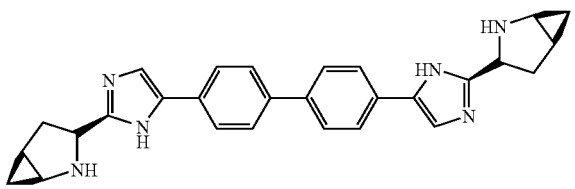

4 N HCl in dioxane (5 mL) was added to a ice-water cooled dioxane (16 mL) solution of carbamate M122b (0.8 g, 1.2 mmol), the ice-water bath was removed and the mixture was stirred at ambient condition for 4 hr. Big chunks of solid that formed during the reaction were broken up with a spatula. Removal of the volatile component in vacuo afforded pyrrolidine M122c (0.4 HCl) as yellow solid (0.73 g). ¹H NMR (DMSO-d₆, δ=2.5 ppm, 400 MHz): δ 7.90 (d, J=8.3, 4H), 7.84 (br s, 2H), 7.79 (d, J=8.3, 4H), 5.24 (m, 2H), 3.38 (m, 2H), 2.71 (m, 2H), ~2.50 (2H, overlapped with solvent signal), 1.93 (m, 2H), 1.38 (m, 2H), 0.96 (m, 2H). LC (Cond. 1): RT=1.03 min; LC/MS: Anal. Calcd. for [M+H]⁺ $C_{28}H_{29}N_6$: 449.25; found 449.59.

Example M122

The TFA salt of Example M122 was prepared from M122c and Cap-51 according to the procedure described for Example 1. LC (Cond. 1): RT=1.34 min; LC/MS: Anal. Calcd. for [M+H]⁺ $C_{42}H_{51}N_8O_6$: 763.39; found 763.73.

Section R

Scheme 1

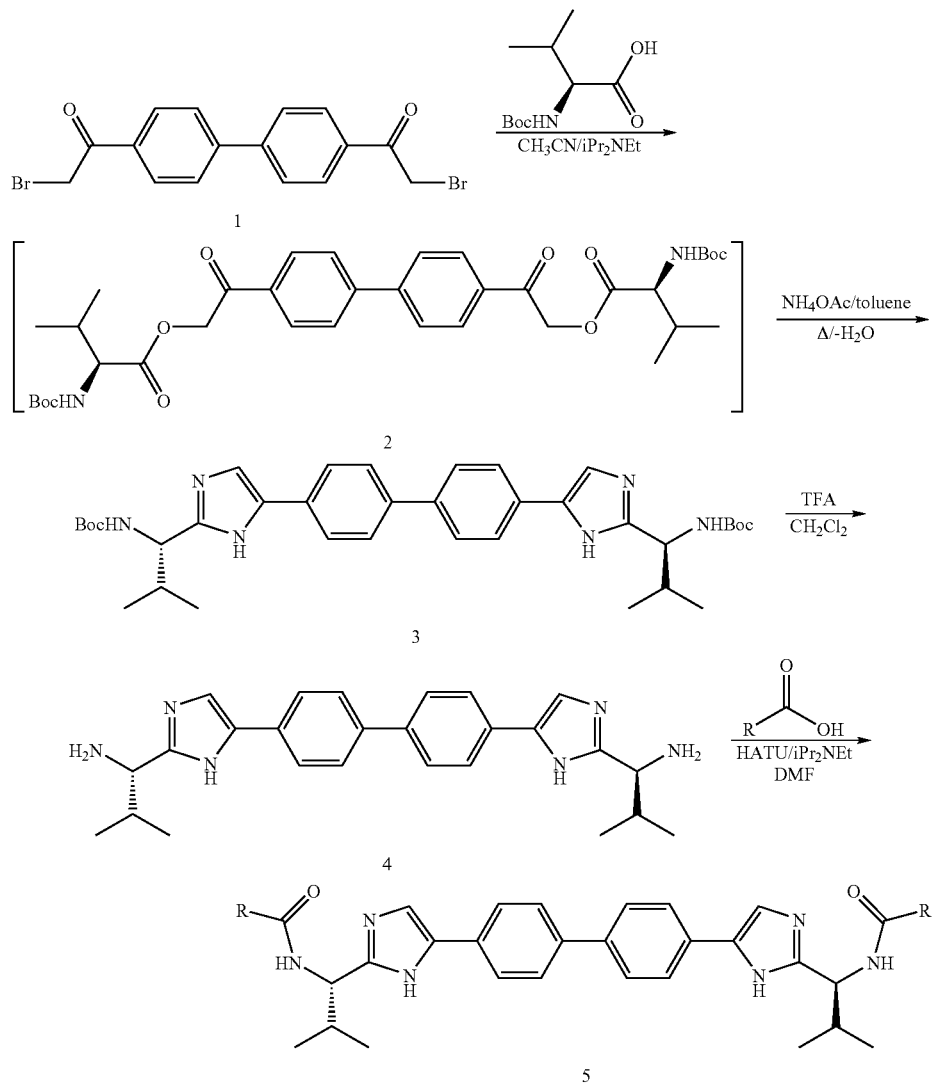

Example R1 tert-butyl(1S,1'S)-1,1'-(5,5'-(biphenyl-4,4'-diyl)bis(1H-imidazole-5,2-diyl))bis(2-methylpropane-1,1-diyl)dicarbamate (3)

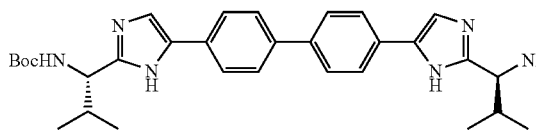

A solution of 1,1'-(biphenyl-4,4'-diyl)bis(2-bromoethanone) (1) (5.14 g, 18.4 mmol) and N-Boc-L-Valine (8.00 g, 36.8 mmol) in dry $CH_3CN$ (40 mL) was treated with $iPr_2NEt$ (7.05 mL, 40.5 mmol) and the solution was allowed to stir at rt overnight. The solvent was removed in vacuo and the resulting slurry was partitioned between EtOAc and $H_2O$. The layers were separated and the aq phase was extracted with EtOAc. The combined organic layers were dried over $MgSO_4$, filtered, and concentrated in vacuo. The residue was suspended in toluene (100 mL) and $NH_4OAc$ (14.2 g, 184.2 mmol) was added. The mixture was heated reflux for 16 h with azeotropic removal of $H_2O$ (Dean-Stark). The mixture was cooled to rt and concentrated to dryness in vacuo. The residue was purified column chromatography (biotage) eluting with 0 to 40% $CH_3CN$ in $CH_2Cl_2$ and then 10% MeOH in $CH_2Cl_2$ to afford the title compound (5.77 g, 50%) as a yellow foam. $^1$HNMR (500 MHz, DMSO-$d_6$) δ 11.77-11.93 (m, 2H), 7.80 (s, br, 4H), 7.66-7.68 (m, 4H), 7.53 (s, br, 2H), 6.89 (d, J=7.7 Hz, 2H), 4.43 (app t, J=8.2 Hz, 2H), 2.05-2.11 (m, 2H), 1.38 (s, 18H), 0.90 (d, J=6.6 Hz, 6H), 0.78 (d, J=6.6 Hz, 6H). LCMS: Anal. Calcd. for $C_{36}H_{48}N_6O_4$: 628; found: 629 (M+H)$^+$.

Example R2 tert-butyl (1R,1'R)-1,1'-(5,5'-(biphenyl-4,4'-diyl)bis(1H-imidazole-5,2-diyl))bis(2-methylpropane-1,1-diyl)dicarbamate

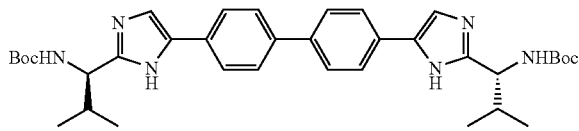

The title compound was prepared according to the method in Example R1 starting with 1,1'-(biphenyl-4,4'-diyl)bis(2-bromoethanone) (1) and N-Boc-D-Valine. LCMS: Anal. Calcd. for $C_{36}H_{48}N_6O_4$: 628; found: 629 (M+H)$^+$.

Example R3

(1S,1'S)-1,1'-(5,5'-(biphenyl-4,4'-diyl)bis(1H-imidazole-5,2-diyl))bis(2-methylpropan-1-amine)

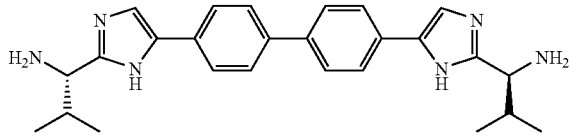

A solution of tert-butyl(1R,1'R)-1,1'-(5,5'-biphenyl-4,4'-diyl)bis(1H-imidazole-5,2-diyl))bis(2-methylpropane-1,1-diyl)dicarbamate (1.00 g, 1.59 mmol) in $CH_2Cl_2$ (30 mL) was added TFA (20 mL) and the solution was allowed to stir at rt for 5 h. The solvents were removed in vacuo, the residue was dissolved in $CH_2Cl_2$: MeOH (1:1) (ca. 10 mL) and absorbed onto an MCX cation exchange cartridge (Oasis). The resin was washed with MeOH and the desired material was released by elution with $NH_3$ in MeOH (2M). The solvents were removed in vacuo to afford the title compound (0.622 g, 91%) as a yellow foam which was sufficiently pure for use in subsequent steps. $^1$HNMR (300 MHz, $CD_3OD$) δ 7.76 (app d, J=8.4 Hz, 4H), 7.68 (app d, J=8.4 Hz, 4H), 7.38 (s, 2H), 3.77 (d, J=7.3 Hz, 2H), 2.07 (sept, J=7.0 Hz, 2H), 1.03 (d, J=7.0 Hz, 6H), 0.88 (d, J=7.0 Hz, 6H). LCMS: Anal. Calcd. for $C_{26}H_{32}N_6$: 428; found: 429 (M+H)$^+$.

Example R4

(1R,1'R)-1,1'-(5,5'-(biphenyl-4,4'-diyl)bis(1H-imidazole-5,2-diyl))bis(2-methylpropan-1-amine)

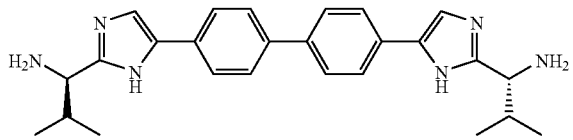

The title compound was prepared according to the method given in Example R3 starting with tert-butyl (1R,1'R)-1,1'-(5,5'-(biphenyl-4,4'-diyl)bis(1H-imidazole-5,2-diyl))bis(2-methylpropane-1,1-diyl)dicarbamate. LCMS: Anal. Calcd. for $C_{26}H_{32}N_6$: 428; found: 429 (M+H)$^+$.

Example R5 dimethyl(4,4'-biphenyldiylbis(1H-imidazole-4,2-diyl((1S)-2-methyl-1,1-propanediyl)imino((2S)-1-oxo-1,2-propanediyl)))biscarbamate

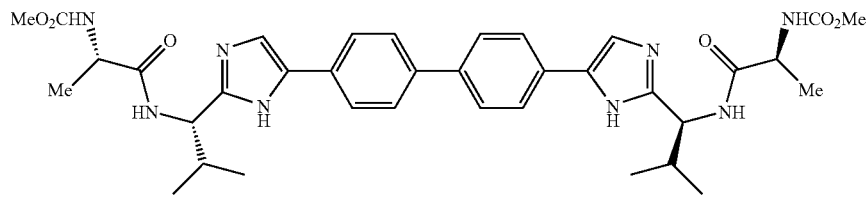

A solution of (1S,1'S)-1,1'-(5,5'-(biphenyl-4,4'-diyl)bis(1H-imidazole-5,2-diyl))bis(2-methylpropan-1-amine) (120 mg, 0.280 mmol), (S)-2-(methoxycarbonylamino)propanoic acid (124 mg, 0.840 mmol) and iPr$_2$NEt (0.489 mL, 2.80 mmol) in DMF (5 mL) was treated with HATU (426 mg, 1.12 mmol) and the reaction mixture was stirred at rt for 2 h. The reaction mixture was partitioned between H$_2$O and EtOAc, the layers separated and the aq phase was extracted with EtOAc. The combined organic layers were concentrated in vacuo and purified by column chromatography (Biotage, 25S eluting with 0 to 40% CH$_3$CN in CH$_2$Cl$_2$ and then 10% MeOH in CH$_2$Cl$_2$. The appropriate fractions were concentrated in vacuo and the residue was purified by prep HPLC (CH$_3$CN—H$_2$O-TFA). Two subsequent purifications by prep HPLC (CH$_3$CN—H$_2$O—NH$_4$OAc) followed by a final prep HPLC (CH$_3$CN—H$_2$O-TFA) afforded the TFA salt of the title compound (4.9 mg, 2%) as a colorless solid. $^1$HNMR (300 MHz, CD$_3$OD) δ 7.89 (s, 2H), 7.86 (s, 8H), 4.87 (d, J=8.5 Hz, 2H), 4.19 (q, J=7.0 Hz, 2H), 3.65 (s, 6H), 1.33 (d, J=7.0 Hz, 6H), 1.14 (d, J=7.0 Hz, 6H), 0.96 (d, J=7.0 Hz, 6H). LCMS: Anal. Calcd. for C$_{36}$H$_{46}$N$_8$O$_6$: 686; found: 687 (M+H)$^+$.

TABLE 1A

The following were prepared similarly starting with the appropriate amine and substitute amino acid.

| Example | Compound Name | Structure | Analytical Data |
|---|---|---|---|
| Example R6 | dimethyl (4,4'-biphenyldiylbis(1H-imidazole-4,2-diyl((1S)-2-methyl-1,1-propanediyl)imino((2S,3R)-3-methoxy-1-oxo-1,2-butanediyl)))biscarbamate | 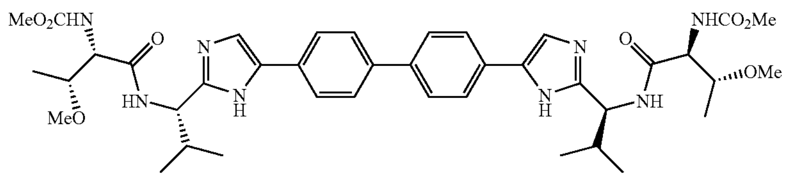 | LCMS: Anal. Calcd. for C$_{40}$H$_{54}$N$_8$O$_8$: 774; found: 775 (M + H)$^+$. |
| Example R7 | dimethyl (4,4'-biphenyldiylbis(1H-imidazole-4,2-diyl((1S)-2-methyl-1,1-propanediyl)imino((2S)-3-methyl-1-oxo-1,2-butanediyl)))biscarbamate | 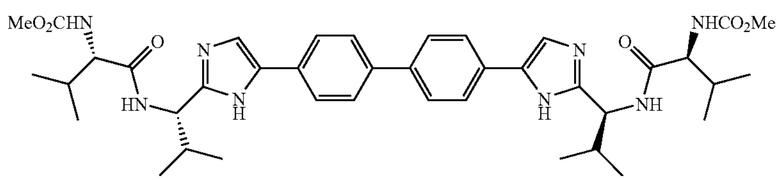 | LCMS: Anal. Calcd. for C$_{40}$H$_{54}$N$_8$O$_6$: 742; found: 743 (M + H)$^+$. |
| Example R8 | dimethyl (4,4'-biphenyldiylbis(1H-imidazole-4,2-diyl((1S)-2-methyl-1,1-propanediyl)imino((2S)-4-methoxy-1-oxo-1,2-butanediyl)))biscarbamate | 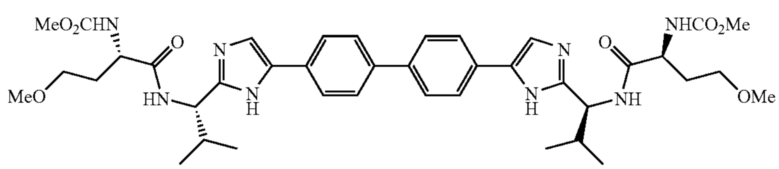 | LCMS: Anal. Calcd. for C$_{40}$H$_{54}$N$_8$O$_8$: 774; found: 775 (M + H)$^+$. |
| Example R9 | dimethyl (4,4'-biphenyldiylbis(1H-imidazole-4,2-diyl((1R)-2-methyl-1,1-propanediyl)imino((2S)-3-methyl-1-oxo-1,2-butanediyl)))biscarbamate | 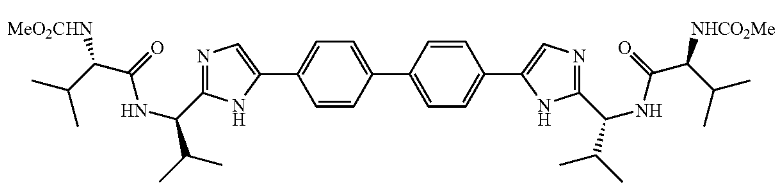 | LCMS: Anal. Calcd. for C$_{40}$H$_{54}$N$_8$O$_6$: 742; found: 743 (M + H)$^+$. |

TABLE 1A-continued

The following were prepared similarly starting with the appropriate amine and substitute amino acid.

| Example | Compound Name | Structure | Analytical Data |
|---|---|---|---|
| Example R10 | dimethyl (4,4'-biphenyldiylbis(1H-imidazole-4,2-diyl((1R)-2-methyl-1,1-propanediyl)imino((2S)-1-oxo-1,2-propanediyl))) biscarbamate | 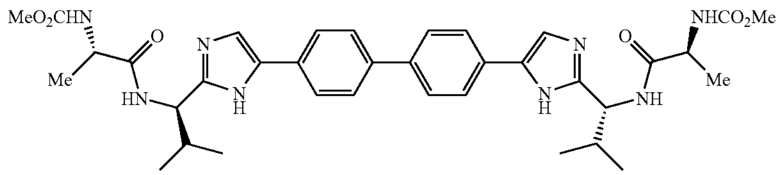 | LCMS: Anal. Calcd. for $C_{36}H_{46}N_8O_6$: 686; found: 687 $(M + H)^+$. |
| Example R11 | dimethyl (4,4'-biphenyldiylbis(1H-imidazole-4,2-diyl((1R)-2-methyl-1,1-propanediyl)imino((2S)-4-methoxy-1-oxo-1,2-butanediyl))) biscarbamate | 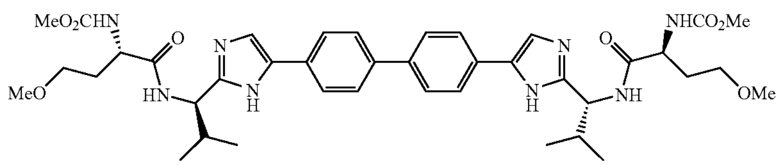 | LCMS: Anal. Calcd. for $C_{40}H_{54}N_8O_8$: 774; found: 775 $(M + H)^+$. |
| Example R12 | dimethyl (4,4'-biphenyldiylbis(1H-imidazole-4,2-diyl((1R)-2-methyl-1,1-propanediyl)imino((2S,3R)-3-methoxy-1-oxo-1,2-butanediyl))) biscarbamate | 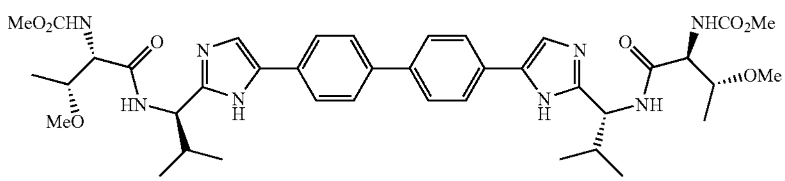 | LCMS: Anal. Calcd. for $C_{40}H_{54}N_8O_8$: 774; found: 775 $(M + H)^+$. |
| Example R13 | dimethyl (4,4'-biphenyldiylbis(1H-imidazole-4,2-diyl((1R)-2-methyl-1,1-propanediyl)imino((2R)-3-methyl-1-oxo-1,2-butanediyl))) biscarbamate | 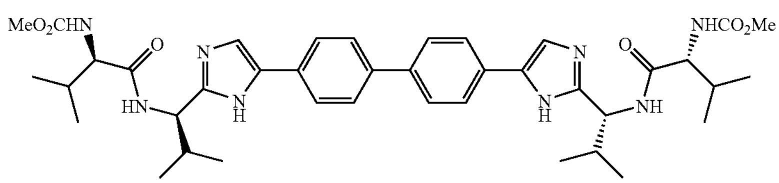 | Anal. Calcd. for $C_{40}H_{54}N_8O_6$: 742; found: 743 $(M + H)^+$. |
| Example R14 | dimethyl (4,4'-biphenyldiylbis(1H-imidazole-4,2-diyl((1S)-2-methyl-1,1-propanediyl)imino((2R)-3-methyl-1-oxo-1,2-butanediyl))) biscarbamate | 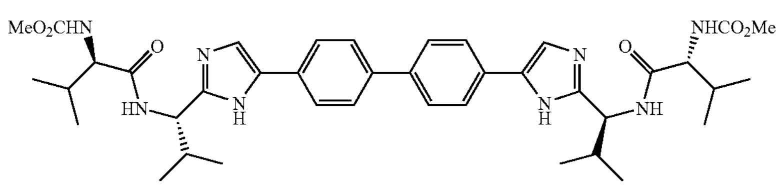 | Anal. Calcd. for $C_{40}H_{54}N_8O_6$: 742; found: 743 $(M + H)^+$. |

Scheme 2

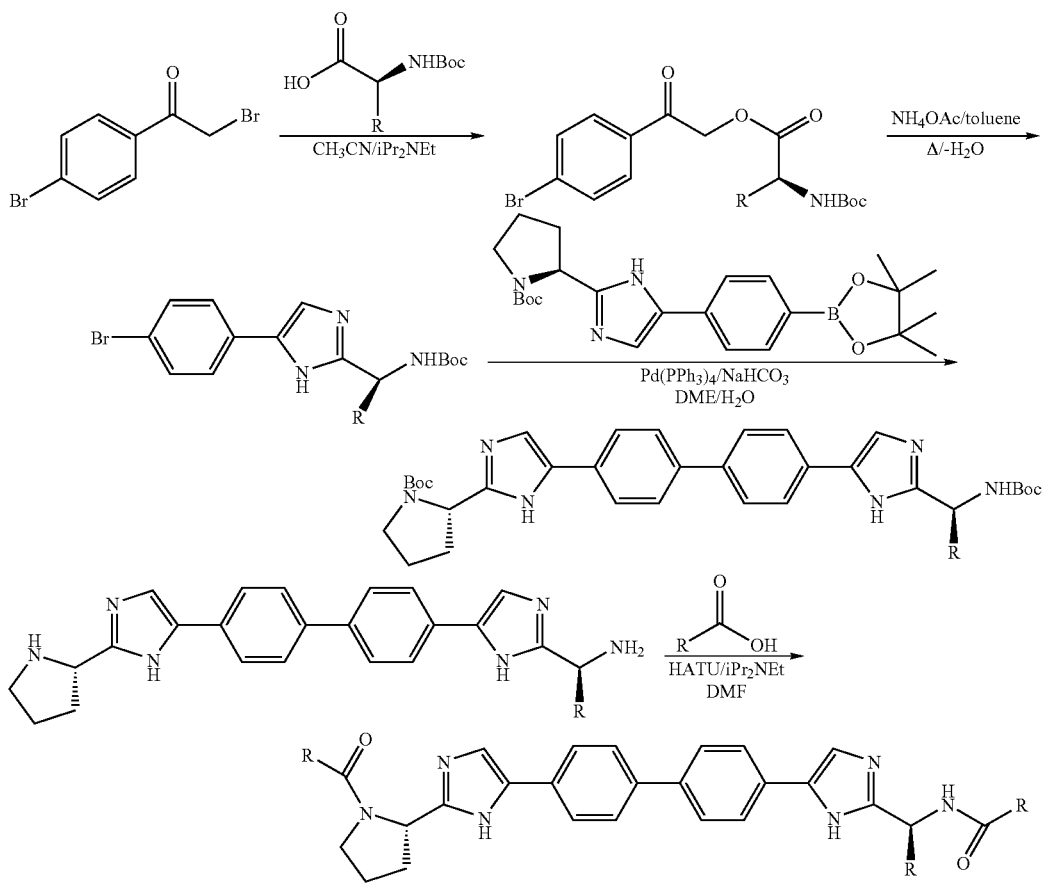

Example R15

(S)-tert-butyl 1-(5-(4-bromophenyl)-1H-imidazol-2-yl)-2-methylpropylcarbamate

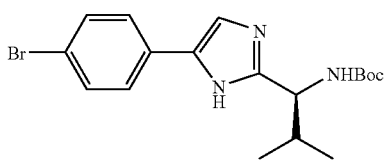

A solution of 2-bromo-1-(4-bromophenyl)ethanone (6.23 g, 22.3 mmol) and N-Boc-L-Valine (5.00 g, 23.0 mmol) in dry CH₃CN (30 mL) was treated with iPr₂NEt (4.40 mL, 25.3 mmol) and the solution was allowed to stir at rt overnight. The solvent was removed in vacuo and the resulting slurry was partitioned between EtOAc and H₂O. The layers were separated and the aq phase was extracted with EtOAc. The combined organic layers were dried over MgSO₄, filtered, and concentrated in vacuo to give a yellow oil. LCMS: Anal. Calcd. for $C_{18}H_{24}BrNO_5$: 413, 415; found: 412, 414 (M−H)⁻. The residue was suspended in toluene (60 mL) and NH₄OAc (8.61 g, 111.7 mmol) was added. The mixture was heated reflux for 16 h with azeotropic removal of H₂O (Dean-Stark). The mixture was cooled to rt and concentrated to dryness in vacuo. The residue was purified column chromatography (biotage) eluting with 10% MeOH in CH₂Cl₂ to afford the title compound (8.55 g, 94%) as a yellow foam. ¹HNMR (500 MHz, CD₃OD) δ 7.84 (s, 1H), 7.66 (app d, J=8.9 Hz, 2H), 7.64 (app d, J=8.9 Hz, 2H), 4.65 (d, J=7.7 Hz, 1H), 2.23-2.27 (m, 1H), 1.42 (s, 9H), 1.07 (d, J=6.5 Hz, 3H), 0.93 (d, J=6.5 Hz, 3H). LCMS: Anal. Calcd. for $C_{18}H_{24}BrN_3O_2$: 393, 395; found: 394, 396 (M+H)⁺.

Example R16

(R)-tert-butyl 1-(5-(4-bromophenyl)-1H-imidazol-2-yl)-2-methylpropylcarbamate

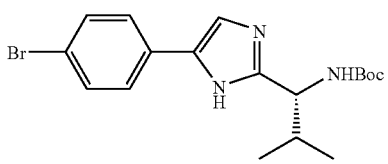

The title compound was prepared starting from 2-bromo-1-(4-bromophenyl)ethanone and N-Boc-D-Valine using the method given in Example 15. ¹HNMR (500 MHz, CD₃OD) δ 7.83 (s, 1H), 7.68 (app d, J=8.7 Hz, 2H), 7.64 (app d, J=8.7 Hz, 2H), 4.65 (d, J=7.3 Hz, 1H), 2.22-2.26 (m, 1H), 1.42 (s, 9H), 1.08 (d, J=6.7 Hz, 3H), 0.93 (d, J=6.7 Hz, 3H). LCMS: Anal. Calcd. for $C_{18}H_{24}BrN_3O_2$: 393, 395; found: 394, 396 (M+H)⁺.

Example R17

(S)-tert-butyl 2-(5-(4'-(2-((S)-1-(tert-butoxycarbonylamino)-2-methylpropyl)-1H-imidazol-5-yl)biphenyl-4-yl)-1H-imidazol-2-yl)pyrrolidine-1-carboxylate

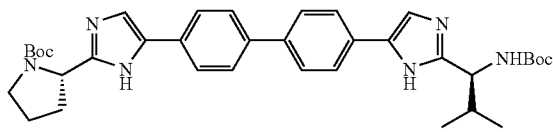

A solution of (S)-tert-butyl 1-(5-(4-bromophenyl)-1H-imidazol-2-yl)-2-methylpropylcarbamate (2.00 g, 5.07 mmol), (S)-tert-butyl 2-(5-(4-(4,4,5,5-tetramethyl-1,3,2-dioxaborolan-2-yl)phenyl)-1H-imidazol-2-yl)pyrrolidine-1-carboxylate (2.23 g, 5.07 mmol) and NaHCO$_3$ (1.49 g, 17.8 mmol) in DME (50 mL) and Water (15 mL) was degassed by evacuating and backfilling with N$_2$.

Tetrakis(triphenylphosphine)palladium(0) (0.293 g, 0.254 mmol) was added and the reaction mixture was heated overnight at 100° C. The mixture was cooled to rt and the DME was removed in vacuo. The residue was partitioned between H$_2$O and EtOAc and the layers separated. The aq phase was extracted with EtOAc and the combined organic layers were concentrated to dryness in vacuo and purified by column chromatography (Biotage) eluting with a gradient of 0 to 40% CH$_3$CN in CH$_2$Cl$_2$ and then 0 to 10% MeOH in CH$_2$Cl$_2$. The title compound (2.05 g, 65% yield) was obtained as a brown foam. This material was used as is in subsequent steps. LCMS: Anal. Calcd. for C$_{36}$H$_{46}$N$_6$O$_4$: 626; found: 627 (M+H)$^+$.

Example R17A (S)-2-methyl-1-(5-(4'-(2-((S)-pyrrolidin-2-yl)-1H-imidazol-5-yl)biphenyl-4-yl)-1H-imidazol-2-yl)propan-1-amine

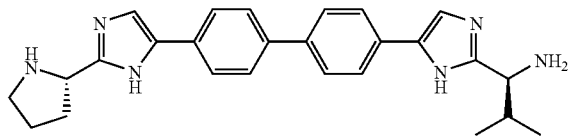

To a solution of (S)-tert-butyl 2-(5-(4'-(2-((S)-1-(tert-butoxycarbonylamino)-2-methylpropyl)-1H-imidazol-5-yl)biphenyl-4-yl)-1H-imidazol-2-yl)pyrrolidine-1-carboxylate (2.05 g, 3.27 mmol) in CH$_2$Cl$_2$ (20 mL) was added TFA (5 mL, 64.9 mmol) and the solution was allowed to stir for 2 h. The solvents were removed in vacuo, the residue was dissolved in CH$_2$Cl$_2$: MeOH (1:1) (ca. 10 mL) and absorbed onto an MCX cation exchange cartridge (Oasis). The resin was washed with MeOH and the desired material was released by elution with NH$_3$ in MeOH (2M). The solvents were removed in vacuo to afford the title compound (0.622 g, 91%) as a yellow foam which was sufficiently pure for use in subsequent steps. $^1$HNMR (500 MHz, CD$_3$OD) δ 7.85-7.88 (m, 4H), 7.75 (m, app d, J=8.2 Hz, 4H), 7.70 (app d, J=5.8 Hz, 2H), 4.96 (t, J=8.2 Hz, 1H), 4.30 (d, J=8.5 Hz, 1H), 3.54-3.57 (m, 1H), 3.47-3.52 (m, 1H), 2.55-2.62 (m, 1H), 2.38-2.46 (m, 1H), 2.28-2.36 (m, 1H), 2.15-2.24 (m, 1H), 1.17 (d, J=6.7 Hz, 3H), 0.94 (d, J=6.7 Hz, 3H). LCMS: Anal. Calcd. for C$_{26}$H$_{30}$N$_6$: 426; found: 427 (M+H)$^+$.

Example R18

N$^2$-(methoxycarbonyl)-N-((1S)-1-(4-(4'-(2-((2S)-1-(N-(methoxycarbonyl)-L-valyl)-2-pyrrolidinyl)-1H-imidazol-4-yl)-4-biphenylyl)-1H-imidazol-2-yl)-2-methylpropyl)-L-valinamide

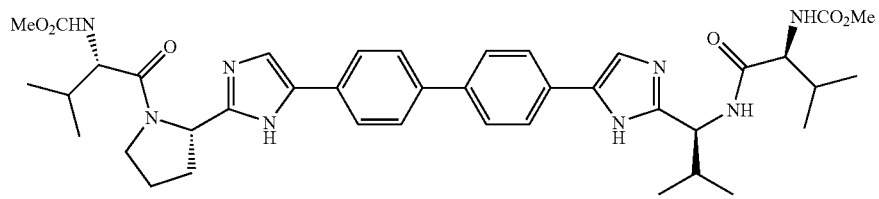

A single neck 50 mL flask equipped with a magnetic stirrer was charged with (S)-2-methyl-1-(5-(4'-(2-((S)-pyrrolidin-2-yl)-1H-imidazol-5-yl)biphenyl-4-yl)-1H-imidazol-2-yl)propan-1-amine (80 mg, 0.188 mmol) and (S)-2-(methoxycarbonylamino)-3-methylbutanoic acid (99 mg, 0.563 mmol) in DMF (5 mL) and DIEA (0.328 mL, 1.875 mmol) was added. To this solution was added HATU (285 mg, 0.750 mmol) added and the reaction was allowed to stir for 4 h rt. The reaction mixture was partitioned between H$_2$O and EtOAc, the layers separated and the aq phase was extracted with EtOAc. The combined organic layers were concentrated in vacuo and purified by column chromatography (Biotage, 25S) eluting with 0 to 40% CH$_3$CN in CH$_2$Cl$_2$ and then 10% MeOH in CH$_2$Cl$_2$. The appropriate fractions were concentrated in vacuo and the residue was purified by prep HPLC (CH$_3$CN—H$_2$O-TFA) and then a subsequent purification by prep HPLC (CH$_3$CN—H$_2$O—NH$_4$OAc) gave the title compound (31.8 mg, 23%) as a colorless solid. $^1$HNMR (500 MHz, CD$_3$OD) δ 7.71 (m, 4H), 7.64-7.67 (m, 4H), 7.35 (s, 1H), 7.32 (s, 1H), 5.33-5.34 (m, 0.2H), 5.17 (dd, J=7.6, 5.5 Hz, 0.8H), 4.77 (d, J=9.2 Hz, 1H), 4.22 and 4.10 (d, J=7.6 Hz, 1H, rotamers 4:1 ratio), 3.97-4.01 (m, 1H), 3.94 (d, J=7.0 Hz, 1H), 3.84-3.89 (m, 1H), 3.64 (s, 6H), 2.28-2.35 (m, 1H), 2.18-2.27 (m, 3H), 1.98-2.08 (m, 3H), 1.05 (d, J=6.7 Hz, 3H), 0.98 and 0.94 (d, J=6.7 Hz, 3H), 0.90 (d, J=6.7 Hz, 6H), 0.88 (d, J=6.7 Hz, 3H), 0.86 (d, J=6.7 Hz, 3H). LCMS: Anal. Calcd. for C$_{40}$H$_{52}$N$_8$O$_6$: 740; found: 741 (M+H)$^+$.

TABLE 2A

The following were prepared similarly starting with the appropriate amine and substitute amino acid.

| Example | Compound Name | Structure | Analytical Data |
|---|---|---|---|
| Example R19 | methyl ((1S,2R)-2-methoxy-1-(((2S)-2-(4-(4'-(2-((1S)-1-((N-(methoxycarbonyl)-O-methyl-L-threonyl)amino)-2-methylpropyl)-1H-imidazol-4-yl)-4-biphenylyl)-1H-imidazol-2-yl)-1-pyrrolidinyl)carbonyl)propyl)carbamate | 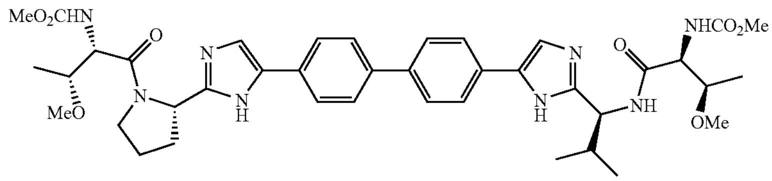 | LCMS: Anal. Calcd. for $C_{40}H_{52}N_8O_8$: 772 found: 773 $(M + H)^+$. |
| Example R20 | methyl ((1S)-3-methoxy-1-(((2S)-2-(4-(4'-(2-((1S)-1-((N-(methoxycarbonyl)-O-methyl-L-homoseryl)amino)-2-methylpropyl)-1H-imidazol-4-yl)-4-biphenylyl)-1H-imidazol-2-yl)-1-pyrrolidinyl)carbonyl)propyl)carbamate | 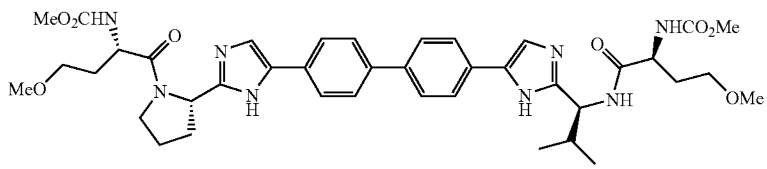 | LCMS: Anal. Calcd. for $C_{40}H_{52}N_8O_8$: 772 found: 773 $(M + H)^+$. |
| Example R21 | methyl ((1S)-2-((2S)-2-(4-(4'-(2-((1S)-1-((N-(methoxycarbonyl)-L-alanyl)amino)-2-methylpropyl)-1H-imidazol-4-yl)-4-biphenylyl)-1H-imidazol-2-yl)-1-pyrrolidinyl)-1-methyl-2-oxoethyl)carbamate | 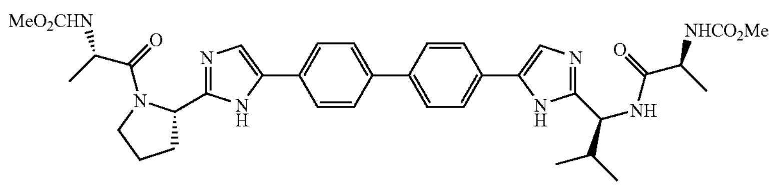 | LCMS: Anal. Calcd. for $C_{36}H_{44}N_8O_6$: 684; found: 685 $(M + H)^+$. |
| Example R22 | $N^2$-(methoxy-carbonyl)-N-((1R)-1-(4-(4'-(2-((2S)-1-(N-(methoxycarbonyl)-L-valyl)-2-pyrrolidinyl)-1H-imidazol-4-yl)-4-biphenylyl)-1H-imidazol-2-yl)-2-methylpropyl)-L-valinamide | 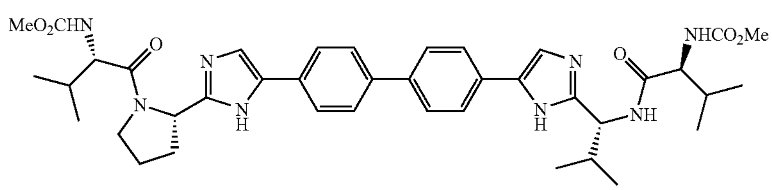 | LCMS: Anal. Calcd. for $C_{40}H_{52}N_8O_6$: 740; found: 741 $(M + H)^+$. |
| Example R23 | methyl ((1S,2R)-2-methoxy-1-(((2S)-2-(4-(4'-(2-((1R)-1-((N-(methoxycarbonyl)-O-methyl-L-threonyl)amino)-2-methylpropyl)-1H-imidazol-4-yl)-4-biphenylyl)-1H-imidazol-2-yl)-1-pyrrolidinyl)carbonyl)propyl)carbamate | 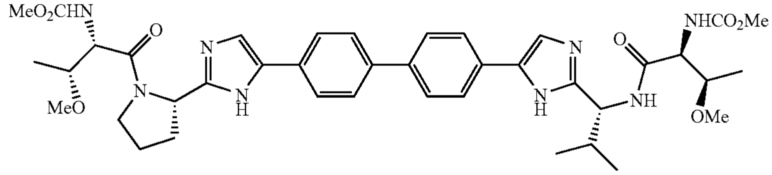 | LCMS: Anal. Calcd. for $C_{40}H_{52}N_8O_8$: 772 found: 773 $(M + H)^+$. |

TABLE 2A-continued

The following were prepared similarly starting with the appropriate amine and substitute amino acid.

| Example | Compound Name | Structure | Analytical Data |
|---|---|---|---|
| Example R24 | methyl ((1S)-3-methoxy-1-(((2S)-2-(4-(4'-(2-((1R)-1-((N-(methoxycarbonyl)-O-methyl-L-homoseryl)amino)-2-methylpropyl)-1H-imidazol-4-yl)-4-biphenylyl)-1H-imidazol-2-yl)-1-pyrrolidinyl)carbonyl)propyl)carbamate | 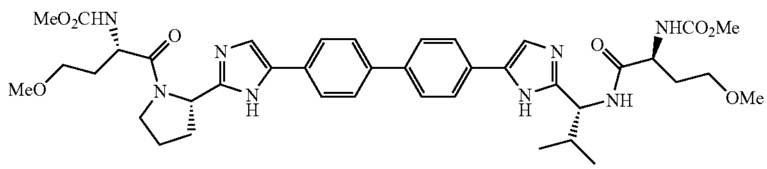 | LCMS: Anal. Calcd. for $C_{40}H_{52}N_8O_8$: 772; found: 773 (M + H)+. |
| Example R25 | methyl ((1S)-2-((2S)-2-(4-(4'-(2-((1R)-1-((N-(methoxycarbonyl)-L-alanyl)amino)-2-methylpropyl)-1H-imidazol-4-yl)-4-biphenylyl)-1H-imidazol-2-yl)-1-pyrrolidinyl)-1-methyl-2-oxoethyl)carbamate | 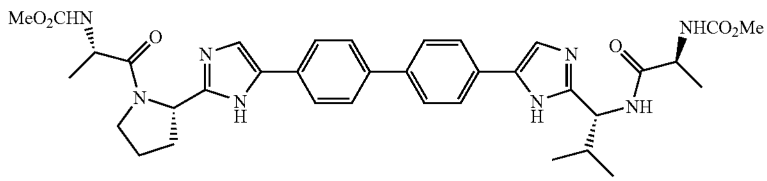 | LCMS: Anal. Calcd. for $C_{36}H_{44}N_8O_6$: 684; found: 685 (M + H)+. |

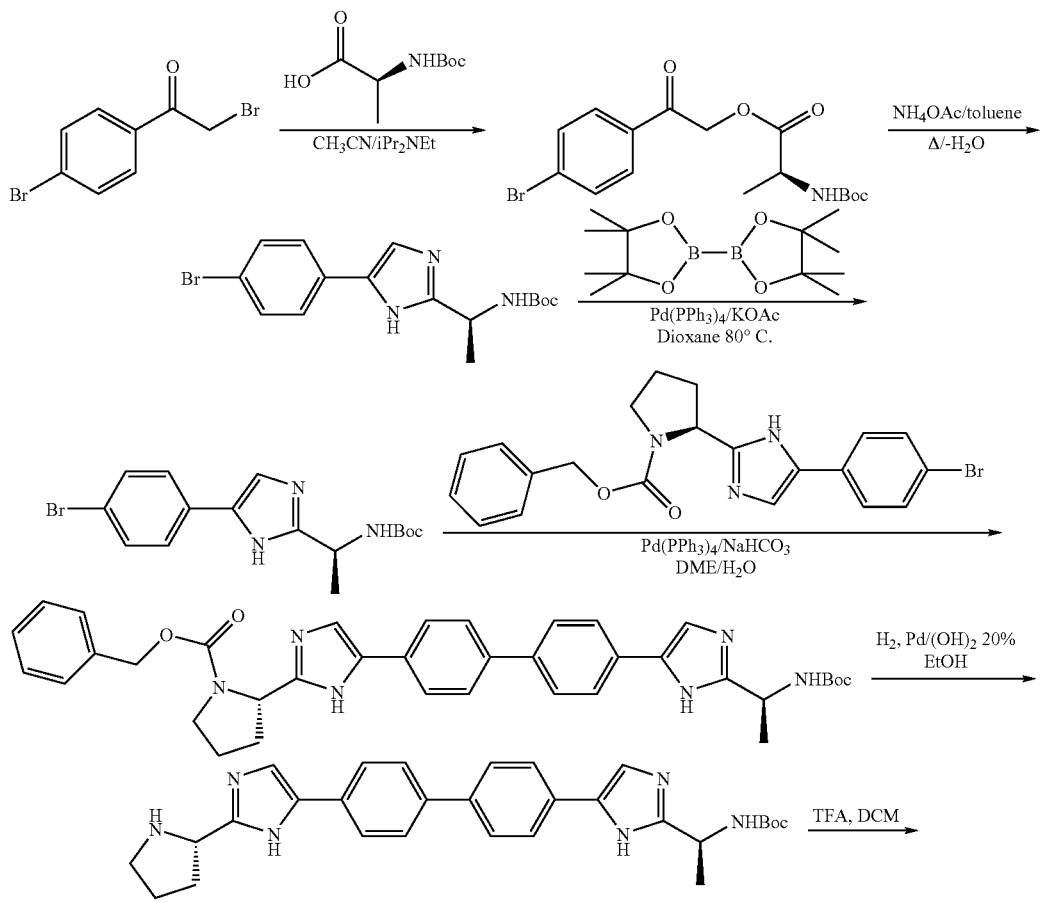

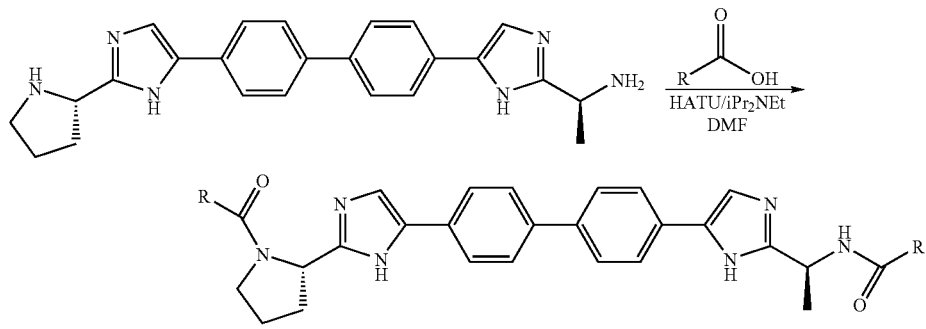

| Example | Structure | Analytical Data |
|---|---|---|
| Example A | 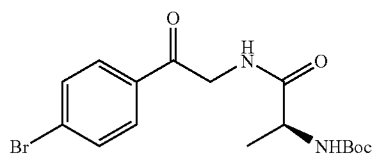 | LCMS: Anal. Calcd. for $C_{16}H_{21}BrN_2O_4$: 385 found: 386 (M + H)+. |
| Example B | 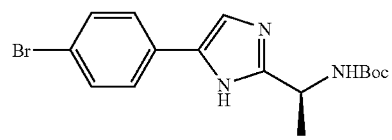 | LCMS: Anal. Calcd. for $C_{16}H_{21}BrN_3O_2$: 366 found: 367 (M + H)+. |
| Example C | 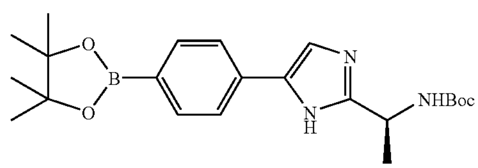 | LCMS: Anal. Calcd. for $C_{22}H_{32}BN_3O_4$: 413; found: 414 (M + H)+. |
| Example D | 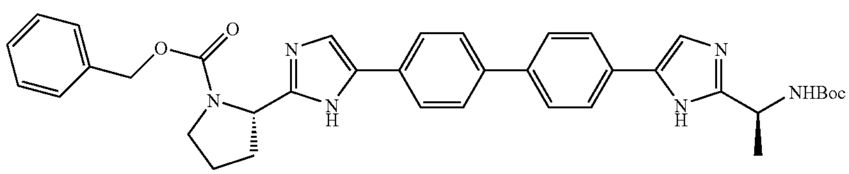 | LCMS: Anal. Calcd. for $C_{37}H_{40}N_6O_4$: 632; found: 633 (M + H)+. |
| Example E | 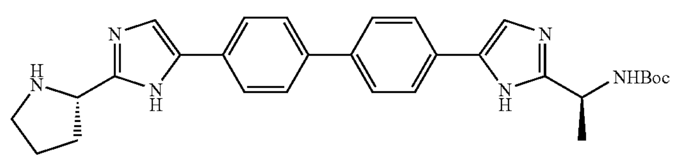 | LCMS: Anal. Calcd. for $C_{29}H_{34}N_6O_2$: 498 found: 499 (M + H)+. |
| Example F | 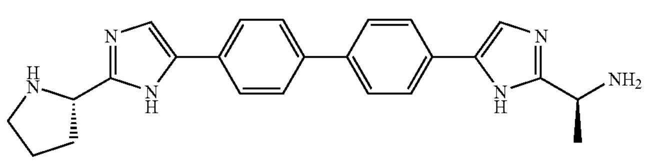 | LCMS: Anal. Calcd. for $C_{24}H_{26}N_6$: 398; found: 399 (M + H)+. |
| Example R26 | 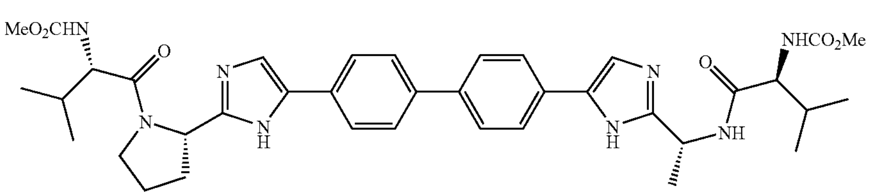 | LCMS: Anal. Calcd. for $C_{38}H_{48}N_8O_6$: 712; found: 713 (M + H)+. |

-continued
| Example | Structure | Analytical Data |
|---|---|---|
| Example R27 | 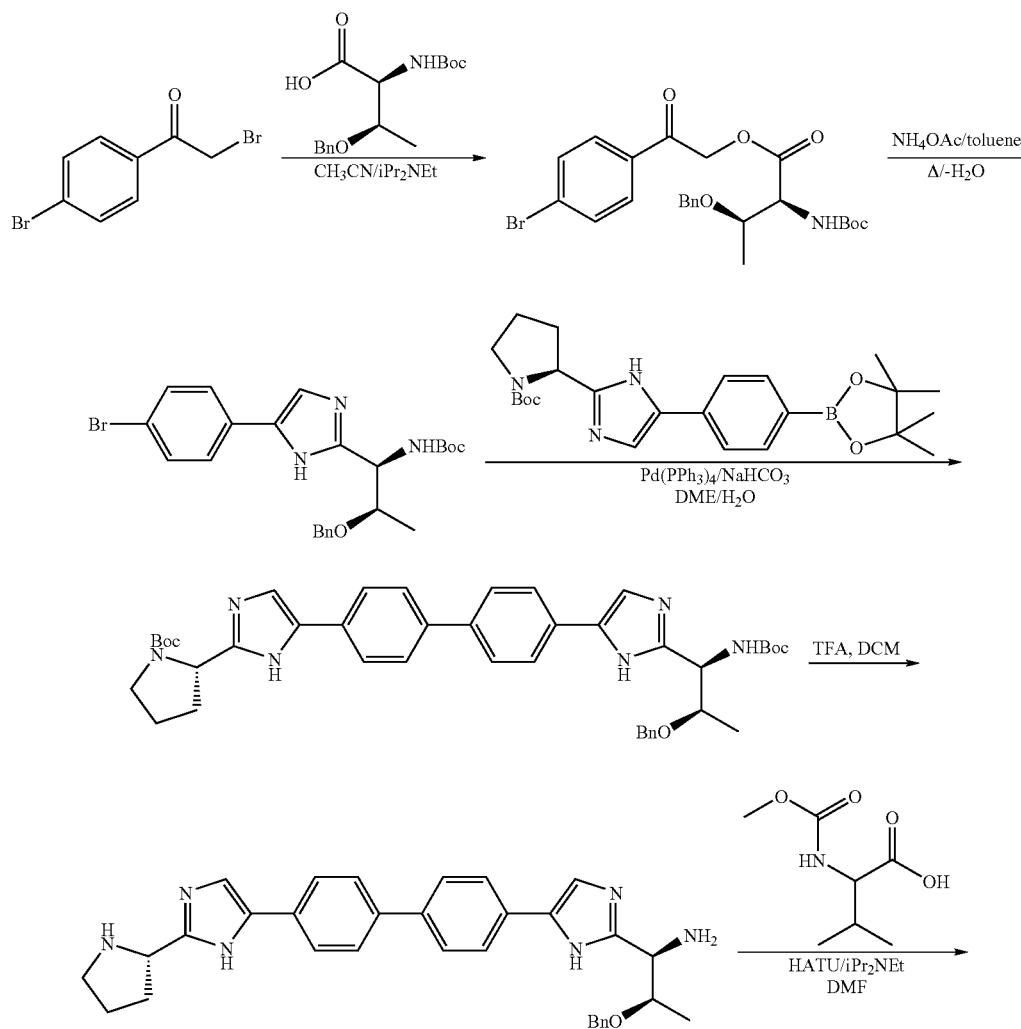 | LCMS: Anal. Calcd. for $C_{38}H_{48}N_8O_8$: 744; found: 745 $(M + H)^+$. |
| Example R28 | 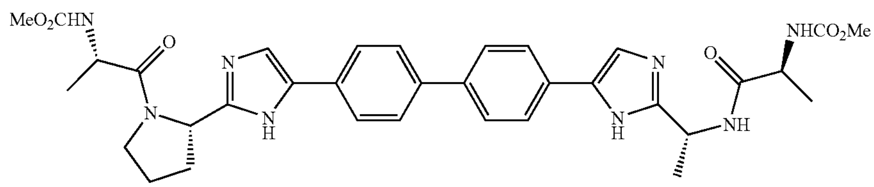 | LCMS: Anal. Calcd. for $C_{34}H_{40}N_8O_6$: 756; found: 757 $(M + H)^+$. |

-continued

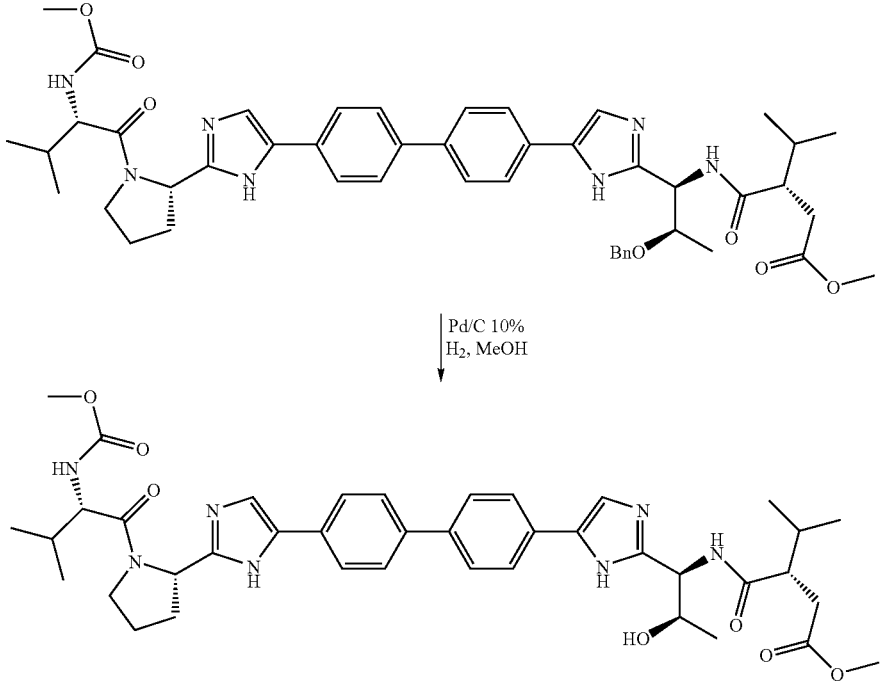

Example R29

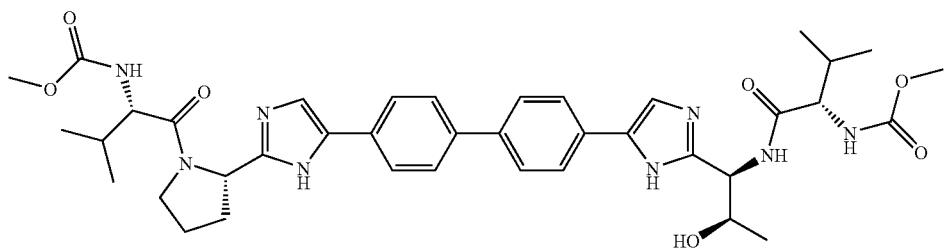

A single neck 50 mL flask equipped with a magnetic stirrer was charged with a compound from, Example E (150 mg, 180 mmol) in Methanol (5 mL). To this solution was added a slurry of Palladium on carbon 10% (100 mg) in Methanol (2 mL). The mixture was purged with 60 psi of Hydrogen. The mixture was shaked on a Parr overnight at room temperature. The contain of the reactor was analyzed by LC-MS and showed a 20% completion. A slurry of Palladium Hydroxide on carbon 20% (100 mg) in Acetic acid (2 mL) was added. The mixture was purged with hydrogen and shake on a Parr shaker with 60 psi of Hydrogen over the weekend. The reaction was filtered through a pad of Celite and the filtrate was evaporated in vacuo. The residue was purified by prep HPLC ($CH_3CN$—$H_2O$-TFA) to give the compound (Example 29) 32 mg 23% yield as a white solid. LCMS: Anal. Calcd. for $C_{39}H_{50}N_8O_7$: 742; found: 743 (M+H)$^+$

| Example | Structure | Analytical Data |
|---------|-----------|-----------------|
| Example G | 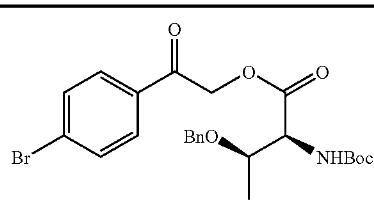 | LCMS: Anal. Calcd. for $C_{24}H_{28}BrNO_6$: 506 found: No ionization (M + H)$^+$. |

-continued
| Example | Structure | Analytical Data |
|---|---|---|
| Example H | 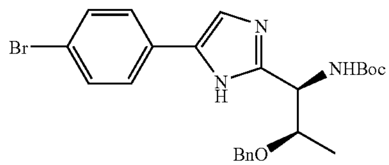 | LCMS: Anal. Calcd. for $C_{24}H_{28}BrN_3O_3$: 486 found: 487 $(M + H)^+$. |
| Example I | 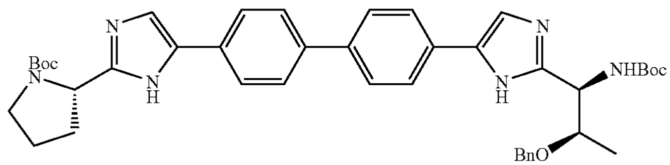 | LCMS: Anal. Calcd. for $C_{42}H_{50}BN_6O_5$: 718 found: 719 $(M + H)^+$. |
| Example J | 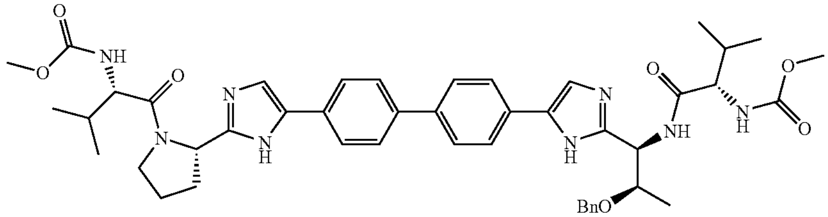 | LCMS: Anal. Calcd. for $C_{46}H_{56}N_8O_7$: 832; found: 833 $(M + H)^+$. |
| Example R29 | 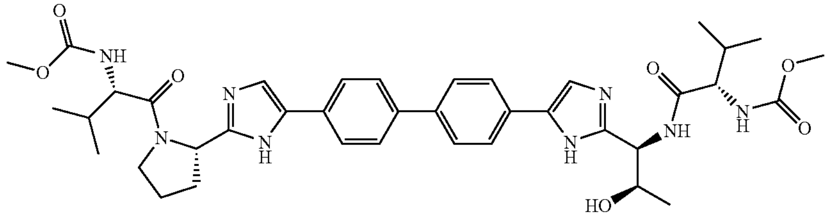 | LCMS: Anal. Calcd. for $C_{46}H_{56}N_8O_7$: 742 found: 743 $(M + H)^+$. |
Scheme 3
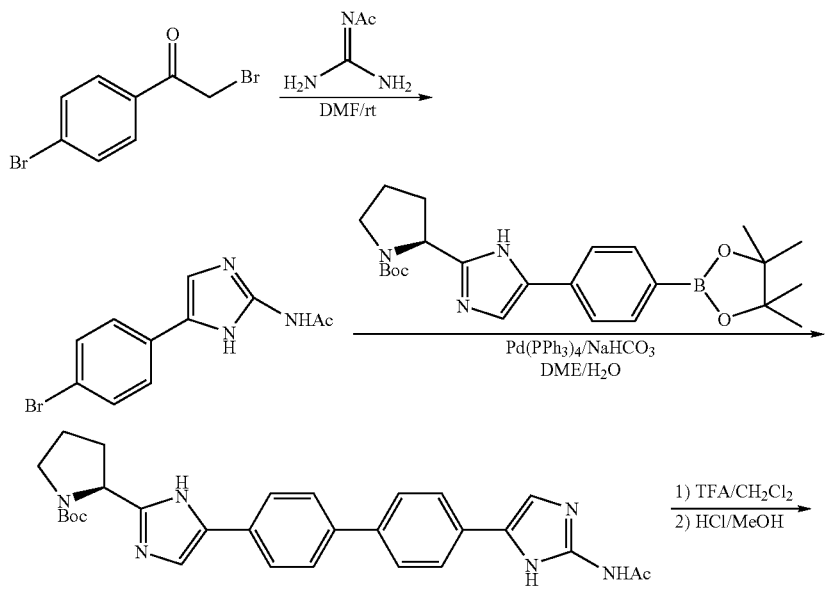

-continued

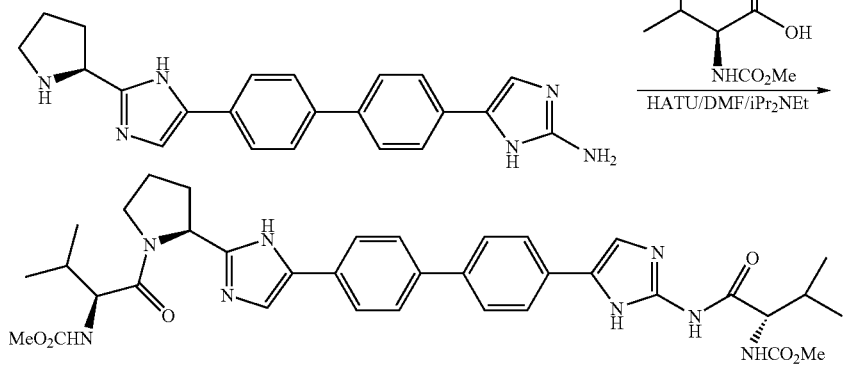

Example R30

N-(5-(4-bromophenyl)-1H-imidazol-2-yl)acetamide

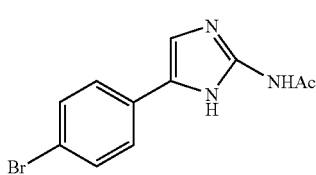

A mixture of 2-bromo-1-(4-bromophenyl)ethanone (2.00 g, 7.20 mmol) and acetylguanidine (2.18 g, 21.6 mmol) in DMF (40 mL) was stirred at rt for 48 h. The solution was concentrated to dryness in vacuo and the resulting brown solid was of sufficient purity for use in the next step. LCMS: Anal. Calcd. for $C_{11}H_{10}BrN_3O$: 279, 281; found: 280, 282 $(M+H)^+$.

Example R31

(S)-tert-butyl 2-(5-(4'-(2-acetamido-1H-imidazol-5-yl)biphenyl-4-yl)-1H-imidazol-2-yl)pyrrolidine-1-carboxylate

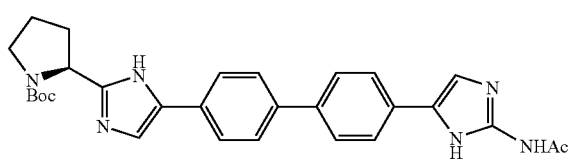

A mixture of N-(5-(4-bromophenyl)-1H-imidazol-2-yl)acetamide (0.604 g, 2.16 mmol), (S)-tert-butyl 2-(5-(4-(4,4,5,5-tetramethyl-1,3,2-dioxaborolan-2-yl)phenyl)-1H-imidazol-2-yl)pyrrolidine-1-carboxylate (0.950 g, 2.16 mmol), NaHCO$_3$ (0.636 g, 7.57 mmol) in DME (20 mL) and H$_2$O (5 mL) was degassed by evacuating and back-filling with N$_2$ (×3). To this solution Pd(PPh$_3$)$_4$ (0.125 g, 0.11 mmol) was added and the suspension heated at 125° C. for 24 h. The mixture was evaporated to dryness in vacuo and the residue was purified by column chromatography (Biotage) eluting with a gradient of 0 to 10% MeOH in CH$_2$C$_2$. The material was then purified by prep HPLC (CH$_3$CN—H$_2$O—NH$_4$OAc) to afford the title compound as a colorless solid. 7.76 (app dd, J=8.4, 2.2 Hz, 4H), 7.69 (app d, J=8.4 Hz, 2H), 7.66 (app d, J=8.4 Hz, 2H), 7.45 (s, 1H), 7.23 (s, 1H), 3.66-3.72 (m, 1H), 3.48-3.53 (s, 1H), 2.34-2.46 (m, 1H), 2.18 (s, 3H), 1.96-2.10 (m, 3H), 1.46, 1.25 (s, 9H, rotamers, 1:2 ratio). LCMS: Anal. Calcd. for $C_{29}H_{32}N_6O_3$: 512; found: 513, 282 $(M+H)^+$.

Example R32

(S)-5-(4'-(2-(pyrrolidin-2-yl)-1H-imidazol-5-yl)biphenyl-4-yl)-1H-imidazol-2-amine

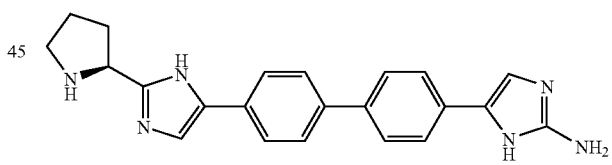

Step 1. A solution of (S)-tert-butyl 2-(5-(4'-(2-acetamido-1H-imidazol-5-yl)biphenyl-4-yl)-1H-imidazol-2-yl)pyrrolidine-1-carboxylate (55.0 mg, 0.11 mmol) in CH$_2$Cl$_2$ (5 mL) and TFA (1 mL) was allowed to stir at rt for 3 h. The reaction mixture was concentrated in vacuo to give the TFA salt of the title compound (55.0 mg) which was carried directly to the next step. LCMS: Anal. Calcd. for $C_{24}H_{24}N_6O$: 412; found: 413 $(M+H)^+$.

Step 2. The brown oil from Step 1 was suspended in 25% conc. HCl in MeOH (10 mL) and heated at reflux for 3 h. The volatiles were removed under reduced pressure and the residue was purified by prep HPLC (CH$_3$CN—H$_2$O-TFA) to give the TFA salt of the title compound (20 mg, 42%). LCMS: Anal. Calcd. for $C_{22}H_{22}N_6$: 370; found: 371 $(M+H)^+$.

Example R33

(S)-2-methoxycarbonylamino-N-(5-(4'-(2-((S)-1-((S)-2-methoxycarbonylamino-3-methylbutanoyl)pyrrolidin-2-yl)-1H-imidazol-5-yl)biphenyl-4-yl)-1H-imidazol-2-yl)-3-methylbutanamide

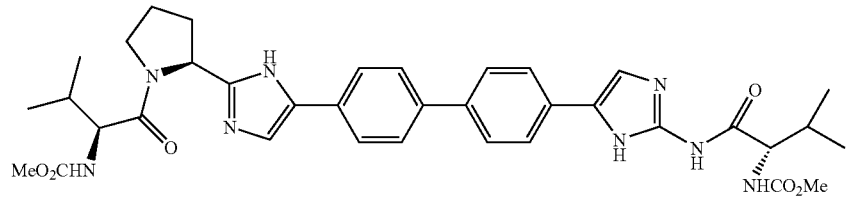

To a solution of (S)-5-(4'-(2-(pyrrolidin-2-yl)-1H-imidazol-5-yl)biphenyl-4-yl)-1H-imidazol-2-amine trifluoroacetic acid salt (20 mg, 0.04 mmol), (S)-2-(methoxycarbonylamino)-3-methylbutanoic acid (25 mg, 0.14 mmol) and iPr$_2$NEt (0.09 mL, 0.53 mmol) in DMF (5 mL) was added HATU (54 mg, 0.14 mmol). The solution was allowed to stir for 3 h and then poured into H$_2$O. The mixture was concentrated to dryness in vacuo and the residue was purified by prep HPLC (CH$_3$CN—H$_2$O-TFA) affording the title compound and recovered starting material. The recovered starting material was resubjected to the reaction conditions and purified as above. The two lots of product were then purified by prep HPLC (CH$_3$CN—H$_2$O—NH$_4$OAc) to give the title compound as a tan solid (18 mg, 76%). $^1$HNMR (400 MHz, CD$_3$OD) δ 7.80-7.88 (m, 9H), 7.56 (s, 1H), 5.24 (app t, J=7.6 Hz, 1H), 4.23 (d, J=7.1 Hz, 1H), 4.18 (d, J=6.6 Hz, 1H), 4.08-4.13 (m, 1H), 3.83-3.90 (m, 1H), 3.68 (s, 3H), 3.65 (s, 3H), 2.54-2.63 (m, 1H), 2.17-2.30 (m, 4H), 2.01-2.09 (m, 1H). LCMS: Anal. Calcd. for C$_{36}$H$_{44}$N$_8$O$_6$: 684; found: 685 (M+H)$^+$.

The following Examples were prepared as described in the above examples using the appropriate starting materials:

Example R34

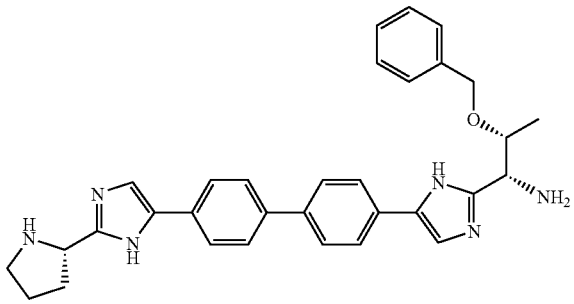

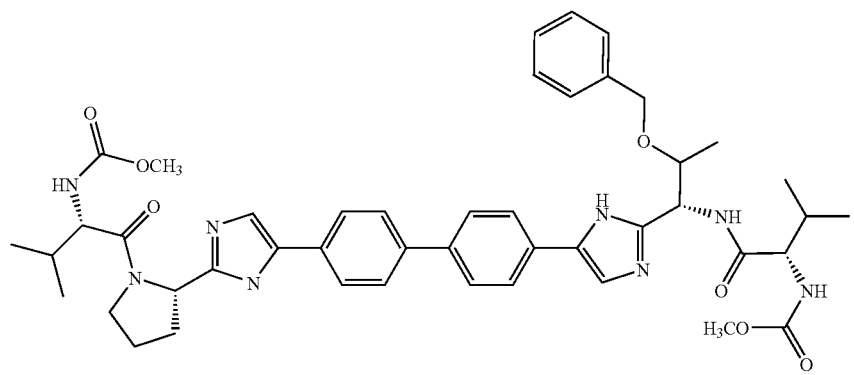

Example R35

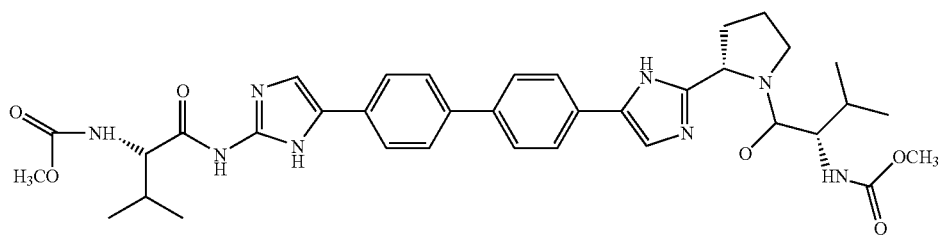

Example R36

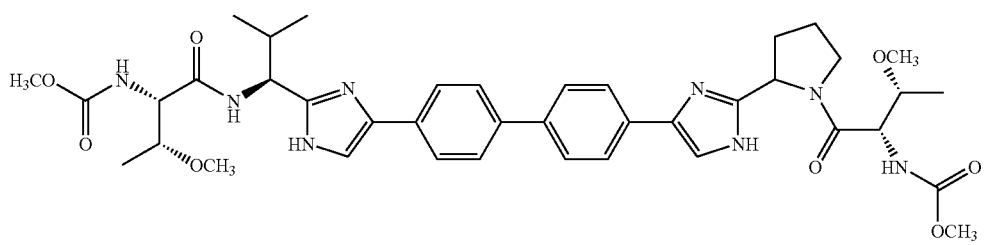

Example R37

Biological Activity

An HCV Replicon assay was utilized in the present disclosure, and was prepared, conducted and validated as described in commonly owned PCT/US2006/022197 and in O'Boyle et. al. *Antimicrob Agents Chemother.* 2005 April; 49(4):1346-53.

HCV 1b-377-neo replicon cells were used to test the currently described compound series as well as cells resistant to compound A due to a Y2065H mutation in NS5A (described in application PCT/US2006/022197). The compounds tested were determined to have more than 10-fold less inhibitory activity on cells resistant to compound A than wild-type cells indicating a related mechanism of action between the two compound series. Thus, the compounds of the present disclosure can be effective to inhibit the function of the HCV NS5A protein and are understood to be as effective in combinations as previously described in application PCT/US2006/022197 and commonly owned WO/O4014852. Further, the compounds of the present disclosure can be effective against the HCV 1b genotype. It should also be understood that the compounds of the present disclosure can inhibit multiple genotypes of HCV. Table 2 shows the EC50 values of representative compounds of the present disclosure against the HCV 1b genotype. In one embodiment compounds of the present disclosure are active against the 1a, 1b, 2a, 2b, 3a, 4a, and 5a genotypes. EC50 ranges against HCV 1b are as follows: A=1-10 μM; B=100-999 nM; C=1-99 nM; and D=1-999 μM.

The compounds of the present disclosure may inhibit HCV by mechanisms in addition to or other than NS5A inhibition. In one embodiment the compounds of the present disclosure inhibit HCV replicon and in another embodiment the compounds of the present disclosure inhibit NS5A.

TABLE 2

| Example | Range |
| --- | --- |
| 1 | D |
| 24-4e | C |
| 24-4f | B |
| 24-4g | A |
| 25-1 | D |
| 25-2 | D |
| 25-3 | D |
| 25-4 | D |
| 25-5 | D |
| 25-6 | C |
| 25-7 | C |
| 25-8 | D |
| 24-4h | D |
| 120-9 | D |
| 120 | D |
| 120-5 | C |
| 120-6 | C |
| 120-7 | D |
| 120-8 | C |
| 103-3 | D |
| 103-4 | D |
| 103-1 | D |
| 103-2 | D |
| 103-5 | D |
| 103-6 | C |
| 103-8 | D |
| 103-7 | D |
| 151 isomer 1 | C |
| 151 isomer 2 | B |
| 152j-9 | C |
| 152j-10 | C |
| 152j-1 | C |
| 152j-2 | D |
| 153c-5 | C |
| 153c-6 | C |
| 153c-2 | C |
| 153c-1 | C |
| 152j-7 | C |
| 152j-8 | D |
| 153c-3 | A |

TABLE 2-continued

| Example | Range |
|---|---|
| 153c-4 | A |
| 152j-11 | D |
| 152j-12 | D |
| 152j-15 | D |
| 152j-28 | D |
| 152j-13 | C |
| 152j-14 | C |
| 152j-19 | D |
| 152j-16 | D |
| 152j-3 | D |
| 152j-20 | C |
| 152j-17 | D |
| 152j-18 | D |
| 152j-3 | D |
| 152j-5 | D |
| 152j-6 | D |
| 152l-2 | D |
| 152l-1 | D |
| 152j-24 | D |
| 152j-23 | D |
| 153c-7 | C |
| 152j-22 | D |
| 24-18-2 | D |
| 24-18-1 | D |
| 24-18-4 | D |
| 24-18-5 | D |
| 24-18-6 | D |
| 24-18-3 | D |
| 152j-21 | D |
| 152l-3 | D |
| 131.1-2 | D |
| 131.1-1 | D |
| 24-4a | D |
| 120-1 | D |
| 120-2 | D |
| 120-3 | D |
| 120-4 | D |
| 24-10 | D |
| 24-9 | D |
| 24-8 | D |
| 24-11 | C |
| 24-12 | C |
| 11 | C |
| 24-16 | D |
| 24-18 | D |
| 24-17 | D |
| 24-15 | C |
| 24-13 | B |
| 24-14 | C |
| 24-4b | C |
| 24-4c | D |
| 24-4d | D |
| 148 | C |
| 149 | D |
| 150 | C |
| 24-5 | D |
| 24-6 | D |
| 24-7 | D |
| 24-1 | D |
| 24-2 | D |
| 24-3 | D |
| 28-1 | D |
| 28-2 | D |
| 28-3 | D |
| 28-4 | D |
| 28-5 | D |
| 84-1 | D |
| 84-2 | D |
| 84-3 | D |
| 84-4 | D |
| 84-7 | C |
| 84-10 | C |
| 84-12 | D |
| 84-14 | C |
| 84-15 | C |
| 84-17 | D |
| 84-18 | C |

TABLE 2-continued

| Example | Range |
|---|---|
| 84-19 | C |
| 84-20 | C |
| 84-24 | D |
| 84-26 | D |
| 84-27 | D |
| 84-28 | D |
| 84-32 | D |
| 84-33 | D |
| 84-34 | C |
| 84-35 | D |
| 84-36 | D |
| 84-38 | D |
| 84-39 | D |
| 84-40 | D |
| 84-44 | D |
| 84-46 | D |
| 84-47 | D |
| 84-48 | D |
| 84-49 | D |
| 84-50 | D |
| 84-51 | D |
| 84-52 | D |
| 84-53 | D |
| 84-54 | D |
| 84-55 | D |
| 84-56 | D |
| 84-57 | D |
| 84-58 | D |
| 84-59 | D |
| 84-60 | D |
| 84-61 | D |
| 84-62 | D |
| 84-63 | D |
| 84-64 | D |
| 84-65 | C-D |
| 84-66 | C-D |
| 84-67 | D |
| 84-68 | C |
| 84-69 | D |
| 84-70 | C |
| 84-71 | C |
| 84-72 | C |
| 84-73 | C |
| 84-74 | D |
| 84-75 | C |
| 84-76 | D |
| 84-77 | D |
| 84-78 | D |
| 84-79 | D |
| 84-80 | D |
| 84-81 | D |
| 84-82 | D |
| 84-83 | D |
| 84-84 | D |
| 84-85 | D |
| 84-86 | D |
| 84-87 | D |
| 94-1 | D |
| 94-2 | C |
| 94-3 | D |
| 94-6 | C-D |
| 94-9 | D |
| 94-10 | D |
| 94-12 | C |
| 94-13 | D |
| 94-17 | D |
| 94-19 | D |
| 94-20 | C |
| 94-24 | D |
| 94-25 | D |
| 94-26 | D |
| 94-27 | C |
| 94-30 | D |
| 94-32 | C |
| 94-33 | C |
| 94-34 | C |
| 94-36 | D |

TABLE 2-continued

| Example | Range |
|---|---|
| 94-37 | C |
| 94-38 | D |
| 94-42 | D |
| 94-44 | D |
| 94-45 | D |
| 94-46 | D |
| 94-47 | D |
| 94-48 | D |
| 94-49 | D |
| 94-50 | D |
| 94-51 | D |
| 94-52 | D |
| 94-53 | D |
| 94-54 | D |
| 94-55 | D |
| 94-56 | D |
| 107-1 | D |
| 107-2 | D |
| 107-3 | D |
| 107-4 | D |
| 107-5 | D |
| 107-6 | D |
| 107-7 | D |
| 107-8 | D |
| 107-9 | D |
| 107-10 | D |
| 107-11 | D |
| 107-12 | D |
| 107-13 | D |
| 107-14 | D |
| 107-15 | D |
| 107-16 | D |
| 107-17 | D |
| 107-18 | D |
| 107-19 | D |
| 107-20 | D |
| 107-21 | D |
| 107-22 | D |
| 107-23 | D |
| 107-24 | D |
| 107-25 | D |
| 107-26 | D |
| 107-27 | D |
| 107-28 | D |
| 107-29 | D |
| 107-30 | D |
| 107-31 | D |
| 107-32 | D |
| 107-33 | D |
| 107-34 | D |
| 107-35 | D |
| 107-36 | D |
| 107-37 | D |
| 107-38 | D |
| 107-39 | D |
| 107-40 | D |
| 107-41 | D |
| 107-42 | D |
| 107-43 | D |
| 107-44 | D |
| 2 | D |
| 3 | D |
| 4 | D |
| 5 | C |
| 6 | C |
| 7 | D |
| 8 | D |
| 24-23 | D |
| 9 | C |
| 10 | C |
| 11 | C |
| 12 | C |
| 13 | C |
| 14 | B |
| 15 | C |
| 16 | C |
| 17 | D |

TABLE 2-continued

| Example | Range |
|---|---|
| 18 | D |
| 19 | D |
| 20 | C |
| 21 | D |
| 22 | D |
| 23 | D |
| 24 | C |
| 25 | D |
| 26 | C |
| 27 | C |
| 28 | C |
| 29 | D |
| 30 | C |
| 31 | D |
| 32 | C |
| 33 | D |
| 34 | D |
| 35 | D |
| 36 | D |
| 37 | D |
| 38 | D |
| 39 | D |
| 40 | D |
| 41 | D |
| 42 | D |
| 43 | D |
| 44 | D |
| 45 | D |
| 46 | D |
| 47 | D |
| 48 | D |
| 49 | D |
| 50 | B |
| 51 | D |
| 52 | D |
| 53 | D |
| 54 | D |
| 55 | D |
| 56 | D |
| 57 | D |
| 58 | D |
| 59 | D |
| 60 | D |
| 61 | D |
| 62 | D |
| 63 | D |
| 64 | D |
| 65 | C |
| 67 | D |
| 68 | D |
| 69 | D |
| 70 | C |
| 71 | D |
| 72 | C |
| 73 | D |
| 74 | D |
| 75 | D |
| 76 | D |
| 77 | D |
| 78 | D |
| 79 | D |
| 80 | D |
| 81 | D |
| 82 | D |
| 83 | D |
| 84 | D |
| 85 | D |
| 86 | D |
| 87 | D |
| 88 | D |
| 89 | D |
| 90 | D |
| 91 | D |
| 92 | D |
| 93 | D |
| 94 | D |
| 95 | D |

TABLE 2-continued

| Example | Range |
|---|---|
| 96 | D |
| 97 | D |
| 98 | D |
| 99 | D |
| 100 | D |
| 101 | D |
| 102 | D |
| 103 | D |
| 104 | D |
| 105 | D |
| 106 | D |
| 107 | D |
| 108 | D |
| 109 | C |
| 110 | D |
| 111 | D |
| 112 | D |
| 113 | D |
| 114 | D |
| 115 | D |
| 116 | D |
| 117 | D |
| 118 | D |
| 119 | D |
| 120 | D |
| 121 | D |
| 122 | D |
| 123 | D |
| 124 | D |
| 125 | D |
| 126 | D |
| 127 | D |
| 128 | D |
| 129 | D |
| 130 | D |
| 131 | D |
| 132 | D |
| 133 | C |
| 134 | D |
| 135 | D |
| 136 | D |
| 138 | D |
| 139 | D |
| 140 | D |
| 141 | D |
| 142 | C |
| 143 | D |
| 144 | D |
| 145 | D |
| 146 | D |
| 147 | D |
| LS2 | C |
| LS3 | C |
| LS4 | C |
| LS16 | C |
| LS6 | B |
| LS11 | A |
| LS14 | D |
| LS20 | D |
| LS21 | D |
| LS22 | D |
| LS23 | D |
| LS24 | D |
| LS25 | D |
| LS26 | D |
| LS27 D'mer 1 | D |
| LS27 D'mer 2 | D |
| LS36 | D |
| LS37 | D |
| F5 | D |
| F6 | D |
| F7 | D |
| F8 | D |
| F14 | D |
| F15 | D |
| F16 | D |
| F17 | D |

TABLE 2-continued

| Example | Range |
|---|---|
| F20 | B |
| F21 | B |
| F22 | B |
| F25 | D |
| F26 | C |
| F27 | C |
| F28 | C |
| F29 | C |
| F30 | C |
| F32 | B |
| F33 | B |
| F34 | C |
| F35 | B |
| F37 | B |
| F38 | D |
| F39 | D |
| Diastereomers | |
| F41 | D |
| F43 | D |
| F48 | D |
| F49 | C |
| F51 | D |
| F52 | D |
| F53 | D |
| F54 | D |
| F55 | D |
| F56 | D |
| F57 | D |
| F58 | D |
| F60 | D |
| F61 | C |
| F62 | C |
| F63 | D |
| F64 | C |
| F65 | B |
| F66 | C |
| F67 | C |
| F69 | B |
| F70 | B |
| F71 | D |
| cj-48 | B |
| cj-49 | C |
| cj-50 | D |
| cj-51 | D |
| cj-52 | D |
| cj-53 | D |
| cj-54 | D |
| cj-55 | D |
| cj-56 | D |
| cj-57 | D |
| cj-58 | D |
| cj-59 | D |
| cj-60 | D |
| cj-61 | D |
| cj-62 | D |
| cj-63 | D |
| cj-64 | D |
| cj-65 | D |
| cj-66 | D |
| cj-67 | D |
| cj-68 | D |
| cj-69 | D |
| cj-70 | D |
| cj-71 | D |
| cj-72 | D |
| cj-73 | D |
| cj-74 | C |
| cj-75 | D |
| cj-76 | D |
| cj-77 | D |
| cj-78 | D |
| cj-79 | D |
| cj-80 | D |
| cj-81 | D |
| cj-82 | D |
| cj-83 | D |
| cj-84 | D |

TABLE 2-continued

| Example | Range |
|---|---|
| cj-85 | D |
| cj-86 | D |
| cj-87 | D |
| cj-88 | D |
| cj-89 | D |
| cj-90 | D |
| cj-91 | D |
| cj-92 | C |
| cj-93 | D |
| cj-94 | D |
| cj-95 | D |
| cj-96 | D |
| cj-97 | D |
| cj-98 | D |
| cj-99 | D |
| cj-100 | D |
| cj-101 | D |
| cj-102 | D |
| cj-103 | D |
| cj-104 | D |
| cj-105 | D |
| cj-106 | D |
| cj-107 | D |
| cj-108 | D |
| cj-109 | D |
| cj-110 | D |
| cj-111 | D |
| cj-112 | D |
| cj-113 | D |
| cj-114 | D |
| cj-115 | D |
| cj-116 | D |
| cj-117 | D |
| cj-118 | D |
| cj-119 | D |
| cj-120 | D |
| cj-121 | D |
| cj-122 | D |
| cj-45 | D |
| cj-41 | D |
| cj-47 | C |
| cj-43 | D |
| cj-44 | D |
| cj-40 | D |
| cj-46 | D |
| cj-42 | D |
| cj-36 | D |
| cj-37 | D |
| cj-38 | D |
| cj-39 | D |
| cj-32 | D |
| cj-33 | D |
| cj-34 | D |
| cj-35 | C |
| cj-136 | D |
| cj-137 | C |
| cj-138 | A |
| cj-139 | C |
| cj-140 | B |
| cj-141 | A |
| cj-142 | A |
| cj-143 | A |
| cj-144 | D |
| cj-145 | C |
| cj-146 | B |
| cj-147 | C |
| cj-148 | C |
| cj-149 | C |
| cj-150 | C |
| cj-151 | C |
| cj-152 | C |
| cj-153 | D |
| cj-154 | D |
| cj-155 | C |
| cj-156 | D |
| cj-126 | D |
| cj-127 | C |
| cj-128 | D |
| cj-129 | D |
| cj-130 | D |
| cj-131 | C |
| cj-132 | B |
| cj-133 | C |
| cj-134 | C |
| cj-135 | C |
| cj-125 | C |
| cj-15c | D |
| cj-20c | D |
| cj-20b | D |
| cj-20a | D |
| cj-17 | D |
| cj-16 | D |
| cj-20d | D |
| cj-20 | D |
| cj-15a | D |
| cj-15 | D |
| cj-15d | D |
| cj-11n | C |
| cj-11o | C |
| cj-11p | D |
| cj-11m | C |
| cj-11h | D |
| cj-11i | D |
| cj-11j | D |
| cj-11k | D |
| cj-11e | A |
| cj-11f | C |
| cj-11g | C |
| cj-11d | D |
| cj-11b | D |
| cj-11 | D |
| cj-11a | D |
| cj-11c | D |
| JG-3 | D |
| JG-4 | C |
| JG-5 | D |
| JG-6 | C |
| JG-7 | D |
| JG-8 | D |
| JG-9 | D |
| JG-10 | C |
| JG-12 | D |
| JG-13 | C |
| JG-14 | D |
| JG-15 | D |
| JG-16 | D |
| JG-17 | D |
| OL-1 | D |
| OL-2 | D |
| OL-3 | C |
| OL-4 | D |
| OL-5 | D |
| OL-6 | D |
| OL-7 | D |
| OL-8 | D |
| OL-9 | D |
| OL-10 | D |
| OL-11 | D |
| OL-12 | D |
| OL-13 | D |
| OL-19 | D |
| OL-20 | C |
| OL-21 | D |
| D73 | D |
| D74 | D |
| D75 | D |
| D76 | D |
| D77 | D |
| J16 | D |
| J17 | D |
| J18 | D |
| J19 | D |
| J20 | D |
| J21 | D |

TABLE 2-continued

| Example | Range |
| --- | --- |
| J22 | D |
| J23 | D |
| J24 | D |
| J25 | D |
| J26 | D |
| J27 | D |
| J28 | C |
| J29 | D |
| J30 | C |
| J31 | D |
| J37 | D |
| J38 | D |
| J39 | D |
| J40 | D |
| J41 | D |
| J42 | D |
| J42.a | D |
| J45 | D |
| J46 | D |
| J47 | D |
| J48 | D |
| J49 | D |
| J50 | D |
| J51 | C |
| D33 | D |
| D34 | D |
| D35 | D |
| D36 | D |
| D37 | D |
| D38 | D |
| D39 | D |
| D40 | D |
| D41 | D |
| D42 | D |
| D43 | D |
| D44 | D |
| D45 | D |
| D46 | D |
| D47 | D |
| D48 | D |
| D49 | D |
| D50 | D |
| D51 | D |
| D52 | D |
| D53 | D |
| D54 | D |
| D55 | D |
| D56 | D |
| D57 | D |
| D58 | D |
| D59 | D |
| D60 | D |
| D61 | D |
| D62 | D |
| D63 | D |
| D64 | D |
| D65 | D |
| D66 | D |
| D67 | D |
| D68 | D |
| D69 | D |
| D70 | D |
| M1 | >A |
| M2 | C |
| M3 | C |
| M4 | B |
| M5 | A |
| M6 | A |
| M7 | >A |
| M8 | A |
| M9 | B |
| M10 | >A |
| M11 | C |
| M12 | C |
| M13 | B |
| M14 | B |
| M15 | B |

TABLE 2-continued

| Example | Range |
| --- | --- |
| M16 | A |
| M17 | B |
| M18 | A |
| M19 | >A |
| M21 | C |
| M22 | A |
| M23 | C |
| M24 | C |
| M25 | C |
| M26 | B |
| M27 | C |
| M28 | A |
| M28-2 | B |
| M29 | >A |
| M30 | C |
| M31 | C |
| M32 | B |
| M33 | C |
| M34 | C |
| M35 | C |
| M36 | C |
| M37 | C |
| M38 | C |
| M39 | C |
| M40 | C |
| M41 | C |
| M42 | C |
| M43 | C |
| M44 | B |
| M45 | C |
| M46 | C |
| M47 | C |
| M48 | C |
| M49 | C |
| M50 | C |
| M51 | C |
| M52 | C |
| M53 | C |
| M54 | C |
| M55 | C |
| M56 | C |
| M57 | C |
| M58 | C |
| M59 | C |
| M60 | C |
| M61 | C |
| M62 | C |
| M63 | C |
| M64 | C |
| M65 | C |
| M66a | B |
| M66b | B |
| M66x | C |
| M67a | B |
| M67b | B |
| M68 | B |
| M69 | B |
| M70 | C |
| M71 | C |
| M72 | C |
| M73 | B |
| M74 | C |
| M75 | C |
| M76 | C |
| M77 | C |
| M78 | C |
| M79 | C |
| M80 | C |
| M81 | B |
| M82 | C |
| M83 | C |
| M84 | C |
| M85 | C |
| M86 | C |
| M87 | C |
| M88 | C |
| M89 | C |

TABLE 2-continued

| Example | Range |
|---|---|
| M90 | A |
| M91 | C |
| M91x | C |
| M91y | B |
| M92 | A |
| M93 | C |
| M94 | C |
| M95 | C |
| M96 | B |
| M97 | C |
| M98 | C |
| M99 | C |
| M100 | C |
| M101 | B |
| M102 | C |
| M103 | B |
| M104 | B |
| M105 | C |
| M106 | C |
| M107 | C |
| M108 | C |
| M109 | C |
| M110 | C |
| M111 | A |
| M112 | C |
| M113 | C |
| M114 | >A |
| M115 | >A |
| M116 | >A |
| M117 | >A |
| M118 | >A |
| M119 | B |
| M120 | B |
| M121 | B |
| M122 | C |
| M123 | A |
| M124 | C |
| M125 | C |
| M126 | C |
| M127 | C |
| M128 | C |
| M129 | A |
| M130 | C |
| R26 | D |
| R27 | D |
| R28 | D |
| R34 | D |
| R35 | B |
| R29 | D |
| R36 | D |
| R20 | D |
| R37 | D |
| R33 | C |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

The compounds of the present disclosure may inhibit HCV by mechanisms in addition to or other than NS5A inhibition. In one embodiment the compounds of the present disclosure inhibit HCV replicon and in another embodiment the compounds of the present disclosure inhibit NS5A. Compounds of the present disclosure may inhibit multiple genotypes of HCV.

What is claimed is:
1. A compound selected from
dimethyl(4,4'-biphenyldiylbis(1H-imidazole-4,2-diyl ((1S)-2-methyl-1,1-propanediyl)imino((2S)-1-oxo-1,2-propanediyl)))biscarbamate;
dimethyl(4,4'-biphenyldiylbis(1H-imidazole-4,2-diyl ((1S)-2-methyl-1,1-propanediyl)imino((2S,3R)-3-methoxy-1-oxo-1,2-butanediyl)))biscarbamate;
dimethyl(4,4'-biphenyldiylbis(1H-imidazole-4,2-diyl ((1S)-2-methyl-1,1-propanediyl)imino((2S)-3-methyl-1-oxo-1,2-butanediyl)))biscarbamate;
dimethyl(4,4'-biphenyldiylbis(1H-imidazole-4,2-diyl ((1S)-2-methyl-1,1-propanediyl)imino((2S)-4-methoxy-1-oxo-1,2-butanediyl)))biscarbamate;
dimethyl(4,4'-biphenyldiylbis(1H-imidazole-4,2-diyl ((1R)-2-methyl-1,1-propanediyl)imino((2S)-3-methyl-1-oxo-1,2-butanediyl)))biscarbamate;
dimethyl(4,4'-biphenyldiylbis(1H-imidazole-4,2-diyl ((1R)-2-methyl-1,1-propanediyl)imino((2S)-1-oxo-1,2-propanediyl)))biscarbamate;
dimethyl(4,4'-biphenyldiylbis(1H-imidazole-4,2-diyl ((1R)-2-methyl-1,1-propanediyl)imino((2S)-4-methoxy-1-oxo-1,2-butanediyl)))biscarbamate;
dimethyl(4,4'-biphenyldiylbis(1H-imidazole-4,2-diyl ((1R)-2-methyl-1,1-propanediyl)imino((2S,3R)-3-methoxy-1-oxo-1,2-butanediyl)))biscarbamate;
dimethyl(4,4'-biphenyldiylbis(1H-imidazole-4,2-diyl ((1R)-2-methyl-1,1-propanediyl)imino((2R)-3-methyl-1-oxo-1,2-butanediyl)))biscarbamate;
dimethyl(4,4'-biphenyldiylbis(1H-imidazole-4,2-diyl ((1S)-2-methyl-1,1-propanediyl)imino((2R)-3-methyl-1-oxo-1,2-butanediyl)))biscarbamate;
$N^2$-(methoxycarbonyl)-N-((1S)-1-(4-(4'-(2-((2S)-1-(N-(methoxycarbonyl)-L-valyl)-2-pyrrolidinyl)-1H-imidazol-4-yl)-4-biphenylyl)-1H-imidazol-2-yl)-2-methylpropyl)-L-valinamide;
methyl(((1S,2R)-2-methoxy-1-(((2S)-2-(4-(4'-(2-((1S)-1-((N-(methoxycarbonyl)-O-methyl-L-threonyl)amino)-2-methylpropyl)-1H-imidazol-4-yl)-4-biphenylyl)-1H-imidazol-2-yl)-1-pyrrolidinyl)carbonyl)propyl) carbamate;
methyl(((1S)-3-methoxy-1-(((2S)-2-(4-(4'-(2-((1S)-1-((N-(methoxycarbonyl)-O-methyl-L-homoseryl)amino)-2-methylpropyl)-1H-imidazol-4-yl)-4-biphenylyl)-1H-imidazol-2-yl)-1-pyrrolidinyl)carbonyl)propyl) carbamate;
methyl(((1S)-2-((2S)-2-(4-(4'-(2-((1S)-1-((N-(methoxycarbonyl)-L-alanyl)amino)-2-methylpropyl)-1H-imidazol-4-yl)-4-biphenylyl)-1H-imidazol-2-yl)-1-pyrrolidinyl)-1-methyl-2-oxoethyl)carbamate;
$N^2$-(methoxycarbonyl)-N-((1R)-1-(4-(4'-(2-((2S)-1-(N-(methoxycarbonyl)-L-valyl)-2-pyrrolidinyl)-1H-imidazol-4-yl)-4-biphenylyl)-1H-imidazol-2-yl)-2-methylpropyl)-L-valinamide;
methyl(((1S,2R)-2-methoxy-1-(((2S)-2-(4-(4'-(2-((1R)-1-((N-(methoxycarbonyl)-O-methyl-L-threonyl)amino)-2-methylpropyl)-1H-imidazol-4-yl)-4-biphenylyl)-1H-imidazol-2-yl)-1-pyrrolidinyl)carbonyl)propyl) carbamate;
methyl(((1S)-3-methoxy-1-(((2S)-2-(4-(4'-(2-((1R)-1-((N-(methoxycarbonyl)-O-methyl-L-homoseryl)amino)-2-methylpropyl)-1H-imidazol-4-yl)-4-biphenylyl)-1H-imidazol-2-yl)-1-pyrrolidinyl)carbonyl)propyl) carbamate;
methyl(((1S)-2-((2S)-2-(4-(4'-(2-((1R)-1-((N-(methoxycarbonyl)-L-alanyl)amino)-2-methylpropyl)-1H-imi- dazol-4-yl)-4-biphenylyl)-1H-imidazol-2-yl)-1-pyrrolidinyl)-1-methyl-2-oxoethyl)carbamate;
dimethyl(4,4'-biphenyldiylbis(1H-imidazole-4,2-diyl((1S)-2-methyl-1,1-propanediyl)imino((2S)-1-oxo-1,2-propanediyl)))biscarbamate;
dimethyl(4,4'-biphenyldiylbis(1H-imidazole-4,2-diyl((1S)-2-methyl-1,1-propanediyl)imino((2S,3R)-3-methoxy-1-oxo-1,2-butanediyl)))biscarbamate;
dimethyl(4,4'-biphenyldiylbis(1H-imidazole-4,2-diyl((1S)-2-methyl-1,1-propanediyl)imino((2S)-3-methyl-1-oxo-1,2-butanediyl)))biscarbamate;
dimethyl(4,4'-biphenyldiylbis(1H-imidazole-4,2-diyl((1S)-2-methyl-1,1-propanediyl)imino((2S)-4-methoxy-1-oxo-1,2-butanediyl)))biscarbamate;
dimethyl(4,4'-biphenyldiylbis(1H-imidazole-4,2-diyl((1R)-2-methyl-1,1-propanediyl)imino((2S)-3-methyl-1-oxo-1,2-butanediyl)))biscarbamate;
dimethyl(4,4'-biphenyldiylbis(1H-imidazole-4,2-diyl((1R)-2-methyl-1,1-propanediyl)imino((2S)-1-oxo-1,2-propanediyl)))biscarbamate;
dimethyl(4,4'-biphenyldiylbis(1H-imidazole-4,2-diyl((1R)-2-methyl-1,1-propanediyl)imino((2S)-4-methoxy-1-oxo-1,2-butanediyl)))biscarbamate;
dimethyl(4,4'-biphenyldiylbis(1H-imidazole-4,2-diyl((1R)-2-methyl-1,1-propanediyl)imino((2S,3R)-3-methoxy-1-oxo-1,2-butanediyl)))biscarbamate;
dimethyl(4,4'-biphenyldiylbis(1H-imidazole-4,2-diyl((1R)-2-methyl-1,1-propanediyl)imino((2R)-3-methyl-1-oxo-1,2-butanediyl)))biscarbamate;
dimethyl(4,4'-biphenyldiylbis(1H-imidazole-4,2-diyl((1S)-2-methyl-1,1-propanediyl)imino((2R)-3-methyl-1-oxo-1,2-butanediyl)))biscarbamate;
$N^2$-(methoxycarbonyl)-N-((1S)-1-(4-(4'-(2-((2S)-1-(N-(methoxycarbonyl)-L-valyl)-2-pyrrolidinyl)-1H-imidazol-4-yl)-4-biphenylyl)-1H-imidazol-2-yl)-2-methylpropyl)-L-valinamide;

methyl((1S,2R)-2-methoxy-1-(((2S)-2-(4-(4'-(2-((1S)-1-((N-(methoxycarbonyl)-O-methyl-L-threonyl)amino)-2-methylpropyl)-1H-imidazol-4-yl)-4-biphenylyl)-1H-imidazol-2-yl)-1-pyrrolidinyl)carbonyl)propyl)carbamate;
methyl((1S)-3-methoxy-1-(((2S)-2-(4-(4'-(2-((1S)-1-((N-(methoxycarbonyl)-O-methyl-L-homoseryl)amino)-2-methylpropyl)-1H-imidazol-4-yl)-4-biphenylyl)-1H-imidazol-2-yl)-1-pyrrolidinyl)carbonyl)propyl)carbamate;
methyl((1S)-2-((2S)-2-(4-(4'-(2-((1S)-1-((N-(methoxycarbonyl)-L-alanyl)amino)-2-methylpropyl)-1H-imidazol-4-yl)-4-biphenylyl)-1H-imidazol-2-yl)-1-pyrrolidinyl)-1-methyl-2-oxoethyl)carbamate;
$N^2$-(methoxycarbonyl)-N-((1R)-1-(4-(4'-(2-((2S)-1-(N-(methoxycarbonyl)-L-valyl)-2-pyrrolidinyl)-1H-imidazol-4-yl)-4-biphenylyl)-1H-imidazol-2-yl)-2-methylpropyl)-L-valinamide;
methyl((1S,2R)-2-methoxy-1-(((2S)-2-(4-(4'-(2-((1R)-1-((N-(methoxycarbonyl)-O-methyl-L-threonyl)amino)-2-methylpropyl)-1H-imidazol-4-yl)-4-biphenylyl)-1H-imidazol-2-yl)-1-pyrrolidinyl)carbonyl)propyl)carbamate;
methyl((1S)-3-methoxy-1-(((2S)-2-(4-(4'-(2-((1R)-1-((N-(methoxycarbonyl)-O-methyl-L-homoseryl)amino)-2-methylpropyl)-1H-imidazol-4-yl)-4-biphenylyl)-1H-imidazol-2-yl)-1-pyrrolidinyl)carbonyl)propyl)carbamate; and
methyl((1S)-2-((2S)-2-(4-(4'-(2-((1R)-1-((N-(methoxycarbonyl)-L-alanyl)amino)-2-methylpropyl)-1H-imidazol-4-yl)-4-biphenylyl)-1H-imidazol-2-yl)-1-pyrrolidinyl)-1-methyl-2-oxoethyl)carbamate;
or a pharmaceutically acceptable salt thereof.

2. A compound selected from

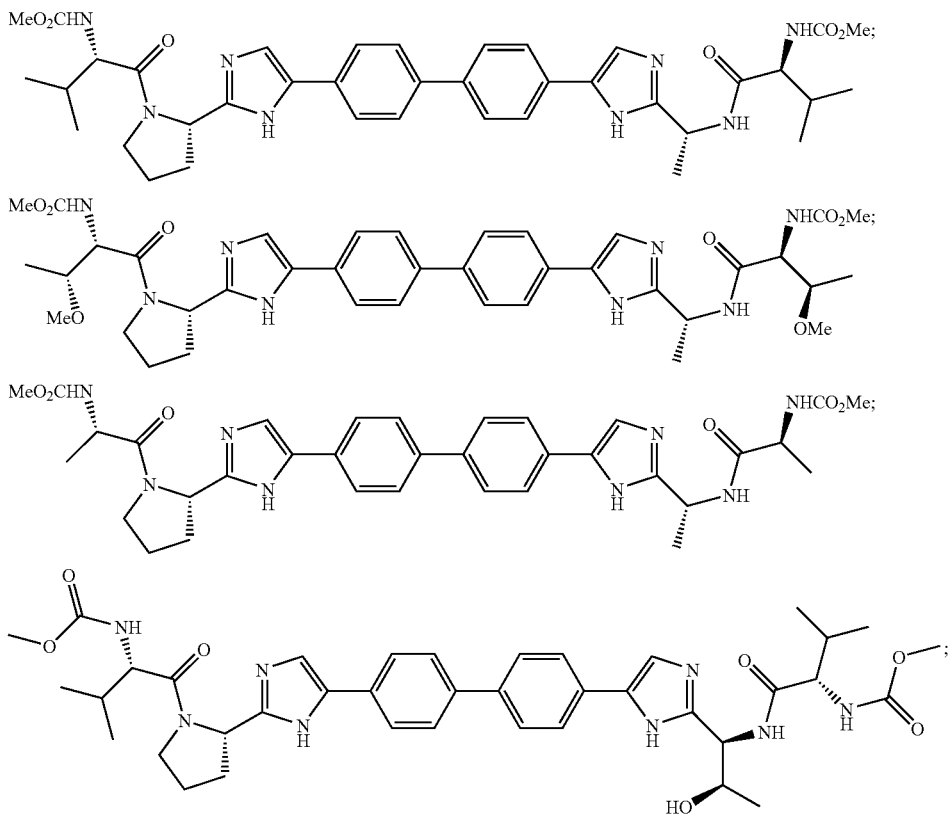

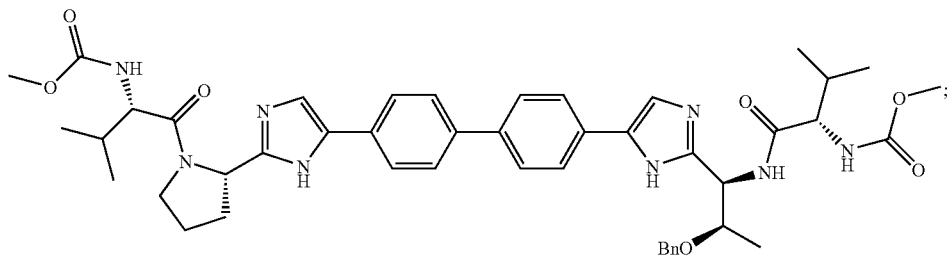
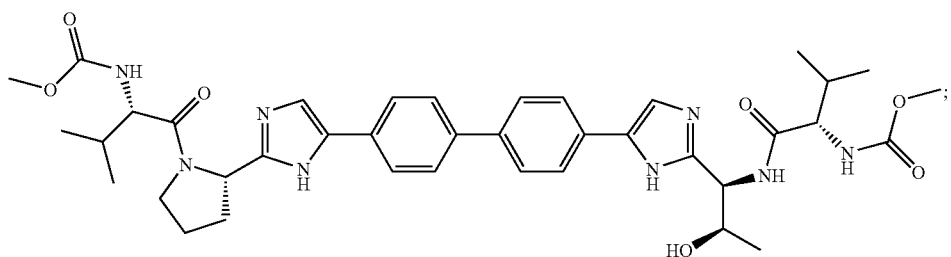
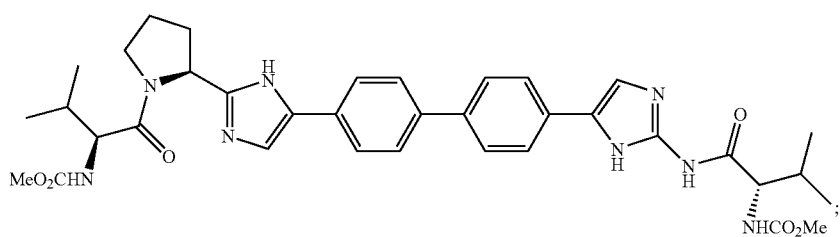
Chiral
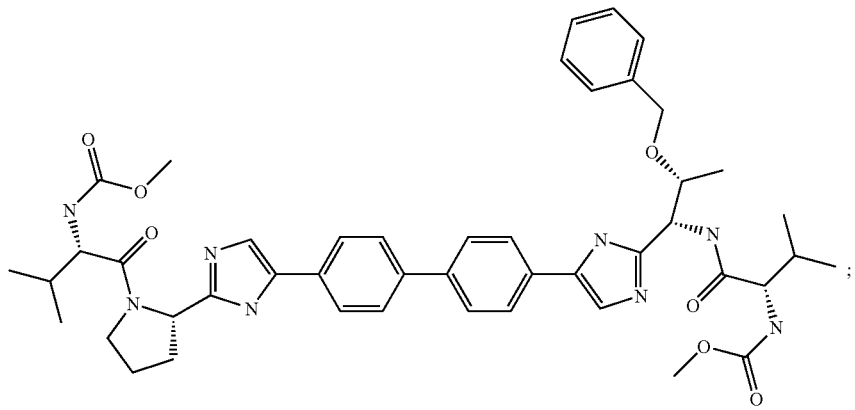
Chiral
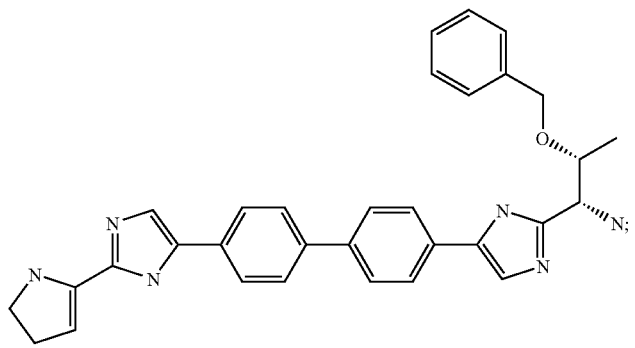

-continued

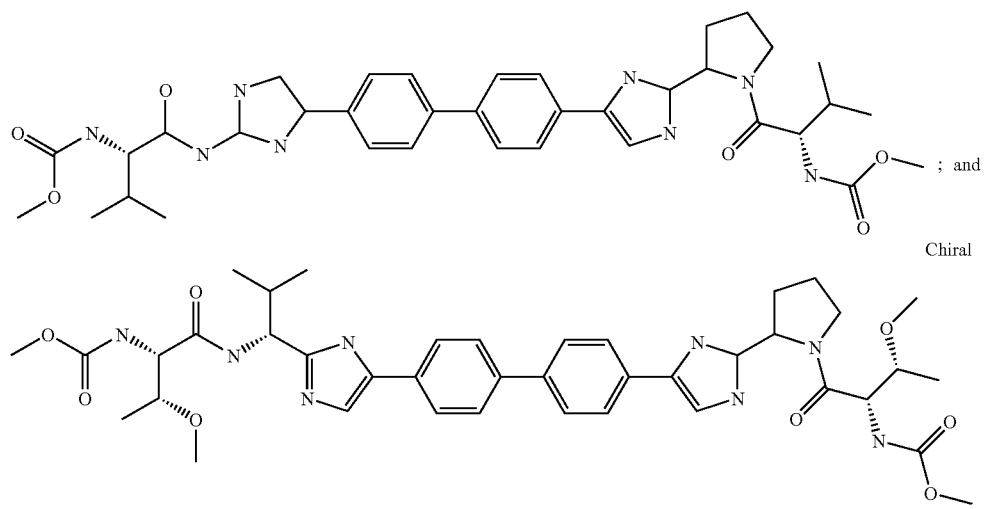

or a pharmaceutically acceptable salt thereof.

3. A composition comprising a compound of claim 1, or a pharmaceutically acceptable salt thereof, and a pharmaceutically acceptable carrier.

4. The composition of claim 3 further comprising one or two additional compounds having anti-HCV activity.

5. The composition of claim 4 wherein at least one of the additional compounds is an interferon or a ribavirin.

6. The composition of claim 5 wherein the interferon is selected from interferon alpha 2B, pegylated interferon alpha, consensus interferon, interferon alpha 2A, and lymphoblastoid interferon tau.

7. The composition of claim 4 wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5'-monophosphate dehydrogenase inhibitor, amantadine, and rimantadine.

8. The composition of claim 4 wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

9. A composition comprising a compound of claim 2, or a pharmaceutically acceptable salt thereof, and a pharmaceutically acceptable carrier.

10. The composition of claim 9 further comprising one or two additional compounds having anti-HCV activity.

11. The composition of claim 10 wherein at least one of the additional compounds is an interferon or a ribavirin.

12. The composition of claim 11 wherein the interferon is selected from interferon alpha 2B, pegylated interferon alpha, consensus interferon, interferon alpha 2A, and lymphoblastoid interferon tau.

13. The composition of claim 10 wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5'-monophosphate dehydrogenase inhibitor, amantadine, and rimantadine.

14. The composition of claim 10 wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

15. A method of treating an HCV infection in a patient, comprising administering to the patient a therapeutically effective amount of a compound of claim 1, or a pharmaceutically acceptable salt thereof.

16. The method of claim 15 further comprising administering one or two additional compounds having anti-HCV activity prior to, after or simultaneously with the compound of claim 1, or a pharmaceutically acceptable salt thereof.

17. The method of claim 16 wherein at least one of the additional compounds is an interferon or a ribavirin.

18. The method of claim 17 wherein the interferon is selected from interferon alpha 2B, pegylated interferon alpha, consensus interferon, interferon alpha 2A, and lymphoblastoid interferon tau.

19. The method of claim 16 wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5'-monophosphate dehydrogenase inhibitor, amantadine, and rimantadine.

20. The method of claim 16 wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

21. A method of treating an HCV infection in a patient, comprising administering to the patient a therapeutically effective amount of a compound of claim 2, or a pharmaceutically acceptable salt thereof.

22. The method of claim 21 further comprising administering one or two additional compounds having anti-HCV activity prior to, after or simultaneously with the compound of claim 2, or a pharmaceutically acceptable salt thereof.

23. The method of claim 22 wherein at least one of the additional compounds is an interferon or a ribavirin.

24. The method of claim 23 wherein the interferon is selected from interferon alpha 2B, pegylated interferon alpha, consensus interferon, interferon alpha 2A, and lymphoblastoid interferon tau.

25. The method of claim 22 wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5'-monophosphate dehydrogenase inhibitor, amantadine, and rimantadine.

26. The method of claim 22 wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

* * * * *

UNITED STATES PATENT AND TRADEMARK OFFICE
CERTIFICATE OF CORRECTION

| | |
|---|---|
| PATENT NO. | : 7,745,636 B2 |
| APPLICATION NO. | : 12/029680 |
| DATED | : June 29, 2010 |
| INVENTOR(S) | : Carol Bachand et al. |

It is certified that error appears in the above-identified patent and that said Letters Patent is hereby corrected as shown below:

In the Specification:

Column 4, line 55, change "Imiqimod" to -- Imiquimod --.
Column 5, line 27, change "Imiqimod" to -- Imiquimod --.

In the Claims:

Claim 2:

Columns 367 and 368, lines 2 to 22, change

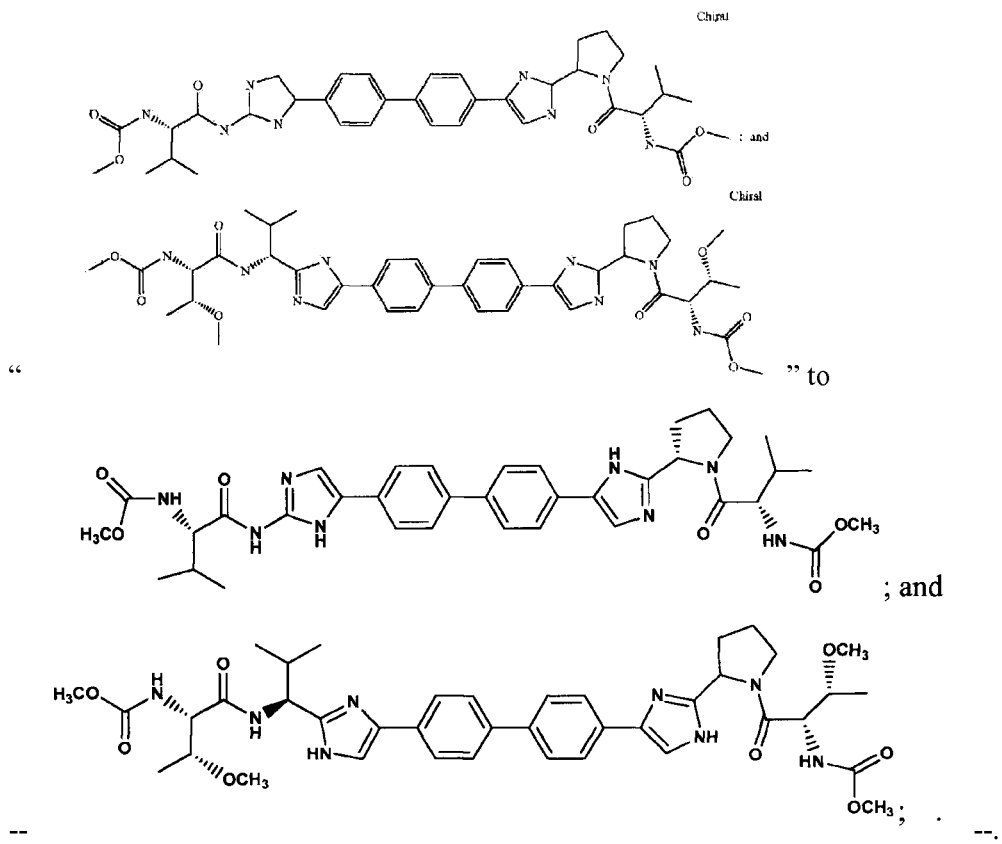

Signed and Sealed this
Seventh Day of August, 2012

David J. Kappos
*Director of the United States Patent and Trademark Office*

CERTIFICATE OF CORRECTION (continued)
U.S. Pat. No. 7,745,636 B2

In the Claims:

Claim 7:

Column 367, line 43, change "Imiqimod" to -- Imiquimod --.

Claim 13:

Column 368, line 25, change "Imiqimod" to -- Imiquimod --.

Claim 19:

Column 368, line 53, change "Imiqimod" to -- Imiquimod --.

Claim 25:

Column 370, line 2, change "Imiqimod" to -- Imiquimod --.